US012295971B2

(12) United States Patent
Roybal et al.

(10) Patent No.: US 12,295,971 B2
(45) Date of Patent: May 13, 2025

(54) COMPOSITIONS AND METHODS FOR ENHANCING ADOPTIVE T CELL THERAPEUTICS

(71) Applicants: The Regents of the University of California, Oakland, CA (US); Northwestern University, Evanston, IL (US)

(72) Inventors: Kole Roybal, San Francisco, CA (US); Julie Garcia, San Francisco, CA (US); Iowis Zhu, San Francisco, CA (US); Jaehyuk Choi, Chicago, IL (US); Jay Daniels, Chicago, IL (US)

(73) Assignees: The Regents of the University of California, Oakland, CA (US); Northwestern University, Evanston, IL (US)

( * ) Notice: Subject to any disclaimer, the term of this patent is extended or adjusted under 35 U.S.C. 154(b) by 0 days.

(21) Appl. No.: 18/630,828

(22) Filed: Apr. 9, 2024

(65) Prior Publication Data

US 2024/0270802 A1 Aug. 15, 2024

Related U.S. Application Data

(63) Continuation of application No. PCT/US2023/075738, filed on Oct. 2, 2023.

(Continued)

(51) Int. Cl.
*A61K 35/17* (2025.01)
*A61K 40/11* (2025.01)
(Continued)

(52) U.S. Cl.
CPC .............. *A61K 35/17* (2013.01); *A61K 40/11* (2025.01); *A61K 40/31* (2025.01); *A61K 40/32* (2025.01);
(Continued)

(58) Field of Classification Search
CPC . C07K 14/4702; A61K 39/4632; A61P 35/00; C12N 9/16; C12N 9/22; C12N 15/63; C12N 2310/20
See application file for complete search history.

(56) References Cited

U.S. PATENT DOCUMENTS 7,452,967 B2 * 11/2008 Bertin ................ C07K 14/4747 530/300
2017/0073423 A1 3/2017 Juillerat et al.
(Continued)

FOREIGN PATENT DOCUMENTS

KR 2016091483 A * 8/2016 ......... C07K 14/4702
WO WO-2021/233551 A1 11/2021

OTHER PUBLICATIONS

Rodríguez-Caparrós A, et al., Int J Mol Sci., Nov. 11, 2020; 21(22):8478. doi: 10.3390/ijms21228478 (Year: 2020).*
(Continued)

*Primary Examiner* — Ram R Shukla
*Assistant Examiner* — Shabana S Meyering
(74) *Attorney, Agent, or Firm* — Mintz, Levin, Cohn, Ferris, Glovsky and Popeo, P.C.

(57) ABSTRACT

The present disclosure relates generally to compositions and methods for improving T cell therapy. In particular, the disclosure provides polypeptides and recombinant nucleic acid constructs and/or recombinant nucleic acids encoding polypeptides having mutations capable of altering T cell signaling, cytokine production, and/or in vivo persistence in tumors of therapeutic T cells comprising the mutation. The T cell signaling can be by NFAT, NF-κB and/or AP-1 pathways. The disclosure also provides vectors and cells including the polypeptides and/or recombinant nucleic acid constructs and/or recombinant nucleic acids of the disclosure as well as methods of preparing a T cell for use in cell
(Continued)

CJ5 therapy, and methods of identifying a mutation useful for improving T cell therapy.

27 Claims, 67 Drawing Sheets

Specification includes a Sequence Listing.

Related U.S. Application Data

(60) Provisional application No. 63/412,300, filed on Sep. 30, 2022.

(51) Int. Cl.

| | |
|---|---|
| ***A61K 40/31*** | (2025.01) |
| ***A61K 40/32*** | (2025.01) |
| ***A61K 40/42*** | (2025.01) |
| ***A61P 35/00*** | (2006.01) |
| ***C07K 14/47*** | (2006.01) |
| ***C07K 14/82*** | (2006.01) |
| ***C07K 16/28*** | (2006.01) |
| ***C12N 5/0783*** | (2010.01) |
| ***C12N 9/16*** | (2006.01) |
| ***C12N 9/22*** | (2006.01) |
| ***C12N 15/63*** | (2006.01) |

(52) U.S. Cl.

CPC ........ *A61K 40/4211* (2025.01); *A61K 40/424* (2025.01); *A61K 40/4251* (2025.01); *A61P 35/00* (2018.01); *C07K 14/4702* (2013.01); *C07K 14/4747* (2013.01); *C07K 14/82* (2013.01); *C07K 16/2803* (2013.01); *C12N 5/0636* (2013.01); *C12N 9/16* (2013.01); *C12N 9/22* (2013.01); *C12N 15/63* (2013.01); *A61K 2239/13* (2023.05); *C12N 2310/20* (2017.05); *C12N 2510/00* (2013.01)

(56) References Cited

U.S. PATENT DOCUMENTS

| | | | |
|---|---|---|---|
| 2021/0062227 A1 | 3/2021 | Qi et al. | |
| 2022/0133790 A1* | 5/2022 | Gehrke .................. | A61P 35/00 424/93.71 |
| 2022/0401537 A1* | 12/2022 | Salter ............. | A61K 39/464402 |
| 2024/0165161 A1 | 5/2024 | Roybal et al. | |

OTHER PUBLICATIONS

Machine Translation of KR-2016091483-A (Year: 2016).*
International Search Report mailed on Mar. 14, 2024, for PCT Application No. PCT/US2023/075738, filed Oct. 2, 2023, 5 pages.
Written Opinion mailed on Mar. 14, 2024, for PCT Application No. PCT/US2023/075738, filed Oct. 2, 2023, 5 pages.

* cited by examiner

T Cell Lymphoma Mutation In Vitro Jurkat Screen Signaling Results

Figure 7A-C CARD11-PIK3R3 Fusion Variants and Variant Function

CJ4

CARD11-PIK3R3 Fusion Function in CBM Complex

BCL10 binding-deficient mutant

MALT1 substrate cleavage

Figure 9A-B CARD11-PIK3R3 Fusion Phosphorylation Signaling Dynamics

T Cell Growth After Anti-CD3/Anti-CD28 Bead Stimulation

CD3+ Cytokine Secretion After Co-Culture with CD19-K562s

CJ7

CJ2

Schematic of Syngeneic TCR-transgenic Melanoma Model

CARD11-PIK3R3 OT-Is Preferentially Expand and Accumulate in Tumors

Tumor infiltrating lymphocytes

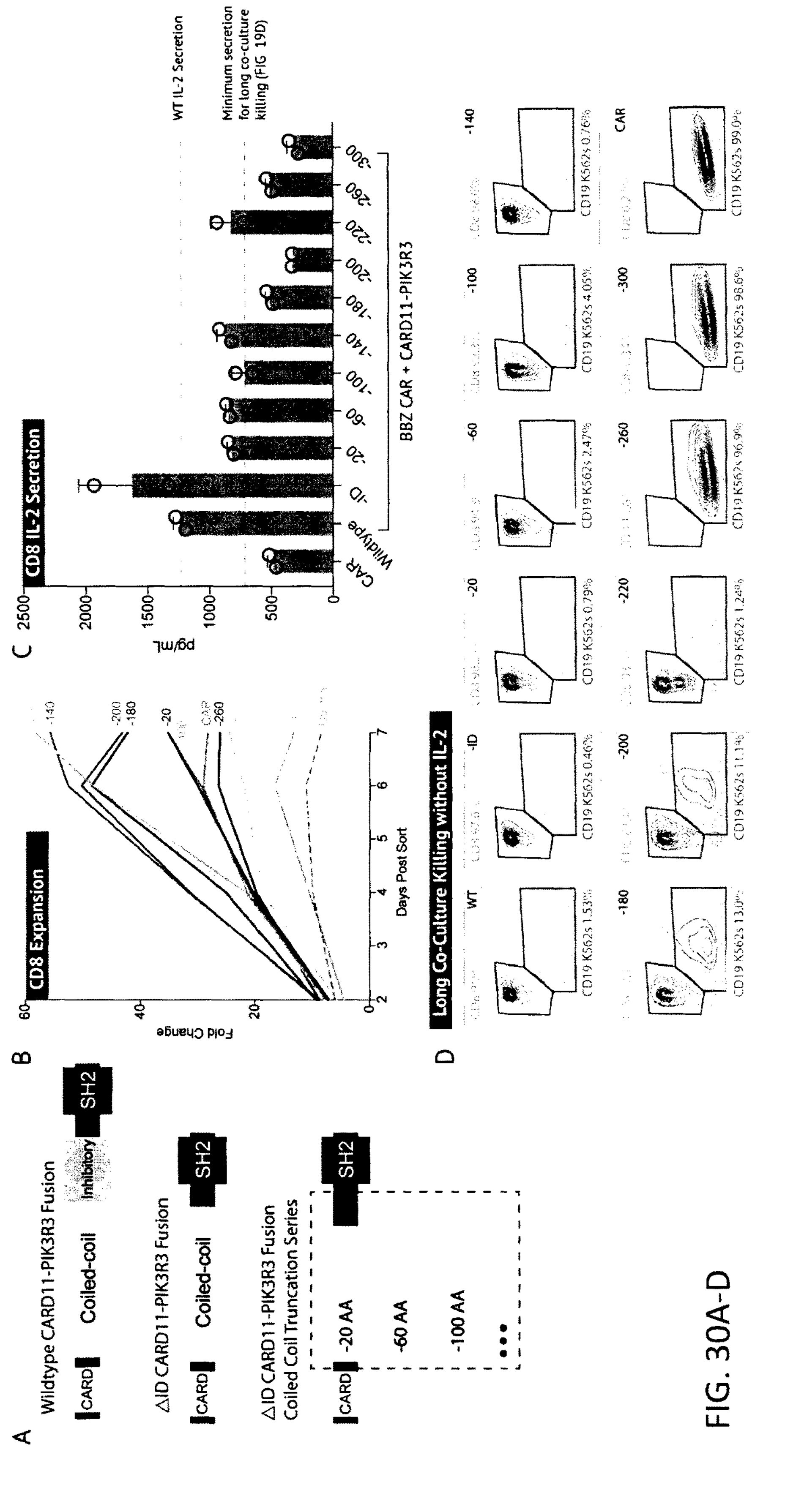
FIG. 30A-D
CJ5

BRAF

CARD11 point mutations

COMPOSITIONS AND METHODS FOR ENHANCING ADOPTIVE T CELL THERAPEUTICS

CROSS-REFERENCE TO RELATED APPLICATION

This application is a continuation, filed under 35 U.S.C. § 120, of PCT/US2023/075738 on Oct. 2, 2023, which claims the benefit of priority to U.S. Provisional Patent Application No. 63/412,300 filed Sep. 30, 2022, the entire contents of which are incorporated by reference herein and for all purposes, including any drawings.

STATEMENT REGARDING FEDERALLY SPONSORED R&D

This invention was made with government support under grant no. OD025751 and 1DP2AI136599-01 awarded by The National Institutes of Health. The government has certain rights in the invention.

STATEMENT REGARDING SEQUENCE LISTING

The Sequence Listing XML associated with this application is provided in XML file format and is hereby incorporated by reference into the specification. The name of the XML file containing the Sequence Listing XML is 048536-737001WO_ST26.xml. The XML file is 720,329 bytes, and was created on Oct. 2, 2023, and is being submitted electronically via USPTO Patent Center.

FIELD

The present disclosure relates generally to compositions and methods for enhancing T cell therapeutics. The disclosure provides recombinant nucleic acid constructs and/or recombinant nucleic acids encoding polypeptides that promote T cell signaling, efficacy and/or in vivo persistence, cells that comprise such recombinant nucleic acids, methods for preparing T cells for use in cell therapies, as well as methods for identifying mutations useful for improving T cell therapy.

BACKGROUND

Adoptive T cell therapies, including chimeric antigen receptor (CAR) T cells, have revolutionized cancer therapy. However, impressive responses are limited to a subset of patients with hematological cancers and have not been unlocked in patients with solid tumors, which represent 90% of adult cancers. In both treatment-resistant hematological and solid cancers, adoptive T cell therapy is limited by a complex combination of factors including fitness of engineered T cells in tumors, T cell exhaustion, poor in vivo persistence and immunosuppressive environmental factors. Despite significant recent advances, rational design has failed to overcome the problems associated with such factors.

Another approach to identify modifications that improve T cell function in vitro and in vivo, besides rational design, is unbiased screening. For example, the vast majority of screening efforts, have focused on genome-scale or genome-wide alterations which modify expression of endogenous wild-type genes via CRISPR-Cas9 or short hairpin RNA (shRNA) or cDNA overexpression.

Chimeric antigen receptors (CARs) are synthetic receptors that include an antigen specific extracellular single chain variable fragment (scFv) attached to a flexible linker (hinge) region, transmembrane domain, and intracellular signaling domains. The intracellular portion of the receptor consists of T cell signaling domains such as 41BB, CD28 and CD3zeta, designed to mimic T cell receptor (TCR) stimulation and the immunological synapse upon engagement with the antigen specified by the scFv. CAR constructs do not require antigen presentation by MHC molecules, and therefore have been used to effectively redirect a patient's own T cells against a tumor specific cell surface antigen. To date, five CD19 targeted CAR-T cell therapies have been approved by the FDA for use against hematological B cell cancers. While these therapies have proven highly effective in refractory B cell malignancies, CAR-T cell therapies have yet to provide robust, long-term efficacy against solid tumors. In the solid tumor setting, CAR-T cells can become exhausted and struggle to proliferate and perform effector function, ultimately resulting in the inability to control tumor growth or prevent relapse. Therefore, to create effective targeted cellular therapies against solid tumors the proliferative capacity, persistence and effector function of CAR-T cells needs to be improved.

An avenue under investigation is genetically modifying CAR-T cells to improve their functionality in solid tumors. A recent case study described a chronic lymphocytic leukemia (CLL) patient who experienced a delayed yet complete response after treatment with a CD19 CAR-T cell therapy. It was later discovered that, within a single T cell clone, the CD19 CAR cassette had integrated into the one allele of TET2, a known T cell lymphoma tumor suppressor, rendering it nonfunctional. Interestingly, the second TET2 allele of this patient was also mutated, resulting in a lack of function of TET2 in the CD19 CAR-T cells dosed to this patient. This single TET2 knockout CAR-T cell clone exhibited altered T cell differentiation and improved overall effector function. Ultimately, this clone expanded to become a majority of the CAR-T cell population, and mediated a complete response against the patient's relapsed CLL. In a second example, a similar complete response was mediated in a patient when the CD22 CAR cassette integrated into the T cell lymphoma tumor suppressor CBL. These case studies demonstrate that genetic knockout of T cell lymphoma tumor suppressors, such as TET2 and CBL, can have remarkable beneficial effects on CAR-T cell therapies. In preclinical studies, genome wide knockout assays have revealed genes, such as REGNASE, that upon knockout improve T cell fitness and anti-tumor efficacy in vivo. Additionally, other studies have found that the knockout of genes related to T cell exhaustion and memory formation, such as the NR4A family of genes, can result in improved and prolonged CAR-T cell response to tumors.

While these examples indicate that CAR-T cell functionality can be improved through genetic manipulation, particularly through manipulation of tumor suppressor genes, these studies are often extremely broad in their scope (examining the entire genome) and focus solely on the effect of constitutive genetic knockouts. Somatic single nucleotide variant (SSNV) mutations, translocations and gene deletions that naturally arise in cancers offer biologically rational candidates for genetic manipulation alongside CAR expression.

There remains a need in the art for alternative solutions to address the significant unmet need for effective adoptive T cell therapies and for enhancing engineered T cell fitness.

SUMMARY

This section provides a general summary of the disclosure, and is not comprehensive of its full scope or all of its features.

The disclosure provides recombinant nucleic acid constructs and/or recombinant nucleic acids and methods for enhancing adoptive T cell therapies. The recombinant nucleic acid constructs and/or recombinant nucleic acids of the disclosure encode polypeptides with mutations wherein the mutations enhance the therapeutic efficacy of T cells by altering T cell signaling, decreasing T cell exhaustion and/or by enhancing in vivo persistence and fitness of engineered T cells.

In one aspect, the disclosure provides a polypeptide comprising: (a) a caspase-associated recruitment domain (CARD) containing protein or a functional fragment thereof; and (b) a domain capable of binding to (i) a substrate localized to the intracellular side of the plasma membrane of a cell and/or (ii) a target polypeptide comprising a phosphorylated tyrosine. In some embodiments, the domain in b) is capable of binding to a substrate indirectly localized to the intracellular side of the plasma membrane through binding to another polypeptide or lipid that is directly localized to the intracellular side. In some embodiments, the CARD containing protein comprises or consists of a sequence having at least 75%, 80%, 85%, 90%, 95%, 96%, 97%, 98%, 99%, or 100% identity to any one of SEQ ID NO: 261-289. In some embodiments, the CARD containing protein is selected from CARD9, CARD10, CARD11, and CARD14. In some embodiments, the CARD containing protein comprises or consists of a sequence having at least 75%, 80%, 85%, 90%, 95%, 96%, 97%, 98%, 99%, or 100% identity to any one of SEQ ID NO: 261-264. In some embodiments, the functional fragment of the CARD containing protein is derived from CARD11 and comprises or consists of a sequence having at least 75%, 80%, 85%, 90%, 95%, 96%, 97%, 98%, 99%, or 100% identity to SEQ ID NO: 263.

In some embodiments, the function of the CARD containing protein or the functional fragment thereof is to bind to a CARD domain on BCL10. In some embodiments, the functional fragment thereof comprises at least 40, at least 50, at least 60, at least 70, at least 80, at least 90, at least 100, at least 150, at least 200, at least 300, at least 400, or at least 500 amino acids.

In some embodiments, the cell is a T cell, a macrophage, a monocyte, or a natural killer (NK) cell. In some embodiments, activation of the cell produces the substrate localized to the intracellular side of the plasma membrane. In some embodiments, the substrate localized to the intracellular side of the plasma membrane of a cell is a phosphoinositide. In some embodiments, the phosphoinositide is selected from phosphatidylinositol (3,4,5)-trisphosphate (PIP3), phosphatidylinositol 4,5-bisphosphate (PI(4,5)P2). In some embodiments, the polypeptide binds to the phosphoinositide with a Kd of less than 50 μM, 10 μM, 5 μM, 1 μM, 0.5 μM, 0.1 μM, 0.05 μM, or 0.01 μM, and wherein the Kd is analyzed using SPR.

In some embodiments, the target polypeptide comprises or consists of a sequence having at least 75%, 80%, 85%, 90%, 95%, 96%, 97%, 98%, 99%, or 100% identity to any one of SEQ ID NOs: 298-304. In some embodiments, the target polypeptide is derived from IGF-IR, CTLA-4, or CD28. In some embodiments, the phosphorylated tyrosine is located at the position corresponding to pY1221 of SEQ ID NO: 302. In some embodiments, the phosphorylated tyrosine is located at the position corresponding to pY1346 of SEQ ID NO: 301.

In some embodiments, the polypeptide binds to the target polypeptide with a Kd of less than 10 μM, 5 μM, 1 μM, 0.5 μM, 0.1 μM, 0.05 μM, or 0.01 μM, and wherein the Kd is analyzed by fluorescence polarization assay. In some embodiments, the polypeptide has a higher affinity for the target polypeptide comprising the phosphorylated tyrosine than a control polypeptide without phosphorylation at the corresponding tyrosine position. In some embodiments, the polypeptide has at least 2-fold, at least 5-fold, at least 10-fold, at least 50-fold, or at least 100-fold, higher affinity (lower Kd) for the target polypeptide comprising the phosphorylated tyrosine than a control polypeptide without phosphorylation at the corresponding tyrosine position.

In some embodiments, the domain in (b) is, or comprises, a SH3 domain. In some embodiments, the domain in (b) is, or comprises, a phosphotyrosine-binding (PTB) domain. In some embodiments, the domain in (b) is, or comprises, a pleckstrin homology (PH) domain. In some embodiments, the domain in (b) is, or comprises, a SH2 domain.

In one aspect, the disclosure provides a polypeptide comprising: (i) a caspase-associated recruitment domain (CARD) containing protein or a functional fragment thereof; and (ii) a SH2 domain. In some embodiments, the CARD containing protein is CARD11. In some embodiments, the SH2 domain is capable of binding to a polypeptide comprising a phosphorylated tyrosine. In some embodiments, the SH2 domain comprises or consists of a sequence having at least 75%, 80%, 85%, 90%, 95%, 96%, 97%, 98%, 99%, or 100% identity to any one of SEQ ID NOs: 305 and 307-437. In some embodiments, the SH2 domain comprises the motif of a conserved arginine residue in the FLVR motif.

In some embodiments, the SH2 domain comprises or consists of a sequence having at least 75%, 80%, 85%, 90%, 95%, 96%, 97%, 98%, 99%, or 100% identity to SEQ ID NO: 305. In some embodiments, the SH2 domain is an engineered SH2 domain with an enhanced affinity for phosphotyrosine. In some embodiments, the SH2 domain comprises or consists of a sequence having at least 75%, 80%, 85%, 90%, 95%, 96%, 97%, 98%, 99%, or 100% identity to any one of SEQ ID NOs: 313-15.

In one aspect, the disclosure provides a polypeptide comprising: (i) a CARD domain derived from CARD11 protein; and (ii) a second polypeptide portion derived from PIK3R3 protein. In some embodiments, the second polypeptide portion comprises or consists of a sequence having at least 75%, 80%, 85%, 90%, 95%, 96%, 97%, 98%, 99%, or 100% identity to any one of SEQ ID NO: 205, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 246, SEQ ID NO: 247, SEQ ID NO: 249, SEQ ID NO: 251, SEQ ID NO: 253, and SEQ ID NO: 255.

In some embodiments, the polypeptide does not comprise a Coiled-coil domain or a portion thereof. In some embodiments, the polypeptide comprises a Coiled-coil domain or a portion thereof. In some embodiments, the Coiled-coil domain comprises or consists of a sequence having at least 75%, 80%, 85%, 90%, 95%, 96%, 97%, 98%, 99%, or 100% identity to any one of SEQ ID NOs: 290-293. In some embodiments, the Coiled-coil domain comprises or consists of a sequence having at least 75%, 80%, 85%, 90%, 95%, 96%, 97%, 98%, 99%, or 100% identity to any one of SEQ ID NO: 290.

In some embodiments, the polypeptide comprises or consists of about 10, about 20, about 30, about 40, about 50, about 60, about 80, about 100, about 120, about 140, about 150, about 160, about 180, about 200, about 220, about 240, about 250, about 260, about 280, or about 300 amino acids of the N-terminal portion of the Coiled-coil domain. In some embodiments, the polypeptide comprises no more than 10, 20, 30, 40, 50, 60, 80, 100, 120, 140, 150, 160, 180, 200, 220, 240, 250, 260, 280, or 300 amino acids of the N-terminal portion of the Coiled-coil domain.

In some embodiments, the domain in (b), or the SH2 domain, or the second polypeptide portion, is located at the N-terminus or the CARD domain, between the CARD domain and the Coiled-coil domain, or at the C-terminus of the CARD domain and/or the Coiled-coil domain. In some embodiments, the CARD domain is derived from a CARD11 protein followed by the Coiled-coil domain derived from the CARD11 protein.

In some embodiments, the domain in (b), or the SH2 domain, or the second polypeptide portion, is located close to the C-terminus of the polypeptide, wherein the polypeptide has no more than 50, 40, 30, 20, 15, 10, or 5 amino acids at the C-terminus of the domain in (b), or the SH2 domain, or the second polypeptide portion.

In some embodiments, the polypeptide does not comprise an inhibitory domain (ID) or a portion thereof. In some embodiments, the polypeptide comprises an inhibitory domain (ID) or a portion thereof. In some embodiments, the inhibitory domain (ID) comprises or consists of a sequence having at least 75%, 80%, 85%, 90%, 95%, 96%, 97%, 98%, 99%, or 100% identity to SEQ ID NO: 294. In some embodiments, the inhibitory domain (ID) comprises or consists of a sequence having at least 75%, 80%, 85%, 90%, 95%, 96%, 97%, 98%, 99%, or 100% identity to SEQ ID NO: 295.

In some embodiments, the polypeptide comprises or consists of about 10, about 20, about 30, about 40, about 50, about 60, about 80, about 100, about 120, about 140, about 150, about 160, about 180, or about 200 amino acids of the N-terminal portion of the inhibitory domain (ID). In some embodiments, the second polypeptide portion comprises no more than 10, 20, 30, 40, 50, 60, 80, 100, 120, 140, 150, 160, 180, or 200 amino acids of the N-terminal portion of the inhibitory domain (ID).

In some embodiments, the polypeptide does not comprise a sequence that is at least 90%, 95%, 96%, 97%, 98%, 99%, or 100% identical to SEQ ID NO: 297. In some embodiments, the polypeptide comprises one or more mutations corresponding to S615F, D357N, Y361C, E634K, and/or S655C of SEQ ID NO: 26.

In some embodiments, expression of the polypeptide in a T cell promotes its in vivo accumulation in tumors. In some embodiments, the T cell expresses an engineered immune receptor that binds to a target on a tumor cell. In some embodiments, the T cell is selected from the group consisting of a regulatory (Treg), a gamma delta T cell, an invariant iNKT cell, a MAIT cell, a CAR T cell, a tumor-infiltrating lymphocyte, and an engineered T cell comprising a transcriptional receptor.

In one aspect, the disclosure provides a polypeptide, comprising a mutation capable of: (i) altering T cell signaling through NFAT, NF-κB and/or AP-1 pathways, (ii) altering cytokine production, (iii) altering JAK/STAT signaling in T cells, (iv) altering co-stimulatory molecule signaling in T cells, (v) altering RAS/MEK/ERK signaling in T cells, (vi) altering phospholipase gamma signaling, (vii) altering a transcription factor activity in T cells, and/or (viii) altering or enhancing in vivo persistence in tumors of T cells comprising the mutation.

In one aspect, the disclosure provides a recombinant nucleic acid encoding a polypeptide described herein. In some embodiments, the nucleic acid comprises a promoter. In some embodiments, the promoter is a constitutive promoter. In some embodiments, the constitutive promoter is CD4 promoter, CD8a promoter, CD8b promoter, TCRa promoter, TCRb promoter, CD3d promoter, CD3g promoter, CD3e promoter, or CD3z promoter. In some embodiments, the promoter is a minimal TATA promoter, a pGK, actin promoter, CD25 promoter, IL2 promoter, IL7 promoter, IL15 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, CD69 promoter, GzmB promoter, T-bet promoter, IFNgamma promoter, TIM3 promoter, IL4 promoter, GATA3 promoter, IL1 promoter, IL5 promoter, IL6 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, c-Kit promoter, nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, TGF-beta promoter, T-bet promoter, Eomes promoter, GATA3 promoter, CD45RA promoter, 2B4 promoter, Type I interferon (IFN) alpha, Type I IFN beta promoter, IFN gamma promoter, IRF3 promoter, IRF7 promoter, NFkB promoter, AP-1 promoter, TNF-alpha promoter, CD130 promoter, NR4A1 promoter, NR4A2, or NR4A3 promoter.

In one aspect, the disclosure provides a vector comprising a recombinant nucleic acid construct as described herein. In some embodiments, the vector is a viral vector selected from a retrovirus vector, an adenovirus vector, and an adeno-associated virus vector. In some embodiments, the retrovirus is a lentivirus.

In one aspect, the disclosure provides a cell comprising a polypeptide described herein and/or a recombinant nucleic acid as described herein. In some embodiments, the ell is a non-natural cell or has been genetically engineered. In some embodiments, the cell is not a CD4+ T cell. In some embodiments, the cell is not a cancerous cell. In some embodiments, the recombinant nucleic acid is exogenous.

In some embodiments, the cell comprises at least one copy, or at least two copies, of endogenous nucleic acid sequence encoding a CARD11 protein, or a protein comprising a CARD11 CARD domain without any SH2 domain. In some embodiments, the recombinant nucleic acid of the cell is located at the endogenous CARD11-encoding gene locus, or comprises at least a portion of the endogenous CARD11-encoding gene, of the cell.

In some embodiments, the cell comprises a polypeptide comprising a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, and functional variants thereof comprising at least one mutation listed in Table 1.

In some embodiments, the cell comprises a nucleic acid sequence having at least 75%, 80%, 85%, 90%, 95%, 96%, 97%, 98%, 99% or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, or functional variants thereof comprising at least one mutation listed in Table 1.

In some embodiments, the cell further comprises: (i) a chimeric antigen receptor (CAR) having specificity for a target antigen; and/or (ii) a T cell receptor (TCR) having specificity for a target antigen. In some embodiments, the cell is selected from the group consisting of an immune cell, a T cell, a regulatory T cell, a CD8+ cell, a natural killer cell, a tumor infiltrating lymphocyte, and a MAIT cell. In some embodiments, the target antigen is DLL3, LY6G6D, Claudin 6, GCC, p53R175H, or PRAME.

In one aspect, the disclosure provides a method of preparing a T cell for use in a cell therapy, the method comprises expressing in the T cell a polypeptide as described herein. In some embodiments, the method comprises genetically modifying the T cell for expression of the polypeptide. In some embodiments, the method comprises introducing to the T cell a recombinant nucleic acid encoding the polypeptide, or a vector comprising the recombinant nucleic acid. In some embodiments, the method comprises expressing in the T cell an engineered immune receptor that binds to a target in a tumor cell. In some embodiments, the method comprises administering to the subject a cell as described herein, or a T cell prepared by a method described herein.

In some embodiments, the subject has a cancer or an autoimmune disease. In some embodiments, the cancer is a solid tumor. In some embodiments, the cancer is a hematological cancer. In some embodiments, the cancer expresses CD19, B7H3 (CD276), BCMA (CD269), ALPPL2, Claudin 18.2, CD123, CD171, CD179a, CD20, CD213A2, CD22, CD24, CD246, CD272, CD30, CD33, CD38, CD44v6, CD46, CD71, CD97, CEA, Claudin 6(CLDN6), CLECL1, CS-1, DLL-3, EGFR, EGFRvIII, ELF2M, EpCAM, EphA2, Ephrin B2, FAP, FLT3, GCC, GD2, GD3, GM3, GPRC5D, HER2 (ERBB2/neu), IGLL1, IL-11Rα, KIT (CD117), KLK2, LY6G6D, MUC1, NCAM, p53R175H, PAP, PDGFR-β, PRAME, PRSS21, PSCA, PSMA, ROR1, SIRPα, SSEA-4, TAG72, TEM1/CD248, TEM7R, TSHR, VEGFR2, ALPI, citrullinated vimentin, cMet, and/or Axl. In some embodiments, the cancer expresses DLL3, LY6G6D, Claudin 6, GCC, p53R175H, and/or PRAME.

In some embodiments, the cancer is small cell lung cancer, colorectal cancer, testicular cancer, ovarian cancer, melanoma, lymphoma, leukemia, multiple myeloma, prostate cancer, breast cancer, non-small cell lung cancer, gastric cancer, esophageal cancer, liver cancer, kidney cancer, head & neck cancer, glioblastoma, neuroblastoma, soft tissue sarcoma, uterine cancer, brain cancer, skin cancer, renal cancer, bladder cancer, pancreatic cancer, thyroid cancer, eye cancer, gastrointestinal cancer, carcinoma, or sarcoma.

In some embodiments, the method of treatment does not comprise administration of lymphodepletive agents within 7 days prior to administration of the T cell therapy. In some embodiments, the method of treatment does not comprise administration of cyclophosphamide, fludarabine, and/or bendamustine within 7 days prior to administration of the T cell therapy. In some embodiments, the method of treatment does not comprise administration of at least 600,000 IU/kg of IL-2 every 8 hours. In some embodiments, the method of treatment does not comprise a checkpoint therapy which blocks PD-1 or CTLA-4 signaling.

In some embodiments, the cell has reduced exhaustion, increased proliferative capacity, enhanced replicative lifespan, decreased replicative senescence, enhanced anti-tumor effect, reduced dysfunction, enhanced persistence, and/or increase intratumoral presence in vivo. In some embodiments, the cell has increased or decreased signaling through the CARD11-BCL10-MALT1 complex, NF-κB, AP-1, NFAT, JAK/STAT, and/or MEK/ERK pathways.

In some embodiments, the disclosure provides a recombinant nucleic acid construct encoding a polypeptide, wherein the polypeptide includes a mutation capable of altering (i) T cell signaling through NFAT, NF-κB and/or AP-1 pathways, (ii) cytokine production, and/or (iii) in vivo persistence in tumors of therapeutic T cells comprising the mutation.

In some embodiments of the recombinant nucleic acid constructs and/or recombinant nucleic acids of the disclosure, the mutation is a point mutation, a gene fusion, a substitution, a gain-of-function mutation, a stop-gain mutation, an insertion mutation, a deletion mutation, a duplication mutation or a translocation. In some embodiments, the mutation is a T cell lymphoma mutation or a mutation in a clonally expanded population of T cells. In some embodiments, the mutation is capable of altering/promoting/enhancing CARD11-BCL10-MALT1 complex signaling in T cells.

In some embodiments, the mutation is in a gene selected from the group consisting of: caspase recruitment domain family member 11 (CARD11), capping protein regulator and myosin 1 linker 2 (CARMIL2), mucosa-associated lymphoid tissue lymphoma translocation protein 1 (MALT1), B-cell lymphoma 6 (BCL6), B-cell lymphoma 10 (BCL10) and MYCN.

In some embodiments, the polypeptide includes an amino acid sequence having at least about 75%, 80%, 85%, 90%, 95%, 96%, 97%, 98%, 99% or 100% identity to SEQ ID NO: 25 and comprising a substitution at an amino acid position selected from the group consisting of 361, 615, 634, 655, and 357 of SEQ ID NO: 25. In some embodiments, the substitution includes Y361C, S615F, E634K, D357N, S655C, or combinations thereof.

In some embodiments, the mutation is a fusion between a CARD11 polypeptide and a PIK3R3 polypeptide. In some embodiments, the fusion includes a CARD domain, a coiled-coil domain, and an SH2 domain from PIK3R3.

In some embodiments of the recombinant nucleic acid constructs and/or recombinant nucleic acids nucleic acid constructs and/or recombinant nucleic acids of the disclosure, the polypeptide is encoded by a nucleic acid sequence having at least about 75%, 80%, 85%, 90%, 95%, 96%, 97%, 98%, 99%, or 100% sequence identity to SEQ ID NO: 205, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 246, SEQ ID NO: 247, SEQ ID NO: 249, SEQ ID NO: 251, SEQ ID NO: 253, or SEQ ID NO: 255.

In some embodiments of the recombinant nucleic acid constructs and/or recombinant nucleic acids of the disclosure, the polypeptide includes an amino acid sequence having at least about 75%, 80%, 85%, 90%, 95%, 96%, 97%, 98%, 99% or 100% sequence identity to SEQ ID NO: 206, SEQ ID NOS: 226, SEQ ID NOS: 228, SEQ ID NOS: 230, SEQ ID NOS: 232, SEQ ID NOS: 234, SEQ ID NOS: 236, SEQ ID NOS: 238, SEQ ID NOS: 240, SEQ ID NOS: 242, SEQ ID NOS: 244, SEQ ID NOS: 248, SEQ ID NOS: 250, SEQ ID NOS: 252, SEQ ID NOS: 254, or SEQ ID NO:256.

In some embodiments of the recombinant nucleic acid constructs and/or recombinant nucleic acids of the disclosure, the polypeptide includes an amino acid sequence having at least about 75%, 80%, 85%, 90%, 95%, 96%, 97%, 98%, 99% or 100% sequence identity to SEQ ID NO: 4 and comprising a substitution at amino acid 647 of SEQ ID NO: 4, SEQ ID NO: 28 and having a substitution at amino acid 575 of SEQ ID NO: 28, or SEQ ID NO: 114 and having a substitution at amino acid 44 of SEQ ID NO: 114. In some embodiments, the substitution at amino acid 647 of SEQ ID NO: 4 is S647R, wherein the substitution at amino acid 575 of SEQ ID NO: 28 is Q575E, and wherein the substitution at amino acid 44 of SEQ ID NO: 114 is P44L.

In some embodiments of the recombinant nucleic acid constructs and/or recombinant nucleic acids of the disclosure, the polypeptide includes a mutation capable of (i) altering JAK/STAT signaling in T cells (ii) altering cytokine production, and/or (iii) enhancing in vivo persistence of therapeutic T cells comprising the mutation in tumors. In some embodiments, the polypeptide having the mutation includes a JAK1, JAK3, STAT3, or STAT5 polypeptide. In some embodiments, the polypeptide includes an amino acid sequence having at least about 75%, 80%, 85%, 90%, 95%, 96%, 97%, 98%, 99% or 100% sequence identity to: SEQ ID NO: 90 and having a substitution at amino acid position 1097 of SEQ ID NO: 90, or to SEQ ID NO: 94 and having a substitution at an amino acid position 573 of SEQ ID NO: 94, or having SEQ ID NO: 176 and having a substitution at an amino acid position 618, 647, or 661 of SEQ ID NO: 176, or SEQ ID NO: 141 and having a substitution at an amino acid position 628, or at amino acid position 665 of SEQ ID NO: 182.

In some embodiments of the recombinant nucleic acid constructs and/or recombinant nucleic acids of the disclosure, the nucleic acid construct includes a nucleic acid sequence having at least about 75%, 80%, 85%, 90%, 95%, 96%, 97%, 98%, 99% or 100% sequence identity to a sequence selected from the group consisting of SEQ ID NO:87, SEQ ID NO: 91: SEQ ID NO: 169, SEQ ID NO: 171, SEQ ID NO: 173, SEQ ID NO: 177 or SEQ ID NO: 179.

In some embodiments of the recombinant nucleic acid constructs and/or recombinant nucleic acids of the disclosure, the polypeptide comprises a mutation capable of altering co-stimulatory molecule signaling in T cells and persistence in tumors of T cells comprising the mutation. In some embodiments, the polypeptide having the mutation includes a TNFRSF1B, CD28, ICOS, or CTLA4 polypeptide. In some embodiments, the polypeptide includes an amino acid sequence having at least about 75%, 80%, 85%, 90%, 95%, 96%, 97%, 98%, 99% or 100% sequence identity to i) SEQ ID NO: 192 and including a substitution at an amino acid position 256 or at position 377 of SEQ ID NO: 192, or ii) SEQ ID NO: 42 and including a substitution at an amino acid position 51 or 77 of SEQ ID NO: 42, or iii) SEQ ID NO: 220, or iv) SEQ ID NO: 218. In some embodiments, the nucleic acid construct includes a polypeptide having an amino acid sequence having at least about 75%, 80%, 85%, 90%, 95%, 96%, 97%, 98%, 99% or 100% sequence identity to SEQ ID NO: 189, SEQ ID NO: 189, SEQ ID NO: 35, SEQ ID NO: 37, SEQ ID NO: 39, SEQ ID NO:43, SEQ ID NO:217 or SEQ ID NO:219.

In some embodiments, the polypeptide includes a mutation capable of altering RAS/MEK/ERK signaling in T cells and in vivo persistence in tumors of therapeutic T cells comprising the mutation.

In some embodiments, the mutation includes a BRAF gene or a RASGRP1 polypeptide. In some embodiments, the polypeptide includes an amino acid sequence having at least about 75%, 80%, 85%, 90%, 95%, 96%, 97%, 98%, 99% or 100% sequence identity to i) SEQ ID NO: 16 and including an amino acid substitution at amino acid position 469 or at position 594 of SEQ ID NO: 16, or to SEQ ID NO: 158 and including a substitution at amino acid position 261 of SEQ ID NO: 261. In some embodiments, the nucleic acid construct comprises a nucleic acid sequence having at least about 75%, 80%, 85%, 90%, 95%, 96%, 97%, 98%, 99% or 100% sequence identity to SEQ ID NO: 9, SEQ ID NO: 11, SEQ ID NO: 13 or SEQ ID NO: 157.

In some embodiments, the polypeptide includes a mutation capable of altering phospholipase gamma signaling and/or (ii) cytokine production, and/or (iii) in vivo persistence in tumors of therapeutic T cells comprising the mutation. In some embodiments, the mutation is in a Phospholipase C gamma 1 (PLCG1) gene. In some embodiments, the polypeptide includes an amino acid sequence having at least about 75%, 80%, 85%, 90%, 95%, 96%, 97%, 98%, 99% or 100% sequence identity to SEQ ID NO: 142 and having a substitution at amino acid position 47, 48, 520, 1163 or 1165 of SEQ ID NO: 142. In some embodiments, the recombinant nucleic acid construct includes a nucleic acid sequence having at least about 75%, 80%, 85%, 90%, 95%, 96%, 97%, 98%, 99% or 100% sequence identity to SEQ ID NO: 133, SEQ ID NO: 135, SEQ ID NO: 137, SEQ ID NO:139, or SEQ ID NO: 143.

In some embodiments of the recombinant nucleic acid constructs and/or recombinant nucleic acids of the disclosure, the polypeptide includes a mutation capable of altering a transcription factor activity in T cells comprising the mutation. In some embodiments, the polypeptide having the mutation includes a NFKB1, NFKB2 or JUNB polypeptide. In some embodiments, the polypeptide includes an amino acid sequence having at least about 75%, 80%, 85%, 90%, 95%, 96%, 97%, 98%, 99% or 100% sequence identity to SEQ ID NO: 118 and comprising a substitution at amino acid 67 of SEQ ID NO: 118, SEQ ID NO: 122 and comprising a substitution at amino acid 565 of SEQ ID NO: 122, or SEQ ID NO: 98 and comprising a substitution at amino acid 282. In some embodiments, the nucleic acid construct comprises a nucleic acid sequence having at least about 75%, 80%, 85%, 90%, 95%, 96%, 97%, 98%, 99% or 100% sequence identity to SEQ ID NO: 115, SEQ ID NO: 119 and SEQ ID NO: 95.

In some embodiments of the constructs polypeptides and nucleic acids of the disclosure, the mutation is a mutation listed in Table 1.

In some embodiments of the recombinant nucleic acid constructs and/or recombinant nucleic acids of the disclosure, the polypeptide includes a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256, or functional variants thereof having at least one mutation listed in Table 1.

In some embodiments of the recombinant nucleic acid constructs and/or recombinant nucleic acids of the disclosure, the recombinant nucleic acid construct includes a nucleic acid sequence having at least about 75%, 80%, 85%, 90%, 95%, 96%, 97%, 98%, 99% or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, SEQ ID NO: 255, or functional variants thereof comprising at least one mutation listed in Table 1.

In an aspect of the disclosure, provided herein is a recombinant nucleic acid construct encoding a fusion polypeptide wherein the fusion polypeptide includes a first polypeptide encoding a partial CARD11 polypeptide and a second polypeptide encoding a partial PIK3R3 polypeptide and wherein expression of the fusion polypeptide promotes in vivo persistence in tumors of therapeutic T cells comprising the fusion polypeptide.

In some embodiments, the T cell is selected from the group consisting of a regulatory (Treg), a gamma delta T cell, an invariant iNKT cell, a macrophage, a monocyte, a natural killer (NK), a CAR T cell, and an engineered T cell comprising a transcriptional receptor.

In some embodiments of the recombinant nucleic acid constructs and/or recombinant nucleic acids of the disclosure, the first polypeptide includes an amino acid sequence having at least about 75%, 80%, 85%, 90%, 95%, 96%, 97%, 98%, 99% or 100% sequence identity to SEQ ID NO: 258. In some embodiments, the second polypeptide comprises an amino acid sequence having at least about 75%, 80%, 85%, 90%, 95%, 96%, 97%, 98%, 99% or 100% sequence identity to SEQ ID NO: 260. In some embodiments, the first polypeptide includes a CARD domain, a coiled-coil domain, and wherein the second polypeptide comprises an SH2 domain from PIK3R3.

In some embodiments of the recombinant nucleic acid constructs and/or recombinant nucleic acids of the disclosure, the construct comprises a promoter. In some embodiments, the promoter is a constitutive promoter. In some embodiments, the constitutive promoter is a CD4 promoter, CD8a promoter, CD8b promoter, TCRa promoter, TCRb promoter, CD3d promoter, CD3g promoter, CD3e promoter, or CD3z promoter.

In some embodiments, the promoter is a MND promoter, EF1a promoter, sEF1a promoter, gamma retroviral LTR promoter, minimal TATA promoter, a pGK, actin promoter, CD25 promoter, IL2 promoter, IL7 promoter, IL15 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, CD69 promoter, GzmB promoter, T-bet promoter, IFNgamma promoter, TIM3 promoter, IL4 promoter, GATA3 promoter, IL1 promoter, IL5 promoter, IL6 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, c-Kit promoter, nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, TGF-beta promoter, T-bet promoter, Eomes promoter, GATA3 promoter, CD45RA promoter, 2B4 promoter, Type I interferon (IFN) alpha, Type I IFN beta promoter, IFN gamma promoter, IRF3 promoter, IRF7 promoter, NFkB promoter, AP-1 promoter, TNF-alpha promoter, CD130 promoter, NR4A1 promoter, NR4A2, or NR4A3 promoter.

In an aspect of the disclosure, provided herein are recombinant nucleic acid constructs and/or recombinant nucleic acids wherein the cytokine is IL-2, IL-4, 11-5, TNF alpha, IFN-gamma, IL-13 and/or a combination of any thereof.

In an aspect of the disclosure, provided herein are vectors including any of the recombinant nucleic acid constructs and/or recombinant nucleic acids of the disclosure. In some embodiments, the vector is a retrovirus, an adenovirus, or an adeno-associated virus. In some embodiments, the retrovirus is a lentivirus.

In an aspect of the disclosure, provided herein are cells including a nucleic acid construct or a vector of the disclosure. In some embodiments, the cell includes (i) a chimeric antigen receptor (CAR) having specificity for a target antigen; (ii) a T cell receptor (TCR) having specificity for a target antigen; and/or (iii) a transcriptional receptor.

In some embodiments, the cells are selected from the group consisting of an immune cell, a T cell, a regulatory T cell, a CD8+ cell, a natural killer cell, and a tumor infiltrating lymphocyte.

In an aspect, the disclosure provides a target antigen. In some embodiments, the target antigen is selected from the group consisting of DLL3, LY6G6D, Claudin 6, GCC, p53R175H, PRAME, CD1, CD1a, CD1b, CD1c, CD1d, CD1e, CD2, CD3d, CD3e, CD3g, CD38, CD4, CD5, CD7, CD8a, CD8b, CD19, CD20, CD21, CD22, CD23, CD24, CD25, CD27, CD28, CD30, CD33, CD34, CD38, CD40, CD44v6, CD45, CD48, CD52, CD59, CD66, CD70, CD71, CD72, CD73, CD79A, CD79B, CD80 (B7.1), CD86 (B7.2), CD94, CD95, CD97, CD123, CD134, CD140 (PDGFR4), CD152, CD154, CD158, CD171, CD178, CD179, CD179a, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), CEA, CLL-1, CS1, EGFR, FGFR2, AFP, CA125, MUC-1, MAGE, alkaline phosphatase, placental-like 2 (ALPPL2), B-cell maturation antigen (BCMA), green fluorescent protein (GFP), enhanced green fluorescent protein (cGFP), Claudin18.2, PSMA, ROR1, Mesothelin, IL13Ra2, FAP, signal regulatory protein α (SIRPα), TRAC, TCRβ, BCMA, TSHR, EGFRvIII, GD2, GD3, Tn Ag, ROR1, ROR2, GPC1, GPC2, FLT3, FAP, TAG72, CEA, EPCAM, B7H3, KIT, IL-13Ra2, IL-11Ra, PSCA, PRSS21, VEGFR2, LewisY, PDGFR-beta, SSEA-4, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD- CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYPIB1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, LAIR1, FCAR, LILRA2, CD300LF, CLEC12A, BST2, EMR2, LY75, GPC3, FCRL5, IGLL1, AFP, TRAC, TCRβ, BCMA, TSHR, EGFRvIII, GD2, GD3, Tn Ag, PSMA, ROR1, ROR2, GPC1, GPC2, FLT3, FAP, TAG72, CEA, EPCAM, B7H3, KIT, IL-13Ra2, IL-11Ra, PSCA, PRSS21, VEGFR2, LewisY, PDGFR-beta, SSEA-4, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, KRAS, mutant KRAS, KRAS G12D, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, LAIR1, FCAR, LILRA2, CD300LF, CLEC12A, BST2, EMR2, LY75, GPC3, FCRL5, IGLL1, the extracellular portion of the APRIL protein, or any combinations thereof.

In some embodiments, the target antigen is selected from cell surface receptors, adhesion proteins, integrins, mucins, lectins, tumor-associated antigens, and tumor-specific antigens. In some embodiments, the target antigen is a tumor-associated antigen selected from the group consisting of CD19, B7H3 (CD276), BCMA (CD269), ALPPL2, Claudin 18.2, CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRC5D, HER2 (ERBB2/neu), IGLL1, IL-11Ra, KIT (CD117), MUC1, NCAM, PAP, PDGFR-β, PRSS21, PSCA, PSMA, ROR1, SIRPα, SSEA-4, TAG72, TEM1/CD248, TEM7R, TSHR, VEGFR2, ALPI, citrullinated vimentin, cMet, and Axl.

In a further aspect, the disclosure provides methods of preparing a T cell for use in a cell therapy. In some embodiments, the method comprises transducing the T cell with a recombinant nucleic acid construct comprising a mutation capable of altering (i) T cell signaling through NFAT, NF-κB and/or AP-1 pathways, (ii) cytokine production, and/or (iii) in vivo persistence of T cells in tumors. In some embodiments, the recombinant nucleic acid construct includes the recombinant nucleic acid construct of the disclosure.

In some embodiments, the T cell further includes a CAR, a TCR, or a transcriptional receptor.

In a further aspect, the disclosure provides a method for enhancing the in vivo persistence of a T cell in a subject in need thereof, the method including administering to the subject a therapeutically effective amount of the T cell of the disclosure. In some embodiments, the T cell is selected from the group consisting of a regulatory (Treg), a natural killer (NK), a tumor infiltrating lymphocyte, and a CAR T cell.

In some embodiments, the subject has cancer or an autoimmune disease. In some embodiments, the cancer is a solid tumor. In some embodiments, the cancer is a hematological cancer.

Also provided herein, is a method for identifying a mutation useful for improving T cell therapy including a) identifying mutations from a clonal T cell genomic sequencing database; b) identifying a frequency of occurrence of the mutations; and c) applying a statistical test to identify a significant difference in a hotspot genomic region where a mutation occurs more often than expected by chance, thereby identifying a mutation in the hotspot region that is capable of improving T cell therapy. In some embodiments, the statistical test includes using a binomial distribution, a Chi square analysis or any other multivariate analysis. In some embodiments, the mutation is a T cell lymphoma mutation. In some embodiments, the hotspot region is in a coding sequence of a gene.

In I some embodiments, the mutation improves T cell therapy by a) increasing proliferation, and/or b) altering effector function, and/or c) resisting T cell dysfunction, and/or d) enhancing growth of a therapeutic T cell comprising the mutation in a tumor. In some embodiments, the mutation is a mutation listed in Table 1. In some embodiments, the mutation promotes positive T cell selection and/or T cell clonal outgrowth.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 2A-2D show the reporter activity Z score for NFAT, NF-κb and AP-1 for each of the indicated T cell lymphoma mutation constructs. In some cases the PD-1 expression and IL-2 Z scores are also depicted. PD-1 expression was assessed via flow. IL-2 secretion was assessed via ELISA. Z score indicates the mean Z score of two independent biological replicates. FIG. 2A shows the reporter activity for each construct when expressed in CD19-CD28z CAR Jurkat cells and co-cultured with K562 (CD19 negative) cell lines. FIG. 2B shows the reporter activity and IL-2 secretion for each construct when expressed in CD19-CD28z CAR Jurkat cells and co-cultured with CD19-K562 positive cell lines. FIG. 2C shows the reporter activity and PD-1 expression for each construct when expressed in CD19-BBz CAR Jurkat cells and co-cultured with K562 (CD19 negative) cell lines. FIG. 2D shows the reporter activity, IL-2 secretion and PD-1 expression for each construct when expressed in CD19-BBz CAR Jurkat cells and co-cultured with CD19-K562 positive cell lines. FIG. 2E shows a bar graph demonstrating that in both the CD19-CD28z CAR and CD19-BBz CAR settings, point mutation and fusion constructs showed more significantly different effects versus controls in the CD19-K562 condition compared to the parental K562 (CD19 negative) line. FIG.

2F shows a bar graph indicating the number of T cell lymphoma point mutation or fusion constructs for which expression in CD19-BBz CAR Jurkats resulted in each distinct combination of signaling up or downregulation upon antigenic stimulation. FIG. 2G shows a bar graph indicating percent NFAT, NF-κB, and AP-1 signaling in CD19-BBz CAR cells upon CD19-K562 stimulation of select mutations highlighting a high degree of tunability of signaling outputs. Each point represents a biological replicate.

FIG. 5A shows a waterfall plot of the in vivo screen log 2 fold change for each construct as determined by MAGeCK, compared to baseline (pre-injection). Positive log 2 fold change indicates increased persistence in tumors compared to input. FIG. 5B depicts a bar graph plotting the in vivo fold change of each mutation and splitting constructs into two categories 1) all constructs that did not significantly increase PD-1 expression in the in vitro jurkat screen or 2) constructs that did significantly increase PD-1 expression in the in vitro jurkat screen. These results indicate that PD-1 expression in vitro may help to predict in vivo persistence of T cell lymphoma mutations.

FIG. 8A is a diagram of the variants harboring deletions of various domains of the CARD11-PIK3R3 fusion generated. FIG. 8B depicts reporter activity of CD19-BBz CAR CARD11-PIK3R3 fusion variants in Jurkat cells co-cultured with CD19-K562s.

FIG. 9A is a diagram of the BCL10 binding-deficient CARD11-PIK3R3 mutant containing an alanine substitution for arginine at the 28th amino acid position. FIG. 9B shows the CD19-BBz CAR Jurkat reporter activity of the BCL10 binding-deficient CARD11-PIK3R3 mutant compared to control and CARD11-PIK3R3 expressing cells. **** indicates P value<0.0001, determined by one-way ANOVA followed by Tukey’s multiple comparison test. FIG. 9C shows western blotting of MALT1 substrates in CARD11-PIK3R3 expressing CD19-BBz CAR Jurkat cells or control cells. P/I indicates phorbol myristate acetate/ionomycin treatment. Ct indicates the C-terminal cleavage product. Data representative of 2 independent experiments.

FIG. 10A shows a schematic indicating an experimental approach to study CAR-dependent signaling in primary human CD3+ T cells in accordance with the current disclosure. FIG. 10B shows heatmaps of marker expression determined by mass cytometry by time of flight (CyTOF) for each of the indicated timepoints in CD19-BBz CAR samples. Values indicate mean for three independent T cell donors.

FIG. 11A shows the principal component (PC) analysis of human CD8+ T cells from three independent donors transduced with the indicated constructs and left unstimulated (Unstim) or co-cultured for 8 hours with CD19 expressing A549 cells (Stim). FIG. 11B shows a volcano plot of differentially expressed genes in CD19-BBz CAR T cells either unstimulated or stimulated with CD19 antigen. Select genes of interest are labeled. Positive log 2 fold changes indicate higher expression in CARD11-PIK3R3 expressing CAR-T cells. FIG. 11C shows NF-κB, AP-1, and MALT1 gene signature enrichment in CARD11-PIK3R3 expressing CD19-BBz CAR cells after stimulation with CD19 expressing A549 cells.

FIG. 14A shows activation markers expressed on CD19-BBz CAR T cells, with or without CARD11-PIK3R3, 24 hours post 1:1 co-culture with CD19-K562s. FIG. 14B shows activation markers expressed on untransduced or CARD11-PIK3R3 transduced CD8+ T cells 24 hours post 1:1 co-culture with CD19-K562s. FIG. 14C shows cytokine secretion of CD8+ T cells expressing the CD19-BBz CAR, with or without CARD11-PIK3R3, 48 hours post 1:1 co-culture with CD19-K562s. P values determined by ratio paired T test. Ns indicates not significant, * indicates P value<0.05.

FIG. 15A shows flow plots depicting CD19-BBz CAR transduced CD8+ T cells and CD19-K562 populations after 14-day co-culture together with and without supplemental IL-2, one donor depicted. Bar graph summarizing population percentages from three donors. P values determined by unpaired T test. FIG. 15B shows cell counts of CD19-BB2 CAR transduced CD8+ T cells co-cultured with CD19-K562s on Day 0 and restimulated with targets on Day 6. P values determined by unpaired T test. Ns indicates not significant. * indicates P value<0.05, *** indicates P value<0.0001.

FIG. 18A shows average radiance of luciferase expressing Nalm6 tumor cells measured using in vivo imaging, radiance used as a proxy for tumor burden. Data indicates mean+/−standard deviation. P values determined using unpaired T test of average radiance values at Day 21. Control (n=5), CAR (n=6), CAR+CARD11-PIK3R3 (n=5).  indicates P value<0.01. FIG. 18B shows survival analysis of Nalm6 bearing mice treated with untransduced (control) (n=5), BBz CAR (n=6) or BBz CAR with CARD11-PIK3R3 (n=5) T cells. P values determined using Log-rank (Mantel-Cox) test. * indicates P values<0.001.

FIG. 20A shows accumulation of CD19-BBz CAR T cells in the spleen and tumor 5 days post adoptive cell transfer. P values determined using unpaired Mann-Whitney t test. FIGS. 20B and C show tumor volumes (B) and survival analysis (C) of CD19-B16 tumor bearing animals treated with untransduced (control)(n=5), BBz CAR (n=5) or BBz CAR with CARD11-PIK3R3 (n=5) OT-1 T cells. P values determined using Log-rank (Mantel-Cox) test. * indicates P value<0.05, ** indicates P values<0.01.

FIG. 24A demonstrates expansion via flow cytometry plots. FIG. 24B quantifies fold expansion of CARD11-PIK3R3 OT-Is in tumors in vivo over control. P values determined by ratio paired T test. **** indicates P value<0.0001.

FIG. 28A depicts tumor size and FIG. 28B depicts survival analysis in B16-OVA melanoma bearing mice treated with PBS or OT-I cells ($2\times10^6$) 12 days after tumor inoculation. Complete response was defined as an absence of detectable tumor. **** indicates P value<0.0001.

FIGS. 30A-D shows results of experiments for assessing CARD11-PIK3R3 truncations in CD8+CD19-BBz CAR T cells in vitro. FIG. 30A is a schematic describing the CARD11-PIK3R3 coiled coil truncation designs, ΔID indicates removal of the inhibitory domain, -XX AA indicates the number of amino acids removed from the coiled coil region. FIG. 30B shows cell counts of CD19-BBz CAR CD8+ T cells with CARD11-PIK3R3 truncations over a period of 7 days after removal from anti-CD3/anti-CD28 bead stimulation. FIG. 30C shows CD19-BBz CAR CD8+ T cells with CARD11-PIK3R3 truncations co-cultured at 1:1 ratio with CD19 target cells for 24 hours, after which the supernatant was assessed via ELISA for IL-2 secretion. FIG.

30D show flow cytometry plots depicting CD19-BBz with CARD11-PIK3R3 or fusion variant CD8+ T cells and CD19-K562 populations after 14-day co-culture together without supplemental IL-2.

Figure 31B:
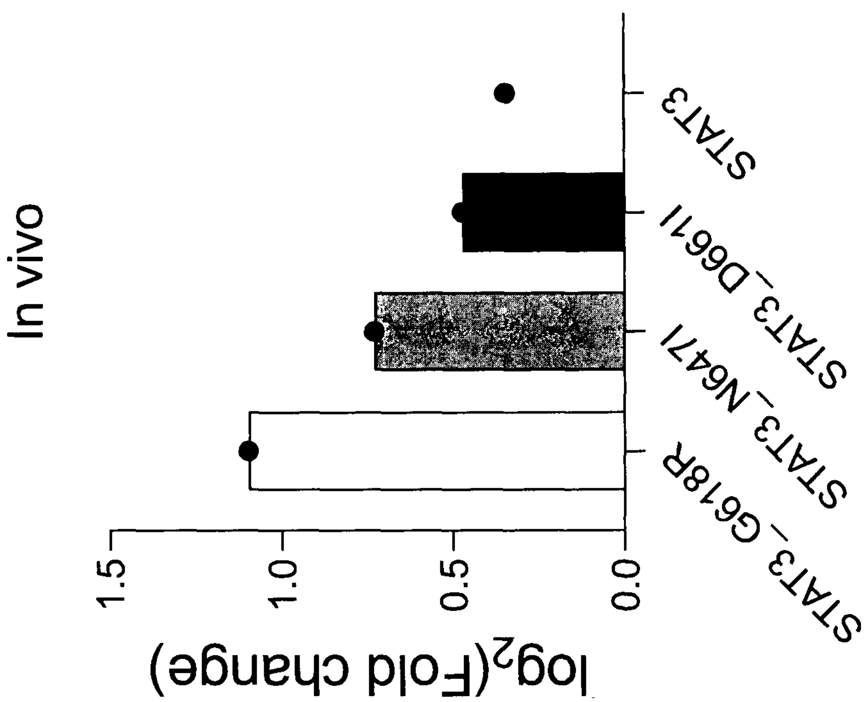
Figure 31A:
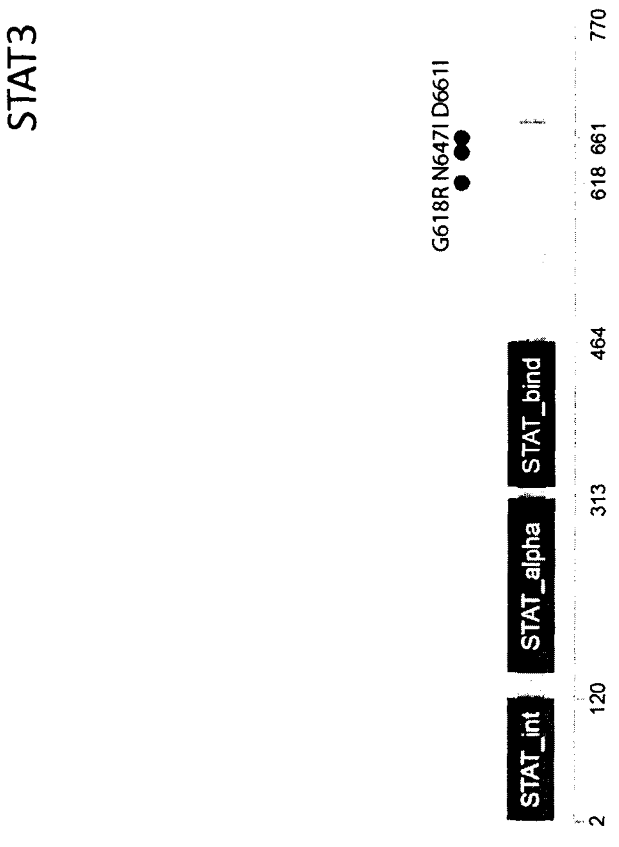

FIG. 31A depicts a lollipop diagram of STAT3 gene point mutations. FIG. 31B shows the in vivo screen log 2 fold change for each STAT mutation and wild-type as determined by MAGeCK, compared to baseline (pre-injection). Positive log 2 fold change indicates increased persistence in tumors compared to input.

Figure 32A:
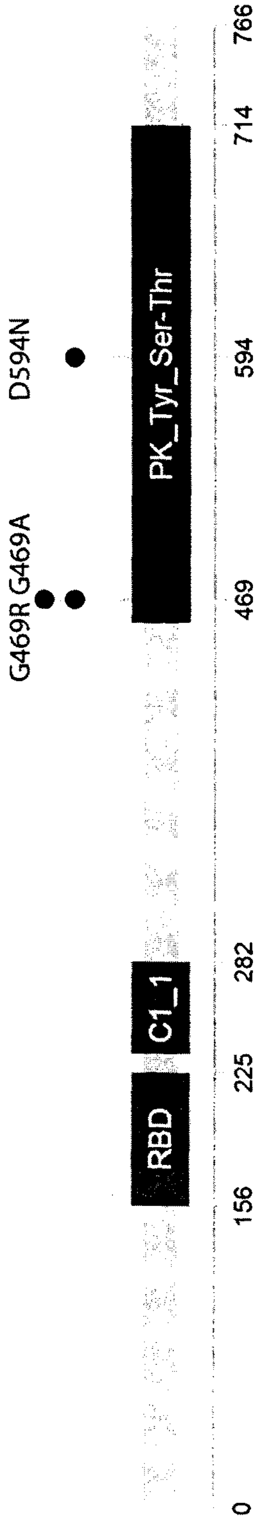
Figure 32B:
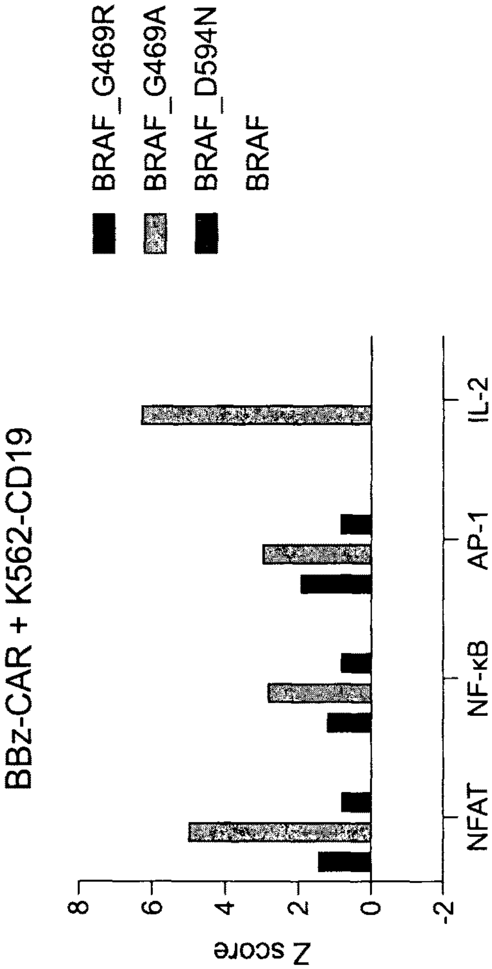

FIG. 32A shows a lollipop diagram depicting BRAF gene point mutations. FIG. 32B shows CD19-BBz CAR Jurkat reporter activity Z score for NFAT, NF-κB, AP-1, and IL-2 for each BRAF mutation or wild-type after co-culture with CD19-K562s. Z score indicates the mean Z score of two independent biological replicates.

Figure 33B:
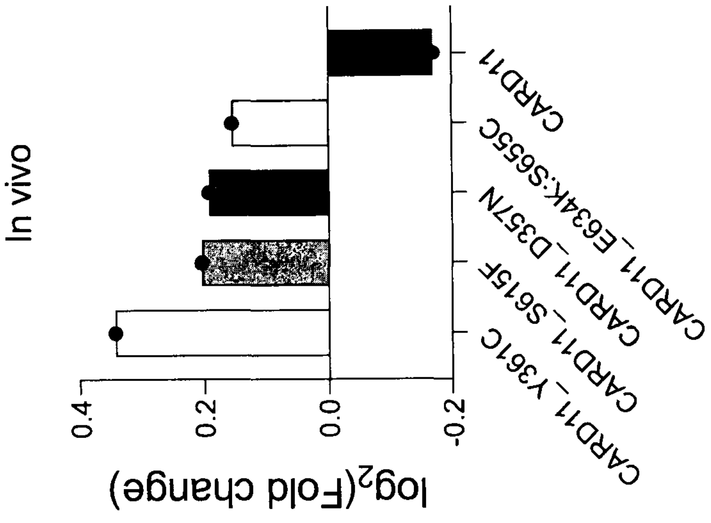
Figure 33A:
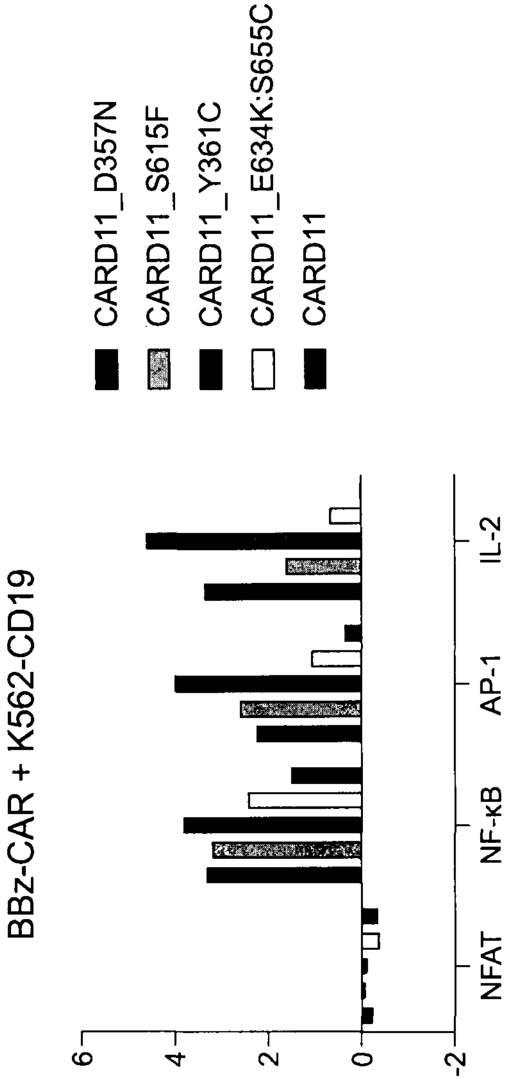

FIGS. 33A-B shows CARD11 mutations. FIG. 33A shows CD19-BBz CAR Jurkat reporter activity Z score for NFAT, NF-κB, AP-1 and IL-2 for each CARD11 mutation or wild-type after co-culture with CD19-K562s. Z score indicates the mean Z score of two independent biological replicates. FIG. 33B shows the in vivo screen log 2 fold change for each CARD11 mutation or wild-type as determined by MAGeCK, compared to baseline (pre-injection). Positive log 2 fold change indicates increased persistence in tumors compared to input.

Figure 34A:
Figure 34B:
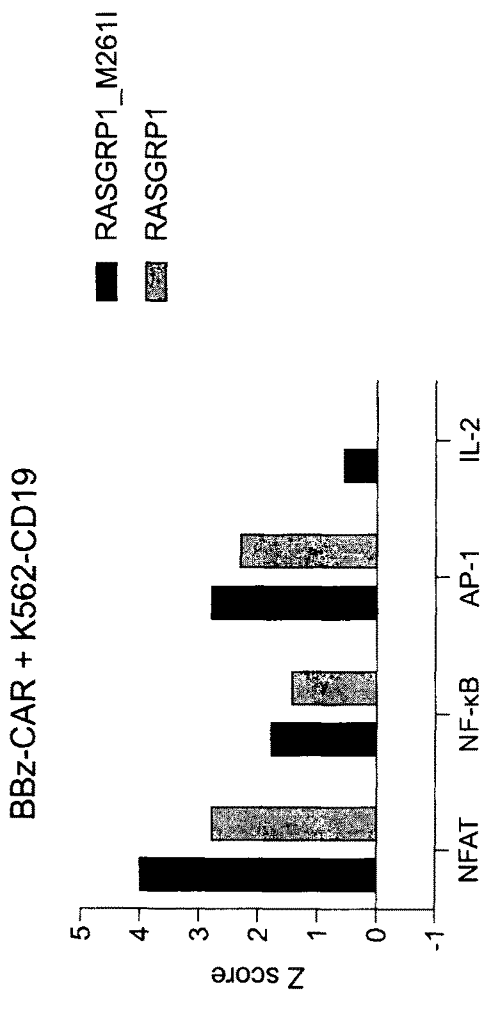
Figure 34C:
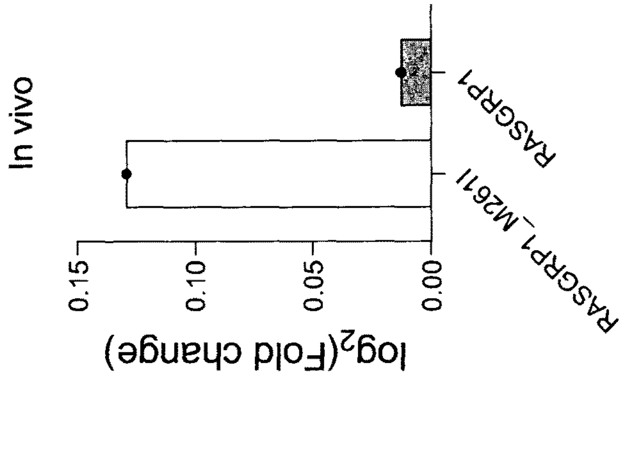

FIG. 34A shows a lollipop diagram depicting RASGRP1 gene point mutations. FIG. 34B CD19-BBz CAR Jurkat reporter activity Z score for NFAT, NF-κB, AP-1 and IL-2 for each RASGRP1 mutation or wild-type after co-culture with CD19-K562s. Z score indicates the mean Z score of two independent biological replicates. FIG. 34C shows the in vivo screen log 2 fold change for each RASGRP1 mutation or wild-type as determined by MAGeCK, compared to baseline (pre-injection). Positive log 2 fold change indicates increased persistence in tumors compared to input.

Figure 35A:
Figure 35B:
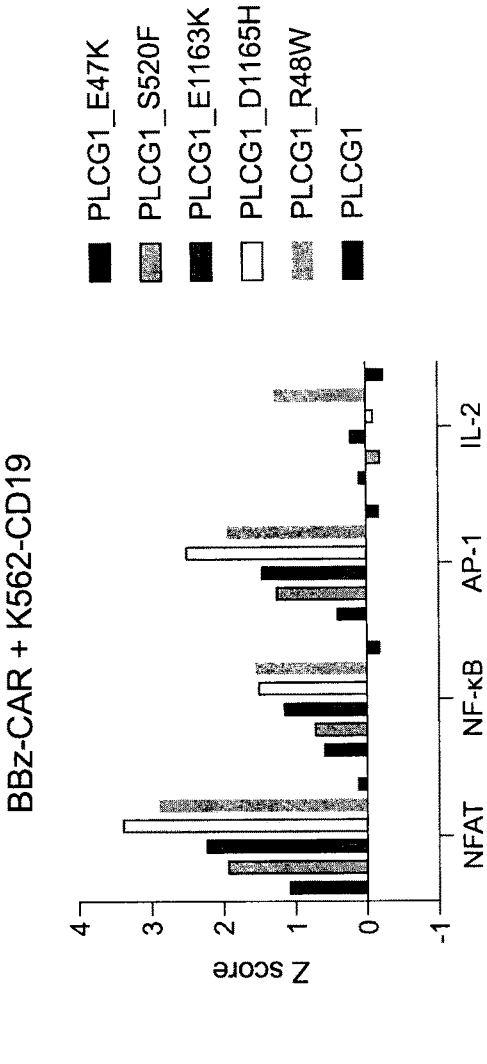

FIG. 35A depicts a lollipop diagram showing various PLCG1 gene point mutations. FIG. 35B is a graph showing CD19-BBz CAR Jurkat reporter activity Z score for NFAT, NF-κB, AP-1 and IL-2 for each PLCG1 mutation after co-culture with CD19-K562s. Z score indicates the mean Z score of two independent biological replicates.

Figure 36A:
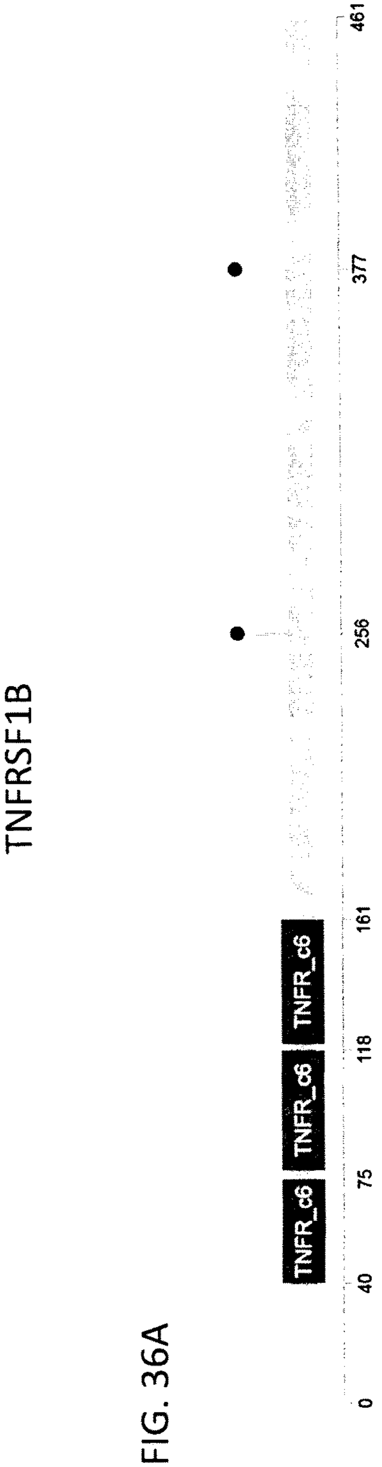
Figure 36B:
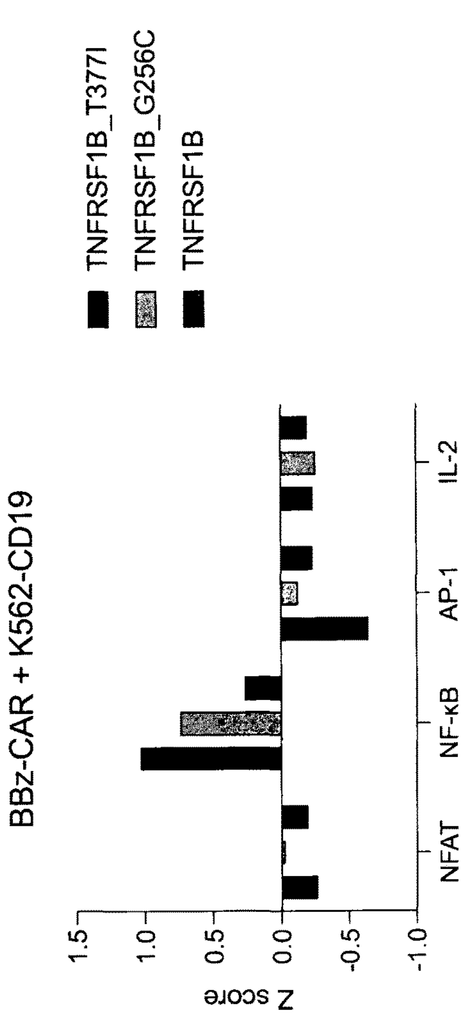
Figure 36C:
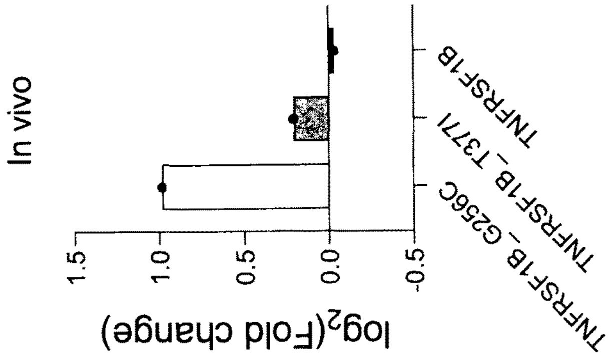

FIG. 36A is a lollipop diagram depicting TNFRSF1B gene point mutations. FIG. 36B shows a bar graph illustrating CD19-BBz CAR Jurkat reporter activity Z score for NFAT, NF-κB, AP-1 and IL-2 for each TNFRSF1B mutation or wild-type after co-culture with CD19-K562s. Z score indicates the mean Z score of two independent biological replicates. FIG. 36C shows the in vivo screen log 2 fold change for each TNFRSF1B mutation or wild-type as determined by MAGeCK, compared to baseline (pre-injection). Positive log 2 fold change indicates increased persistence in tumors compared to input.

Figure 37A:
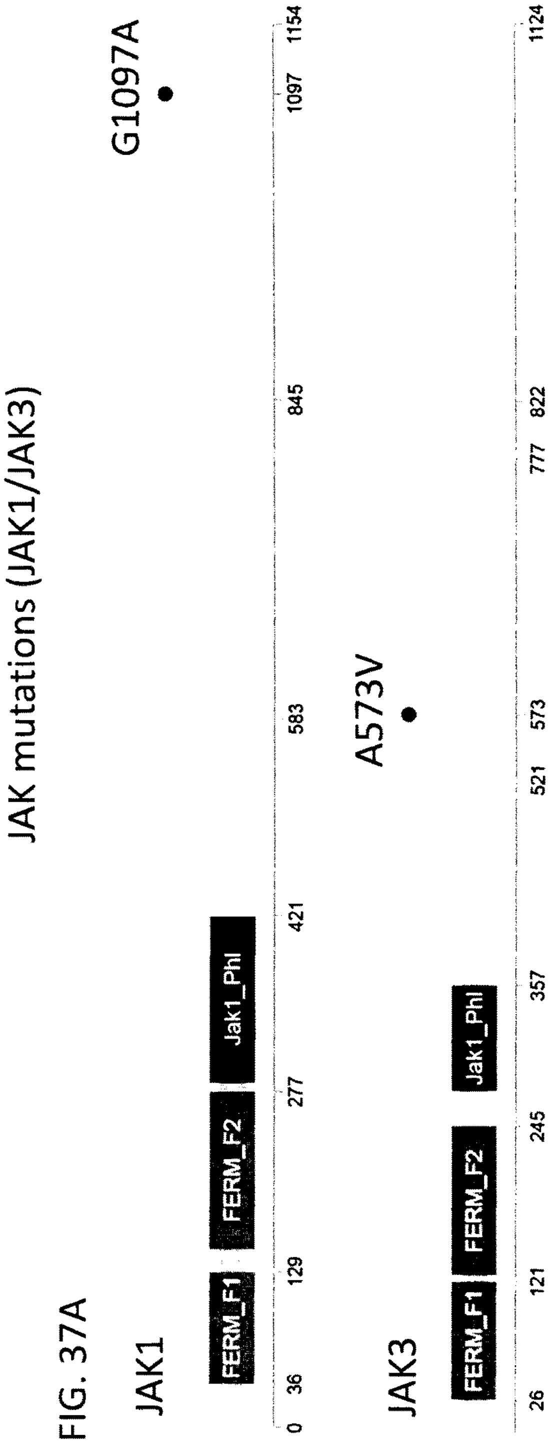
Figure 37B:
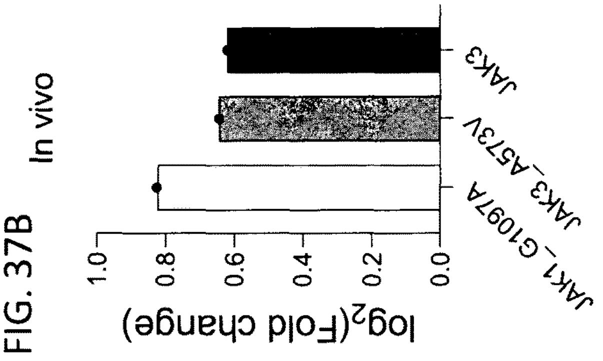

FIG. 37A is a lollipop diagram depicting JAK/JAK3 gene mutations. FIG. 37B shows the in vivo screen log 2 fold change for each JAK1/JAK3 mutation as determined by MAGeCK, compared to baseline (pre-injection). Positive log 2 fold change indicates increased persistence in tumors compared to input.

Figure 38:
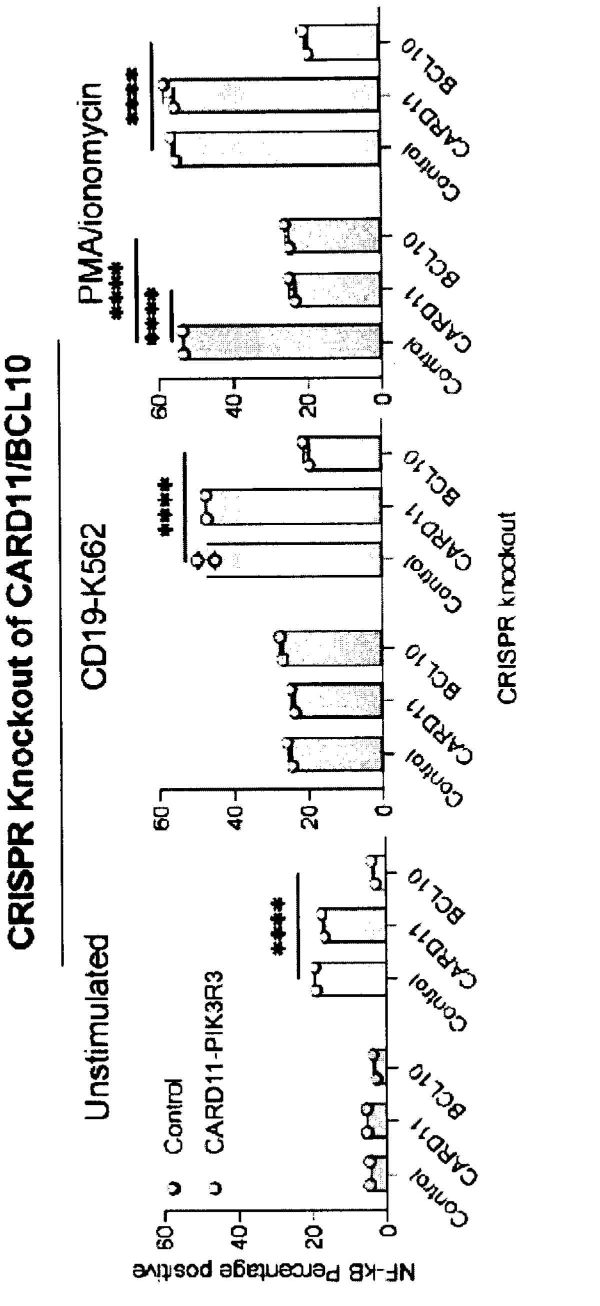

FIG. 38 shows NF-κB reporter activity of control, CARD11, or BCL10 CRISPR knockout BBz-CAR Jurkat cells.

Figure 39B:
Figure 39A:
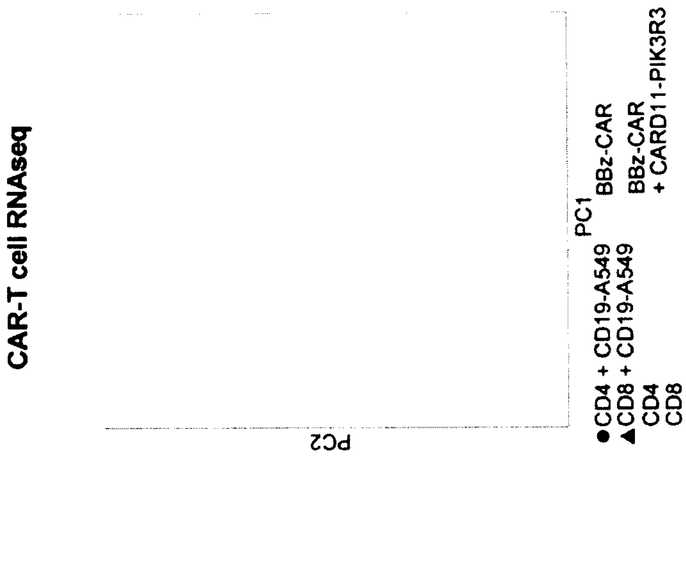
Figure 39C:
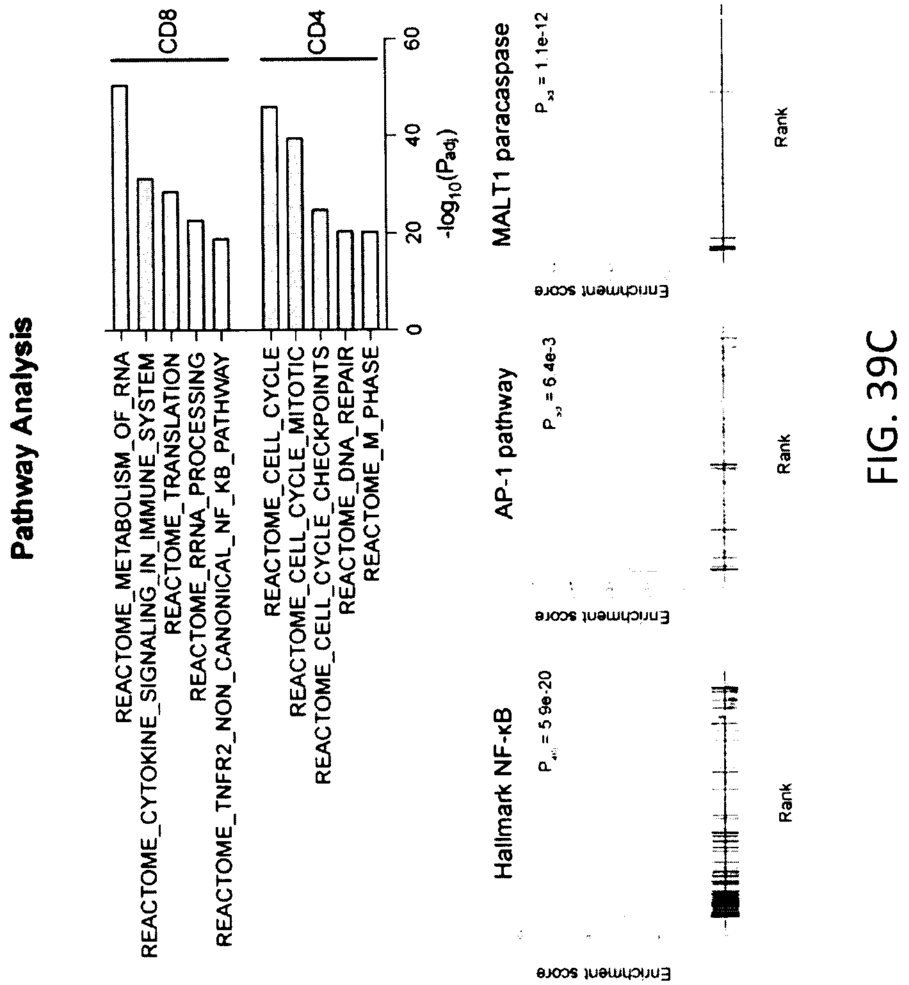

FIG. 39A shows Principal component analysis of transcriptomes of human BBz-CAR T cells. FIG. 39B is a heatmap of significantly upregulated genes in CARD11-PIK3R3 compared to control BBz-CAR T cells after stimulation with CD19 antigen shared among both CD4+ and CD8+ T cells. FIG. 39C shows the top 5 Reactome pathways enriched in CD4+ and CD8+ T cells (top) and NF-κB, AP-1, and MALT1 gene signature enrichment in CARD11-PIK3R3 expressing CD8+ BBz-CAR T cells after stimulation (bottom).

Figure 40:
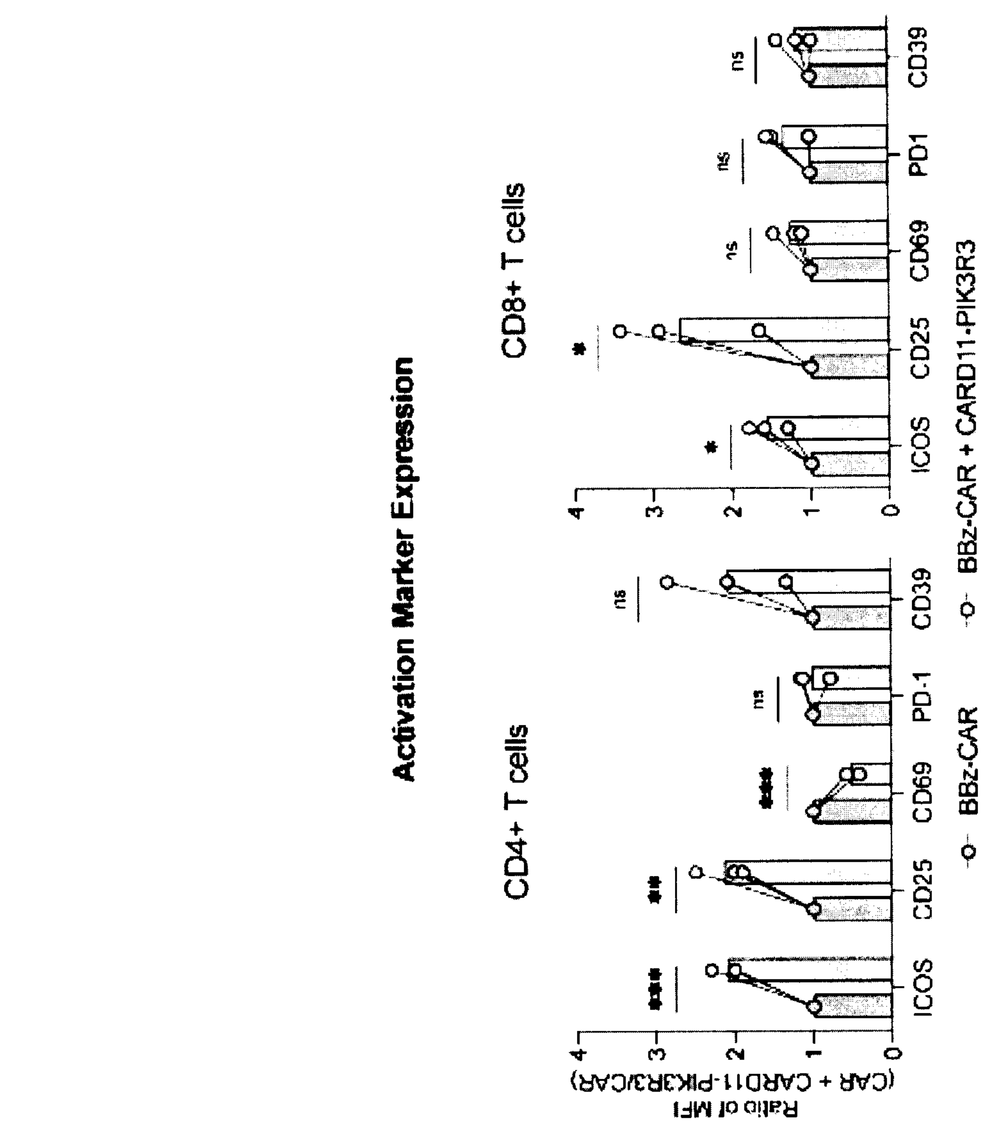

FIG. 40 shows activation markers expressed on transduced CD4 and CD8 T cells 24 hours post 1:1 co-culture with CD19-K562s. Ratio of MFI in CARD11-PIK3R3 relative to control shown. P values determined by unpaired T test.

Figure 41:
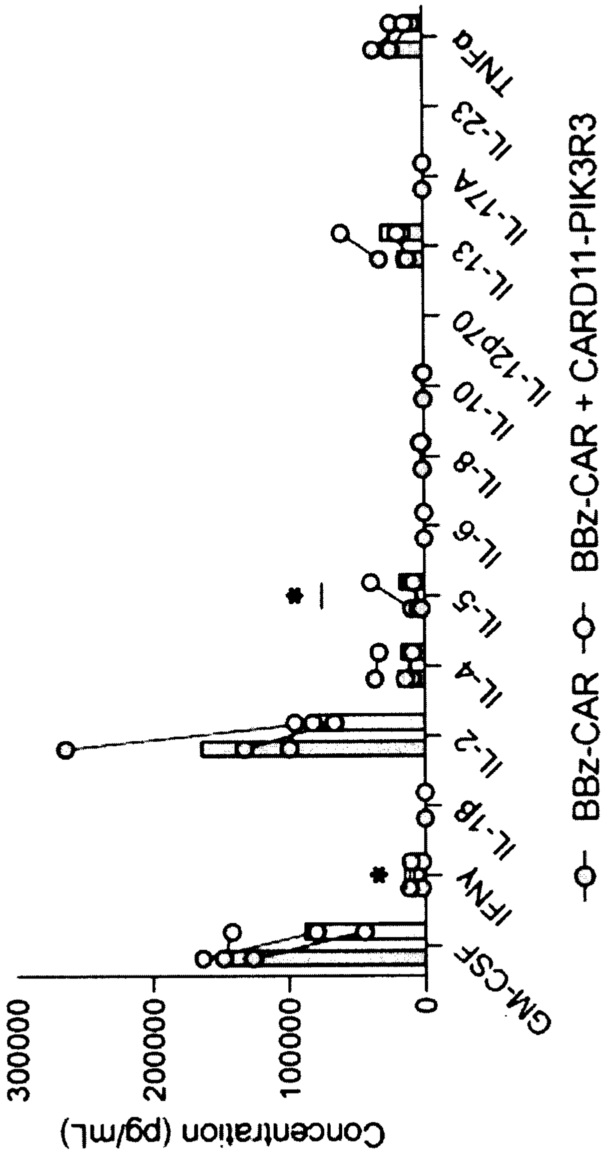

FIG. 41 shows cytokine secretion of CD4+CD19-BBz-CAR T cells and CD19-BB2-CAR+CARD11-PIK3R3 T cells after 48 hours of stimulation.

Figure 42A:
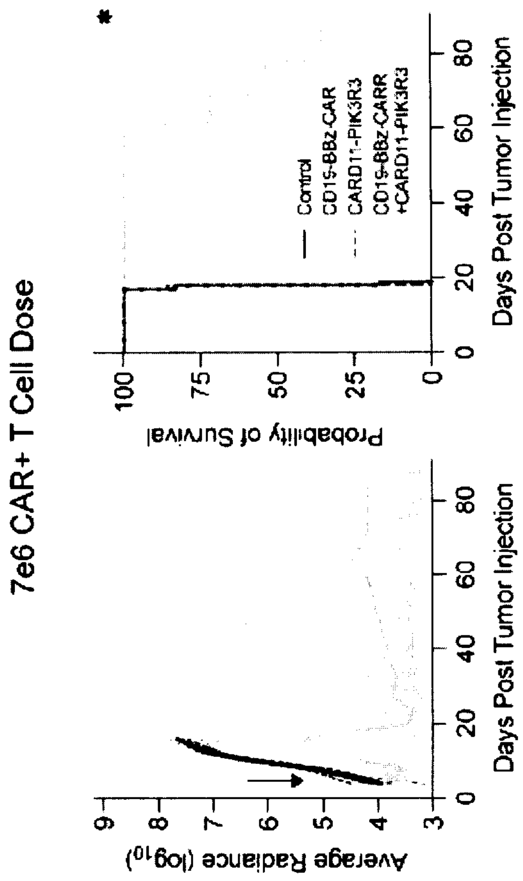
Figure 42C:
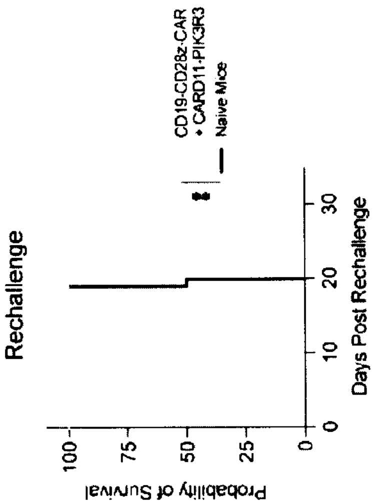
Figure 42B:
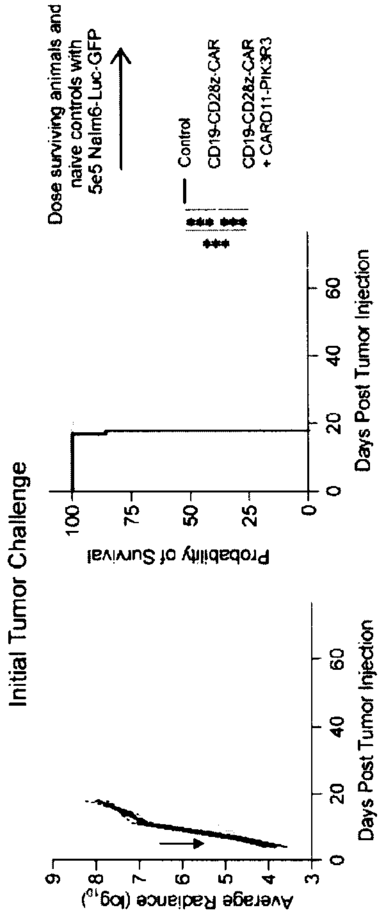
Figure 42D:
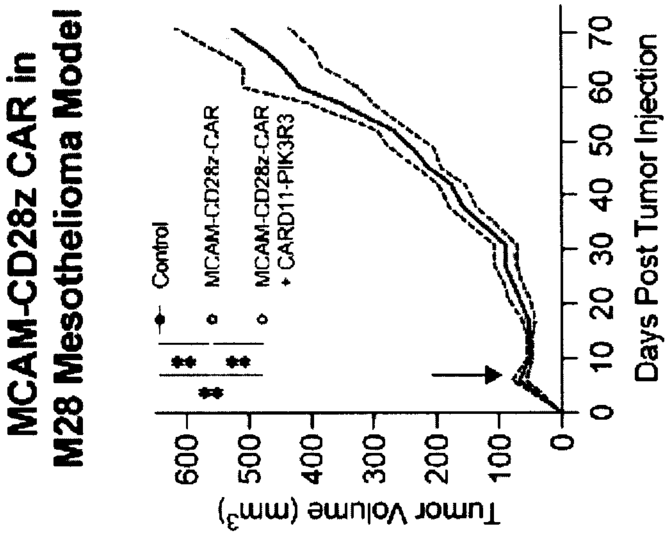

FIG. 42A shows control (n=6), CD19-BBz-CAR (n=7), CD19-BBz-CAR+CARD11-PIK3R3 (n=7) dosed at 7e6 CAR+ T cells. CARD11-PIK3R3 T cell (n=7) dose was equivalent to the total number of CARD11-PIK3R3 expressing T cells dosed in the CD19-BBz-CAR+CARD11-PIK3R3 group. FIG. 42B shows control (n=7), CD19-CD28z-CAR (n=7), CD19-CD282-CAR+CARD11-PIK3R3 (n=7) T cells dosed at 4c5 CAR+ T cells. FIG. 42C shows survival analysis of part (b) surviving CD19-CD28z-CAR+CARD11-PIK3R3 (n=6) animals or naive mice (n=4) rechallenged with 505 Nalm6-Luc-GFP tumors. FIG. 42D shows tumor volumes of M28 tumor bearing animals treated with control (n=5), MCAM-CD282-CAR (n=5), or MCAM-CD282-CAR+CARD11-PIK3R3 (n=5). T cells dosed at 5e5 CAR+ cells, control cells dosed equivalent to highest total T cell dose in other treatment groups.

Figure 43A:
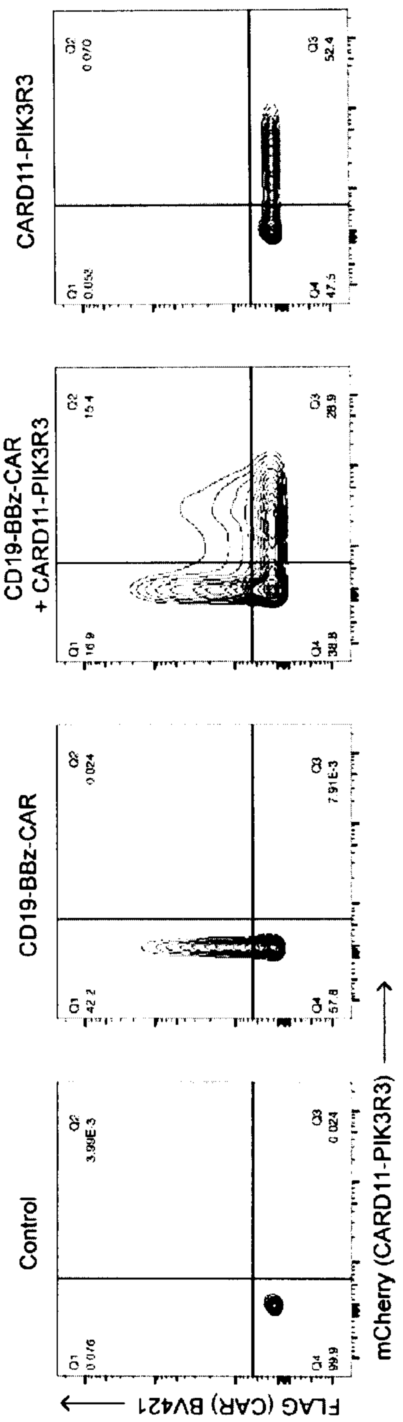
Figure 43B:
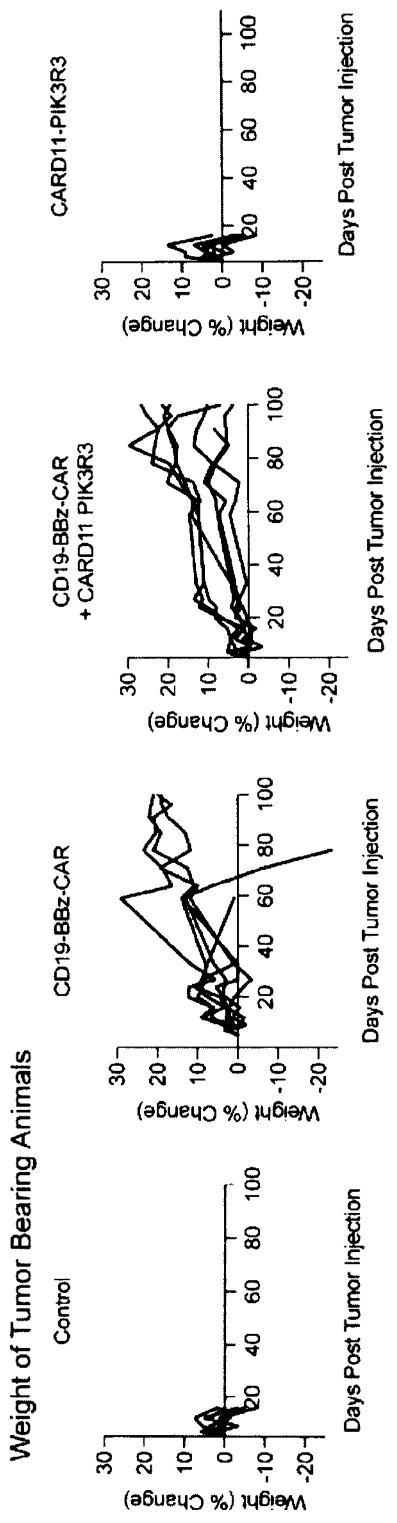
Figure 43C:
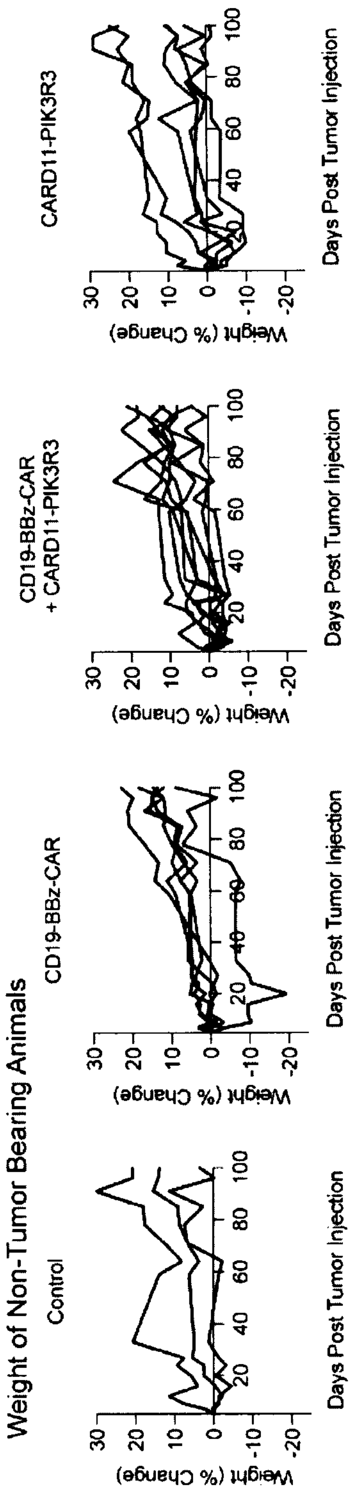
Figure 43D:
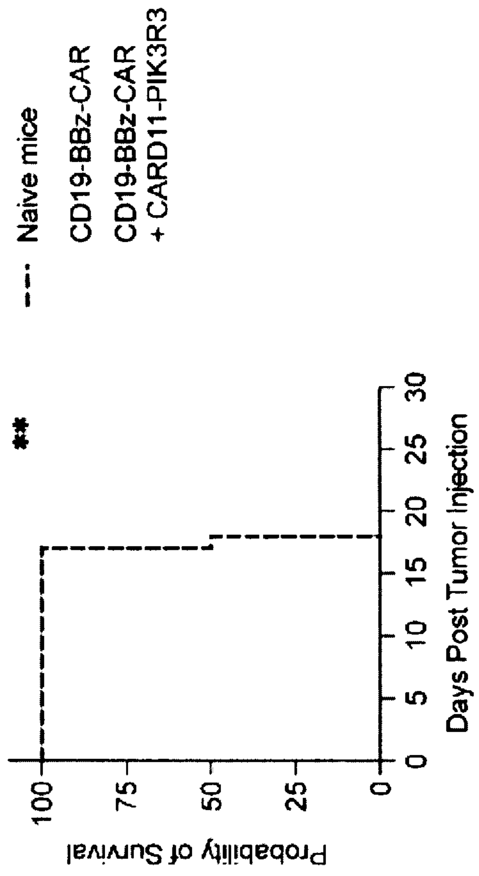

FIG. 43A shows flow cytometry plots indicating CAR (FLAG) and CARD11-PIK3R3 (mCherry) expression in human CD3 T cells. FIG. 43B and FIG. 43C show percent weight change from baseline of (FIG. 43B) tumor bearing or (FIG. 43C) non-tumor bearing animals treated with control, CD19-BBz-CAR, CD19-BBz-CAR+CARD11-PIK3R3 or CARD11-PIK3R3. FIG. 43D shows survival analysis of FIG. 42B surviving CD19-BBz-CAR (n=3), CD19-BB2-CAR+CARD11-PIK3R3 (n=4) animals or naive mice (n=4) rechallenged with 5c5 Nalm6-Luc-GFP tumors. P values determined by Log-rank Mantel-Cox. * indicates P value<0.05.

Figure 44A:
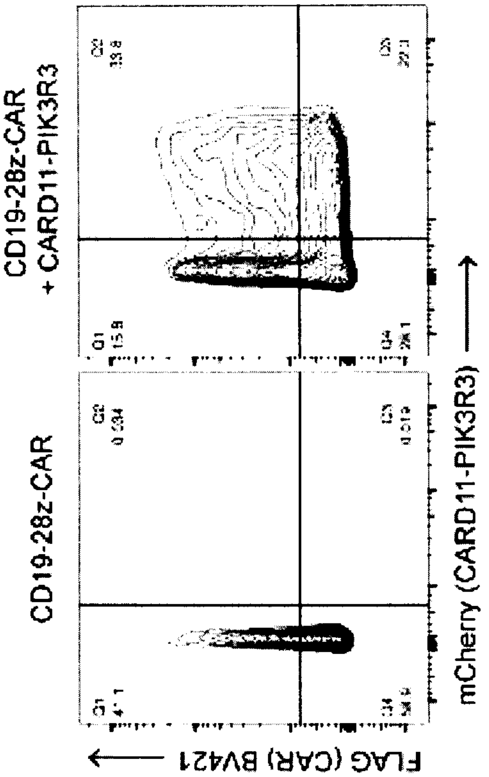
Figure 44B:
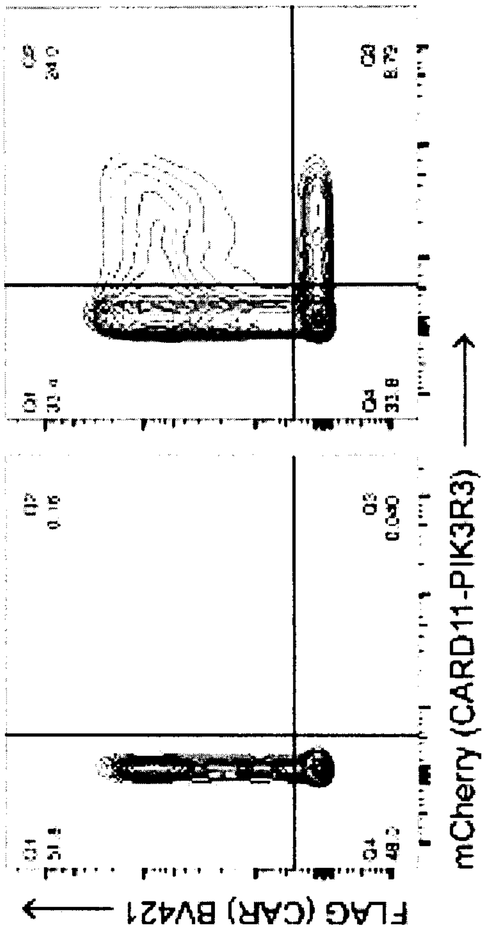
Figure 44C:
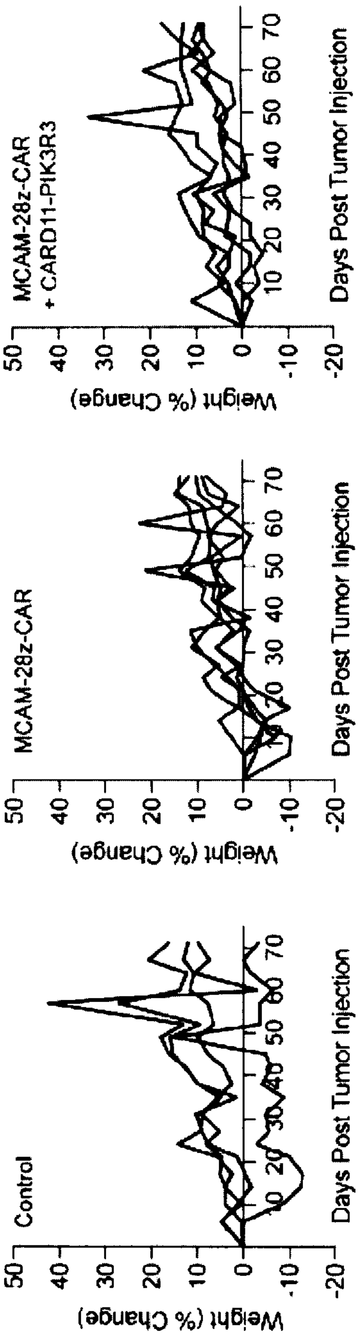

FIG. 44A and FIG. 44B show flow cytometry plots indicating FLAG (CAR) and mCherry (CARD11-PIK3R3) expression in human CD3 T cells. FIG. 44C shows Percent weight change from baseline of control, MCAM-CD282-CAR or MCAM-CD282-CAR+CARD11-PIK3R3 treated M28 tumor bearing animals.

Figure 45:
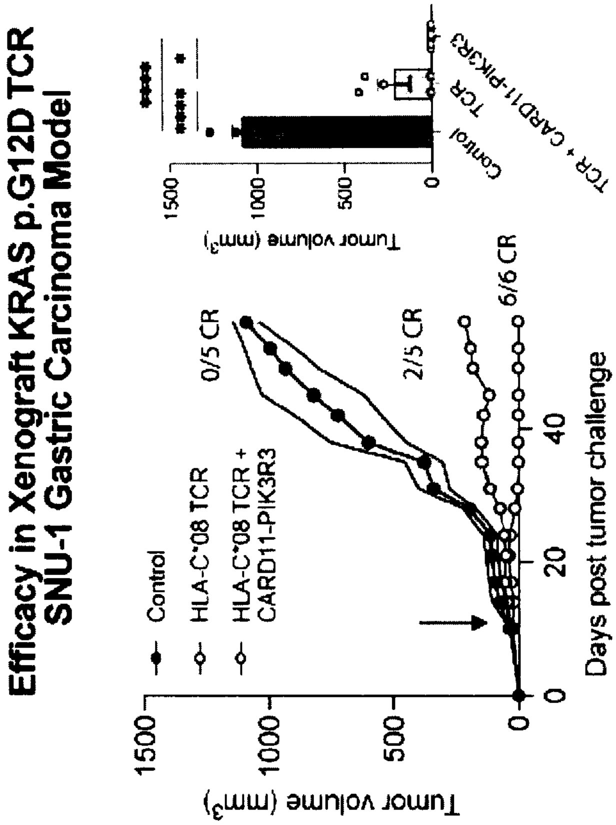

FIG. 45 shows tumor size of SNU-1 HLA-C*08:02 gastric cancer xenograft bearing mice treated with control (n=5), KRAS p.G12D-specific TCR T cells (n=5), or KRAS p.G12D-specific TCRCARD11-PIK3R3 T cells (n=6). Complete response was defined as an absence of a detectable tumor. * indicates P value<0.05, * indicates P values<0.001, ** indicates P value<0.0001.

Figures 46A, 46B, 46C:
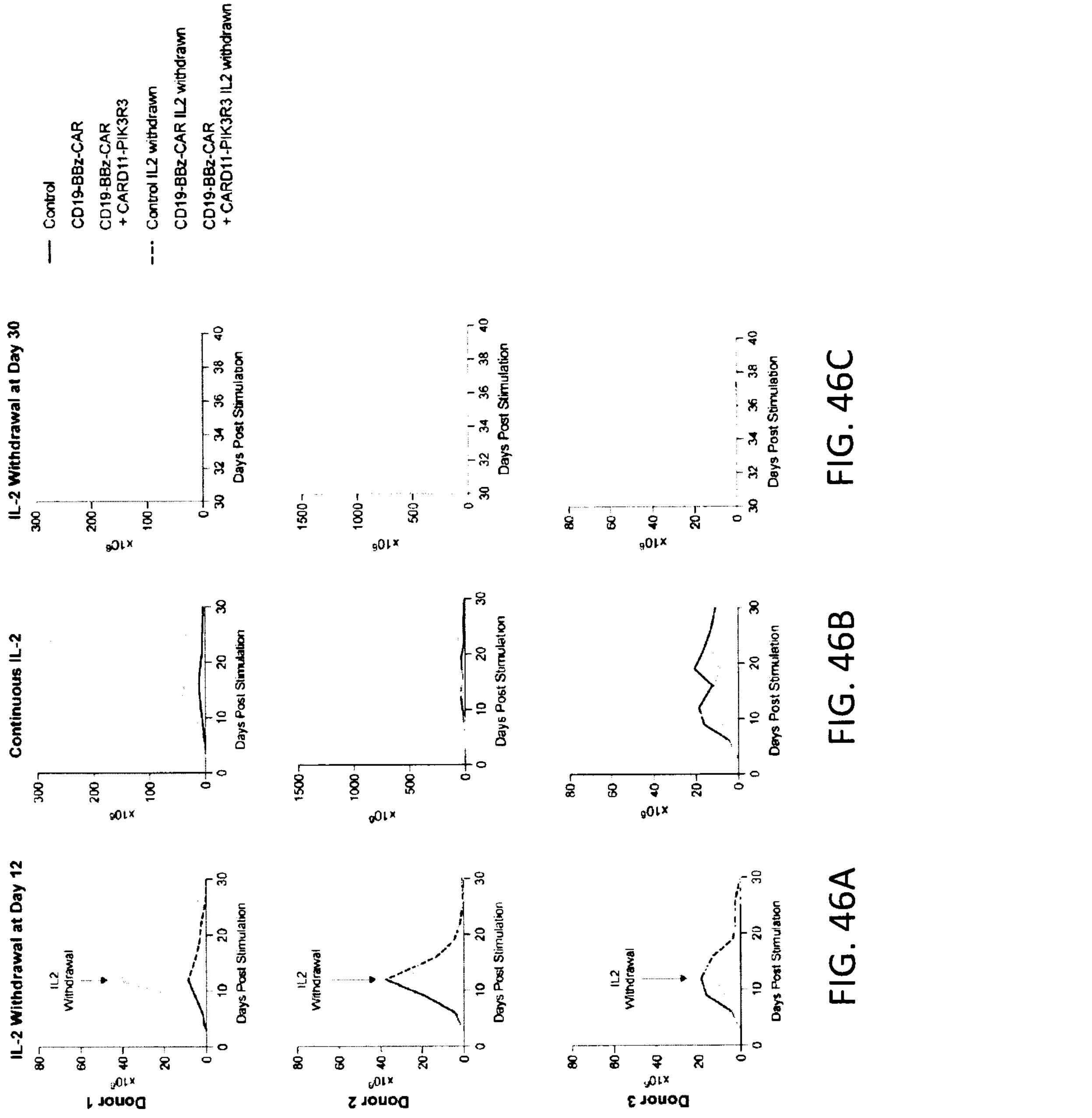

FIG. 46A, FIG. 46B, and FIG. 46C show in vitro expansion of CD19-BB2-CAR T cells with and without CARD11-PIK3R3. FIG. 46A and FIG. 46B show CAR or CAR+CARD11-PIK3R3 were sorted for purity, then expanded with IL-2 for 12 days. On Day 12, cultures were split, reseeding each group without IL-2 (FIG. 46A) and with IL-2 (FIG. 46B). Cells were counted and split from day 12 to day 30. FIG. 46C shows, on Day 30, CD19-BB2-CAR+CARD11-PIK3R3 T cells that were cultured with IL-2 were reseeded without IL-2 and counted and split for an additional 10 days.

Figure 47:
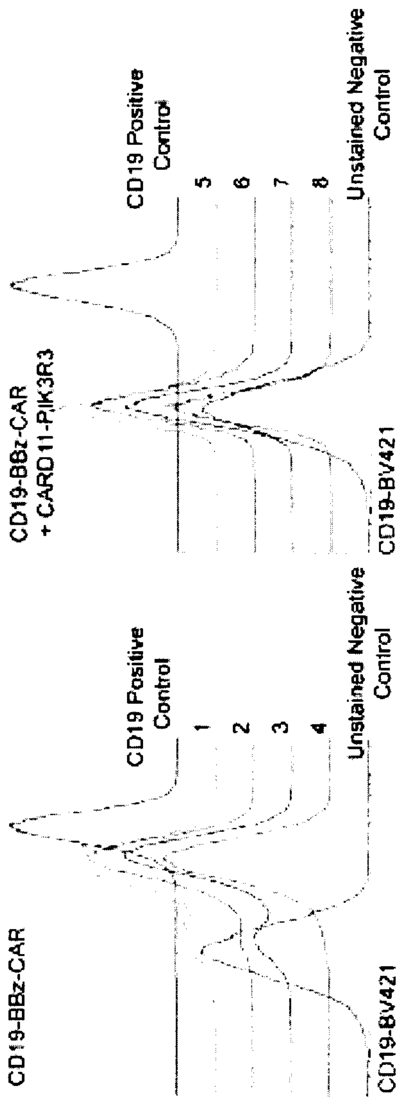

FIG. 47 shows in vivo analysis of CARD11-PIK3R3 expressing CAR T cells. Histograms are shown indicating human CD19 ligand expression on hCD19-B16 tumors, CD19-BBz-CAR or CD19-BBz-CAR+CARD11-PIK3R3 treated with that had reach euthanasia endpoint, compared to known CD19 positive B16 tumor sample.

Figure 48A:
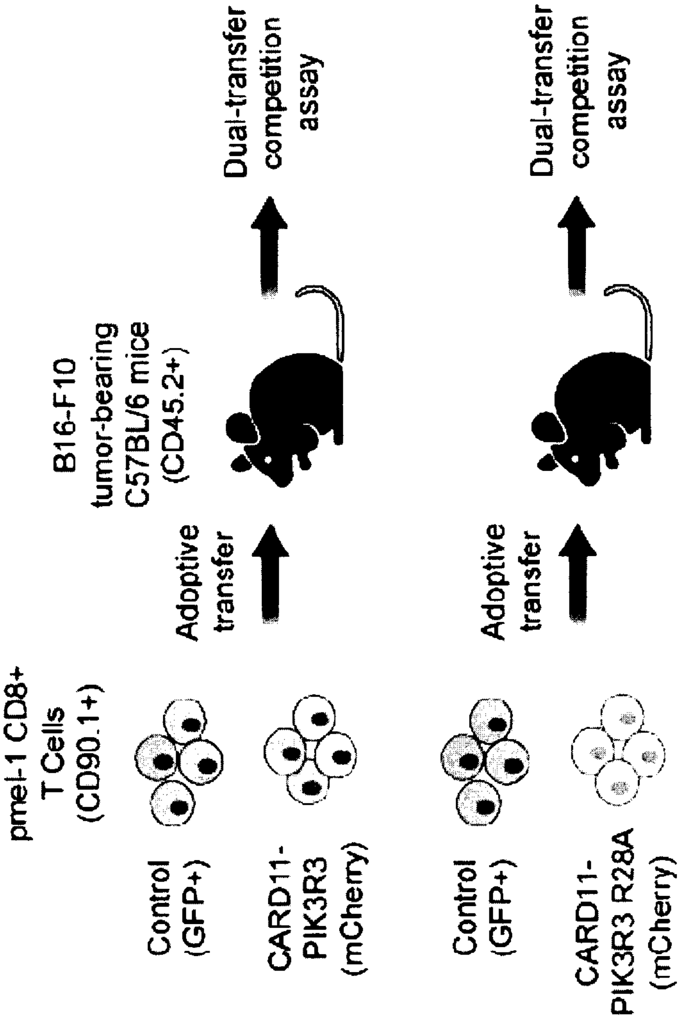
Figure 48C:
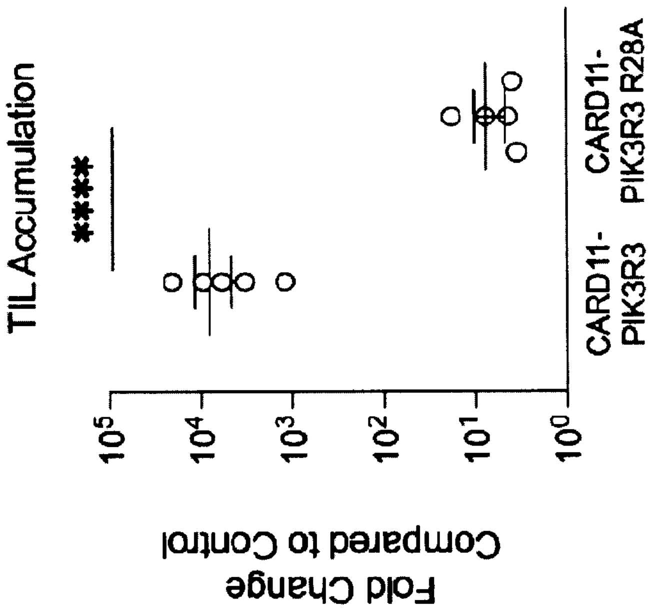
Figure 48B:
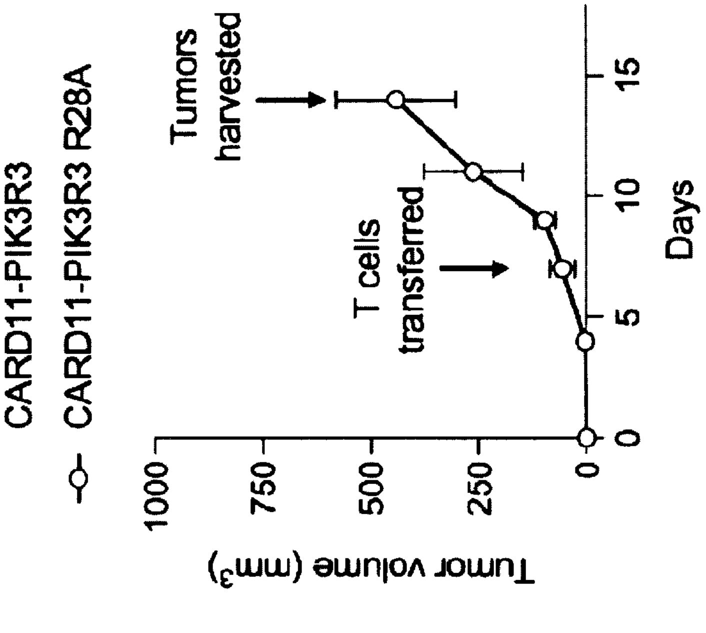

FIG. 48A, FIG. 48B, and FIG. 48C show in vivo analysis of CARD11-PIK3R3 expressing OT-I T cells. FIG. 48A shows a schematic of competition experiments with CARD11-PIK3R3 and CARD11-PIK3R3 R28A pmel-1 CD8 T cells in B16-F10 tumor model.

FIG. 48B shows tumor growth curves of mice described in (a). FIG. 48C shows fold-enrichment in the tumor of wild-type CARD11-PIK3R3 or CARD11-PIK3R3 (p.R28A) expressing pmel-1 CD8 T cells compared to vector control 7 days after adoptive transfer. All P values determined by ratio paired T test.

Figure 49A:
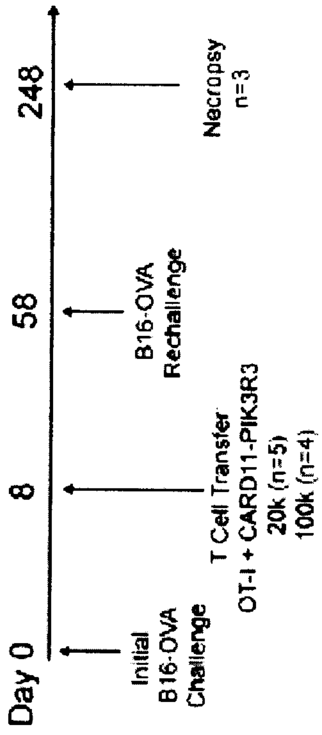
Figure 49B:
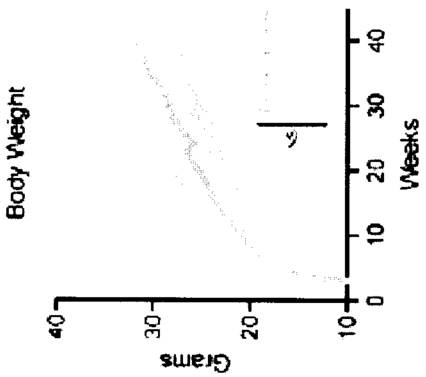
Figure 49C:
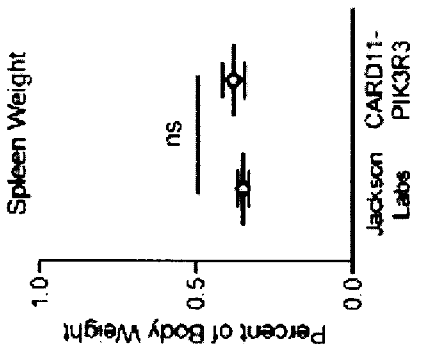
Figure 49D:
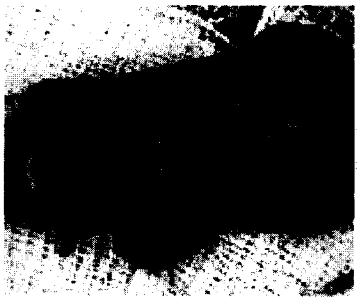
Figure 49E:
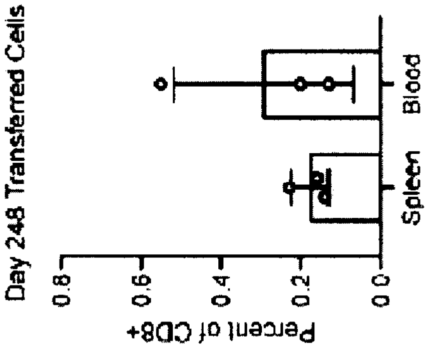
Figure 49F:
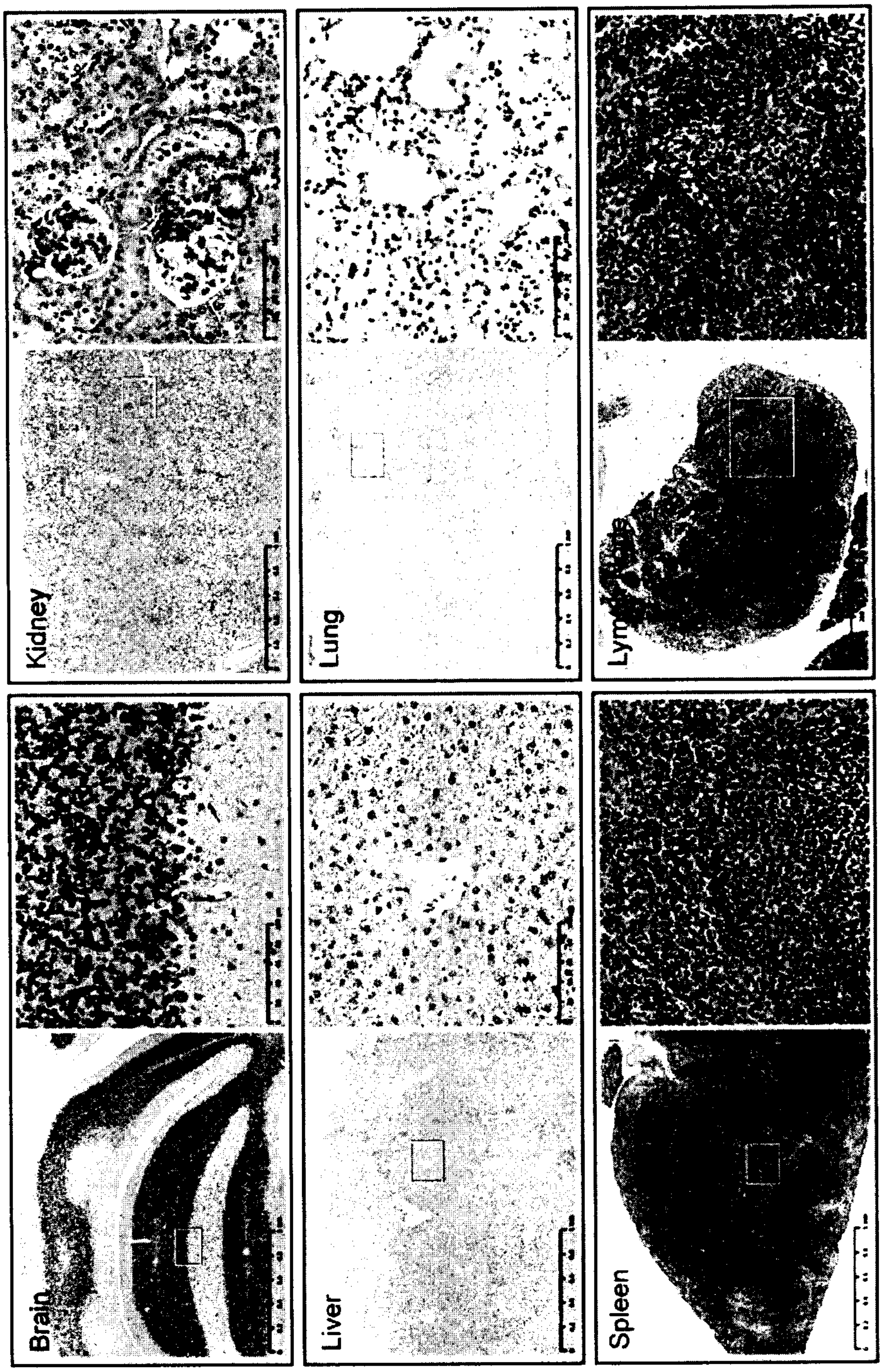
Figure 49G:
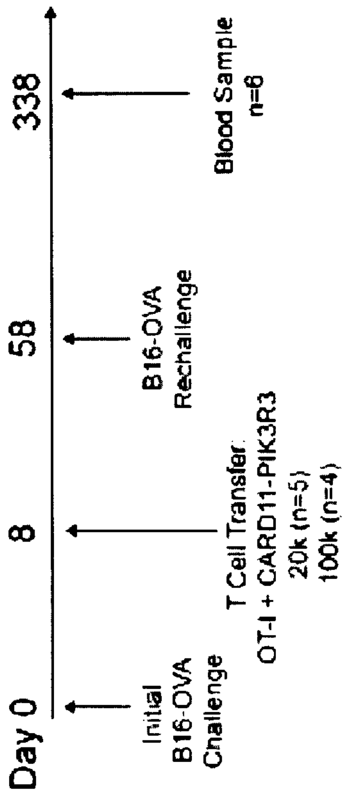
Figure 49H:
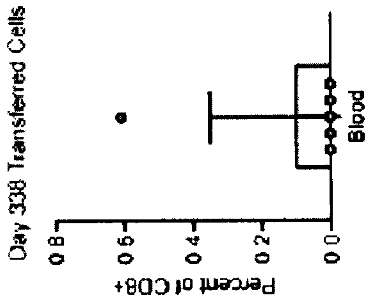
Figure 49I:
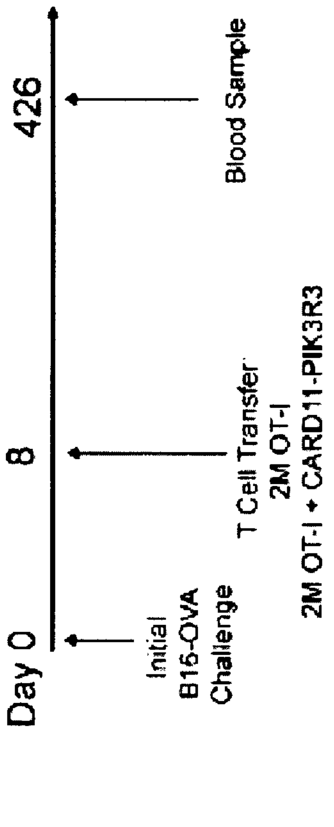
Figure 49J:
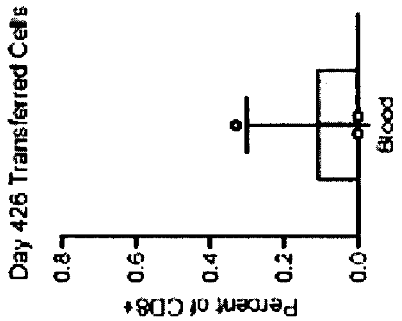

FIGS. 49A-49J show long-term evaluation of B6 mice treated with CARD11-PIK3R3 expressing OT-I T cells. FIG. 49A shows mice that cleared B16-F10-OVA were monitored for up to 240 days after adoptive T cell transfer. Necropsies were performed in as outlined in this schematic. FIG. 49B shows body weights of all CARD11-PIK3R3 infused mice from FIGS. 29A-29B were measured weekly and compared to expected weight curves published by The Jackson Laboratory Research Institute. FIG. 49C shows spleen weight for three animals that underwent necropsy on day 240. This was calculated as percent of body weight and compared to expected spleen weight published by The Jackson Laboratory Research Institute FIG. 49D shows necropsy of one representative animal. None of the three animals had gross pathology. FIG. 49E shows the Percentage of CD8 T cells in spleen and blood that express CARD11-PIK3R3 240 days after adoptive transfer. FIG. 49F shows representative hematoxylin and cosin-stained tissue sections from select organs where nodal or extranodal lymphomas can occur. Animals were subject to full-body necropsies. Tissues did not show evidence of nuclear atypia, changes in cellular architecture, or presence of neoplastic disease. Representative images at low (left) and high (right)-power magnification are shown with size bars. White box reflects the site of high-magnification image. FIG. 49G and FIG. 49I show a schematic of blood sampling of mice presented in FIGS. 29A-29B 330 days after adoptive transfer (FIG. 49G) or of 2e6 OT-I CARD11-PIK3R3 treated mice 418 days after adoptive transfer (FIG. 49I). FIG. 49H and FIG. 49J shows the percentage of CD8 T cells in blood that express CARD11-PIK3R3.

In the following detailed description, reference is made to the Figures, which form a part hereof. In the Figures, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

DETAILED DESCRIPTION OF THE DISCLOSURE

Overview

In general, the present disclosure relates, inter alia, to compositions and methods for improving adoptive T cell therapy. The disclosers have discovered ways to improve the therapeutic efficacy of T cells by altering T cell signaling, decreasing T cell exhaustion and/or by enhancing in vivo persistence and fitness of engineered T cells. T cell cancers can undergo positive selection of beneficial genetic alterations (e.g., mutations). In some embodiments, the present disclosure relates to exploiting such beneficial mutations to improve the effectiveness of T cell therapeutics.

The disclosure also relates to polypeptides having one or more mutations that can alter or promote or enhance signaling in T cells. The disclosure also relates to recombinant nucleic acid constructs and/or recombinant nucleic acids encoding polypeptides having one or more mutations that can alter or promote or enhance signaling in T cells. Non-limiting examples of such mutations are shown in Table 1. Non-limiting examples of signaling in T cells include: 1) CARD11-BCL10-MALT1 complex signaling, 2) JAK/STAT signaling, 3) co-stimulatory molecule signaling, 4) RAS/MEK/ERK signaling, 5) phospholipase gamma signaling, 6) transcription factor activity and/or other signaling pathways.

In some embodiments, the mutation alters a TCR transcriptional signaling output. In some embodiments, the mutation inhibits or reduces a TCR transcriptional signaling output e.g., NFAT, NF-κB or AP-1 signaling) or cytokine outputs (e.g., IL-2)

The disclosure also relates to polypeptides having one or more mutations, that can reduce T cell exhaustion, increase proliferation, alter effector function, resist T cell dysfunction, increase T cell fitness, enhance in vivo persistence, and/or increase intratumoral presence of therapeutic T cells. The disclosure further relates to recombinant nucleic acid constructs and/or recombinant nucleic acids encoding polypeptides having one or more mutations, that can reduce T cell exhaustion, increase proliferation, alter effector function, resist T cell dysfunction, increase T cell fitness, enhance in vivo persistence, and/or increase intratumoral presence of therapeutic T cells.

Reprograming T cells for proliferation, cytokine production and differentiation towards effector cells after engagement of a T cell receptor complex can depend on activating costimulatory signals and can be counteracted by coinhibitory molecules. The transcription factors NF-κB, NFAT and AP-1 have a major role in inducing the transcriptional program that is required for T cell activation and differentiation. Measuring the expression of such transcription factors are within the methods of the current disclosure and can be indicative to the major changes in T cell function for the mutations of the disclosure.

Definitions

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. All publications, patent applications, patents, GenBank or other accession numbers and other references mentioned herein are incorporated by reference in their entirety for all purposes.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B."

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is understood that aspects and embodiments of the disclosure described herein include "comprising," "consisting," and "consisting essentially of" aspects and embodiments. As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or step.

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then the to be "substantially identical." This definition also refers to, or may be applied to, the complement of a test sequence. This definition also includes sequences that have deletions and/or additions, as well as those that have substitutions. Generally, sequence identity can exist over a region that is at least about 20 amino acids or nucleotides in length, or over a region that is 10-100 amino acids or nucleotides in length, or over the entire length of a given sequence If necessary, sequence identity can be calculated using published techniques and widely available computer programs, such as the GCS program package (Devereux et al, Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

As used herein, the term "mutation" refers to a point mutation, a gene fusion, a substitution, a gain-of-function mutation, a stop-gain mutation, an insertion mutation, a deletion mutation, a duplication mutation and/or a translocation. The mutation may be in one or more genes. The mutation may be naturally occurring. Alternatively, the mutation may be induced or engineered. As used herein, the term "vector" refers to a recombinant polynucleotide construct designed for transfer between host cells, and that may be used for the purpose of transformation, e.g., the introduction of heterologous DNA into a host cell. As such, in some embodiments, the vector can be a replicon, such as a plasmid, phage, or cosmid, into which another DNA segment may be inserted so as to bring about the replication of the inserted segment. In some embodiments, the expression vector can be an integrating vector.

As used herein, the term "viral vector" refers either to a nucleic acid molecule (e.g., a transfer plasmid) that includes virus-derived nucleic acid elements that generally facilitate transfer of the nucleic acid molecule or integration into the genome of a cell or to a viral particle that mediates nucleic acid transfer. Viral particles will generally include various viral components and sometimes also host cell components in addition to nucleic acid(s). The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.). For example, a recombinant polypeptide as disclosed herein can be produced in a eukaryotic host, such as a mammalian cells (e.g., COS cells, NIH 3T3 cells, or Hela cells). These cells are available from many sources, including the American Type Culture Collection (Manassas, VA). In selecting an expression system, care should be taken to ensure that the components are compatible with one another. Artisans or ordinary skill are able to make such a determination. Furthermore, if guidance is required in selecting an expression system, skilled artisans may consult P. Jones, "Vectors: Cloning Applications", John Wiley and Sons, New York, N.Y., 2009).

As used herein, the term "retroviral vector" refers to a viral vector or plasmid containing structural and functional genetic elements, or portions thereof, that are primarily derived from a retrovirus. The retroviral vector can be a lentiviral vector. As used herein, the term "lentiviral vector" refers to a viral vector or plasmid containing structural and functional genetic elements, or portions thereof, including LTRs that are primarily derived from a lentivirus, which is a genus of retrovirus. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

As used herein, the term "pharmaceutically acceptable carrier" as used herein means any suitable carriers, diluents or excipients. These include all aqueous and non-aqueous isotonic sterile injection solutions, which may contain antioxidants, buffers and solutes, which render the composition isotonic with the blood of the intended recipient; aqueous and non-aqueous sterile suspensions, which may include suspending agents and thickening agents, dispersion media, antifungal and antibacterial agents, isotonic and absorption agents and the like. It will be understood that compositions of the present disclosure may also include other supplementary physiologically active agents. The carrier must be pharmaceutically "acceptable" in the sense of being compatible with the other ingredients of the composition and not injurious to the subject.

As used herein, the term "PEGylation" refers to modifying a protein by covalently attaching polyethylene glycol (PEG) to the protein, with "PEGylated" referring to a protein having a PEG attached. A range of PEG, or PEG derivative sizes with optional ranges of from about 10,000 Daltons to about 40,000 Daltons may be attached to the recombinant polypeptides of the disclosure using a variety of chemistries. In some embodiments, the average molecular weight of the PEG, or PEG derivative, is about 1 kD to about 200 kD such as, e.g., about 10 kD to about 150 kD, about 50 kD to about 100 kD, about 5 kD to about 100 kD, about 20 kD to about 80 kD, about 30 kD to about 70 kD, about 40 kD to about 60 kD, about 50 kD to about 100 kD, about 100 kD to about 200 kD, or about 1 150 kD to about 200 kD. In some embodiments, the average molecular weight of the PEG, or PEG derivative, is about 5 kD, about 10 kD, about 20 kD, about 30 kD, about 40 kD, about 50 kD, about 60 kD, about 70 kD, or about 80 kD. In some embodiments, the average molecular weight of the PEG, or PEG derivative, is about 40 kD.

As used herein, the terms "administration" and "administering" refer to the delivery of a bioactive composition or formulation by an administration route including, but not limited to, oral, intravenous, intra-arterial, intramuscular, intraperitoneal, subcutaneous, intramuscular, and topical administration, or combinations thereof. The term includes, but is not limited to, administering by a medical professional and self-administering.

As used herein, the term "injection" includes intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion.

The term "cancer" generally refers to the presence of cells possessing characteristics typical of cancer-causing cells, such as uncontrolled proliferation, immortality, metastatic potential, rapid growth and proliferation rate, and certain characteristic morphological features. Cancer cells can be in the form of a tumor, but such cells can exist alone within an animal subject, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In some embodiments, the cancer is a solid tumor, a soft tissue tumor, or a metastatic lesion.

As used herein, and unless otherwise specified, a "therapeutically effective" or "pharmaceutically effective" amount or number of a subject construct, nucleic acid, cell, or composition of the disclosure generally refer to an amount or number sufficient for a construct, nucleic acid, cell, or composition to accomplish a stated purpose relative to the absence of the composition, e.g., to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent. An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition including a "therapeutically effective amount" will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins)

As used herein, a "subject" or an "individual" includes animals, such as human (e.g., human subjects) and non-human animals. In some embodiments, a "subject" or "individual" is a patient under the care of a physician. Thus, the subject can be a human patient or an individual who has, is at risk of having, or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, e.g. non-human primates, and non-mammals, e.g., sheep, dogs, cows, chickens, amphibians, reptiles, etc.

Headings, e.g., (a), (b), (i) etc., are presented merely for case of reading the specification and claims. The use of headings in the specification or claims does not require the steps or elements be performed in alphabetical or numerical order or the order in which they are presented. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

TCR Signaling

Upon engagement of a peptide-MHC complex, the immunoreceptor tyrosine-based activation motifs (ITAMs) contained within the intracellular tails of the TCR complex become phosphorylated and recruit Zap70. Zap70 then recruits and activates the downstream LAT signalosome containing LAT, PLCy, Slp76. This signalosome causes the activation of the Ras/MAPK/ERK signaling leading to AP-1 transcriptional activity, the activation of PKCθ leading to NF-κB transcriptional activity and finally the influx of calcium which is responsible for NFAT transcriptional activity. Additionally, signaling from costimulatory receptors, such as 41BB, and cytokine support from IL-2 enhances these signaling pathways, and is required for T cells to undergo full activation and avoid anergic cell death. When fully activated, T cells rapidly proliferate and differentiate, secrete inflammatory cytokines, and cytotoxic cells begin performing target killing through release of cytotoxic granules. After resolution of this acute response, activated T cells undergo contraction to a form a small population of long-lived memory T cells that surveil the body, ready to respond to future encounters with the antigen.

T Cell Signaling

T cells become fully activated through T cell receptor (TCR) engagement, costimulatory signaling and cytokine support. TCR activation induces NFAT, NF-κB and AP-1 transcription factors signaling, IL-2 and other inflammatory cytokine secretion.

T Cell Exhaustion

T cell exhaustion is a state of hypo-responsiveness induced in effector T cell populations after chronic exposure to antigen. Exhaustion is marked by the upregulation of surface inhibitory receptors such as PD-1, TIM-3, LAG-3 and CTLA-4 among others, and the inability to proliferate long term, secrete inflammatory cytokines and kill target cells effectively. Exhausted T cells exist in a distinct transcriptional and epigenetic landscape. While exhaustion has been well characterized in chronic viral infections, it is also implicated in cancer, in which tumor infiltrating T cells, and engineered T cell therapies exhibit signs of exhaustion and fail to control tumor growth. To better treat chronic infections or cancer, T cell exhaustion must be prevented or overcome. In fact, checkpoint therapies which block signaling from the PD-1 or CTLA-4 axis of inhibition have proven somewhat effective in reinvigorating T cell responses in certain cancers leading to limited but effective tumor control.

NFAT Signaling:

The transcription factor nuclear factor of activated T cells (NFAT) is involved in T cell activation as well as programs of T cell exhaustion. At resting state, NFAT transcription factors are found in the cytoplasm in a phosphorylated state, unable to translocate to the nucleus to induce signaling. The extracellular influx of $Ca^{2+}$ that occurs during T cell activation activates the calcium dependent phosphatase calcineurin, resulting in dephosphorylation of NFAT, and its subsequent translocation and signaling in the nucleus. NFAT binds DNA in multiple ways, as a monomer, dimer or as a complex with other transcription factors. In particular NFAT is known to cooperatively bind with the transcription factor AP-1, inducing transcription of activation associated genes critical for effector T cell function. In contrast, when NFAT is not bound by AP-1, but is instead partnerless, it has been found to induce the expression of exhaustion associated genes, such as the inhibitory receptor PD-1. Additionally, studies have determined that exhaustion induced by partnerless NFAT can be remedied in CAR T cells by overexpressing the AP-1 family member, cJun. NFAT induces the expression of transcription factors TOX and NR4A1/2/3, which have been associated with T cell exhaustion and deletion or knockdown of these transcription factors has improved T cell phenotype and in vivo tumor control.

As NFAT signaling is key to successful T cell activation, but also plays a role in exhaustion, particularly in the absence of AP-1, it can be used to determine how genetic modifications in T cells influences the dynamics of NFAT signaling. Targeting the NFAT transcriptional pathway can be beneficial for T cell therapeutics.

NF-κB Signaling:

NF-κB (nuclear factor kappa light chain enhancer of B cells) is a family of transcription factors that induces transcriptional programs critical for T cell activation and effector function. NF-κB signaling occurs in many cell types. In T cells, NF-κB signaling induces a wide range of transcriptional programs responsible for proliferation and memory formation, resistance to apoptosis, cytokine secretion, and the production of a robust effector T cell response. NF-κB signaling is induced through two pathways, the canonical and noncanonical pathways.

In the canonical pathway NFKB1 is bound in the cytoplasm by IkBa and IkB-like molecule p105, forming a complex that prevents the nuclear translocation of NKFB1. When activated, TCR signaling induces activation of PKCθ, which in turn phosphorylates and activates CARD11. Activated CARD11 forms a complex with BCL10 and MALT1, and ultimately causes the phosphorylation and degradation of IkBa and IkB-like molecule p105, releasing NF-κB to translocate to the nucleus.

The non-canonical pathway is triggered by signaling through tumor necrosis factor receptor (TNFR) family members, which includes the costimulatory domain 41BB. At rest, the NFKB2 is bound by p100, during activation NF-κB-inducing kinase (NIK) activates IKKa, which in turn phosphorylates p100 and leads to the release and translocation of NKFB2 to the nucleus.

In syngeneic models of solid tumors, endogenous T cells that can respond to the tumors required NF-κB signaling to mediate tumor clearance. While NF-κB is induced through TCR signaling, it is also stimulated through the costimulatory domain 41BB (a TNFRS superfamily member), which is used clinically in FDA approved chimeric antigen receptor (CARs) therapies. CAR therapies using 41BB costimulatory domains have been found to persist longer in patients as compared to CAR therapies using other costimulatory domains, such as CD28. The persistence of 41BB CARs is directly linked to NF-κB signaling, which improves CAR T resistance to apoptosis through suppression of apoptotic proteins such as Bim.

AP-1 Signaling:

AP-1 transcription factors are a family of homo or heterodimeric proteins formed from complexes of JUN, FOS, ATF or MAF proteins. AP-1 signaling is induced by the phosphorylation cascade called the Mitogen Activated Protein Kinase (MAPK) pathway, triggered by TCR, cytokine/chemokine, or growth factor signaling. AP-1 often signals in complex with NFAT, and as indicated in the NFAT section, the loss of AP-1 causes partnerless NFAT to induce exhaustion programs in T cells, however this exhaustion can be remedied by overexpression of the AP-1 family member c-Jun. Related to this, loss of AP-1 is also known to induce an anergic cell state, where the T cell has partially activated through the TCR, but does not have enough costimulatory and cytokine signaling to induce full activation.

AP-1 dimers are activated by a plethora of physiological and pathological stimuli. Studies have reported that AP-1 proteins, mostly those that belong to the Jun group, control cell life and death through their ability to regulate the expression and function of cell cycle regulators such as Cyclin D1, p53, p21(cip1/waf1), p19(ARF) and p16. Amongst the Jun proteins, c-Jun is unique in its ability to positively regulate cell proliferation through the repression of tumor suppressor gene expression and function, and induction of cyclin D1 transcription. These actions are antagonized by JunB, which upregulates tumor suppressor genes and represses cyclin D1. An important target for AP-1 effects on cell life and death is the tumor suppressor p53, whose expression as well as transcriptional activity, are modulated by AP-1 proteins.

The concomitant induction of NFAT and AP-1 takes concerted activation of two different signaling pathways: calcium/calcineurin, which promotes NFAT dephosphorylation, nuclear translocation and activation; and protein kinase C (PKC)/Ras, which promotes the synthesis, phosphorylation, and activation of members of the Fos and Jun families of transcription factors. (Shaulian E, Karin M. AP-1 as a regulator of cell life and death. Nat Cell Biol 2002 45. 2002; 4(5):E131-E136.)

IL-2 Signaling:

IL-2 is a pleiotropic cytokine required for activation, proliferation differentiation, and maintenance of T cells. Naïve T cells express a low affinity IL-2 receptor requiring high volumes of IL-2 to initiate activation, while memory and regulatory T cells express a high affinity IL-2 receptor requiring much lower amounts of IL-2 for effective signaling. The IL-2 receptor makes use of the JAK/STAT signaling cascade, resulting in wide ranging transcriptional changes. Though CD8+ T cells are responsible for the cytotoxic effector response to foreign antigens, CD8+ T cells themselves cannot effectively produce IL-2 and rely instead on helper CD4+ T cells to produce IL-2 and other cytokine support.

IL-2 is so critical for T cell persistence and proliferation that high dose IL-2 therapy has been FDA approved for certain cancers, with the hopes of expanding endogenous cytotoxic T cell populations to induce tumor rejection. In metastatic melanoma and renal cell carcinoma trials, high dose IL-2 therapy induces limited (7%) long term response rates.

However this therapy is not well tolerated by patients, causing multiple deaths, and likely contributes to the expansion of CD4+CD25+FoxP3+ regulatory T cells. Regulatory T cells are known to be pro-tumorigenic and high numbers of regulatory T cells (Tregs) are correlated with poor prognosis in solid tumor settings. Toxicity and the expansion of pro-tumor Treg populations present so much of a challenge to IL-2 therapy that synthetic orthogonal IL-2 cytokine therapies have recently been developed to target the effects of IL-2 cytokine therapy to cytotoxic T cells and avoid expansion of Tregs.

IL-2 secretion is highly relevant for the persistence and proliferation of T cell therapeutic products, therefore the inventors/disclosers assessed IL-2 secretion capacity of each mutation when expressed in CAR Jurkat cell lines and after co-culture with target cells. As a follow up for relevant hits, the inventors/disclosers assessed the capacity for mutations to improve CAR T cell in vitro target killing when cultured without supplemental IL-2. This setting, where IL-2 is withheld, better reflects the challenges of the tumor microenvironment, where IL-2 is scarce and autocrine secretion of IL-2 would be beneficial for maintenance of proliferation and long-term killing capabilities.

In Vivo Screening of Mutations:

A major barrier to the success of cell therapy is the accumulation and persistence of T cells within tumors. The inventors/disclosers sought to systematically screen mutations in primary human CAR T cells in a xenograft model. To uncover mutations that improve persistence in highly adverse conditions, the inventors/disclosers utilized a difficult to control K562 subcutaneous tumor model in which T cell efficacy is limited.

The inventors/disclosers found that clinically relevant CD19 targeted BBz CAR T cells are ineffective in controlling CD19-K562 tumors in a subcutaneous xenograft model, likely failing due to low CAR T cell infiltration, and the lack of persistence and expansion within the tumor microenvironment. These challenges mirror some of the CAR T cell clinical failures observed when treating solid tumors. The inventors/disclosers opted to screen the mutations in this high bar "failure" model with the hopes of finding mutations that greatly improve CAR T cell persistence within solid tumors.

While adoptive cell therapies have proven highly effective in refractory B cell malignancies, CAR-T cell therapies have yet to provide robust, long-term efficacy against solid tumors. In the solid tumor setting, CAR-T cells become exhausted and struggle to proliferate and perform effector function, ultimately resulting in the inability to control tumor growth or prevent relapse. Therefore, the inventors/disclosers opted to create effective targeted cellular therapies against solid tumors by improving the proliferative capacity, persistence, and effector function of CAR-T cells.

CARD11-BCL10-Malt Signalosome

Formation of a CARD11-BCL10-MALT (CBM) signaling complex is a key event in T- and B cell receptor-induced gene expression. After exposure to distinct immune triggers, these molecules form self-organizing filaments with MALT1 protease activity to regulate canonical nuclear factor-κB (NF-κB) and mitogen-activated protein kinase (MAPK) signalling pathways and the degradation of mRNA-binding proteins, which provides two layers of control of inflammatory gene expression. Deregulation of CARD11, BCL10 or MALT1 expression or CBM signaling have been associated with cancer, immunodeficiency, and autoimmunity (J. Ruland, L. Hartjes, CARD-BCL-10-MALT1 signalling in protective and pathological immunity. Nat Rev Immunol 19, 118-134 (2019).

In normal T cells, T cell receptor (TCR) signaling activates PKCθ, which in turn promotes the assembly of the CARD11-BCL10-MALT1 (CBM) signalosome. The CBM complex subsequently has three major outputs: NF-κB transcriptional activity, AP-1 transcriptional activity and MALT1 proteolytic activity (FIG. 5). The assembly of the CARD11-BCL10-MALT1 signalosome complex is an essential step in regulating NF-κB in lymphoid immune cells.

An inhibitory domain present in CARD11 may allow for intramolecular autoinhibition which can prevent CARD11 binding to BCL10 in the absence of upstream signals. Upon phosphorylation of the inhibitory domain in normal T cells, CARD11 autoinhibition can be relieved and the CARD11 protein can oligomerize and promote prion-like assembly of the CBM complex with recruitment of BCL10-MALT1 filaments, which then can allow for CBM complex signaling.

Genes involved in CBM signaling include but are not limited to caspase recruitment domain family member 11 (CARD11), capping protein regulator and myosin 1 linker 2 (CARMIL2), mucosa-associated lymphoid tissue lymphoma translocation protein 1 (MALT1), B-cell lymphoma 10 (BCL10). CARD11 can be involved in both the innate and adaptive immune systems. CARD11 is implicated in the activation of NF-κB by the TCR complex.

JAK/STAT Signaling

The biochemistry of JAK/STAT signaling is well known to a person of skill in the art. Briefly, signaling begins with extracellular association of cytokines or growth factors with their corresponding transmembrane receptors. This facilitates trans-activation of receptor-bound Janus kinases (JAKS) by putting them in spatial proximity and by prompting conformational changes that distance their kinase domains from inhibitory pseudokinase domains. Activated JAKS then phosphorylate latent STAT monomers, leading to dimerization, nuclear translocation, and DNA binding. In mammals, 4 JAKS (JAK1, JAK2, JAK3, TYK2) and 7 STATs (STAT1, STAT2, STAT3, STAT4, STAT5a, STAT5b, and STAT6) are employed by more than 50 cytokines and growth factors. (Villarino A V., Kanno Y, O'Shea J J. Mechanisms and consequences of JAK-STAT signaling in the immune system. Nat Immunol 2017 184. 2017; 18(4): 374-384).

Co-Stimulatory Molecule Signaling

Co-stimulatory and co-inhibitory molecules are cell surface receptors and ligands that are classified into various families on the basis of their structure and functions.

Co-stimulatory and co-inhibitory receptors determine the functional outcome of T cell receptor (TCR) signaling. The specific recognition of cognate antigenic peptides presented by MHC molecules triggers T cell receptor signaling, but it is co-stimulatory and co-inhibitory receptors on T cells that direct T cell function and determine T cell fate. T cell co-signaling receptors have been broadly defined as cell-surface molecules that can transduce signals into T cells to positively (co-stimulatory receptors) or negatively (co-inhibitory receptors) modulate TCR signaling. Examples of co-stimulatory or co-inhibitory receptors includes CD28 and CTLA-4, both of which bind to ligands B7-1 and 7-2. Other genes involved in co-stimulatory molecule signaling include TNFR2, TNFRS1B, and ICOS (Chen L, Flies D B. Molecular mechanisms of T cell co-stimulation and co-inhibition. Nat Rev Immunol 2013 134. 2013; 13(4):227-242.)

RAS/MEK/ERK

As is known by the skilled in the art, the sarcoma/mitogen-activated protein kinase kinase/extracellular receptor kinase (RAS/MEK/ERK) is a conserved signaling pathway that plays pivotal roles in cell proliferation, survival and differentiation. The aberrant activation of the RAS/MEK/ERK signaling pathway induces tumors. Efforts have been dedicated to targeting this signaling pathway for cancer treatment. The aberrant activation of the signaling pathway contributes to tumorigenesis and tumor development.

It is also known that triggering of a T-cell receptor by its cognate antigen results in nearly immediate activation of downstream signaling cascades, including the RAS/MEK/ERK pathway. Studies have also shown that RAS/MEK/ERK signaling is memory stage-dependent in human T cells, conferring susceptibility to alloreactive T-cell selective inhibition.

As an important upstream molecular marker of the RAS-RAF-MEK-ERK pathway, RAS serves as a molecular switch by binding GTP/GDP, and it includes four isoforms: HRAS, KRAS4A, KRAS4B, and NRAS. KRAS is the most frequent isoform in all human cancers. KRAS4A and KRAS4B are the different splicing isoforms of the same gene. When the transmembrane receptors (receptor tyrosine kinase, RTKs) are activated, the complexes of growth-factor-receptor bound protein 2 (GRB2) and son of sevenless (SOS) in the cytoplasm are recruited to the inner surface of cell membrane. (McCubrey J A, Steelman L S, Basecke J, Martelli A M. Raf/mek/erk signaling. Target Ther Acute Myeloid Leuk. January 2015:275-305.)

Several mutations identified by the inventors/disclosers are in genes having various roles in this signaling pathway.

Phospholipase C Gamma Signaling

Phospholipase C (PLC) is an essential mediator of cellular signaling. PLC regulates multiple cellular processes by generating bioactive molecules such as inositol-1,4,5-triphosphate (IP3) and diacylglycerol (DAG). These products propagate and regulate cellular signaling via calcium ($Ca^{2+}$) mobilization and activation of protein kinase C (PKC), other kinases, and ion channels. PLCγ1, one of the primary subtypes of PLC, is directly activated by membrane receptors, including receptor tyrosine kinases (RTKs), and adhesion receptors such as integrin. PLCγ1 mediates signaling through direct interactions with other signaling molecules via SH domains, as well as its lipase activity. PLCγ1 is frequently enriched and mutated in various cancers, and is involved in the processes of tumorigenesis, including proliferation, migration, and invasion. (Jang H J, Suh P G, Lee Y J, Shin K J, Cocco L, Chae Y C. PLCγ1: Potential arbitrator of cancer progression. Adv Biol Regul. 2018; 67:179-189, and Patterson R L, Van Rossum D B, Nikolaidis N, Gill D L, Snyder S H. Phospholipase C-γ: diverse roles in receptor-mediated calcium signaling. Trends Biochem Sci. 2005; 30(12):688-697

The phospholipase C gamma signaling pathway has been implicated in T cell lymphomas and primarily in cutaneous T cell lymphomas (CTCL). Nine PLCG1 mutations (p.R48W, p.S312L, p.D342N, p.S345F, p.S520F, p.R1158H, p.E1163K, p.D1165H, and the in-frame indel p. VYEEDM1161V) have been identified in Sezary Syndrome, the leukemic variant of CTCL. (V. M. Patel et al., Frequent and Persistent PLCG1 Mutations in Sezary Cells Directly Enhance PLCγ1 Activity and Stimulate NFkB, AP-1, and NFAT Signaling. J Invest Dermatol 140, 380-389.e384 (2020).

Recombinant Nucleic Acid Constructs and/or Recombinant Nucleic Acids and Polypeptides Certain aspects of the disclosure are directed to polypeptides, recombinant nucleic acid constructs, and recombinant nucleic acids encoding polypeptides, wherein the polypeptides include a mutation capable of altering T cell signaling.

Exemplary mutations in the polypeptides encoded by the recombinant nucleic acid constructs and/or recombinant nucleic acids of the disclosure are described in Table 1. In some embodiments of the recombinant nucleic constructs and/or recombinant nucleic acids of the disclosure, the polypeptides can include more than one mutation. For example, one or two or three or four or five or more mutations. In some embodiments, the mutations are a combination of different types of mutations. The different types of mutations can be point mutations, gene fusions, substitutions, gain-of-function mutations, stop-gain mutations, insertion mutations, deletion mutations, duplication mutations or translocations. The mutation can be a T cell lymphoma mutation or a mutation in a clonally expanded population of T cells. In some embodiments, the mutation is a point mutation or substitution.

In some embodiments, the mutation is a gene fusion. In some embodiments, the gene fusion comprises a polypeptide comprising a caspase-associated recruitment domain (CARD). In some embodiments, the gene fusion comprises a polypeptide comprising a CARD containing protein or a functional fragment thereof. A functional fragment of a CARD containing protein can be, for example, a fragment that provides NF-κB transcriptional activity, AP-1 transcriptional activity, and/or MALT1 proteolytic activity at a level at least 70%, 75%, 80%, 85%, 90%, or 95% of that of a full-length protein, as determined by the in vitro CAR Jurkat assay shown in FIG. 1 and described herein. In some embodiments, the gene fusion comprises a domain capable of binding to (i) a substrate localized to the intracellular side of the plasma membrane of a cell and/or (ii) a target polypeptide comprising a phosphorylated tyrosine (pTyr). In some embodiments, the gene fusion comprises a CARD containing protein and a domain capable of binding to (i) a substrate localized to the intracellular side of the plasma membrane of a cell and/or (ii) a target polypeptide comprising a pTyr.

In some embodiments, the domain is capable of binding to a substrate indirectly localized to the intracellular side of the plasma membrane. Indirect localization can refer to localization of the substrate to the intracellular side of the plasma membrane through, for example, binding of the substrate to another polypeptide or lipid that is directly localized to the intracellular side of the plasma membrane. Indirect localization can refer to localization of the substrate to the intracellular side of the plasma membrane through, for example, interaction of the substrate with another polypeptide or lipid that is directly localized to the intracellular side of the plasma membrane. In some embodiments, the domain is capable of binding to a substrate directly localized to the intracellular side of the plasma membrane. Direct localization can refer to localization of the substrate to the intracellular side of the plasma membrane through, for example, binding of the substrate to the intracellular side of the plasma membrane itself. Direct localization can refer to localization of the substrate to the intracellular side of the plasma membrane through, for example, interaction of the substrate with the intracellular side of the plasma membrane itself.

In some embodiments, the mutation is a T cell lymphoma mutation. T cell lymphoma mutation can be a mutation occurring in, or identified in, a T cell lymphoma. T cell lymphomas are a heterogeneous group of lymphoid malignancies that occur in nodal and extranodal sites.

There are two main types of T cell lymphomas namely T-lymphoblastic lymphoma and Peripheral T-cell lymphomas classified based on clinical manifestations and cytogenetic mutations. Peripheral T cell lymphoma can be further divided into cutaneous T cell lymphoma, adult T cell lymphoma, angioimmunoblastic T cell lymphoma, natural killer T cell lymphoma, enteropathy associated T cell lymphoma, and anaplastic large cell lymphoma. In some embodiments, the T cell lymphoma mutation occurs in a T lymphoblastic lymphoma. In some embodiments, the T cell lymphoma mutation occurs in a Peripheral T cell lymphoma.

In some embodiments, the mutation is a mutation in a clonally expanded population of T cells. As used herein, a clonally expanded population of T cells can be a population of T cells that are descended from a single progenitor cell. T cells within the clonally expanded population can express the same T cell receptor.

The polypeptides of the disclosure, or the recombinant nucleic acid constructs and/or recombinant nucleic acids of the disclosure, can alter T cell signaling in various ways. In some embodiments, the altering of the T cell signaling can be by enhancing, promoting, improving, reducing, regulating, or modulating the signaling pathway within a T cell. In some embodiments, the altering of the T cell signaling can be by activating, increasing, suppressing, inhibiting, or other means of changing the signaling.

The polypeptides of the disclosure, or the recombinant nucleic acid constructs and/or recombinant nucleic acids of the disclosure, can alter T cell signaling through one or more T cell signaling pathways. In some embodiments, the polypeptides or recombinant nucleic acid constructs and/or recombinant nucleic acids of the disclosure can alter T cell signaling by increasing one or more pathways and/or reducing one or more pathways, or by a combination of enhancing and/or reducing various pathways, for example as shown in FIG. 2F. In some embodiments, the mutation can alter cytokine production. The cytokine can be, without limitation, IL-2, IL-4, IL-5, TNF alpha, IFN-gamma, IL-13 and/or other cytokines. In some embodiments, the cytokine is IL-2. In some embodiments, the cytokine is IL-2, and the production of IL-2 is increased.

In some embodiments, the polypeptides or recombinant nucleic acid constructs and/or recombinant nucleic acids of the disclosure can alter T cell signaling through one or more T cell signaling pathways. Signaling pathways can be, without limitation, the NFAT pathway, NF-κB pathway, AP-1 pathway, JAK/STAT pathway, RAS/MEK/ERK, and/or phospholipase gamma signaling, or described elsewhere herein.

In some embodiments, the polypeptides or recombinant nucleic acid constructs and/or recombinant nucleic acids of the disclosure can alter CARD11-BCL10-MALT1 complex signaling, co-stimulatory molecule signaling, cytokine production and/or transcription factor activity in T cells.

The disclosure also relates to polypeptides having one or more mutations that can reduce T cell exhaustion, increase proliferation, alter effector function, resist T cell dysfunction, increase T cell fitness, enhance in vivo persistence, and/or increase intratumoral presence of therapeutic T cells. The disclosure further relates to recombinant nucleic acids encoding polypeptides having one or more mutations, that can reduce T cell exhaustion, increase proliferation, alter effector function, resist T cell dysfunction, increase T cell fitness, enhance in vivo persistence, and/or increase intratumoral presence of therapeutic T cells.

T cell fitness can refer to the ability of a T cell to generate an immune response. The ability of a T cell to perform T cell functions such as signaling, cytokine production, survival, and persistence in a tumor, may contribute to the fitness of a T cell. T cell exhaustion may contribute to reducing its fitness.

In some embodiments, polypeptides of the disclosure, or the recombinant nucleic acid constructs and/or recombinant nucleic acids of the disclosure can alter in vivo persistence in tumors of therapeutic T cells including the mutation. The in vivo persistence of therapeutic T cells can refer to the length of time that the therapeutic T cells exist within the tumor of the host after infusion. In some embodiments, in vivo persistence of therapeutic T cells is enhanced. Enhanced in vivo persistence of therapeutic T cells can include at least a positive log 2 fold change in therapeutic T cells as compared to the input total.

In some embodiments, the polypeptides or recombinant nucleic acid constructs and/or recombinant nucleic acids of the disclosure can alter the in vivo persistence in tumors or the other functions or activities of T cells described herein, through one or more of the following genes: BCL6, BCOR, BRAF, CARD11, CARMIL2, CCND3, CD28, CD3E, CSNK1A1, CSNK2B, ECSIT, EIFS1, FYN, GATA, GNAQ, IRF4, ITGB2, JAK1, JAK3, JUNB, KCNQ1, LATS1, MSC, MYCN, NFKB1, NFKB2, NRAS, PDCD1, PLCG1, PRKCB1, RARA, RASGRP1, RHOA, SMARCB1, STAT3, STAT5, TBL1XR1, TNFRSF1B, TP53 and VAV1.

In some embodiments, the genes include caspase recruitment domain family member 11 (CARD11). In some embodiments, the genes include capping protein regulator and myosin 1 linker 2 (CARMIL2), mucosa-associated lymphoid tissue lymphoma translocation protein 1 (MALT1), B-cell lymphoma 6 (BCL6), B-cell lymphoma 10 (BCL10), and MYCN. In some embodiments, the gene can be a STAT3, STAT5B, JAK1, JAK2, or JAK3 gene. In some embodiments, the gene can be BRAF, or RASGRP1. In some embodiments, the gene can be phospholipase C gamma 1 (PLCG1) gene. In some embodiments, the gene can be NFKB1, NFKB2, or JUNB gene. In some embodiments, the gene can be TNFRSF1B.

In some embodiments, the polypeptides of the disclosure, or the recombinant nucleic acid constructs and/or recombinant nucleic acids of the disclosure can alter the therapeutic efficacy of engineered T cells. Alteration of therapeutic efficacy can include, without limitation, a decrease in T cell exhaustion, increased proliferative capacity, enhanced anti-tumor effect, enhanced replicative lifespan, decreased replicative senescence, enhanced ability to kill, enhanced fitness of engineered T cells and/or other functions or activities of T cells. In some embodiments, the nucleic acid constructs and/or recombinant nucleic acids of the disclosure encodes a polypeptide comprising an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188, SEQ ID NO: 190, SEQ ID NO: 192, SEQ ID NO: 194, SEQ ID NO: 196, SEQ ID NO: 198, SEQ ID NO: 200, SEQ ID NO: 202, SEQ ID NO: 204, SEQ ID NO: 206, SEQ ID NO: 208, SEQ ID NO: 210, SEQ ID NO: 212, SEQ ID NO: 214, SEQ ID NO: 216, SEQ ID NO: 218, SEQ ID NO: 220, SEQ ID NO: 222, SEQ ID NO: 224, SEQ ID NO: 226, SEQ ID NO: 228, SEQ ID NO: 230, SEQ ID NO: 232, SEQ ID NO: 234, SEQ ID NO: 236, SEQ ID NO: 238, SEQ ID NO: 240, SEQ ID NO: 242, SEQ ID NO: 244, SEQ ID NO: 246, SEQ ID NO: 248, SEQ ID NO: 250, SEQ ID NO: 252, SEQ ID NO: 254, SEQ ID NO: 256 or a variant thereof wherein the amino acid sequence includes one or more of the mutations listed in Table 1 for the same gene.

In some embodiments, the nucleic acids constructs and/or recombinant nucleic acids of the disclosure include a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 195, SEQ ID NO: 197, SEQ ID NO: 199, SEQ ID NO: 201, SEQ ID NO: 203, SEQ ID NO: 205, SEQ ID NO: 207, SEQ ID NO: 209, SEQ ID NO: 211, SEQ ID NO: 213, SEQ ID NO: 215, SEQ ID NO: 217, SEQ ID NO: 219, SEQ ID NO: 221, SEQ ID NO: 223, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 247, SEQ ID NO: 249, SEQ ID NO: 251, SEQ ID NO: 253, or SEQ ID NO: 255 or a variant thereof wherein the variant includes one or more of the mutations listed in Table 1 for the same gene.

In some embodiments, the polypeptides of the disclosure have, or the nucleic acid constructs and/or recombinant nucleic acids of the disclosure encode a polypeptide sequence having, at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 25 and comprising a substitution at an amino acid position 361, 615, 634, 655, 357 or combinations thereof. In some embodiments, the substitution is Y361C, S615F, E634K, S655C and/or D357N. In some embodiments the nucleic acid constructs and/or recombinant nucleic acids of the disclosure encode a polypeptide a sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 25 and comprising at least one, two or more substitutions at an amino acid position 361, 615, 634, 655, 357. In some embodiments, the nucleic acid constructs and/or recombinant nucleic acids encode a polypeptide having E634K and S655C mutations. In some embodiments, the recombinant nucleic acid construct encodes a substitution selected from the group consisting of: Y361C, S615F, E634K, D357N, S655C, and any combination thereof.

In some embodiments, the disclosure relates to polypeptides, or to recombinant nucleic acids encoding polypeptides, comprising a caspase-associated recruitment domain (CARD) containing protein, or a functional fragment thereof. CARD is a conserved homology domain comprising a 6-helix bundle or 5-helix bundle. CARDs can mediate protein-protein interactions between key apoptotic signaling molecules. Non-limiting examples of CARDS include CARD6, CARD8, CARD9, CARD10, CARD11, CARD14, CARD16, CARD18, and CARD19. Non-limiting examples of proteins comprising CARDs include those described in Boyle and Monie bioRxiv 087908; doi: https://doi.org/10.1101/087908; and/or Park. In *J Mol Med.* 2019 March; 43(3): 1119-1127, such as human caspase-1, -2, -4, and -5, mouse caspase-1, -2, -11, and -12, ASC, NOD1, NOD2, Apaf-1, BCL-10, and RIG-I. In some embodiments, the CARD comprises or consists of a sequence having at least 75%, 80%, 85%, 90%, 95%, 96%, 97%, 98%, 99%, or 100% identity to any one of SEQ ID NO: 261-289. In some embodiments, the CARD containing protein, or functional fragment thereof, is derived from a CARD protein selected from CARD9 (UniProt #Q9H257), CARD10 (UniProt #Q9BWT7) CARD11 (UniProt #Q9BXL7), or CARD14 (UniProt #Q9H257) (Wang et al. J Biol Chem. 2001 Jun. 15; 276(24):21405-9; Bertin et al. J Biol Chem. 2001 Apr. 13; 276(15):11877-82). In some embodiments, the CARD containing protein, or functional fragment thereof, is derived from a CARD11 protein (UniProt #Q9BXL7), or a functional fragment thereof. In some embodiments, the CARD containing protein comprises or consists of a sequence having at least 75%, 80%, 85%, 90%, 95%, 96%, 97%, 98%, 99%, or 100% identity to any one of SEQ ID NOs: 261-264. In some embodiments, the functional fragment of the CARD containing protein is derived from CARD11 and comprises or consists of a sequence having at least 75%, 80%, 85%, 90%, 95%, 96%, 97%, 98%, 99%, or 100% identity to SEQ ID NO: 263.

In some embodiments, the function of the CARD containing protein or the functional fragment thereof is to bind to a CARD domain on BCL10 (Bertin et al. J. Biol Chem. 201 Apr; 276(15): 11877-11882). In some embodiments, the functional fragment thereof comprises at least 40, at least 50, at least 60, at least 70, at least 80, at least 90, at least 100, at least 150, at least 200, at least 300, at least 400, or at least 500 amino acids. Non-limiting examples of a cell include a T cell, a macrophage, a monocyte, and a natural killer (NK) cell. In some embodiments, activation of the cell produces the substrate localized to the intracellular side of the plasma membrane. In some embodiments, the substrate localized to the intracellular side of the plasma membrane of a cell is a phosphoinositide. Non-limiting examples of phosphoinosities include those described in Posor et al. Nat Rev Mol Cell Biol. 2022 December; 23(12):797-816. In some embodiments, the phosphoinositide is selected from phosphatidylinositol (3,4,5)-trisphosphate (PIP3), phosphatidylinositol 4,5-bisphosphate (PI(4,5)P2) (Hawse and Cattley J. Bio. Chem. 2019 March; 294(13):4793-4805; Sun et al. PLOS ONE. 2011 November; 6(11): e27227). In some embodiments, the polypeptide binds to the phosphoinositide with a Kd of less than 100 μM, 50 μM, 10 μM, 5 μM, 1 μM, 0.5 μM, 0.1 μM, 0.05 μM, or 0.01 μM, and wherein the Kd is analyzed using SPR as described in Yu et al. *Molecular Cell.* 2004 March; 13(5): p 677-688.

The disclosure further relates to polypeptides comprising a domain capable of binding to (i) a substrate localized to the intracellular side of the plasma membrane of a cell and/or (ii) a target polypeptide comprising a phosphorylated tyrosine (pTyr). In some embodiments, the domain is capable of binding to a substrate indirectly localized to the intracellular side of the plasma membrane. Indirect localization can refer to localization of the substrate to the intracellular side of the plasma membrane through, for example, binding of the substrate to another polypeptide or lipid that is directly localized to the intracellular side of the plasma membrane. Indirect localization can refer to localization of the substrate to the intracellular side of the plasma membrane through, for example, interaction of the substrate with another polypeptide or lipid that is directly localized to the intracellular side of the plasma membrane. In some embodiments, the domain is capable of binding to a substrate directly localized to the intracellular side of the plasma membrane. Direct localization can refer to localization of the substrate to the intracellular side of the plasma membrane through, for example, binding of the substrate to the intracellular side of the plasma membrane itself. Direct localization can refer to localization of the substrate to the intracellular side of the plasma membrane through, for example, interaction of the substrate with the intracellular side of the plasma membrane itself.

Non-limiting examples of domains capable of binding to (i) and/or (ii) include Src Homology region 2 (SH2) domains, Src Homology region 3 (SH3) domains, pleckstrin homology (PH) domains, and phosphytyrosine-binding (PTB) domains. SH2 and PTB domains mediate protein-protein interactions involved in many signal transduction pathways. SH2, SH3, and PTB domains that can be used in the disclosure include, for example, those disclosed in Schlessinger et al. *Sci STKE.* 2003 Jul. 15; 2003(191):RE12. SH2 containing proteins can bind to plasma membrane lipids through a different binding pocket than the pTyr binding pocket; most SH2 domains bind plasma membrane lipids and many have high phosphoinositide specificity (Park et al., Cell. 2016 Apr. 7; 62(1):7-20). In some embodiments, the domain is, or comprises, an SH3 domain. In some embodiments, the domain is, or comprises, a PTB domain. In some embodiments, the domain is, or comprises, a PH domain. In some embodiments, the domain is, or comprises, an SH2 domain. In some embodiments, the SH2 domain comprises or consists of a sequence having at least 75%, 80%, 85%, 90%, 95%, 96%, 97%, 98%, 99%, or 100% identity to any one of SEQ ID NOs: 305 and 307-437. In some embodiments, the SH2 domain is from a PIK3R3 protein (UniProt #Q92569). In some embodiments, the SH2 domain comprises the motif of a conserved arginine residue in the FLVR motif (Arg βB5 or Arg175 in the v-Src SH2 domain). Most conserved resides are clustered on the βB strand, and the conserved arginine residue in the FLVR motif plays the central role in forming a double hydrogen bond with the phosphate group of pTyr. Additional residues that are key for phosphopeptide binding are His βD4, Lys βD6, and Arg αA2, which coordinate and anchor the aromatic ring of the phosphotyrosine (Diop et al. Int J Mol Sci. 2022 Dec. 15; 23(24): 15944). In some embodiments, the SH2 domain comprises or consists of a sequence having at least 75%, 80%, 85%, 90%, 95%, 96%, 97%, 98%, 99%, or 100% identity to SEQ ID NO: 305In some embodiments, the SH2 domain is an engineered SH2 domain with an enhanced affinity for phosphotyrosine. In some embodiments, the SH2 domain comprises or consists of a sequence having at least 75%, 80%, 85%, 90%, 95%, 96%, 97%, 98%, 99%, or 100% identity to any one of SEQ ID NO: 313-315 (e.g., Veggiani et al. Protein Sci. 2019 February; 28(2):403-413).

Non-limiting examples of target polypeptides comprising a pTyr include P110α/PIK3CA, P110β/PIK3CB, P110δ/PIK3CD, IGF-IR, ErbB2, CTLA-4, and CD28. In some embodiments, the target polypeptide is derived from IGF-IR, CTLA-4, or CD28. In some embodiments, the target polypeptide comprises or consists of a sequence having at least 75%, 80%, 85%, 90%, 95%, 96%, 97%, 98%, 99%, or 100% identity to any one of SEQ ID NOS: 298-304. In some embodiments, the pTyr is located at the position corresponding to pY1346 of SEQ ID NO: 301. In some embodiments, the pTyr is located at the position corresponding to pY1221 of SEQ ID NO: 302. In some embodiments, the polypeptide binds to the target polypeptide with a Kd of less than 100 μM, 50 μM, 10 μM, 5 μM, 1 μM, 0.5 μM, 0.1 μM, 0.05 μM, or 0.01 μM, wherein the Kd is analyzed by fluorescence polarization assay as described in Hause et al. PLOS One. 2012; 7(9):e44471. In some embodiments, the polypeptide has a higher affinity for the target polypeptide comprising the pTyr than a control polypeptide without phosphorylation at the corresponding tyrosine position. In some embodiments, the polypeptide has at least 2-fold, at least 5-fold, at least 10-fold, at least 50-fold, or at least 100-fold, higher affinity (lower Kd) for the target polypeptide comprising the phosphorylated tyrosine than a control polypeptide without phosphorylation at the corresponding tyrosine position.

Furthermore, the disclosure relates to polypeptides comprising a CARD containing protein or a functional fragment thereof, and a domain capable of binding to (i) a substrate localized to the intracellular side of the plasma membrane of a cell and/or (ii) a target polypeptide comprising a phosphorylated tyrosine (also called a CARD fusion polypeptide), as disclosed herein. In some embodiments, the polypeptide comprises a CARD containing protein, or a functional fragment thereof, and an SH2 domain (also called a CARD-SH2 fusion polypeptide). In some embodiments, the disclosure relates to a polypeptide comprising a functional fragment of a CARD containing protein derived from a CARD11 protein and an SH2 domain from a PIK3R3 protein (also called a CARD11-PIK3R3 fusion polypeptide).

Furthermore, the disclosure relates to recombinant nucleic acids encoding polypeptides comprising a CARD containing protein or a functional fragment thereof and a domain capable of binding to (i) a substrate localized to the intracellular side of the plasma membrane of a cell and/or (ii) a target polypeptide comprising a phosphorylated tyrosine, as disclosed herein. In some embodiments, the recombinant nucleic acid encodes a polypeptide comprising a CARD containing protein or a functional fragment thereof and an SH2 domain. In some embodiments, the recombinant nucleic acid encodes a functional fragment of a CARD containing protein derived from a CARD11 protein and an SH2 domain from a PIK3R3 protein. In some embodiments, the recombinant nucleic acid encodes a functional fragment of a CARD containing protein derived from a CARD9 protein and an SH2 domain from a PIK3R3 protein.

In some embodiments, the polypeptide is a CARD11-PIK3R3 fusion polypeptide. In some embodiments, the recombinant nucleic acid constructs and/or recombinant nucleic acids encode a CARD11-PIK3R3 fusion polypeptide or any truncations thereof. In some embodiments, the polypeptide includes, or the nucleic acid constructs and/or recombinant nucleic acid encodes a CARD11-PIK3R3 fusion polypeptide or truncations thereof, including an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOS: 206, SEQ ID NOS: 226, SEQ ID NOS: 228, SEQ ID NOS: 230, SEQ ID NOS: 232, SEQ ID NOS: 234, SEQ ID NOS: 236, SEQ ID NOS: 238, SEQ ID NOS: 240, SEQ ID NOS: 242, SEQ ID NOS: 244, SEQ ID NOS: 248, SEQ ID NOS: 250, SEQ ID NOS: 252, SEQ ID NOS: 254, or SEQ ID NO:256. In some embodiments, the truncations are encoded by a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 205, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 246, SEQ ID NO: 247, SEQ ID NO: 249, SEQ ID NO: 251, SEQ ID NO: 253, or SEQ ID NO: 255.

The disclosure further relates to a second polypeptide portion derived from PIK3R3. Non-limiting examples of polypeptides derived from PIK3R3 include either of two SH2 domains, a catalytic subunit, and a regulatory subunit. In some embodiments, the second polypeptide portion comprises or consists of a sequence having at least 75%, 80%, 85%, 90%, 95%, 96%, 97%, 98%, 99%, or 100% identity to any one of SEQ ID NO: 205, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 246, SEQ ID NO: 247, SEQ ID NO: 249, SEQ ID NO: 251, SEQ ID NO: 253, and SEQ ID NO: 255. In some embodiments, the polypeptide does not comprise a Coiled-coil domain or a portion thereof. In some embodiments, the polypeptide comprises a Coiled-coil domain or a portion thereof. In some embodiments, the Coiled-coil domain comprises or consists of a sequence having at least 75%, 80%, 85%, 90%, 95%, 96%, 97%, 98%, 99%, or 100% identity to any one of SEQ ID NOs: 290-294. In some embodiments, the Coiled-coil domain comprises or consists of a sequence having at least 75%, 80%, 85%, 90%, 95%, 96%, 97%, 98%, 99%, or 100% identity to SEQ ID NO: 290. In some embodiments, the polypeptide comprises or consists of about 10, about 20, about 30, about 40, about 50, about 60, about 80, about 100, about 120, about 140, about 150, about 160, about 180, about 200, about 220, about 240, about 250, about 260, about 280, or about 300 amino acids of the N-terminal portion of the Coiled-coil domain. In some embodiments, the polypeptide comprises no more than 10, 20, 30, 40, 50, 60, 80, 100, 120, 140, 150, 160, 180, 200, 220, 240, 250, 260, 280, or 300 amino acids of the N-terminal portion of the Coiled-coil domain.

The present disclosure further relates to polypeptides wherein the domain capable of binding to the target polypeptide comprising the phosphorylated tyrosine, or the SH2 domain, or the second polypeptide portion, is located at the N-terminus of the CARD containing protein or functional fragment thereof, between the CARD containing protein and the Coiled-coil domain, or at the C-terminus of the CARD containing protein and/or the Coiled-coil domain. In some embodiments, the polypeptide comprises the CARD domain derived from a CARD11 protein followed by the Coiled-coil domain derived from the CARD11 protein. The present disclosure further relates to polypeptides wherein the domain capable of binding to the target polypeptide comprising the phosphorylated tyrosine, or the SH2 domain, or the second polypeptide portion, is located close to the C-terminus of the polypeptide, wherein the polypeptide has no more than 50, 40, 30, 20, 15, 10, or 5 amino acids at the C-terminus of the domain in (b), or the SH2 domain, or the second polypeptide portion.

In some embodiments, the polypeptide does not comprise an inhibitory domain (ID) or a portion thereof. In other embodiments, the polypeptide comprises an ID or a portion thereof. In some embodiments, the ID comprises or consists of a sequence having at least 75%, 80%, 85%, 90%, 95%, 96%, 97%, 98%, 99%, or 100% identity to SEQ ID NO: 294. In some embodiments, the inhibitory domain (ID) comprises or consists of a sequence having at least 75%, 80%, 85%, 90%, 95%, 96%, 97%, 98%, 99%, or 100% identity to SEQ ID NO: 295. In some embodiments, the polypeptide comprises or consists of about 10, about 20, about 30, about 40, about 50, about 60, about 80, about 100, about 120, about 140, about 150, about 160, about 180, or about 200 amino acids of the N-terminal portion of the ID. In some embodiments, the second polypeptide portion comprises no more than 10, 20, 30, 40, 50, 60, 80, 100, 120, 140, 150, 160, 180, or 200 amino acids of the N-terminal portion of the ID. In some embodiments, the polypeptide does not comprise a sequence that is at least 90%, 95%, 96%, 97%, 98%, 99%, or 100% identical to SEQ ID NO: 297. In some embodiments, the polypeptide comprises one or more mutations corresponding to S615F, D357N, Y361C, E634K, and/or S655C of SEQ ID NO: 26.

In some embodiments, the CARD11-PIK3R3 fusion polypeptide includes a CARD domain (i.e., containing protein or functional fragment thereof), a CARD inhibitory domain (ID), a coiled-coil domain, and an SH2 domain from PIK3R3. In some embodiments, the CARD11-PIK3R3 fusion polypeptide includes a functional fragment of a CARD containing protein derived from CARD11 domain, a coiled-coil domain, and an SH2 domain from PIK3R3.

In some embodiments, the recombinant nucleic acid constructs and/or recombinant nucleic acids of the disclosure, includes a CARD11-PIK3R3 fusion polypeptide encoded by a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 205, SEQ ID NO: 225, SEQ ID NO: 227, SEQ ID NO: 229, SEQ ID NO: 231, SEQ ID NO: 233, SEQ ID NO: 235, SEQ ID NO: 237, SEQ ID NO: 239, SEQ ID NO: 241, SEQ ID NO: 243, SEQ ID NO: 245, SEQ ID NO: 246, SEQ ID NO: 247, SEQ ID NO: 249, SEQ ID NO: 251, SEQ ID NO: 253, SEQ ID NO: 255, or SEQ ID NO: 296.

In some embodiments, the polypeptide of the disclosure has, or the recombinant nucleic acid constructs and/or recombinant nucleic acids of the disclosure encodes, a polypeptide comprising a BCL3 polypeptide having a substitution at amino acid 647. In some embodiments of the recombinant nucleic acid constructs and/or recombinant nucleic acids of the disclosure, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4 and including a substitution at amino acid 647. In some embodiments, the substitution at amino acid 647 of SEQ ID NO: 4 is S647R.

In some embodiments, the polypeptide of the disclosure has, or the recombinant nucleic acid constructs and/or recombinant nucleic acids of the disclosure encodes, a polypeptide comprising a CARMIL2 polypeptide having a substitution at amino acid 575. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 28 and including a substitution at amino acid 575. In some embodiments, the substitution at amino acid 575 of SEQ ID NO: 28 is Q575E.

In some embodiments, the polypeptide of the disclosure has, or the recombinant nucleic acid constructs and/or recombinant nucleic acids of the disclosure encodes a polypeptide comprising a MYCN polypeptide having a substitution at amino acid 44. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 114 and including a substitution at amino acid 44. In some embodiments, the substitution at amino acid 44 of SEQ ID NO: 114 is P44L.

In some embodiments, the polypeptide is encoded by a nucleic acid sequence comprising at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:1. SEQ ID NO: 111 or SEQ ID 129. In some embodiments, the polypeptide includes a mutation capable of (i) altering JAK/STAT signaling in T cells (ii) altering cytokine production, and/or (iii) enhancing in vivo persistence of therapeutic T cells comprising the mutation in tumors. In some embodiments the mutation is in a JAK1, JAK3 STAT3, or STAT5 gene. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to (i) SEQ ID NO: 90 and comprising a substitution at amino acid position 1097 of SEQ ID NO: 90, (ii) SEQ ID NO: 94 and comprising a substitution at an amino acid position 573 of SEQ ID NO: 94, (iii) SEQ ID NO: 176 and comprising a substitution at an amino acid position 618, 647, or 661 of SEQ ID NO: 176 or a combination thereof, (iv) SEQ ID NO: 182 and comprising a substitution at an amino acid position 628, or at amino acid position 665 of SEQ ID NO: 182 or a combination thereof.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:87 wherein the nucleic acid sequence encodes a JAK1 polypeptide with a G1097A substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 91 wherein the nucleic acid encodes a JAK3 polypeptide with an A573V substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:169 and encoding a STAT3 polypeptide having an N6471 substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 171 and encoding a STAT3 polypeptide having a G618R substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 173 and encoding a STAT3 polypeptide having a D661I substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 177 and encoding a STAT5 polypeptide with a T628S substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 179 and encoding a STAT5 polypeptide with a Y665F substitution.

In some embodiments of the recombinant nucleic acid constructs and/or recombinant nucleic acids of the disclosure, the polypeptide includes a mutation capable of altering co-stimulatory molecule signaling in T cells and persistence in tumors of T cells including the mutation. In some embodiments, the mutation is in a TNFR2, TNFRS1B, CD28, ICOS, CTLA4 gene, or a combination thereof.

In some embodiments of the recombinant nucleic acid constructs and/or recombinant nucleic acids of the disclosure, the nucleic acid encodes a polypeptide comprising a TNFRSF1B polypeptide having a substitution at amino acid 256 and/or 377. In some embodiments of the recombinant nucleic acid constructs and/or recombinant nucleic acids of the disclosure, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 192 and comprising a substitution at an amino acid position 256 and/or at position 377 of SEQ ID NO: 192 or a combination thereof.

In some embodiments of the recombinant nucleic acid constructs and/or recombinant nucleic acids of the disclosure, the nucleic acid encodes a polypeptide comprising a TNFRSF1B polypeptide having a substitution at amino acid 337. In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 187 and encoding a TNFRSF1B polypeptide with a T337I substitution.

In some embodiments of the recombinant nucleic acid constructs and/or recombinant nucleic acids of the disclosure, the nucleic acid encodes a polypeptide comprising a TNFRSF1B polypeptide having a substitution at amino acid 256. In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 189 and encoding a TNFRSF1B polypeptide with a G256C substitution.

In some embodiments of the recombinant nucleic acid constructs and/or recombinant nucleic acids of the disclosure, the nucleic acid encodes a polypeptide comprising a CD28 polypeptide having a substitution at amino acid 51 and/or 77. In some embodiments of the recombinant nucleic acid constructs and/or recombinant nucleic acids of the disclosure, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 42 and encoding a CD28 polypeptide including a substitution at an amino acid position 51 and/or 77 of SEQ ID NO: 42 or a combination thereof.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 35 and encoding a CD28 polypeptide with a F51V substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 37 and encoding a CD28 polypeptide with a F51I substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 39 and encoding a CD28 polypeptide with a Q77P substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:43 and encoding a CD28 polypeptide with a T195P substitution.

In some embodiments of the recombinant nucleic acid constructs and/or recombinant nucleic acids of the disclosure, the nucleic acid encodes a polypeptide comprising an ICOS-CD28 polypeptide. In some embodiments of the recombinant nucleic acid constructs and/or recombinant nucleic acids of the disclosure, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 220.

In some embodiments of the recombinant nucleic acid construct of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:219.

In some embodiments of the recombinant nucleic acid constructs and/or recombinant nucleic acids of the disclosure, the nucleic acid encodes a polypeptide comprising a CD28-CTLA4 polypeptide. In some embodiments of the recombinant nucleic acid constructs and/or recombinant nucleic acids of the disclosure, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 218.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:217

In some embodiments of the recombinant nucleic acid constructs and/or recombinant nucleic acids of the disclosure, the polypeptide includes a mutation capable of altering RAS/MEK/ERK signaling in T cells and in vivo persistence in tumors of therapeutic T cells including the mutation. In some embodiments, the mutation is in a BRAF gene. In some embodiments, the polypeptide includes an amino acid sequence having at least about 75%, 80%, 85%, 90%, 95%, 96%, 97%, 98%, 99% or 100% sequence identity to SEQ ID NO: 16, and including an amino acid substitution at amino acid position 469 or 594 or a combination thereof. In some embodiments, the amino acid substitution is G469R. In some embodiments, the amino acid substitution is G469A. In some embodiments, the substitution is D594N.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 9 and encoding a BRAF polypeptide with a G469R substitution. In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:11 and encodes a BRAF polypeptide with a G469A substitution.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 13 and encodes a BRAF polypeptide with a D594N substitution.

In some embodiments n some embodiments of the recombinant nucleic acid constructs and/or recombinant nucleic acids of the disclosure, the polypeptide includes a mutation capable of altering RAS/MEK/ERK signaling in T cells and in vivo persistence in tumors of therapeutic T cells including the mutation. In some embodiments, the mutation is in a RASGRP1 gene. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 158 and including a substitution at amino acid position 261.

In some embodiments of the recombinant nucleic acid constructs and/or recombinant nucleic acids of the disclosure, the nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 157 and encoding a RASGRP1 polypeptide with a M261I substitution.

In some embodiments of the recombinant nucleic acid constructs and/or recombinant nucleic acids of the disclosure, the polypeptide includes a mutation capable of altering phospholipase gamma signaling and/or (ii) cytokine production, and/or (iii) in vivo persistence in tumors of therapeutic T cells comprising the mutation. In some embodiments, the mutation is in a Phospholipase C gamma 1 (PLCG1) gene. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 142 and including a substitution at amino acid position 47, 48, 520, 1163, 1165 or any combination thereof. In some embodiments, the substitution is E47K. In some embodiments, the substitution is R48W. In some embodiments, the substitution is S520F. In some embodiments, the substitution is E1163K. In some embodiments, the substitution is D1165H.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 133 and encodes a PLCG1 polypeptide having a E47K substitution.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 135 and encodes a PLCG1 polypeptide with a S520F substitution.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to, SEQ ID NO: 137 and encodes a PLCG1 polypeptide with a substitution E1163K.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:139 and encodes a PLCG1 polypeptide with a D1165H substitution.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 143 and encodes a PLCG1 polypeptide with a R48W substitution.

In some embodiments of the recombinant nucleic acid constructs and/or recombinant nucleic acids of the disclosure, the polypeptide includes a mutation capable of altering a transcription factor activity in T cells including the mutation. In some embodiments, the mutation is in a NFKB1, NFKB2 or JUNB gene.

In some embodiments of the recombinant nucleic acid constructs and/or recombinant nucleic acids of the disclosure, the nucleic acid encodes a polypeptide comprising an NFKB1 polypeptide having a substitution at amino acid 67. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 118 and including a substitution at amino acid 67 of SEQ ID NO:118. In some embodiments, the substitution is H67Y.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 115 and encodes a NFKB1 polypeptide with a H67Y substitution.

In some embodiments of the recombinant nucleic acid constructs and/or recombinant nucleic acids of the disclosure, the nucleic acid encodes a polypeptide comprising an NFKB2 polypeptide having a substitution at amino acid 656. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 122 and including a substitution at amino acid 656 of SEQ ID NO:122. In some embodiments, the substitution is K656X.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 119 and encodes a NFKB2 polypeptide with a K656X mutation.

In some embodiments of the recombinant nucleic acid constructs and/or recombinant nucleic acids of the disclosure, the nucleic acid encodes a polypeptide comprising a JUNB polypeptide having a substitution at amino acid 282. In some embodiments, the polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 98 and including a substitution at amino acid 282 of SEQ ID NO:98. In some embodiments, the substitution is A282V.

In some embodiments, the recombinant nucleic acid construct includes a nucleic acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 95 and encodes a JUNB polypeptide with a A282V substitution.

In some embodiments, the polypeptide includes a first polypeptide encoding a partial CARD 11 polypeptide and a second polypeptide encoding a partial PIK3R3 polypeptide. In some embodiments, the first polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 258. In some embodiments, the first polypeptide includes an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 260.

In some embodiments, the recombinant nucleic acid constructs and/or recombinant nucleic acids of the disclosure includes a promoter. The promoter can be any promoter. The promoter can be a T cell promoter, or an inducible promoter. The promoter can be active in a subset of T cells.

In some embodiments, the promoter can be a constitutive promoter. Examples of constitutive promoters include but are not limited to a MND promoter, EF1a promoter, sEF1 promoter, gamma retroviral LTR promoter, CD4 promoter, CD8a promoter, CD8b promoter, TCRa promoter, TCRb promoter, CD3d promoter, CD3g promoter, CD3e promoter, or a CD32 promoter. In some embodiments, the promoter is a minimal TATA promoter, a pGK, actin promoter, CD25 promoter, IL2 promoter, IL7 promoter, IL15 promoter, KLRG-1 promoter, HLA-DR promoter, CD38 promoter, CD69 promoter, Ki-67 promoter, CD11a promoter, CD58 promoter, CD99 promoter, CD62L promoter, CD103 promoter, CCR4 promoter, CCR5 promoter, CCR6 promoter, CCR9 promoter, CCR10 promoter, CXCR3 promoter, CXCR4 promoter, CLA promoter, Granzyme A promoter, Granzyme B promoter, Perforin promoter, CD57 promoter, CD161 promoter, IL-18Ra promoter, CD69 promoter, GzmB promoter, T-bet promoter, IFNgamma promoter, TIM3 promoter, IL4 promoter, GATA3 promoter, IL1 promoter, IL5 promoter, IL6 promoter, IL13 promoter, IL10 promoter, IL17A promoter, IL6 promoter, IL21 promoter, IL23R promoter, FoxP3 promoter, CTLA4 promoter, CD25 promoter, PD1 promoter, CD45RO promoter, CCR7 promoter, CD28 promoter, CD95 promoter, CD28 promoter, CD27 promoter, CD127 promoter, PD-1 promoter, CD122 promoter, CD132 promoter, c-Kit promoter, nuclear factor of activated T cells (NFAT) promoter, programmed death 1 (PD-1) promoter, T cell immunoglobulin mucin-3 (TIM-3) promoter, cytotoxic T lymphocyte antigen-4 (CTLA4) promoter, lymphocyte-activation protein 3 (LAG-3) promoter, tumor necrosis factor (TNF)-related apoptosis-inducing ligand (TRAIL) promoter, B- and T-lymphocyte attenuator (BTLA) promoter, CD25 promoter, CD69 promoter, Fas ligand (FasL) promoter, TIGIT promoter, TGF-beta promoter, T-bet promoter, Eomes promoter, GATA3 promoter, CD45RA promoter, 2B4 promoter, Type I interferon (IFN) alpha, Type I IFN beta promoter, IFN gamma promoter, IRF3 promoter, IRF7 promoter, NF-κB promoter, AP-1 promoter, TNF-alpha promoter, and CD130 promoter, NR4A1 promoter, NR4A2, or NR4A3 promoter.

The disclosure also provides vectors including the recombinant nucleic acid constructs and/or recombinant nucleic acids of the disclosure.

The nucleic acid molecules can be contained within a vector that is capable of directing their expression in, for example, a cell that has been transformed/transduced with the vector. Suitable vectors for use in eukaryotic and prokaryotic cells are known in the art and are commercially available, or readily prepared by a skilled artisan. See for example, Sambrook, J., & Russell, D. W. (2012). Molecular Cloning: A Laboratory Manual (4th ed.). Cold Spring Harbor, NY: Cold Spring Harbor Laboratory and Sambrook, J., & Russel, D. W. (2001). Molecular Cloning: A Laboratory Manual (3rd ed.). Cold Spring Harbor, NY: Cold Spring Harbor Laboratory (jointly referred to herein as "Sambrook"); Ausubel, F. M. (1987). Current Protocols in Molecular Biology. New York, NY: Wiley (including supplements through 2014); Bollag, D. M. et al. (1996). Protein Methods. New York, NY: Wiley-Liss; Huang, L. et al. (2005). Nonviral Vectors for Gene Therapy. San Diego: Academic Press; Kaplitt, M. G. et al. (1995). Viral Vectors: Gene Therapy and Neuroscience Applications. San Diego, CA: Academic Press; Lefkovits, I. (1997). The Immunology Methods Manual: The Comprehensive Sourcebook of Techniques. San Diego, CA: Academic Press; Doyle, A. et al. (1998). Cell and Tissue Culture: Laboratory Procedures in Biotechnology. New York, NY: Wiley; Mullis, K. B., Ferré, F. & Gibbs, R. (1994). PCR: The Polymerase Chain Reaction. Boston: Birkhauser Publisher; Greenfield, E. A. (2014). Antibodies: A Laboratory Manual (2nd ed.). New York, NY: Cold Spring Harbor Laboratory Press; Beaucage, S. L. et al. (2000). Current Protocols in Nucleic Acid Chemistry. New York, NY: Wiley, (including supplements through 2014); and Makrides, S. C. (2003). Gene Transfer and Expression in Mammalian Cells. Amsterdam, NL: Elsevier Sciences B.V., the disclosures of which are incorporated herein by reference).

DNA vectors can be introduced into eukaryotic cells via conventional transformation or transfection techniques. Suitable methods for transforming or transfecting host cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

In some embodiments, the expression vector can be a viral vector.

Host Cells

The nucleic acid of the present disclosure can be introduced into a host cell, such as, for example, a human T lymphocyte, to produce a recombinant or engineered cell containing the nucleic acid molecule. Accordingly, some embodiments of the disclosure relate to methods for making a recombinant or engineered cell, including (a) providing a cell capable of protein expression and (b) contacting the provided cell with a recombinant nucleic acid of the disclosure.

Introduction of the nucleic acid molecules of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Accordingly, in some embodiments, the nucleic acid molecules can be delivered by viral or non-viral delivery vehicles known in the art. For example, the nucleic acid molecule can be stably integrated in the host genome, or can be episomally replicating, or present in the recombinant host cell as a mini-circle expression vector for transient expression. Accordingly, in some embodiments, the nucleic acid molecule is maintained and replicated in the recombinant host cell as an episomal unit. In some embodiments, the nucleic acid molecule is stably integrated into the genome of the recombinant cell. Stable integration can be achieved using classical random genomic recombination techniques or with more precise techniques such as guide RNA-directed CRISPR/Cas9 genome editing, or DNA-guided endonuclease genome editing with NgAgo (Natronobacterium gregoryi Argonaute), or TALENs genome editing (transcription activator-like effector nucleases). In some embodiments, the nucleic acid molecule is present in the recombinant host cell as a mini-circle expression vector for transient expression.

The nucleic acid molecules can be encapsulated in a viral capsid or a lipid nanoparticle, or can be delivered by viral or non-viral delivery means and methods known in the art, such as electroporation. For example, introduction of nucleic acids into cells may be achieved by viral transduction. In a non-limiting example, adeno-associated virus (AAV) is engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral-derived vector systems are also useful for nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

In some embodiments, host cells can be genetically engineered (e.g., transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the polypeptides of interest. Host cells can be either untransformed cells or cells that have already been transfected with at least one nucleic acid molecule.

Certain aspects of the disclosure relate to cells comprising the constructs and or/recombinant nucleic acid or the vectors of the disclosure. In some embodiments, the recombinant cell is a prokaryotic cell or a eukaryotic cell. In some embodiments, the cell is in vivo. In some embodiments, the cell is ex vivo. In some embodiments, the cell is in vitro. In some embodiments, the recombinant cell is a eukaryotic cell. In some embodiments, the recombinant cell is an animal cell. In some embodiments, the animal cell is a mammalian cell. In some embodiments, the animal cell is a human cell. In some embodiments, the cell is a non-human primate cell. In some embodiments, the cell is a non-natural cell or has been genetically engineered. In some embodiments, the cell is not a cancerous cell. In some embodiments, the recombinant nucleic acid is exogenous. In some embodiments, the mammalian cell is an immune cell, a neuron, an epithelial cell, and endothelial cell, or a stem cell. In some embodiments, the cell is not a CD4+ T cell. In some embodiments, the cell can be an immune cell, a T cell, a CD4+ cell, a CD8+ cell, a regulatory T cell, a gamma delta T cell, an invariant iNKT cell, a MAIT cell, a macrophage, a monocyte, a natural killer cell (NK), or a tumor infiltrating lymphocyte (TIL). In some embodiments, the cell comprises at least one copy, or at least two copies, of endogenous nucleic acid sequence encoding a CARD11 protein, or a protein comprising a CARD11 CARD domain without any SH2 domain. In some embodiments, the recombinant nucleic acid of the cell is located at the endogenous CARD11-encoding gene locus, or comprises at least a portion of the endogenous CARD11-encoding gene, of the cell.

The T cells of the disclosure or precursors thereof can be immune cells of the lymphoid lineage. In some embodiments, the T cell expresses an engineered immune receptor that binds to a target on a tumor cell. In some embodiments, the T cell can express a T cell receptor (TCR). A TCR as known by the skilled in the art can be composed of two different, an alpha chain and a beta chain, each consisting of a constant region that anchors the chain inside the T cell surface membrane, and a variable region which can recognize and bind an antigen presented by MHCs. The TCR complex can be associated with six polypeptides forming two heterodimers, CD3γε and CD3δε, and one homodimer, CD3ζ, which together forms the CD3 complex. TCRs can be engineered to utilize the modification of T cells that retain these complexes to specifically target the antigens expressed by particular tumor cells. As used herein, a TCR can be a naturally-occurring or an engineered TCR.

In some embodiments, the T cells can be CD4+ or CD8+ and can include, but are not limited to, regulatory T cells, cytotoxic T lymphocytes, T helper cells, and memory T cells, including central memory T cells (TCM), stem memory T cells (TSCM), stem-cell-like memory T cells (or stem-like memory T cells), and effector memory T cells such as, for example, TEM cells and TEMRA (CD45RA+) cells, effector T cells, Th1 cells, Th2 cells, Th9 cells, Th17 cells, Th22 cells, Tfh (follicular helper) cells, T regulatory cells, natural killer T cells, mucosal associated invariant T cells (MAIT), and γδ T cells. Major T cell subtypes include TSCM (stem cell memory), TCM (central memory), TTM (Transitional Memory), TEM (Effector memory), TTE (Terminal Effector) and TN (naive).

In some embodiments, the T cells of the disclosure, or precursors thereof, can be cells that mediate an immune response, i.e. immunostimulatory cells. Immunostimulatory T cells include, but are not limited to, T helper cells (CD4+), cytotoxic T cells and memory T cells, including central memory T cells (TCM), stem memory T cells (TSCM), stem-cell-like memory T cells (or stem-like memory T cells), and effector memory T cells, for example, TEM cells and TEMRA (CD45RA+) cells, effector T cells, Th1 cells, Th2 cells, Th9 cells, Th17 cells, Th22 cells, Tfh (follicular helper) cells, natural killer T cells, mucosal associated invariant T cells (MAIT), and γδ T cells.

In some embodiments, the T cells of the disclosure can be immunoinhibitory cells, i.e., cells that inhibit an immune response. Immunoinhibitory T cells include regulatory T cells (T regulatory cells, Treg) and follicular regulatory T cells (Tfh) cells.

In some embodiments, the T cells of the disclosure can be hematopoietic stem and/or progenitor cells of the lymphoid lineage that can differentiate into T cells. Hematopoietic stem and/or progenitor cells can be derived from bone marrow, umbilical cord blood, and adult peripheral blood.

In some aspects, the cell further includes (i) a chimeric antigen receptor (CAR) having specificity for a target antigen; and/or (ii) a T cell receptor (TCR) having specificity for a target antigen.

In some embodiments, the T cells of the disclosure can be engineered to express a transgene, such as a CAR or a transcriptional regulator. Transcriptional regulators include synthetic receptors such as the synthetic notch receptors described in U.S. Pat. No. 11,202,801 or other synthetic receptors, such as, for example, those described in provisional application nos: 62/905,251, 63/15,428, 62/905,268, 62/905,263, 62/935,024 and 62/905,248, which are herein incorporated by reference in their entirety.

The T cells can be genetically engineered for recombinant expression of a transgene. Such T cells can but need not express a CAR or a transcriptional receptor that binds to a target antigen, since the cells already are target antigen-specific so that their immune response (for example, cytotoxicity) is stimulated specifically by such target antigen. Such T cells that recognize and are sensitized to a target antigen can be obtained by known methods, by way of example, in vitro sensitization methods using naive T cells or hematopoietic progenitor cells (described, for example, by Wolfl et al., Nat. Protocols 9:950-966 (2014), or by van Lent et al., J Immunol. 179:4959-4968 (2007)), or obtained from a subject that has been exposed to and is mounting an immune response against the target antigen (i.e., in vivo sensitized T cells).

In some aspects, the cell, e.g., T cell, NK cell, and/or TIL, comprises a CAR. In some aspects, the cell that can be prepared to express a CAR (e.g., a CAR T cell) is, e.g., a CD8+ T cell or CD4+ T cell. In some aspects, a CAR-expressing cell disclosed herein is a CAR T cell, e.g., a mono CAR T cell, a genome-edited CAR T cell, a dual CAR T cell, or a tandem CAR T cell.

In some embodiments, the target antigen can be cell surface receptors, adhesion proteins, integrins, mucins, lectins, tumor-associated antigens, and tumor-specific antigens.

In some embodiments, the target antigen can be a tumor-associated antigen. Non-limiting exemplary tumor-associated antigens suitable for the compositions and methods of the disclosure include CD19, B7H3 (CD276), BCMA (CD269), ALPPL2, Claudin 18.2, CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, DLL-3, EGFR, EGFRvIII, ELF2M, EpCAM, EphA2, Ephrin B2, FAP, FLT3, GCC, GD2, GD3, GM3, GPRC5D, HER2 (ERBB2/neu), IGLL1, IL-11Ra, KIT (CD117), KLK2, LY6G6D, MUC1, NCAM, p53R175H, PAP, PDGFR-β, PRAME, PRSS21, PSCA, PSMA, ROR1, SIRPα, SSEA-4, TAG72, TEM1/CD248, TEM7R, TSHR, VEGFR2, ALPI, citrullinated vimentin, cMet, and Axl.

In some embodiments, the target antigen can be CD1, CD1a, CD1b, CD1c, CD1d, CD1e, CD2, CD3d, CD3e, CD3g, CD3ε, CD4, CD5, CD7, CD8a, CD8b, CD19, CD20, CD21, CD22, CD23, CD24, CD25, CD27, CD28, CD30, CD33, CD34, CD38, CD40, CD44v6, CD45, CD48, CD52, CD59, CD66, CD70, CD71, CD72, CD73, CD79A, CD79B, CD80 (B7.1), CD86 (B7.2), CD94, CD95, CD97, CD123, CD134, CD140 (PDGFR4), CD152, CD154, CD158, CD171, CD178, CD179, CD179a, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), CEA, CLL-1, CS1, EGFR, FGFR2, AFP, CA125, MUC-1, MAGE, alkaline phosphatase, placental-like 2 (ALPPL2), B-cell maturation antigen (BCMA), green fluorescent protein (GFP), enhanced green fluorescent protein (cGFP), Claudin18.2, PSMA, ROR1, Mesothelin, IL13Ra2, FAP, signal regulatory protein α (SIRPα), TRAC, TCRβ, BCMA, TSHR, EGFRvIII, GD2, GD3, Tn Ag, ROR1, ROR2, GPC1, GPC2, FLT3, FAP, TAG72, CEA, EPCAM, B7H3, KIT, IL-13Ra2, IL-11Ra, PSCA, PRSS21, VEGFR2, LewisY, PDGFR-beta, SSEA-4, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, KRAS, mutant KRAS, KRAS G12D, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, LAIR1, FCAR, LILRA2, CD300LF, CLEC12A, BST2, EMR2, LY75, GPC3, FCRL5, IGLL1, AFP, TRAC, TCRβ, BCMA, TSHR, EGFRvIII, GD2, GD3, Tn Ag, PSMA, ROR1, ROR2, GPC1, GPC2, FLT3, FAP, TAG72, CEA, EPCAM, B7H3, KIT, IL-13Ra2, IL-11Ra, PSCA, PRSS21, VEGFR2, LewisY, PDGFR-beta, SSEA-4, , folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, LAIR1, FCAR, LILRA2, CD300LF, CLEC12A, BST2, EMR2, LY75, GPC3, FCRL5, IGLL1, the extracellular portion of the APRIL protein, or any combinations thereof.

In some aspects, the TCR targets AFP, CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMW-MAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, KRAS, mutant KRAS, KRAS G12D, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, the extracellular portion of the APRIL protein, or any combinations thereof.

A CAR may comprise a costimulatory signaling domain, e.g., to increase signaling potency. See U.S. Pat. Nos. 7,741,465, and 6,319,494, as well as Krause et al. and Finney et al. (supra), Song et al., Blood 119:696-706 (2012); Kalos et al, Sci Transl. Med. 3:95 (2011); Porter et al, N. Engl. J. Med. 365:725-33 (2011), and Gross et al, Annu. Rev. Pharmacol. Toxicol. 56:59-83 (2016). Signals generated through a TCR alone may be insufficient for full activation of a T cell and a secondary or co-stimulatory signal may increase activation. Thus, in some embodiments, a signaling domain further comprises one or more additional signaling domains (e.g., costimulatory signaling domains) that activate one or more immune cell effector functions (e.g., a native immune cell effector function described herein). In some embodiments, a portion of such costimulatory signaling domains may be used, as long as the portion transduces the effector function signal. In some embodiments, a cytoplasmic domain described herein comprises one or more cytoplasmic sequences of a T cell co-receptor (or fragment thereof). Non-limiting examples of such T cell co-receptors comprise CD27, CD28, 4-1BB (CD137), 0X40, CD30, CD40, PD-1, ICOS, lymphocyte function-associated antigen-1 (LFA-1), MYD88, CD2, CD7, LIGHT, NKG2C, B7-H3, and a ligand that binds with CD83. An exemplary costimulatory protein has the amino acid sequence of a costimulatory protein found naturally on T cells, the complete native amino acid sequence of which costimulatory protein is described in NCBI Reference Sequence: NP_006130.1.

In various embodiments, a mechanism of modulating (e.g., decreasing) binding activity of the target antigen is desired, e.g., to minimize or curtail adverse events resulting from binding activity. It may also be desired to comprise an inducible "on" or "accelerator" switch in immune cells. Suitable techniques comprise use of inducible caspase-9 (U.S. Appl. 2011/0286980) or a thymidine kinase, before, after, or at the same time, as the cells are transduced with the CAR construct of the present disclosure. Additional methods for introducing suicide genes and/or "on" switches comprise TALENS, zinc fingers, RNAi, siRNA, shRNA, antisense technology, and other techniques.

In accordance with the present disclosure, on-off or other types of control switch techniques may be incorporated herein. These techniques may comprise use of dimerization domains and optional activators of such domain dimerization, e.g., as disclosed by Wu et al., Science 2015 October; 350(6258):aab4077 utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of each of which is also incorporated by reference herein with respect to dimerization technology. Additional dimerization pairs may comprise cyclosporine-A/cyclophilin, receptor, estrogen/estrogen receptor (optionally using tamoxifen, 4-hydroxytamoxifen, or endoxifen), glucocorticoids/glucocorticoid receptor, tetracycline/tetracycline receptor, and/or vitamin D/vitamin D receptor. Further examples of dimerization technology may be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

In some embodiments, the T cell may comprise a bicistronic CAR. Bicistronic CARs can comprise two CARs that bind different targets and are encoded by a single vector. A bicistronic CAR may comprise a first CAR sequence and a second CAR sequence expressed as a single polypeptide comprising a cleavable linker between the first and second CARs. Non-limiting examples of first and/or second CAR sequences include CD19, CD20, BCMA, CD22, CD70, DLL3, LY6G6D, Claudin 6, GCC, p53R175H, and PRAME. An exemplary cleavable linker is Furin-GSG-T2A (see, e.g., Chng et al. MAbs. 2015 March-April; 7(2): 403-412, which is herein incorporated by reference with respect to cleavable linkers; see also Guedan et al. Mol Ther Methods Clin Dev. 2019 Mar. 15; 12: 145-156, which is incorporated herein by reference with respect to bicistronic CAR design).

In some embodiments, the T cell may comprise a bispecific CAR. In some embodiments, a first binding motif and a second binding motif (e.g., distinct anti-CD20 and anti-CD 19 binding motifs) are both comprised in single bispecific CAR. In such bispecific CARs, a CAR molecule itself may be engineered to recognize more than one antigen. In tandem bispecific CARs, the first and second binding motifs are extracellular and may be characterized as a membrane-proximal binding motif and a membrane-distal binding motif.

Sources for the T cells include, but are not limited to, peripheral blood, bone marrow, or other sources of hematopoietic cells. T cells can be isolated by methods well known in the art, including commercially available isolation methods (see, for example, Rowland-Jones et al., Lymphocytes: A Practical Approach, Oxford University Press, New York (1999), Su et al., Methods Mol. Biol. 806:287-299 (2012); Bluestone et al., Sci. Transl. Med. 7(315) (doi: 10.1126/scitranslmed.aad4134)(2015); Miyara et al., Nat. Rev. Rheumatol. 10:543-551 (2014); Liu et al., J. Exp. Med. 203:1701-1711 (2006); Seddiki et al., J. Exp. Med. 203: 1693-1700 (2006); Ukena et al., Exp. Hematol. 39:1152-1160 (2011); Chen et al., J. Immunol. 183:4094-4102 (2009); Putnam et al., Diabetes 58:652-662 (2009); Putnam et al., Am. Tranplant. 13:3010-3020 (2013); Lee et al., Cancer Res. 71:2871-2881 (2011); MacDonald et al., J Clin. Invest. 126:1413-1424 (2016)).

Various known techniques can be employed to isolate or enrich for desired immune cells such as T cells. If a particular type of T cell is to be isolated, various cell surface markers or combinations of markers, including but not limited to, CD3, CD4, CD8, CD34 (for hematopoietic stem and progenitor cells) and the like, can be used to separate the cells, as is well known in the art (see Kearse, T Cell Protocols: Development and Activation, Humana Press, Totowa N.J. (2000); De Libero, T Cell Protocols, Vol. 514 of Methods in Molecular Biology, Humana Press, Totowa N.J. (2009)) Negative selection methods can be used to remove cells that are not the desired immune cells. Additionally, positive selection methods can be used to isolate or enrich for desired T cells. In some instances, a combination of both positive and negative selection methods can be used.

Pharmaceutical Compositions

In some embodiments, the recombinant nucleic acid constructs and/or recombinant nucleic acids of the disclosure and recombinant cells of the disclosure can be incorporated into compositions, including pharmaceutical compositions. Such compositions generally include the recombinant nucleic acids, recombinant polypeptides, and/or recombinant cells of the disclosure, and a pharmaceutically acceptable excipient, e.g., carrier.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Systemic administration of the subject recombinant nucleic acid constructs and/or recombinant nucleic acids and recombinant cells of the disclosure can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the recombinant nucleic acid constructs and/or recombinant nucleic acids and recombinant cells of the disclosure can also be administered by transfection or infection using methods known in the art, including but not limited to the methods described in McCaffrey et al. (Nature 418:6893, 2002), Xia et al. (Nature Biotechnol. 20: 1006-1010, 2002), or Putnam (Am. J. Health Syst. Pharm. 53: 151-160, 1996, erratum at Am. J. Health Syst. Pharm. 53:325, 1996).

In some embodiments, the recombinant nucleic acid constructs and/or recombinant nucleic acids and recombinant cells of the disclosure are prepared with carriers that will protect the recombinant polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811. As described in greater detail below, the polypeptides of the present disclosure may also be modified to achieve extended duration of action such as by PEGylation, acylation, Fc fusions, linkage to molecules such as albumin, etc. In some embodiments, the recombinant polypeptides can be further modified to prolong their half-life in vivo and/or ex vivo. Non-limiting examples of known strategies and methodologies suitable for modifying the recombinant polypeptides of the disclosure include (1) chemical modification of a recombinant polypeptide described herein with highly soluble macromolecules such as polyethylene glycol ("PEG") which prevents the recombinant polypeptides from contacting with proteases; and (2) covalently linking or conjugating a recombinant polypeptide described herein with a stable protein such as, for example, albumin. Accordingly, in some embodiments, the polypeptides of the disclosure can be fused to a stable protein, such as, albumin. For example, human albumin is known as one of the most effective proteins for enhancing the stability of polypeptides fused thereto and there are many such fusion proteins reported.

In some embodiments, the pharmaceutical compositions of the disclosure include one or more PEGEylation reagents. In some embodiments, the PEGylation reagent is selected from methoxy polyethylene glycol-succinimidyl propionate (mPEG-SPA), mPEG-succinimidyl butyrate (mPEG-SBA), mPEG-succinimidyl succinate (mPEG-SS), mPEG-succinimidyl carbonate (mPEG-SC), mPEG-Succinimidyl Glutarate (mPEG-SG), mPEG-N-hydroxyl-succinimide (mPEG-NHS), mPEG-tresylate and mPEG-aldehyde. In some embodiments, the PEGylation reagent is polyethylene glycol. In some embodiments, the PEGylation reagent is polyethylene glycol with an average molecular weight of 20 kD covalently bound to the N-terminal methionine residue of the recombinant polypeptides of the disclosure, or about 80 kD covalently bound to the N-terminal methionine residue of the polypeptides of the disclosure. In some embodiments, the PEGylation reagent is polyethylene glycol with an average molecular weight of about 40 kD covalently bound to the N-terminal methionine residue of the polypeptides of the disclosure.

Accordingly, in some embodiments, recombinant nucleic acid constructs and/or recombinant nucleic acids and recombinant cells of the disclosure are chemically modified with one or more polyethylene glycol moieties, e.g., PEGylated; or with similar modifications, e.g. PASylated. In some embodiments, the PEG molecule or PAS molecule is conjugated to one or more amino acid side chains of the disclosed recombinant polypeptide. In some embodiments, the PEGylated or PASylated polypeptide contains a PEG or PAS moiety on only one amino acid. In other embodiments, the PEGylated or PASylated polypeptide contains a PEG or PAS moiety on two or more amino acids, e.g., attached to two or more, five or more, ten or more, fifteen or more, or twenty or more different amino acid residues. In some embodiments, the PEG or PAS chain is 2000, greater than 2000, 5000, greater than 5,000, 10,000, greater than 10,000, greater than 10,000, 20,000, greater than 20,000, and 30,000 Da. The PASylated polypeptide may be coupled directly to PEG or PAS (e.g., without a linking group) through an amino group, a sulfhydryl group, a hydroxyl group, or a carboxyl group. In some embodiments, the recombinant polypeptide of the disclosure is covalently bound to a polyethylene glycol with an average molecular weight of 20,000 Daltons. In some embodiments, the recombinant polypeptide of the disclosure is covalently bound to a polyethylene glycol with an average molecular weight ranging from about 1 kD to about 200 kD such as, e.g., about 10 kD to about 150 kD, about 50 kD to about 100 kD, about 5 kD to about 100 kD, about 20 kD to about 80 kD, about 30 kD to about 70 kD, about 40 kD to about 60 kD, about 50 kD to about 100 kD, about 100 kD to about 200 kD, or about 1 150 kD to about 200 kD. In some embodiments, the recombinant polypeptide of the disclosure is covalently bound to a polyethylene glycol with an average molecular weight of about 5 kD, about 10 kD, about 20 kD, about 30 kD, about 40 kD, about 50 kD, about 60 kD, about 70 kD, or about 80 kD. In some embodiments, the recombinant polypeptide of the disclosure is covalently bound to a polyethylene glycol with an average molecular weight of about 40 kD Methods of the Disclosure The disclosure also relates to methods including the polypeptides, recombinant nucleic acid constructs and/or recombinant nucleic acids or the cells of the disclosure.

Methods for Identifying a Mutation Useful for Improving T Cell Therapy

In an aspect, the disclosure relates to methods for identifying a mutation useful (beneficial) for improving T cell therapy (e.g., as described in Example 1). The mutation can be identified from genomic sequencing data of T cell lymphomas or from clonal T cells or other T cells. The methods can include applying a statistical test to determine a mutation that occurs more often than expected by chance in a hotspot region of a coding sequence. As used herein, a hotspot region can be a segment of DNA that is prone to genetic alteration. In some embodiments, the hotspot region is in a coding sequence of a gene. In some embodiments, the statistical tests employ a binomial distribution. In some embodiments, the statistical tests employ Chi square analysis or any other multivariate analysis.

The binomial distributions can be employed across gene lengths in the entire genome of a cell. The statistical tests can employ various false discovery rates. In some embodiments, the discovery rate can be 0.05. In some embodiments, it can be controlled for by the Benjamini-Hochberg algorithm. In some embodiments, heterogeneity due to transcription couple repair can be accounted for.

In some embodiments, a mutation useful or beneficial for improving T cell therapy, can be identified by selecting a mutation that has occurred in patients. In some embodiments, a mutation can be identified by performing a statistical analysis of genomic sequencing data of clonal T cells, including T cell lymphomas, from public and/or private databases. In some embodiments, a mutation is identified by using binomial distributions across gene lengths in the entire genome and a false discovery rate of 0.05 controlled for by the Benjamini-Hochberg algorithm. In some embodiments, the mutation is identified in hotspot regions where the mutation occurred more often than expected by chance alone in the hotspot regions. In some embodiments, a mutation is identified by permuting the background rate of mutations across the genome accounting for heterogeneity due to transcription couple repair thereby identifying genes that harbor mutations that occur more often than expected by chance using the permuted background rate of mutations.

The identified mutation can be a mutation that increases proliferation of therapeutic T cells, or alters effector function, or resists T cell dysfunction, and/or T cell enhances growth, or reduces T cell exhaustion or promotes in vivo persistence of T cells. Increasing proliferation of therapeutic T cells can include clonal expansion, increase in replication rate of T cells and/or increase in the number of T cells. The mutation can be any mutation listed in Table 1.

T-cell effector functions can involve the interaction of an armed effector T cell with a target cell displaying specific antigen. The effector proteins released by these T cells are focused on the appropriate target cell by mechanisms that are activated by recognition of antigen on the target cell.

In some embodiments, the method for identifying a mutation useful (beneficial) for improving T cell therapy includes various steps such as a) identifying mutations from a clonal T cell genomic sequencing database; b) identifying a frequency of occurrence of the mutations; and c) applying a statistical test to identify a significant difference in a hotspot genomic region where a mutation occurs more often than expected by chance, thereby identifying a mutation in the hotspot region that is capable of improving T cell therapy. The mutation can improve T cell therapy by increasing proliferation, altering effector function, resisting T cell dysfunction, and/or enhancing growth, of a therapeutic T cell including the mutation, in a tumor. The mutation can promote positive T cell selection and/or T cell clonal outgrowth. The mutation can be any mutation listed in Table 1.

Methods for Preparing T Cells for Use in Cell Therapy

The disclosure also provides methods for preparing a T cell for use in cell therapy. The T cell can further comprise a CAR, a TCR, and a transcriptional receptor. The T cell can be an NK cell or a tumor infiltrating lymphocyte from a patient with cancer. Preparing the cell can include introducing (e.g., by transducing) into a cell any one or more of the recombinant nucleic acid constructs and/or recombinant nucleic acids of the disclosure. Preparing the cell can include introducing (e.g., by transducing) into a cell any one or more vectors comprising any one or more of the recombinant nucleic acid constructs and/or recombinant nucleic acids of the disclosure. Preparing the cell can include expressing in the cell any one or more of the polypeptides of the disclosure. The cell can be genetically modified for expression of the polypeptide. The cell can further comprise expression of an engineered immune receptor that binds to a target in a tumor cell.

The cells can be transduced with a recombinant nucleic acid construct that can alter T cell signaling via the NFAT pathway, NF-κB pathway, AP-1 pathway, JAK/STAT pathway, RAS/MEK/ERK, phospholipase gamma signaling or other T cell signaling pathways.

The methods of preparing a T cell according to the disclosure can include transducing T cells with recombinant nucleic acid constructs and/or recombinant nucleic acids capable of enhancing or promoting or improving or reducing or regulating or modulating the pathway or activating or increasing or suppressing or inhibiting or other means of changing T cell signaling. The methods of preparing a T cell according to the disclosure can include transducing cells with recombinant nucleic acid constructs and/or recombinant nucleic acids that can alter CARD11-BCL10-MALT1 complex signaling, co-stimulatory molecule signaling, and cytokine production and/or transcription factor activity in T cells.

In an embodiment, the method of preparing a T cell for use in a cell therapy includes transducing the T cell with a recombinant nucleic acid construct and/or recombinant nucleic acid having a mutation capable of altering (i) T cell signaling through NFAT, NF-κB and/or AP-1 pathways, (ii) cytokine production, and/or (iii) in vivo persistence of T cells in tumors.

In some embodiments of the methods of preparing a T cell for use in a cell therapy includes polypeptides and/or recombinant nucleic constructs and/or recombinant nucleic acids that can alter in vivo persistence in tumors of therapeutic T cells including the mutation. In some embodiments, the recombinant nucleic acid constructs and/or recombinant nucleic acids of the disclosure can alter the therapeutic efficacy, decrease T cell exhaustion, increase proliferative capacity, enhance anti-tumor effect, enhance the replicative lifespan, decrease replicative senescence, and enhance ability to kill, enhance the fitness of engineered T cells and/or other functions or activities of T cells.

Figure 2A:
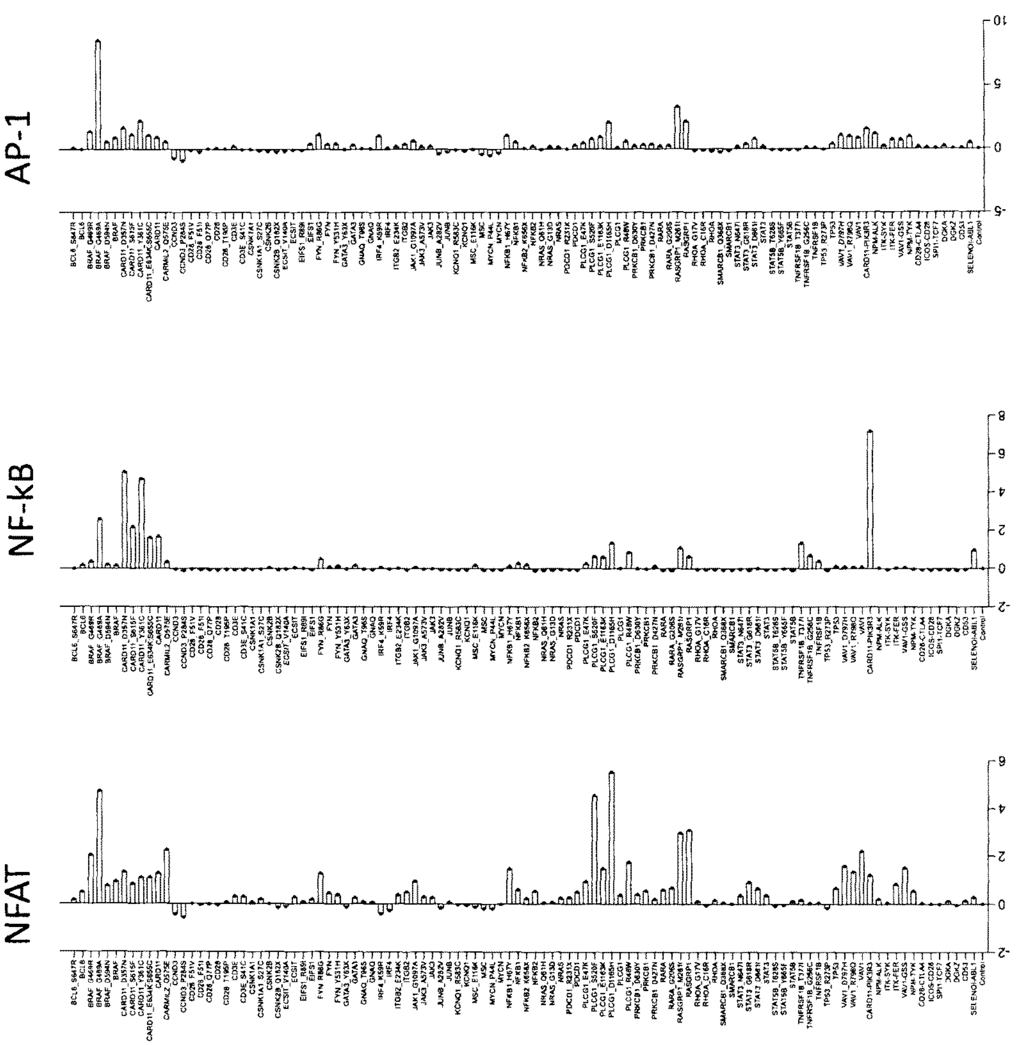
FIGS. 2A-2G show the detailed signaling results of the in vitro T cell lymphoma mutation screen.
Figure 2B:
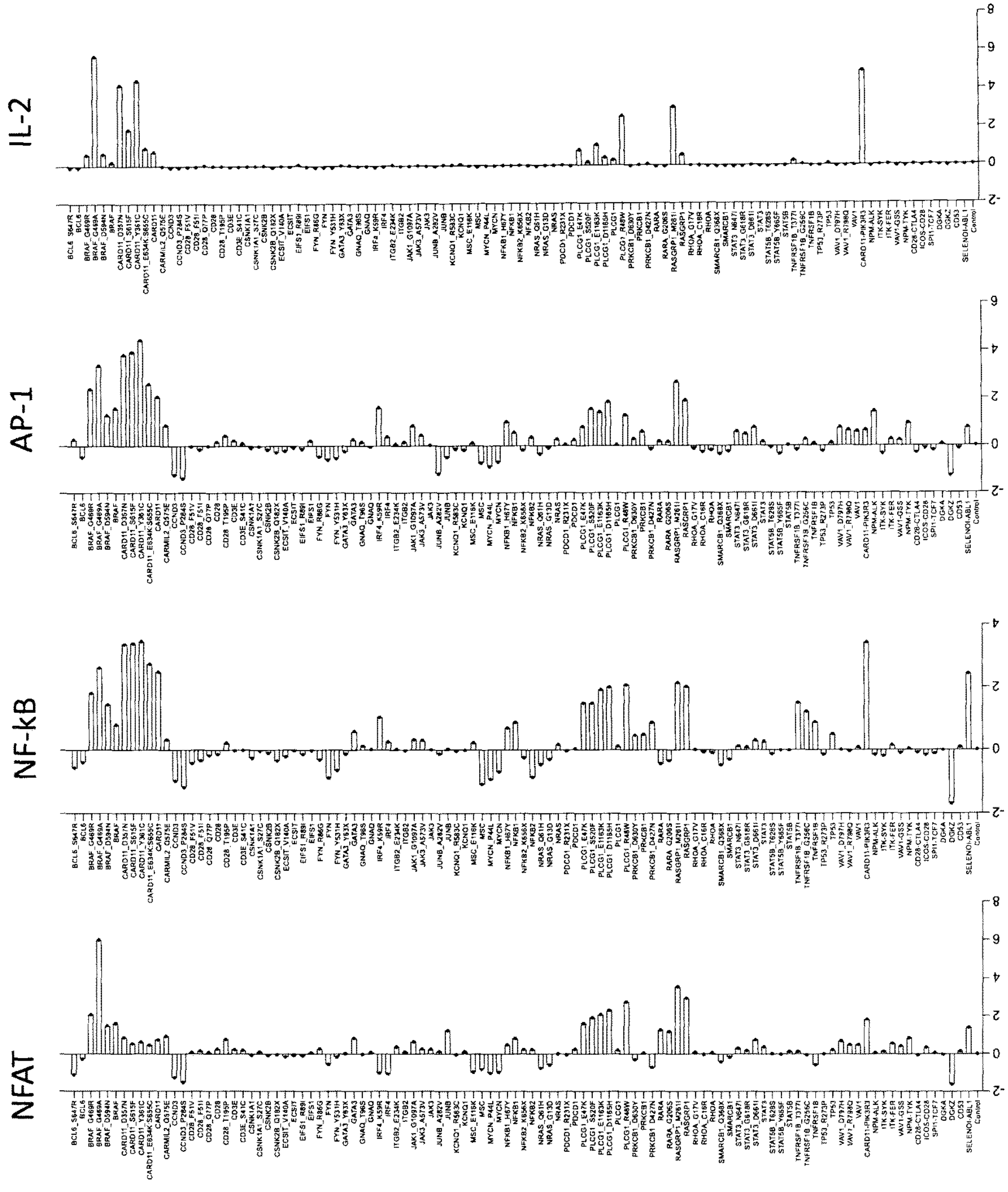
Figure 2C:
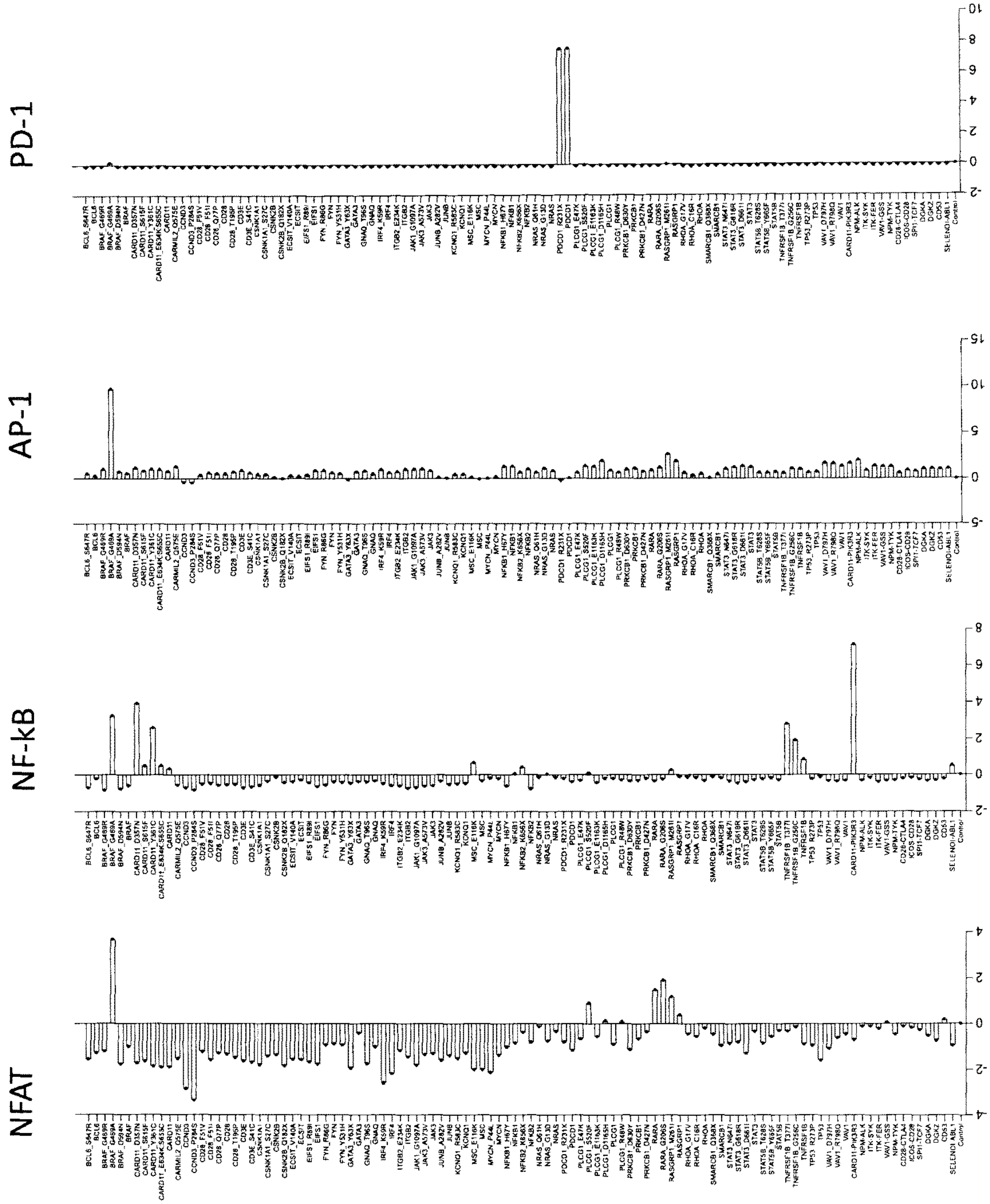
Figure 2D:
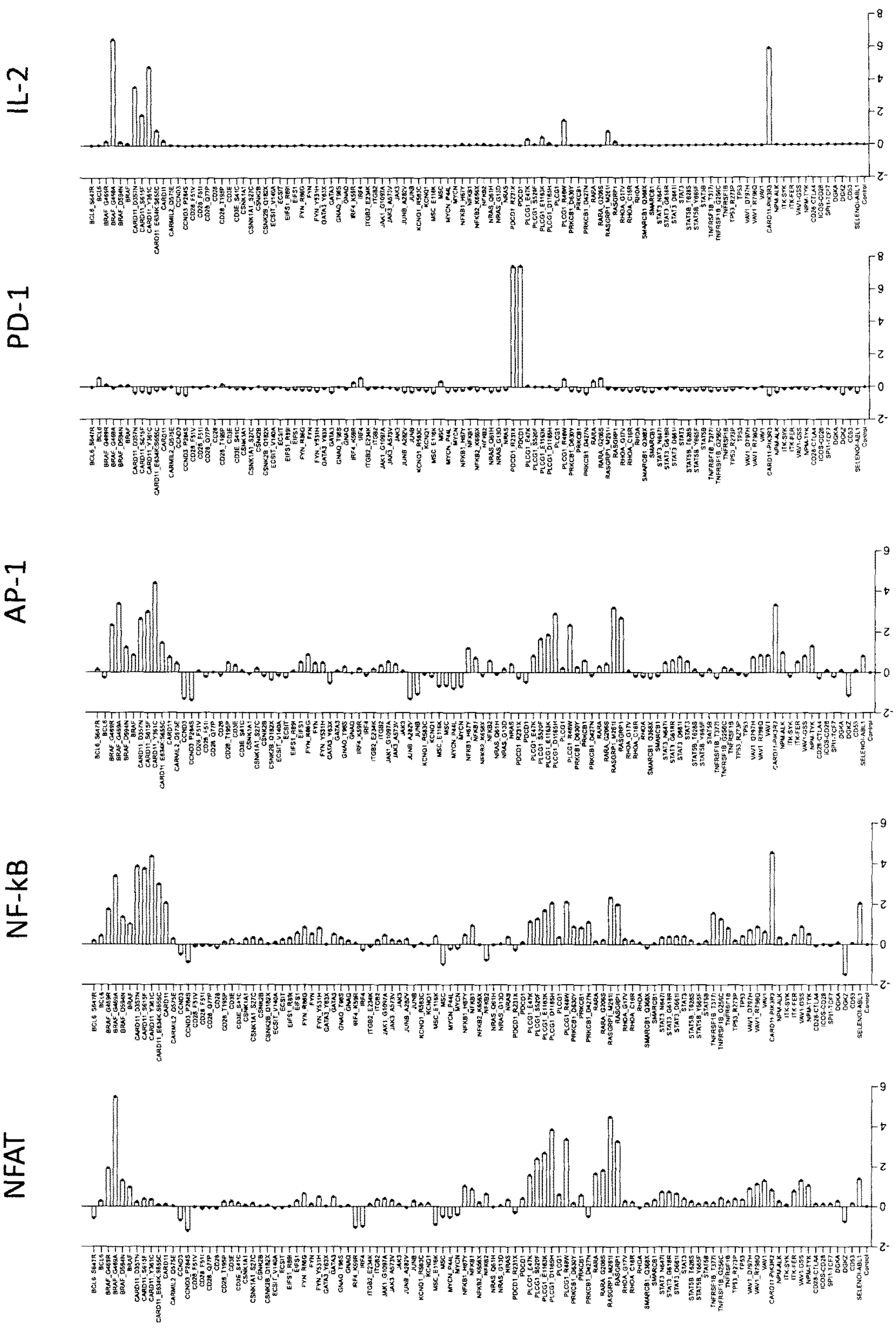

In some embodiments, the polypeptides or recombinant nucleic acid constructs and/or recombinant nucleic acids of the disclosure can alter the in vivo persistence in tumors, in vivo accumulation in tumors, or the other functions or activities of T cells described herein, through a mutation in one or more of the forty one genes listed in Table 1 or FIG. 2A. In some embodiments, the genes include caspase recruitment domain family member 11 (CARD11). In some embodiments, the genes include capping protein regulator and myosin 1 linker 2 (CARMIL2), mucosa-associated lymphoid tissue lymphoma translocation protein 1 (MALT1), B-cell lymphoma 6 (BCL6), B-cell lymphoma 10 (BCL10) and MYCN. The gene can be a signal transducer and activator of transcription gene (STAT) including STAT3, STAT5B. The gene can be a janus kinase gene such as JAK1, JAK2, or JAK3 gene. The gene can be v-raf murine sarcoma viral oncogene homolog B1 (BRAF). The gene can be RAS Guanyl Releasing Protein 1 (RASGRP1). The gene can be Tumor necrosis factor receptor superfamily member 1B (TNFRSF1B). The gene can be phospholipase C gamma 1 (PLCG1) gene. The gene can be nuclear factor kappa light chain enhancer of activated B cells (NF-κB1), or (NF-κB2) or JunB Proto-Oncogene, AP-1 Transcription Factor Subunit (JUNB) gene.

Methods for Treating a Subject

The disclosure also provides methods of treating a subject in need of cell therapy, comprising administering to the subject a cell as described herein or a T-cell prepared by any of the methods described herein. The disclosure also provides methods for enhancing the in vivo persistence of a T cell (e.g., a therapeutic T cell) in a subject in need thereof, by administering to the subject a therapeutically effective amount of the T cells of the disclosure. The T cells can include any of the recombinant nucleic acid constructs and/or recombinant nucleic acids of the disclosure.

This administering step can be accomplished using any method of implantation delivery in the art. For example, the recombinant cells of the disclosure can be infused directly in the individual's bloodstream or otherwise administered to the individual.

In some embodiments, the methods disclosed herein include administering which term is used interchangeably with the terms "introducing," implanting," and "transplanting," recombinant cells into an individual, by a method or route that results in at least partial localization of the introduced cells at a desired site such that a desired effect(s) is/are produced. The recombinant cells or their differentiated progeny can be administered by any appropriate route that results in delivery to a desired location in the individual where at least a portion of the administered cells or components of the cells remain viable. The period of viability of the cells after administration to an individual can be as short as a few hours, e.g., twenty-four hours, to a few days, to as long as several years, or even the lifetime of the individual, i.e., long-term engraftment.

When provided prophylactically, the recombinant cells described herein can be administered to an individual in advance of any symptom of a disease or condition to be treated. Accordingly, in some embodiments the prophylactic administration of a recombinant cell population prevents the occurrence of symptoms of the disease or condition.

When provided therapeutically in some embodiments, recombinant cells are provided at (or after) the onset of a symptom or indication of a disease or condition, e.g., upon the onset of disease or condition.

For use in the various embodiments described herein, an effective amount of recombinant cells as disclosed herein, can be at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The recombinant cells can be derived from one or more donors or can be obtained from an autologous source. In some embodiments, the recombinant cells are expanded in culture prior to administration to an individual in need thereof.

In some embodiments, the delivery of a recombinant cell composition (e.g., a composition including a plurality of recombinant cells according to any of the cells described herein) into an individual by a method or route results in at least partial localization of the cell composition at a desired site. A composition including recombinant cells can be administered by any appropriate route that results in effective treatment in the individual, e.g., administration results in delivery to a desired location in the individual where at least a portion of the composition delivered, e.g., at least $1\times10^4$ cells, is delivered to the desired site for a period of time. Modes of administration include injection, infusion, and instillation. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous. For the delivery of cells, delivery by injection or infusion is a preferred mode of administration.

In some embodiments, the recombinant cells are administered systemically, e.g., via infusion or injection. For example, a population of recombinant cells are administered other than directly into a target site, tissue, or organ, such that it enters the individual's circulatory system and, thus, is subject to metabolism and other similar biological processes.

The efficacy of a treatment including any of the compositions provided herein for the treatment of a disease or condition can be determined by a skilled clinician. However, one skilled in the art will appreciate that a treatment is considered effective if any one or all of the signs or symptoms or markers of disease are improved or ameliorated. Efficacy can also be measured by failure of an individual to worsen as assessed by decreased hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

As discussed above, a therapeutically effective amount includes an amount of a therapeutic composition that is sufficient to promote a particular beneficial effect when administered to an individual, such as one who has, is suspected of having, or is at risk for a disease. In some embodiments, an effective amount includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

In some embodiments of the disclosed methods, the individual is a mammal. In some embodiments, the mammal is a human. In some embodiments, the individual has or is suspected of having a disease associated with inhibition of cell signaling mediated by a cell surface ligand or antigen. The diseases suitable for being treated by the compositions and methods of the disclosure include, but are not limited to, cancers, autoimmune diseases, inflammatory diseases, and infectious diseases. In some embodiments, the disease is a cancer or a chronic infection.

Methods for CAR design, delivery and expression in T cells, and the manufacturing of clinical-grade CAR-T cell populations are known in the art. See, for example, Lee et al., Clin Cancer Res (2012) 18(10):2780-90, hereby incorporated by reference in its entirety. For example, the engineered CARs may be introduced into T cells using retroviruses, which efficiently and stably integrate a nucleic acid sequence encoding the chimeric antigen receptor into the target cell genome.

Other methods known in the art include, but are not limited to, lentiviral transduction, transposon-based systems, direct RNA transfection, and CRISPR/Cas systems (e.g., type I, type II, or type III systems using a suitable Cas protein such Cas3, Cas4, Cas5, Cas5c (or CasD), Cas6, Cas6e, Cas6f, Cas7, Cas8a1, Cas8a2, Cas8b, Cas8c, Cas9, Cas10, Cas10d, Cas12a (Cpf1), Cas13a (C2c2), Cas13b, Cas13d, CasF, CasG, CasH, Csy1, Csy2, Csy3, Cse1 (or CasA), Csc2 (or CasB), Csc3 (or CasE), CasX, CasY, Csc4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966, etc.).

In some embodiments, a recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV requires that the following components are present within a single cell (denoted herein as a packaging cell): a rAAV genome, AAV rep and cap genes separate from (e.g., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692.

The CAR-T cells, once they have been expanded ex vivo in response to, for example, an autoimmune disease antigen, can be reinfused into the subject in a therapeutically effective amount.

The precise amount of CAR T cells to be administered can be determined by a physician with consideration of individual differences in age, weight, extent of disease and condition of the subject.

Administration of T cell therapies may be defined by number of total cells per infusion or number of cells per kilogram of body weight, especially for pediatric subjects (e.g., patients). As T cells replicate and expand after transfer, the administered cell dose may not resemble the final steady-state number of cells. In some embodiments, a pharmaceutical composition including the CAR T cells of the present disclosure may be administered at a dosage of $10^4$ to $10^{10}$ total cells. In another embodiment, a pharmaceutical composition including the CAR T cells of the present disclosure may be administered at a dosage of $10^3$ to $10^8$ cells/kg body weight, including all integer values within those ranges.

Compositions including the CAR T cells of the present disclosure may also be administered multiple times at these dosages. The cells can be administered by using infusion techniques that are known in the art (see, for example, Rosenberg et al., New Engl J Med, (1988) 319:1676). The optimal dosage and treatment regimen for a particular subject can be determined by one skilled in the art by monitoring the subject for signs of disease and adjusting the treatment accordingly.

In some embodiments, administration of any of the compositions embodied herein, for the treatment of, for example, an autoimmune or inflammatory disease, can be combined with other cell-based therapies, for example, stem cells, antigen presenting cells, pancreatic islets etc.

The composition of the present disclosure may be prepared in a manner known in the art and in a manner suitable for parenteral administration to mammals, particularly humans, including a therapeutically effective amount of the composition alone, with one or more pharmaceutically acceptable carriers or diluents.

The term "pharmaceutically acceptable carrier" as used herein means any suitable carriers, diluents or excipients. These include all aqueous and non-aqueous isotonic sterile injection solutions, which may contain anti-oxidants, buffers and solutes, which render the composition isotonic with the blood of the intended recipient; aqueous and non-aqueous sterile suspensions, which may include suspending agents and thickening agents, dispersion media, antifungal and antibacterial agents, isotonic and absorption agents and the like. It will be understood that compositions of the present disclosure may also include other supplementary physiologically active agents.

The carrier must be pharmaceutically "acceptable" in the sense of being compatible with the other ingredients of the composition and not injurious to the subject. Compositions include those suitable for parenteral administration, including subcutaneous, intramuscular, intravenous and intradermal administration. The compositions may conveniently be presented in unit dosage form and may be prepared by any method well known in the art of pharmacy. Such methods include preparing the carrier for association with the CAR-T cells. In general, the compositions are prepared by uniformly and intimately bringing into association any active ingredients with liquid carriers.

In some embodiments, the composition is suitable for parenteral administration. In another embodiment, the composition is suitable for intravenous administration.

Compositions suitable for parenteral administration include aqueous and nonaqueous isotonic sterile injection solutions which may contain anti-oxidants, buffers, bactericides and solutes, which render the composition isotonic with the blood of the intended recipient; and aqueous and non-aqueous sterile suspensions which may include suspending agents and thickening agents.

Enhancing the in vivo persistence of a T cell in a subject can be enhancing the fitness or enhancing the function and/or enhancing the efficacy of the therapeutic T cells. The enhancing can be measured by determining the accumulation of the number of T cell in a tumor (for example as described in Example 13 below).

In some embodiments, in vivo persistence can be by promoting the intra-tumoral increase of effector cytokines. In some embodiments, the in vivo persistence can be by increasing the expression of the stemness-associated transcription factor TCF1 in TILs. In some embodiments, the in vivo persistence can be by increasing the expression of TNF-α, IFN-γ, and/or IL-2.

In some embodiments, enhancing the in vivo persistence can be measured by measuring differences in gene expression. In some embodiments, the genes include but are not limited to activation markers (IL2RA, CD69), cytotoxic and effector molecules (IFNG, TNF, IL4, IL5, IL13, GZMA, GZMB), chemokines (CCL4, CCL20, CCL8), and co-stimulatory molecules (ICOS, OX40, 4-1BB, GITR).

In some embodiments, the subject has cancer or an autoimmune disease. In some embodiments, the cancer can be a solid tumor. In some embodiments, the cancer can be a hematological cancer. In some embodiments, the cancer expresses a tumor-associated antigen, as described herein. In some embodiments, the cancer expresses DLL3, LY6G6D, Claudin 6, GCC, p53R175H, and/or PRAME.

Exemplary solid tumors include, without limitation, small cell lung cancer, colorectal cancer, testicular cancer, ovarian cancer, or melanoma, lymphoma, leukemia, multiple myeloma, prostate cancer, breast cancer, non-small cell lung cancer, gastric cancer, esophageal cancer, liver cancer, kidney cancer, head & neck cancer, glioblastoma, neuroblastoma, soft tissue sarcoma, uterine cancer, brain cancer, skin cancer, renal cancer, bladder cancer, pancreatic cancer, thyroid cancer, eye cancer, gastrointestinal cancer, carcinoma, and sarcoma.

In some embodiments, the method of treatment does not comprise administration of lymphodepletive agents within 7 days prior to administration of the T cell therapy. Non-limiting examples of lymphodepletive agents include cyclophosphamide, fludarabine, and/or bendamustine within 7 days prior to administration of the T cell therapy. In some embodiments, the method of treatment does not comprise administration of at least 600,000 IU/kg of IL-2 every 8 hours. In some embodiments, the method of treatment does not comprise a checkpoint therapy which blocks PD-1 or CTLA-4 signaling.

In some embodiments, the method of treatment comprises a cell with reduced exhaustion, increased proliferative capacity, enhanced replicative lifespan, decreased replicative senescence, enhanced anti-tumor effect, reduced dysfunction, enhanced persistence, and/or increase intratumoral presence in vivo. In some embodiments, the method of treatment comprises a cell with increased or decreased signaling through the CARD11-BCL10-MALT1 complex, NF-κB, AP-1, NFAT, JAK/STAT, and/or MEK/ERK pathways.

The cells of the methods of the disclosure can be regulatory (Treg), natural killer (NK) cells, a gamma delta T cell, an invariant iNKT cell, a macrophage, a monocyte, TILs or engineered T cells. In some embodiments, the engineered T cells can express a recombinant TCR or a CAR or a transcriptional receptor.

The engineered T cells can be autologous or allogeneic/non-autologous to the subject to which they are administered in the methods of the disclosure. For example, autologous cells can be isolated from the subject to which the T cells are to be administered. The autologous cells can be isolated from the subject to which the engineered cells recombinantly expressing a CAR or a transcriptional receptor are to be administered. Optionally, the cells can be obtained by leukapheresis, where leukocytes are selectively removed from withdrawn blood, engineered and made recombinant, and then retransfused into the donor. Alternatively, allogeneic cells from an allogeneic/non-autologous donor that is not the subject can be used. In the case of an allogeneic/non-autologous donor, the cells are typed and matched for human leukocyte antigen (HLA) to determine an appropriate level of compatibility, as is well known in the art. For both autologous and allogeneic/cells, methods for genetic manipulation and/or administration to a subject are well known in the art. In some situations, the cells can be optionally preserved (e.g., cryopreserved) until ready to be used.

Procedures for separation of cells include, but are not limited to, flow cytometry, affinity chromatography, density gradient centrifugation, magnetic separation with antibody-coated magnetic beads, conjugation to particles that modify cell density, cytotoxic agents joined to or used in conjunction with a monoclonal antibody (mAb) or any other appropriate technique.

In some embodiments, the isolated T cells are genetically engineered ex vivo for recombinant expression of a transgene. In some embodiments, isolated T cells are genetically engineered ex vivo for recombinant expression of a CAR or a transcriptional receptor as described in more details supra. In some embodiments, the cells can be genetically engineered for recombinant expression. Methods suitable for genetically engineering cells for recombinant expression are well known in the art.

Systems and Kits

Systems or kits of the present disclosure include one or more of any of the recombinant nucleic acids, recombinant cells, or pharmaceutical compositions disclosed herein as well as syringes (including pre-filled syringes) and/or catheters (including pre-filled syringes) used to administer any of the recombinant nucleic acids, recombinant cells, or pharmaceutical compositions to a subject. The kits also include written instructions for using of any of the recombinant nucleic acids, recombinant cells, or pharmaceutical compositions disclosed herein as well as syringes and/or catheters for use with their administration.

Any of the above-described systems and kits can further include one or more additional reagents, where such additional reagents can be selected from: dilution buffers; reconstitution solutions, wash buffers, control reagents, control expression vectors, negative control polypeptides, positive control polypeptides, reagents for in vitro production of the chimeric receptor polypeptides.

In some embodiments, the components of a system or kit can be in separate containers. In some other embodiments, the components of a system or kit can be combined in a single container.

In some embodiments, a system or kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors/disclosers reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature cited above.

Additional embodiments are disclosed in further detail in the following examples, which are provided by way of illustration and are not in any way intended to limit the scope of this disclosure or the claims.

Example 1

Identification of Mutations

This Example describes the design and implementation of a statistical test to identify mutations for improving T cell therapy by altering signaling pathways, reducing T cell exhaustion, increasing therapeutic T cell proliferation, altering T cell effector function, resisting T cell dysfunction, enhancing growth in harsh tumor microenvironment, increasing in vivo persistence of therapeutic T cells and/or by other means.

In order to identify a mutation useful or beneficial for improving T cell therapy, the inventors/disclosers either 1—selected mutations that occurred in patients or 2—performed a statistical analysis of genomic sequencing data of clonal T cells, including T cell lymphomas, and have identified, from public and private databases, using binomial distributions across gene lengths in the entire genome and a false discovery rate of 0.05 controlled for by the Benjamini-Hochberg algorithm, hotspot regions and mutations that occur more often than expected by chance alone in the hotspot regions. In particular, the inventors/disclosers permuted the background rate of mutations across the genome accounting for heterogeneity due to transcription couple repair. Then they identified genes that harbor mutations that occur more often than expected by chance assuming the background rate of mutations.

Using the methods, the inventors/disclosers identified and cloned 62 point mutations (encoding non-synonymous amino acid substitutions and putative gain-of-function truncating mutations) in 40 different genes. In addition, the inventors/disclosers identified 10 gene fusions.

Example 2

Library Construction and In Vitro Mutation Screening

This Example describes the design and construction of the library of mutations shown in Table 1 and the screening of the constructs in order to identify the constructs that could improve in vivo persistence of human CAR T cells.

The inventors/disclosers cloned the 62 identified point mutations and the 10 fusion polypeptides. For each point mutation construct, a wild-type control of the same gene was generated to control for the effects of overexpression of the wild-type form of the gene. Five control constructs were also cloned. These targets were cloned into a barcoded lentiviral construct to enable pooled screening. In total, the library for T cell lymphoma mutation screening included 117 unique constructs (FIGS. 1 and 2A-D).

Wildtype genes of the mutation library were ordered as plasmids through DNASU, and point mutations were introduced through PCR site directed mutagenesis. For some mutated genes the genes were synthesized by Twist Biosciences (South San Francisco, CA). Wild type or mutated gene fragments were cloned into a modified pHR' SIN:CSW vector containing a PGK promoter followed by a T2A self-cleaving sequence, a unique barcode and the fluorescent tag mCherry used to identify transduced cells. Wild type or mutant gene fragments were cloned via a Sbf1 site in the multiple cloning site 3' to the PGK promoter sequence. All constructs were cloned via Infusion cloning (Clontech #ST0345) or Gibson assembly.

Intracellular domains containing the appropriate costimulatory domain, and CD3zeta domain were synthesized as synthesized by Twist. Receptors were built by fusing the CD19 scFv to the corresponding receptor scaffold and intracellular tail. All receptors contained an n-terminal CD8a signal peptide (MALPVTALLLPLALLLHAARP SEQ ID NO: 261) for membrane targeting and a flag-tag (DYKDDDDK SEQ ID NO: 262) for easy determination of surface expression with α-flag PE (Biolegend 637310). In some cases the receptors additionally contained a T2A self-cleaving sequence followed by a tNGFR sequence, used in downstream applications for T cell isolations. The receptors were cloned into a modified pHR'SIN:CSW vector containing a PGK promoter for all primary T cell experiments.

Triple reporter Jurkat cells (a human T cell line) that stably express NFAT-cGFP, NF-κB-eCFP, and AP-1-iRFP fluorescent protein reporter constructs were generated.

These triple reporter cells were then transduced to express a CD19-CD282 or CD19-BBz CAR, which led to CD19 antigen dependent signaling and IL-2 production.

Figure 1:
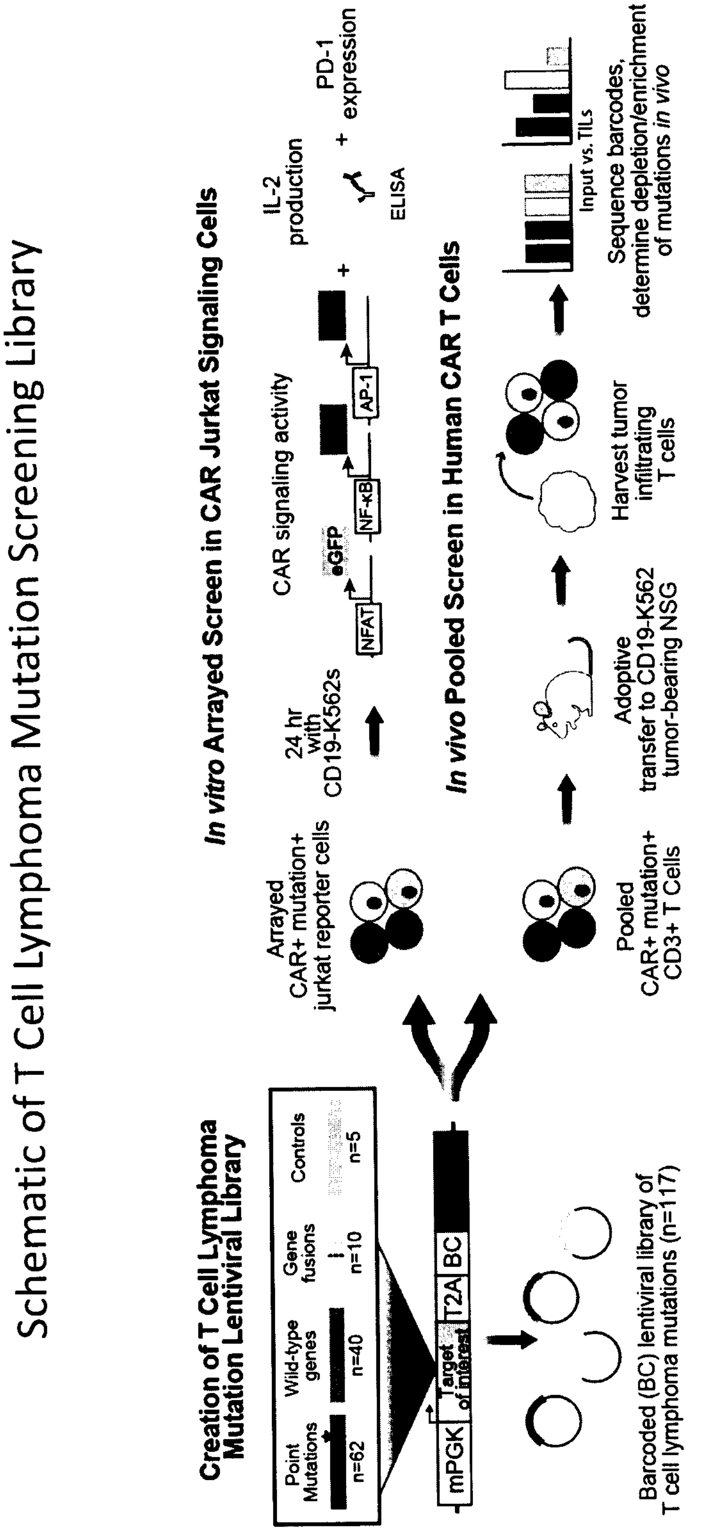
FIG. 1 is a schematic depicting the present disclosure's approach to creation of a screening library of mutations identified in T cell lymphomas, and in vitro and in vivo screening analysis of the library.

The effects of most of the mutations had not been fully characterized in the context of T cell signaling and effector function. To elucidate their functions, the inventors/disclosers transduced the triple reporter line with each construct in the library. Collectively, the reporter cells enabled elucidation of the mutations' effects on biochemical signaling pathways, the effects of antigen and the evaluation of effector cytokine production. A schematic of the in vitro and in vivo screens of the mutations to uncover effects of the mutations on T cell signaling pathways using triple reporter Jurkat cells (a human T cell line) stably expressing NFATcGFP, NF-κB-eCFP and AP-1-iRFP fluorescent protein reporter constructs is illustrated in FIG. 1.

To screen the effects of T cell lymphoma mutations on CAR signaling, triple reporter CAR cells were transduced with a CD19-CD28z or a CD19-BBz chimeric antigen receptor (CAR). Then co-cultured with K652 or K562-CD19 cells, and NFAT, NF-κB, and AP-1 reporter activity was determined by flow cytometry. As a readout of effector functions, supernatants from the K562-CD19 condition were collected and analyzed for IL-2 by ELISA. Each screen was performed twice with independent transductions and was highly reproducible across biological replicates. In vitro screens uncovered numerous mutations with significant impacts on CAR signaling and cytokine production (FIG. 2, Table 3-5). For the CD19-BB2 CAR screen, PD-1 levels were assessed by flow cytometry.

Figure 3:
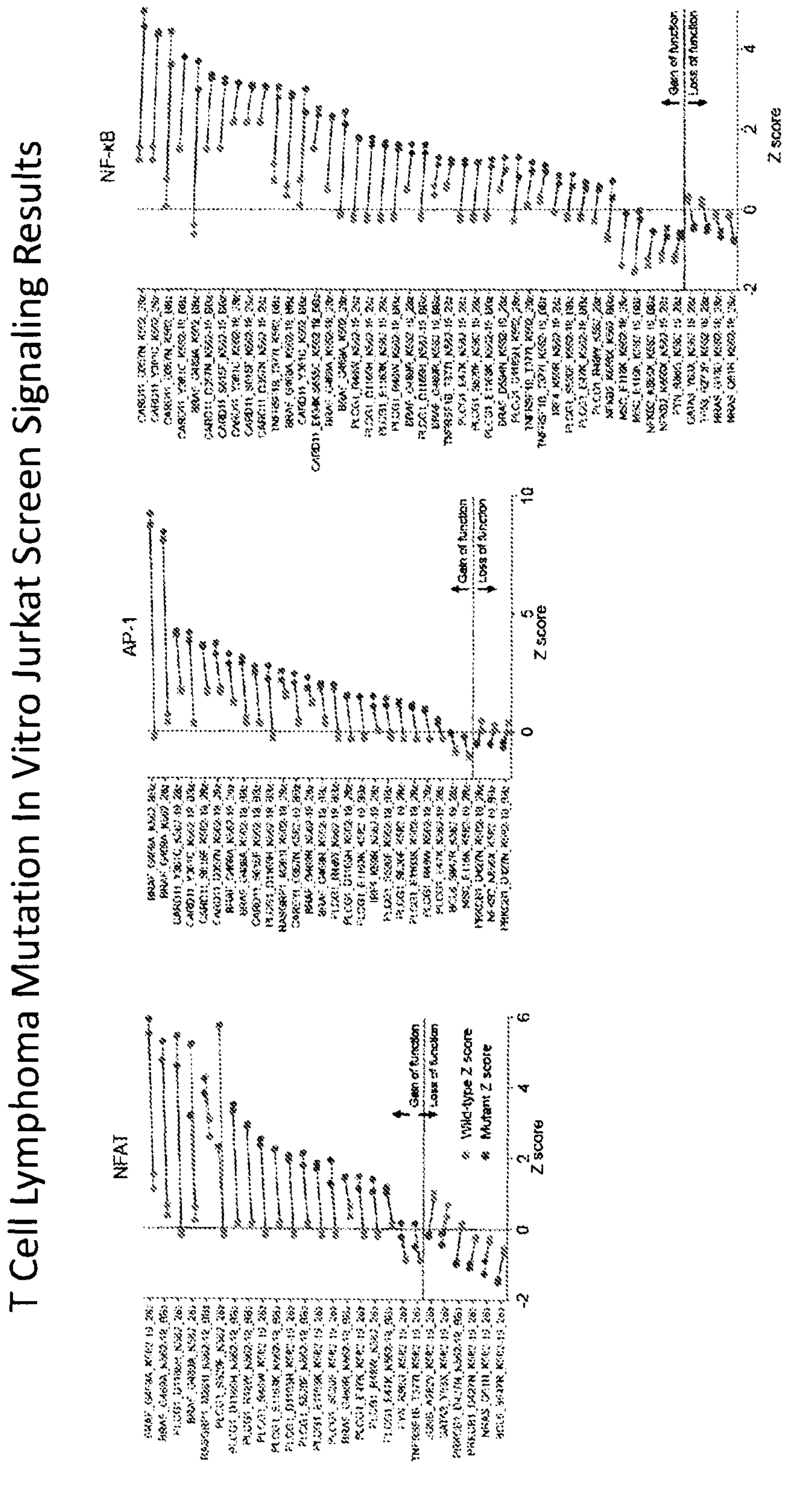
FIG. 3 shows the Z score for NFAT, AP-1 and NF-κB signaling of mutations that showed a statistically significant difference from their wildtype controls, ordering the mutations based on the Z-score from positive (top of y-axis) to negative (bottom of y-axis). This ordering demonstrates that some mutations induce a gain of function (increase the signaling output as compared to wildtype), while others cause a loss of function (reduce the signaling output as compared to wildtype).

Mutations altered signaling in ways that were unachievable via expression of the wild-type form of the gene. Twenty-five point mutation constructs showed significant differences versus their wild-type counterparts, demonstrating substantial increases or decreases of signaling endowed by the mutations not attributable to overexpression of the wild-type genes (FIG. 3). Therefore, this mutation library allows for the alteration of T cell signaling in ways that are not possible with overexpression of wild-type genes. This feature of the mutation library differentiates it from approaches were expression of wild-type genes are enhanced or elevated.

In vitro screening uncovered numerous mutations with significant impacts on CAR signaling and cytokine production. These screens were highly reproducible across two biological replicates. Similar effects were observed when mutations were paired with either the CD19-CD28z CAR or CD19-BBz CAR. Mutations previously reported to upregulate TCR dependent signaling (e.g. PLCG1) had effects that were consistent with these previous findings, suggesting our assay effectively captures known positives. In addition, expression of the negative control construct DGKZ, which encodes diacyl glycerol kinase zeta, a known inhibitor of T cell receptor signaling, significantly reduced CAR dependent signaling, as expected.

Figure 2E:
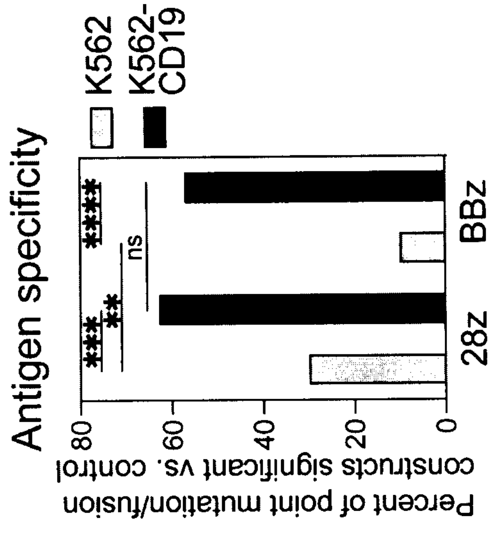
Figure 2F:
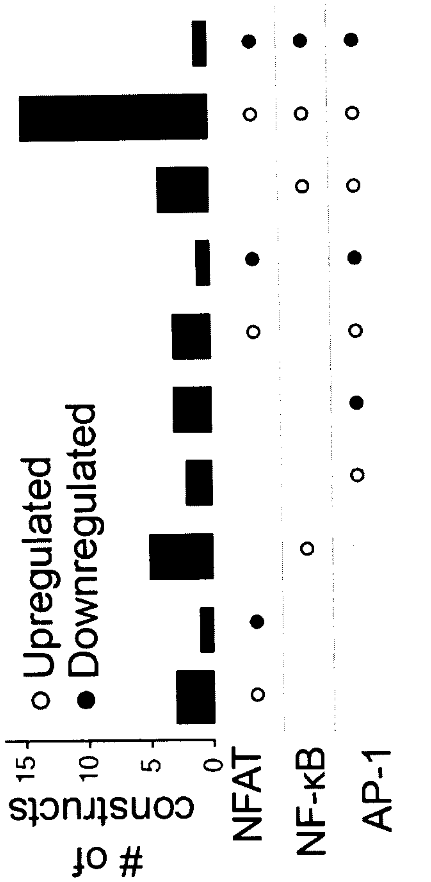

The mutation constructs showed a significant degree of antigenic specificity. For both the CD19-CD28z CAR and the CD19-BBz CAR, mutation constructs showed significantly more effects upon antigenic stimulation than in the absence of antigen (FIG. 2E).

The mutations produced a striking diversity of effects on TCR-dependent signaling (FIG. 2F). For the CD19-BBz CAR, a total of 10 different combinations of signaling pathway up- or down-regulation induced by mutations were observed. Some of these modifications may be desirable. For example, imbalances between NFAT and AP-1 signaling may contribute to T cell exhaustion. Therefore, mutations that increase AP-1 but not NFAT may be beneficial to T cell therapies. 25 mutation constructs showed significant differences versus their wild-type counterparts, demonstrating substantial increases or decreases of signaling endowed by the mutations not attributable to overexpression of the wild-type genes (FIG. 3).

Figure 2G:
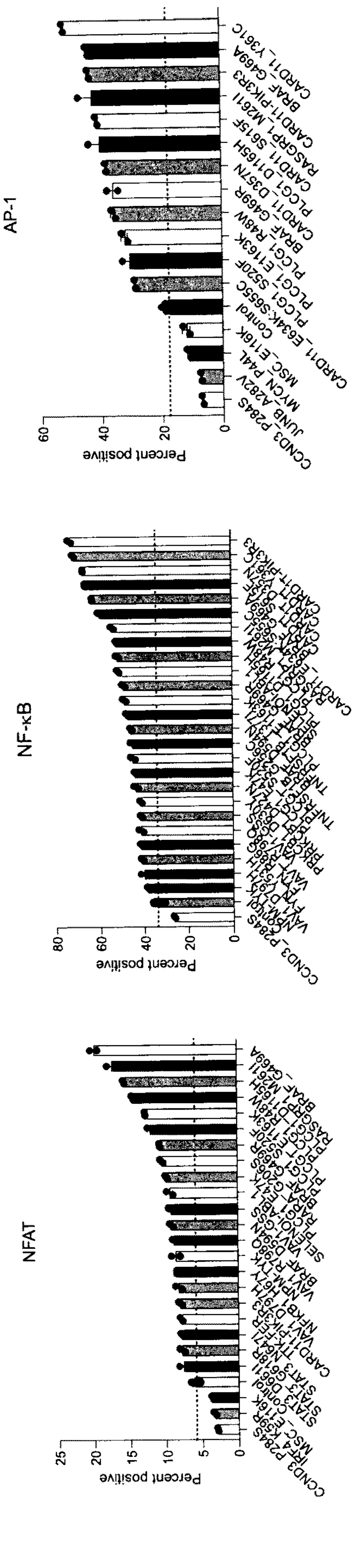

Moreover, these mutations provide effect sizes unachievable with changes in gene expression alone, enabling tunable changes over wide dynamic ranges. As an example of this tunability, AP-1 reporter expression could be tuned down or up over a range of 0.4 fold to nearly 3 fold the levels induced by CAR activation in controls (FIG. 2G).

Example 3

In Vivo Mutation Screening

Figure 4:
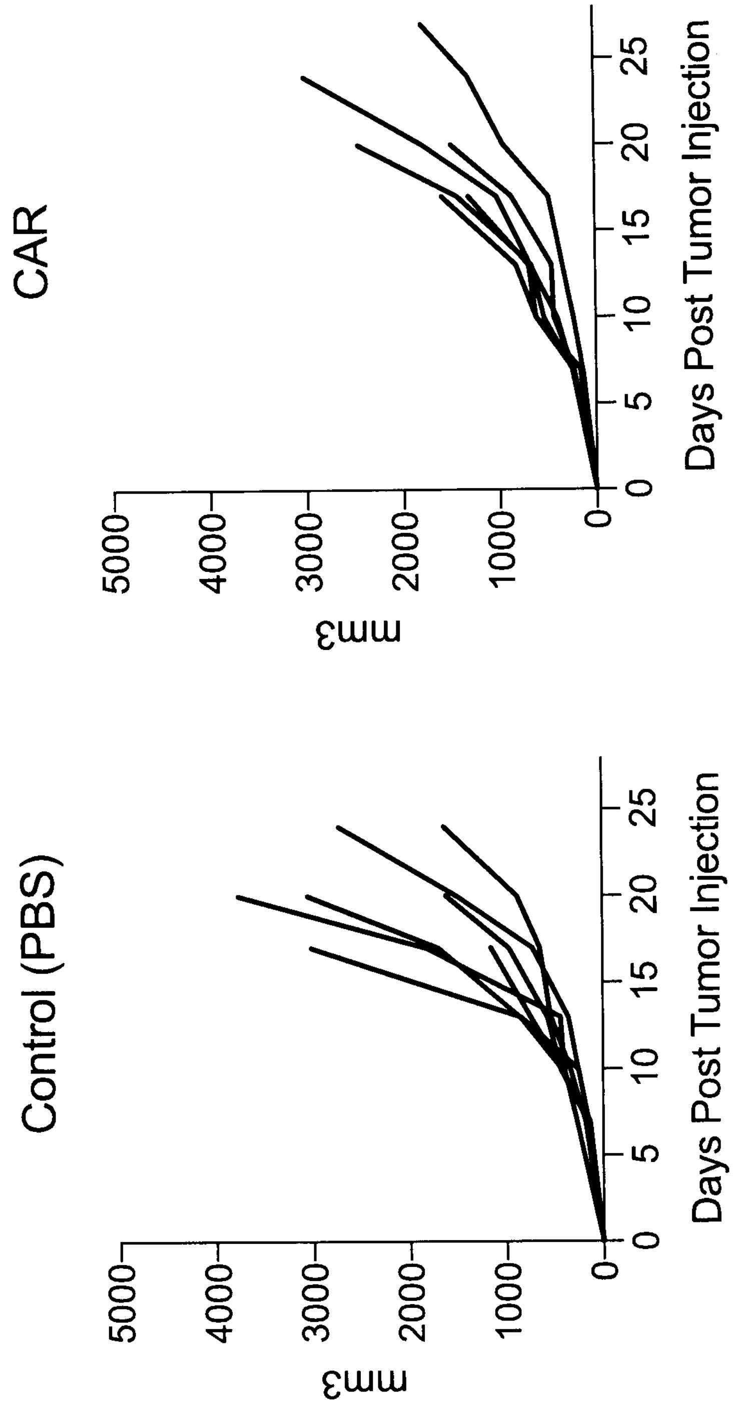
FIG. 4 shows tumor growth curves of CD19-K562 tumor bearing animals treated with PBS or CD19-BBz CAR T cells.
Figure 5A:
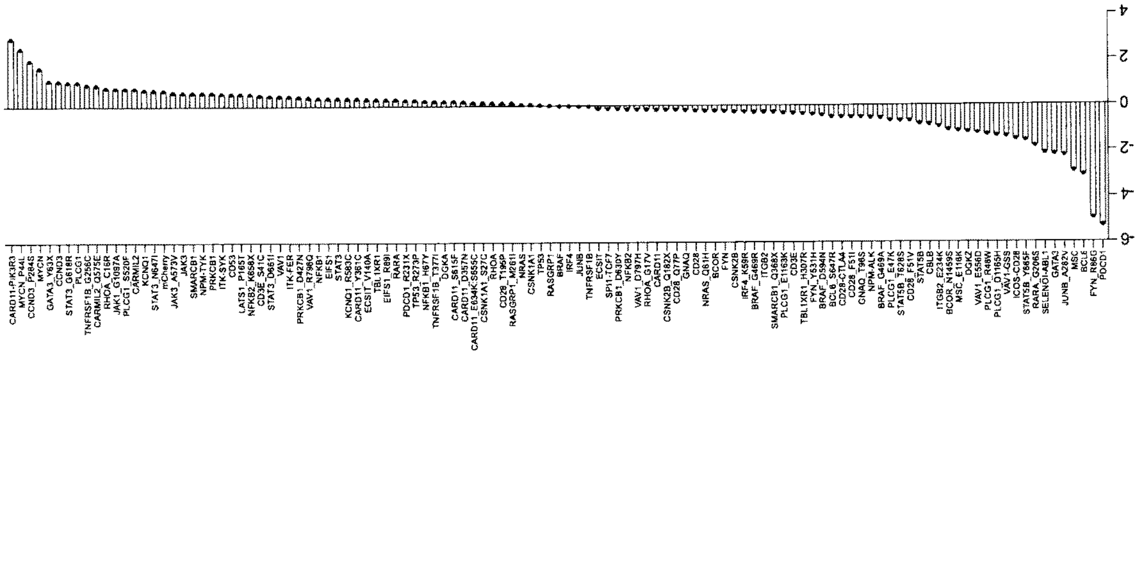
FIGS. 5A and 5B show the correlation between results of the in vivo screen and PD-1 in vitro studies on the identified mutations of the disclosure.

Next, the inventors/disclosers systematically screened T cell lymphoma mutations to identify constructs which could improve in vivo persistence of human CAR-T cells as follows. Primary human CD3+ T cells were co-transduced with a CD19-BBz CAR and T cell lymphoma mutation constructs. Cells expressing both the CAR and the mutation constructs were pooled, sorted, and then injected into immunodeficient mice bearing subcutaneous CD19-K562 tumors (FIG. 1). A sample of this pre-injection pooled library was taken for sequencing of barcodes. Barcode frequency in tumors were compared to the pre-injection T cell pool to determine constructs which were depleted or enriched in vivo. The single most depleted construct in the library was PDCD1, which encodes the co-inhibitory receptor and immunotherapy target PD-1, suggesting that the in vivo screen was able to identify therapeutically relevant targets (FIG. 5A). The K562 subcutaneous xenograft model generally shows poor T cell infiltration and persistence, and a lack of anti-tumor efficacy of CAR-T cells (FIG. 4). This model was employed to identify constructs which enable T cells to overcome the harsh solid tumor microenvironment that limits therapeutic T cell efficacy. $1\times10^6$ CD19-K562s were injected subcutaneously to NSG mice on day 0, followed by intravenous injection of $5\times10^6$ CD19-BB2 CAR cell or PBS vector control cells on Day 4. These data show that CD19-BBz CAR cells control CD19-K562 growth poorly, suggesting T cell function is limited in this model and providing rationale for using this model to screen for mutation constructs which improve T cell function. Constructs which improve the infiltration and/or persistence in this model could be valuable for improving the anti-tumor efficacy of cell therapies against solid tumors.

In vivo screening identified 35 mutation constructs with positive log 2 fold changes in vivo (FIG. 5A). Positive log 2 fold changes indicate mutations, which were enriched in tumors compared to pre-injection samples. Enrichment in tumors suggests these constructs enable T cells to accumulate or persist or expand in tumors in vivo, which is a favorable feature for cellular therapies. These include the following mutation constructs: CARD11-PIK3R3, MYCN_P44L, CCND3_P284S, GATA3_Y63X, STAT3_G618R, TNFRSF1B_G256C, CARMIL2_Q575E, RHOA_C16R, JAK1_G1097A, PLCG1_S520F, STAT3_N6471, JAK3_A573V, NPM-TYK, ITK-SYK, LATS1_P165T, NFKB2_K656X, CD3E_S41C, STAT3_D661I , ITK-FER, PRKCB1_D427N, VAV1_R798Q, KCNQ1_R583C, CARD11_Y361C, ECSIT_V140A, EIFS1_R89I, PDCD1_R231X, TP53_R273P, NFKB1_H67Y, TNFRSF1B_T377I, CARD11_S615F, CARD11_D357N, CARD11_E634K:S655C, CSNK1A1_S27C, CD28_T195P, RASGRP1_M261I.

Mutation constructs altered in vivo persistence in ways unattainable by wild-type gene overexpression (Table 3). For example, while wild-type CARD11 showed a negative log 2 fold change, the CARD11-PIK3R3 fusion and 4 CARD11 point mutations (CARD11 p.Y361C, p.S615F, p.D357N, and p. E634K:S655C) all showed positive log 2 fold change. Similarly, TNFRSF1B p.G256C and p.T377I mutation showed positive log 2 fold change while TNFRSF1B wild-type showed a negative log 2 fold change in tumors in vivo. Therefore, mutations can allow for improvement of in vivo persistence in tumors beyond the levels allowed by wild-type gene expression.

Figure 5B:
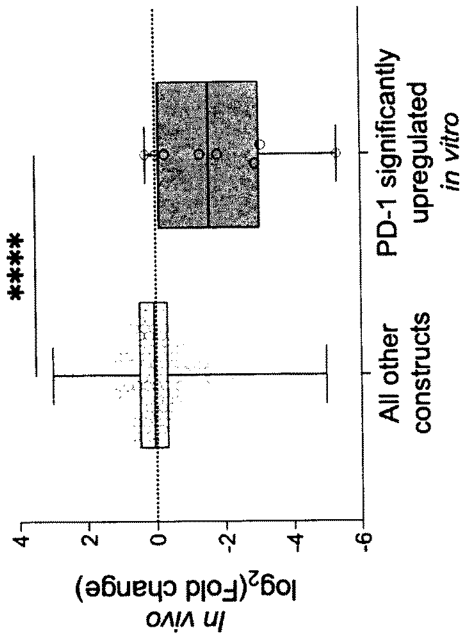

In vitro screening results showed correlation with in vivo screening results. Consistent with a role for PD-1 levels in regulating the in vivo persistence of CAR cells, staining for PD-1 in CD19-BBz CAR Jurkat cells showed that constructs which significantly upregulated PD-1 in response to antigen had worse persistence (FIG. 5B).

Example 4

Analysis of the Various Domains of the CARD11-PIK3R3 Gene Fusion

This experiment was done to elucidate which domains of the CARD11-PIK3R3 gene fusion were responsible for the gain of function of CARD11-PIK3R3.

The CARD11-PIK3R3 fusion was initially identified in a patient with CD4+ leukemic cutaneous T cell lymphoma (L. Wang et al., Genomic profiling of Sezary syndrome identifies alterations of key T cell signaling and differentiation genes. *Nature Genetics* 47, 1426-1434 (2015)).

Figure 6:
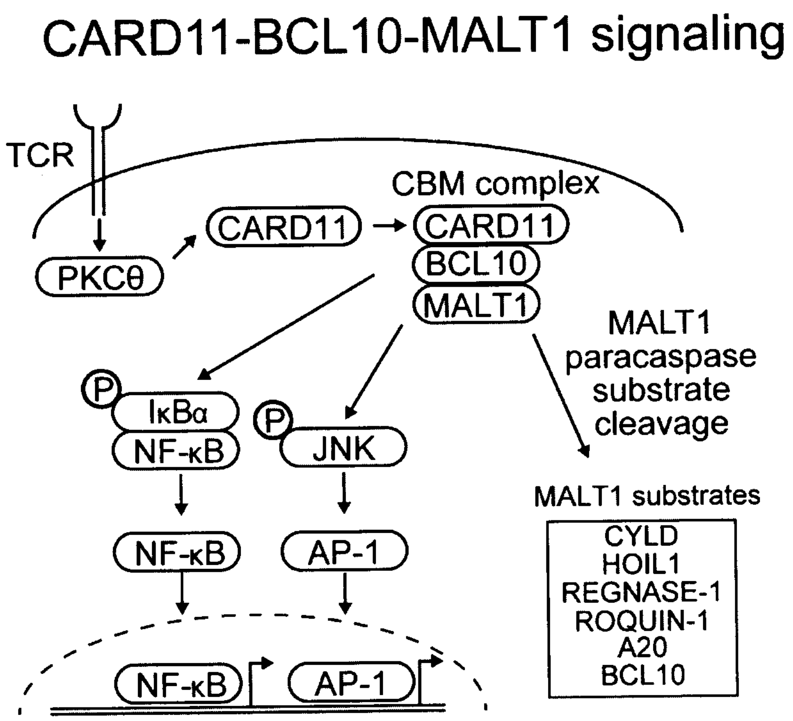
FIG. 6 is a schematic indicating signaling by the CARD11-BCL10-MALT1 (CBM) complex in T cells. In normal T cells, T cell receptor (TCR) signaling activates PKCθ, which in turn promotes the assembly of the CBM signalosome. The CBM complex subsequently has three major outputs: NF-κB transcriptional activity, AP-1 transcriptional activity and MALT1 proteolytic activity.
Figure 7:
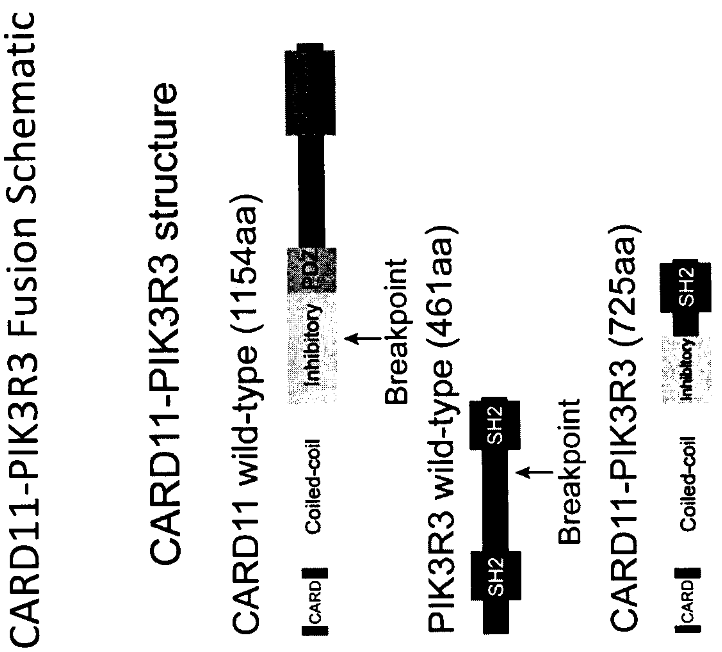
FIG. 7 shows a schematic of the CARD11-PIK3R3 fusion according to the disclosure. The topmost diagram shows the structure and domains of wild-type CARD11 comprising 1154 amino acids and the location of the breakpoint where the C-terminal component is lost and the PIK3R3 polypeptide is attached in the fusion protein. The middle diagram depicts the structure of wild-type PIK3R3 which comprises 461 amino acids and the location of the breakpoint where the C-terminal component of PIK3R3 is attached in the fusion protein. The bottom diagram depicts the CARD11-PIK3R3 fusion protein having 725 amino acids with the CARD, Coiled-coil and truncated inhibitory domains derived from the N-terminus of CARD11 and an SH2 domain derived from the C-terminus of PIK3R3. The truncation of CARD11 is at the location in the wildtype gene shown in topmost structure and labelled “Breakpoint”, and the truncation of PIK3R3 is at the location in the wildtype gene shown in the middle structure and labelled “Breakpoint”.

The product of the translocation between CARD11 and PIK3R3, (SEQ ID NO: 160) results in a gene fusion of the N-terminal CARD11 protein CARD domain, coiled-coil domain, and part of the inhibitory domain with an SH2 domain from the C-terminus of PIK3R3 (FIG. 7). Because of the important role of CARD11 in mediating antigen dependent signaling in T cells (FIG. 6) and the partial lack of inhibitory domain in the fusion protein, the CARD11-PIK3R3 fusion was tested to determine if it alters CBM complex signaling.

Figures 8A, 8B:
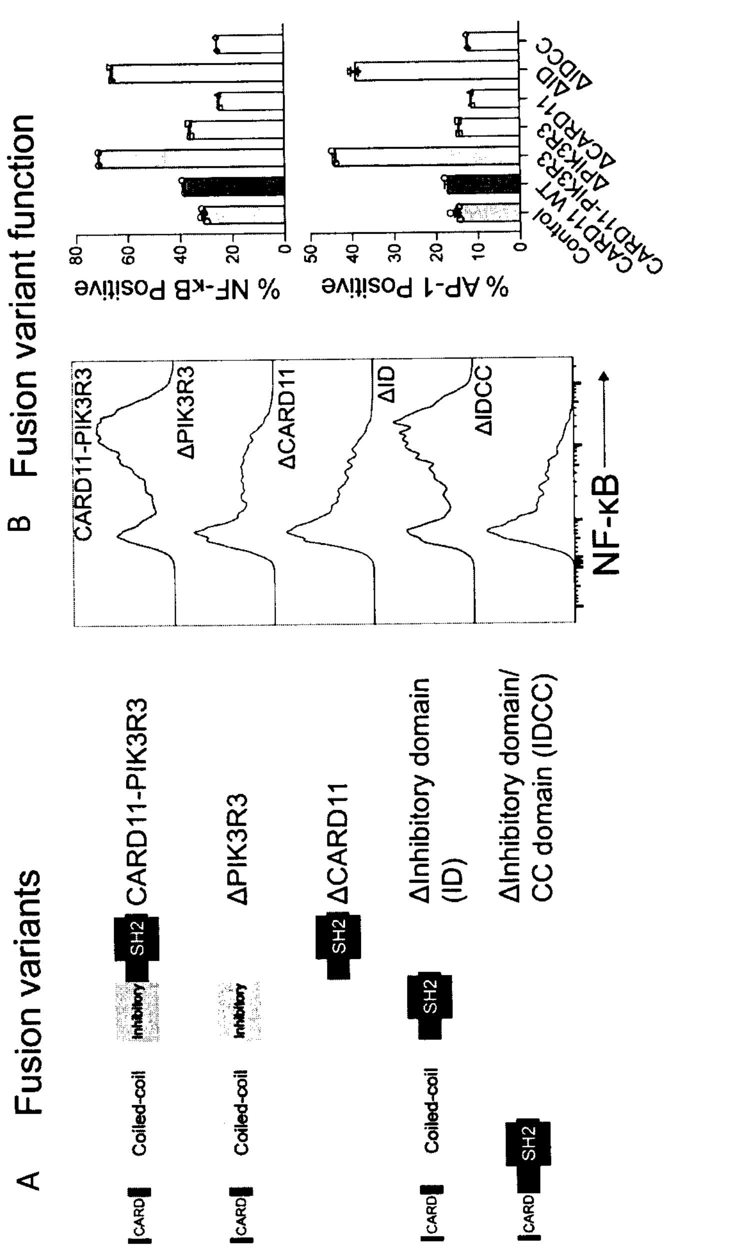
FIGS. 8A-B depict various CARD11-PIK3R3 fusion variants and their function.

The inventor/disclosers generated variants lacking specific domains and tested their ability to induce NF-κB and AP-1 signaling (FIG. 8A-8B). Deletion of the PIK3R3 component of the fusion abolished signaling activity, but the PIK3R3 component was not sufficient on its own to induce these pathways. Therefore, the CARD11-PIK3R3 fusion does not gain function simply by truncating part of the CARD11 protein, but rather requires the C-terminal PIK3R3 to activate downstream signaling cascades. The remaining part of the inhibitory domain was not required for fusion gain-of-function, however removing the coiled-coil domain or the entire CARD11 portion of the fusion component prevented function.

Example 5

Truncations of the CARD11-PIK3R3 Gene Fusion

This experiment was done to characterize the structure-function relationship of the CARD11-PIK3R3 gene fusion (SEQ ID NO: 206).

The inventors/disclosers introduced various truncations of the fusion polypeptide (SEQ ID NO: 226, 228, 230, 232, 234, 236, 238, 240, 242, 244, 246, 248, 250, 252, 254, 256) as shown in FIG. 30A. SEQ ID NOS: 226, 228, 230, 232, 234, 236, 238, 240, 242, 244, 246, 248, 250, 252, 254, 256 contain the sequence of SEQ ID NO: 206 with a 20, 40, 60, 80, 100, 120, 140, 160, 180, 200, 220, 240, 260, 280 or 300 amino acid deletion respectively. The various truncations were assessed in CD8+ CD19-BBz CAR T cells over a period of 7 days after removal from anti-CD3/anti-CD28 bead stimulation (FIG. 30B). IL-2 secretions were analyzed by ELISA after co-culturing CD19-BBz CAR CD8+ T cells with CARD11-PIK3R3 truncations at 1:1 ratio with CD19 target cells for 24 hours. CD8+ and CD19K562 populations after 14-day co-culture together without supplemental IL-2 were assessed and the results are shown in FIG. 30D. The long co-culture killing assay (FIG. 30D) demonstrated that some truncated versions of the fusion (-ID, -20, -60, -100, -140, -220) induced persistent target cell killing without IL-2 supplementation similar to that of the WT (full length) version of the fusion. In contrast, some truncated versions of the fusion (-180, -200, -260, -300) were not able to induce persistent target cell killing without IL-2 supplementation and looked more similarly to the CAR alone condition. These results indicate that the coiled-coil domain of CARD11 could be truncated without losing the established phenotype of the full-length fusion, though certain truncations lead to loss of function. Additionally, the IL-2 secretion data (FIG. 30C) indicates that only the -ID fusion variant produces similar amounts of IL-2 as compared to the WT (full length) version of the fusion (dotted line labeled WT IL-2 secretion). However, when comparing the IL-2 secretion data to the long co-culture killing data, the inventors/disclosers hypothesize that there is a minimum threshold of IL-2 secretion required to observe the long co-culture killing without IL-2 phenotype. In FIG. 30C this minimum threshold is indicated with a labeled dotted line. The fusion variants that were unable to killing CD19-K562 targets in the long co-culture killing without IL-2 assay (FIG. 30D) are the variants that fall below the hypothesized IL-2 secretion minimum threshold in FIG. 30C.

Example 6

CARD11-PIK3R3 Promotes Assembly and Signaling of the CBM Complex

Figure 9A:
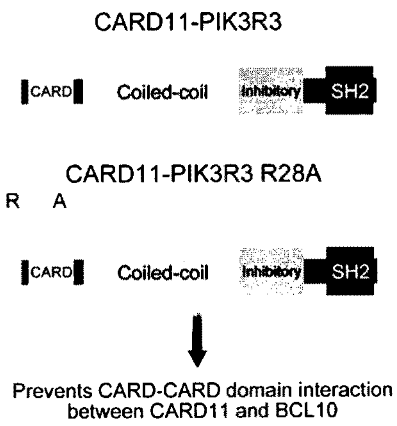
FIGS. 9A-C illustrate CARD11-PIK3R3 fusion function in the CBM complex.
Figure 9B:
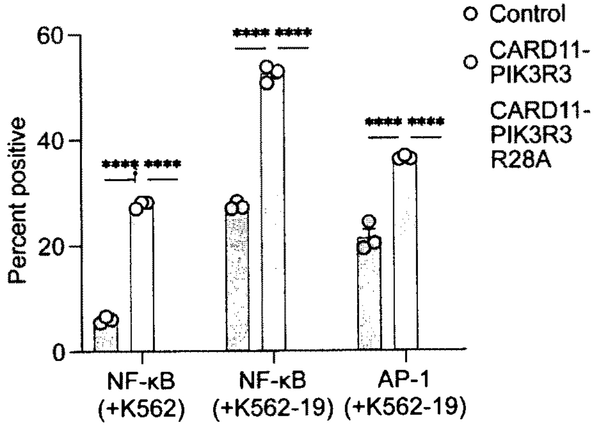
Figure 9C:
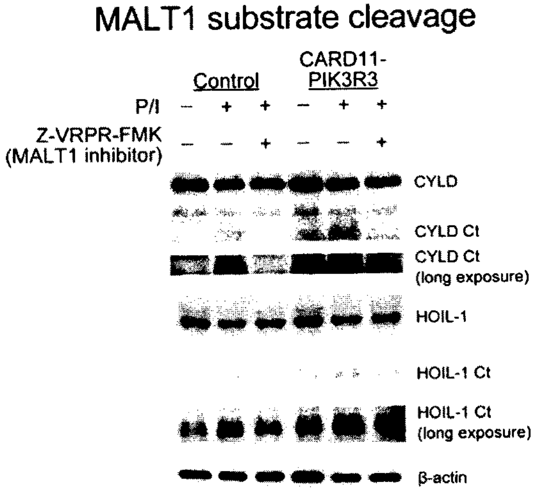

To test whether CARD11-PIK3R3 promotes assembly and signaling of the CBM complex through binding to BCL10, a mutant version of CARD11-PIK3R3 was generated with an amino acid substitution (R28A) at the BCL10 binding interface of the CARD domain of CARD11, previously reported to be essential for CARD11-BCL10 binding. It was observed that BCL10 binding was important for both tonic NF-κB and CAR signaling induced NF-κB and AP-1 (FIGS. 9A and 9B). In addition, western blotting of canonical MALT1 substrates CYLD and HOIL-1 indicated increased tonic and stimulation-induced cleavage of these proteins in the presence of the fusion (FIG. 9C). MALT1 inhibitor treatment demonstrated cleavage of these proteins was indeed MALT1 dependent (FIG. 9C). Altogether, these data indicated that the CARD11-PIK3R3 fusion protein enhances CBM complex signaling.

To test whether CARD11 or BCL10 were required for the function of CARD11-PIK3R3, CRISPR knockout experiments were performed. CRISPR/Cas9 was used to knock out CARD11 or BCL10 in the BBz-CAR Jurkat signaling cell line. In unstimulated, CAR-stimulated, and pharmacological TCR stimulated conditions, a reliance of CARD11-PIK3R3 on BCL10 but not wild-type CARD11 was observed (FIG. 38). In contrast, control cells relied on both CARD11 and BCL10 for TCR-triggered activation of NF-κB as expected. Interestingly, cells lacking CARD11-PIK3R3 did not depend on either CARD11 or BCL10 for CAR-dependent signaling, indicating that CBM may not be optimally engaged during CAR-T cell signaling (FIG. 38).

Example 7

Effects of CARD11-PIK3R3 Expression on Signaling in Primary Human T Cells

This example was to examine CARD11-PIK3R3 fusion expression in primary human T cells.

Figure 10A:
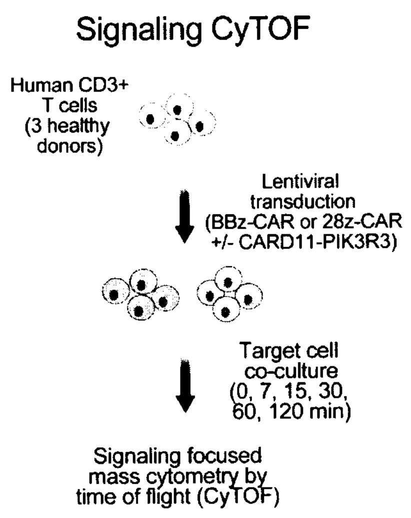
FIGS. 10A-B show CARD11-PIK3R3 fusion phosphorylation signaling dynamics.
Figure 10B:
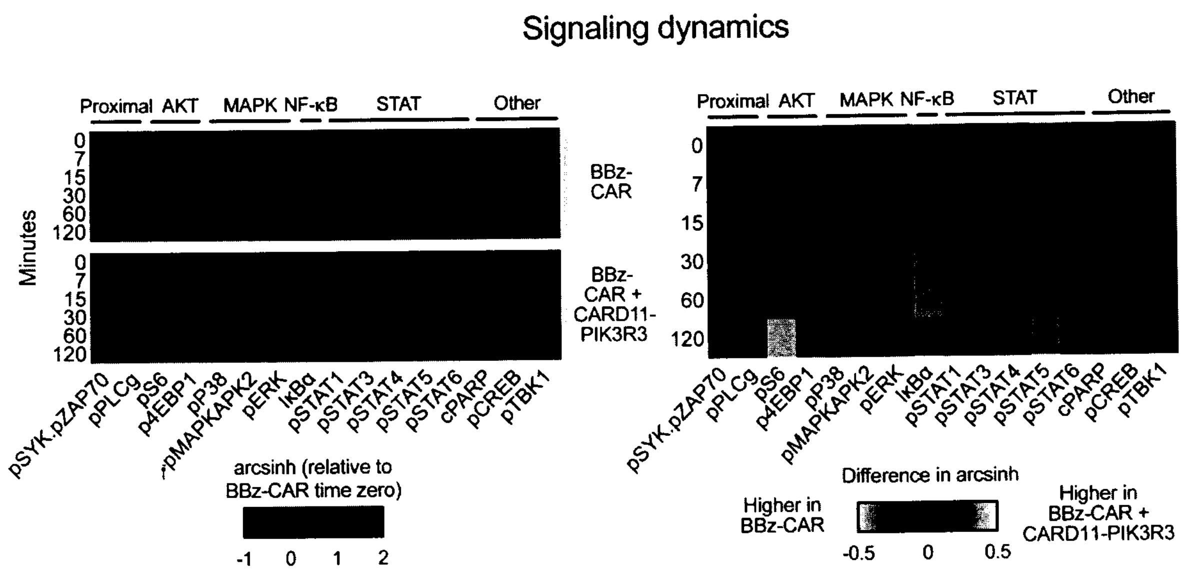

Human CD3+ T cells from three healthy donors were lentivirally transduced with CD19-CD28z or BBz CARs, with or without the CARD11-PIK3R3 fusion. CAR T cells were analyzed by CyTOF at 0, 7, 15, 30, 60, and 120 minute time points of co-culture with CD19 expressing cells (FIG. 10A). Consistent with activation of NF-κB signaling induced in Jurkat cells, both CD19-CD28z and CD19-BBz CAR cells expressing the CARD11-PIK3R3 fusion displayed significantly reduced levels of IκBα, a negative regulator of NF-κB which is degraded downstream of CBM complex activation (FIG. 10B). Furthermore, CD19-BBz CAR cells showed enhanced signaling through two pathways downstream of the CBM complex, PI3K/Akt (p4EBP1) and MAPK, though these were not significantly different in CD19-CD28z CAR cells. Consistent with signaling differences being mediated through the fusion itself and not differences in transduction from the CAR, no differences were observed in proximal signaling events.

This data indicated that CARD11-PIK3R3 expression altered downstream signaling events in primary cells following CAR engagement.

Example 8

CARD11-PIK3R3 Enhances Gene Expression

Figures 11A, 11B, 11C:
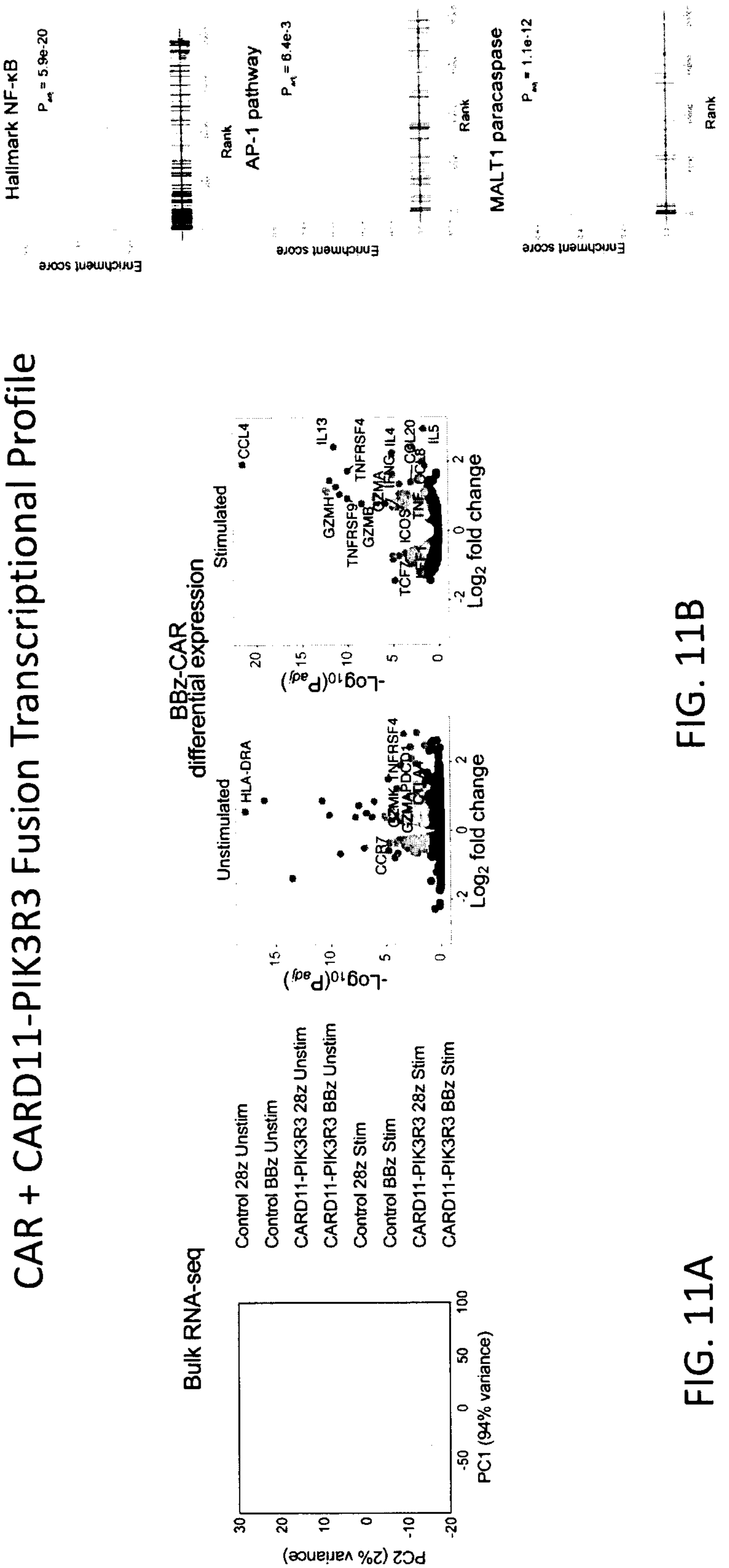
FIGS. 11A-C show CARD11-PIK3R3 fusion transcriptional landscape.

To examine potential difference in gene expression, bulk RNA-sequencing of human CD8+ T cells from three healthy donors was performed with and without CAR stimulation through co-culture with CD19 expressing targets. Principal component analysis revealed strong transcriptional differences due to stimulation, but minimal global differences in the transcriptomes of CARD11-PIK3R3 cells from controls (FIG. 11A). Differential expression analysis revealed that genes significantly upregulated in CARD11-PIK3R3 CD19-BBz CAR cells compared to controls in the stimulated state were genes normally induced in control cells by CAR signaling, that were enhanced in the presence of the fusion (FIG. 11B). This suggests that rather than inducing an entirely distinct transcriptional state, CARD11-PIK3R3 expression augments the expression of a subset of CAR induced genes. These include activation markers (IL2RA, CD69), cytotoxic and effector molecules (IFNG, TNF, IL4, IL5, IL13, GZMA, GZMB), chemokines (CCL4, CCL20, CCL8), and co-stimulatory molecules (ICOS, OX40, 4-1BB, GITR). Consistent with the inventors/disclosers' biochemical analyses, gene set enrichment utilizing a previously reported set of genes which are downregulated in response to MALT1 paracaspase inhibition in human T cells revealed significant enrichment of these genes in CARD11-PIK3R3 expressing cells, as well as NF-κB and AP-1 induced genes (FIG. 11C).

RNA-sequencing of human CD4+ and CD8+ T cells from three healthy donors, with and without antigen stimulation (Supplemental Table 2). Principal component analysis demonstrated the most dramatic transcriptional differences were induced by CAR-dependent stimulation, suggesting that CARD11-PIK3R3 expression is not sufficient to cause primary cells to adopt a fully antigen activated phenotype (FIG. 39A). By comparing transcripts upregulated in both CD4+ and CD8+ T cells upon CAR stimulation, we identified a core group of 43 genes modulated by CARD11-PIK3R3 (FIG. 39B) These included several transcripts with important roles in CAR T cell function and effector cytokine production (FIG. 39B), including activation markers (IL2RA), cytotoxic and effector molecules (IFNG, TNF, IL4, IL5, IL13), chemokines (CCL4), and co-stimulatory molecules (ICOS, TNFRSF4[OX40]). Several of these genes, such as ICOS48 and OX4049, have been previously suggested to favorably impact anti-tumor responses. Interestingly, CARD11-PIK3R3 expressing CD4+ T cells were enriched for gene signatures related to cell cycle as compared to CD8+ T cells, which were enriched most for RNA metabolism, cytokine signaling, and translation signatures (FIG. 39C). Consistent with our biochemical analyses, gene set enrichment identified enrichment of NF-κB, AP-1, and MALT1 paracaspase signatures (FIG. 39C).

Example 9

CARD11-PIK3R3 Provides Proliferative Advantage to CD3 T Cells

The following experiment shows how increased CBM complex signaling affects the activation state and effector phenotypes in primary CAR T cells.

Figure 12A:
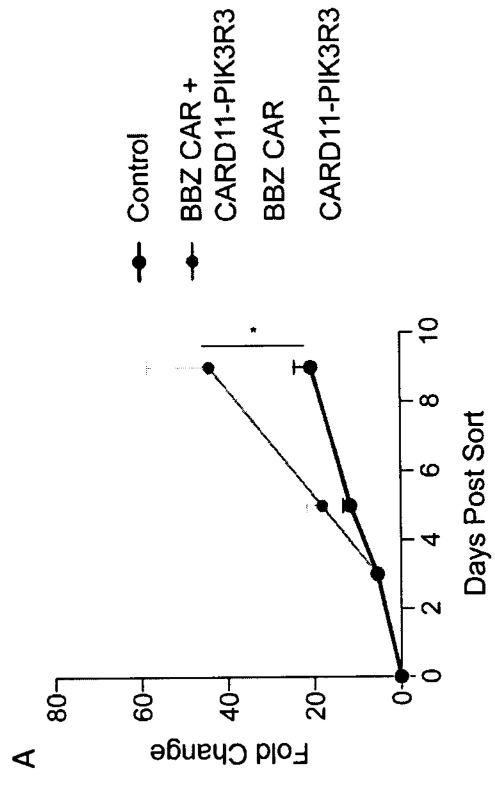
FIGS. 12A-B show the results of experiments of CD3+ T cell growth after anti-CD3/anti-CD28 bead stimulation. Cells counts of CD19-BBz CAR (FIG. 12A) or CD19-CD28z CAR (FIG. 12B) CD3+ T cells over a period of 9 days after removal from anti-CD3/anti-CD28 bead stimulation. Ns indicates not significant, * indicates P value<0.05.
Figure 12B:
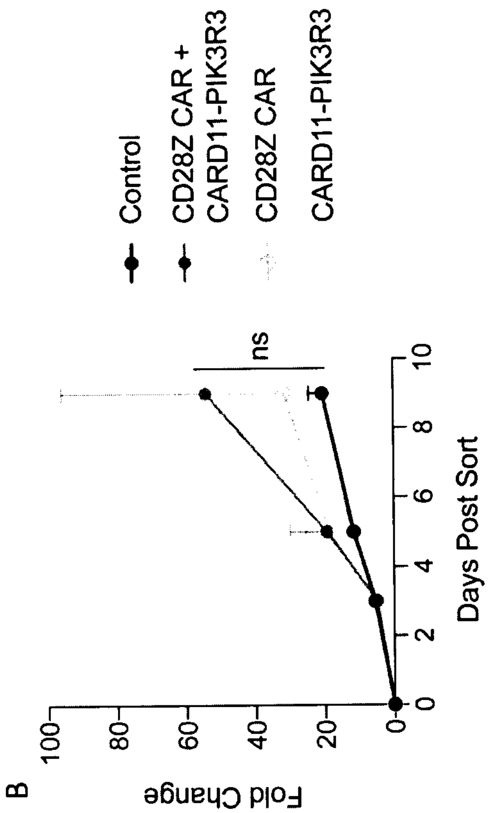

Primary T cells were co-transduced with a CD19-BBz or CD19-CD28z CAR and the CARD11-PIK3R3 fusion protein. After removing anti-CD3/CD28 beads and sorting for a purified population, cells were expanded and rested in culture for approximately one week. In transduced CD3 T cells, greater expansion of CD19-BBZ CAR with CARD11-PIK3R3 T cells was observed as compared to the CD19-BBz CAR T cells alone (FIG. 12A). However, this observation was not replicated in the CD19-CD2z T cell only population (FIG. 12B), suggesting the fusion provides a proliferative advantage particularly when paired with a BBz CAR.

Further experiments were performed to determine if CARD11-PIK3R3 could induce cytokine independent growth in primary CAR T cells. To do so, we co-transduced primary T cells with a CD19-BBz-CAR and CARD11-PIK3R3. After removing anti-CD3/CD28 stimulation and sorting for a purified population, cells were expanded and rested in culture with IL-2. CARD11-PIK3R3 improved the expansion of CAR-T cells in the presence of IL-2, however removal of IL-2 either early or late in the culture led to rapid T cell population contraction (FIGS. 46A-46C).

Example 10

Antigen-Induced Activation States

To assess antigen-induced activation states, CD8+ T cells were co-cultured with K562-CD19 targets for 24 hours, and then assessed the expression of activation markers via flow.

Figures 14A, 14B, 14C:
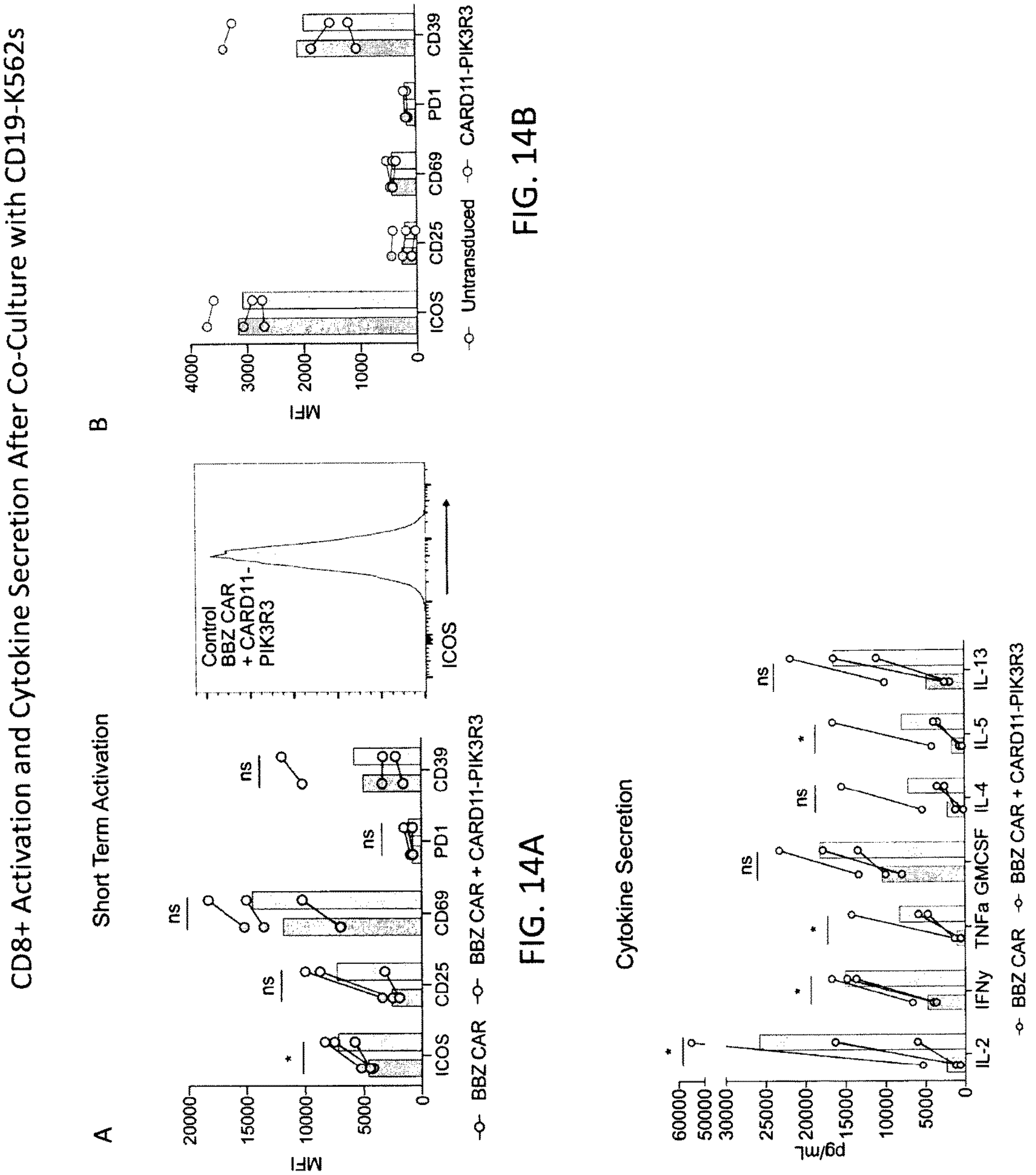
FIGS. 14A-C shows activation and cytokine secretion of CD8+ T cells after co-culture with CD19-K562s.

Most short term activation markers (CD25, CD69, PD-1, CD39) by both CD19-BBz CAR T cells and CD19-BBz CAR with CARD11-PIK3R3 fusion protein T cells were upregulated (FIG. 14A). Consistent with the bulk RNAseq data, ICOS was found to be significantly upregulated in CD19-BBz CAR with CARD11-PIK3R3 fusion T cells as compared to CAR T cells alone. These observations were similar in the CD19-CD28z CAR setting. Interestingly, while Jurkat signaling data suggested that the CARD11-PIK3R3 fusion protein leads to higher basal expression of NF-κB, the inventors/disclosers did not find that CD8+ T cells expressing only the CARD11-PIK3R3 fusion had significantly higher expression of activation markers as compared to control (untransduced) T cells (FIG. 14B). This suggested that while the fusion does induce some basal NF-κB signaling, it is not significant enough to cause antigen independent activation of the cell.

Further experiments were performed using both CD8+ and CD4+ T cells. Equivalent expression of some activation markers (PD-1, CD39) in CD19-BBz-CAR T cells with and without CARD11-PIK3R3 was observed (FIG. 40). Consistent with the bulk RNAseq data, CD25 (IL2RA) and ICOS were found to be significantly upregulated in CARD11-PIK3R3 CD19-BBz CAR T cells as compared to CAR T cells alone (FIG. 40).

Example 11

CARD11-PIK3R3 Upregulated Cytokines

This Example shows how CARD11-PIK3R3 upregulates various cytokines.

Bulk RNAseq analysis of activated CD19-BBz CAR with CARD11-PIK3R3 fusion T cells identified numerous upregulated cytokines (TNFα, IFN-γ, IL-5, and IL-13).

Figure 13A:
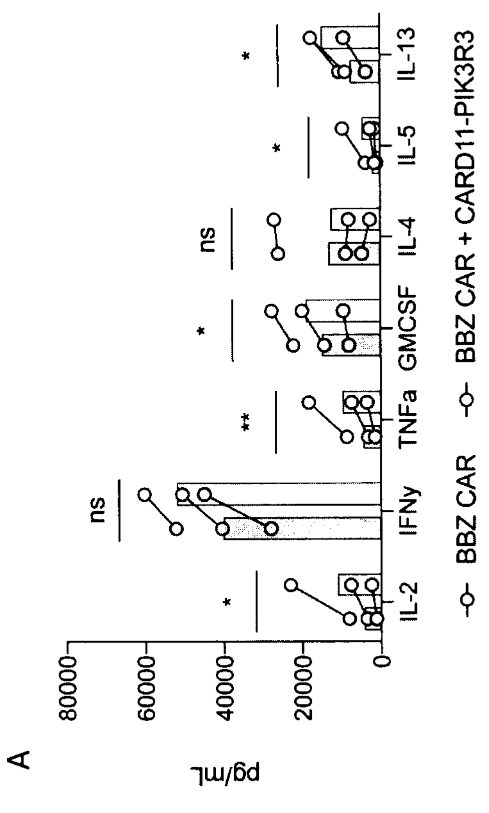
FIGS. 13A-B show CD3+ cytokine secretion after co-culture with CD19-K562s. Cytokine secretion profiles of CD19-BBz CAR (FIG. 13A) or CD19-CD28z CAR (FIG. 13B) CD3+ T cells co-cultured for 48 hours at 1:1 ratio with CD19-K562s. P values determined by ratio paired T test. Ns indicates not significant, * indicates P value<0.05, ** indicates P value<0.01.
Figure 13B:
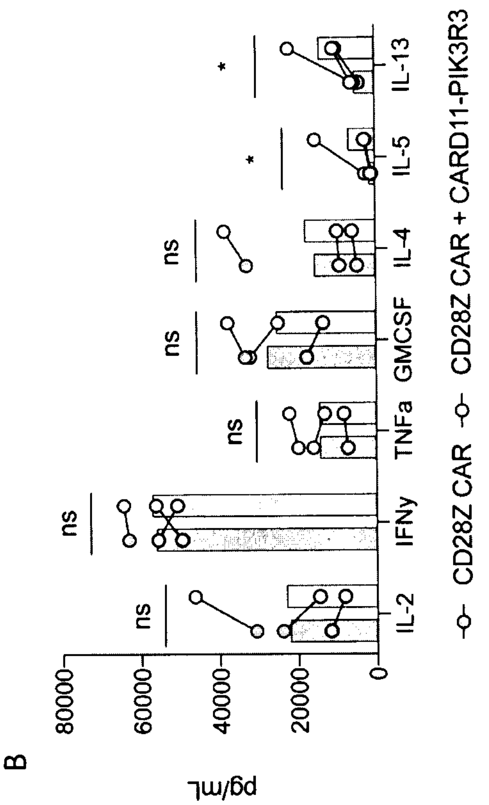

To confirm these findings at the protein level the inventors/disclosers co-cultured transduced CD8+ T cells with CD19-K562 targets for 48 hours and assessed the supernatant for a variety of cytokines. Verifying the Jurkat ELISA results, they found that the CARD11-PIK3R3 fusion induced higher secretion of IL-2, in addition to other inflammatory cytokines such as IFN-γ, TNFα and GMCSF (though not significantly increased) (FIG. 14C). Surprisingly, while cytokine secretion was substantially increased in CD8+ CARD11-PIK3R CAR T cells, this was less so in CD4+ CARD11-PIK3R CAR T cells, despite being originally observed in a CD4+ T cell cancer (FIG. 41) Interestingly, Th2 cytokines IL-5 was also significantly increased by expression of the fusion, indicating that the fusion induces a unique cytokine profile. Similar trends were observed in CD8+ T cells with the CD19-CD282 CAR and bulk CD3 T cells with either CD19-BBz or CD19-CD28z CAR, however in some cases the increase observed in fusion transduced cells was not significant (FIG. 13A-B).

Example 12

CARD11-PIK3R3, Cytotoxicity, and Growth

To understand how the expression of the CARD11-PIK3R3 fusion shaped CAR T cell cytotoxicity and growth, the following experiment was conducted.

Figures 15A, 15B:
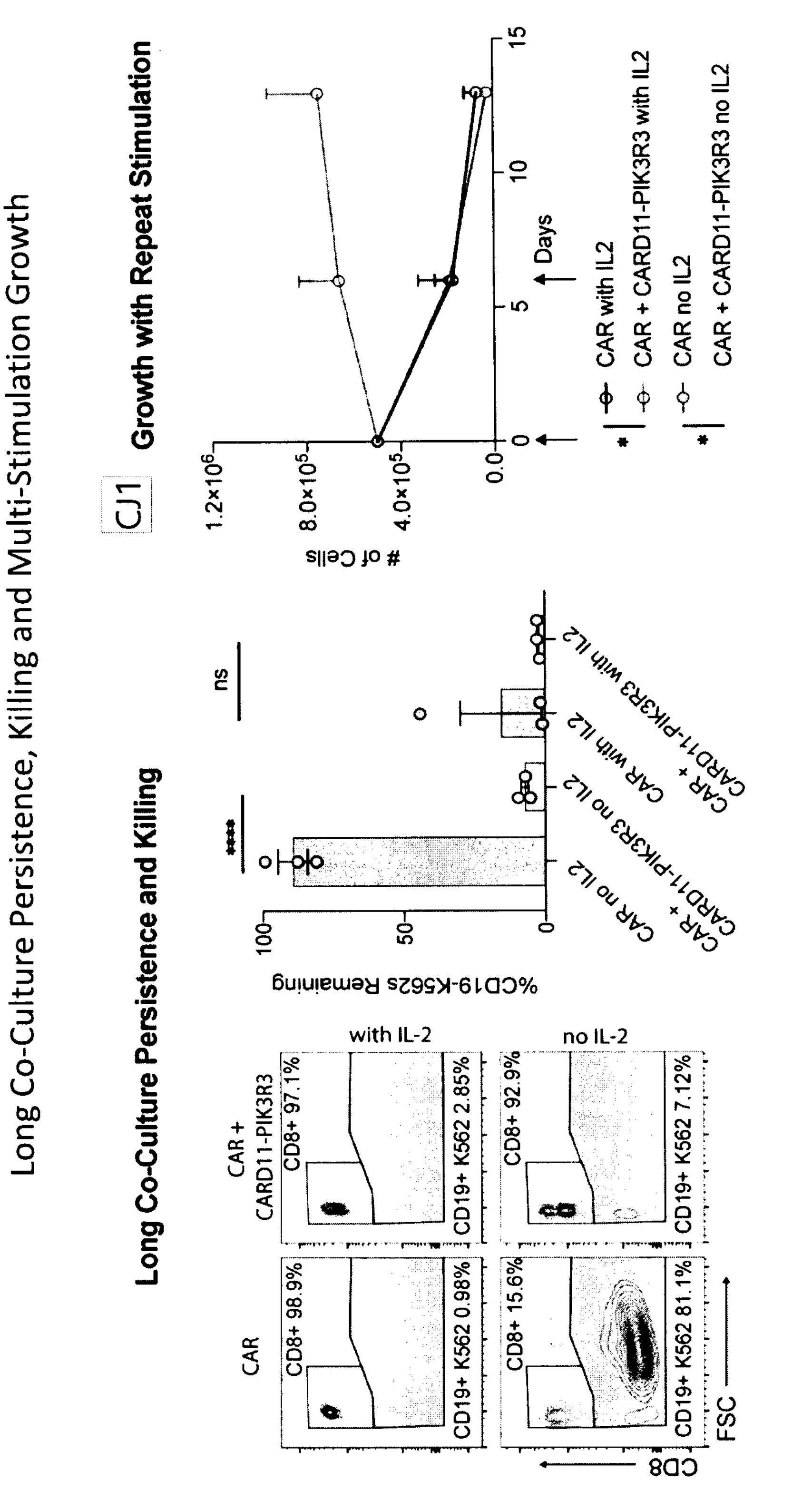
FIGS. 15A-B show the results of experiments on long co-culture persistence, killing and multi-stimulation growth.

As tumor microenvironments often lack pro-survival signaling required by cytotoxic T cells, such as IL-2, the inventors/disclosers did experiments to reveal how the CARD11-PIK3R3 fusion would affect engineered T cell killing in a state of IL-2 starvation. A long-term assay was set up, where transduced T cells were mixed with CD19-K562s at a 1:1 ratio and maintained in culture for two weeks with or without supplemental IL-2. Interestingly, after two weeks of culture both the CD19-BBz CAR alone and CAR with CARD11-PIK3R3 were able to efficiently clear the CD19-K562 targets, however when cultured without supplemental IL-2, only the CD19-BBz CAR with CARD11-PIK3R3 was able to efficiently clear the CD19-K562 targets (FIG. 15A). Less dramatic differences in killing were observed for the CD19-CD282 CAR in the long co-culture killing assay.

Figures 16A, 16B:
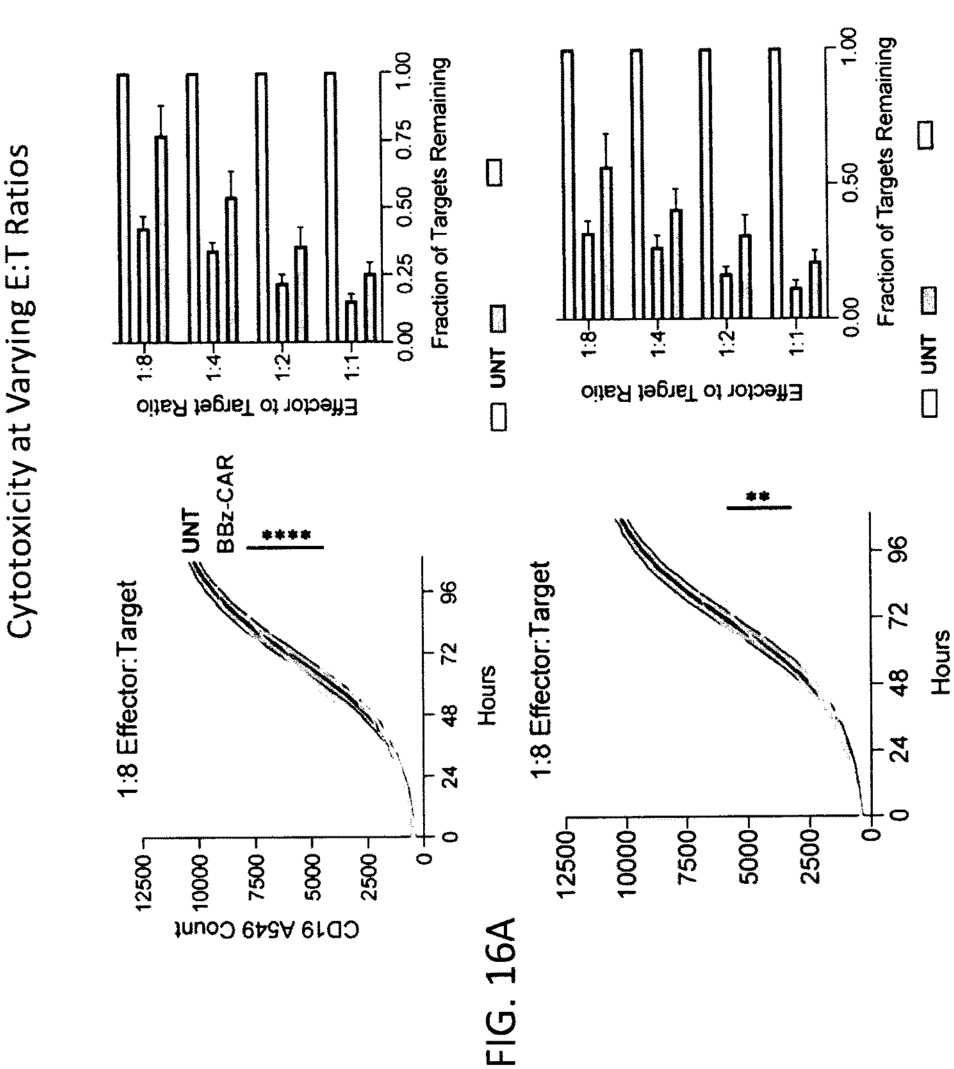
FIGS. 16A and B show cytotoxicity at varying effector to target ratios. Growth of CD19-A549 mKate2+ targets co-cultured with CD19-BBz CAR (A) or CD19-CD28z CAR (B) CD8+ T cells over 108 hour period. Bar graph indicates target cell counts at hour 108, standardized to control. P values calculated by 1-way ANOVA followed by Tukey's multiple comparison test.  indicates P value<0.01, ** indicates P value<0.0001.

When stimulated twice in a two-week period, the inventors/disclosers noticed that regardless of supplemental IL-2, the CD19-BBz CAR alone decreased in numbers, while the CD19-BBz CAR with CARD11-PIK3R3 efficiently expanded (with IL-2), or maintained a higher number of cells (without IL-2) over time (FIG. 15B). Finally, the inventors/disclosers assessed target killing at varying ratios over time and found that at every ratio tested, the CD19-BBz CAR with CARD11-PIK3R3 better controlled target cell growth as compared to the CD19-BBz CAR alone (FIG. 16). Similar trends were noted for CD19-28z CAR with and without the CARD11-PIK3R3 fusion.

Example 13

CARD11-PIK3R3 Improves Fitness, Function and Efficacy of Therapeutic T Cells

This Example showed how the CARD11-PIK3R3 fusion improved the fitness, function, and efficacy of therapeutic T cells in a fully immunocompetent, syngeneic setting.

Figure 23:
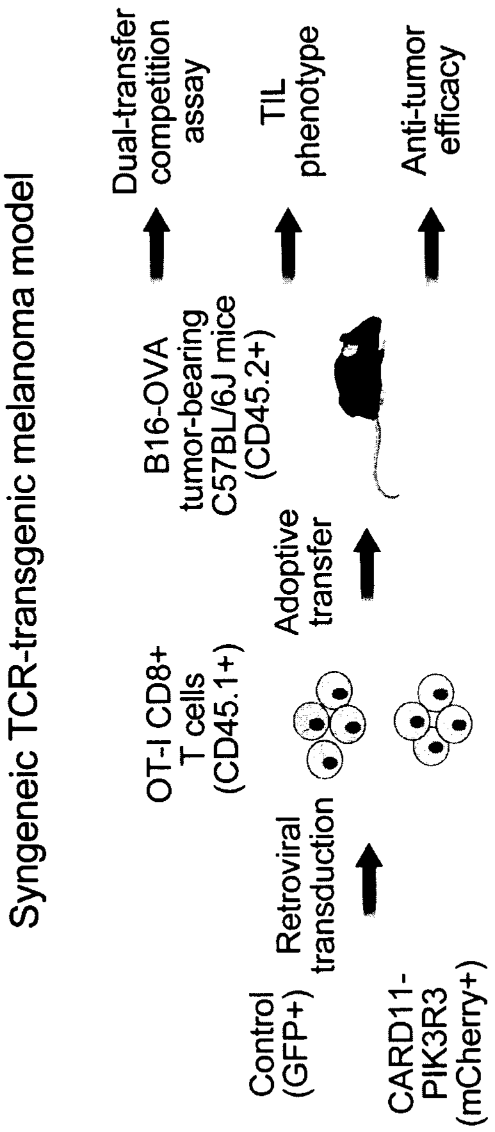
FIG. 23 is a schematic indicating the syngeneic TCR-transgenic Melanoma Model used to assess CARD11-PIK3R3 therapeutic function in T cells in vivo OT-I CD8+ T cells=T cells collected from CD45.1 C57BL/6-Tg(TcraT-crb)1100Mjb/J mice.

Transgenic TCR-expressing murine OT-I CD8+ T cells, which are specific for chicken ovalbumin (OVA), were collected from CD45.1 C57BL/6-Tg(TcraTcrb) 1100Mjb/J (OT-I) mice. These cells were used in B16-OVA mouse model, in which B16 melanoma cells express the OVA antigen (FIG. 23).

Figure 24A:
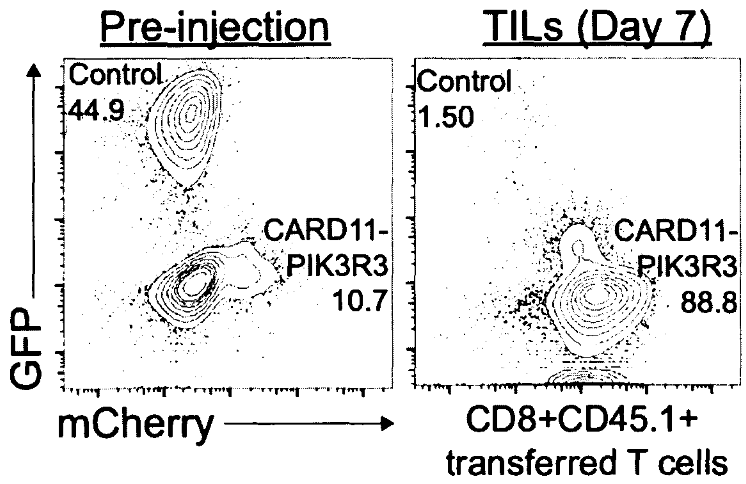
FIGS. 24A-B shows that CARD11-PIK3R3 OT-I cells preferentially expand and accumulate in tumors. It shows accumulation of TILs in the dual-transfer competition assay 7 days post T cell transfer.
Figure 24B:
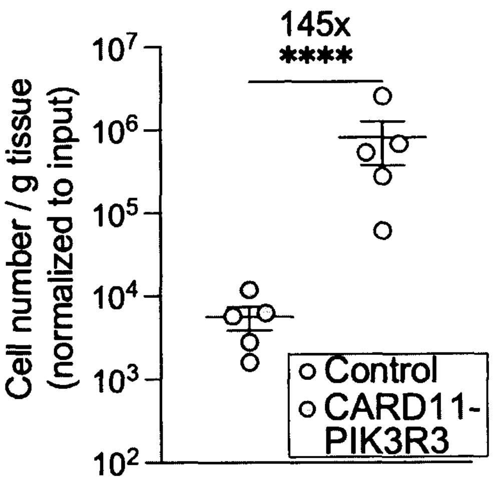

CD45.1+ OT-I CD8+ T cells were transduced with either control (GFP+) or CARD11-PIK3R3 (mCherry+) retroviruses, enabling tracking of adoptively transferred cells in CD45.2+ C57BL/6J hosts bearing B16-OVA melanoma tumors. To analyze in vivo accumulation, a dual-transfer system was used in which competition between transferred T cells in the same tumor can be determined. The inventors/disclosers generated a mixture of CD45.1+ OT-I T cells in which approximately 10% of the cells were mCherry positive (corresponding to CARD11-PIK3R3 expressing cells) to directly compare in vivo to GFP+ control cells. Strikingly, a ~145 fold increase in cell number (normalized to input) of CARD11-PIK3R3 expressing cells was observed compared to control cells among the TILs 7 days following transfer (FIGS. 24A and B).

We confirmed enhanced competitive accumulation of CARD11-PIK3R3 in a second transgenic TCR mouse model, pmel-1 T cells (which recognize gp100, an endogenous melanoma antigen) against B16-F10 tumors (FIGS. 48A-48C). We performed this assay with both the wildtype CARD11-PIK3R3 and the R28A mutant to assess the dependence of the in vivo phenotypes on BCL10 interactions. Mutating the R28A binding site reduced accumulation in vivo by 1257-fold (FIGS. 48A-48C).

This corresponded to a significantly increased fraction of transferred cells among total CD8+ T cells, even without normalization to input numbers. Therefore, within the same tumor microenvironment, CARD11-PIK3R3 expressing T cells have dramatically improved accumulation compared to control cells.

Example 14

Characterization of the Phenotype of Cells Following Adoptive Transfer of CARD11-PIK3R3

The following test was used to characterize the phenotype of cells following adoptive transfer of either CARD11-PIK3R3 or control transduced OT-I cells.

Figure 25:
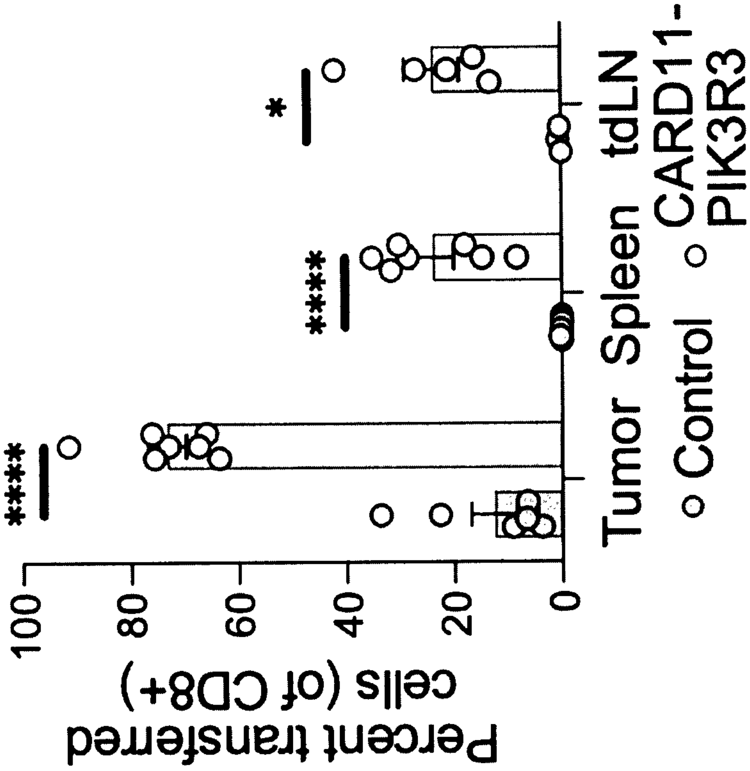
FIG. 25 shows accumulation of CARD11-PIK3R3 OT-I in tumor, spleen and draining lymph node 7 days post transfer of $1\times10^6$ CARD11-PIK3R3 or control OT-Is. P values determined by unpaired T test. * indicates P value<0.05, **** indicates P value<0.0001.

In accordance with the data obtained from the competitive dual-transfer assay, there was also enhanced accumulation of CARD11-PIK3R3 expressing cells in the tumor when transferred separately. In addition, the inventors/disclosers detected a higher proportion of CARD11-PIK3R3 OT-I cells compared to control OT-I cells in the spleen and tumor draining lymph node, though to a lesser extent than observed in the tumor. (FIG. 25)

Example 15

Effector Functions of CARD11-PIK3R3

The following test was used to characterize the effector functions of the CARD11-PIK3R3 fusion protein.

Figure 26A:
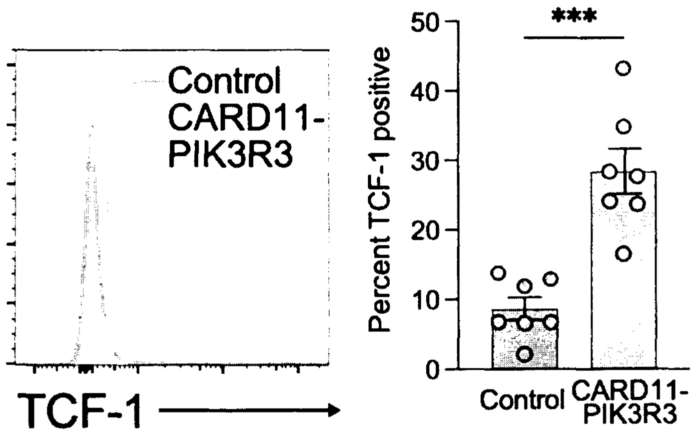
FIG. 26A shows TCF-1 expression in OT-I+CARD11-PIK3R3 TILs. TCF-1 expression of TIL cells 7 days post transfer of $1\times10^6$ CARD11-PIK3R3 or control OT-Is.
Figure 26B:
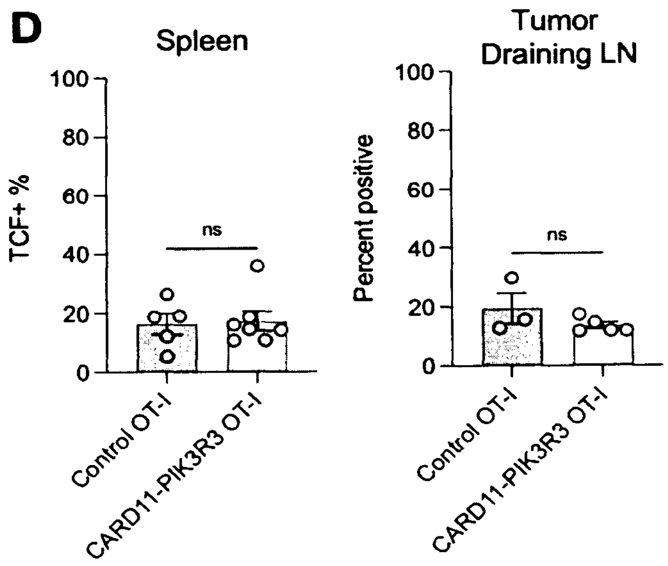
FIG. 26B shows the frequency of TCF-1+OT-I cells in spleen and tumor draining lymph node (LN) of mice bearing B16-OVA subcutaneous tumors. P values determined by unpaired T test. ns indicates not significant, *** indicates P values<0.001.
Figure 27:
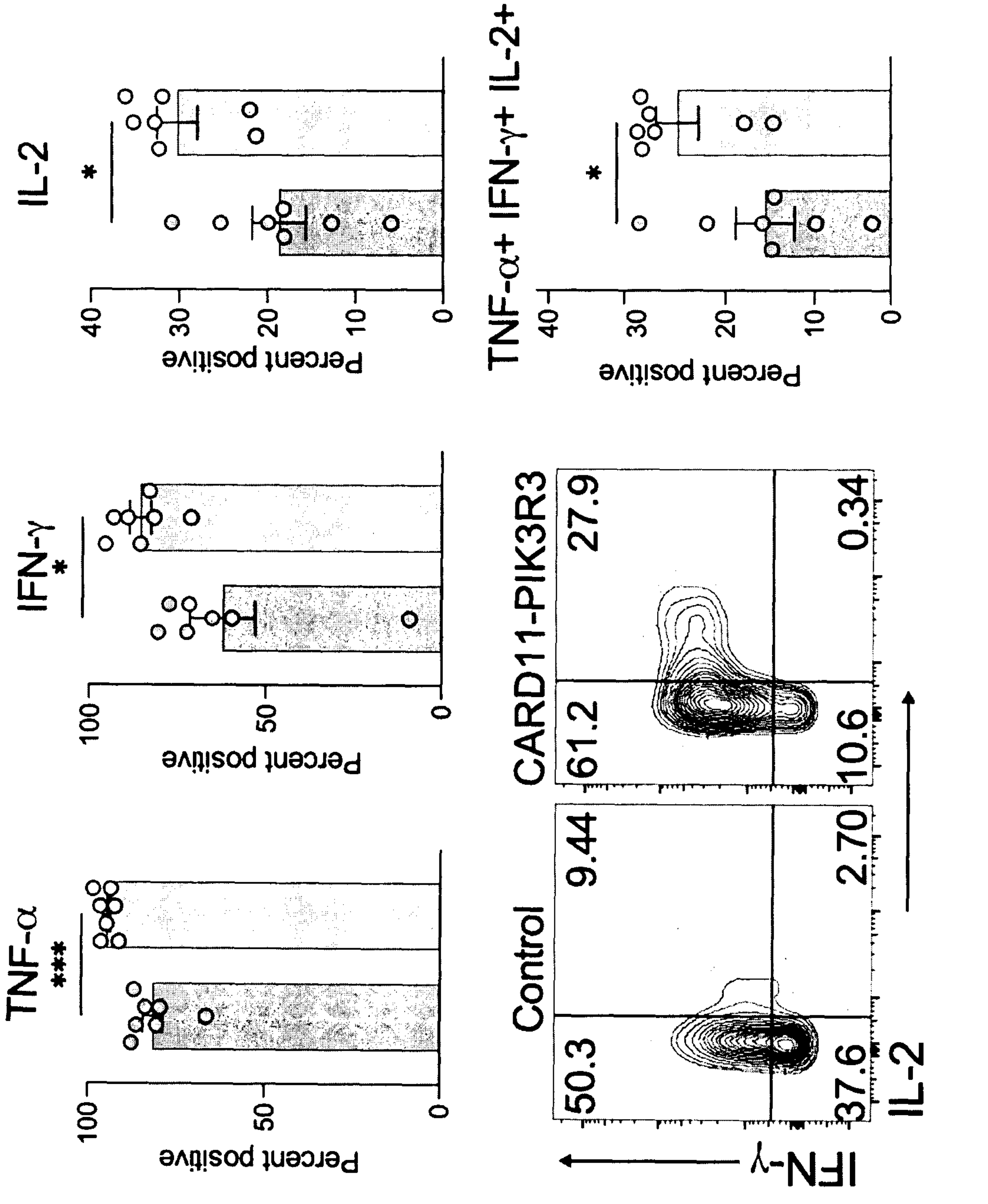
FIG. 27 shows that CARD11-PIK3R3 OT-Is have improved functionality in vivo. It depicts ex vivo cytokine production of TILs isolated 7 days post transfer of $1\times10^6$ CARD11-PIK3R3 or control OT-Is, and restimulated ex vivo with PMA/Ionomycin. P values determined by unpaired T test. * indicates P value<0.05, *** indicates P values<0.001.

Ex vivo restimulation and intracellular cytokine staining of CARD11-PIK3R3 OT-I cells revealed enhanced effector functions of fusion expressing cells, including higher production of TNF-α, IFN-γ, and IL-2 (FIG. 27). Furthermore, the proportion of polyfunctional cells producing all three of these effector cytokines was significantly elevated in CARD11-PIK3R3 OT-I cells. Additionally, CARD11-PIK3R3 expression substantially increased the expression of the stemness-associated transcription factor TCF1 in TILs (FIG. 26A). Consistent with tumor-specific reprogramming, TCF1 expression was not significantly different in either tumor draining lymph nodes or spleen. (FIG. 26B)

These results indicate that CARD11-PIK3R3 promotes the intra-tumoral accumulation of highly functional, stem-like T cells.

Example 16

Anti-Tumor Efficacy of CARD11-PIK3R3 in a Syngeneic, TCR Transgenic Melanoma Mouse Model The following experiment was done to determine the effects of CARD11-PIK3R3 on the therapeutic efficacy of T cells in a syngeneic, immunocompetent systems.

Figures 28A, 28B:
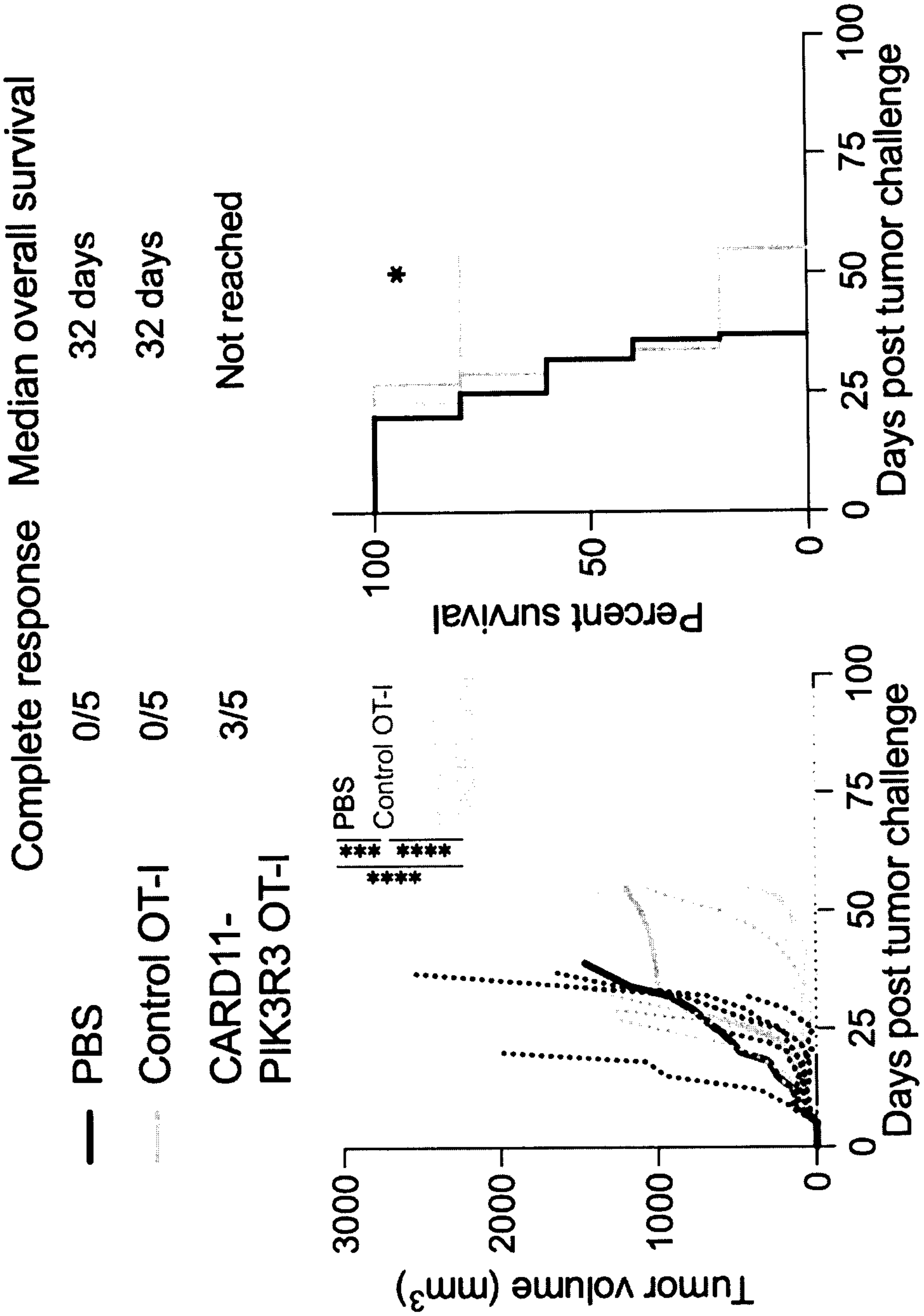
FIGS. 28A and 28B show that CARD11-PIK3R3 OT-Is demonstrate improved anti-tumor efficacy in vivo.
Figure 29A:
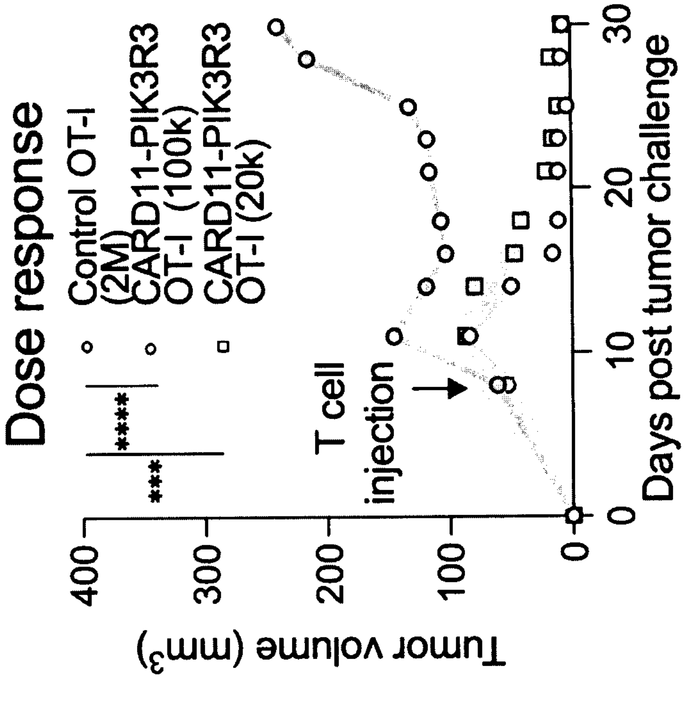
FIGS. 29A and 29B show that CARD11-PIK3R3 OT-Is demonstrate improved functionality in vivo at low doses and during tumor rechallenge. Tumor size of B16-OVA melanoma bearing mice treated with OT-I CARD11-PIK3R3 T cells at $1\times10^5$ (n=4) or $2\times10^5$ (n=5) T cell dose as compared to $2\times10^6$ control OT-I T cells (n=5) (A) and mice with cleared tumors from the dose response experiment rechallenged with B16-OVA melanoma tumors subcutaneously on the contralateral flank (B). * indicates P values<0.001, ** indicates P value<0.0001.

On day 12 following inoculation with B16-OVA tumors subcutaneously, mice were treated with PBS control or $2\times10^6$ OT-I cells transduced with either control or CARD11-PIK3R3 retrovirus, without pre-conditioning or lymphodepletion. CARD11-PIK3R3 cells mediated significantly enhanced control of tumor volume (FIG. 28A). In addition, CARD11-PIK3R3 OT-I cells promoted prolonged overall survival (FIG. 28B). 60% of mice (3/5) receiving the CARD11-PIK3R3 OT-Is achieved complete clearance of tumors at 85 days following tumor challenge, at which point no PBS or control OT-I treated mice survived. Altogether, these data indicate that CARD11-PIK3R3 expressing T cells have superior therapeutic function in vivo. Reduced cell numbers are routinely used as "stress tests" to quantify relative efficacy of modified T cell therapies. Moreover, these data suggest that the CARD11-PIK3R3 fusion may overcome one key limitation of cell therapies, i.e. the ability to manufacture sufficient cells for therapeutic efficacy in humans. To test this, therapeutic efficacy of 20,000 and 100,000 CARD11-PIK3R3 transduced OT-I cells against 2 million control OT-I cells in B16-OVA tumor bearing mice was compared. Strikingly, CARD11-PIK3R3 enabled tumor control with both 20-fold and 100-fold lower dose than control cells (FIG. 29A)

Figure 29B:
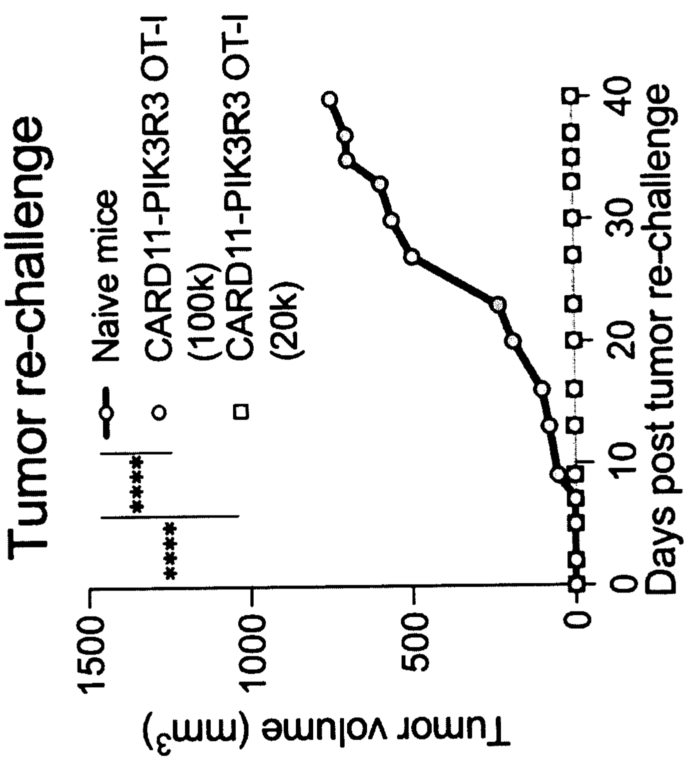

Current T cell therapies often lack long term persistence, failing to form memory populations after clearance of the primary tumor, resulting in high incidence of relapse. After more than two weeks of initial tumor clearance, CARD11-PIK3R3 OT-1 treated animals treated with low cell doses or naïve controls were rechallenged with B16-OVA tumor cells in the contralateral flank. The CARD11-PIK3R3 OT-I treated animals were protected from tumor development compared to naïve, untreated mice (FIG. 29B). The rejection of a secondary tumor challenge suggests the CARD11-PIK3R3 OT-Is develop a long term, memory phenotype that is capable of responding to and suppressing tumor reoccurrence. This phenotype is highly desirable in cancer therapies, allowing for a single engineered therapy to respond to primary tumors and to prevent relapse, inducing durable clinical remission. Altogether, these data indicate that CARD11-PIK3R3 expressing T cells have superior therapeutic function in vivo.

Example 17

Enhancement of Other Cell Types than the Original Cell by Mutation Constructs

The CARD11-PIK3R3 fusion was initially uncovered in a patient with CD4+ T cell lymphoma (Wang et al., Genomic profiling of Sezary syndrome identifies alterations of key T cell signaling and differentiation genes. *Nature Genetics* 47, 1426-1434 (2015). The OT-I data described in Example 16 is a CD8+ only cell therapy model, and the CARD11-PIK3R3 fusion dramatically enhanced the function of these CD8+ T cells in vivo, despite being a sequence derived from a CD4+ T cell. Therefore, mutations described herein can have therapeutic value in cell types that differ from those the mutations originally occur in.

Example 18

Figure 19:
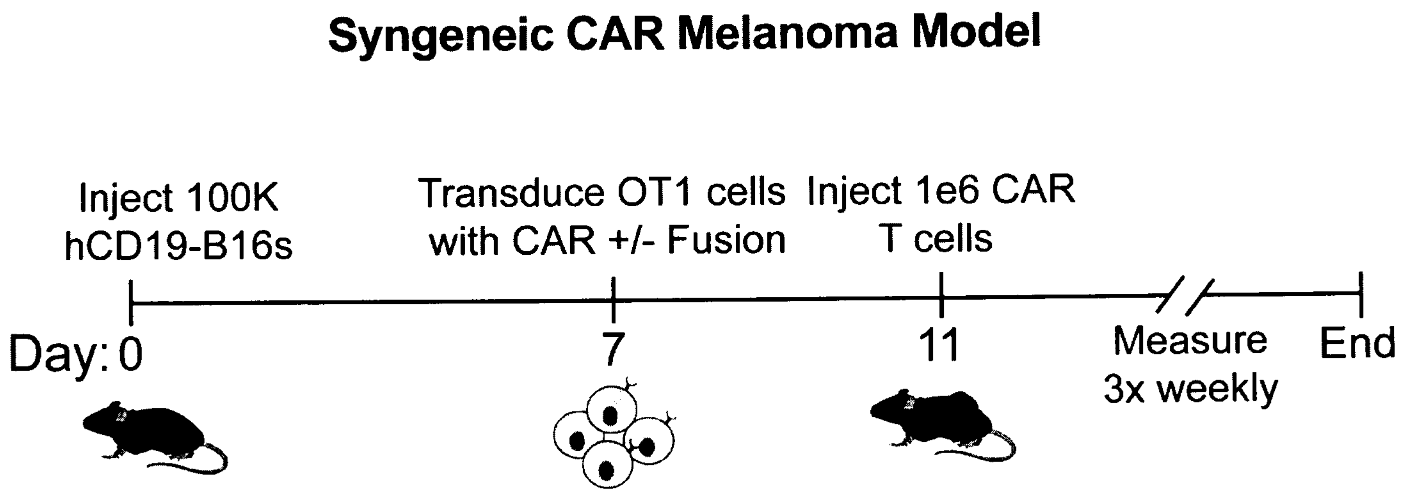
FIG. 19 is a schematic of the syngeneic CAR Melanoma Model used to assess CARD11-PIK3R3 therapeutic function in CD19-BBz CAR T cells in vivo. hCD19-B16s=B16 tumor cells expressing human CD19. OT-I cells=T cells collected from C57BL/6-Tg(TcraTcrb) 1100Mjb/J mice

CARD11-PIK3R3 Improves the Anti-Tumor Efficacy of Mouse CAR T Cells in a Syngeneic Melanoma Model T cells were collected from C57BL/6-Tg(TcraTcrb) 1100Mjb/J (OT-I) mice and transduced with a hCD19-CAR (CD19-BBz CAR), with or without the CARD11-PIK3R3 fusion (FIG. 19). T cells were transferred to mice bearing hCD19-B16 melanoma tumors. In this model B6.SJL-Ptprca Pepcb/BoyJ mice receive a subcutaneous injection of $1\times10^5$ hCD19 expressing B16 tumor cells in the hind flank. Eleven days after tumor inoculation, $1\times10^6$ CAR+ mouse T cells were dosed to tumor bearing animals, and tumor growth was tracked via calipers measurements taken 3× weekly. Tumor volume was calculated using the following equation: (Length×Width×Width)/2, where length is the longest measurement. Mice were euthanized when the tumor reaches 2000 mm3 or 2 cm in either length or width.

Figure 20A:
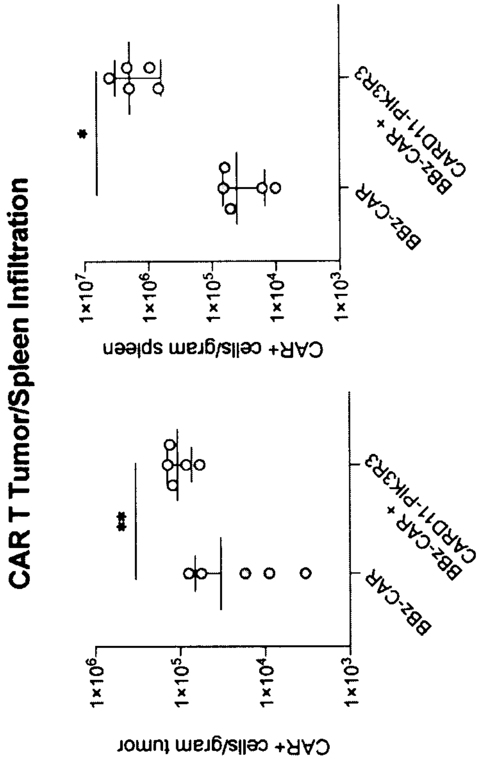
FIGS. 20A-C shows results of experiments with CD19-BBz CAR with CARD11-PIK3R3 fusion in controlling hCD19 B16 tumors.
Figure 20B:
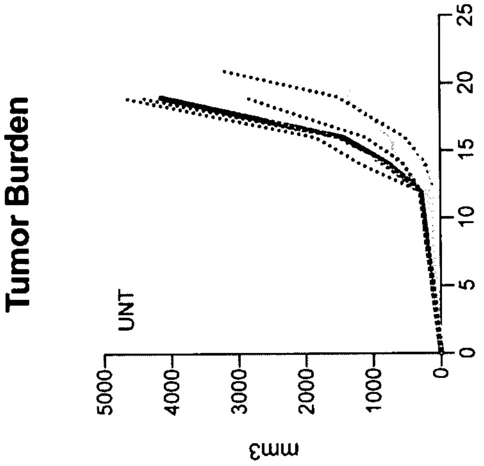
Figure 20C:
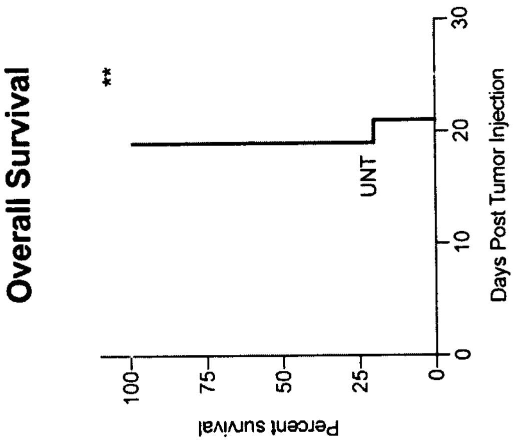

CARD11-PIK3R3 CAR T cells had significantly increased accumulation in the tumor and the spleen, significantly increased ability to control tumor volume, and significantly increased overall survival (FIG. 20). Therefore, CARD11-PIK3R3 enhances the efficacy of CAR T cells in vivo, in a syngeneic setting without lymphodepletion, radiation, or chemotherapy.

In a repeated study, CD19-BBz-CAR and CARD11-PIK3R3 CD19-BBz-CAR T cell treated tumors were assessed at tumor endpoint by flow cytometry. CD19-BBz-CAR treated tumors maintained CD19 expression, while CARD11-PIK3R3 CD19-BB2-CAR T cell treated tumors were uniformly CD19 negative, suggesting antigen loss as the mechanism of relapse (FIG. 47).

Example 19

Figure 17:
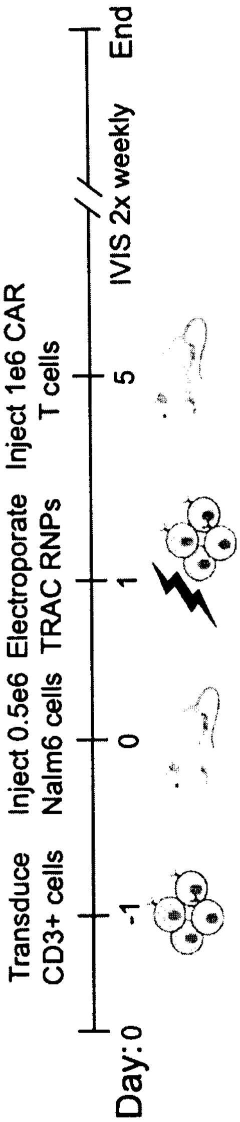
FIG. 17 shows a schematic indicating a xenograft CAR leukemic model used to assess CARD11-PIK3R3 therapeutic function in T cells in vivo. In this model NOD.Cg-Prkdcscid I12rgtm 1 Wjl/SzJ (NSG) mice are dosed with $5\times10^5$ Nalm6-GFP-Luciferase cells via tail vein injection. Primary human CD3+ T cells are transduced to express the CD19-BBz CAR (with or without co-expression of CARD11-PIK3R3) and electroporated with TRAC RNPs to knockout expression of the human TCR. TRAC RNPs are CRISPR/Cas9 ribonuclear protein complexes targeting the human T cell receptor alpha constant region gene. Nalm6 bearing mice are dosed with $1\times10^6$ CD19-BBz CAR T cells and tumor burden is assessed twice weekly via bioluminesce imaging using an IVIS imaging system. Mice are euthanized at first signs of hind limb paralysis.
Figure 18A:
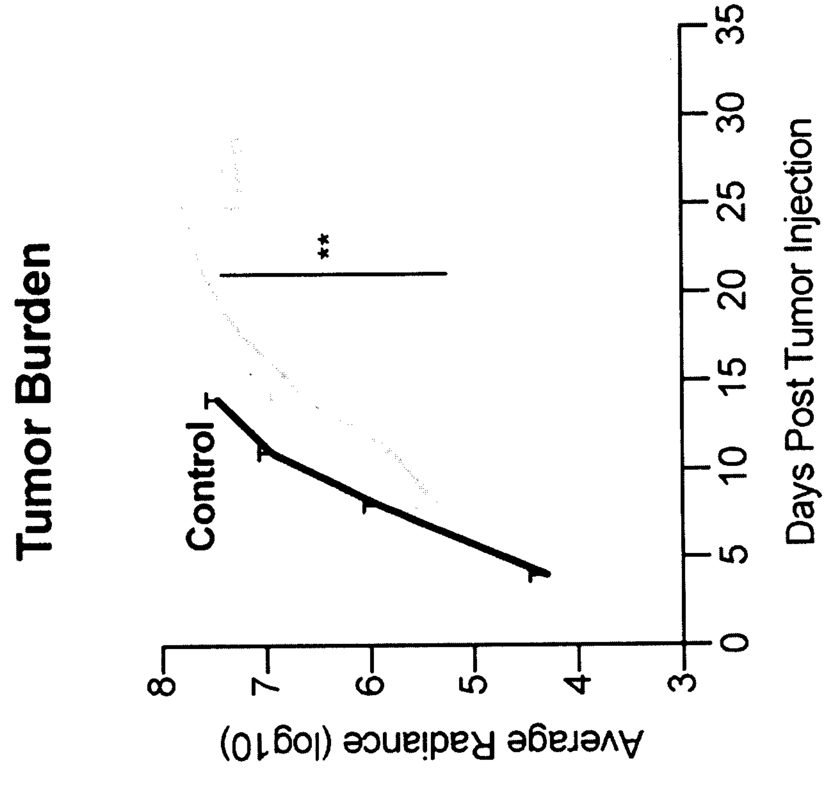
FIG. 18A-B demonstrate that CD19-BBz CAR expressing the CARD11-PIK3R3 fusion control Nalm6 leukemia in vivo.
Figure 18B:
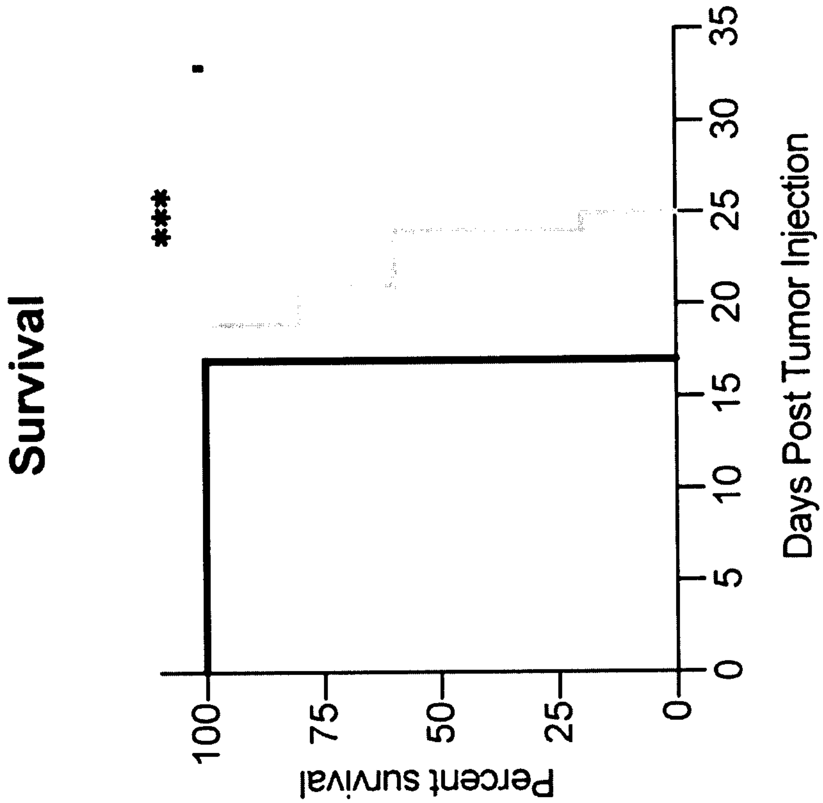

CARD11-PIK3R3 Improves the Anti-Tumor Efficacy of Human CAR T Cells in a Xenograft Leukemia Model Human CD3+ T cells were transduced with a CD19-BBz CAR with or without the CARD11-PIK3R3 fusion. T cells were then electroporated with Cas9 RNPs targeting the TCR alpha locus to knockout the endogenous T cell receptor. NSG mice bearing Nalm-6-luciferase leukemia were injected with CAR T cells (FIG. 17). Mice treated with CARD11-PIK3R3 CAR T cells had significantly lower tumor burden and a significantly improved survival (FIG. 18).

The improved efficacy of CD19-BBz-CAR T cells was also observed at higher doses of $7\times10^6$ CAR+ T cells, where 4 of 7 CD19-BBz-CAR treated animals that initially controlled tumor began relapsing with NALM-6 disease, while 7 of 7 CARD11-PIK3R3 CD19-BBz-CAR T cell treated animals did not relapse (FIG. 42A, FIG. 43A). We also determined that CARD11-PIK3R3 expressing T cells alone had no anti-tumor effect, demonstrating that the anti tumor effects observed are antigen-specific, and dependent on CAR activity (FIG. 42A). To address safety concerns, we also determined that NALM-6 bearing animals that controlled tumors with CAR or CARD11-PIK3R3 CAR T cell treatment gained weight over the course of 100 days, losing weight only when NALM-6 relapse occurred (FIG. 42A, FIG. 43B). Similarly, non-tumor bearing mice tolerated high doses of control T cells, CAR T cells, CAR+CARD11-PIK3R3 T cells (FIG. 43C). Finally, upon $5\times10^5$ NALM-6 tumor rechallenge (to animals that had eliminated the leukemia and had not developed symptoms of GVHD), we found that CD19-BBz-CAR treated animals succumbed to NALM-6 disease at a similar rate as naïve age matched controls, while CARD11-PIK3R3 CD19-BB2-CAR T cells prevented leukemic growth (FIG. 43D). These data indicate that CARD11-PIK3R3 enhances therapeutic efficacy while maintaining safety, even at high T cell doses, in vivo.

We next determined whether CARD11-PIK3R3 could improve CD19-CD28z-CAR T cell activity at low doses in the NALM6 leukemia model described above. We thus dosed NALM6-bearing mice with $4\times10^5$ CD19-CD282-CAR T cells, or CARD11-PIK3R3 CD19-CD282-CAR T cells (FIG. 44A) and found that CAR T cell treated animals succumbed to disease, while CARD11-PIK3R3 CAR T cells cleared two successive NALM6 challenges (FIGS. 42B-42C). Therefore, the anti-tumor efficacy of CARD11-PIK3R3 expression is not limited to CARs with 4-1BB costimulatory domains, but also improves those with CD28 domains, suggesting that CARD11-PIK3R3 expression could broadly benefit CAR T cell therapies.

Finally, we sought to determine how CARD11-PIK3R3 could perform in a xenograft solid tumor model. Here, we used the subcutaneous model of mesothelioma (M28), which naturally expresses the tumor associated antigen MCAM55. We manufactured and dosed tumor bearing animals with $5\times10^5$ MCAM targeted CD282-CAR T cells with or without CARD11-PIK3R3, or control T cells (FIG. 44B). Animals maintained weight throughout the study (FIG. 44C), indicating therapy was well tolerated. While MCAM-CD282-CAR treatment delayed tumor growth compared to the control, both control and CAR T cell treated tumors progressively increased in size (FIG. 42D). In contrast, CARD11-PIK3R3 MCAM CD28z-CAR T cell treated animals controlled M28 tumor growth over the course of approximately 70 days (FIG. 42D). Therefore, CARD11-PIK3R3 safely improves the long-term therapeutic efficacy of human CAR T cells in vivo in both hematological and solid tumor settings. Furthermore, CARD11-PIK3R3 CAR T cells protect from relapse (rechallenge) as compared to CAR T cells alone.

Example 20

CARD11-PIK3R3 Improves the Anti-Tumor Efficacy of Human CAR T Cells in a Human TCR-Based Xenograft Model To further extend these TCR efficacy findings to human engineered TCR T cells, we developed a human TCR-based xenograft model. KRAS p.G12D, a common mutation present in human solid tumors, can be presented on various human HLA alleles and has been targeted by adoptive T cell therapies in small studies in humans. Utilizing HLA-C*08:02 over-expressing SNU-1 gastric carcinoma cells which harbor a KRAS p.G12D mutation and a clinically validated TCR against HLA-C*08:02 presented KRAS p.G12D, we observed significantly enhanced tumor clearance with CARD11-PIK3R3 expression (FIG. 45). Therefore, CARD11-PIK3R3 expression enhances the function of both human and mouse therapeutic TCR cells. Altogether, these data indicate that CARD11-PIK3R3 expressing T cells have superior therapeutic function in vivo in multiple immunotherapy refractory tumor models, including CAR and TCR-transgenic based models.

Example 21

Figure 21:
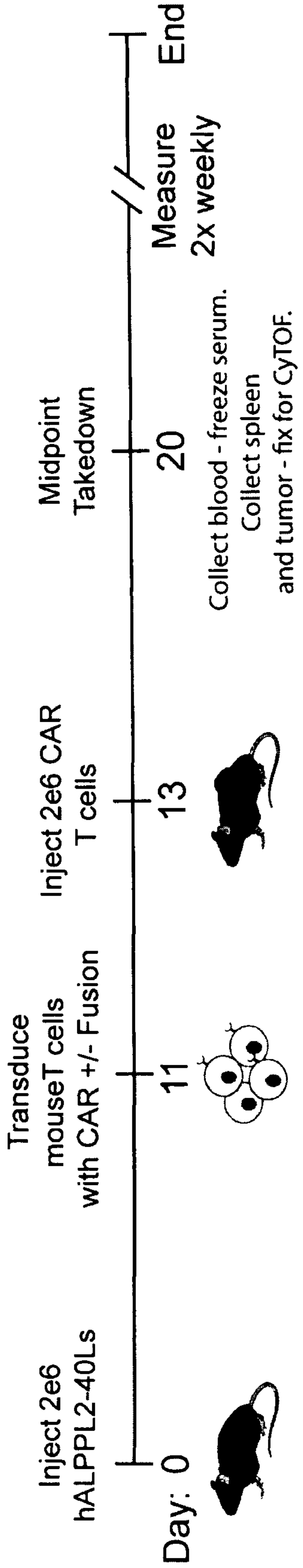
FIG. 21 shows a schematic indicating the syngeneic CAR Mesothelioma Model used to assess CARD11-PIK3R3 therapeutic function in CAR T cells in vivo. hALPPL2-40Ls=hALPPL2-expressing tumor cells.
Figure 22:
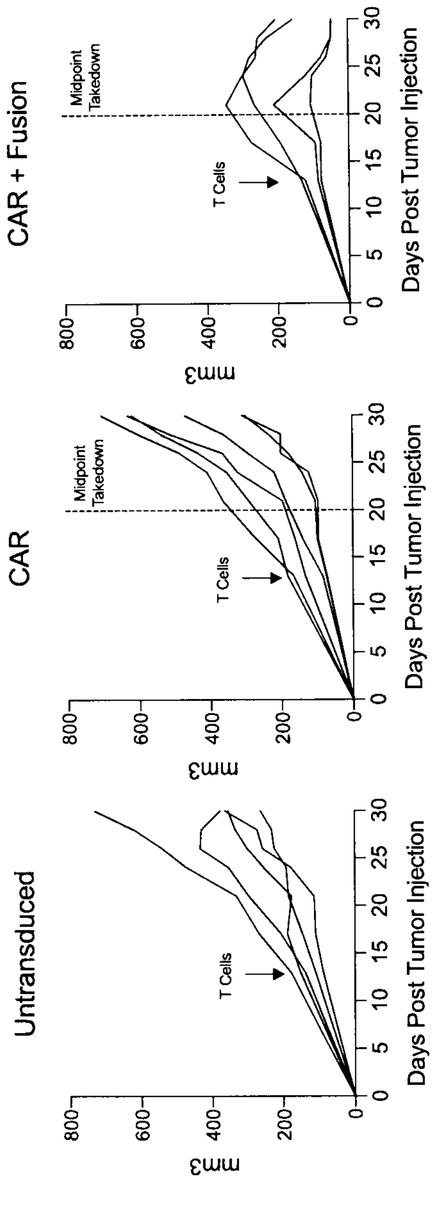
FIG. 22 shows tumor growth curves of hALPPL2 expressing 40L (mesothelioma) tumors injected subcutaneously and treated with untransduced, ALPPL2-BBz CAR or ALPPL2-BBz CAR with CARD11-PIK3R3 T cells. This data demonstrates that ALPPL2-BBz CAR T cells with CARD11-PIK3R3 expression induce some tumor control in the 40L model.

CARD11-PIK3R3 Improves the Anti-Tumor Efficacy of Mouse CAR T Cells in a Syngeneic Mesothelioma Model Mouse T cells were transduced with a hAPPL2-CAR, with or without the CARD11-PIK3R3 fusion (FIG. 21). T cells were transferred to mice bearing hAPPL2-40L mesothelioma tumors. In this model, C57BL/6J mice receive a subcutaneous injection of $2\times10^6$ hALPPL2-expressing 40L (mesothelioma) tumor cells in the hind flank. T cells were collected from B6.SJL-Ptprca Pepcb/BoyJ (CD45.1) mice and transduced to express ALPPL2-BBz CAR with or without co-expression of CARD11-PIK3R3. Thirteen days after tumor inoculation, $2\times10^6$ CAR+ mouse T cells were dosed to tumor bearing animals, and tumor growth was tracked via calipers measurements taken 3× weekly. Tumor volume was calculated using the following equation: (Length×Width×Width)/2, where length is the longest measurement. Mice were euthanized when the tumor reaches 2000 mm3 or 2 cm in either length or width. CARD11-PIK3R3 CAR T cells had significantly increased ability to control tumor volume (FIG. 22).

The approach used by the inventors/disclosers allowed the identification of a CARD11-PIK3R3 gene fusion which dramatically enhances therapeutic T cell function and efficacy through engaging the CBM complex. Furthermore, expression of the fusion enables superior tumor control at 100-fold lower cell doses than control cells in a fully immunocompetent murine model without lymphodepletion. Notably, the gene fusion the inventors/disclosers have identified would be inaccessible through previous T cell screening efforts such as loss of function, CRISPR activation, or wild-type gene overexpression screens. Therefore, naturally occurring mutations which have undergone positive selection in humans in vivo represent a novel and powerful set of tools to enhance cell therapy. The results obtained by the inventors/disclosers suggest that further testing of additional mutations identified in T cell lymphomas, or even other somatic mutations occurring in T cells including autoimmune disease, may hold promise for identifying additional approaches to enhance T cell function. Furthermore, this approach provides a platform for modifying other immune cell types with naturally occurring mutations for cell therapy, such as macrophages, NK cells, gamma delta T cells, or B cells. The potential utility of this approach is highlighted in the fact that while discovered in CD4+ T cells, the CARD11-PIK3R3 fusion dramatically enhances CD8+ T cell function.

The results presented herein implicate the CBM signalosome as a key regulator of therapeutic T cell function. Several individual outputs of CBM signaling, such as inducing AP-1 and NF-κB transcriptional activity and downregulation of MALT1 cleavage substrates REGNASE-1 and ROQUIN, have each been implicated independently as approaches to improve T cell therapy. This raises the possibility that a unifying feature of these various approaches is that they partly address a relative deficiency of CBM signaling. CARD11-PIK3R3 expression represents a powerful engineering solution to enhance each of these separate CBM outputs simultaneously. Further investigation of T cell lymphoma mutations in the context of adoptively transferred T cells may improve cellular therapies and elucidate new T cell biology.

Example 22

Safety in OT-I Mice

To address concerns of toxicity or transformation, we monitored the mice from FIG. 29 for up to 418 days after T cell transfer (FIG. 49A). Throughout this time, CARD11-PIK3R3 OT-I T cell treated animals gained weight similarly to that of published controls (FIG. 49B). To assess for occult disease, we performed necropsy on three mice on day 240 after T cell transfer. Their spleens were of normal weight and gross appearance (FIGS. 49C-49D). Additionally, CARD11-PIK3R3 OT-I T cells made up less than 1% of total CD8+ T cells in the spleen and blood (FIG. 49E). We performed hematoxylin and eosin (H&E) staining of common extra-nodal sites of lymphoma, as well as the spleen and lymph nodes. Pathology review failed to identify any evidence of nuclear atypia, destruction of normal cellular architecture, or neoplastic disease (FIG. 49F).

For the remaining 9 animals, we monitored the blood for evidence of leukemic disease for 330-418 after adoptive transfer. There were no atypical cells in the blood. Moreover, tail bleeds of CARD11-PIK3R3 OT-I treated animals revealed CARD11-PIK3R3 OT-I T cells were present at less than 1% of the overall CD8 population (FIGS. 49G-49J). This data suggests contraction of CARD11-PIK3R3 OT-I T cell population after exposure to initial or rechallenge tumors. Altogether, these data demonstrate a favorable safety profile of CARD11-PIK3R3 expressing anti-tumor T cells and a lack of evidence of malignant transformation in vivo over long time periods.

Example 23

STAT3 Putative Gain-of-Function Mutations

STAT3 is a transcription factor which is phosphorylated by receptor associated Janus kinases (JAKs). JAK/STAT signaling is critical for responses to signaling molecules such as cytokines. STAT3 is essential for T cell mediated control of infection. STAT3 plays an important role in T cell differentiation, including Th17 and Tfh differentiation. Additionally, STAT3 promotes the survival of T cells through inhibiting apoptosis (Oh et al. 2011. J. Biol. Chem. 286(35):30888-30897). Modulation of STAT3 signaling by expression of mutated versions of STAT3 may therefore be advantageous in the context of T cell therapies by modulation of one or more of the above mentioned roles of STAT3 in T cells.

STAT3 mutations tested include the following: STAT3_G618R, STAT3_N6471, and STAT3_D661I.

These mutations occurred in the SH2 domain. SH2 mutations in STAT3 can lead to increased STAT3 activity, as determined by phosphorylated STAT3 levels. SH2 mutations in STAT3 can also lead to cytokine independent growth of cell lines (Küçük et. al., 2015, *Nature Communications*. 6, Article number 6025)

STAT3 mutations improved the in vivo accumulation and/or persistence of CAR T cells. In vivo screening identified positive log 2 fold change for all three STAT3 variants tested, suggesting that these mutations are advantageous for the in vivo accumulation and/or persistence of cell therapy (FIG. 31).

Example 24

BRAF Putative Gain-of-Function Mutations

BRAF is a serine/threonine kinase which plays a key role in regulating cell growth in response to signaling from receptor tyrosine kinases. The RAF/MEK/ERK pathway is essential for T cell development and T cell functions. This pathway is activated downstream of T cell receptor signaling. MEK/ERK signaling are required for IL-2 production and proliferation of naïve T cells in response to TCR stimulation. Therefore, modulation of this key signaling pathway in T cells may be advantageous to improving adoptive T cell therapies.

BRAF mutations tested include the following: BRAF_G469R, BRAF_D594N and BRAF_G469A.

These mutations occurred in the BRAF kinase domain (FIG. 32). Kinase domain mutations in BRAF such as G469A can increase BRAF signaling as determined by kinase cascade (Davies, H. et. al. 2002. Nature. 417, 949-954)

BRAF mutations strongly enhanced CAR-dependent NFAT, NF-κB, and AP-1 signaling and IL-2 production (FIG. 32). Modulation of BRAF signaling by expression of BRAF mutations may therefore be used to alter CAR-T cell signaling.

Example 25

CARD11 Putative Gain-of-Function Mutations

CARD11 is a key signaling molecule in the CARD11-BCL10-MALT1 signalosome. CARD11-PIK3R3 fusion expression improves anti-tumor efficacy and enhances CARD11-BCL10-MALT1 signaling. Point mutations in CARD11 can similarly be used to enhance CARD11-BCL10-MALT1 signaling in therapeutic T cells.

CARD11 mutations tested include the following: CARD11_S615F, CARD11_D357N, CARD11_Y361C, and CARD11_E634K:S655C.

These mutations occurred in the inhibitory domain or the coiled coil domain. These mutations can increase NF-κB signaling and other CARD11-BCL10-MALT1 signalosome outputs (Da Silva Almeida et al. 2015. *Nature Genetics*. 47(12): 1465-1470)

CARD11 mutations enhanced CAR-dependent NF-κB and AP-1 signaling and IL-2 production (FIG. 33). These mutations also increased the in vivo accumulation of CAR T cells. Modulation of CARD11-BCL10-MALT1 signaling by expression of CARD11 point mutations may therefore be used to alter CAR-T cell signaling and improve in vivo function.

Example 26

RASGRP1 Putative Gain-of-Function Mutation

RASGRP1 plays an important role in mediating TCR-dependent activation of Erk signaling. RASGRP1 plays a role in positive selection in the thymus and in TCR dependent T cell activation, as loss of RASGRP1 impairs these processes.

The RASGRP1 mutation tested was M261I. This mutation occurred in the RasGEF domain (FIG. 34). This domain is the catalytic domain of the protein which promotes guanyl nucleotide exchange.

RASGRP1 mutation enhances CAR-dependent NFAT, NF-κB and AP-1 signaling and IL-2 production compared to wild-type RASGRP1 (FIG. 34). This mutation also increased the in vivo accumulation of CAR T cells (FIG. 34). RASGRP1 mutation may therefore be used to alter CAR-T cell signaling and improve in vivo function.

Example 27

PLCG1 Putative Gain-of-Function Mutations

PLCG1 is a critical signaling molecule in T cells downstream of TCR activation. Upon activation, PLCG1 catalyzes the formation of IP3 and DAG from PI-4,5BP. IP3 and DAG in turn activate additional signaling cascades, including NF-κB and NFAT signaling. PLCG1 is required for the development, activation, proliferation, and cytokine production of T cells (Fu et al., 2010. *J. Exp Med.* 207(2):309-318)

The PLCG1 mutations tested include the following: PLCG1_D1165H, PLCG1_E1163K, PLCG1_E47K, PLCG1_R48W, PLCG1_S520F.

These mutations occurred in numerous regions of the PLCG1 protein including the C2 domain (FIG. 35). Several of these mutations have been previously characterized to activate NFAT, NF-κB, and AP-1 signaling basally (Fu et al., 2010. *J. Exp Med.* 207(2):309-318).

PLCG1 mutations enhanced CAR-dependent NFAT, NF-κB and AP-1 signaling and IL-2 production compared to wild-type PLCG1 (FIG. 35). PLCG1 mutation may therefore be used to alter CAR-T cell signaling.

Example 28

TNFRSF1B Putative Gain-of-Function Mutations

TNFRSF1B (TNFR2) is a co-stimulatory molecule expressed on activated T cells. TNFR2 binds to TNFα and LTa3. Upon binding, TNFR2 signals through TRAF2 to activate NF-κB signaling. TNFR2 is required for T cell expansion and effector differentiation (Ward-Kavanagh. 2016. Cell. Immunity. 44:1005-1019).

The TNFRSF1B mutations tested include TNFRSF1B_G256C and TNFRSF1B_T377I. The T377I mutation has been previously characterized to activate NF-κB signaling (Ungewickell et al. 2015. Nature Genetics. 47:1056-1060).

TNFRSF1B mutations activated CAR-dependent NF-κB to a greater extent than wild-type TNFRSF1B (FIG. 36). The TNFRSF1B mutations also led to higher in vivo accumulation than wild-type TNFRSF1B (FIG. 36). These mutations can therefore be leveraged to alter CAR signaling and enhance in vivo persistence.

Example 29

JAK Family Putative Gain-of-Function Mutations

JAK/STAT signaling plays a critical role in the biology of T cells, particularly in response to cytokines. Cytokine receptors that have recognized their ligand lead to the trans-activation of JAK proteins that are bound to the receptor. JAKs then phosphorylate STATs, which dimerize and translocate to the nucleus to affect transcription (Villarino et al. 2015. *J. of Immunology.* 194(1):21-27).

JAK/STAT signaling in T cells has previously been modified in numerous ways in order to potentiate cell therapies, through methods including synthetic cytokines, synthetic cytokine receptors including switch receptors, and through incorporation of JAK/STAT signaling domains in CAR constructs. The JAK1/JAK3 mutations tested include the following: JAK1_G1097A and JAK3_A573V.

The JAK3 mutation has previously been shown to increase STAT3 and STAT5 phosphorylation and the expansion of NK cells (Picod et al. 2022. *Haematologica.* 107(9): 2218-2225).

These mutations occurred in the kinase or pseudokinase domains of JAK1/JAK3 (FIG. 37). JAK1/JAK3 mutations had positive effects on in vivo accumulation (FIG. 37). These mutations can therefore be leveraged to enhance in vivo persistence in CAR T cells.

Example 30

Materials and Methods

Receptor and Mutation Screening Construct Construction

Intracellular domains containing the appropriate costimulatory domain and CD3zeta domain were synthesized by Twist. Receptors were built by fusing the CD19 scFv1 to the corresponding receptor scaffold and intracellular tail. All receptors contain an n-terminal CD8a signal peptide (MALPVTALLLPLALLLHAARP SEQ ID NO:261) for membrane targeting and a flag-tag (DYKDDDDK SEQ ID NO: 262) for easy determination of surface expression with α-flag PE or BV421 (Biolegend 637310, 637322). In some cases the receptors additionally contained a T2A self-cleaving sequence followed by a tNGFR sequence, used in downstream applications for T cell isolations. The receptors were cloned into a modified pHR'SIN:CSW vector containing a PGK promoter for all primary T cell experiments.

Primary Human T Cell Isolation and Culture

Primary CD3+, CD4+ and CD8+ T cells were isolated from anonymous donor blood after apheresis by negative selection (Biolegend Mojo Sort #480129, 480130, 480131). Blood was obtained from Blood Centers of the Pacific (San Francisco, CA) as approved by the University Institutional Review Board. T cells were cryopreserved in RPMI-1640 (UCSF cell culture core) with 20% human AB serum (Valley Biomedical Inc., #HP1022) and 10% DMSO. After thawing, T cells were cultured in human T cell medium consisting of X-VIVO 15 (Lonza #04-418Q), 5% Human AB serum and 10 mM neutralized N-acetyl L-Cysteine (Sigma-Aldrich #A9165) supplemented with 30 units/mL IL-2 (NCI BRB Preclinical Repository) for all experiments unless otherwise noted. In vivo experiments were completed with bulk CD3+ cells isolated in a similar manner.

Lentiviral Transduction of Human T Cells

Pantropic VSV-G pseudotyped lentivirus was produced via transfection of Lenti-X 293T cells (Clontech #11131D) with a pHR'SIN:CSW transgene expression vector and the viral packaging plasmids pCMVdR8.91 and pMD2.G using Mirus TransIT-Lenti (Mirus #MIR 6606). Primary T cells were thawed the same day, and after 24 hours in culture, were stimulated with Human T-Activator CD3/CD28 Dynabeads (Life Technologies #11131D) at a 1:3 cell:bead ratio. At 48 hours, viral supernatant was harvested and the primary T cells were exposed to the virus for 24 hours. At day 5 post T cell stimulation, the Dynabeads were removed, T cells were sorted, and the T cells expanded until day 10-14 when they were rested and could be used in vitro or in vivo assays. T cells were sorted for assays with a Beckton Dickinson (BD) FACs ARIA II.

TCR Knockout and Lentiviral Transduction of Human T Cells

For TCR KO experiments, primary T cells were cultured in human T cell medium consisting of X-VIVO 15 (Lonza #04-418Q), 5% Human AB serum and 10 mM neutralized N-acetyl L-Cysteine (Sigma-Aldrich #A9165) supplemented with 100 units/mL IL-7 (Miltenyi #130-095-362) and 100 units/mL IL-15 (Miltenyi #130-095-765). Primary T cells were thawed, rested for 1 hour then stimulated with Human T-Activator CD3/CD28 Dynabeads (Life Technologies #11131D) at a 1:3 cell:bead ratio. One day after activation, T cells were transduced with concentrated virus. 24 hours later, virus and Dynabeads were removed, cells were rested for 24 hours, then resuspended at $1\times100^6$ cells per mL in P3 electroporation buffer (Lonza #V4SP-3960) with gRNA (CAGGGTTCTGGATATCTGT) targeting the human TRAC locus and Cas9. 23 uL of this mixture was aliquoted to each well of a 96 well nucleofection plate (Lonza #V4SP-3960) and immediately electroporated using a 4-D Lonza Nucleofector with program EH115. Cells were resuspended in pre-warmed human T cell medium and recovered for 30 minutes in the incubator before being transferred to culture. Electroporated cells were assessed for TCR KO and lentiviral transduction via flow before injection to mice.

Cell Lines

This Example describes the various cell lines used in the experiments of this study. The cancer cell lines used were K562 myelogenous leukemia cells (ATCC #CCL-24 3), Jurkat cells (Clone E6-1, ATCC #TIB-152), B16-F10 melanoma cells (ATCC #CRL-6475) and A549 lung epithelial carcinoma cells (ATCC #CCL-18). K562s and A549s were lentivirally transduced to stably express human CD19. CD19 levels were determined by flow cytometry (Biolegend, clone HIB19). A549s were additionally transduced to express the nuclear stain mkate2. All cell lines were sorted for expression of the transgenes. Jurkat cells were transduced with retroviruses encoding fluorescent reporter constructs (Addgene 118095, 118094, and 118031) and stimulated with PMA/ionomycin to sort a line with high induction of each reporter. To enable screening with our mCherry expressing lentiviral constructs, an iRFP fluorescent reporter was subcloned to replace mCherry in the previously described AP1-mCherry construct. Triple reporter cells were then transduced with a CD19-CD28z CAR or CD19-BBz-CAR. Jurkat and K562 cells were cultured in RPMI+10% FBS with penicillin/streptomycin and sodium pyruvate. B16-OVA and A549 cells were cultured in DMEM+10% FBS with penicillin/streptomycin. All cell lines were routinely tested for *mycoplasma* contamination (Southern Biotech).

In Vitro Primary T Cell Assays

For in vitro co-culture assays, transduced primary T cells were co-cultured with target cells at effector to target ratios and co-culture time courses. For Luminex assays, cells were co-cultured in media lacking exogenous IL-2, supernatants were collected 48 hours after start, frozen at −80C and sent for analysis to Eve Technologies. For IL-2 ELISA assays, supernatant was collected from 24-hour co-cultures of transduced T cells and target cells. Supernatants were assessed for IL-2 secretion using the Invitrogen Instant IL-2 ELISA kit (Invitrogen #BMS221INST). For repeat stimulation assay, transduced T cells were co-cultured on the adherent CD19 expressing A549 cell line, after 1 week T cells were removed from co-culture without disturbing adherent cells, counted and replated on CD19 expressing A549 cells seeded 24 hours prior. For co-culture assays performed over a period of days to weeks, media was supplemented regularly. For Mass cytometry by time of flight (CyTOF) transduced CD3+ T cells were co-cultured with CD19-K562s for 7.5, 15, 30, 60 or 120 minutes, then immediately fixed with 1.6% PFA for 10 minutes at room temperature. Cells were then pelleted, washed, and stored at −80C until ready for barcoding and staining. All primary T cell in vitro assays were performed with three donors.

Flow Cytometry

For all in vitro primary T cell assays, cells were washed with PBS 2% FBS twice, stained with surface staining markers at room temperature for 20 minutes, washed twice, and resuspended in PBS 2% FBS with DRAQ7 (diluted 1:1000) before analysis on a BD FACSymphony X-50 Flow Cytometer. The following antibodies were used: CD8 (SK1), CD25 (M-A251), CD39 (A1), CD69 (FN50), CD271 (ME20.4), CD278 (C398.4A), CD279 (EH12.2H7)

K562 In Vivo Xenograft Assays

NOD.Cg-Prkdcscid Il2rgtm 1 Wjl/SzJ (NSG) mice were dosed with $1\times10^6$ CD19 expressing K562 cells via subcutaneous injection. 5 days post tumor injection, 3 to $6\times10^6$ transduced or control T cells were dosed to tumor bearing animals via retro-orbital injection. Tumors were measured with calipers twice weekly, and tumor volume was calculated using the following formula: (length×width2)/2. Throughout experiment animal drinking water was supplemented with Clavomox to prevent bacterial infections.

Nalm6 In Vivo Xenograft Assays

NOD.Cg-Prkdcscid Il2rgtm 1 Wjl/SzJ (NSG) mice were dosed with $5\times10^5$ luciferase expressing Nalm6 cells via intravenous tail vein injection. 5 days post tumor injection, $1\times10^6$ transduced or control T cells were dosed to tumor bearing animals via retro-orbital injection. Tumor burden was measured twice weekly via bioluminescence imaging after 200 uL intraperontineal injection of D-Luciferin (15 mg/mL, Goldbio), image analysis performed using Living Image (Perkin-Elmer). Animal drinking water was supplemented with Clavomox to prevent bacterial infections.

Jurkat Reporter Screening and Analysis

CAR triple reporter Jurkat cells were transduced in 96 well plate format with individual T cell lymphoma mutation lentiviruses. 48 hours post-transduction, cells were plated at approximately a 1:1 ratio with K562 or K562-CD19 cells. Plates were spun at 300 g for 2 minutes to promote interaction of CAR cells and target cells. Following 24 hours of co-culture, supernatants were removed for IL-2 ELISA (ELISA MAX™ Deluxe Set Human IL-2, Biolegend) and cells were washed in FACS buffer (PBS+2% FBS) and analyzed by FACS. For the CD19-BBz CAR screen, cells were stained with anti-PD-1 (Biolegend, clone EH12.2H7) prior to FACS analysis. Each screen was performed in biological replicate with separate lentiviral transductions. For analysis, the percentage positive for each reporter in each condition (i.e. each CAR and co-culture cell type) was compared to the mCherry only controls and the corresponding wild-type gene control when available by T test followed by Bonferroni correction. Z scores were calculated for each condition as $(x-\mu)/\sigma$ (where x is the observed value, $\mu$ is the mean, and $\sigma$ is the standard deviation).

In Vivo Screening and Analysis

Human CD3 T cells were lentivirally co-transduced with a CD19-BBZ CAR with tNGFR and the mutant construct library in an arrayed fashion. CD3+ T cells were assessed via flow for CD19-BBZ CAR (FLAG) and mutant construct (mCherry) expression. T cells were pooled based on mCherry expression and sorted for a purified dual positive population. $6\times10^6$ library T cells were injected to 15 CD19-K562 tumor bearing animals. T cells were isolated from the tumor and spleen by positive selection using the tNGFR (CELLection™ Biotin Binder Kit) at 7, 14, and 21 days post injection. gDNA was isolated from these T cells (Nucleo-Spin Tissue, Machery Nagel), and quantified by NanoDrop Spectrophotometry and adjusted to 8 ng/uL. PCR amplification of the samples was performed using primers (Table 2) to enrich for the mutations barcodes (PCR1). PCRs were performed with Kappa HiFi, in reaction volumes of 50 μL with between 10 and 1090 ng of gDNA, all reactions underwent 7 cycles of amplification. For the subsequent PCR to add Illumina barcodes and adapters to the products (PCR2), all products from PCR1 were quantified with a Qubit 1× dsDNA High Sensitivity Assay kit (Invitrogen) and up to 10 ng of template was used in a 25 μL reaction with Kappa Hifi. Different forward and reverse primers were used for each sample for PCR2 to add unique custom Illumina 15 and 17 barcode sequences to each sample. Finally, PCR2 products were again quantified using Quibit, and these products were pooled at 1:1 molar ratio, diluted, loaded, and run on a MiniSeq 75 cycle cartridge using the standard manufacturer protocols.

Bulk RNAseq and Analysis

For bulk RNAseq, T cells from 3 independent healthy donors transduced with the indicated constructs were either unstimulated or stimulated via co-culture with CD19 expressing A549 cells for 8 hours. RNA was then isolated (Nucleospin RNA XS, Machery-Nagel and cDNA libraries were constructed using SMART-Seqv4 Ultra Low Input RNA Kit (Takara Bio) and Nextera XT (Illumina). Sequencing reads were aligned using STAR, transcripts quantified using HT-Seq, and differentially expressed genes were identified using DESeq2 as previously described. (Love M I, Huber W, Anders S. Moderated estimation of fold change and dispersion for RNA-seq data with DESeq2. Genome Biol. 2014; 15(12):1-21.)

Immunoblot Analysis

Jurkat cells ($1-5\times10^6$) were pre-treated for 30 minutes with the MALT1 inhibitor Z-VRPR-FMK (75 μM) or vehicle control. Cells were then treated with PMA/ionomycin as indicated for 2 hours. Whole-cell lysates were generated and analyzed by immunoblotting with the following antibodies: anti-HOIL1 (Millipore Sigma, MABC576), anti-CYLD (Santa Cruz, sc-74435), and anti-β-actin (Cell Signaling Technologies, 4967).

Mass Cytometry by Time of Flight (CyTOF)

Cells were thawed on ice for 15 minutes, washed, and barcoded with distinct combinations of stable Pd isotopes for 15 min at room temperature on a shaker in Maxpar Barcode Perm Buffer (Fluidigm, cat #201057) (Mass tag cellular barcodes; Bodenmiller B, Zunder E R, Finck R, et al. Multiplexed mass cytometry profiling of cellular states perturbed by small-molecule regulators. Nat Biotechnol 2012 309. 2012; 30(9):858-867). Cells were washed twice with cell staining media (PBS with 0.5% BSA and 0.02% NaN3) and pooled into a single cluster tube. Cells were stained with surface staining antibodies for 30 min at room temperature on a shaker. After staining, cells were washed two times with cell staining media followed by permeabilization with methanol for 10 min at 4° C. Permeabilized cells were washed twice in cell-staining media and stained with intracellular antibodies for 30 min at room temperature on a shaker. Cells were washed twice in cell-staining media and then stained with 1 ml of 1:4000 191/193Ir DNA intercalator (Fluidigm) diluted in PBS with 1.6% PFA overnight. Cells were diluted in Cell Acquisition Solution containing bead standards (Fluidigm, Cat #201078) to and analyzed on a Helios mass cytometer (Fluidigm) equilibrated with Cell Acquisition Solution. After acquisition, the data from the pooled samples underwent bead standard data normalization and de-barcoding using the R package from the PICI institute available at https://github.com/ParkerICI/premessa.

Mouse T Cell Purification and Retroviral Transduction

CD8+ T cells were isolated from the spleens of CD45.1+ or CD45.2 OT-I mice using a mouse CD8+ T cell isolation kit (Stemcell Technologies) or Mouse Pan CD3+ T cell isolation kit (Biolegend). T cells were then cultured with 100 U/mL recombinant human IL-2 (Peprotech), anti-CD3e (1 ug/mL) and anti-CD28 (0.5 ug/mL) overnight. For CAR experiments, T cells were stimulated overnight with anti-CD3/CD28 beads (ThermoFisher). Retroviral supernatants were added to T cells in Retronectin (Takara) coated plates and spinduction was performed for 1 hour at 2000 rpm at 30° ° C. Following transduction, T cells were resuspended and cultured in fresh media containing 100 U/mL IL-2 until adoptive transfer. Transduction efficiency was determined by flow cytometry prior to adoptive transfer.

B16-OVA Melanoma Tumor Model

Female C57BL/6 mice age 6-8 weeks were injected subcutaneously with $5\times10^5$ B16-OVA melanoma cells. Mice with similar sized tumors were randomized to receive treatments of OT-I T cells. 100 μL of T cells (or PBS control) were retro-orbitally injected on day 8-12 post tumor inoculation. For dual-transfer competitive assay and tumor infiltrating lymphocyte analysis experiments, $1\times10^6$ T cells were transferred. For anti-tumor efficacy, $2\times10^6$ T cells were transferred. Tumor lengths and widths were determined every 2-3 days by digital caliper measurement and tumor volume was calculated as length×width×[(length×width) 0.5]×π/6 as previously described (Wei, J., Long, L., Zheng, W. et al. Targeting REGNASE-1 programs long-lived effector T cells for cancer therapy. Nature 576, 471-476 (2019). https://doi.org/10.1038/s41586-019-1821-z).

Death was defined as a progressively growing tumor that reaches 15 mm in its longest axis or developing ulceration or necrosis. For the anti-tumor efficacy experiment, measurement of tumors and determination of survival endpoint was blinded to experimental condition. Experiments were performed in accordance with Northwestern University Institutional Animal Care and Use Committee approved protocols.

B16-OVA Tumor Infiltrating Lymphocyte (TIL) Isolation and Analysis

To isolate TILs, B16-OVA tumors were excised, minced, and digested using collagenase IV (1 mg/mL) and DNAse I (50 ug/mL) for 30 minutes at 37° C. in a shaking incubator at 200 rpm. TILs were filtered through a 70 uM cell strainer and isolated over Percoll density centrifugation. For dual-transfer experiments, the isolated TILs were subjected to Fc receptor blocking, live/dead staining (Live/Dead Violet) and surface marker staining for flow cytometric analysis. For intracellular cytokine staining, cells were restimulated ex vivo in media containing brefeldin and monensin (Invitrogen), phorbol myristate acetate, and ionomycin for four hours. Following Fc blocking, live/dead staining, and cell surface marker staining, cells were fixed (BD CytoFix), permeabilized (Invitrogen 10× Perm), and stained for intracellular proteins.

CD19-B16 Melanoma Tumor Model

Male B6.SJL-Ptprca Pepcb/BoyJ mice age 6-12 weeks were injected subcutaneously with $1\times10^5$ CD19-B16 melanoma cells. Mice with similar sized tumors were randomized to receive treatments of CAR T cells. $2\times10^6$ CAR+ or untransduced (control) T cells were retro-orbitally injected on day 12 post tumor inoculation. Tumor lengths and widths were determined every 2-3 days by digital caliper measurement and tumor volume was calculated using the following formula: (length×width2)/2. Death was defined as a progressively growing tumor that reaches, 2000 mm3 or 20 mm in its longest axis, whichever comes first.

ALPPL2-40L Mesothelioma Tumor Model

Male B6.SJL-Ptprca Pepcb/BoyJ mice age 6-12 weeks were injected subcutaneously with $2\times10^6$ ALPPL2-40L mesothelioma cells. Mice with similar sized tumors were randomized to receive treatments of CAR T cells. $2\times10^6$ CAR+ or untransduced (control) T cells were retro-orbitally injected on day 12 post tumor inoculation. Tumor lengths and widths were determined every 2-3 days by digital caliper measurement and tumor volume was calculated using the following formula: (length×width2)/2. Death was defined as a progressively growing tumor that reaches, 2000 mm3 or 20 mm in its longest axis, whichever comes first.

CARD11 and BCL10 CRISPR Knock-Out

CARD11 and BCL10 CRISPR knock-out CRISPR knockout was performed in triple reporter Jurkat cells using the SE Cell Line 4D Nucleofector Kit (Lonza). $1\times10^6$ cells were nucleofected with Cas9 only or ribonuclear protein complexes of Cas9 with CARD11 gRNA (CAATGACCTTACACTGACGC SEQ ID NO: 263) or BCL10 gRNA (TCGCCGAATAGATTCAACAA SEQ ID NO: 264).

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

TABLE 2

| LIST OF PCR1 PRIMERS | |
|---|---|
| PCR1F_1 | TCGTCGGCAGCGTCAGATGTGTATAAGAGACAGacgtagaagagaatcctgggc |
| PCR1F_2 | TCGTCGGCAGCGTCAGATGTGTATAAGAGACAGNacgtagaagagaatcctgggc |
| PCR1F_3 | TCGTCGGCAGCGTCAGATGTGTATAAGAGACAGNNacgtagaagagaatcctgggc |
| PCR1F_4 | TCGTCGGCAGCGTCAGATGTGTATAAGAGACAGNNNacgtagaagagaatcctgggc |
| PCR1F_5 | TCGTCGGCAGCGTCAGATGTGTATAAGAGACAGNNNNacgtagaagagaatcctgggc |
| PCR1R_1 | GTCTCGTGGGCTCGGAGATGTGTATAAGAGACAGttggtcaccttcagcttggc |
| PCR1R_2 | GTCTCGTGGGCTCGGAGATGTGTATAAGAGACAGNttggtcaccttcagcttggc |
| PCR1R_3 | GTCTCGTGGGCTCGGAGATGTGTATAAGAGACAGNNttggtcaccttcagcttqqc |
| PCR1R_4 | GTCTCGTGGGCTCGGAGATGTGTATAAGAGACAGNNNttggtcaccttcagcttggc |
| PCR1R_5 | GTCTCGTGGGCTCGGAGATGTGTATAAGAGACAGNNNNttggtcaccttcagcttggc |

TABLE 3

RESULTS OF IN VIVO MUTATION SCREENING

| Construct | In vivo log2 fold change |
|---|---|
| CARD11-PIK3R3 | 3.0005 |
| MYCN_P44L | 2.5543 |
| CCND3_P284S | 2.0288 |
| MYCN | 1.7046 |
| GATA3_Y63X | 1.1711 |
| CCND3 | 1.1358 |
| STAT3_G618R | 1.0989 |
| PLCG1 | 1.0924 |
| TNFRSF1B_G256C | 0.98454 |
| CARMIL2_Q575E | 0.95534 |
| RHOA_C16R | 0.83989 |
| JAK1_G1097A | 0.82419 |
| PLCG1_S520F | 0.81648 |
| CARMIL2 | 0.81511 |
| KCNQ1 | 0.74451 |
| STAT3_N647I | 0.73129 |
| mCherry | 0.71787 |
| JAK3_A573V | 0.64517 |
| JAK3 | 0.6204 |
| SMARCB1 | 0.61464 |
| NPM-TYK | 0.61211 |
| PRKCB1 | 0.60187 |
| ITK-SYK | 0.57059 |
| CD53 | 0.55832 |
| LATS1_P165T | 0.55327 |
| NFKB2_K656X | 0.54768 |
| CD3E_S41C | 0.49715 |
| STAT3_D661I | 0.47289 |
| VAV1 | 0.46373 |
| ITK-FER | 0.45221 |
| PRKCB1_D427N | 0.42466 |
| VAV1_R798Q | 0.38758 |
| NFKB1 | 0.36173 |
| EIFS1 | 0.35107 |
| STAT3 | 0.34767 |

TABLE 3-continued

RESULTS OF IN VIVO MUTATION SCREENING

| Construct | In vivo log2 fold change |
| --- | --- |
| KCNQ1__R583C | 0.34574 |
| CARD11__Y361C | 0.34369 |
| ECSIT__V140A | 0.30825 |
| TBL1XR1 | 0.3019 |
| EIFS1__R89I | 0.294 |
| RARA | 0.29369 |
| PDCD1__R231X | 0.26309 |
| TP53__R273P | 0.2616 |
| NFKB1__H67Y | 0.23355 |
| TNFRSF1B__T377I | 0.20846 |
| DGKA | 0.20622 |
| CARD11__S615F | 0.20484 |
| CARD11__D357N | 0.19285 |
| CARD11__E634K: S655C | 0.15507 |
| CSNK1A1__S27C | 0.14252 |
| RHOA | 0.1348 |
| CD28__T195P | 0.13182 |
| RASGRP1__M261I | 0.1296 |
| NRAS | 0.067501 |
| CSNK1A1 | 0.061897 |
| TP53 | 0.043614 |
| RASGRP1 | 0.013008 |
| BRAF | −0.0035971 |
| IRF4 | −0.010882 |
| JUNB | −0.025732 |
| TNFRSF1B | −0.032402 |
| ECSIT | −0.12417 |
| SPI1-TCF7 | −0.12925 |
| PRKCB1__D630Y | −0.13355 |
| NFKB2 | −0.15157 |
| VAV1__D797H | −0.15363 |
| RHOA__G17V | −0.16445 |
| CARD11 | −0.16964 |
| CSNK2B__Q182X | −0.17317 |
| CD28__Q77P | −0.17518 |
| GNAQ | −0.19753 |
| CD28 | −0.22358 |
| NRAS__Q61H | −0.23431 |
| BCOR | −0.23446 |
| FYN | −0.24392 |
| CSNK2B | −0.27225 |
| IRF4__K59R | −0.27748 |
| BRAF__G469R | −0.28717 |
| ITGB2 | −0.28743 |
| SMARCB1__Q368X | −0.28979 |
| PLCG1__E1163K | −0.33003 |
| CD3E | −0.34196 |
| TBL1XR1__H307R | −0.36523 |
| FYN__Y531H | −0.38263 |
| BRAF__D594N | −0.42484 |
| BCL6__S647R | −0.50434 |
| CD28-CTLA4 | −0.51046 |
| CD28__F51I | −0.52077 |
| GNAQ__T96S | −0.5295 |
| NPM-ALK | −0.54833 |
| BRAF__G469A | −0.56155 |
| PLCG1__E47K | −0.68232 |
| STAT5B__T628S | −0.68373 |
| CD28__F51V | −0.68501 |
| STAT5B | −0.82356 |
| CBLB | −0.85465 |
| ITGB2__E234K | −0.93692 |
| BCOR__N1459S | −1.0945 |
| MSC__E116K | −1.1425 |
| DGKZ | −1.183 |
| VAV1__E556D | −1.2374 |
| PLCG1__R48W | −1.3029 |
| PLCG1__D1165H | −1.3605 |
| VAV1-GSS | −1.3956 |
| ICOS-CD28 | −1.5123 |
| STAT5B__Y665F | −1.5667 |
| RARA__G206S | −1.8206 |
| SELENOI-ABL1 | −2.1187 |
| GATA3 | −2.1676 |
| JUNB__A282V | −2.2295 |
| MSC | −2.9114 |
| BCL6 | −3.088 |
| FYN__R86G | −4.9583 |
| PDCD1 | −5.2934 |

TABLE 4

RESULTS OF IN VITRO MUTATION SCREENING

| Construct | condition | group | CAR | nfat_zscore | nfkb_zscore | ap1_zscore | il2_zscore | pd1_zscore |
| --- | --- | --- | --- | --- | --- | --- | --- | --- |
| BCL6 | K562 | Wild-type | 28z | −0.04037972 | −0.0955831 | −0.41976843 | NA | NA |
| BCL6 | K562 | Wild-type | BBz | −0.42494348 | −0.14672375 | −0.48966525 | NA | −0.14045184 |
| BCL6 | K562-19 | Wild-type | 28z | −0.60059827 | −0.70834113 | −0.81444001 | −0.34152766 | NA |
| BCL6 | K562-19 | Wild-type | BBz | −0.18288789 | −0.11036598 | −0.65804064 | −0.21448862 | 0.53255809 |
| BCL6_S647R | K562 | Mutant | 28z | −0.35915673 | −0.29389965 | −0.30193543 | NA | NA |
| BCL6_S647R | K562 | Mutant | BBz | −0.69736303 | −0.63294304 | −0.27092471 | NA | −0.15216875 |
| BCL6_S647R | K562-19 | Mutant | 28z | −1.4472224 | −0.87572869 | −0.06785586 | −0.34164038 | NA |
| BCL6_S647R | K562-19 | Mutant | BBz | −1.0354498 | −0.36073958 | −0.23781412 | −0.2349297 | −0.06574864 |
| BRAF | K562 | Wild-type | 28z | 0.41734257 | −0.12651894 | 0.53507192 | NA | NA |
| BRAF | K562 | Wild-type | BBz | −0.15086105 | −0.5089276 | −0.22431594 | NA | −0.14240422 |
| BRAF | K562-19 | Wild-type | 28z | 1.29334332 | 0.51574434 | 1.23532286 | −0.07349989 | NA |
| BRAF | K562-19 | Wild-type | BBz | 0.4989266 | 0.48421561 | 0.47549493 | −0.11387979 | 0.07579773 |
| BRAF_D594N | K562 | Mutant | 28z | 0.23749219 | −0.06506305 | 0.23140873 | NA | NA |
| BRAF_D594N | K562 | Mutant | BBz | −0.90612685 | −0.69591963 | −0.03449949 | NA | −0.13537424 |
| BRAF_D594N | K562-19 | Mutant | 28z | 1.17145567 | 1.15905427 | 0.95419286 | 0.38641353 | NA |
| BRAF_D594N | K562-19 | Mutant | BBz | 0.83238883 | 0.83616754 | 0.85878988 | −0.01315878 | 0.05440468 |
| BRAF_G469A | K562 | Mutant | 28z | 4.19343309 | 2.29844317 | 8.27352879 | NA | NA |
| BRAF_G469A | K562 | Mutant | BBz | 4.53554578 | 3.36214342 | 8.97191503 | NA | 0.13955362 |
| BRAF_G469A | K562-19 | Mutant | 28z | 5.687353 | 2.32667926 | 3.05616511 | 5.55025808 | NA |
| BRAF_G469A | K562-19 | Mutant | BBz | 5.00458398 | 2.85478237 | 3.00208717 | 6.30688486 | −0.10690446 |
| BRAF_G469R | K562 | Mutant | 28z | 1.52300962 | 0.08415717 | 1.0106096 | NA | NA |
| BRAF_G469R | K562 | Mutant | BBz | −0.34720489 | −0.75881493 | 0.2378824 | NA | −0.12170792 |
| BRAF_G469R | K562-19 | Mutant | 28z | 1.76072274 | 1.52697931 | 2.06857341 | 0.35364478 | NA |
| BRAF_G469R | K562-19 | Mutant | BBz | 1.46193293 | 1.21983288 | 1.96356853 | 0.00654301 | 0.09843618 |
| CARD11 | K562 | Wild-type | 28z | 0.76432902 | 1.40268456 | 0.57314851 | NA | NA |
| CARD11 | K562 | Wild-type | BBz | −1.03720751 | 0.42615385 | 0.01644312 | NA | −0.12678245 |
| CARD11 | K562-19 | Wild-type | 28z | 0.44778195 | 2.19188712 | 1.73088915 | 0.49655187 | NA |

TABLE 4-continued

RESULTS OF IN VITRO MUTATION SCREENING

| Construct | condition | group | CAR | nfat_zscore | nfkb_zscore | ap1_zscore | il2_zscore | pd1_zscore |
|---|---|---|---|---|---|---|---|---|
| CARD11 | K562-19 | Wild-type | BBz | −0.34811726 | 1.52691894 | 0.37366488 | 0.04741407 | −0.17274699 |
| CARD11_D357N | K562 | Mutant | 28z | 0.81660002 | 4.77616697 | 1.31667239 | NA | NA |
| CARD11_D357N | K562 | Mutant | BBz | −0.86215615 | 4.04596443 | 0.38224895 | NA | −0.14513877 |
| CARD11_D357N | K562-19 | Mutant | 28z | 0.55371145 | 3.06936424 | 3.5186095 | 4.03791094 | NA |
| CARD11_D357N | K562-19 | Mutant | BBz | −0.23505497 | 3.32790316 | 2.25349661 | 3.3844891 | −0.41758481 |
| CARD11_E634K: S655C | K562 | Mutant | 28z | 0.58427801 | 1.34030602 | 0.72247509 | NA | NA |
| CARD11_E634K: S655C | K562 | Mutant | BBz | −1.04901776 | 0.57885195 | 0.22322985 | NA | −0.12951579 |
| CARD11_E634K: S655C | K562-19 | Mutant | 28z | 0.14528109 | 2.45027526 | 2.26857329 | 0.69828143 | NA |
| CARD11_E634K: S655C | K562-19 | Mutant | BBz | −0.37563674 | 2.4486072 | 1.07736493 | 0.68266188 | −0.27479898 |
| CARD11_S615F | K562 | Mutant | 28z | 0.31394837 | 1.90037921 | 0.75928438 | NA | NA |
| CARD11_S615F | K562 | Mutant | BBz | −0.77510162 | 0.58107106 | 0.06433776 | NA | −0.14552813 |
| CARD11_S615F | K562-19 | Mutant | 28z | 0.22611254 | 3.09528996 | 3.63508187 | 1.66924451 | NA |
| CARD11_S615F | K562-19 | Mutant | BBz | −0.07758086 | 3.21725938 | 2.61699929 | 1.62726411 | −0.34556963 |
| CARD11_Y361C | K562 | Mutant | 28z | 0.57506305 | 4.41637671 | 1.85631617 | NA | NA |
| CARD11_Y361C | K562 | Mutant | BBz | −1.00449277 | 2.71705204 | 0.2478598 | NA | −0.14162271 |
| CARD11_Y361C | K562-19 | Mutant | 28z | 0.32389953 | 3.168582 | 4.14743406 | 4.27085752 | NA |
| CARD11_Y361C | K562-19 | Mutant | BBz | −0.11740999 | 3.82923422 | 4.01651052 | 4.62183388 | −0.42416689 |
| CARD11-PIK3R3 | K562 | Fusion | 28z | 0.69354179 | 6.90840923 | 1.20497724 | NA | NA |
| CARD11-PIK3R3 | K562 | Fusion | BBz | 0.1466756 | 7.22743303 | 0.85507554 | NA | −0.14435763 |
| CARD11-PIK3R3 | K562-19 | Fusion | 28z | 1.51517617 | 3.13320621 | 0.3049936 | 4.66564406 | NA |
| CARD11-PIK3R3 | K562-19 | Fusion | BBz | 0.37107759 | 4.00945098 | 2.95110071 | 5.69050212 | −0.53650972 |
| CARMIL2_Q575E | K562 | Mutant | 28z | 1.72977003 | 0.06737486 | 0.21901141 | NA | NA |
| CARMIL2_Q575E | K562 | Mutant | BBz | −0.66414944 | −0.477902 | 0.53793429 | NA | −0.10647467 |
| CARMIL2_Q575E | K562-19 | Mutant | 28z | 0.63637423 | 0.02116175 | 0.51849677 | −0.25751396 | NA |
| CARMIL2_Q575E | K562-19 | Mutant | BBz | −0.44119459 | −0.26441597 | 0.06724462 | −0.21628463 | −0.04312157 |
| CCND3 | K562 | Wild-type | 28z | −0.95864479 | −0.32481792 | −1.14022793 | NA | NA |
| CCND3 | K562 | Wild-type | BBz | −2.00046112 | −0.62346197 | −1.19086847 | NA | −0.16232143 |
| CCND3 | K562-19 | Wild-type | 28z | −1.58580772 | −1.29423889 | −1.56376981 | −0.34298667 | NA |
| CCND3 | K562-19 | Wild-type | BBz | −1.12445669 | −1.02722958 | −1.69420663 | −0.24816655 | −0.4710794 |
| CCND3_P284S | K562 | Mutant | 28z | −1.09502855 | −0.41842547 | −1.30374901 | NA | NA |
| CCND3_P284S | K562 | Mutant | BBz | −2.50537585 | −0.75280415 | −1.24360496 | NA | −0.17013348 |
| CCND3_P284S | K562-19 | Mutant | 28z | −1.85171994 | −1.48521031 | −1.71008355 | −0.34298667 | NA |
| CCND3_P284S | K562-19 | Mutant | BBz | −1.65191799 | −1.4182088 | −1.76611827 | −0.26181593 | −0.55667426 |
| CD28 | K562 | Wild-type | 28z | −0.58014083 | −0.3764552 | −0.29434623 | NA | NA |
| CD28 | K562 | Wild-type | BBz | −0.47872898 | −0.45757179 | −0.2707104 | NA | −0.14592009 |
| CD28 | K562-19 | Wild-type | 28z | −0.05505631 | −0.45761568 | −0.16829841 | −0.26499215 | NA |
| CD28 | K562-19 | Wild-type | BBz | −0.5443677 | −0.69953906 | −0.52164624 | −0.25884193 | −0.04189137 |
| CD28_F51I | K562 | Mutant | 28z | −0.57621223 | −0.34975894 | −0.62237231 | NA | NA |
| CD28_F51I | K562 | Mutant | BBz | −0.72070639 | −0.3765616 | −0.1941139 | NA | −0.15529191 |
| CD28_F51I | K562-19 | Mutant | 28z | −0.15470396 | −0.65172335 | −0.49779072 | −0.29299669 | NA |
| CD28_F51I | K562-19 | Mutant | BBz | −0.55989238 | −0.62514142 | −0.59278357 | −0.22804159 | −0.07851296 |
| CD28_F51V | K562 | Mutant | 28z | −0.51884618 | −0.32456415 | −0.48693454 | NA | NA |
| CD28_F51V | K562 | Mutant | BBz | −0.36977225 | −0.42444839 | −0.38081091 | NA | −0.1498244 |
| CD28_F51V | K562-19 | Mutant | 28z | −0.23571422 | −0.73386965 | −0.37360963 | −0.30394058 | NA |
| CD28_F51V | K562-19 | Mutant | BBz | −0.48915964 | −0.65072433 | −0.31805897 | −0.24965553 | −0.030371 |
| CD28_Q77P | K562 | Mutant | 28z | −0.53216238 | −0.35701187 | −0.38039333 | NA | NA |
| CD28_Q77P | K562 | Mutant | BBz | −0.42416747 | −0.47278101 | −0.23361863 | NA | −0.15138761 |
| CD28_Q77P | K562-19 | Mutant | 28z | −0.24138729 | −0.48806784 | −0.35292875 | −0.23546789 | NA |
| CD28_Q77P | K562-19 | Mutant | BBz | −0.51274029 | −0.5997123 | −0.37119695 | −0.25269648 | 0.00707333 |
| CD28_T195P | K562 | Mutant | 28z | −0.44590801 | −0.34711941 | −0.37264683 | NA | NA |
| CD28_T195P | K562 | Mutant | BBz | −0.62145361 | −0.43013779 | −0.06551116 | NA | −0.13225238 |
| CD28_T195P | K562-19 | Mutant | 28z | 0.46152183 | −0.08448582 | 0.09520837 | −0.26199817 | NA |
| CD28_T195P | K562-19 | Mutant | BBz | −0.2143554 | −0.41628433 | 0.09413578 | −0.24803365 | 0.1375158 |
| CD28-CTLA4 | K562 | Fusion | 28z | −0.47332426 | −0.36779612 | −0.2118667 | NA | NA |
| CD28-CTLA4 | K562 | Fusion | BBz | 0.71391578 | −0.14055481 | −0.23057066 | NA | −0.14865473 |
| CD28-CTLA4 | K562-19 | Fusion | 28z | −0.3741551 | −0.40850329 | −0.64424609 | −0.26715955 | NA |
| CD28-CTLA4 | K562-19 | Fusion | BBz | −0.32034873 | −0.6219302 | −0.6635623 | −0.249844 | −0.08015496 |
| CD3E | K562 | Wild-type | 28z | −0.20869157 | −0.36252031 | −0.15002519 | NA | NA |
| CD3E | K562 | Wild-type | BBz | −0.77432561 | −0.63649336 | 0.10336625 | NA | −0.13186032 |
| CD3E | K562-19 | Wild-type | 28z | −0.07655176 | −0.33187641 | −0.12152951 | −0.30548728 | NA |
| CD3E | K562-19 | Wild-type | BBz | −0.20130779 | −0.30622441 | −0.03709553 | −0.23060918 | −0.04641549 |
| CD3E_S41C | K562 | Mutant | 28z | −0.22277297 | −0.36653084 | −0.44028483 | NA | NA |
| CD3E_S41C | K562 | Mutant | BBz | −0.84042023 | −0.59300352 | −0.18473182 | NA | −0.14318508 |
| CD3E_S41C | K562-19 | Mutant | 28z | −0.11814801 | −0.31809851 | −0.23428394 | −0.29767783 | NA |
| CD3E_S41C | K562-19 | Mutant | BBz | −0.28441598 | −0.51332993 | −0.30931003 | −0.21643876 | −0.17027997 |
| CD53 | K562 | Wild-type | 28z | −0.36542757 | −0.35020662 | −0.2877231 | NA | NA |
| CD53 | K562 | Wild-type | BBz | 1.03246777 | −0.14741347 | 0.20596587 | NA | −0.14748358 |
| CD53 | K562-19 | Wild-type | 28z | −0.15998843 | −0.22181842 | −0.46156325 | −0.27093551 | NA |
| CD53 | K562-19 | Wild-type | BBz | −0.29143329 | −0.48906853 | −0.28471326 | −0.22034481 | −0.15093587 |
| CSNK1A1 | K562 | Wild-type | 28z | −0.44874715 | −0.33704702 | −0.42349776 | NA | NA |
| CSNK1A1 | K562 | Wild-type | BBz | −0.92780734 | −0.48795022 | −0.33677387 | NA | −0.15997838 |
| CSNK1A1 | K562-19 | Wild-type | 28z | −0.35891914 | −0.57390489 | −0.43016389 | −0.28566222 | NA |

TABLE 4-continued

RESULTS OF IN VITRO MUTATION SCREENING

| Construct | condition | group | CAR | nfat_zscore | nfkb_zscore | ap1_zscore | il2_zscore | pd1_zscore |
|---|---|---|---|---|---|---|---|---|
| CSNK1A1 | K562-19 | Wild-type | BBz | −0.38452477 | −0.27172985 | −0.44943316 | −0.22846393 | −0.1521738 |
| CSNK1A1_S27C | K562 | Mutant | 28z | −0.31294661 | −0.30901164 | −0.52438639 | NA | NA |
| CSNK1A1_S27C | K562 | Mutant | BBz | −0.56733553 | −0.27275759 | −0.35643497 | NA | −0.14123307 |
| CSNK1A1_S27C | K562-19 | Mutant | 28z | −0.20514256 | −0.34914646 | −0.37183918 | −0.26088941 | NA |
| CSNK1A1_S27C | K562-19 | Mutant | BBz | −0.30094182 | −0.19923758 | −0.18489185 | −0.24110229 | −0.09909219 |
| CSNK2B | K562 | Wild-type | 28z | −0.51786169 | −0.24503595 | −0.56053973 | NA | NA |
| CSNK2B | K562 | Wild-type | BBz | −0.50168434 | −0.04736048 | −0.67212366 | NA | −0.14709013 |
| CSNK2B | K562-19 | Wild-type | 28z | −0.3803699 | −0.40786621 | −0.49920708 | −0.24916952 | NA |
| CSNK2B | K562-19 | Wild-type | BBz | −0.43728406 | −0.27377335 | −0.55126321 | −0.23935517 | −0.00568437 |
| CSNK2B_Q182X | K562 | Mutant | 28z | −0.67970208 | −0.34188232 | −0.62332948 | NA | NA |
| CSNK2B_Q182X | K562 | Mutant | BBz | −0.98270142 | −0.35146927 | −0.75707037 | NA | −0.150606 |
| CSNK2B_Q182X | K562-19 | Mutant | 28z | −0.3451449 | −0.65386662 | −0.61408605 | −0.32332219 | NA |
| CSNK2B_Q182X | K562-19 | Mutant | BBz | −0.39709762 | −0.51274607 | −0.76661099 | −0.23277307 | −0.19291069 |
| DGKA | K562 | Wild-type | 28z | −0.39000468 | −0.36890619 | −0.15889508 | NA | NA |
| DGKA | K562 | Wild-type | BBz | 0.30986127 | −0.26049532 | 0.22635721 | NA | −0.14748237 |
| DGKA | K562-19 | Wild-type | 28z | −0.34400475 | −0.32754857 | −0.27622474 | −0.32293663 | NA |
| DGKA | K562-19 | Wild-type | BBz | −0.19168181 | −0.45998248 | −0.27295276 | −0.24893913 | −0.11761202 |
| DGKZ | K562 | Wild-type | 28z | −0.55927303 | −0.40663331 | −0.35859179 | NA | NA |
| DGKZ | K562 | Wild-type | BBz | 0.11179913 | −0.23052019 | 0.24430382 | NA | −0.14982672 |
| DGKZ | K562-19 | Wild-type | 28z | −1.95081386 | −2.01088233 | −1.60264003 | −0.34298667 | NA |
| DGKZ | K562-19 | Wild-type | BBz | −1.19877096 | −2.04362801 | −1.53464225 | −0.25612365 | −0.4965937 |
| ECSIT | K562 | Wild-type | 28z | −0.23687303 | −0.24493021 | −0.46175394 | NA | NA |
| ECSIT | K562 | Wild-type | BBz | −0.72081725 | −0.20094585 | −0.52462183 | NA | −0.13849964 |
| ECSIT | K562-19 | Wild-type | 28z | −0.39929618 | −0.34501722 | −0.42268011 | −0.30511933 | NA |
| ECSIT | K562-19 | Wild-type | BBz | −0.50135184 | −0.28970695 | −0.63286958 | −0.23625678 | −0.04642178 |
| ECSIT_V140A | K562 | Mutant | 28z | −0.64210503 | −0.33154217 | −0.58523506 | NA | NA |
| ECSIT_V140A | K562 | Mutant | BBZ | −0.70911786 | −0.30636496 | −0.4532958 | NA | −0.15099537 |
| ECSIT_V140A | K562-19 | Mutant | 28z | −0.46486066 | −0.52145765 | −0.55558429 | −0.26915792 | NA |
| ECSIT_V140A | K562-19 | Mutant | BBz | −0.52833077 | −0.43089642 | −0.52594927 | −0.25689741 | −0.12295566 |
| EIFS1 | K562 | Wild-type | 28z | −0.33400571 | −0.34881446 | 0.0336754 | NA | NA |
| EIFS1 | K562 | Wild-type | BBz | −0.90712457 | −0.55524309 | 0.11098623 | NA | −0.14826305 |
| EIFS1 | K562-19 | Wild-type | 28z | −0.24866653 | −0.34009359 | −0.12706579 | −0.30538397 | NA |
| EIFS1 | K562-19 | Wild-type | BBz | −0.1668651 | 0.03097729 | 0.11486094 | −0.22898211 | −0.1920877 |
| EIFS1_R89I | K562 | Mutant | 28z | −0.43376759 | −0.27968626 | −0.47256045 | NA | NA |
| EIFS1_R89I | K562 | Mutant | BBz | −0.8080935 | −0.33537153 | −0.38488282 | NA | −0.15490199 |
| EIFS1_R89I | K562-19 | Mutant | 28z | −0.40268728 | −0.4565814 | −0.47281287 | −0.20454285 | NA |
| EIFS1_R89I | K562-19 | Mutant | BBz | −0.44297121 | −0.22071782 | −0.29790811 | −0.23771353 | −0.18385599 |
| FYN | K562 | Wild-type | 28z | −0.05799779 | −0.20253699 | −0.00215442 | NA | NA |
| FYN | K562 | Wild-type | BBz | −0.01905981 | −0.31568471 | −0.15599027 | NA | −0.11975312 |
| FYN | K562-19 | Wild-type | 28z | −0.85921924 | −1.1977602 | −0.92289747 | −0.34298667 | NA |
| FYN | K562-19 | Wild-type | BBZ | −0.3281698 | −0.00308721 | 0.08058235 | −0.25575489 | −0.25875356 |
| FYN_R86G | K562 | Mutant | 28z | 0.75297246 | 0.21942135 | 0.80158894 | NA | NA |
| FYN_R86G | K562 | Mutant | BBz | −0.07484076 | −0.47378958 | 0.08973765 | NA | −0.12561306 |
| FYN_R86G | K562-19 | Mutant | 28z | −0.04036374 | −0.62345576 | −0.79588366 | −0.34164038 | NA |
| FYN_R86G | K562-19 | Mutant | BBz | 0.18905917 | 0.31539973 | 0.48388528 | −0.18699662 | −0.22665185 |
| FYN_Y531H | K562 | Mutant | 28z | −0.14062917 | −0.1530213 | 0.05741357 | NA | NA |
| FYN_Y531H | K562 | Mutant | BBz | −0.07367675 | −0.3354128 | −0.23575382 | NA | −0.12678393 |
| FYN_Y531H | K562-19 | Mutant | 28z | −0.46888288 | −0.96120984 | −0.85903648 | −0.34287395 | NA |
| FYN_Y531H | K562-19 | Mutant | BBz | 0.0378552 | 0.28382445 | 0.10854927 | −0.2305466 | −0.28673403 |
| GATA3 | K562 | Wild-type | 28z | −0.25312402 | −0.10426333 | −0.04252235 | NA | NA |
| GATA3 | K562 | Wild-type | BBz | 0.42846653 | −0.29107382 | −0.06983707 | NA | −0.12639411 |
| GATA3 | K562-19 | Wild-type | 28z | 0.52722908 | 0.29999748 | −0.07303806 | −0.24319387 | NA |
| GATA3 | K562-19 | Wild-type | BBz | 0.03539228 | −0.02472126 | −0.29166927 | −0.21948347 | −0.3636831 |
| GATA3_Y63X | K562 | Mutant | 28z | −0.65513429 | −0.30733058 | −0.40944273 | NA | NA |
| GATA3_Y63X | K562 | Mutant | BBz | −1.07125254 | −0.37426247 | −0.91994707 | NA | −0.14904382 |
| GATA3_Y63X | K562-19 | Mutant | 28z | −0.27944967 | −0.43875685 | −0.56807322 | −0.24868349 | NA |
| GATA3_Y63X | K562-19 | Mutant | BBz | −0.44090309 | −0.52955546 | −0.93240665 | −0.23567896 | −0.11513939 |
| GNAQ | K562 | Wild-type | 28z | −0.44688316 | −0.35104536 | −0.33518606 | NA | NA |
| GNAQ | K562 | Wild-type | BBZ | −0.15075019 | −0.25073099 | −0.28754576 | NA | −0.15411937 |
| GNAQ | K562-19 | Wild-type | 28z | −0.23181408 | −0.29396016 | −0.39681704 | −0.29613938 | NA |
| GNAQ | K562-19 | Wild-type | BBz | −0.39717757 | −0.35328757 | −0.41451023 | −0.20870113 | −0.14517238 |
| GNAQ_T96S | K562 | Mutant | 28z | −0.4353353 | −0.32822234 | −0.33067469 | NA | NA |
| GNAQ_T96S | K562 | Mutant | BBz | −0.89625661 | −0.3048718 | 0.04248594 | NA | −0.13889039 |
| GNAQ_T96S | K562-19 | Mutant | 28z | −0.3181088 | −0.18469656 | −0.18184961 | −0.31291166 | NA |
| GNAQ_T96S | K562-19 | Mutant | BBz | −0.4363487 | −0.20902502 | −0.0973324 | −0.22998832 | −0.04394915 |
| ICOS-CD28 | K562 | Fusion | 28z | −0.51884618 | −0.38236185 | −0.26868927 | NA | NA |
| ICOS-CD28 | K562 | Fusion | BBz | 0.6594097 | −0.11098172 | 0.05786873 | NA | −0.14006563 |
| ICOS-CD28 | K562-19 | Fusion | 28z | 0.03735682 | −0.4839386 | −0.45996985 | −0.3169841 | NA |
| ICOS-CD28 | K562-19 | Fusion | BBz | −0.32080934 | −0.54095634 | −0.27775725 | −0.26181593 | −0.0118555 |
| IRF4 | K562 | Wild-type | 28z | −0.80277896 | −0.30963891 | −0.28951135 | NA | NA |
| IRF4 | K562 | Wild-type | BBz | −1.333691 | −0.51429436 | −0.14121072 | NA | −0.15763533 |
| IRF4 | K562-19 | Wild-type | 28z | −1.37738118 | −0.05069881 | 0.03311782 | −0.32231906 | NA |
| IRF4 | K562-19 | Wild-type | BBz | −1.44081503 | −0.823781 | −0.50723276 | −0.26181593 | 0.53667093 |
| IRF4_K59R | K562 | Mutant | 28z | −0.9342683 | −0.22734071 | 0.67516944 | NA | NA |
| IRF4_K59R | K562 | Mutant | BBz | −1.73863237 | −0.40137383 | 0.19384536 | NA | −0.14709078 |
| IRF4_K59R | K562-19 | Mutant | 28z | −1.3313861 | 0.75404077 | 1.27079425 | −0.34156794 | NA |

TABLE 4-continued

RESULTS OF IN VITRO MUTATION SCREENING

| Construct | condition | group | CAR | nfat_zscore | nfkb_zscore | ap1_zscore | il2_zscore | pd1_zscore |
|---|---|---|---|---|---|---|---|---|
| IRF4_K59R | K562-19 | Mutant | BBZ | −1.48668861 | −0.4887766 | −0.19041351 | −0.26181593 | 0.26097145 |
| ITGB2 | K562 | Wild-type | 28z | −0.02169084 | −0.34878973 | −0.00313834 | NA | NA |
| ITGB2 | K562 | Wild-type | BBZ | −0.60005026 | −0.64766956 | 0.20716443 | NA | −0.11545778 |
| ITGB2 | K562-19 | Wild-type | 28z | −0.19610073 | −0.3393405 | −0.1822037 | −0.29301631 | NA |
| ITGB2 | K562-19 | Wild-type | BBz | −0.10175371 | −0.3230338 | −0.03494402 | −0.23935517 | −0.11225607 |
| ITGB2_E234K | K562 | Mutant | 28z | −0.15081928 | −0.26040171 | −0.16747267 | NA | NA |
| ITGB2_E234K | K562 | Mutant | BBz | −0.31537702 | −0.52119303 | −0.06812259 | NA | −0.11740942 |
| ITGB2_E234K | K562-19 | Mutant | 28z | 0.0755843 | −0.2849073 | −0.26479808 | −0.24113582 | NA |
| ITGB2_E234K | K562-19 | Mutant | BBz | −0.33917759 | −0.6567167 | −0.21644462 | −0.25459582 | −0.15834883 |
| ITK-FER | K562 | Fusion | 28z | 0.30650175 | −0.26552591 | 0.339244 | NA | NA |
| ITK-FER | K562 | Fusion | BBZ | 0.62763726 | −0.30559963 | 0.56295316 | NA | −0.15841731 |
| ITK-FER | K562-19 | Fusion | 28z | 0.25918967 | −0.1613113 | −0.08105297 | −0.25876702 | NA |
| ITK-FER | K562-19 | Fusion | BBZ | 0.3190046 | −0.0643324 | 0.13673189 | −0.23981607 | −0.10443676 |
| ITK-SYK | K562 | Fusion | 28z | −0.46775096 | −0.34064177 | −0.13857165 | NA | NA |
| ITK-SYK | K562 | Fusion | BBz | 0.72555975 | −0.09117297 | 0.05354281 | NA | −0.15138751 |
| ITK-SYK | K562-19 | Fusion | 28z | −0.16785575 | −0.51165169 | −0.68242105 | −0.28232082 | NA |
| ITK-SYK | K562-19 | Fusion | BBz | −0.36070427 | −0.49155775 | −0.56230655 | −0.25434095 | −0.13118414 |
| JAK1_G1097A | K562 | Mutant | 28z | 0.42310718 | −0.20649125 | 0.30278053 | NA | NA |
| JAK1_G1097A | K562 | Mutant | BBz | −0.95031926 | −0.61664585 | 0.231969 | NA | −0.11936376 |
| JAK1_G1097A | K562-19 | Mutant | 28z | 0.34262633 | 0.01806679 | 0.50105059 | −0.29272241 | NA |
| JAK1_G1097A | K562-19 | Mutant | BBz | −0.0592784 | −0.07528756 | 0.14885098 | −0.23495171 | −0.03242997 |
| JAK3 | K562 | Wild-type | 28z | −0.25558056 | −0.2954291 | −0.1403376 | NA | NA |
| JAK3 | K562 | Wild-type | BBz | −0.45715935 | −0.5203064 | 0.06271058 | NA | −0.13654595 |
| JAK3 | K562-19 | Wild-type | 28z | −0.06437501 | −0.30261584 | −0.32223756 | −0.29898304 | NA |
| JAK3 | K562-19 | Wild-type | BBZ | −0.33314729 | −0.36073958 | −0.2982667 | −0.22208007 | −0.17727392 |
| JAK3_A573V | K562 | Mutant | 28z | −0.22464628 | −0.33008657 | −0.15794237 | NA | NA |
| JAK3_A573V | K562 | Mutant | BBz | −0.4910381 | −0.54463151 | 0.2654254 | NA | −0.11701858 |
| JAK3_A573V | K562-19 | Mutant | 28z | −0.04707723 | −0.00158642 | 0.10858252 | −0.26096146 | NA |
| JAK3_A573V | K562-19 | Mutant | BBz | −0.14718084 | −0.31542799 | 0.02177982 | −0.23573164 | −0.06699879 |
| JUNB | K562 | Wild-type | 28z | −0.44669186 | −0.33746281 | −0.62478529 | NA | NA |
| JUNB | K562 | Wild-type | BBz | −0.54504532 | −0.43211554 | −0.71144585 | NA | −0.16856981 |
| JUNB | K562-19 | Wild-type | 28z | 0.94164374 | −0.28510589 | −0.82050743 | −0.23656332 | NA |
| JUNB | K562-19 | Wild-type | BBz | −0.18029336 | −0.63961538 | −1.46348391 | −0.23480652 | −0.33817152 |
| JUNB_A282V | K562 | Mutant | 28z | −0.69517854 | −0.35490786 | −0.76877835 | NA | NA |
| JUNB_A282V | K562 | Mutant | BBz | −0.74210974 | −0.26477095 | −0.63257923 | NA | −0.16232162 |
| JUNB_A282V | K562-19 | Mutant | 28z | −0.17477039 | −0.44149591 | −1.51788904 | −0.33009102 | NA |
| JUNB_A282V | K562-19 | Mutant | BBz | −0.49771866 | −0.27830607 | −1.70377976 | −0.25632839 | −0.33775973 |
| KCNQ1 | K562 | Wild-type | 28z | −0.57289484 | −0.35789649 | −0.56554082 | NA | NA |
| KCNQ1 | K562 | Wild-type | BBz | −0.42433376 | −0.39318396 | −0.31942259 | NA | −0.16114991 |
| KCNQ1 | K562-19 | Wild-type | 28z | −0.18270476 | −0.32187185 | −0.53166871 | −0.19437329 | NA |
| KCNQ1 | K562-19 | Wild-type | BBz | −0.29417356 | −0.57486705 | −0.58833766 | −0.23668669 | −0.2603987 |
| KCNQ1_R583C | K562 | Mutant | 28z | −0.54665436 | −0.35848146 | −0.44108024 | NA | NA |
| KCNQ1_R583C | K562 | Mutant | BBz | −0.66620031 | −0.40875584 | −0.35545072 | NA | −0.16622722 |
| KCNQ1_R583C | K562-19 | Mutant | 28z | −0.35436554 | −0.35407009 | −0.48565588 | −0.24148623 | NA |
| KCNQ1_R583C | K562-19 | Mutant | BBz | −0.32406186 | −0.48074073 | −0.46693104 | −0.23464042 | −0.19908496 |
| MSC | K562 | Wild-type | 28z | −0.72181095 | −0.39528524 | −0.83416068 | NA | NA |
| MSC | K562 | Wild-type | BBz | −1.14727283 | −0.23939536 | −0.83007119 | NA | −0.15919771 |
| MSC | K562-19 | Wild-type | 28z | −1.13520336 | −1.39933196 | −1.06386155 | −0.34164038 | NA |
| MSC | K562-19 | Wild-type | BBz | −0.93974045 | −1.53484494 | −1.06220362 | −0.26166008 | 0.31445534 |
| MSC_E116K | K562 | Mutant | 28z | −0.66286786 | −0.10499992 | −0.4270475 | NA | NA |
| MSC_E116K | K562 | Mutant | BBz | −1.1472174 | 0.76604342 | −0.67473508 | NA | −0.16349332 |
| MSC_E116K | K562-19 | Mutant | 28z | −1.26808291 | −0.07448126 | −0.22644608 | −0.30387608 | NA |
| MSC_E116K | K562-19 | Mutant | BBz | −1.35047797 | −0.12937266 | −1.09519074 | −0.23662239 | −0.39577403 |
| MYCN | K562 | Wild-type | 28z | −0.53441829 | −0.36907896 | −0.73052664 | NA | NA |
| MYCN | K562 | Wild-type | BBz | −0.52375283 | −0.13385621 | −0.61985549 | NA | −0.15490153 |
| MYCN | K562-19 | Wild-type | 28z | −1.29255851 | −1.00813766 | −1.02119153 | −0.291337 | NA |
| MYCN | K562-19 | Wild-type | BBz | −0.84821898 | −0.72716547 | −1.1055169 | −0.23523482 | −0.23694413 |
| MYCN_P44L | K562 | Mutant | 28z | −0.71896248 | −0.37573976 | −0.89470367 | NA | NA |
| MYCN_P44L | K562 | Mutant | BBz | −1.26831696 | −0.09690238 | −0.74096526 | NA | −0.16115074 |
| MYCN_P44L | K562-19 | Mutant | 28z | −1.35072167 | −1.23801831 | −1.21374971 | −0.29281915 | NA |
| MYCN_P44L | K562-19 | Mutant | BBz | −0.98499353 | −0.77057168 | −1.19572933 | −0.2517801 | −0.29414444 |
| NFKB1 | K562 | Wild-type | 28z | 0.08092883 | −0.01440897 | 0.16505587 | NA | NA |
| NFKB1 | K562 | Wild-type | BBz | 0.00262068 | 0.14160741 | 0.53206058 | NA | −0.14982551 |
| NFKB1 | K562-19 | Wild-type | 28z | 0.53398727 | 0.58764619 | 0.21810224 | −0.28627586 | NA |
| NFKB1 | K562-19 | Wild-type | BBz | 0.39541034 | 0.39096508 | 0.32482993 | −0.20340792 | −0.14681573 |
| NFKB1_H67Y | K562 | Mutant | 28z | 0.9437595 | −0.15284853 | 0.70554411 | NA | NA |
| NFKB1_H67Y | K562 | Mutant | BBz | −0.17276325 | −0.53781539 | 0.5342513 | NA | −0.12639411 |
| NFKB1_H67Y | K562-19 | Mutant | 28z | 0.17675038 | 0.40592624 | 0.66606231 | −0.26262686 | NA |
| NFKB1_H67Y | K562-19 | Mutant | BBz | 0.5531618 | −0.06316469 | 0.80722912 | −0.16511798 | −0.24351568 |
| NFKB2 | K562 | Wild-type | 28z | 0.01532298 | −0.41819285 | −0.1576144 | NA | NA |
| NFKB2 | K562 | Wild-type | BBz | 0.03594513 | −0.69011208 | 0.23364379 | NA | −0.11975423 |
| NFKB2 | K562-19 | Wild-type | 28z | −0.06337762 | −1.17143728 | 0.01956663 | −0.29264744 | NA |
| NFKB2 | K562-19 | Wild-type | BBz | 0.16688863 | −1.31005425 | 0.19252285 | −0.14371182 | −0.09538002 |
| NFKB2_K656X | K562 | Mutant | 28z | −0.28259556 | −0.0751247 | −0.36198869 | NA | NA |
| NFKB2_K656X | K562 | Mutant | BBz | 0.45197618 | 0.51393383 | −0.1155886 | NA | −0.16076017 |
| NFKB2_K656X | K562-19 | Mutant | 28z | −0.07854653 | −0.56524921 | −0.53738204 | −0.25383021 | NA |

TABLE 4-continued

RESULTS OF IN VITRO MUTATION SCREENING

| Construct | condition | group | CAR | nfat_zscore | nfkb_zscore | ap1_zscore | il2_zscore | pd1_zscore |
|---|---|---|---|---|---|---|---|---|
| NFKB2_K656X | K562-19 | Mutant | BBz | −0.25300012 | −0.54124827 | −0.52824367 | −0.17765405 | −0.25998173 |
| NPM-ALK | K562 | Fusion | 28z | −0.29188751 | −0.24869056 | 0.82144494 | NA | NA |
| NPM-ALK | K562 | Fusion | BBz | 0.71469179 | −0.25182085 | 1.16339034 | NA | −0.11975637 |
| NPM-ALK | K562-19 | Fusion | 28z | −0.25193555 | −0.47250257 | 1.0881593 | −0.33706929 | NA |
| NPM-ALK | K562-19 | Fusion | BBz | −0.19015425 | −0.19324521 | 0.60686912 | −0.22966099 | −0.34680161 |
| NPM-TYK | K562 | Fusion | 28z | 0.03245347 | −0.32985395 | 0.60945468 | NA | NA |
| NPM-TYK | K562 | Fusion | BBz | 0.37423759 | −0.22600195 | 0.46904507 | NA | −0.13498571 |
| NPM-TYK | K562-19 | Fusion | 28z | 0.53919769 | −0.2843115 | 0.60809169 | −0.34123768 | NA |
| NPM-TYK | K562-19 | Fusion | BBz | 0.5999941 | −0.01448809 | 0.92705852 | −0.2552337 | −0.1826134 |
| NRAS | K562 | Wild-type | 28z | −0.26714708 | −0.3438383 | −0.23332688 | NA | NA |
| NRAS | K562 | Wild-type | BBz | 0.49650117 | −0.05882057 | 0.05050276 | NA | −0.16661918 |
| NRAS | K562-19 | Wild-type | 28z | −0.29809741 | −0.13872043 | −0.06267367 | −0.27460561 | NA |
| NRAS | K562-19 | Wild-type | BBz | −0.12336034 | −0.1656188 | 0.02084694 | −0.21096022 | −0.2089562 |
| NRAS_G13D | K562 | Mutant | 28z | −0.44424465 | −0.37768858 | −0.20491114 | NA | NA |
| NRAS_G13D | K562 | Mutant | BBz | 0.09045122 | 0.11465611 | 0.29224607 | NA | −0.14240645 |
| NRAS_G13D | K562-19 | Mutant | 28z | −0.88362946 | −0.61201973 | −0.44925137 | −0.27116567 | NA |
| NRAS_G13D | K562-19 | Mutant | BBz | −0.40551089 | −0.51157836 | −0.21164013 | −0.20718884 | −0.26779935 |
| NRAS_Q61H | K562 | Mutant | 28z | −0.47321929 | −0.40909683 | −0.44480065 | NA | NA |
| NRAS_Q61H | K562 | Mutant | BBz | 0.71552322 | −0.05664085 | −0.12450236 | NA | −0.14631215 |
| NRAS_Q61H | K562-19 | Mutant | 28z | −1.07258633 | −0.77392917 | −0.69597225 | −0.32639748 | NA |
| NRAS_Q61H | K562-19 | Mutant | BBz | −0.46875157 | −0.55776573 | −0.47173554 | −0.21659873 | −0.30071955 |
| PDCD1 | K562 | Wild-type | 28z | −0.02032376 | −0.36001807 | −0.07108648 | NA | NA |
| PDCD1 | K562 | Wild-type | BBz | −0.30395477 | −0.30850404 | −0.70926304 | NA | 7.59073915 |
| PDCD1 | K562-19 | Wild-type | 28z | −0.05106677 | −0.28077806 | −0.09978636 | −0.30768851 | NA |
| PDCD1 | K562-19 | Wild-type | BBz | −0.04306742 | −0.42768521 | −0.89246352 | −0.249844 | 7.43334981 |
| PDCD1_R231X | K562 | Mutant | 28z | −0.24256996 | −0.35055896 | −0.39878905 | NA | NA |
| PDCD1_R231X | K562 | Mutant | BBz | 0.04648052 | −0.13083113 | −1.02023688 | NA | 7.55949913 |
| PDCD1_R231X | K562-19 | Mutant | 28z | −0.35566046 | −0.33910061 | −0.29796789 | −0.24374415 | NA |
| PDCD1_R231X | K562-19 | Mutant | BBz | −0.73519419 | −0.80156311 | −0.65710776 | −0.24165014 | 7.41689166 |
| PLCG1 | K562 | Wild-type | 28z | −0.14592485 | −0.27006513 | −0.27255806 | NA | NA |
| PLCG1 | K562 | Wild-type | BBz | −0.0511094 | −0.13591652 | 0.06682219 | NA | −0.12717747 |
| PLCG1 | K562-19 | Wild-type | 28z | −0.10502891 | −0.18763421 | −0.30261895 | 0.03183223 | NA |
| PLCG1 | K562-19 | Wild-type | BBz | 0.14712442 | −0.17993896 | −0.17291563 | −0.25344572 | −0.20360229 |
| PLCG1_D1165H | K562 | Mutant | 28z | 5.0043194 | 1.06939699 | 1.74380332 | NA | NA |
| PLCG1_D1165H | K562 | Mutant | BBz | 0.96482113 | −0.12252247 | 1.14691213 | NA | −0.07289151 |
| PLCG1_D1165H | K562-19 | Mutant | 28z | 1.99928762 | 1.71191811 | 1.51415128 | 0.16042837 | NA |
| PLCG1_D1165H | K562-19 | Mutant | BBz | 3.39863359 | 1.52384586 | 2.50979045 | −0.1017419 | 0.02518722 |
| PLCG1_E1163K | K562 | Mutant | 28z | 0.95874839 | 0.32092343 | 0.57719243 | NA | NA |
| PLCG1_E1163K | K562 | Mutant | BBZ | 0.27698025 | −0.34953342 | 0.51171685 | NA | −0.13420541 |
| PLCG1_E1163K | K562-19 | Mutant | 28z | 1.78122081 | 1.6305662 | 1.08474755 | 0.83569131 | NA |
| PLCG1_E1163K | K562-19 | Mutant | BBZ | 2.24403946 | 1.16736121 | 1.47865923 | 0.23789494 | −0.03118194 |
| PLCG1_E47K | K562 | Mutant | 28z | 0.42241897 | −0.02241964 | 0.10582477 | NA | NA |
| PLCG1_E47K | K562 | Mutant | BBz | 0.17678517 | −0.23237601 | −0.10701616 | NA | −0.14552971 |
| PLCG1_E47K | K562-19 | Mutant | 28z | 1.30608581 | 1.1979222 | 0.44967853 | 0.54289919 | NA |
| PLCG1_E47K | K562-19 | Mutant | BBz | 1.09976681 | 0.61371227 | 0.43268311 | 0.11867278 | 0.06017267 |
| PLCG1_R48W | K562 | Mutant | 28z | 1.22927865 | 0.56336014 | 0.22803413 | NA | NA |
| PLCG1_R48W | K562 | Mutant | BBz | 0.92157101 | −0.20925892 | −0.14827507 | NA | −0.11819362 |
| PLCG1_R48W | K562-19 | Mutant | 28z | 2.42644478 | 1.78223119 | 0.94506778 | 2.3504768 | NA |
| PLCG1_R48W | K562-19 | Mutant | BBz | 2.908172 | 1.57544174 | 1.95503529 | 1.28637241 | 0.46261435 |
| PLCG1_S520F | K562 | Mutant | 28z | 4.00894029 | 0.35879209 | 0.41078202 | NA | NA |
| PLCG1_S520F | K562 | Mutant | BBz | 1.75612741 | 0.18380354 | 0.56354848 | NA | −0.0775803 |
| PLCG1_S520F | K562-19 | Mutant | 28z | 1.61058144 | 1.19299858 | 1.21818287 | −0.08617912 | NA |
| PLCG1_S520F | K562-19 | Mutant | BBz | 1.95371054 | 0.74087351 | 1.26861741 | −0.1929633 | −0.01965869 |
| PRKCB1 | K562 | Wild-type | 28z | 0.04214668 | −0.31159131 | −0.04847615 | NA | NA |
| PRKCB1 | K562 | Wild-type | BBz | 0.1781709 | −0.22737381 | 0.30788287 | NA | −0.15021608 |
| PRKCB1 | K562-19 | Wild-type | 28z | −0.25562587 | 0.20157412 | 0.25791851 | −0.24507385 | NA |
| PRKCB1 | K562-19 | Wild-type | BBz | 0.11061361 | 0.30283114 | 0.20944644 | −0.23705736 | −0.27273543 |
| PRKCB1_D427N | K562 | Mutant | 28z | −0.31794602 | −0.15959751 | 0.00657155 | NA | NA |
| PRKCB1_D427N | K562 | Mutant | BBz | 0.48496806 | −0.12986446 | −0.03132451 | NA | −0.14631057 |
| PRKCB1_D427N | K562-19 | Mutant | 28z | −1.02109531 | 0.57795624 | −0.47941142 | −0.20952336 | NA |
| PRKCB1_D427N | K562-19 | Mutant | BBz | −0.94284723 | 0.58316658 | −0.53218811 | −0.24893913 | −0.42704698 |
| PRKCB1_D630Y | K562 | Mutant | 28z | −0.1190055 | −0.29334981 | −0.1422876 | NA | NA |
| PRKCB1_D630Y | K562 | Mutant | BBz | −0.28188628 | −0.26412693 | 0.19992547 | NA | −0.14709366 |
| PRKCB1_D630Y | K562-19 | Mutant | 28z | −0.61693134 | 0.16072021 | −0.04535664 | −0.30064774 | NA |
| PRKCB1_D630Y | K562-19 | Mutant | BBz | −0.27342234 | 0.33878534 | −0.11196159 | −0.2480327 | −0.265738 |
| RARA | K562 | Wild-type | 28z | 0.07357786 | −0.39766059 | −0.16504631 | NA | NA |
| RARA | K562 | Wild-type | BBz | 2.33556585 | −0.25638037 | 0.10486643 | NA | −0.14201467 |
| RARA | K562-19 | Wild-type | 28z | 0.97211566 | −0.75526894 | −0.15952742 | −0.33095303 | NA |
| RARA | K562-19 | Wild-type | BBz | 1.18566693 | −0.39465029 | −0.09539659 | −0.2605096 | 0.35151419 |
| RARA_G206S | K562 | Mutant | 28z | 0.15758565 | −0.40171701 | −0.10434602 | NA | NA |
| RARA_G206S | K562 | Mutant | BBz | 2.76202142 | −0.15996026 | 0.38169332 | NA | −0.14201504 |
| RARA_G206S | K562-19 | Mutant | 28z | 0.8819208 | −0.65958464 | −0.17755264 | −0.34298667 | NA |
| RARA_G206S | K562-19 | Mutant | BBz | 1.34330094 | −0.31338449 | 0.03224886 | −0.26181593 | 0.52022127 |
| RASGRP1 | K562 | Wild-type | 28z | 2.57715222 | 0.35289874 | 1.81260038 | NA | NA |
| RASGRP1 | K562 | Wild-type | BBz | 1.22692702 | −0.03808012 | 1.06901393 | NA | −0.09085726 |
| RASGRP1 | K562-19 | Wild-type | 28z | 2.61980049 | 1.72855108 | 1.5701744 | 0.302134 | NA |

TABLE 4-continued

RESULTS OF IN VITRO MUTATION SCREENING

| Construct | condition | group | CAR | nfat_zscore | nfkb_zscore | ap1_zscore | il2_zscore | pd1_zscore |
|---|---|---|---|---|---|---|---|---|
| RASGRP1 | K562-19 | Wild-type | BBz | 2.80678965 | 1.4525213 | 2.32405964 | −0.02974785 | −0.12870888 |
| RASGRP1_M261I | K562 | Mutant | 28z | 2.45896976 | 0.80454914 | 2.99486157 | NA | NA |
| RASGRP1_M261I | K562 | Mutant | BBz | 2.04185381 | 0.35441582 | 1.86018033 | NA | −0.02485699 |
| RASGRP1_M261I | K562-19 | Mutant | 28z | 3.24928982 | 1.85592042 | 2.35935963 | 2.81543692 | NA |
| RASGRP1_M261I | K562-19 | Mutant | BBz | 4.01905476 | 1.79848086 | 2.80839464 | 0.57657597 | −0.1377674 |
| RHOA | K562 | Wild-type | 28z | −0.36170892 | −0.34721799 | −0.60897323 | NA | NA |
| RHOA | K562 | Wild-type | BBz | 0.63839436 | −0.2408085 | −0.27940985 | NA | −0.15255839 |
| RHOA | K562-19 | Wild-type | 28z | −0.23892652 | −0.40592153 | −0.53738204 | −0.32101367 | NA |
| RHOA | K562-19 | Wild-type | BBz | −0.49691491 | −0.48074073 | −0.59421791 | −0.26181593 | −0.24804846 |
| RHOA_C16R | K562 | Mutant | 28z | −0.58532221 | −0.3704851 | −0.5324475 | NA | NA |
| RHOA_C16R | K562 | Mutant | BBz | 0.28845793 | −0.07225337 | −0.45950291 | NA | −0.17208688 |
| RHOA_C16R | K562-19 | Mutant | 28z | −0.3381322 | −0.39317792 | −0.60018076 | −0.28372207 | NA |
| RHOA_C16R | K562-19 | Mutant | BBz | −0.23165669 | −0.34334633 | −0.56639387 | −0.25164868 | −0.28508287 |
| RHOA_G17V | K562 | Mutant | 28z | −0.40410474 | −0.33326553 | −0.56151919 | NA | NA |
| RHOA_G17V | K562 | Mutant | BBZ | 0.39591808 | −0.05345318 | −0.17230969 | NA | −0.17052395 |
| RHOA_G17V | K562-19 | Mutant | 28z | −0.21093773 | −0.29630203 | −0.46709954 | −0.28010727 | NA |
| RHOA_G17V | K562-19 | Mutant | BBz | −0.18783708 | −0.28371458 | −0.30966861 | −0.249844 | −0.2077192 |
| SELENOI-ABL1 | K562 | Fusion | 28z | −0.22444566 | 0.69022259 | 0.11938116 | NA | NA |
| SELENOI-ABL1 | K562 | Fusion | BBz | −0.10689035 | 0.59579253 | 0.24426412 | NA | −0.14435902 |
| SELENOI-ABL1 | K562-19 | Fusion | 28z | 1.09377981 | 2.13372187 | 0.41757099 | −0.313734 | NA |
| SELENOI-ABL1 | K562-19 | Fusion | BBz | 0.91589183 | 1.49637324 | 0.42809432 | −0.232441 | −0.36655742 |
| SMARCB1 | K562 | Wild-type | 28z | −0.50171568 | −0.37922877 | −0.54617456 | NA | NA |
| SMARCB1 | K562 | Wild-type | BBz | −0.10711207 | −0.0955718 | −0.33591663 | NA | −0.16154085 |
| SMARCB1 | K562-19 | Wild-type | 28z | −0.47709412 | −0.61833354 | −0.57484882 | −0.3284938 | NA |
| SMARCB1 | K562-19 | Wild-type | BBz | −0.12126392 | −0.49360125 | −0.54875311 | −0.26181593 | −0.31511976 |
| SMARCB1_Q368X | K562 | Mutant | 28z | −0.46137514 | −0.36617492 | −0.67273352 | NA | NA |
| SMARCB1_Q368X | K562 | Mutant | BBz | 0.38671299 | −0.04578918 | −0.71877212 | NA | −0.16349416 |
| SMARCB1_Q368X | K562-19 | Mutant | 28z | −0.71601326 | −0.79437677 | −0.68366037 | −0.34298667 | NA |
| SMARCB1_Q368X | K562-19 | Mutant | BBz | −0.27759608 | −0.70115249 | −0.65804064 | −0.26181593 | −0.322116 |
| SPI1-TCF7 | K562 | Fusion | 28z | −0.53040337 | −0.34621007 | −0.30420449 | NA | NA |
| SPI1-TCF7 | K562 | Fusion | BBz | 0.57235517 | −0.19235583 | −0.05235878 | NA | −0.16193225 |
| SPI1-TCF7 | K562-19 | Fusion | 28z | −0.26228599 | −0.4424889 | −0.54969392 | −0.25682659 | NA |
| SPI1-TCF7 | K562-19 | Fusion | BBz | −0.3100131 | −0.61710555 | −0.60310973 | −0.21940929 | −0.14846273 |
| STAT3 | K562 | Wild-type | 28z | −0.15080995 | −0.36655557 | −0.19152097 | NA | NA |
| STAT3 | K562 | Wild-type | BBz | 0.49677831 | −0.21131734 | 0.43387418 | NA | −0.16115093 |
| STAT3 | K562-19 | Wild-type | 28z | 0.08732942 | −0.04676817 | −0.16794432 | −0.32161814 | NA |
| STAT3 | K562-19 | Wild-type | BBz | −0.04533294 | −0.13170809 | 0.18183811 | −0.24073363 | −0.20237081 |
| STAT3_D661I | K562 | Mutant | 28z | 0.13870547 | −0.29602839 | 0.41702812 | NA | NA |
| STAT3_D661I | K562 | Mutant | BBz | −0.43614401 | −0.31233699 | 0.5539521 | NA | −0.13967422 |
| STAT3_D661I | K562-19 | Mutant | 28z | 0.45653491 | −0.00714714 | 0.42912679 | −0.29108867 | NA |
| STAT3_D661I | K562-19 | Mutant | BBZ | 0.20309873 | −0.12688344 | 0.39309856 | −0.26181593 | −0.10072875 |
| STAT3_G618R | K562 | Mutant | 28z | 0.39559527 | −0.38318303 | −0.00474699 | NA | NA |
| STAT3_G618R | K562 | Mutant | BBz | 0.03605599 | −0.37983119 | 0.42350786 | NA | −0.13771841 |
| STAT3_G618R | K562-19 | Mutant | 28z | −0.12323466 | −0.22181842 | 0.15247081 | −0.3398235 | NA |
| STAT3_G618R | K562-19 | Mutant | BBZ | 0.27884646 | −0.15143677 | 0.22034689 | −0.25164868 | −0.14557882 |
| STAT3_N647I | K562 | Mutant | 28z | −0.16335163 | −0.32806715 | −0.19958653 | NA | NA |
| STAT3_N647I | K562 | Mutant | BBz | −0.00774842 | −0.26404627 | 0.21457802 | NA | −0.12990961 |
| STAT3_N647I | K562-19 | Mutant | 28z | −0.00585759 | −0.19061317 | 0.26322985 | −0.3424531 | NA |
| STAT3_N647I | K562-19 | Mutant | BBz | 0.28169004 | −0.18301204 | 0.10589629 | −0.26181593 | −0.10731252 |
| STAT5B | K562 | Wild-type | 28z | −0.40487927 | −0.39818928 | −0.50856541 | NA | NA |
| STAT5B | K562 | Wild-type | BBz | 0.53914157 | −0.20078768 | −0.10050743 | NA | −0.1634936 |
| STAT5B | K562-19 | Wild-type | 28z | −0.17880463 | −0.32302214 | −0.32294574 | −0.31367221 | NA |
| STAT5B | K562-19 | Wild-type | BBz | −0.25081455 | −0.37433775 | −0.22820513 | −0.24893913 | −0.22582368 |
| STAT5B_T628S | K562 | Mutant | 28z | −0.59579927 | −0.37637061 | −0.45966002 | NA | NA |
| STAT5B_T628S | K562 | Mutant | BBz | 0.00178924 | −0.15911175 | −0.18991499 | NA | −0.15841722 |
| STAT5B_T628S | K562-19 | Mutant | 28z | −0.28776931 | −0.44463217 | −0.40412377 | −0.33107617 | NA |
| STAT5B_T628S | K562-19 | Mutant | BBz | −0.19976608 | −0.34071898 | −0.24247574 | −0.25164868 | −0.24434292 |
| STAT5B_Y665F | K562 | Mutant | 28z | −0.55909106 | −0.31539753 | −0.51453704 | NA | NA |
| STAT5B_Y665F | K562 | Mutant | BBz | 0.27637053 | −0.10626277 | −0.16922203 | NA | −0.16622861 |
| STAT5B_Y665F | K562-19 | Mutant | 28z | −0.31376501 | −0.32044038 | −0.69008188 | −0.30260997 | NA |
| STAT5B_Y665F | K562-19 | Mutant | BBz | −0.31075105 | −0.513038 | −0.54036276 | −0.25074722 | −0.23282391 |
| TNFRSF1B | K562 | Wild-type | 28z | −0.4745957 | 0.110219 | −0.2970961 | NA | NA |
| TNFRSF1B | K562 | Wild-type | BBz | −0.0403523 | 0.94032292 | 0.2084503 | NA | −0.15177781 |
| TNFRSF1B | K562-19 | Wild-type | 28z | −0.87041062 | 0.59058385 | −0.25496482 | −0.30627317 | NA |
| TNFRSF1B | K562-19 | Wild-type | BBz | −0.19335512 | 0.27300743 | −0.23121669 | −0.19391559 | −0.2443408 |
| TNFRSF1B_G256C | K562 | Mutant | 28z | −0.48399263 | 0.40692893 | −0.25995884 | NA | NA |
| TNFRSF1B_G256C | K562 | Mutant | BBz | 0.6930113 | 2.03443779 | 0.28157813 | NA | −0.13225321 |
| TNFRSF1B_G256C | K562-19 | Mutant | 28z | −0.35020921 | 0.92972811 | −0.08211524 | −0.23223905 | NA |
| TNFRSF1B_G256C | K562-19 | Mutant | BBz | −0.02784839 | 0.74686588 | −0.12709225 | −0.25434095 | −0.22088768 |
| TNFRSF1B_T377I | K562 | Mutant | 28z | −0.33576472 | 1.06097378 | −0.50435526 | NA | NA |
| TNFRSF1B_T377I | K562 | Mutant | BBz | 0.51757194 | 2.93772452 | −0.20383729 | NA | −0.14787192 |
| TNFRSF1B_T377I | K562-19 | Mutant | 28z | −0.16911799 | 1.21364477 | −0.52453902 | −0.03812957 | NA |
| TNFRSF1B_T377I | K562-19 | Mutant | BBz | −0.2620997 | 1.03465333 | −0.64377003 | −0.23336602 | −0.28508185 |
| TP53 | K562 | Wild-type | 28z | 0.14251044 | −0.17236928 | 0.01138413 | NA | NA |
| TP53 | K562 | Wild-type | BBz | −0.74044687 | −0.0501042 | −0.09734038 | NA | −0.14943476 |
| TP53 | K562-19 | Wild-type | 28z | −0.09228641 | 0.20709354 | −0.22786243 | −0.20325183 | NA |

TABLE 4-continued

| RESULTS OF IN VITRO MUTATION SCREENING | | | | | | | | |
|---|---|---|---|---|---|---|---|---|
| Construct | condition | group | CAR | nfat_zscore | nfkb_zscore | ap1_zscore | il2_zscore | pd1_zscore |
| TP53 | K562-19 | Wild-type | BBz | −0.10002875 | −0.11519063 | −0.52200483 | −0.23889748 | −0.0739801 |
| TP53_R273P | K562 | Mutant | 28z | −0.69547482 | −0.39234249 | −0.46029367 | NA | NA |
| TP53_R273P | K562 | Mutant | BBz | −0.09641039 | −0.17315171 | −0.15547434 | NA | −0.15998051 |
| TP53_R273P | K562-19 | Mutant | 28z | −0.30416944 | −0.47095509 | −0.57591109 | −0.30374806 | NA |
| TP53_R273P | K562-19 | Mutant | BBz | −0.07456323 | −0.34071898 | −0.47101836 | −0.25344572 | −0.20360195 |
| VAV1 | K562 | Wild-type | 28z | 1.69015501 | −0.19419154 | 0.49339655 | NA | NA |
| VAV1 | K562 | Wild-type | BBz | 0.38771072 | −0.25044963 | 0.54144266 | NA | −0.09671506 |
| VAV1 | K562-19 | Wild-type | 28z | 0.19924322 | −0.22773503 | 0.25898077 | −0.3009065 | NA |
| VAV1 | K562-19 | Wild-type | BBz | 0.83381309 | 0.07656514 | 0.4638773 | −0.25344572 | −0.0081329 |
| VAV1_D797H | K562 | Mutant | 28z | 1.07978864 | −0.19517831 | 0.68582311 | NA | NA |
| VAV1_D797H | K562 | Mutant | BBz | −0.23880245 | −0.25206283 | 0.8836107 | NA | −0.11545778 |
| VAV1_D797H | K562-19 | Mutant | 28z | 0.38905639 | −0.30849115 | 0.42452363 | −0.33597073 | NA |
| VAV1_D797H | K562-19 | Mutant | BBz | 0.44839533 | 0.18150847 | 0.37631785 | −0.2480327 | −0.07932764 |
| VAV1_R798Q | K562 | Mutant | 28z | 0.83286034 | −0.20416535 | 0.61914673 | NA | NA |
| VAV1_R798Q | K562 | Mutant | BBz | 0.23384099 | −0.28740408 | 0.81943633 | NA | −0.10804196 |
| VAV1_R798Q | K562-19 | Mutant | 28z | 0.20522753 | −0.35800073 | 0.29963436 | −0.32318256 | NA |
| VAV1_R798Q | K562-19 | Mutant | BBZ | 0.66830636 | 0.33205532 | 0.46029144 | −0.2552337 | −0.12130254 |
| VAV1-GSS | K562 | Fusion | 28z | 0.99509265 | −0.21842428 | 0.32021909 | NA | NA |
| VAV1-GSS | K562 | Fusion | BBz | 0.9002231 | −0.23806478 | 0.49522281 | NA | −0.1463102 |
| VAV1-GSS | K562-19 | Fusion | 28z | 0.1197961 | −0.41402271 | −0.11209824 | −0.34298667 | NA |
| VAV1-GSS | K562-19 | Fusion | BBz | 0.8401066 | 0.33030375 | 0.42909725 | −0.2471248 | −0.11184598 |

TABLE 5

| RESULTS OF IN VITRO MUTATION SCREENING (CONTINUED) | | | | | | | |
|---|---|---|---|---|---|---|---|
| construct | condition | group | CAR | ctrl_pval_nfat | ctrl_pval_nfkb | ctrl_pval_ap1 | ctrl_pval_il2 |
| BCL6 | K562 | Wild-type | 28z | 1 | 1 | 1 | NA |
| BCL6 | K562 | Wild-type | BBz | 1 | 1 | 1 | NA |
| BCL6 | K562-19 | Wild-type | 28z | 1 | 0.001197 | 0.423738 | 1 |
| BCL6 | K562-19 | Wild-type | BBz | 1 | 0.761292 | 1 | 1 |
| BCL6_ S647R | K562 | Mutant | 28z | 1 | 1 | 1 | NA |
| BCL6_ S647R | K562 | Mutant | BBz | 1 | 0.912114 | 1 | NA |
| BCL6_ S647R | K562-19 | Mutant | 28z | 6.39E−19 | 3.90E−09 | 1 | 1 |
| BCL6_ S647R | K562-19 | Mutant | BBz | 0.4788 | 1 | 1 | 1 |
| BRAF | K562 | Wild-type | 28z | 0.241794 | 1 | 1 | NA |
| BRAF | K562 | Wild-type | BBz | 1 | 1 | 1 | NA |
| BRAF | K562-19 | Wild-type | 28z | 2.01E−36 | 4.02E−20 | 2.32E−29 | 1 |
| BRAF | K562-19 | Wild-type | BBz | 1.51E−06 | 2.17E−13 | 4.12E−08 | 1 |
| BRAF_ D594N | K562 | Mutant | 28z | 1 | 1 | 1 | NA |
| BRAF_ D594N | K562 | Mutant | BBz | 1 | 0.256158 | 1 | NA |
| BRAF_ D594N | K562-19 | Mutant | 28z | 6.37E−32 | 3.50E−56 | 2.61E−20 | 2.20E−05 |
| BRAF_ D594N | K562-19 | Mutant | BBz | 5.24E−13 | 3.71E−24 | 4.57E−18 | 1 |
| BRAF_ G469A | K562 | Mutant | 28z | 3.45E−61 | 1.11E−71 | 3.09E−64 | NA |
| BRAF_ G469A | K562 | Mutant | BBz | 0.043092 | 1.02E−46 | 1.57E−46 | NA |
| BRAF_ G469A | K562-19 | Mutant | 28z | 5.70E−209 | 1.36E−127 | 4.74E−99 | 3.18E−129 |
| BRAF_ G469A | K562-19 | Mutant | BBz | 2.28E−137 | 2.13E−103 | 6.75E−97 | 1.25E−10 |
| BRAF_ G469R | K562 | Mutant | 28z | 3.57E−13 | 1 | 1 | NA |
| BRAF_ G469R | K562 | Mutant | BBz | 1 | 0.0684684 | 1 | NA |
| BRAF_ G469R | K562-19 | Mutant | 28z | 3.85E−56 | 1.66E−79 | 2.97E−60 | 0.00010855 |
| BRAF_ G469R | K562-19 | Mutant | BBz | 1.27E−28 | 1.02E−37 | 7.59E−57 | 1 |
| CARD11 | K562 | Wild-type | 28z | 0.00030883 | 9.36E−36 | 1 | NA |
| CARD11 | K562 | Wild-type | BBz | 1 | 1 | 1 | NA |
| CARD11 | K562-19 | Wild-type | 28z | 4.40E−08 | 8.38E−120 | 2.75E−47 | 1.85E−07 |
| CARD11 | K562-19 | Wild-type | BBz | 1 | 1.06E−49 | 4.57E−06 | 1 |

TABLE 5-continued

RESULTS OF IN VITRO MUTATION SCREENING (CONTINUED)

| | | | | | | | |
|---|---|---|---|---|---|---|---|
| CARD11_ D357N | K562 | Mutant | 28z | 6.85E−05 | 8.36E−167 | 0.1726074 | NA |
| CARD11_ D357N | K562 | Mutant | BBz | 1 | 2.39E−63 | 1 | NA |
| CARD11_ D357N | K562-19 | Mutant | 28z | 4.19E−11 | 6.22E−168 | 6.94E−117 | 6.88E−101 |
| CARD11_ D357N | K562-19 | Mutant | BBZ | 1 | 7.18E−122 | 8.93E−68 | 0.0100868 |
| CARD11_ E634K: S655C | K562 | Mutant | 28z | 0.0128079 | 3.57E−33 | 1 | NA |
| CARD11_ E634K: S655C | K562 | Mutant | BBz | 1 | 1 | 1 | NA |
| CARD11_ E634K: S655C | K562-19 | Mutant | 28z | 0.081396 | 1.40E−134 | 3.21E−68 | 8.32E−12 |
| CARD11_ E634K: S655C | K562-19 | Mutant | BBZ | 1 | 3.54E−87 | 9.29E−25 | 1 |
| CARD11_ S615F | K562 | Mutant | 28z | 1 | 2.66E−55 | 1 | NA |
| CARD11_ S615F | K562 | Mutant | BBz | 1 | 1 | 1 | NA |
| CARD11_ S615F | K562-19 | Mutant | 28z | 0.00175241 | 2.68E−169 | 4.00E−121 | 6.91E−40 |
| CARD11_ S615F | K562-19 | Mutant | BBz | 1 | 1.33E−117 | 5.03E−82 | 1 |
| CARD11_ Y361C | K562 | Mutant | 28z | 0.0113715 | 3.42E−154 | 0.00046683 | NA |
| CARD11_ Y361C | K562 | Mutant | BBz | 1 | 6.61E−32 | 1 | NA |
| CARD11_ Y361C | K562-19 | Mutant | 28z | 2.13E−05 | 5.72E−173 | 1.14E−139 | 4.31E−106 |
| CARD11_ Y361C | K562-19 | Mutant | BBz | 1 | 1.24E−140 | 2.54E−134 | 1.13E−05 |
| CARD11-PIK3R3 | K562 | Fusion | 28z | 0.0013957 | 5.17E−231 | 0.519498 | NA |
| CARD11-PIK3R3 | K562 | Fusion | BBz | 1 | 1.64E−138 | 1 | NA |
| CARD11-PIK3R3 | K562-19 | Fusion | 28z | 8.45E−46 | 3.09E−171 | 0.00044528 | 4.18E−113 |
| CARD11-PIK3R3 | K562-19 | Fusion | BBz | 0.00016806 | 3.61E−147 | 6.27E−95 | 1.05E−08 |
| CARMIL2_ Q575E | K562 | Mutant | 28z | 1.67E−16 | 1 | 1 | NA |
| CARMIL2_ Q575E | K562 | Mutant | BBz | 1 | 1 | 1 | NA |
| CARMIL2_ Q575E | K562-19 | Mutant | 28z | 3.76E−13 | 0.061047 | 2.29E−08 | 1 |
| CARMIL2_ Q575E | K562-19 | Mutant | BBz | 1 | 1 | 0.81396 | 1 |
| CCND3 | K562 | Wild-type | 28z | 1 | 1 | 1 | NA |
| CCND3 | K562 | Wild-type | BBz | 1 | 1 | 1 | NA |
| CCND3 | K562-19 | Wild-type | 28z | 1.20E−23 | 2.32E−28 | 1.21E−17 | 1 |
| CCND3 | K562-19 | Wild-type | BBz | 0.044289 | 0.1393308 | 1.02E−19 | 1 |
| CCND3_ P284S | K562 | Mutant | 28z | 1 | 1 | 1 | NA |
| CCND3_ P284S | K562 | Mutant | BBz | 0.246582 | 0.0761292 | 1 | NA |
| CCND3_ P284S | K562-19 | Mutant | 28z | 1.11E−33 | 4.86E−39 | 4.52E−22 | 1 |
| CCND3_ P284S | K562-19 | Mutant | BBz | 9.50E−11 | 2.18E−09 | 6.03E−22 | 1 |
| CD28 | K562 | Wild-type | 28z | 1 | 1 | 1 | NA |
| CD28 | K562 | Wild-type | BBz | 1 | 1 | 1 | NA |
| CD28 | K562-19 | Wild-type | 28z | 1 | 1 | 1 | 1 |
| CD28 | K562-19 | Wild-type | BBz | 1 | 1 | 1 | 1 |
| CD28_ F51I | K562 | Mutant | 28z | 1 | 1 | 1 | NA |
| CD28_ F51I | K562 | Mutant | BBz | 1 | 1 | 1 | NA |
| CD28_ F51I | K562-19 | Mutant | 28z | 1 | 0.0306432 | 1 | 1 |
| CD28_ F51I | K562-19 | Mutant | BBz | 1 | 1 | 1 | 1 |
| CD28_ F51V | K562 | Mutant | 28z | 1 | 1 | 1 | NA |

TABLE 5-continued

| RESULTS OF IN VITRO MUTATION SCREENING (CONTINUED) | | | | | | | |
|---|---|---|---|---|---|---|---|
| CD28_F51V | K562 | Mutant | BBz | 1 | 1 | 1 | NA |
| CD28_F51V | K562-19 | Mutant | 28z | 1 | 0.00020469 | 1 | 1 |
| CD28_F51V | K562-19 | Mutant | BBz | 1 | 1 | 1 | 1 |
| CD28_Q77P | K562 | Mutant | 28z | 1 | 1 | 1 | NA |
| CD28_Q77P | K562 | Mutant | BBz | 1 | 1 | 1 | NA |
| CD28_Q77P | K562-19 | Mutant | 28z | 1 | 1 | 1 | 1 |
| CD28_Q77P | K562-19 | Mutant | BBz | 1 | 1 | 1 | 1 |
| CD28_T195P | K562 | Mutant | 28z | 1 | 1 | 1 | NA |
| CD28_T195P | K562 | Mutant | BBz | 1 | 1 | 1 | NA |
| CD28_T195P | K562-19 | Mutant | 28z | 1.92E−08 | 1 | 0.84987 | 1 |
| CD28_T195P | K562-19 | Mutant | BBz | 1 | 1 | 0.301644 | 1 |
| CD28-CTLA4 | K562 | Fusion | 28z | 1 | 1 | 1 | NA |
| CD28-CTLA4 | K562 | Fusion | BBz | 1 | 1 | 1 | NA |
| CD28-CTLA4 | K562-19 | Fusion | 28z | 1 | 1 | 1 | 1 |
| CD28-CTLA4 | K562-19 | Fusion | BBz | 1 | 1 | 1 | 1 |
| CD3E | K562 | Wild-type | 28z | 1 | 1 | 1 | NA |
| CD3E | K562 | Wild-type | BBz | 1 | 0.847476 | 1 | NA |
| CD3E | K562-19 | Wild-type | 28z | 1 | 1 | 1 | 1 |
| CD3E | K562-19 | Wild-type | BBz | 1 | 1 | 1 | 1 |
| CD3E_S41C | K562 | Mutant | 28z | 1 | 1 | 1 | NA |
| CD3E_S41C | K562 | Mutant | BBz | 1 | 1 | 1 | NA |
| CD3E_S41C | K562-19 | Mutant | 28z | 1 | 1 | 1 | 1 |
| CD3E_S41C | K562-19 | Mutant | BBz | 1 | 1 | 1 | 1 |
| CD53 | K562 | Wild-type | 28z | 1 | 1 | 1 | NA |
| CD53 | K562 | Wild-type | BBz | 1 | 1 | 1 | NA |
| CD53 | K562-19 | Wild-type | 28z | 1 | 1 | 1 | 1 |
| CD53 | K562-19 | Wild-type | BBz | 1 | 1 | 1 | 1 |
| CSNK1A1 | K562 | Wild-type | 28z | 1 | 1 | 1 | NA |
| CSNK1A1 | K562 | Wild-type | BBz | 1 | 1 | 1 | NA |
| CSNK1A1 | K562-19 | Wild-type | 28z | 1 | 1 | 1 | 1 |
| CSNK1A1 | K562-19 | Wild-type | BBz | 1 | 1 | 1 | 1 |
| CSNK1A1_S27C | K562 | Mutant | 28z | 1 | 1 | 1 | NA |
| CSNK1A1_S27C | K562 | Mutant | BBz | 1 | 1 | 1 | NA |
| CSNK1A1_S27C | K562-19 | Mutant | 28z | 1 | 1 | 1 | 1 |
| CSNK1A1_S27C | K562-19 | Mutant | BBz | 1 | 1 | 1 | 1 |
| CSNK2B | K562 | Wild-type | 28z | 1 | 1 | 1 | NA |
| CSNK2B | K562 | Wild-type | BBz | 1 | 1 | 1 | NA |
| CSNK2B | K562-19 | Wild-type | 28z | 1 | 1 | 1 | 1 |
| CSNK2B | K562-19 | Wild-type | BBz | 1 | 1 | 1 | 1 |
| CSNK2B_Q182X | K562 | Mutant | 28z | 1 | 1 | 1 | NA |
| CSNK2B_Q182X | K562 | Mutant | BBz | 1 | 1 | 1 | NA |
| CSNK2B_Q182X | K562-19 | Mutant | 28z | 1 | 0.0246582 | 1 | 1 |
| CSNK2B_Q182X | K562-19 | Mutant | BBz | 1 | 1 | 1 | 1 |
| DGKA | K562 | Wild-type | 28z | 1 | 1 | 1 | NA |
| DGKA | K562 | Wild-type | BBz | 1 | 1 | 1 | NA |
| DGKA | K562-19 | Wild-type | 28z | 1 | 1 | 1 | 1 |
| DGKA | K562-19 | Wild-type | BBz | 1 | 1 | 1 | 1 |
| DGKZ | K562 | Wild-type | 28z | 1 | 1 | 1 | NA |
| DGKZ | K562 | Wild-type | BBz | 1 | 1 | 1 | NA |
| DGKZ | K562-19 | Wild-type | 28z | 1.33E−37 | 4.69E−71 | 8.69E−19 | 1 |
| DGKZ | K562-19 | Wild-type | BBz | 0.00447678 | 2.59E−28 | 3.14E−15 | 1 |

TABLE 5-continued

RESULTS OF IN VITRO MUTATION SCREENING (CONTINUED)

| | | | | | | | |
|---|---|---|---|---|---|---|---|
| ECSIT | K562 | Wild-type | 28z | 1 | 1 | 1 | NA |
| ECSIT | K562 | Wild-type | BBz | 1 | 1 | 1 | NA |
| ECSIT | K562-19 | Wild-type | 28z | 1 | 1 | 1 | 1 |
| ECSIT | K562-19 | Wild-type | BBz | 1 | 1 | 1 | 1 |
| ECSIT_ V140A | K562 | Mutant | 28z | 1 | 1 | 1 | NA |
| ECSIT_ V140A | K562 | Mutant | BBz | 1 | 1 | 1 | NA |
| ECSIT_ V140A | K562-19 | Mutant | 28z | 1 | 1 | 1 | 1 |
| ECSIT_ V140A | K562-19 | Mutant | BBz | 1 | 1 | 1 | 1 |
| EIFS1 | K562 | Wild-type | 28z | 1 | 1 | 1 | NA |
| EIFS1 | K562 | Wild-type | BBz | 1 | 1 | 1 | NA |
| EIFS1 | K562-19 | Wild-type | 28z | 1 | 1 | 1 | 1 |
| EIFS1 | K562-19 | Wild-type | BBz | 1 | 0.00397404 | 0.2001384 | 1 |
| EIFS1_ R89I | K562 | Mutant | 28z | 1 | 1 | 1 | NA |
| EIFS1_ R89I | K562 | Mutant | BBz | 1 | 1 | 1 | NA |
| EIFS1_ R89I | K562-19 | Mutant | 28z | 1 | 1 | 1 | 1 |
| EIFS1_ R89I | K562-19 | Mutant | BBz | 1 | 1 | 1 | 1 |
| FYN | K562 | Wild-type | 28z | 1 | 1 | 1 | NA |
| FYN | K562 | Wild-type | BBz | 1 | 1 | 1 | NA |
| FYN | K562-19 | Wild-type | 28z | 0.00318402 | 2.22E−23 | 0.01022238 | 1 |
| FYN | K562-19 | Wild-type | BBz | 1 | 0.01970262 | 0.452466 | 1 |
| FYN_ R86G | K562 | Mutant | 28z | 0.00040459 | 0.0591318 | 1 | NA |
| FYN_ R86G | K562 | Mutant | BBz | 1 | 1 | 1 | NA |
| FYN_ R86G | K562-19 | Mutant | 28z | 1 | 0.1630314 | 0.763686 | 1 |
| FYN_ R86G | K562-19 | Mutant | BBz | 0.0567378 | 5.41E−09 | 2.97E−08 | 1 |
| FYN_ Y531H | K562 | Mutant | 28z | 1 | 1 | 1 | NA |
| FYN_ Y531H | K562 | Mutant | BBz | 1 | 1 | 1 | NA |
| FYN_ Y531H | K562-19 | Mutant | 28z | 1 | 1.97E−12 | 0.0988722 | 1 |
| FYN_ Y531H | K562-19 | Mutant | BBz | 1 | 3.69E−08 | 0.1623132 | 1 |
| GATA3 | K562 | Wild-type | 28z | 1 | 1 | 1 | NA |
| GATA3 | K562 | Wild-type | BBz | 1 | 1 | 1 | NA |
| GATA3 | K562-19 | Wild-type | 28z | 2.56E−10 | 1.05E−10 | 1 | 1 |
| GATA3 | K562-19 | Wild-type | BBz | 1 | 0.0469224 | 1 | 1 |
| GATA3_ Y63X | K562 | Mutant | 28z | 1 | 1 | 1 | NA |
| GATA3_ Y63X | K562 | Mutant | BBz | 1 | 1 | 1 | NA |
| GATA3_ Y63X | K562-19 | Mutant | 28z | 1 | 1 | 1 | 1 |
| GATA3_ Y63X | K562-19 | Mutant | BBz | 1 | 1 | 0.043092 | 1 |
| GNAQ | K562 | Wild-type | 28z | 1 | 1 | 1 | NA |
| GNAQ | K562 | Wild-type | BBz | 1 | 1 | 1 | NA |
| GNAQ | K562-19 | Wild-type | 28z | 1 | 1 | 1 | 1 |
| GNAQ | K562-19 | Wild-type | BBz | 1 | 1 | 1 | 1 |
| GNAQ_ T96S | K562 | Mutant | 28z | 1 | 1 | 1 | NA |
| GNAQ_ T96S | K562 | Mutant | BBz | 1 | 1 | 1 | NA |
| GNAQ_ T96S | K562-19 | Mutant | 28z | 1 | 1 | 1 | 1 |
| GNAQ_ T96S | K562-19 | Mutant | BBZ | 1 | 1 | 1 | 1 |
| ICOS- CD28 | K562 | Fusion | 28z | 1 | 1 | 1 | NA |
| ICOS- CD28 | K562 | Fusion | BBz | 1 | 1 | 1 | NA |
| ICOS- CD28 | K562-19 | Fusion | 28z | 1 | 1 | 1 | 1 |
| ICOS- CD28 | K562-19 | Fusion | BBz | 1 | 1 | 1 | 1 |
| IRF4 | K562 | Wild-type | 28z | 1 | 1 | 1 | NA |
| IRF4 | K562 | Wild-type | BBz | 1 | 1 | 1 | NA |

TABLE 5-continued

| RESULTS OF IN VITRO MUTATION SCREENING (CONTINUED) | | | | | | | |
|---|---|---|---|---|---|---|---|
| IRF4 | K562-19 | Wild-type | 28z | 1.10E−16 | 1 | 1 | 1 |
| IRF4 | K562-19 | Wild-type | BBz | 8.47E−07 | 1 | 1 | 1 |
| IRF4_ K59R | K562 | Mutant | 28z | 1 | 1 | 1 | NA |
| IRF4_ K59R | K562 | Mutant | BBz | 1 | 1 | 1 | NA |
| IRF4_ K59R | K562-19 | Mutant | 28z | 4.09E−15 | 1.07E−32 | 1.90E−30 | 1 |
| IRF4_ K59R | K562-19 | Mutant | BBz | 1.27E−07 | 1 | 1 | 1 |
| ITGB2 | K562 | Wild-type | 28z | 1 | 1 | 1 | NA |
| ITGB2 | K562 | Wild-type | BBz | 1 | 0.641592 | 1 | NA |
| ITGB2 | K562-19 | Wild-type | 28z | 1 | 1 | 1 | 1 |
| ITGB2 | K562-19 | Wild-type | BBz | 1 | 1 | 1 | 1 |
| ITGB2_ E234K | K562 | Mutant | 28z | 1 | 1 | 1 | NA |
| ITGB2_ E234K | K562 | Mutant | BBz | 1 | 1 | 1 | NA |
| ITGB2_ E234K | K562-19 | Mutant | 28z | 1 | 1 | 1 | 1 |
| ITGB2_ E234K | K562-19 | Mutant | BBz | 1 | 1 | 1 | 1 |
| ITK-FER | K562 | Fusion | 28z | 1 | 1 | 1 | NA |
| ITK-FER | K562 | Fusion | BBz | 1 | 1 | 1 | NA |
| ITK-FER | K562-19 | Fusion | 28z | 0.00066553 | 1 | 1 | 1 |
| ITK-FER | K562-19 | Fusion | BBz | 0.00089057 | 0.1989414 | 0.0687078 | 1 |
| ITK-SYK | K562 | Fusion | 28z | 1 | 1 | 1 | NA |
| ITK-SYK | K562 | Fusion | BBz | 1 | 1 | 1 | NA |
| ITK-SYK | K562-19 | Fusion | 28z | 1 | 1 | 1 | 1 |
| ITK-SYK | K562-19 | Fusion | BBz | 1 | 1 | 1 | 1 |
| JAK1_ G1097A | K562 | Mutant | 28z | 0.1671012 | 1 | 1 | NA |
| JAK1_ G1097A | K562 | Mutant | BBz | 1 | 1 | 1 | NA |
| JAK1_ G1097A | K562-19 | Mutant | 28z | 1.03E−05 | 0.0924084 | 4.43E−08 | 1 |
| JAK1_ G1097A | K562-19 | Mutant | BBz | 1 | 0.241794 | 0.0440496 | 1 |
| JAK3 | K562 | Wild-type | 28z | 1 | 1 | 1 | NA |
| JAK3 | K562 | Wild-type | BBz | 1 | 1 | 1 | NA |
| JAK3 | K562-19 | Wild-type | 28z | 1 | 1 | 1 | 1 |
| JAK3 | K562-19 | Wild-type | BBZ | 1 | 1 | 1 | 1 |
| JAK3_ A573V | K562 | Mutant | 28z | 1 | 1 | 1 | NA |
| JAK3_ A573V | K562 | Mutant | BBz | 1 | 1 | 1 | NA |
| JAK3_ A573V | K562-19 | Mutant | 28z | 1 | 0.253764 | 0.576954 | 1 |
| JAK3_ A573V | K562-19 | Mutant | BBz | 1 | 1 | 1 | 1 |
| JUNB | K562 | Wild-type | 28z | 1 | 1 | 1 | NA |
| JUNB | K562 | Wild-type | BBz | 1 | 1 | 1 | NA |
| JUNB | K562-19 | Wild-type | 28z | 2.04E−23 | 1 | 0.34713 | 1 |
| JUNB | K562-19 | Wild-type | BBz | 1 | 1 | 3.54E−13 | 1 |
| JUNB_ A282V | K562 | Mutant | 28z | 1 | 1 | 1 | NA |
| JUNB_ A282V | K562 | Mutant | BBz | 1 | 1 | 1 | NA |
| JUNB_ A282V | K562-19 | Mutant | 28z | 1 | 1 | 2.51E−16 | 1 |
| JUNB_ A282V | K562-19 | Mutant | BBz | 1 | 1 | 4.19E−20 | 1 |
| KCNQ1 | K562 | Wild-type | 28z | 1 | 1 | 1 | NA |
| KCNQ1 | K562 | Wild-type | BBz | 1 | 1 | 1 | NA |
| KCNQ1 | K562-19 | Wild-type | 28z | 1 | 1 | 1 | 1 |
| KCNQ1 | K562-19 | Wild-type | BBz | 1 | 1 | 1 | 1 |
| KCNQ1_ R583C | K562 | Mutant | 28z | 1 | 1 | 1 | NA |
| KCNQ1_ R583C | K562 | Mutant | BBz | 1 | 1 | 1 | NA |

TABLE 5-continued

RESULTS OF IN VITRO MUTATION SCREENING (CONTINUED)

| | | | | | | | |
|---|---|---|---|---|---|---|---|
| KCNQ1_ R583C | K562-19 | Mutant | 28z | 1 | 1 | 1 | 1 |
| KCNQ1_ R583C | K562-19 | Mutant | BBz | 1 | 1 | 1 | 1 |
| MSC | K562 | Wild-type | 28z | 1 | 1 | 1 | NA |
| MSC | K562 | Wild-type | BBz | 1 | 1 | 1 | NA |
| MSC | K562-19 | Wild-type | 28z | 1.30E−09 | 3.06E−34 | 3.04E−05 | 1 |
| MSC | K562-19 | Wild-type | BBz | 1 | 2.14E−12 | 0.00031361 | 1 |
| MSC_ E116K | K562 | Mutant | 28z | 1 | 1 | 1 | NA |
| MSC_ E116K | K562 | Mutant | BBZ | 1 | 1 | 1 | NA |
| MSC_ E116K | K562-19 | Mutant | 28z | 3.93E−13 | 1 | 1 | 1 |
| MSC_ E116K | K562-19 | Mutant | BBz | 2.63E−05 | 1 | 7.97E−05 | 1 |
| MYCN | K562 | Wild-type | 28z | 1 | 1 | 1 | NA |
| MYCN | K562 | Wild-type | BBz | 1 | 1 | 1 | NA |
| MYCN | K562-19 | Wild-type | 28z | 3.38E−14 | 1.55E−14 | 0.00019631 | 1 |
| MYCN | K562-19 | Wild-type | BBz | 1 | 1 | 4.55E−05 | 1 |
| MYCN_ P44L | K562 | Mutant | 28z | 1 | 1 | 1 | NA |
| MYCN_ P44L | K562 | Mutant | BBz | 1 | 1 | 1 | NA |
| MYCN_ P44L | K562-19 | Mutant | 28z | 9.74E−16 | 1.55E−25 | 1.97E−08 | 1 |
| MYCN_ P44L | K562-19 | Mutant | BBz | 1 | 1 | 7.09E−07 | 1 |
| NFKB1 | K562 | Wild-type | 28z | 1 | 1 | 1 | NA |
| NFKB1 | K562 | Wild-type | BBz | 1 | 1 | 1 | NA |
| NFKB1 | K562-19 | Wild-type | 28z | 1.04E−10 | 1.00E−23 | 0.01474704 | 1 |
| NFKB1 | K562-19 | Wild-type | BBz | 6.85E−05 | 6.85E−11 | 4.69E−05 | 1 |
| NFKB1_ H67Y | K562 | Mutant | 28z | 1.63E−06 | 1 | 1 | NA |
| NFKB1_ H67Y | K562 | Mutant | BBz | 1 | 1 | 1 | NA |
| NFKB1_ H67Y | K562-19 | Mutant | 28z | 0.0265734 | 5.31E−15 | 4.62E−12 | 1 |
| NFKB1_ H67Y | K562-19 | Mutant | BBz | 1.54E−07 | 0.1989414 | 8.98E−17 | 1 |
| NFKB2 | K562 | Wild-type | 28z | 1 | 1 | 1 | NA |
| NFKB2 | K562 | Wild-type | BBz | 1 | 0.256158 | 1 | NA |
| NFKB2 | K562-19 | Wild-type | 28z | 1 | 4.88E−22 | 1 | 1 |
| NFKB2 | K562-19 | Wild-type | BBz | 0.0928872 | 6.22E−07 | 0.00871416 | 1 |
| NFKB2_ K656X | K562 | Mutant | 28z | 1 | 1 | 1 | NA |
| NFKB2_ K656X | K562 | Mutant | BBz | 1 | 1 | 1 | NA |
| NFKB2_ K656X | K562-19 | Mutant | 28z | 1 | 1 | 1 | 1 |
| NFKB2_ K656X | K562-19 | Mutant | BBz | 1 | 1 | 1 | 1 |
| NPM- ALK | K562 | Fusion | 28z | 1 | 1 | 1 | NA |
| NPM- ALK | K562 | Fusion | BBz | 1 | 1 | 1 | NA |
| NPM- ALK | K562-19 | Fusion | 28z | 1 | 1 | 1.66E−24 | 1 |
| NPM- ALK | K562-19 | Fusion | BBz | 1 | 1 | 2.73E−11 | 1 |
| NPM- TYK | K562 | Fusion | 28z | 1 | 1 | 1 | NA |
| NPM- TYK | K562 | Fusion | BBz | 1 | 1 | 1 | NA |
| NPM- TYK | K562-19 | Fusion | 28z | 2.56E−10 | 1 | 1.27E−10 | 1 |
| NPM- TYK | K562-19 | Fusion | BBz | 2.56E−08 | 0.0306432 | 3.69E−20 | 1 |
| NRAS | K562 | Wild-type | 28z | 1 | 1 | 1 | NA |
| NRAS | K562 | Wild-type | BBz | 1 | 1 | 1 | NA |
| NRAS | K562-19 | Wild-type | 28z | 1 | 1 | 1 | 1 |
| NRAS | K562-19 | Wild-type | BBz | 1 | 1 | 1 | 1 |
| NRAS_ G13D | K562 | Mutant | 28z | 1 | 1 | 1 | NA |
| NRAS_ G13D | K562 | Mutant | BBz | 1 | 1 | 1 | NA |
| NRAS_ G13D | K562-19 | Mutant | 28z | 0.00094802 | 0.241794 | 1 | 1 |

TABLE 5-continued

| RESULTS OF IN VITRO MUTATION SCREENING (CONTINUED) | | | | | | | |
|---|---|---|---|---|---|---|---|
| NRAS_ G13D | K562-19 | Mutant | BBz | 1 | 1 | 1 | 1 |
| NRAS_ Q61H | K562 | Mutant | 28z | 1 | 1 | 1 | NA |
| NRAS_ Q61H | K562 | Mutant | BBZ | 1 | 1 | 1 | NA |
| NRAS_ Q61H | K562-19 | Mutant | 28z | 4.19E−08 | 1.05E−05 | 1 | 1 |
| NRAS_ Q61H | K562-19 | Mutant | BBz | 1 | 1 | 1 | 1 |
| PDCD1 | K562 | Wild-type | 28z | 1 | 1 | 1 | NA |
| PDCD1 | K562 | Wild-type | BBz | 1 | 1 | 1 | NA |
| PDCD1 | K562-19 | Wild-type | 28z | 1 | 1 | 1 | 1 |
| PDCD1 | K562-19 | Wild-type | BBz | 1 | 1 | 0.1587222 | 1 |
| PDCD1_ R231X | K562 | Mutant | 28z | 1 | 1 | 1 | NA |
| PDCD1_ R231X | K562 | Mutant | BBz | 1 | 1 | 1 | NA |
| PDCD1_ R231X | K562-19 | Mutant | 28z | 1 | 1 | 1 | 1 |
| PDCD1_ R231X | K562-19 | Mutant | BBz | 1 | 1 | 1 | 1 |
| PLCG1 | K562 | Wild-type | 28z | 1 | 1 | 1 | NA |
| PLCG1 | K562 | Wild-type | BBz | 1 | 1 | 1 | NA |
| PLCG1 | K562-19 | Wild-type | 28z | 1 | 1 | 1 | 1 |
| PLCG1 | K562-19 | Wild-type | BBz | 0.1671012 | 1 | 1 | 1 |
| PLCG1_ D1165H | K562 | Mutant | 28z | 7.01E−80 | 1.41E−23 | 0.00179311 | NA |
| PLCG1_ D1165H | K562 | Mutant | BBz | 1 | 1 | 1 | NA |
| PLCG1_ D1165H | K562-19 | Mutant | 28z | 1.06E−66 | 1.11E−90 | 3.02E−39 | 0.111222 |
| PLCG1_ D1165H | K562-19 | Mutant | BBz | 1.50E−88 | 1.81E−49 | 2.80E−78 | 1 |
| PLCG1_ E1163K | K562 | Mutant | 28z | 1.51E−06 | 0.00113236 | 1 | NA |
| PLCG1_ E1163K | K562 | Mutant | BBz | 1 | 1 | 1 | NA |
| PLCG1_ E1163K | K562-19 | Mutant | 28z | 2.25E−57 | 1.06E−85 | 2.66E−24 | 7.95E−16 |
| PLCG1_ E1163K | K562-19 | Mutant | BBz | 8.07E−52 | 9.46E−36 | 1.33E−38 | 1 |
| PLCG1_ E47K | K562 | Mutant | 28z | 0.1584828 | 1 | 1 | NA |
| PLCG1_ E47K | K562 | Mutant | BBz | 1 | 1 | 1 | NA |
| PLCG1_ E47K | K562-19 | Mutant | 28z | 5.39E−37 | 8.91E−59 | 5.77E−07 | 1.34E−08 |
| PLCG1_ E47K | K562-19 | Mutant | BBz | 3.71E−19 | 4.24E−17 | 2.87E−07 | 1 |
| PLCG1_ R48W | K562 | Mutant | 28z | 1.69E−09 | 7.21E−09 | 1 | NA |
| PLCG1_ R48W | K562 | Mutant | BBz | 1 | 1 | 1 | NA |
| PLCG1_ R48W | K562-19 | Mutant | 28z | 1.82E−85 | 3.66E−95 | 6.37E−20 | 3.64E−59 |
| PLCG1_ R48W | K562-19 | Mutant | BBz | 6.25E−73 | 1.48E−51 | 2.36E−56 | 1 |
| PLCG1_ S520F | K562 | Mutant | 28z | 5.29E−61 | 0.00028489 | 1 | NA |
| PLCG1_ S520F | K562 | Mutant | BBz | 1 | 1 | 1 | NA |
| PLCG1_ S520F | K562-19 | Mutant | 28z | 2.05E−49 | 1.53E−58 | 1.03E−28 | 1 |
| PLCG1_ S520F | K562-19 | Mutant | BBz | 8.50E−43 | 4.31E−21 | 2.26E−31 | 1 |
| PRKCB1 | K562 | Wild-type | 28z | 1 | 1 | 1 | NA |
| PRKCB1 | K562 | Wild-type | BBz | 1 | 1 | 1 | NA |
| PRKCB1 | K562-19 | Wild-type | 28z | 1 | 4.62E−07 | 0.00270522 | 1 |
| PRKCB1 | K562-19 | Wild-type | BBz | 0.421344 | 1.03E−08 | 0.00421344 | 1 |
| PRKCB1_ D427N | K562 | Mutant | 28z | 1 | 1 | 1 | NA |
| PRKCB1_ D427N | K562 | Mutant | BBz | 1 | 1 | 1 | NA |
| PRKCB1_ D427N | K562-19 | Mutant | 28z | 9.48E−07 | 1.57E−23 | 1 | 1 |
| PRKCB1_ D427N | K562-19 | Mutant | BBz | 1 | 3.14E−16 | 1 | 1 |

TABLE 5-continued

RESULTS OF IN VITRO MUTATION SCREENING (CONTINUED)

| | | | | | | | |
|---|---|---|---|---|---|---|---|
| PRKCB1_ D630Y | K562 | Mutant | 28z | 1 | 1 | 1 | NA |
| PRKCB1_ D630Y | K562 | Mutant | BBz | 1 | 1 | 1 | NA |
| PRKCB1_ D630Y | K562-19 | Mutant | 28z | 1 | 1.12E−05 | 1 | 1 |
| PRKCB1_ D630Y | K562-19 | Mutant | BBz | 1 | 1.46E−09 | 1 | 1 |
| RARA | K562 | Wild-type | 28z | 1 | 1 | 1 | NA |
| RARA | K562 | Wild-type | BBz | 1 | 1 | 1 | NA |
| RARA | K562-19 | Wild-type | 28z | 1.95E−24 | 4.17E−05 | 1 | 1 |
| RARA | K562-19 | Wild-type | BBz | 2.73E−21 | 1 | 1 | 1 |
| RARA_ G206S | K562 | Mutant | 28z | 1 | 1 | 1 | NA |
| RARA_ G206S | K562 | Mutant | BBz | 1 | 1 | 1 | NA |
| RARA_ G206S | K562-19 | Mutant | 28z | 6.39E−21 | 0.01970262 | 1 | 1 |
| RARA_ G206S | K562-19 | Mutant | BBZ | 1.90E−25 | 1 | 1 | 1 |
| RASGRP1 | K562 | Wild-type | 28z | 1.41E−30 | 0.00025616 | 0.00094563 | NA |
| RASGRP1 | K562 | Wild-type | BBz | 1 | 1 | 1 | NA |
| RASGRP1 | K562-19 | Wild-type | 28z | 3.73E−94 | 4.24E−92 | 2.39E−41 | 0.00095524 |
| RASGRP1 | K562-19 | Wild-type | BBz | 8.43E−70 | 1.05E−46 | 8.95E−71 | 1 |
| RASGRP1_ M261I | K562 | Mutant | 28z | 1.12E−28 | 2.22E−15 | 2.92E−11 | NA |
| RASGRP1_ M261I | K562 | Mutant | BBz | 1 | 1 | 0.01560888 | NA |
| RASGRP1_ M261I | K562-19 | Mutant | 28z | 1.04E−120 | 1.28E−99 | 1.02E−71 | 2.97E−70 |
| RASGRP1_ M261I | K562-19 | Mutant | BBz | 3.57E−108 | 1.74E−60 | 5.51E−90 | 1 |
| RHOA | K562 | Wild-type | 28z | 1 | 1 | 1 | NA |
| RHOA | K562 | Wild-type | BBz | 1 | 1 | 1 | NA |
| RHOA | K562-19 | Wild-type | 28z | 1 | 1 | 1 | 1 |
| RHOA | K562-19 | Wild-type | BBz | 1 | 1 | 1 | 1 |
| RHOA_ C16R | K562 | Mutant | 28z | 1 | 1 | 1 | NA |
| RHOA_ C16R | K562 | Mutant | BBz | 1 | 1 | 1 | NA |
| RHOA_ C16R | K562-19 | Mutant | 28z | 1 | 1 | 1 | 1 |
| RHOA_ C16R | K562-19 | Mutant | BBz | 1 | 1 | 1 | 1 |
| RHOA_ G17V | K562 | Mutant | 28z | 1 | 1 | 1 | NA |
| RHOA_ G17V | K562 | Mutant | BBz | 1 | 1 | 1 | NA |
| RHOA_ G17V | K562-19 | Mutant | 28z | 1 | 1 | 1 | 1 |
| RHOA_ G17V | K562-19 | Mutant | BBz | 1 | 1 | 1 | 1 |
| SELENOI-ABL1 | K562 | Fusion | 28z | 1 | 4.02E−12 | 1 | NA |
| SELENOI-ABL1 | K562 | Fusion | BBz | 1 | 1 | 1 | NA |
| SELENOI-ABL1 | K562-19 | Fusion | 28z | 3.47E−29 | 2.02E−116 | 2.68E−06 | 1 |
| SELENOI-ABL1 | K562-19 | Fusion | BBz | 8.28E−15 | 1.52E−48 | 5.39E−07 | 1 |
| SMARCB1 | K562 | Wild-type | 28z | 1 | 1 | 1 | NA |
| SMARCB1 | K562 | Wild-type | BBz | 1 | 1 | 1 | NA |
| SMARCB1 | K562-19 | Wild-type | 28z | 1 | 0.1989414 | 1 | 1 |
| SMARCB1 | K562-19 | Wild-type | BBz | 1 | 1 | 1 | 1 |
| SMARCB1_ Q368X | K562 | Mutant | 28z | 1 | 1 | 1 | NA |
| SMARCB1_ Q368X | K562 | Mutant | BBZ | 1 | 1 | 1 | NA |
| SMARCB1_ Q368X | K562-19 | Mutant | 28z | 0.761292 | 2.54E−06 | 1 | 1 |
| SMARCB1_ Q368X | K562-19 | Mutant | BBz | 1 | 1 | 1 | 1 |
| SPI1-TCF7 | K562 | Fusion | 28z | 1 | 1 | 1 | NA |
| SPI1-TCF7 | K562 | Fusion | BBz | 1 | 1 | 1 | NA |
| SPI1-TCF7 | K562-19 | Fusion | 28z | 1 | 1 | 1 | 1 |

TABLE 5-continued

RESULTS OF IN VITRO MUTATION SCREENING (CONTINUED)

| | | | | | | | |
|---|---|---|---|---|---|---|---|
| SPI1-TCF7 | K562-19 | Fusion | BBz | 1 | 1 | 1 | 1 |
| STAT3 | K562 | Wild-type | 28z | 1 | 1 | 1 | NA |
| STAT3 | K562 | Wild-type | BBz | 1 | 1 | 1 | NA |
| STAT3 | K562-19 | Wild-type | 28z | 0.643986 | 1 | 1 | 1 |
| STAT3 | K562-19 | Wild-type | BBz | 1 | 1 | 0.0140049 | 1 |
| STAT3_D661I | K562 | Mutant | 28z | 1 | 1 | 1 | NA |
| STAT3_D661I | K562 | Mutant | BBz | 1 | 1 | 1 | NA |
| STAT3_D661I | K562-19 | Mutant | 28z | 1.92E−08 | 0.253764 | 1.98E−06 | 1 |
| STAT3_D661I | K562-19 | Mutant | BBz | 0.0306432 | 1 | 1.85E−06 | 1 |
| STAT3_G618R | K562 | Mutant | 28z | 0.265734 | 1 | 1 | NA |
| STAT3_G618R | K562 | Mutant | BBz | 1 | 1 | 1 | NA |
| STAT3_G618R | K562-19 | Mutant | 28z | 1 | 1 | 0.137655 | 1 |
| STAT3_G618R | K562-19 | Mutant | BBz | 0.00318402 | 1 | 0.00327978 | 1 |
| STAT3_N647I | K562 | Mutant | 28z | 1 | 1 | 1 | NA |
| STAT3_N647I | K562 | Mutant | BBz | 1 | 1 | 1 | NA |
| STAT3_N647I | K562-19 | Mutant | 28z | 1 | 1 | 0.00270522 | 1 |
| STAT3_N647I | K562-19 | Mutant | BBz | 0.0029925 | 1 | 0.2001384 | 1 |
| STAT5B | K562 | Wild-type | 28z | 1 | 1 | 1 | NA |
| STAT5B | K562 | Wild-type | BBz | 1 | 1 | 1 | NA |
| STAT5B | K562-19 | Wild-type | 28z | 1 | 1 | 1 | 1 |
| STAT5B | K562-19 | Wild-type | BBz | 1 | 1 | 1 | 1 |
| STAT5B_T628S | K562 | Mutant | 28z | 1 | 1 | 1 | NA |
| STAT5B_T628S | K562 | Mutant | BBz | 1 | 1 | 1 | NA |
| STAT5B_T628S | K562-19 | Mutant | 28z | 1 | 1 | 1 | 1 |
| STAT5B_T628S | K562-19 | Mutant | BBz | 1 | 1 | 1 | 1 |
| STAT5B_Y665F | K562 | Mutant | 28z | 1 | 1 | 1 | NA |
| STAT5B_Y665F | K562 | Mutant | BBz | 1 | 1 | 1 | NA |
| STAT5B_Y665F | K562-19 | Mutant | 28z | 1 | 1 | 1 | 1 |
| STAT5B_Y665F | K562-19 | Mutant | BBz | - | 1 | 1 | 1 |
| TNFRSF1B | K562 | Wild-type | 28z | 1 | 1 | 1 | NA |
| TNFRSF1B | K562 | Wild-type | BBz | 1 | 0.0464436 | 1 | NA |
| TNFRSF1B | K562-19 | Wild-type | 28z | 0.00191999 | 6.42E−24 | 1 | 1 |
| TNFRSF1B | K562-19 | Wild-type | BBz | 1 | 6.89E−08 | 1 | 1 |
| TNFRSF1B_G256C | K562 | Mutant | 28z | 1 | 2.04E−05 | 1 | NA |
| TNFRSF1B_G256C | K562 | Mutant | BBz | 1 | 8.16E−18 | 1 | NA |
| TNFRSF1B_G256C | K562-19 | Mutant | 28z | 1 | 1.45E−42 | 1 | 1 |
| TNFRSF1B_G256C | K562-19 | Mutant | BBz | 1 | 2.80E−21 | 1 | 1 |
| TNFRSF1B_T377I | K562 | Mutant | 28z | 1 | 2.20E−23 | 1 | NA |
| TNFRSF1B_T377I | K562 | Mutant | BBz | 1 | 2.05E−36 | 1 | NA |
| TNFRSF1B_T377I | K562-19 | Mutant | 28z | 1 | 1.01E−59 | 1 | 1 |
| TNFRSF1B_T377I | K562-19 | Mutant | BBz | 1 | 4.72E−31 | 1 | 1 |
| TP53 | K562 | Wild-type | 28z | 1 | 1 | 1 | NA |
| TP53 | K562 | Wild-type | BBz | 1 | 1 | 1 | NA |
| TP53 | K562-19 | Wild-type | 28z | 1 | 3.42E−07 | 1 | 1 |
| TP53 | K562-19 | Wild-type | BBz | 1 | 0.914508 | 1 | 1 |
| TP53_R273P | K562 | Mutant | 28z | 1 | 1 | 1 | NA |
| TP53_R273P | K562 | Mutant | BBz | 1 | 1 | 1 | NA |

TABLE 5-continued

RESULTS OF IN VITRO MUTATION SCREENING (CONTINUED)

| | | | | | | | |
|---|---|---|---|---|---|---|---|
| TP53_R273P | K562-19 | Mutant | 28z | 1 | 1 | 1 | 1 |
| TP53_R273P | K562-19 | Mutant | BBz | 1 | 1 | 1 | 1 |
| VAV1 | K562 | Wild-type | 28z | 3.33E−151 | 1 | 1 | NA |
| VAV1 | K562 | Wild-type | BBz | | 1 | 1 | NA |
| VAV1 | K562-19 | Wild-type | 28z | 0.00821142 | 1 | 0.00270522 | 1 |
| VAV1 | K562-19 | Wild-type | BBz | 3.93E−13 | 0.00093605 | 5.72E−08 | 1 |
| VAV1_D797H | K562 | Mutant | 28z | 1.67E−07 | 1 | 1 | NA |
| VAV1_D797H | K562 | Mutant | BBZ | 1 | 1 | 1 | NA |
| VAV1_D797H | K562-19 | Mutant | 28z | 2.30E−06 | 1 | 1.98E−06 | 1 |
| VAV1_D797H | K562-19 | Mutant | BBz | 8.50E−06 | 7.95E−06 | 3.40E−06 | 1 |
| VAV1_R798Q | K562 | Mutant | 28z | 5.94E−05 | 1 | 1 | NA |
| VAV1_R798Q | K562 | Mutant | BBz | 1 | 1 | 1 | NA |
| VAV1_R798Q | K562-19 | Mutant | 28z | 0.00821142 | 1 | 0.00057935 | 1 |
| VAV1_R798Q | K562-19 | Mutant | BBz | 1.00E−09 | 2.82E−09 | 5.72E−08 | 1 |
| VAV1-GSS | K562 | Fusion | 28z | 1.19E−06 | 1 | 1 | NA |
| VAV1-GSS | K562 | Fusion | BBz | 1 | 1 | 1 | NA |
| VAV1-GSS | K562-19 | Fusion | 28z | 0.2353302 | 1 | 1 | 1 |
| VAV1-GSS | K562-19 | Fusion | BBz | 2.94E−13 | 2.82E−09 | 2.87E−07 | 1 |

| construct | ctrl_pval_pd1 | wt_pval_nfat | wt_pval_nfkb | wt_pval_ap1 | wt_pval_il2 | wt_pval_pd1 |
|---|---|---|---|---|---|---|
| BCL6 | NA | NA | NA | NA | NA | NA |
| BCL6 | 1 | NA | NA | NA | NA | NA |
| BCL6 | NA | NA | NA | NA | NA | NA |
| BCL6 | 1.54E−27 | NA | NA | NA | NA | NA |
| BCL6_S647R | NA | 1 | 1 | 1 | NA | NA |
| BCL6_S647R | 1 | 1 | 1 | 1 | NA | 1 |
| BCL6_S647R | NA | 5.00E−05 | 1 | 0.01982232 | 1 | NA |
| BCL6_S647R | 1 | 0.0871416 | 1 | 1 | 1 | 4.43E−19 |
| BRAF | NA | NA | NA | NA | NA | NA |
| BRAF | 1 | NA | NA | NA | NA | NA |
| BRAF | NA | NA | NA | NA | NA | NA |
| BRAF | 1 | NA | NA | NA | NA | NA |
| BRAF_D594N | NA | 1 | 1 | 1 | NA | NA |
| BRAF_D594N | 1 | 1 | 1 | 1 | NA | 1 |
| BRAF_D594N | NA | 1 | 5.41E−06 | 1 | 1 | NA |
| BRAF_D594N | 1 | 1 | 1 | 1 | 1 | 1 |
| BRAF_G469A | NA | 4.64E−25 | 2.24E−40 | 1.30E−32 | NA | NA |
| BRAF_G469A | 0.0316008 | 0.1201788 | 2.61E−37 | 1.47E−24 | NA | 0.00049316 |
| BRAF_G469A | NA | 4.55E−109 | 2.44E−49 | 8.07E−22 | 9.08E−98 | NA |
| BRAF_G469A | 1 | 2.12E−72 | 6.97E−38 | 4.07E−39 | 1.84E−05 | 1 |
| BRAF_G469R | NA | 1 | 1 | 1 | NA | NA |
| BRAF_G469R | 1 | 1 | 1 | 1 | NA | 1 |
| BRAF_G469R | NA | 1 | 5.39E−17 | 0.00189365 | 1 | NA |
| BRAF_G469R | 1 | 0.0073017 | 0.01558494 | 2.54E−14 | 1 | 1 |
| CARD11 | NA | NA | NA | NA | NA | NA |
| CARD11 | 1 | NA | NA | NA | NA | NA |
| CARD11 | NA | NA | NA | NA | NA | NA |

TABLE 5-continued

| RESULTS OF IN VITRO MUTATION SCREENING (CONTINUED) | | | | | | |
|---|---|---|---|---|---|---|
| CARD11 | 0.588924 | NA | NA | NA | NA | NA |
| CARD11_ D357N | NA | 1 | 7.47E−69 | 1 | NA | NA |
| CARD11_ D357N | 1 | 1 | 5.05E−33 | 1 | NA | 1 |
| CARD11_ D357N | NA | 1 | 1.60E−12 | 3.14E−21 | 3.81E−60 | NA |
| CARD11_ D357N | 1.69E−15 | 1 | 6.87E−23 | 1.46E−22 | 1 | 0.0378252 |
| CARD11_ E634K: S655C | NA | 1 | 1 | 1 | NA | NA |
| CARD11_ E634K: S655C | 1 | 1 | 1 | 1 | NA | 1 |
| CARD11_ E634K: S655C | NA | 1 | 1 | 1 | 1 | NA |
| CARD11_ E634K: S655C | 6.10E−06 | 1 | 3.50E−05 | 0.0892962 | 1 | 1 |
| CARD11_ S615F | NA | 1 | 1 | 1 | NA | NA |
| CARD11_ S615F | 1 | 1 | 1 | 1 | NA | 1 |
| CARD11_ S615F | NA | 1 | 2.35E−13 | 6.42E−24 | 2.18E−10 | NA |
| CARD11_ S615F | 2.23E−10 | 1 | 3.23E−20 | 1.59E−31 | 1 | 1 |
| CARD11_ Y361C | NA | 1 | 1.06E−57 | 1 | NA | NA |
| CARD11_ Y361C | 1 | 1 | 1.83E−13 | 1 | NA | 1 |
| CARD11_ Y361C | NA | 1 | 1.04E−15 | 4.69E−37 | 3.33E−65 | NA |
| CARD11_ Y361C | 5.43E−16 | 1 | 4.33E−36 | 1.44E−70 | 0.0287574 | 0.02271906 |
| CARD11- PIK3R3 | NA | NA | NA | NA | NA | NA |
| CARD11- PIK3R3 | 1 | NA | NA | NA | NA | NA |
| CARD11- PIK3R3 | NA | NA | NA | NA | NA | NA |
| CARD11- PIK3R3 | 8.04E−25 | NA | NA | NA | NA | NA |
| CARMIL2_ Q575E | NA | NA | NA | NA | NA | NA |
| CARMIL2_ Q575E | 1 | NA | NA | NA | NA | NA |
| CARMIL2_ Q575E | NA | NA | NA | NA | NA | NA |
| CARMIL2_ Q575E | 1 | NA | NA | NA | NA | NA |
| CCND3 | NA | NA | NA | NA | NA | NA |
| CCND3 | 1 | NA | NA | NA | NA | NA |
| CCND3 | NA | NA | NA | NA | NA | NA |
| CCND3 | 1.37E−19 | NA | NA | NA | NA | NA |
| CCND3_ P284S | NA | 1 | 1 | 1 | NA | NA |
| CCND3_ P284S | 1 | 1 | 1 | 1 | NA | 1 |
| CCND3_ P284S | NA | 1 | 1 | 1 | 1 | NA |
| CCND3_ P284S | 1.81E−26 | 1 | 1 | 1 | 1 | 1 |
| CD28 | NA | NA | NA | NA | NA | NA |
| CD28 | 1 | NA | NA | NA | NA | NA |
| CD28 | NA | NA | NA | NA | NA | NA |
| CD28 | 1 | NA | NA | NA | NA | NA |
| CD28_ F51I | NA | 1 | 1 | 1 | NA | NA |
| CD28_ F51I | 1 | 1 | 1 | 1 | NA | 1 |
| CD28_ F51I | NA | 1 | 1 | 1 | 1 | NA |
| CD28_ F51I | 1 | 1 | 1 | 1 | 1 | 1 |

TABLE 5-continued

| RESULTS OF IN VITRO MUTATION SCREENING (CONTINUED) | | | | | | |
|---|---|---|---|---|---|---|
| CD28_ F51V | NA | 1 | 1 | 1 | NA | NA |
| CD28_ F51V | 1 | 1 | 1 | 1 | NA | 1 |
| CD28_ F51V | NA | 1 | 1 | 1 | 1 | NA |
| CD28_ F51V | 1 | 1 | 1 | 1 | 1 | 1 |
| CD28_ Q77P | NA | 1 | 1 | 1 | NA | NA |
| CD28_ Q77P | 1 | 1 | 1 | 1 | NA | 1 |
| CD28_ Q77P | NA | 1 | 1 | 1 | 1 | NA |
| CD28_ Q77P | 1 | 1 | 1 | 1 | 1 | 1 |
| CD28_ T195P | NA | 1 | 1 | 1 | NA | NA |
| CD28_ T195P | 1 | 1 | 1 | 1 | NA | 1 |
| CD28_ T195P | NA | 1 | 1 | 1 | 1 | NA |
| CD28_ T195P | 0.495558 | 1 | 1 | 0.655956 | 1 | 1 |
| CD28- CTLA4 | NA | NA | NA | NA | NA | NA |
| CD28- CTLA4 | 1 | NA | NA | NA | NA | NA |
| CD28- CTLA4 | NA | NA | NA | NA | NA | NA |
| CD28- CTLA4 | 1 | NA | NA | NA | NA | NA |
| CD3E | NA | NA | NA | NA | NA | NA |
| CD3E | 1 | NA | NA | NA | NA | NA |
| CD3E | NA | NA | NA | NA | NA | NA |
| CD3E | 1 | NA | NA | NA | NA | NA |
| CD3E_ S41C | NA | 1 | 1 | 1 | NA | NA |
| CD3E_ S41C | 1 | 1 | 1 | 1 | NA | 1 |
| CD3E_ S41C | NA | 1 | 1 | 1 | 1 | NA |
| CD3E_ S41C | 0.737352 | 1 | 1 | 1 | 1 | 1 |
| CD53 | NA | NA | NA | NA | NA | NA |
| CD53 | 1 | NA | NA | NA | NA | NA |
| CD53 | NA | NA | NA | NA | NA | NA |
| CD53 | 1 | NA | NA | NA | NA | NA |
| CSNK1A1 | NA | NA | NA | NA | NA | NA |
| CSNK1A1 | 1 | NA | NA | NA | NA | NA |
| CSNK1A1 | NA | NA | NA | NA | NA | NA |
| CSNK1A1 | 1 | NA | NA | NA | NA | NA |
| CSNK1A1_ S27C | NA | 1 | 1 | 1 | NA | NA |
| CSNK1A1_ S27C | 1 | 1 | 1 | 1 | NA | 1 |
| CSNK1A1_ S27C | NA | 1 | 1 | 1 | 1 | NA |
| CSNK1A1_ S27C | 1 | 1 | 1 | 1 | 1 | 1 |
| CSNK2B | NA | NA | NA | NA | NA | NA |
| CSNK2B | 1 | NA | NA | NA | NA | NA |
| CSNK2B | NA | NA | NA | NA | NA | NA |
| CSNK2B | 1 | NA | NA | NA | NA | NA |
| CSNK2B_ Q182X | NA | 1 | 1 | 1 | NA | NA |
| CSNK2B_ Q182X | 1 | 1 | 1 | 1 | NA | 1 |
| CSNK2B_ Q182X | NA | 1 | 1 | 1 | 1 | NA |
| CSNK2B_ Q182X | 0.0866628 | 1 | 1 | 1 | 1 | 1 |
| DGKA | NA | NA | NA | NA | NA | NA |
| DGKA | 1 | NA | NA | NA | NA | NA |
| DGKA | NA | NA | NA | NA | NA | NA |
| DGKA | 1 | NA | NA | NA | NA | NA |
| DGKZ | NA | NA | NA | NA | NA | NA |
| DGKZ | 1 | NA | NA | NA | NA | NA |

TABLE 5-continued

| RESULTS OF IN VITRO MUTATION SCREENING (CONTINUED) | | | | | | |
|---|---|---|---|---|---|---|
| DGKZ | NA | NA | NA | NA | NA | NA |
| DGKZ | 1.32E−21 | NA | NA | NA | NA | NA |
| ECSIT | NA | NA | NA | NA | NA | NA |
| ECSIT | 1 | NA | NA | NA | NA | NA |
| ECSIT | NA | NA | NA | NA | NA | NA |
| ECSIT | 1 | NA | NA | NA | NA | NA |
| ECSIT_V140A | NA | 1 | 1 | 1 | NA | NA |
| ECSIT_V140A | 1 | 1 | 1 | 1 | NA | 1 |
| ECSIT_V140A | NA | 1 | 1 | 1 | 1 | NA |
| ECSIT_V140A | 1 | 1 | 1 | 1 | 1 | 1 |
| EIFS1 | NA | NA | NA | NA | NA | NA |
| EIFS1 | 1 | NA | NA | NA | NA | NA |
| EIFS1 | NA | NA | NA | NA | NA | NA |
| EIFS1 | 0.0940842 | NA | NA | NA | NA | NA |
| EIFS1_R89I | NA | 1 | 1 | 1 | NA | NA |
| EIFS1_R89I | 1 | 1 | 1 | 1 | NA | 1 |
| EIFS1_R89I | NA | 1 | 1 | 1 | 1 | NA |
| EIFS1_R89I | 0.2099538 | 1 | 1 | 1 | 1 | 1 |
| FYN | NA | NA | NA | NA | NA | NA |
| FYN | 1 | NA | NA | NA | NA | NA |
| FYN | NA | NA | NA | NA | NA | NA |
| FYN | 4.91E−05 | NA | NA | NA | NA | NA |
| FYN_R86G | NA | 1 | 1 | 1 | NA | NA |
| FYN_R86G | 1 | 1 | 1 | 1 | NA | 1 |
| FYN_R86G | NA | 0.00011491 | 0.00017093 | 1 | 1 | NA |
| FYN_R86G | 0.00234612 | 1 | 1 | 1 | 1 | 1 |
| FYN_Y531H | NA | 1 | 1 | 1 | NA | NA |
| FYN_Y531H | 1 | 1 | 1 | 1 | NA | 1 |
| FYN_Y531H | NA | 1 | 1 | 1 | 1 | NA |
| FYN_Y531H | 1.22E−06 | 1 | 1 | 1 | 1 | 1 |
| GATA3 | NA | NA | NA | NA | NA | NA |
| GATA3 | 1 | NA | NA | NA | NA | NA |
| GATA3 | NA | NA | NA | NA | NA | NA |
| GATA3 | 1.29E−11 | NA | NA | NA | NA | NA |
| GATA3_Y63X | NA | 1 | 1 | 1 | NA | NA |
| GATA3_Y63X | 1 | 1 | 1 | 1 | NA | 1 |
| GATA3_Y63X | NA | 0.00022312 | 1.55E−08 | 1 | 1 | NA |
| GATA3_Y63X | 1 | 1 | 1 | 0.363888 | 1 | 0.0284886 |
| GNAQ | NA | NA | NA | NA | NA | NA |
| GNAQ | 1 | NA | NA | NA | NA | NA |
| GNAQ | NA | NA | NA | NA | NA | NA |
| GNAQ | 1 | NA | NA | NA | NA | NA |
| GNAQ_T96S | NA | 1 | 1 | 1 | NA | NA |
| GNAQ_T96S | 1 | 1 | 1 | 1 | NA | 1 |
| GNAQ_T96S | NA | 1 | 1 | 1 | 1 | NA |
| GNAQ_T96S | 1 | 1 | 1 | 1 | 1 | 1 |
| ICOS-CD28 | NA | NA | NA | NA | NA | NA |
| ICOS-CD28 | 1 | NA | NA | NA | NA | NA |
| ICOS-CD28 | NA | NA | NA | NA | NA | NA |
| ICOS-CD28 | 1 | NA | NA | NA | NA | NA |

TABLE 5-continued

| RESULTS OF IN VITRO MUTATION SCREENING (CONTINUED) | | | | | | |
|---|---|---|---|---|---|---|
| IRF4 | NA | NA | NA | NA | NA | NA |
| IRF4 | 1 | NA | NA | NA | NA | NA |
| IRF4 | NA | NA | NA | NA | NA | NA |
| IRF4 | 7.06E−28 | NA | NA | NA | NA | NA |
| IRF4_ K59R | NA | 1 | 1 | 1 | NA | NA |
| IRF4_ K59R | 1 | 1 | 1 | 1 | NA | 1 |
| IRF4_ K59R | NA | 1 | 1.82E−10 | 1.02E−09 | 1 | NA |
| IRF4_ K59R | 2.51E−07 | 1 | 1 | 1 | 1 | 0.00313614 |
| ITGB2 | NA | NA | NA | NA | NA | NA |
| ITGB2 | 1 | NA | NA | NA | NA | NA |
| ITGB2 | NA | NA | NA | NA | NA | NA |
| ITGB2 | 1 | NA | NA | NA | NA | NA |
| ITGB2_ E234K | NA | 1 | 1 | 1 | NA | NA |
| ITGB2_ E234K | 1 | 1 | 1 | 1 | NA | 1 |
| ITGB2_ E234K | NA | 1 | 1 | 1 | 1 | NA |
| ITGB2_ E234K | 1 | 1 | 1 | 1 | 1 | 1 |
| ITK- FER | NA | NA | NA | NA | NA | NA |
| ITK- FER | 1 | NA | NA | NA | NA | NA |
| ITK- FER | NA | NA | NA | NA | NA | NA |
| ITK- FER | 1 | NA | NA | NA | NA | NA |
| ITK- SYK | NA | NA | NA | NA | NA | NA |
| ITK- SYK | 1 | NA | NA | NA | NA | NA |
| ITK- SYK | NA | NA | NA | NA | NA | NA |
| ITK- SYK | 1 | NA | NA | NA | NA | NA |
| JAK1_ G1097A | NA | NA | NA | NA | NA | NA |
| JAK1_ G1097A | 1 | NA | NA | NA | NA | NA |
| JAK1_ G1097A | NA | NA | NA | NA | NA | NA |
| JAK1_ G1097A | 1 | NA | NA | NA | NA | NA |
| JAK3 | NA | NA | NA | NA | NA | NA |
| JAK3 | 1 | NA | NA | NA | NA | NA |
| JAK3 | NA | NA | NA | NA | NA | NA |
| JAK3 | 0.390222 | NA | NA | NA | NA | NA |
| JAK3_ A573V | NA | 1 | 1 | 1 | NA | NA |
| JAK3_ A573V | 1 | 1 | 1 | 1 | NA | 1 |
| JAK3_ A573V | NA | 1 | 1 | 1 | 1 | NA |
| JAK3_ A573V | 1 | 1 | 1 | 1 | 1 | 1 |
| JUNB | NA | NA | NA | NA | NA | NA |
| JUNB | 1 | NA | NA | NA | NA | NA |
| JUNB | NA | NA | NA | NA | NA | NA |
| JUNB | 6.99E−10 | NA | NA | NA | NA | NA |
| JUNB_ A282V | NA | 1 | 1 | 1 | NA | NA |
| JUNB_ A282V | 1 | 1 | 1 | 1 | NA | 1 |
| JUNB_ A282V | NA | 5.63E−10 | 1 | 0.0734958 | 1 | NA |
| JUNB_ A282V | 7.45E−10 | 1 | 1 | 1 | 1 | 1 |
| KCNQ1 | NA | NA | NA | NA | NA | NA |
| KCNQ1 | 1 | NA | NA | NA | NA | NA |
| KCNQ1 | NA | NA | NA | NA | NA | NA |
| KCNQ1 | 3.97E−05 | NA | NA | NA | NA | NA |
| KCNQ1_ R583C | NA | 1 | 1 | 1 | NA | NA |

TABLE 5-continued

RESULTS OF IN VITRO MUTATION SCREENING (CONTINUED)

| | | | | | | |
|---|---|---|---|---|---|---|
| KCNQ1_ R583C | 1 | 1 | 1 | 1 | NA | 1 |
| KCNQ1_ R583C | NA | 1 | 1 | 1 | 1 | NA |
| KCNQ1_ R583C | 0.0464436 | 1 | 1 | 1 | 1 | 1 |
| MSC | NA | NA | NA | NA | NA | NA |
| MSC | 1 | NA | NA | NA | NA | NA |
| MSC | NA | NA | NA | NA | NA | NA |
| MSC | 8.74E−11 | NA | NA | NA | NA | NA |
| MSC_ E116K | NA | 1 | 1 | 1 | NA | NA |
| MSC_ E116K | 1 | 1 | 0.378252 | 1 | NA | 1 |
| MSC_ E116K | NA | 1 | 1.61E−28 | 0.00150822 | 1 | NA |
| MSC_ E116K | 6.80E−14 | 1 | 7.68E−14 | 1 | 1 | 9.38E−26 |
| MYCN | NA | NA | NA | NA | NA | NA |
| MYCN | 1 | NA | NA | NA | NA | NA |
| MYCN | NA | NA | NA | NA | NA | NA |
| MYCN | 0.00071102 | NA | NA | NA | NA | NA |
| MYCN_ P44L | NA | 1 | 1 | 1 | NA | NA |
| MYCN_ P44L | 1 | 1 | 1 | 1 | NA | 1 |
| MYCN_ P44L | NA | 1 | 1 | 1 | 1 | NA |
| MYCN_ P44L | 4.38E−07 | 1 | 1 | 1 | 1 | 1 |
| NFKB1 | NA | NA | NA | NA | NA | NA |
| NFKB1 | 1 | NA | NA | NA | NA | NA |
| NFKB1 | NA | NA | NA | NA | NA | NA |
| NFKB1 | 1 | NA | NA | NA | NA | NA |
| NFKB1_ H67Y | NA | 1 | 1 | 1 | NA | NA |
| NFKB1_ H67Y | 1 | 1 | 1 | 1 | NA | 1 |
| NFKB1_ H67Y | NA | 1 | 1 | 1 | 1 | NA |
| NFKB1_ H67Y | 0.00032319 | 1 | 1 | 1 | 1 | 1 |
| NFKB2 | NA | NA | NA | NA | NA | NA |
| NFKB2 | 1 | NA | NA | NA | NA | NA |
| NFKB2 | NA | NA | NA | NA | NA | NA |
| NFKB2 | 1 | NA | NA | NA | NA | NA |
| NFKB2_ K656X | NA | 1 | 1 | 1 | NA | NA |
| NFKB2_ K656X | 1 | 1 | 0.01869714 | 1 | NA | 1 |
| NFKB2_ K656X | NA | 1 | 4.29E−05 | 1 | 1 | NA |
| NFKB2_ K656X | 4.19E−05 | 1 | 0.00471618 | 0.0462042 | 1 | 1 |
| NPM- ALK | NA | NA | NA | NA | NA | NA |
| NPM- ALK | 1 | NA | NA | NA | NA | NA |
| NPM- ALK | NA | NA | NA | NA | NA | NA |
| NPM- ALK | 1.85E−10 | NA | NA | NA | NA | NA |
| NPM- TYK | NA | NA | NA | NA | NA | NA |
| NPM- TYK | 1 | NA | NA | NA | NA | NA |
| NPM- TYK | NA | NA | NA | NA | NA | NA |
| NPM- TYK | 0.2360484 | NA | NA | NA | NA | NA |
| NRAS | NA | NA | NA | NA | NA | NA |
| NRAS | 1 | NA | NA | NA | NA | NA |
| NRAS | NA | NA | NA | NA | NA | NA |
| NRAS | 0.01656648 | NA | NA | NA | NA | NA |
| NRAS_ G13D | NA | 1 | 1 | 1 | NA | NA |
| NRAS_ G13D | 1 | 1 | 1 | 1 | NA | 1 |

TABLE 5-continued

RESULTS OF IN VITRO MUTATION SCREENING (CONTINUED)

| | | | | | | |
|---|---|---|---|---|---|---|
| NRAS_G13D | NA | 0.225036 | 0.01838592 | 1 | 1 | NA |
| NRAS_G13D | 1.53E−05 | 1 | 1 | 1 | 1 | 1 |
| NRAS_Q61H | NA | 1 | 1 | 1 | NA | NA |
| NRAS_Q61H | 1 | 1 | 1 | 1 | NA | 1 |
| NRAS_Q61H | NA | 0.00057456 | 6.68E−06 | 0.363888 | 1 | NA |
| NRAS_Q61H | 1.74E−07 | 1 | 1 | 1 | 1 | 1 |
| PDCD1 | NA | NA | NA | NA | NA | NA |
| PDCD1 | 7.16E−273 | NA | NA | NA | NA | NA |
| PDCD1 | NA | NA | NA | NA | NA | NA |
| PDCD1 | 1.12E−264 | NA | NA | NA | NA | NA |
| PDCD1_R231X | NA | 1 | 1 | 1 | NA | NA |
| PDCD1_R231X | 2.00E−272 | 1 | 1 | 1 | NA | 1 |
| PDCD1_R231X | NA | 1 | 1 | 1 | 1 | NA |
| PDCD1_R231X | 1.95E−264 | 1 | 1 | 1 | 1 | 1 |
| PLCG1 | NA | NA | NA | NA | NA | NA |
| PLCG1 | 1 | NA | NA | NA | NA | NA |
| PLCG1 | NA | NA | NA | NA | NA | NA |
| PLCG1 | 0.0292068 | NA | NA | NA | NA | NA |
| PLCG1_D1165H | NA | 3.42E−45 | 9.29E−13 | 1 | NA | NA |
| PLCG1_D1165H | 1 | 1 | 1 | 1 | NA | 1 |
| PLCG1_D1165H | NA | 4.14E−35 | 2.51E−53 | 8.07E−22 | 1 | NA |
| PLCG1_D1165H | 1 | 5.10E−43 | 1.71E−20 | 1.16E−43 | 1 | 0.1264032 |
| PLCG1_E1163K | NA | 1 | 0.517104 | 1 | NA | NA |
| PLCG1_E1163K | 1 | 1 | 1 | 1 | NA | 1 |
| PLCG1_E1163K | NA | 6.37E−29 | 1.10E−49 | 1.48E−12 | 0.00015164 | NA |
| PLCG1_E1163K | 1 | 3.71E−19 | 1.22E−12 | 1.15E−17 | 1 | 1 |
| PLCG1_E47K | NA | 1 | 1 | 1 | NA | NA |
| PLCG1_E47K | 1 | 1 | 1 | 1 | NA | 1 |
| PLCG1_E47K | NA | 2.78E−16 | 5.41E−31 | 0.01668618 | 0.39078 | NA |
| PLCG1_E47K | 1 | 0.00998298 | 0.00232936 | 0.758898 | 1 | 0.00845082 |
| PLCG1_R48W | NA | 0.049077 | 0.00052668 | 1 | NA | NA |
| PLCG1_R48W | 1 | 1 | 1 | 1 | NA | 1 |
| PLCG1_R48W | NA | 3.11E−48 | 1.20E−56 | 6.06E−10 | 1.65E−33 | NA |
| PLCG1_R48W | 7.40E−22 | 2.61E−32 | 9.43E−22 | 9.15E−29 | 1 | 4.31E−23 |
| PLCG1_S520F | NA | 3.50E−32 | 0.2348514 | 1 | NA | NA |
| PLCG1_S520F | 1 | 1 | 1 | 1 | NA | 1 |
| PLCG1_S520F | NA | 7.83E−24 | 7.76E−31 | 3.09E−15 | 1 | NA |
| PLCG1_S520F | 1 | 4.45E−14 | 3.50E−05 | 1.98E−13 | 1 | 1 |
| PRKCB1 | NA | NA | NA | NA | NA | NA |
| PRKCB1 | 1 | NA | NA | NA | NA | NA |
| PRKCB1 | NA | NA | NA | NA | NA | NA |
| PRKCB1 | 8.02E−06 | NA | NA | NA | NA | NA |
| PRKCB1_D427N | NA | 1 | 1 | 1 | NA | NA |
| PRKCB1_D427N | 1 | 1 | 1 | 1 | NA | 1 |
| PRKCB1_D427N | NA | 0.00080917 | 0.703836 | 0.02355696 | 1 | NA |

TABLE 5-continued

| RESULTS OF IN VITRO MUTATION SCREENING (CONTINUED) | | | | | | |
|---|---|---|---|---|---|---|
| PRKCB1_ D427N | 3.30E−16 | 0.00089057 | 1 | 0.0280098 | 1 | 1 |
| PRKCB1_ D630Y | NA | 1 | 1 | 1 | NA | NA |
| PRKCB1_ D630Y | 1 | 1 | 1 | 1 | NA | 1 |
| PRKCB1_ D630Y | NA | 1 | 1 | 1 | 1 | NA |
| PRKCB1_ D630Y | 2.00E−05 | 1 | 1 | 1 | 1 | 1 |
| RARA | NA | NA | NA | NA | NA | NA |
| RARA | 1 | NA | NA | NA | NA | NA |
| RARA | NA | NA | NA | NA | NA | NA |
| RARA | 2.23E−13 | NA | NA | NA | NA | NA |
| RARA_ G206S | NA | 1 | 1 | 1 | NA | NA |
| RARA_ G206S | 1 | 1 | 1 | 1 | NA | 1 |
| RARA_ G206S | NA | 1 | 1 | 1 | 1 | NA |
| RARA_ G206S | 1.59E−26 | 1 | 1 | 1 | 1 | 1 |
| RASGRP1 | NA | NA | NA | NA | NA | NA |
| RASGRP1 | 1 | NA | NA | NA | NA | NA |
| RASGRP1 | NA | NA | NA | NA | NA | NA |
| RASGRP1 | 1 | NA | NA | NA | NA | NA |
| RASGRP1_ M261I | NA | 1 | 1 | 1 | NA | NA |
| RASGRP1_ M261I | 1 | 1 | 1 | 1 | NA | 1 |
| RASGRP1_ M261I | NA | 0.0739746 | 1 | 0.00687078 | 1.26E−36 | NA |
| RASGRP1_ M261I | 1 | 1.39E−05 | 1 | 1 | 1 | 1 |
| RHOA | NA | NA | NA | NA | NA | NA |
| RHOA | 1 | NA | NA | NA | NA | NA |
| RHOA | NA | NA | NA | NA | NA | NA |
| RHOA | 0.00018601 | NA | NA | NA | NA | NA |
| RHOA_ C16R | NA | 1 | 1 | 1 | NA | NA |
| RHOA_ C16R | 1 | 1 | 1 | 1 | NA | 1 |
| RHOA_ C16R | NA | 1 | 1 | 1 | 1 | NA |
| RHOA_ C16R | 1.53E−06 | 1 | 1 | 1 | 1 | 1 |
| RHOA_ G17V | NA | 1 | 1 | 1 | NA | NA |
| RHOA_ G17V | 1 | 1 | 1 | 1 | NA | 1 |
| RHOA_ G17V | NA | 1 | 1 | 1 | 1 | NA |
| RHOA_ G17V | 0.01888866 | 1 | 1 | 1 | 1 | 1 |
| SELENOI-ABL1 | NA | NA | NA | NA | NA | NA |
| SELENOI-ABL1 | 1 | NA | NA | NA | NA | NA |
| SELENOI-ABL1 | NA | NA | NA | NA | NA | NA |
| SELENOI-ABL1 | 8.16E−12 | NA | NA | NA | NA | NA |
| SMARCB1 | NA | NA | NA | NA | NA | NA |
| SMARCB1 | 1 | NA | NA | NA | NA | NA |
| SMARCB1 | NA | NA | NA | NA | NA | NA |
| SMARCB1 | 2.20E−08 | NA | NA | NA | NA | NA |
| SMARCB1_ Q368X | NA | 1 | 1 | 1 | NA | NA |
| SMARCB1_ Q368X | 1 | 1 | 1 | 1 | NA | 1 |
| SMARCB1_ Q368X | NA | 1 | 1 | 1 | 1 | NA |
| SMARCB1_ Q368X | 7.83E−09 | 1 | 1 | 1 | 1 | 1 |
| SPI1-TCF7 | NA | NA | NA | NA | NA | NA |
| SPI1-TCF7 | 1 | NA | NA | NA | NA | NA |

TABLE 5-continued

| RESULTS OF IN VITRO MUTATION SCREENING (CONTINUED) | | | | | | |
|---|---|---|---|---|---|---|
| SPI1-TCF7 | NA | NA | NA | NA | NA | NA |
| SPI1-TCF7 | 1 | NA | NA | NA | NA | NA |
| STAT3 | NA | NA | NA | NA | NA | NA |
| STAT3 | 1 | NA | NA | NA | NA | NA |
| STAT3 | NA | NA | NA | NA | NA | NA |
| STAT3 | 0.0330372 | NA | NA | NA | NA | NA |
| STAT3_D661I | NA | 1 | 1 | 1 | NA | NA |
| STAT3_D661I | 1 | 1 | 1 | 1 | NA | 1 |
| STAT3_D661I | NA | 1 | 1 | 0.876204 | 1 | NA |
| STAT3_D661I | 1 | 1 | 1 | 1 | 1 | 1 |
| STAT3_G618R | NA | 1 | 1 | 1 | NA | NA |
| STAT3_G618R | 1 | 1 | 1 | 1 | NA | 1 |
| STAT3_G618R | NA | 1 | 1 | 1 | 1 | NA |
| STAT3_G618R | 1 | 1 | 1 | 1 | 1 | 1 |
| STAT3_N647I | NA | 1 | 1 | 1 | NA | NA |
| STAT3_N647I | 1 | 1 | 1 | 1 | NA | 1 |
| STAT3_N647I | NA | 1 | 1 | 1 | 1 | NA |
| STAT3_N647I | 1 | 1 | 1 | 1 | 1 | 1 |
| STAT5B | NA | NA | NA | NA | NA | NA |
| STAT5B | 1 | NA | NA | NA | NA | NA |
| STAT5B | NA | NA | NA | NA | NA | NA |
| STAT5B | 0.00258552 | NA | NA | NA | NA | NA |
| STAT5B_T628S | NA | 1 | 1 | 1 | NA | NA |
| STAT5B_T628S | 1 | 1 | 1 | 1 | NA | 1 |
| STAT5B_T628S | NA | 1 | 1 | 1 | 1 | NA |
| STAT5B_T628S | 0.00029207 | 1 | 1 | 1 | 1 | 1 |
| STAT5B_Y665F | NA | 1 | 1 | 1 | NA | NA |
| STAT5B_Y665F | 1 | 1 | 1 | 1 | NA | 1 |
| STAT5B_Y665F | NA | 1 | 1 | 1 | 1 | NA |
| STAT5B_Y665F | 0.00115151 | 1 | 1 | 1 | 1 | 1 |
| TNFRSF1B | NA | NA | NA | NA | NA | NA |
| TNFRSF1B | 1 | NA | NA | NA | NA | NA |
| TNFRSF1B | NA | NA | NA | NA | NA | NA |
| TNFRSF1B | 0.00029207 | NA | NA | NA | NA | NA |
| TNFRSF1B_G256C | NA | 1 | 1 | 1 | NA | NA |
| TNFRSF1B_G256C | 1 | 1 | 0.090972 | 1 | NA | 1 |
| TNFRSF1B_G256C | NA | 1 | 1 | 1 | 1 | NA |
| TNFRSF1B_G256C | 0.00450072 | 1 | 1 | 1 | 1 | 1 |
| TNFRSF1B_T377I | NA | 1 | 9.96E−06 | 1 | NA | NA |
| TNFRSF1B_T377I | 1 | 1 | 5.03E−10 | 1 | NA | 1 |
| TNFRSF1B_T377I | NA | 0.0108927 | 1.54E−05 | 1 | 1 | NA |
| TNFRSF1B_T377I | 1.53E−06 | 1 | 0.0056259 | 1 | 1 | 1 |
| TP53 | NA | NA | NA | NA | NA | NA |
| TP53 | 1 | NA | NA | NA | NA | NA |
| TP53 | NA | NA | NA | NA | NA | NA |
| TP53 | 1 | NA | NA | NA | NA | NA |
| TP53_R273P | NA | 1 | 1 | 1 | NA | NA |

TABLE 5-continued

| RESULTS OF IN VITRO MUTATION SCREENING (CONTINUED) | | | | | | |
|---|---|---|---|---|---|---|
| TP53_ R273P | 1 | 1 | 1 | 1 | NA | 1 |
| TP53_ R273P | NA | 1 | 6.15E−07 | 1 | 1 | NA |
| TP53_ R273P | 0.0292068 | 1 | 1 | 1 | 1 | 1 |
| VAV1 | NA | NA | NA | NA | NA | NA |
| VAV1 | 1 | NA | NA | NA | NA | NA |
| VAV1 | NA | NA | NA | NA | NA | NA |
| VAV1 | 1 | NA | NA | NA | NA | NA |
| VAV1_ D797H | NA | 1 | 1 | 1 | NA | NA |
| VAV1_ D797H | 1 | 1 | 1 | 1 | NA | 1 |
| VAV1_ D797H | NA | 1 | 1 | 1 | 1 | NA |
| VAV1_ D797H | 1 | 1 | 1 | 1 | 1 | 1 |
| VAV1_ R798Q | NA | 1 | 1 | 1 | NA | NA |
| VAV1_ R798Q | 1 | 1 | 1 | 1 | NA | 1 |
| VAV1_ R798Q | NA | 1 | 1 | 1 | 1 | NA |
| VAV1_ R798Q | 1 | 1 | 1 | 1 | 1 | 1 |
| VAV1- GSS | NA | NA | NA | NA | NA | NA |
| VAV1- GSS | 1 | NA | NA | NA | NA | NA |
| VAV1- GSS | NA | NA | NA | NA | NA | NA |
| VAV1- GSS | 1 | NA | NA | NA | NA | NA |

REFERENCES

1 H., O'Connor. R. S., Kawalckar. O. U., Ghassemi, S. & Milone. M. C. CAR T cell immunotherapy for human cancer. *Science* 359. 1361-1365. doi:10.1126/science.aar6711 (2018).

2 Hou, A. J., Chen, L. C. & Chen, Y. Y. Navigating CAR-T cells through the solid-tumour microenvironment. *Nature Reviews Drug Discovery* 20, 531-550, doi:10.1038/s41573-021-00189-2 (2021).

3 Larson, R. C. & Maus, M. V. Recent advances and discoveries in the mechanisms and functions of CAR T cells. *Nature Reviews Cancer* 21, 145-161, doi:10.1038/s41568-020-00323-z (2021).

4 Long, A. H. et al. 4-1B B costimulation ameliorates T cell exhaustion induced by tonic signaling of chimeric antigen receptors. *Nat Med* 21, 581-590, doi:10.1038/nm.3838 (2015).

Maude, S. L. et al. Chimeric Antigen Receptor T Cells for Sustained Remissions in Leukemia. *New England Journal of Medicine* 371, 1507-1517, doi:10.1056/NEJMoa1407222 (2014).

6 Kloss, C. C. et al. Dominant-Negative TGF-Receptor Enhances PSMA-Targeted Human CAR T Cell Proliferation And Augments Prostate Cancer Eradication. *Mol Ther* 26, 1855-1866, doi:10.1016/j.ymthe.2018.05.003 (2018).

7 Wei, J. et al. Targeting REGNASE-1 programs long-lived effector T cells for cancer therapy. *Nature* 576, 471-476, doi:10.1038/s41586-019-1821-2 (2019).

8 Legut, M. et al. A genome-scale screen for synthetic drivers of T cell proliferation. *Nature* 603, 728-735, doi:10.1038/s41586-022-04494-7 (2022).

9 Shifrut, E. et al. Genome-wide CRISPR Screens in Primary Human T Cells Reveal Key Regulators of Immune Function. *Cell* 175, 1958-1971.e1915, doi:https://doi.org/10.1016/j.cell.2018.10.024 (2018).

Schmidt, R. et al. CRISPR activation and interference screens decode stimulation responses in primary human T cells. *Science* 375, cabj4008, doi:10.1126/science.abj4008.

11 Sutra Del Galy, A. et al. In vivo genome-wide CRISPR screens identify SOCSI as intrinsic checkpoint of CD4(+) T(H)1 cell response. *Sci Immunol* 6, cabe8219, doi:10.1126/sciimmunol.abc8219 (2021).

12 Dong, M. B. et al. Systematic Immunotherapy Target Discovery Using Genome-Scale In Vivo CRISPR Screens in CD8 T Cells. *Cell* 178, 1189-1204.c1123, doi:10.1016/j.cell.2019.07.044 (2019).

13 Zhou, P. et al. In vivo discovery of immunotherapy targets in the tumour microenvironment. *Nature* 506, 52-57, doi:10.1038/nature 12988 (2014).

14 Roth, T. L. et al. Pooled Knockin Targeting for Genome Engineering of Cellular Immunotherapies. *Cell* 181, 728-744.c721, doi:10.1016/j.cell.2020.03.039 (2020).

15 Mustjoki, S. & Young, N. S. Somatic Mutations in "Benign" Disease. *N Engl J Med* 384, 2039-2052, doi:10.1056/NEJMra2101920 (2021).

16 Kadin, M. E. et al. Loss of receptors for transforming growth factor beta in human T-cell malignancies. *Proc Natl Acad Sci USA* 91, 6002-6006, doi:10.1073/pnas.91.13.6002 (1994).

17 Park, J. et al. Integrated genomic analyses of cutaneous T-cell lymphomas reveal the molecular bases for disease heterogeneity. *Blood* 138, 1225-1236, doi:10.1182/blood.2020009655 (2021).

18 Wartewig, T. et al. PD-1 is a haploinsufficient suppressor of T cell lymphomagenesis. *Nature* 552, 121-125, doi: 10.1038/nature24649 (2017).

19 Kataoka, K. et al. Integrated molecular analysis of adult T cell leukemia/lymphoma. *Nat Genet* 47, 1304-1315, doi:10.1038/ng.3415 (2015).

20 Kleppe, M. et al. Mutation analysis of the tyrosine phosphatase PTPN2 in Hodgkin's lymphoma and T-cell non-Hodgkin's lymphoma. *Haematologica* 96, 1723-1727, doi:10.3324/haematol.2011.041921 (2011).

21 Stadtmauer Edward, A. et al. CRISPR-engineered T cells in patients with refractory cancer. *Science* 367, caba7365, doi:10.1126/science.aba7365 (2020).

22 Fraictta, J. A. et al. Disruption of TET2 promotes the therapeutic efficacy of CD19-targeted T cells. *Nature* 558, 307-312, doi:10.1038/s41586-018-0178-z (2018).

23 Kumar, J. et al. Deletion of Cbl-b inhibits CD8< sup>+</sup> T-cell exhaustion and promotes CAR T-cell function. *Journal for Immuno Therapy of Cancer* 9, c001688, doi:10.1136/jitc-2020-001688 (2021).

24 Prinzing, B. et al. Deleting DNMT3A in CAR T cells prevents exhaustion and enhances antitumor activity. *Science Translational Medicine* 13, cabh0272, doi:10.1126/scitranslmed.abh0272.

25 Wiede, F. et al. PTPN2 phosphatase deletion in T cells promotes anti-tumour immunity and CAR T-cell efficacy in solid tumours. *The EMBO* Journal 39, c103637, doi: https://doi.org/10.15252/embj.2019103637 (2020).

26 Park, J. et al. Genomic analysis of 220 CTCLs identifies a novel recurrent gain-of-function alteration in RLTPR (p.Q575E). *Blood* 130, 1430-1440, doi:10.1182/blood-2017-02-768234 (2017).

27 Daniels, J. et al. Cellular origins and genetic landscape of cutaneous gamma delta T cell lymphomas. *Nature communications* 11, 1806-1806, doi:10.1038/s41467-020-15572-7 (2020).

28 Jutz, S. et al. Assessment of costimulation and coinhibition in a triple parameter T cell reporter line: Simultaneous measurement of NF-κB, NFAT and AP-1. *J Immunol Methods* 430, 10-20, doi:10.1016/j.jim.2016.01.007 (2016).

29 Patel, V. M. et al. Frequent and Persistent PLCG1 Mutations in Sézary Cells Directly Enhance PLCγ1 Activity and Stimulate NFκB, AP-1, and NFAT Signaling. *J Invest Dermatol* 140, 380-389.c384, doi:10.1016/j.jid.2019.07.693 (2020).

30 Ungewickell, A. et al. Genomic analysis of mycosis fungoides and Sézary syndrome identifies recurrent alterations in TNFR2. *Nature genetics* 47, 1056-1060, doi:10.1038/ng.3370 (2015).

31 Robles-Valero, J. et al. Cancer-associated mutations in VAV1 trigger variegated signaling outputs and T-cell lymphomagenesis. *Embo j* 40, c108125, doi:10.15252/cmbj.2021108125 (2021).

32 Vallois, D. et al. Activating mutations in genes related to TCR signaling in angioimmunoblastic and other follicular helper T-cell-derived lymphomas. *Blood* 128, 1490-1502, doi:10.1182/blood-2016-02-698977 (2016).

33 Chen, S. S., Hu, Z. & Zhong, X.-P. Diacylglycerol Kinases in T Cell Tolerance and Effector Function. *Frontiers in Cell and Developmental Biology* 4, doi:10.3389/fcell.2016.00130 (2016).

34 Martinez, G. J. et al. The transcription factor NFAT promotes exhaustion of activated CD8 T cells. *Immunity* 42, 265-278, doi:10.1016/j.immuni.2015.01.006 (2015).

35 Rafiq, S., Hackett, C. S. & Brentjens, R. J. Engineering strategies to overcome the current roadblocks in CAR T cell therapy. *Nature Reviews Clinical Oncology* 17, 147-167, doi:10.1038/s41571-019-0297-y (2020).

36 Sharma, P. & Allison, J. P. Immune checkpoint targeting in cancer therapy: toward combination strategies with curative potential. *Cell* 161, 205-214, doi:10.1016/j.cell.2015.03.030 (2015).

37 Schmitz, R. et al. Burkitt lymphoma pathogenesis and therapeutic targets from structural and functional genomics. *Nature* 490, 116-120, doi:10.1038/nature 11378 (2012).

38 Liu, Y. et al. The genomic landscape of pediatric and young adult T-lineage acute lymphoblastic leukemia. *Nature genetics* 49, 1211-1218, doi:10.1038/ng.3909 (2017).

39 Lynn, R. C. et al. c-Jun overexpression in CAR T cells induces exhaustion resistance. *Nature* 576, 293-300, doi: 10.1038/s41586-019-1805-2 (2019).

40 Kahan, S. M. et al. Intrinsic IL-2 production by effector CD8 T cells affects IL-2 signaling and promotes fate decisions, stemness, and protection. *Sci Immunol* 7, cab16322, doi:10.1126/sciimmunol.abl6322 (2022).

41 Wang, L. et al. Genomic profiling of Sezary syndrome identifies alterations of key T cell signaling and differentiation genes. *Nature genetics* 47, 1426-1434, doi: 10.1038/ng.3444 (2015).

42 Ruland, J. & Hartjes, L. CARD-BCL-10-MALT1 signalling in protective and pathological immunity. *Nat Rev Immunol* 19, 118-134, doi:10.1038/s41577-018-0087-2 (2019).

43 Jattani, R. P., Tritapoc, J. M. & Pomerantz, J. L. Intramolecular Interactions and Regulation of Cofactor Binding by the Four Repressive Elements in the Caspase Recruitment Domain-containing Protein 11 (CARD11) Inhibitory Domain. *J Biol Chem* 291, 8338-8348, doi: 10.1074/jbc.M116.717322 (2016).

44 Burke, J. E. Structural Basis for Regulation of Phosphoinositide Kinases and Their Involvement in Human Disease. *Molecular Cell* 71, 653-673, doi:https://doi.org/10.1016/j.molcel.2018.08.005 (2018).

45 Kutzner, K. et al. Phosphorylation of serine-893 in CARD11 suppresses the formation and activity of the CARD11-BCL10-MALT1 complex in T and B cells. *Science Signaling* 15, cabk3083, doi:10.1126/scisignal.abk3083.

46 Li, S., Yang, X., Shao, J. & Shen, Y. Structural Insights into the Assembly of CARMA1 and BCL10. *PLOS ONE* 7, c42775, doi:10.1371/journal.pone.0042775 (2012).

47 Minguencau, M. et al. Single-cell mass cytometry of TCR signaling: Amplification of small initial differences results in low ERK activation in NOD mice. *Proceedings of the National Academy of Sciences* 111, 16466-16471, doi:10.1073/pnas. 1419337111 (2014).

48 Yamamoto, Y. & Gaynor, R. B. IkappaB kinases: key regulators of the NF-kappaB pathway. *Trends Biochem Sci* 29, 72-79, doi:10.1016/j.tibs.2003.12.003 (2004).

49 Fan, X., Quezada, S. A., Sepulveda, M. A., Sharma, P. & Allison, J. P. Engagement of the ICOS pathway markedly enhances efficacy of CTLA-4 blockade in cancer immunotherapy. *Journal of Experimental Medicine* 211, 715-725, doi:10.1084/jem.20130590 (2014).

50 Massarelli, E. et al. High OX-40 expression in the tumor immune infiltrate is a favorable prognostic factor of overall survival in non-small cell lung cancer. *J Immunother* Cancer 7, 351, doi:10.1186/s40425-019-0827-2 (2019).

51 Bardet, M. et al. The T-cell fingerprint of MALT1 paracaspase revealed by selective inhibition. *Immunol Cell Biol* 96, 81-99, doi:10.1111/imcb.1018 (2018).

52 Jiang, T., Zhou, C. & Ren, S. Role of IL-2 in cancer immunotherapy. *Oncoimmunology* 5, e1163462, doi: 10.1080/2162402x.2016.1163462 (2016).

53 Thommen, D. S. & Schumacher, T. N. T Cell Dysfunction in Cancer. Cancer Cell 33, 547-562, doi:10.1016/j.ccell.2018.03.012 (2018).

54 Guedan, S. et al. *Enhancing CAR T cell persistence through ICOS and* 4-1BB costimulation. *JCI Insight* 3, doi:10.1172/jci.insight.96976 (2018).

55 Li, Q.-X., Feuer, G., Ouyang, X. & An, X. Experimental animal modeling for immuno-oncology. *Pharmacology & Therapeutics* 173, 34-46, doi:https://doi.org/10.1016/j.pharmthera.2017.02.002 (2017).

56 Kalbasi, A. et al. Potentiating adoptive cell therapy using synthetic IL-9 receptors. *Nature* 607, 360-365, doi: 10.1038/s41586-022-04801-2 (2022).

57 Zhang, Y., Liu, Z., Wei, W. & Li, Y. TCR engineered T cells for solid tumor immunotherapy. *Experimental Hematology & Oncology* 11, 38, doi:10.1186/s40164-022-00291-0 (2022).

58 Overwijk, W. W. & Restifo, N. P. B16 as a mouse model for human melanoma. *Curr Protoc Immunol* Chapter 20, Unit-20.21, doi:10.1002/0471142735.im2001s39 (2001).

59 Eyquem, J. et al. Targeting a CAR to the TRAC locus with CRISPR/Cas9 enhances tumour rejection. *Nature* 543, 113-117, doi:10.1038/nature21405 (2017).

60 McLellan, A. D. & Ali Hosseini Rad, S. M. Chimeric antigen receptor T cell persistence and memory cell formation. *Immunol Cell Biol* 97, 664-674, doi:10.1111/imcb.12254 (2019).

61 Klichinsky, M. et al. Human chimeric antigen receptor macrophages for cancer immunotherapy. *Nat Biotechnol* 38, 947-953, doi:10.1038/s41587-020-0462-y (2020).

62 Rezvani, K. Adoptive cell therapy using engineered natural killer cells. *Bone Marrow Transplantation* 54, 785-788, doi:10.1038/s41409-019-0601-6 (2019).

63 Kabelitz, D., Serrano, R., Kouakanou, L., Peters, C. & Kalyan, S. Cancer immunotherapy with γδ T cells: many paths ahead of us. *Cellular & Molecular Immunology* 17, 925-939, doi:10.1038/s41423-020-0504-x (2020).

64 Wennhold, K., Shimabukuro-Vornhagen, A. & von Bergwelt-Baildon, M. B Cell-Based Cancer Immunotherapy. *Transfusion Medicine and Hemotherapy* 46, 36-46, doi:10.1159/000496166 (2019)\.

65 Zhu, I. et al. Modular design of synthetic receptors for programmed gene regulation in cell therapies. *Cell* 185, 1431-1443.e1416, doi:10.1016/j.cell.2022.03.023 (2022).

66 Zhao, H. et al. Genome-wide fitness gene identification reveals Roquin as a potent suppressor of CD8 T cell expansion and anti-tumor immunity. *Cell Rep* 37, 110083, doi:10.1016/j.celrep.2021.110083 (2021).

67 Chen L, Flies D B. Molecular mechanisms of T cell co-stimulation and co-inhibition. *Nat Rev Immunol* 2013 134. 2013; 13(4):227-242.

68 McCubrey J A, Steelman L S, Basecke J, Martelli A M. Raf/mek/erk signaling. *Target Ther Acute Myeloid Leuk.* January 2015:275-305.

69 Jutz, S. et al. Assessment of costimulation and coinhibition in a triple parameter T cell reporter line: Simultaneous measurement of NF-κB, NFAT and AP-1. *J Immunol Methods* 430, 10-20, doi:10.1016/j.jim.2016.01.007 (2016).

70 Love M I, Huber W, Anders S. Moderated estimation of fold change and dispersion for RNA-seq data with DESeq2. *Genome Biol.* 2014; 15(12):1-21.

71 J. Ruland, L. Hartjes, CARD-BCL-10-MALT1 signalling in protective and pathological immunity. *Nat Rev Immunol* 19, 118-134 (2019). ADDIN EN.REFLIST 72 Müller M R, Rao A. NFAT, immunity and cancer: a transcription factor comes of age. *Nat Rev Immunol* 2010 109. 2010; 10(9):645-656

73 Jang H J, Suh P G, Lee Y J, Shin K J, Cocco L, Chae Y C. PLCγ1: Potential arbitrator of cancer progression. *Adv Biol Regul.* 2018; 67: 179-189.

74 Patterson R L, Van Rossum D B, Nikolaidis N, Gill D L, Snyder S H. Phospholipase C-γ: diverse roles in receptor-mediated calcium signaling. *Trends Biochem Sci.* 2005; 30(12):688-697.

75 Patel V M et al., Frequent and Persistent PLCG1 Mutations in Sézary Cells Directly Enhance PLCγ1 Activity and Stimulate NFκB, AP-1, and NFAT Signaling. *J Invest Dermatol* 140, 380-389.e384 (2020).

76 Park, J. et al. Integrated genomic analyses of cutaneous T-cell lymphomas reveal the molecular bases for disease heterogeneity. *Blood* 138, 1225-1236, doi:10.1182/blood.2020009655 (2021).

77 Porter, D. L., Levine, B. L., Kalos, M., Bagg, A. & June, C. H. Chimeric Antigen Receptor-Modified T Cells in Chronic Lymphoid Leukemia. *New England Journal of Medicine* 365, 725-733, doi:10.1056/NEJMoa1103849 (2011).

78 Shaulian E, Karin M. AP-1 as a regulator of cell life and death. *Nat Cell Biol* 2002 45. 2002; 4(5):E131-E136.

79 Taniguchi K, Karin M. NF-κB, inflammation, immunity and cancer: coming of age. *Nat Rev Immunol* 2018 185. 2018; 18(5):309-324. doi:10.1038/nri.2017.142.

80 Villarino A V., Kanno Y, O'Shea J J. Mechanisms and consequences of Jak-STAT signaling in the immune system. *Nat Immunol* 2017 184. 2017; 18(4):374-384.

81 Wei, J. et al. Targeting REGNASE-1 programs long-lived effector T cells for cancer therapy. *Nature* 576, 471-476, doi:10.1038/s41586-019-1821-z (2019).

82 L. Wang et al., Genomic profiling of Sezary syndrome identifies alterations of key T cell signaling and differentiation genes. *Nature genetics* 47, 1426-1434 (2015).

What is claimed:

1. A nucleic acid construct comprising a nucleic acid sequence encoding a polypeptide, the polypeptide comprising:

a. a caspase-associated recruitment domain (CARD) containing protein; and b. a Src Homology region 2 (SH2) domain, wherein the polypeptide comprises or consists of a sequence having at least 85% identity to SEQ ID NO: 206.

2. The nucleic acid construct of claim 1, further comprising a nucleic acid sequence encoding a chimeric antigen receptor (CAR), a T cell receptor (TCR), a cytokine, a chemokine, or a growth factor.

3. The nucleic acid construct of claim 1, wherein the polypeptide comprises or consists of a sequence having at least 95% identity to SEQ ID NO: 206.

4. A polypeptide encoded by the nucleic acid construct of claim 1.

5. The polypeptide of claim 4, wherein the polypeptide comprises or consists of a sequence having at least 95% identity to SEQ ID NO: 206.

6. A vector comprising the nucleic acid construct of claim 1, wherein the vector is selected from the group consisting of a plasmid, a retrovirus vector, an adenovirus vector, and an adeno-associated virus vector.

7. The vector of claim 6, wherein the polypeptide comprises or consists of a sequence having at least 95% identity to SEQ ID NO: 206.

8. An isolated, in vitro, or ex vivo engineered cell comprising a polypeptide or a nucleic acid encoding the polypeptide, the polypeptide comprising:

a. a caspase-associated recruitment domain (CARD) containing protein; and b. a Src Homology region 2 (SH2) domain, wherein the polypeptide comprises or consists of a sequence having at least 85% identity to SEQ ID NO: 206.

9. The engineered cell of claim 8, wherein the engineered cell is selected from the group consisting of an immune cell, a T cell, a CD4+ T cell, a CD8+ T cell, a regulatory T cell (Treg), a gamma delta T cell (γδT), an invariant natural killer T (iNKT) cell, a mucosal associated invariant T (MAIT) cell, a macrophage, a monocyte, a natural killer (NK) cell, a tumor infiltrating lymphocyte (TIL), a cytotoxic T cell, a T helper cell, a memory T cell, a central memory T (TCM) cell, a stem memory T (TSCM) cell, a stem-cell-like memory T cell (or stem-like memory T cells), an effector memory T (TEM) cell, a TEMRA (CD45RA+) cell, an effector T cell, a Th1 cell, a Th2 cell, a Th9 cell, a Th17 cell, a Th22 cell, a Tfh (follicular helper) cell, a natural killer T (NKT) cell, a transitional memory T (TTM) cell, a terminal effector T (TTE) cell, a naïve T (TN) cell, a hematopoietic stem cell, and a progenitor cell of the lymphoid lineage.

10. The engineered cell of claim 8, wherein the CARD containing protein comprises or consists of a sequence having at least 95% identity to SEQ ID NO: 263.

11. The engineered cell of claim 8, wherein the polypeptide comprises or consists of a sequence having at least 95% identity to SEQ ID NO: 206.

12. The engineered cell of claim 8, wherein the nucleic acid encoding the polypeptide comprises or consists of a sequence having at least 95% identity to SEQ ID NO: 205.

13. The engineered cell of claim 8, wherein the engineered cell further comprises a chimeric antigen receptor (CAR), a T cell receptor (TCR), a cytokine, a chemokine, or a growth factor.

14. The engineered cell of claim 13, wherein the CAR or the TCR have specificity for a target antigen selected from the group consisting of CD1, CD1a, CD1b, CD1c, CD1d, CD1e, CD2, CD3d, CD3e, CD3g, CD3ε, CD4, CD5, CD7, CD8a, CD8b, CD19, CD20, CD21, CD22, CD23, CD24, CD25, CD27, CD28,CD30, CD33, CD34, CD38, CD40, CD44v6, CD45, CD48, CD52, CD59, CD66, CD70, CD71, CD72, CD73, CD79A, CD79B, CD80 (B7.1), CD86 (B7.2), CD94, CD95, CD97, CD123, CD134, CD140 (PDGFR4), CD152, CD154, CD158, CD171, CD178, CD179, CD179a, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), CEA, CLL-1, CS1, DLL3, LY6G6D, Claudin 6, GCC, p53R175H, PRAME, EGFR, FGFR2, AFP, CA125, MUC-1, MAGE, alkaline phosphatase, placental-like 2 (ALPPL2), B-cell maturation antigen (BCMA), green fluorescent protein (GFP), enhanced green fluorescent protein (eGFP), Claudin 18.2, PSMA, ROR1, Mesothelin, IL13Ra2, FAP, signal regulatory protein α (SIRPα), TCRalpha, TCRbeta, TSHR, EGFRvIII, GD2, GD3, Tn Ag, ROR1, ROR2, GPC1, GPC2, FLT3, FAP, TAG72, CEA, EPCAM, KIT, IL-13Ra2, IL-11Ra, PSCA, PRSS21, VEGFR2, LewisY, PDGFR-beta, SSEA-4, folate receptor alpha, ERBB2 (Her2/neu), MUC16, NCAM, prostase, PAP, ELF2M, Ephrin B2, IGF-I receptor, CAIX, LMP2, gp100, bcr-abl, tyrosinase, EphA2, fucosyl GM1, sLe, GM3, TGS5, HMWMAA, o-acetyl-GD2, folate receptor beta, TEM1/CD248, TEM7R, GPRC5D, CXORF61, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, HPV E7, MAGE A1, ETV6-AML, sperm protein 17, XAGE1, Tie 2, MAD-CT-1, MAD-CT-2, Fos-related antigen 1, p53, p53 mutant, KRAS, mutant KRAS, KRAS G12D, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, LAIR1, FCAR, LILRA2, CD300LF, CLEC12A, BST2, EMR2, LY75, GPC3, FCRL5, IGLL1, PSMA, the extracellular portion of the APRIL protein, and any combinations thereof.

15. The engineered cell of claim 13, wherein the CAR or the TCR have specificity for a target antigen selected from the group consisting of BCMA, CD19, CD20, CD22, CD70, CD79A, CD79B, CD276 (B7H3), Claudin 6, Claudin 18.2, DLL3, GCC, GD2, GD3, GPC3, GPRC5D, LY6G6D, p53R175H, PRAME, and ROR1.

16. The engineered cell of claim 8, wherein the engineered cell is selected from the group consisting of a T cell, a macrophage, a monocyte, and a natural killer (NK) cell.

17. The engineered cell of claim 8, wherein expression of the polypeptide is controlled by a promoter.

18. The engineered cell of claim 13, wherein the promoter is selected from the group consisting of an MND promoter, an EF1a promoter, a sEF1a promoter, a gamma retroviral LTR promoter, a CD4 promoter, a CD8a promoter, a CD8b promoter, a TCRa promoter, a TCRb promoter, a CD3d promoter, a CD3g promoter, a CD3e promoter, a CD3z promoter, a minimal TATA promoter, a pGK, actin promoter, a CD25 promoter, an IL2 promoter, an IL7 promoter, an IL15 promoter, a KLRG-1 promoter, a HLA-DR promoter, a CD38 promoter, a CD69 promoter, a Ki-67 promoter, a CD11a promoter, a CD58 promoter, a CD99 promoter, a CD62L promoter, a CD103 promoter, a CCR4 promoter, a CCR5 promoter, a CCR6 promoter, a CCR9 promoter, a CCR10 promoter, a CXCR3 promoter, a CXCR4 promoter, a CLA promoter, a Granzyme A promoter, a Granzyme B promoter, a Perforin promoter, a CD57 promoter, a CD161 promoter, an IL-18Ra promoter, a CD69 promoter, a GzmB promoter, a T-bet promoter, an IFNgamma promoter, an IL4 promoter, a GATA3 promoter, an IL1 promoter, an IL5 promoter, an IL6 promoter, an IL13 promoter, an IL10 promoter, an IL17A promoter, an IL6 promoter, an IL21 promoter, an IL23R promoter, a FoxP3 promoter, a CTLA4 promoter, a CD25 promoter, a CD45RO promoter, a CCR7 promoter, a CD28 promoter, a CD95 promoter, a CD28 promoter, a CD27 promoter, a CD127 promoter, a CD122 promoter, a CD132 promoter, a c-Kit promoter, a nuclear factor of activated T cells (NFAT) promoter, a programmed death 1 (PD-1) promoter, a T cell immunoglobulin mucin-3 (TIM-3) promoter, a cytotoxic T lymphocyte antigen-4 (CTLA4) promoter, a lymphocyte-activation protein 3 (LAG-3) promoter, a tumor necrosis factor (TNF)-related apoptosis-inducing ligand (TRAIL) promoter, a B- and T-lymphocyte attenuator (BTLA) promoter, a CD25 promoter, a CD69 promoter, a Fas ligand (FasL) promoter, a TIGIT promoter, a TGF-beta promoter, a T-bet promoter, an Eomes promoter, a CD45RA promoter, a 2B4 promoter, a Type I interferon (IFN) alpha, a Type I IFN beta promoter, an IFN gamma promoter, an IRF3 promoter, an IRF7 promoter, a NFkB promoter, an AP-1 promoter, a TNF-alpha promoter, a CD130 promoter, a NR4A1 promoter, a NR4A2, a NR4A3 promoter, and any combination thereof.

19. The engineered cell of claim 8, wherein the nucleic acid is introduced into the engineered cell via RNA, a plasmid, a retrovirus vector, an adenovirus vector, or an adeno-associated virus vector.

20. The engineered cell of claim 8, wherein the nucleic acid is inserted in the genome of the engineered cell using a CRISPR/Cas system.

21. The engineered cell of claim 8, wherein the nucleic acid is inserted in a TCR alpha locus of the engineered cell.

22. The engineered cell of claim 8, wherein the engineered cell has reduced or eliminated expression of an endogenous T cell receptor (TCR).

23. The engineered cell of claim 8, wherein the engineered cell is an autologous cell.

24. The engineered cell of claim 8, wherein the engineered cell is an allogeneic cell.

25. The engineered cell of claim 8, wherein the engineered cell comprises a chimeric antigen receptor (CAR) or a T cell receptor (TCR), wherein the CAR or the TCR have specificity for a target antigen selected from the group consisting of BCMA, CD19, CD20, CD22, CD70, CD79A, CD79B, CD276 (B7H3), Claudin 6, Claudin 18.2, DLL3, GCC, GD2, GD3, GPC3, GPRC5D, LY6G6D, p53R175H, PRAME, and ROR1, wherein the polypeptide comprises or consists of a sequence having at least 95% identity to SEQ ID NO: 206, wherein expression of the polypeptide is controlled by a promoter selected from the group consisting of a TCRa promoter, a TCRb promoter, a gamma retroviral LTR promoter, an IL2 promoter, a nuclear factor of activated T cells (NFAT) promoter, an NR4A1 promoter, an MND promoter, an EF1a promoter, and a sEF1a promoter.

26. The engineered cell of claim 25, wherein the engineered cell has reduced cell surface expression of an endogenous T cell receptor (TCR).

27. A method of making an isolated, in vitro, or ex vivo engineered cell, the method comprising, introducing a nucleic acid construct comprising a nucleic acid sequence encoding a polypeptide into the isolated, in vitro, or ex vivo cell, wherein the polypeptide comprises:

i. a caspase-associated recruitment domain (CARD) containing protein; and ii. Src Homology region 2 (SH2) domain, wherein the polypeptide comprises or consists of a sequence having at least 85% identity to SEQ ID NO: 206.

* * * * *

UNITED STATES PATENT AND TRADEMARK OFFICE

CERTIFICATE OF CORRECTION

PATENT NO. : 12,295,971 B2
APPLICATION NO. : 18/630828
DATED : May 13, 2025
INVENTOR(S) : Kole Roybal et al.

It is certified that error appears in the above-identified patent and that said Letters Patent is hereby corrected as shown below:

In the Claims

At Column 376, Claim number 18, Line number 58, delete "13" after the word "claim" and insert --17--.

Signed and Sealed this
Eleventh Day of November, 2025

John A. Squires
*Director of the United States Patent and Trademark Office*

SEQUENCE LISTING

```
Sequence total quantity: 437
SEQ ID NO: 1          moltype = DNA  length = 2118
FEATURE               Location/Qualifiers
source                1..2118
                      mol_type = other DNA
                      organism = Synthetic construct
SEQUENCE: 1
atggcctcgc cggctgacag ctgtatccag ttcacccgcc atgccagtga tgttcttctc  60
aaccttaatc gtctccggag tcgagacatc ttgactgatg ttgtcattgt tgtgagccgt  120
gagcagttta gagcccataa aacggtcctc atggcctgca gtggcctgtt ctatagcatc  180
```

-continued

```
tttacagacc agttgaaatg caaccttagt gtgatcaatc tagatcctga gatcaaccct  240
gagggattct gcatcctcct ggacttcatg tacacatctc ggctcaattt gcgggagggc  300
aacatcatgg ctgtgatggc cacggctatg tacctgcaga tggagcatgt tgtggacact  360
tgccggaagt ttattaaggc cagtgaagca gagatggttt ctgccatcaa gcctcctcgt  420
gaagagttcc tcaacagccg gatgctgatg ccccaagaca tcatggccta tcggggttgt  480
gaggtggtgg agaacaacct gccactgagg agcgcccctg ggtgtgagag cagagccttt  540
gcccccagcc tgtacagtgg cctgtccaca ccgccagcct cttattccat gtacagccac  600
ctccctgtca gcagcctcct cttctccgat gaggagtttc gggatgtccg gatgcctgtg  660
gccaacccct tccccaagga gcgggcactc ccatgtgata gtgccaggcc agtccctggt  720
gagtacagcc ggccgacttt ggaggtgtcc cccaatgtgt gccacagcaa tatctattca  780
cccaaggaaa caatcccaga agaggcacga agtgatatgc actacagtgt ggctgagggc  840
ctcaaacctg ctgccccctc agcccgaaat gccccctact tcccttgtga caaggccagc  900
aaagaagaag agagaccctc ctcggaagat gagattgccc tgcatttcga gccccccaat  960
gcacccctga accggaaggg tctggttagt ccacagagcc cccagaaatc tgactgccag  1020
cccaactcgc ccacagagtc ctgcagcagt aagaatgcct gcatcctcca ggcttctggc  1080
tcccctccag ccaagagccc cactgacccc aaagcctgca actggaagaa atacaagttc  1140
atcgtgctca acagcctcaa tcagaatgcc aaaccagagg ggcctgagca ggctgagctg  1200
ggccgccttt ccccacgagc ctacacggcc ccacctgcct gccagccacc catggagcct  1260
gagaaccttg acctccagtc ccccaaccaag ctgagtgcca gcggggagga ctccaccatc  1320
ccacaagcca gccggctcaa taacatcgtt aacaggtcca tgacgggctc tccccgcagc  1380
agcagcgaga gccactcacc actctacatg cacccccga agtgcacgtc ctgcggctct  1440
cagtccccac agcatgcaga gatgtgcctc cacaccgctg gccccacgtt ccctgaggag  1500
atgggagaga cccagtctga gtactcagat tctagctgtg agaacggggc cttcttctgc  1560
aatgagtgtg actgccgctt ctctgaggag gcctcactca agaggcacac gctgcagacc  1620
cacagtgaca aaccctacaa gtgtgaccgc tgccaggcct ccttccgcta caagggcaac  1680
ctcgccagcc acaagaccgt ccataccggt gagaaaccct atcgttgcaa catctgtggg  1740
gcccagttca accggccagc caacctgaaa acccacactc gaattcactc tggagagaag  1800
ccctacaaat gcgaaacctg cggagccaga tttgtacagg tggcccacct ccgtgcccat  1860
gtgcttatcc acactggtga gaagccctat ccctgtgaaa tctgtggcac ccgtttccgg  1920
caccttcaga ctctgaagcg ccacctgcga atccacacag gagagaaacc ttaccattgt  1980
gagaagtgta acctgcattt ccgtcacaaa agccagctgc gacttcactt gcgccagaag  2040
catggcgcca tcaccaacac caaggtgcaa taccgcgtgt cagccactga cctgcctccg  2100
gagctcccca aagcctgc                                                2118

SEQ ID NO: 2            moltype = AA  length = 706
FEATURE                 Location/Qualifiers
source                  1..706
                        mol_type = protein
                        organism = Synthetic construct
SEQUENCE: 2
MASPADSCIQ FTRHASDVLL NLNRLRSRDI LTDVVIVVSR EQFRAHKTVL MACSGLFYSI  60
FTDQLKCNLS VINLDPEINP EGFCILLDFM YTSRLNLREG NIMAVMATAM YLQMEHVVDT  120
CRKFIKASEA EMVSAIKPPR EEFLNSRMLM PQDIMAYRGC EVVENNLPLR SAPGCESRAF  180
APSLYSGLST PPASYSMYSH LPVSSLLFSD EEFRDVRMPV ANPFPKERAL PCDSARPVPG  240
EYSRPTLEVS PNVCHSNIYS PKETIPEEAR SDMHYSVAEG LKPAAPSARN APYFPCDKAS  300
KEEERPSSED EIALHFEPPN APLNRKGLVS PQSPQKSDCQ PNSPTESCSS KNACILQASG  360
SPPAKSPTDP KACNWKKYKF IVLNSLNQNA KPEGPEQAEL GRLSPRAYTA PPACQPPMEP  420
ENLDLQSPTK LSASGEDSTI PQASRLNNIV NRSMTGSPRS SSESHSPLYM HPPKCTSCGS  480
QSPQHAEMCL HTAGPTFPEE MGETQSEYSD SSCENGAFFC NECDCRFSEE ASLKRHTLQT  540
HSDKPYKCDR CQASFRYKGN LASHKTVHTG EKPYRCNICG AQFNRPANLK THTRIHSGEK  600
PYKCETCGAR FVQVAHLRAH VLIHTGEKPY PCEICGTRFR HLQTLKRHLR IHTGEKPYHC  660
EKCNLHFRHK SQLRLHLRQK HGAITNTKVQ YRVSATDLPP ELPKAC                 706

SEQ ID NO: 3            moltype = DNA  length = 2118
FEATURE                 Location/Qualifiers
source                  1..2118
                        mol_type = genomic DNA
                        organism = Homo sapiens
SEQUENCE: 3
atggcctcgc cggctgacag ctgtatccag ttcacccgcc atgccagtga tgttcttctc  60
aaccttaatc gtctccggag tcgagacatc ttgactgatg ttgtcattgt tgtgagccgt  120
gagcagttta gagcccataa aacggtcctc atggcctgca gtggcctgtt ctatagcatc  180
tttacagacc agttgaaatg caaccttagt gtgatcaatc tagatcctga gatcaaccct  240
gagggattct gcatcctcct ggacttcatg tacacatctc ggctcaattt gcgggagggc  300
aacatcatgg ctgtgatggc cacggctatg tacctgcaga tggagcatgt tgtggacact  360
tgccggaagt ttattaaggc cagtgaagca gagatggttt ctgccatcaa gcctcctcgt  420
gaagagttcc tcaacagccg gatgctgatg ccccaagaca tcatggccta tcggggttgt  480
gaggtggtgg agaacaacct gccactgagg agcgcccctg ggtgtgagag cagagccttt  540
gcccccagcc tgtacagtgg cctgtccaca ccgccagcct cttattccat gtacagccac  600
ctccctgtca gcagcctcct cttctccgat gaggagtttc gggatgtccg gatgcctgtg  660
gccaacccct tccccaagga gcgggcactc ccatgtgata gtgccaggcc agtccctggt  720
gagtacagcc ggccgacttt ggaggtgtcc cccaatgtgt gccacagcaa tatctattca  780
cccaaggaaa caatcccaga agaggcacga agtgatatgc actacagtgt ggctgagggc  840
ctcaaacctg ctgccccctc agcccgaaat gccccctact tcccttgtga caaggccagc  900
aaagaagaag agagaccctc ctcggaagat gagattgccc tgcatttcga gccccccaat  960
gcacccctga accggaaggg tctggttagt ccacagagcc cccagaaatc tgactgccag  1020
cccaactcgc ccacagagtc ctgcagcagt aagaatgcct gcatcctcca ggcttctggc  1080
tcccctccag ccaagagccc cactgacccc aaagcctgca actggaagaa atacaagttc  1140
atcgtgctca acagcctcaa tcagaatgcc aaaccagagg ggcctgagca ggctgagctg  1200
```

-continued

```
ggccgccttt ccccacgagc ctacacggcc ccacctgcct gccagccacc catggagcct  1260
gagaaccttg acctccagtc cccaaccaag ctgagtgcca gcggggagga ctccaccatc  1320
ccacaagcca gccggctcaa taacatcgtt aacaggtcca tgacgggctc tccccgcagc  1380
agcagcgaga gccactcacc actctacatg caccccccga agtgcacgtc ctgcggctct  1440
cagtccccac agcatgcaga gatgtgcctc cacaccgctg gccccacgtt ccctgaggag  1500
atgggagaga cccagtctga gtactcagat tctagctgtg agaacggggc cttcttctgc  1560
aatgagtgtg actgccgctt ctctgaggag gcctcactca agaggcacac gctgcagacc  1620
cacagtgaca aaccctacaa gtgtgaccgc tgccaggcct ccttccgcta caagggcaac  1680
ctcgccagcc acaagaccgt ccataccggt gagaaaccct atcgttgcaa catctgtggg  1740
gcccagttca accggccagc caacctgaaa acccacactc gaattcactc tggagagaag  1800
ccctacaaat gcgaaacctg cggagccaga tttgtacagg tggcccacct ccgtgcccat  1860
gtgcttatcc acactggtga gaagccctat ccctgtgaaa tctgtggcac ccgtttccgg  1920
caccttcaga ctctgaagag ccacctgcga atccacacag gagagaaacc ttaccattgt  1980
gagaagtgta acctgcattt ccgtcacaaa agccagctgc gacttcactt gcgccagaag  2040
catggcgcca tcaccaacac caaggtgcaa taccgcgtgt cagccactga cctgcctccg  2100
gagctcccca aagcctgc                                                 2118

SEQ ID NO: 4            moltype = AA  length = 706
FEATURE                 Location/Qualifiers
source                  1..706
                        mol_type = protein
                        organism = Homo sapiens
SEQUENCE: 4
MASPADSCIQ FTRHASDVLL NLNRLRSRDI LTDVVIVVSR EQFRAHKTVL MACSGLFYSI  60
FTDQLKCNLS VINLDPEINP EGFCILLDFM YTSRLNLREG NIMAVMATAM YLQMEHVVDT  120
CRKFIKASEA EMVSAIKPPR EEFLNSRMLM PQDIMAYRGC EVVENNLPLR SAPGCESRAF  180
APSLYSGLST PPASYSMYSH LPVSSLLFSD EEFRDVRMPV ANPFPKERAL PCDSARPVPG  240
EYSRPTLEVS PNVCHSNIYS PKETIPEEAR SDMHYSVAEG LKPAAPSARN APYFPCDKAS  300
KEEERPSSED EIALHFEPPN APLNRKGLVS PQSPQKSDCQ PNSPTESCSS KNACILQASG  360
SPPAKSPTDP KACNWKKYKF IVLNSLNQNA KPEGPEQAEL GRLSPRAYTA PPACQPPMEP  420
ENLDLQSPTK LSASGEDSTI PQASRLNNIV NRSMTGSPRS SSESHSPLYM HPPKCTSCGS  480
QSPQHAEMCL HTAGPTFPEE MGETQSEYSD SSCENGAFFC NECDCRFSEE ASLKRHTLQT  540
HSDKPYKCDR CQASFRYKGN LASHKTVHTG EKPYRCNICG AQFNRPANLK THTRIHSGEK  600
PYKCETCGAR FVQVAHLRAH VLIHTGEKPY PCEICGTRFR HLQTLKSHLR IHTGEKPYHC  660
EKCNLHFRHK SQLRLHLRQK HGAITNTKVQ YRVSATDLPP ELPKAC                  706

SEQ ID NO: 5            moltype = DNA  length = 5265
FEATURE                 Location/Qualifiers
source                  1..5265
                        mol_type = other DNA
                        organism = Synthetic construct
SEQUENCE: 5
atgctctcag caaccccccct gtatgggaac gttcacagct ggatgaacag cgagagggtc  60
cgcatgtgtg gggcgagcga agacaggaaa atccttgtaa atgatggtga cgcttcaaaa  120
gccagactgg aactgaggga agagaatccc ttgaaccaca acgtggtgga tgcgagcacg  180
gcccatagga tcgatggcct ggcagcactg agcatggacc gcactggcct gatccgggaa  240
gggctgcggg tcccgggaaa catcgtctat tctagcttgt gtggactggg ctcagagaaa  300
ggtcgggagg ctgccacaag cactctaggt ggccttgggt tttcttcgga aagaaatcca  360
gagatgcagt tcaaaccgaa tacacccgag acagtggagg cttctgccgt ctctggaaaa  420
cccccaaatg gcttcagtgc tatatacaaa acaccgcctg gaatacaaaa aagtgctgta  480
gccacagcag aagcgctggg cttggacagg cctgccagcg acaaacagag ccctctcaac  540
atcaatggtg ctagttatct gcggctgccc tgggtcaatc cttacatgga gggtgccacg  600
ccagccatct accctttcct cgactcgcca aataagtatt cactgaacat gtacaaggcc  660
ttgctacctc agcagtccta cagcttggcc cagccgctgt attctccagt ctgcaccaat  720
ggggagcgct ttctctacct gccgccacct cactacgtcg gtccccacat cccatcgtcc  780
ttggcatcac ccatgaggct ctcgacacct tcggcctccc cagccatccc gcctctcgtc  840
cattgcgcag acaaaagcct cccgtggaag atgggcgtca gccctgggaa tcctgttgat  900
tcccacgcct atcctcacat ccagaacagt aagcagccca gggttccctc tgccaaggcg  960
gtcaccagtg gcctgccggg ggacacagct ctcctgttgc cccctcgcc tcggccgtca  1020
ccccgagtcc accttcccac ccagcctgct gcagacacct actcggagtt ccacaagcac  1080
tatgccagga tctccacctc tccttcagtt gccctgtcaa agccatacat gacagttagc  1140
agcgagttcc ccgcggccag gctctccaat ggcaagtatc ccaaggctcc ggaaggggggc  1200
gaaggtgccc agccagtgcc cggcatgcc cggaagacag cggttcaaga cagaaaagat  1260
ggcagctcac ctcctctgtt ggagaagcag accgttacca aagacgtcac agataagcca  1320
ctagacttgt cttctaaagt ggtggatgta gatgcttcca aagctgacca catgaaaaag  1380
atggctccca cggtcctggt tcacagcagg gctggaagtg gcttagtgct ctccggaagt  1440
gagattccga aagaaacact atctcctcca ggaaatggtt gtgctatcta tagatctgaa  1500
atcatcagca ctgctccctc atcctgggtg gtgcccgggc caagtcctaa cgaagagaac  1560
aatggcaaaa gcatgtcgct gaaaaacaag gcattggact gggcgatacc acagcagcgg  1620
agttcatcat gcccgcgcat gggcggcacc gatgctgtca tcactaacgt ttcagggtca  1680
gtgtcgagtg caggccgccc agcctccgca tcacccgccc ccaatgccaa tgcagatggc  1740
accaaaacca gcaggagctc tgtagaaacc acaccatccg ttattcagca cgtgggccag  1800
cccccggcca ctcctgccaa gcacagtagc agcaccagca gcaagggcgc caaagccagc  1860
aacccagaac cgagtttcaa agcaaacgag aacggccttc caccaagctc tatatttctg  1920
tctccaaatg aggcattcag gtccccacca attccctacc ccaggagtta cctcccttac  1980
ccagcccctg agggcattgc tgtaagtccc ctctccttac atggcaaagg acctgtctac  2040
cctcacccag ttttgttacc caatggcagt ctgtttcctg ggcaccttgc cccaaagcct  2100
gggctgccct atgggcttcc caccggccgt ccagagtttg tgacctacca agatgccctg  2160
gggttgggca tggtgcatcc catgttgata ccacacacgc ccatagagat tactaaagag  2220
```

-continued

```
gagaaaccag agaggagatc ccggtcccat gagagagccc gttacgagga cccaaccctc  2280
cggaatcggt tttccgagat tttggaaact agcagcacca agttacatcc agatgtcccc  2340
accgacaaga acctaaagcc gaaccccaac tggaatcaag ggaagactgt tgtcaaaagc  2400
gacaagcttg tctacgtaga ccttctccga gaagaaccag atgctaaaac tgacacaaac  2460
gtgtccaaac ccagctttgc agcagagagt gttggccaga gcgctgagcc ccccaagccc  2520
tcagttgagc cggccctgca gcagcaccgt gatttcatcg ccctgagaga ggagttgggg  2580
cgcatcagtg acttccacga aacttatact ttcaaacagc cagtcttcac cgtaagcaag  2640
gacagtgttc tggcaggtac caacaaagag aacctagggt tgccagtctc gactccattc  2700
ctggagccac ctctggggag cgatggccct gctgtaactt ttggtaaaac ccaagaggat  2760
cccaaaccat tttgtgtggg cagtgcccca ccaagtgtgg atgtgacccc cacctatacc  2820
aaagatggag ctgatgaggc tgaatcaaat gatggcaaag ttctgaaacc gaagccatct  2880
aagctggcaa agagaatcgc caactcagcg ggttacgtgg gtgaccgatt caaatgtgtc  2940
actaccgaac tgtatgcaga ttccagtcag ctcagccggg agcaacgggc attgcagatg  3000
gaaggattac aagaggacag tattttatgt ctacccgctg cttactgtga gcgtgcaatg  3060
atgcgcttct cagagttgga gatgaaagaa agagaaggtg gccacccagc aaccaaagac  3120
tccgagatgt gcaaattcag cccagccgac tgggaaaggt tgaaaggaaa tcaggacaaa  3180
aagccaaagt cggtcaccct ggaggaggcc attgcagaac agaacgaaag tgagagatgc  3240
gagtatagtg ttggaaacaa gcaccgtgat ccctttgaag ccccagagga caaagatctt  3300
cctgtggaga agtactttgt ggagaggcag cctgtgagcg agcctcccgc agaccaggtg  3360
gcctcggaca tgcctcacag ccccaccctc cgggtggaca ggaaacgcaa agtctcaggt  3420
gacagcagcc acactgagac cactgcggag gaggtgccag aggaccctct gctgaaagcc  3480
aaacgccgac gagtctctaa agatgactgg cctgagaggg aaatgacaaa cagttcctct  3540
aaccacttag aagacccaca ttatagtgag ctgaccaacc tgaaggtgtg cattgaatta  3600
acagggctcc atcctaaaaa acaacgccac ttgctgcacc ttagagaacg atgggagcag  3660
caggtgtcgg cagcagatgg caaacctggc cggcaaagca ggaaggaagt gacccaggcc  3720
actcagcctg aggccattcc tcaggggact aacatcactg aagagaaacc tggcaggaaa  3780
agggcagagg ccaaaggcaa cagaagctgg tcggaagagt ctcttaaacc cagtgacaat  3840
gaacaaggct tgcctgtgtt ctccggctct ccgcccatga agagtcttc atccaccagt  3900
gcaggcggca aaaagcaggc tcagccaagc tgcgcaccag cctccaggcc gcctgccaaa  3960
cagcagaaaa ttaaagaaaa ccagaagaca gatgtgctgt gtgcagacga agaagaggat  4020
tgccaggctg cctccctgct gcagaaatac accgacaaca gcgagaagcc atccgggaag  4080
agactgtgca aaaccaaaca cttgatccct caggagtcca ggcggggatt gccactgaca  4140
ggggaatact acgtggagaa tgccgatggc aaggtgactg tccggagatt cagaaagcgg  4200
ccggagccca gttcggacta tgatctgtca ccagccaagc aggagccaaa gcccttcgac  4260
cgcttgcagc aactgctacc agcctcccag tccacacagc tgccatgctc aagttcccct  4320
caggagacca cccagtctcg ccctatgccg ccggaagcac ggagacttat tgtctctaag  4380
aacgctggcg agacccttct gcagcgggca gccaggcttg gctatgagga agtggtcctg  4440
tactgcttag agaacaagat ttgtgatgta aatcatcggg acaacgcagg ttactgcgcc  4500
ctgcatgaag cttgtgctag ggctggctc aacattgtgc gacacctcct tgaatatggc  4560
gctgatgtca actgtagtgc ccaggatgga accaggcctc tgcacgatgc tgttgagaac  4620
gatcacttgg aaattgtccg actacttctc tcttatggtg ctgaccccac cttggctacg  4680
tactcaggta gaaccatcat gaaaatgacc cacagtgaac ttatggaaaa gttcttaaca  4740
gattatttaa atgacctcca gggtcgcaat gatgatgacg ccagtggcac ttgggacttc  4800
tatggcagct ctgtttgtga accagatgat gaaagtggct atgatgtttt agccaacccc  4860
ccaggaccag aagaccagga tgatgatgac gatgcctata gcgatgtgtt tgaatttgaa  4920
ttttcagaga ccccccctctt accgtgttat aacatccaag tatctgtggc tcaggggcca  4980
cgaaactggc tactgctttc ggatgtcctt aagaaattga aaatgtcctc ccgcatattt  5040
cgctgcaatt ttccaaacgt ggaaattgtc accattgcag aggcagaatt ttatcggcag  5100
gtttctgcaa gtctcttgtt ctcttgctcc aaagacctgg aagccttcaa ccctgaaagt  5160
aaggagctgt tagatctggt ggaattcacg aacgaaattc agactctgct gggctcctct  5220
gtagagtggc tccaccccag tgatctggcc tcagacaact actgg                  5265
```

```
SEQ ID NO: 6           moltype = AA  length = 1755
FEATURE                Location/Qualifiers
source                 1..1755
                       mol_type = protein
                       organism = Synthetic construct
SEQUENCE: 6
MLSATPLYGN VHSWMNSERV RMCGASEDRK ILVNDGDASK ARLELREENP LNHNVVDAST  60
AHRIDGLAAL SMDRTGLIRE GLRVPGNIVY SSLCGLGSEK GREAATSTLG GLGFSSERNP  120
EMQFKPNTPE TVEASAVSGK PPNGFSAIYK TPPGIQKSAV ATAEALGLDR PASDKQSPLN  180
INGASYLRLP WVNPYMEGAT PAIYPFLDSP NKYSLNMYKA LLPQQSYSLA QPLYSPVCTN  240
GERFLYLPPP HYVGPHIPSS LASPMRLSTP SASPAIPPLV HCADKSLPWK MGVSPGNPVD  300
SHAYPHIQNS KQPRVPSAKA VTSGLPGDTA LLLPPSPRPS PRVHLPTQPA ADTYSEFHKH  360
YARISTSPSV ALSKPYMTVS SEFPAARLSN GKYPKAPEGG EGAQPVPGHA RKTAVQDRKD  420
GSSPPLLEKQ TVTKDVTDKP LDLSSKVVDV DASKADHMKK MAPTVLVHSR AGSGLVLSGS  480
EIPKETLSPP GNGCAIYRSE IISTAPSSWV VPGPSPNEEN NGKSMSLKNK ALDWAIPQQR  540
SSSCPRMGGT DAVITNVSGS VSSAGRPASA SPAPNANADG TKTSRSSVET TPSVIQHVGQ  600
PPATPAKHSS STSSKGAKAS NPEPSFKANE NGLPPSSIFL SPNEAFRSPP IPYPRSYLPY  660
PAPEGIAVSP LSLHGKGPVY PHPVLLPNGS LFPGHLAPKP GLPYGLPTGR PEFVTYQDAL  720
GLGMVHPMLI PHTPIEITKE EKPERRSRSH ERARYEDPTL RNRFSEILET SSTKLHPDVP  780
TDKNLKPNPN WNQGKTVVKS DKLVYVDLLR EEPDAKTDTN VSKPSFAAES VGQSAEPPKP  840
SVEPALQQHR DFIALREELG RISDFHETYT FKQPVFTVSK DSVLAGTNKE NLGLPVSTPF  900
LEPPLGSDGP AVTFGKTQED PKPFCVGSAP PSVDVTPTYT KDGADEAESN DGKVLKPKPS  960
KLAKRIANSA GYVGDRFKCV TTELYADSSQ LSREQRALQM EGLQEDSILC LPAAYCERAM  1020
MRFSELEMKE REGGHPATKD SEMCKFSPAD WERLKGNQDK KPKSVTLEEA IAEQNESERC  1080
EYSVGNKHRD PFEAPEDKDL PVEKYFVERQ PVSEPPADQV ASDMPHSPTL RVDRKRKVSG  1140
DSSHTETTAE EVPEDPLLKA KRRRVSKDDW PEREMTNSSS NHLEDPHYSE LTNLKVCIEL  1200
TGLHPKKQRH LLHLRERWEQ QVSAADGKPG RQSRKEVTQA TQPEAIPQGT NITEEKPGRK  1260
```

-continued

```
RAEAKGNRSW SEESLKPSDN EQGLPVFSGS PPMKSLSSTS AGGKKQAQPS CAPASRPPAK  1320
QQKIKENQKT DVLCADEEED CQAASLLQKY TDNSEKPSGK RLCKTKHLIP QESRRGLPLT  1380
GEYYVENADG KVTVRRFRKR PEPSSDYDLS PAKQEPKPFD RLQQLLPASQ STQLPCSSSP  1440
QETTQSRPMP PEARRLIVSK NAGETLLQRA ARLGYEEVVL YCLENKICDV NHRDNAGYCA  1500
LHEACARGWL NIVRHLLEYG ADVNCSAQDG TRPLHDAVEN DHLEIVRLLL SYGADPTLAT  1560
YSGRTIMKMT HSELMEKFLT DYLNDLQGRN DDDASGTWDF YGSSVCEPDD ESGYDVLANP  1620
PGPEDQDDDD DAYSDVFEFE FSETPLLPCY NIQVSVAQGP RNWLLLSDVL KKLKMSSRIF  1680
RCNFPNVEIV TIAEAEFYRQ VSASLLFSCS KDLEAFNPES KELLDLVEFT NEIQTLLGSS  1740
VEWLHPSDLA SDNYW                                                   1755

SEQ ID NO: 7           moltype = DNA  length = 5265
FEATURE                Location/Qualifiers
source                 1..5265
                       mol_type = genomic DNA
                       organism = Homo sapiens
SEQUENCE: 7
atgctctcag caacccccct gtatgggaac gttcacagct ggatgaacag cgagagggtc  60
cgcatgtgtg gggcgagcga agacaggaaa atccttgtaa atgatggtga cgcttcaaaa  120
gccagactgg aactgaggga agagaatccc ttgaaccaca acgtggtgga tgcgagcacg  180
gcccatagga tcgatggcct ggcagcactg agcatggacc gcactggcct gatccgggaa  240
gggctgcggg tcccgggaaa catcgtctat tctagcttgt gtggactggg ctcagagaaa  300
ggtcgggagg ctgccacaag cactctaggt ggccttgggt ttcttcgga aagaaatcca  360
gagatgcagt tcaaaccgaa tacacccgag acagtggagg cttctgccgt ctctggaaaa  420
cccccaaatg gcttcagtgc tatatacaaa acaccgcctg gaatacaaaa aagtgctgta  480
gccacagcag aagcgctggg cttggacagg cctgccagcg acaaacagag ccctctcaac  540
atcaatggtg ctagttatct gcggctgccc tgggtcaatc cttacatgga gggtgccacg  600
ccagccatct accctttcct cgactcgcca aataagtatt cactgaacat gtacaaggcc  660
ttgctacctc agcagtccta cagcttggcc cagccgctgt attctccagt ctgcaccaat  720
ggggagcgct ttctctacct gccgccacct cactacgtcg gtccccacat cccatcgtcc  780
ttggcatcac ccatgaggct ctcgacacct tcggcctccc cagccatccc gcctctcgtc  840
cattgcgcag acaaaagcct cccgtggaag atgggcgtca gccctgggaa tcctgttgat  900
tcccacgcct atcctcacat ccagaacagt aagcagccca gggttccctc tgccaaggcg  960
gtcaccagtg gcctgccggg ggacacagct ctcctgttgc ccccctcgcc tcggccgtca  1020
ccccgagtcc accttcccac ccagcctgct gcagacacct actcggagtt ccacaagcac  1080
tatgccagga tctccacctc tccttcagtt gccctgtcaa agccatacat gacagttagc  1140
agcgagttcc ccgcggccag gctctccaat ggcaagtatc ccaaggctcc ggaagggggc  1200
gaaggtgccc agccagtgcc cggcatgccc cggaagacag cggttcaaga cagaaaagat  1260
ggcagctcac ctcctctgtt ggagaagcag accgttacca aagacgtcac agataagcca  1320
ctagacttgt cttctaaagt ggtggatgta gatgcttcca aagctgacca catgaaaaag  1380
atggctccca cggtcctggt tcacagcagg gctggaagtg gcttagtgct ctccggaagt  1440
gagattccga aagaaacact atctcctcca ggaaatggtt gtgctatcta tagatctgaa  1500
atcatcagca ctgctccctc atcctgggtg gtgcccgggc caagtcctaa cgaagagaac  1560
aatggcaaaa gcatgtcgct gaaaaacaag gcattggact gggcgatacc acagcagcgg  1620
agttcatcat gcccgcgcat gggcggcacc gatgctgtca tcactaacgt ttcagggtca  1680
gtgtcgagtg caggccgccc agcctccgca tcacccgccc ccaatgccaa tgcagatggc  1740
accaaaacca gcaggagctc tgtagaaacc acaccatccg ttattcagca cgtgggccag  1800
cccccggcca ctcctgccaa gcacagtagc agcaccagca gcaagggcgc caaagccagc  1860
aacccagaac cgagtttcaa agcaaacgag aacggccttc caccaagctc tatatttctg  1920
tctccaaatg aggcattcag gtccccacca attccctacc ccaggagtta cctcccttac  1980
ccagcccctg agggcattgc tgtaagtccc ctctccttac atggcaaagg acctgtctac  2040
cctcacccag ttttgttacc caatggcagt ctgtttcctg ggcaccttgc cccaaagcct  2100
gggctgccct atgggcttcc caccggccgt ccagagtttg tgacctacca agatgccctg  2160
gggttgggca tggtgcatcc catgttgata ccacacacgc ccatagagat tactaaagag  2220
gagaaaccag agaggagatc ccggtcccat gagagagccc gttacgagga cccaaccctc  2280
cggaatcggt tttccgagat tttggaaact agcagcacca agttacatcc agatgtcccc  2340
accgacaaga acctaaagcc gaaccccaac tggaatcaag ggaagactgt tgtcaaaagc  2400
gacaagcttg tctacgtaga ccttctccga gaagaaccag atgctaaaac tgacacaaac  2460
gtgtccaaac ccagctttgc agcagagagt gttggccaga gcgctgagcc ccccaagccc  2520
tcagttgagc cggccctgca gcagcaccgt gatttcatcg ccctgagaga ggagttgggg  2580
cgcatcagtg acttccacga aacttatact ttcaaacagc cagtcttcac cgtaagcaag  2640
gacagtgttc tggcaggtac caacaaagag aacctagggt tgccagtctc gactccattc  2700
ctggagccac ctctggggag cgatggccct gctgtaactt ttggtaaaac ccaagaggat  2760
cccaaaccat tttgtgtggg cagtgcccca ccaagtgtgg atgtgacccc cacctatacc  2820
aaagatggag ctgatgaggc tgaatcaaat gatggcaaag ttctgaaacc gaagccatct  2880
aagctggcaa agagaatcgc caactcagcg ggttacgtgg gtgaccgatt caaatgtgtc  2940
actaccgaac tgtatgcaga ttccagtcag ctcagccggg agcaacgggc attgcagatg  3000
gaaggattac aagaggacag tattttatgt ctacccgctg cttactgtga gcgtgcaatg  3060
atgcgcttct cagagttgga gatgaaagaa agagaaggtg gccacccagc aaccaaagac  3120
tccgagatgt gcaaattcag cccagccgac tgggaaaggt tgaaaggaaa tcaggacaaa  3180
aagccaaagt cggtcaccct ggaggaggcc attgcagaac agaacgaaag tgagagatgc  3240
gagtatagtg ttggaaacaa gcaccgtgat ccctttgaag ccccagagga caaagatctt  3300
cctgtggaga agtactttgt ggagaggcag cctgtgagcg agcctcccgc agaccaggtg  3360
gcctcggaca tgcctcacag ccccaccctc cgggtggaca ggaaacgcaa agtctcaggt  3420
gacagcagcc acactgagac cactgcggag gaggtgccag aggaccctct gctgaaagcc  3480
aaacgccgac gagtctctaa agatgactgg cctgagaggg aaatgacaaa cagttcctct  3540
aaccacttag aagacccaca ttatagtgag ctgaccaacc tgaaggtgtg cattgaatta  3600
acagggctcc atcctaaaaa acaacgccac ttgctgcacc ttagagaacg atgggagcag  3660
caggtgtcgg cagcagatgg caaacctggc cggcaaagca ggaaggaagt gacccaggcc  3720
actcagcctg aggccattcc tcaggggact aacatcactg aagagaaacc tggcaggaaa  3780
```

```
agggcagagg ccaaaggcaa cagaagctgg tcggaagagt ctcttaaacc cagtgacaat  3840
gaacaaggct tgcctgtgtt ctccggctct ccgcccatga agagtctttc atccaccagt  3900
gcaggcggca aaaagcaggc tcagccaagc tgcgcaccag cctccaggcc gcctgccaaa  3960
cagcagaaaa ttaaagaaaa ccagaagaca gatgtgctgt gtgcagacga agaagaggat  4020
tgccaggctg cctccctgct gcagaaatac accgacaaca gcgagaagcc atccgggaag  4080
agactgtgca aaaccaaaca cttgatccct caggagtcca ggcggggatt gccactgaca  4140
ggggaatact acgtggagaa tgccgatggc aaggtgactg tccggagatt cagaaagcgg  4200
ccggagccca gttcggacta tgatctgtca ccagccaagc aggagccaaa gcccttcgac  4260
cgcttgcagc aactgctacc agcctcccag tccacacagc tgccatgctc aagttcccct  4320
caggagacca cccagtctcg ccctatgccg ccggaagcac ggagacttat tgtcaataag  4380
aacgctggcg agacccttct gcagcgggca gccaggcttg gctatgagga agtggtcctg  4440
tactgcttag agaacaagat ttgtgatgta aatcatcggg acaacgcagg ttactgcgcc  4500
ctgcatgaag cttgtgctag gggctggctc aacattgtgc gacacctcct tgaatatggc  4560
gctgatgtca actgtagtgc ccaggatgga accaggcctc tgcacgatgc tgttgagaac  4620
gatcacttgg aaattgtccg actacttctc tcttatggtg ctgaccccac cttggctacg  4680
tactcaggta gaaccatcat gaaaatgacc cacagtgaac ttatggaaaa gttcttaaca  4740
gattatttaa atgacctcca gggtcgcaat gatgatgacg ccagtggcac ttgggacttc  4800
tatggcagct ctgtttgtga accagatgat gaaagtggct atgatgtttt agccaacccc  4860
ccaggaccag aagaccagga tgatgatgac gatgcctata gcgatgtgtt tgaatttgaa  4920
ttttcagaga cccccctctt accgtgttat aacatccaag tatctgtggc tcaggggcca  4980
cgaaactggc tactgctttc ggatgtcctt aagaaattga aaatgtcctc ccgcatattt  5040
cgctgcaatt ttccaaacgt ggaaattgtc accattgcag aggcagaatt ttatcggcag  5100
gtttctgcaa gtctcttgtt ctcttgctcc aaagacctgg aagccttcaa ccctgaaagt  5160
aaggagctgt tagatctggt ggaattcacg aacgaaattc agactctgct gggctcctct  5220
gtagagtggc tccaccccag tgatctggcc tcagacaact actgg                  5265

SEQ ID NO: 8            moltype = AA  length = 1755
FEATURE                 Location/Qualifiers
source                  1..1755
                        mol_type = protein
                        organism = Homo sapiens
SEQUENCE: 8
MLSATPLYGN VHSWMNSERV RMCGASEDRK ILVNDGDASK ARLELREENP LNHNVVDAST  60
AHRIDGLAAL SMDRTGLIRE GLRVPGNIVY SSLCGLGSEK GREAATSTLG GLGFSSERNP  120
EMQFKPNTPE TVEASAVSGK PPNGFSAIYK TPPGIQKSAV ATAEALGLDR PASDKQSPLN  180
INGASYLRLP WVNPYMEGAT PAIYPFLDSP NKYSLNMYKA LLPQQSYSLA QPLYSPVCTN  240
GERFLYLPPP HYVGPHIPSS LASPMRLSTP SASPAIPPLV HCADKSLPWK MGVSPGNPVD  300
SHAYPHIQNS KQPRVPSAKA VTSGLPGDTA LLLPPSPRPS PRVHLPTQPA ADTYSEFHKH  360
YARISTSPSV ALSKPYMTVS SEFPAARLSN GKYPKAPEGG EGAQPVPGHA RKTAVQDRKD  420
GSSPPLLEKQ TVTKDVTDKP LDLSSKVVDV DASKADHMKK MAPTVLVHSR AGSGLVLSGS  480
EIPKETLSPP GNGCAIYRSE IISTAPSSWV VPGPSPNEEN NGKSMSLKNK ALDWAIPQQR  540
SSSCPRMGGT DAVITNVSGS VSSAGRPASA SPAPNANADG TKTSRSSVET TPSVIQHVGQ  600
PPATPAKHSS STSSKGAKAS NPEPSFKANE NGLPPSSIFL SPNEAFRSPP IPYPRSYLPY  660
PAPEGIAVSP LSLHGKGPVY PHPVLLPNGS LFPGHLAPKP GLPYGLPTGR PEFVTYQDAL  720
GLGMVHPMLI PHTPIEITKE EKPERRSRSH ERARYEDPTL RNRFSEILET SSTKLHPDVP  780
TDKNLKPNPN WNQGKTVVKS DKLVYVDLLR EEPDAKTDTN VSKPSFAAES VGQSAEPPKP  840
SVEPALQQHR DFIALREELG RISDFHETYT FKQPVFTVSK DSVLAGTNKE NLGLPVSTPF  900
LEPPLGSDGP AVTFGKTQED PKPFCVGSAP PSVDVTPTYT KDGADEAESN DGKVLKPKPS  960
KLAKRIANSA GYVGDRFKCV TTELYADSSQ LSREQRALQM EGLQEDSILC LPAAYCERAM  1020
MRFSELEMKE REGGHPATKD SEMCKFSPAD WERLKGNQDK KPKSVTLEEA IAEQNESERC  1080
EYSVGNKHRD PFEAPEDKDL PVEKYFVERQ PVSEPPADQV ASDMPHSPTL RVDRKRKVSG  1140
DSSHTETTAE EVPEDPLLKA KRRRVSKDDW PEREMTNSSS NHLEDPHYSE LTNLKVCIEL  1200
TGLHPKKQRH LLHLRERWEQ QVSAADGKPG RQSRKEVTQA TQPEAIPQGT NITEEKPGRK  1260
RAEAKGNRSW SEESLKPSDN EQGLPVFSGS PPMKSLSSTS AGGKKQAQPS CAPASRPPAK  1320
QQKIKENQKT DVLCADEEED CQAASLLQKY TDNSEKPSGK RLCKTKHLIP QESRRGLPLT  1380
GEYYVENADG KVTVRRFRKR PEPSSDYDLS PAKQEPKPFD RLQQLLPASQ STQLPCSSSP  1440
QETTQSRPMP PEARRLIVNK NAGETLLQRA ARLGYEEVVL YCLENKICDV NHRDNAGYCA  1500
LHEACARGWL NIVRHLLEYG ADVNCSAQDG TRPLHDAVEN DHLEIVRLLL SYGADPTLAT  1560
YSGRTIMKMT HSELMEKFLT DYLNDLQGRN DDDASGTWDF YGSSVCEPDD ESGYDVLANP  1620
PGPEDQDDDD DAYSDVFEFE FSETPLLPCY NIQVSVAQGP RNWLLLSDVL KKLKMSSRIF  1680
RCNFPNVEIV TIAEAEFYRQ VSASLLFSCS KDLEAFNPES KELLDLVEFT NEIQTLLGSS  1740
VEWLHPSDLA SDNYW                                                   1755

SEQ ID NO: 9            moltype = DNA  length = 2298
FEATURE                 Location/Qualifiers
source                  1..2298
                        mol_type = other DNA
                        organism = Synthetic construct
SEQUENCE: 9
atggcggcgc tgagcggtgg cggtggtggc ggcgcggagc cgggccaggc tctgttcaac  60
ggggacatgg agcccgaggc cggcgccggc gccggcgccg cggcctcttc ggctgcggac  120
cctgccattc cggaggaggt gtggaatatc aaacaaatga ttaagttgac acaggaacat  180
atagaggccc tattggacaa atttggtggg gagcataatc caccatcaat atatctggag  240
gcctatgaag aatacaccag caagctagat gcactccaac aaagagaaca acagttattg  300
gaatctctgg ggaacggaac tgatttttct gtttctagct ctgcatcaat ggataccgtt  360
acatcttctt cctcttctag cctttcagtg ctaccttcat ctctttcagt tttcaaaat   420
cccacagatg tggcacggag caaccccaag tcaccacaaa aacctatcgt tagagtcttc  480
ctgcccaaca aacagaggac agtggtacct gcaaggtgtg gagttacagt ccgagacagt  540
ctaaagaaag cactgatgat gagaggtcta atcccagagt gctgtgctgt ttacagaatt  600
```

-continued

```
caggatggag agaagaaacc aattggttgg gacactgata tttcctggct tactggagaa  660
gaattgcatg tggaagtgtt ggagaatgtt ccacttacaa cacacaactt tgtacgaaaa  720
acgtttttca ccttagcatt ttgtgacttt tgtcgaaagc tgcttttcca gggtttccgc  780
tgtcaaacat gtggttataa atttcaccag cgttgtagta cagaagttcc actgatgtgt  840
gttaattatg accaacttga tttgctgttt gtctccaagt tctttgaaca ccacccaata  900
ccacaggaag aggcgtcctt agcagagact gccctaacat ctggatcatc cccttccgca  960
cccgcctcgg actctattgg gccccaaatt ctcaccagtc cgtctccttc aaaatccatt  1020
ccaattccac agcccttccg accagcagat gaagatcatc gaaatcaatt tgggcaacga  1080
gaccgatcct catcagctcc caatgtgcat ataaacacaa tagaacctgt caatattgat  1140
gacttgatta gagaccaagg atttcgtggt gatggaggat caaccacagg tttgtctgct  1200
acccccccctg cctcattacc tggctcacta actaacgtga aagccttaca gaaatctccc  1260
gggcctcagc gagaaaggaa gtcatcttca tcctcagaag acaggaatcg aatgaaaaca  1320
cttggtagac gggactcgag tgatgattgg gagattcctg atgggcagat tacagtggga  1380
caaaagaattg gatctggatc atttcgaaca gtctacaagg gaaagtggca tggtgatgtg  1440
gcagtgaaaa tgttgaatgt gacagcacct acacctcagc agttacaagc cttcaaaaat  1500
gaagtaggag tactcaggaa aacacgacat gtgaatatcc tactcttcat gggctattcc  1560
acaaagccac aactggctat tgttacccag tggtgtgagg gctccagctt gtatcaccat  1620
ctccatatca ttgagaccaa atttgagatg atcaagctta tagatattgc acgacagact  1680
gcacagggca tggattactt acacgccaag tcaatcatcc acagagacct caagagtaat  1740
aatatatttc ttcatgaaga cctcacagta aaaataggtg attttggtct agctacagtg  1800
aaatctcgat ggagtgggtc ccatcagttt gaacagttgt ctgggtccat tttgtggatg  1860
gcaccagaag tcatcagaat gcaagataaa aatccataca gctttcagtc agatgtatat  1920
gcatttggga ttgttctgta tgaattgatg actggacagt taccttattc aaacatcaac  1980
aacagggacc agataatttt tatggtggga cgaggatacc tgtctccaga tctcagtaag  2040
gtacggagta actgtccaaa agccatgaag agattaatgg cagagtgcct caaaaagaaa  2100
agagatgaga gaccactctt tccccaaatt ctcgcctcta ttgagctgct ggcccgctca  2160
ttgccaaaaa ttcaccgcag tgcatcagaa ccctccttga atcgggctgg tttccaaaca  2220
gaggatttta gtctatatgc ttgtgcttct ccaaaaacac ccatccaggc agggggatat  2280
ggtgcgtttc ctgtccac                                                2298

SEQ ID NO: 10          moltype = AA  length = 766
FEATURE                Location/Qualifiers
source                 1..766
                       mol_type = protein
                       organism = Synthetic construct
SEQUENCE: 10
MAALSGGGGG GAEPGQALFN GDMEPEAGAG AGAAASSAAD PAIPEEVWNI KQMIKLTQEH  60
IEALLDKFGG EHNPPSIYLE AYEEYTSKLD ALQQREQQLL ESLGNGTDFS VSSSASMDTV  120
TSSSSSSLSV LPSSLSVFQN PTDVARSNPK SPQKPIVRVF LPNKQRTVVP ARCGVTVRDS  180
LKKALMMRGL IPECCAVYRI QDGEKKPIGW DTDISWLTGE ELHVEVLENV PLTTHNFVRK  240
TFFTLAFCDF CRKLLFQGFR CQTCGYKFHQ RCSTEVPLMC VNYDQLDLLF VSKFFEHHPI  300
PQEEASLAET ALTSGSSPSA PASDSIGPQI LTSPSPSKSI PIPQPFRPAD EDHRNQFGQR  360
DRSSSAPNVH INTIEPVNID DLIRDQGFRG DGGSTTGLSA TPPASLPGSL TNVKALQKSP  420
GPQRERKSSS SSEDRNRMKT LGRRDSSDDW EIPDGQITVG QRIGSGSFRT VYKGKWHGDV  480
AVKMLNVTAP TPQQLQAFKN EVGVLRKTRH VNILLFMGYS TKPQLAIVTQ WCEGSSLYHH  540
LHIIETKFEM IKLIDIARQT AQGMDYLHAK SIIHRDLKSN NIFLHEDLTV KIGDFGLATV  600
KSRWSGSHQF EQLSGSILWM APEVIRMQDK NPYSFQSDVY AFGIVLYELM TGQLPYSNIN  660
NRDQIIFMVG RGYLSPDLSK VRSNCPKAMK RLMAECLKKK RDERPLFPQI LASIELLARS  720
LPKIHRSASE PSLNRAGFQT EDFSLYACAS PKTPIQAGGY GAFPVH                766

SEQ ID NO: 11          moltype = DNA  length = 2298
FEATURE                Location/Qualifiers
source                 1..2298
                       mol_type = other DNA
                       organism = Synthetic construct
SEQUENCE: 11
atggcggcgc tgagcggtgg cggtggtggc ggcgcggagc cgggccaggc tctgttcaac  60
ggggacatgg agcccgaggc cggcgccggc gccggcgccg cggcctcttc ggctgcggac  120
cctgccattc cggaggaggt gtggaatatc aaacaaatga ttaagttgac acaggaacat  180
atagaggccc tattggacaa atttggtggg gagcataatc caccatcaat atatctggag  240
gcctatgaag aatacaccag caagctagat gcactccaac aaagagaaca acagttattg  300
gaatctctgg ggaacggaac tgatttttct gtttctagct ctgcatcaat ggataccgtt  360
acatcttctt cctcttctag cctttcagtg ctaccttcat ctctttcagt ttttcaaaat  420
cccacagatg tggcacggag caaccccaag tcaccacaaa aacctatcgt tagagtcttc  480
ctgcccaaca aacagaggac agtggtacct gcaaggtgtg gagttacagt ccgagacagt  540
ctaaagaaag cactgatgat gagaggtcta atcccagagt gctgtgctgt ttacagaatt  600
caggatggag agaagaaacc aattggttgg gacactgata tttcctggct tactggagaa  660
gaattgcatg tggaagtgtt ggagaatgtt ccacttacaa cacacaactt tgtacgaaaa  720
acgtttttca ccttagcatt ttgtgacttt tgtcgaaagc tgcttttcca gggtttccgc  780
tgtcaaacat gtggttataa atttcaccag cgttgtagta cagaagttcc actgatgtgt  840
gttaattatg accaacttga tttgctgttt gtctccaagt tctttgaaca ccacccaata  900
ccacaggaag aggcgtcctt agcagagact gccctaacat ctggatcatc cccttccgca  960
cccgcctcgg actctattgg gccccaaatt ctcaccagtc cgtctccttc aaaatccatt  1020
ccaattccac agcccttccg accagcagat gaagatcatc gaaatcaatt tgggcaacga  1080
gaccgatcct catcagctcc caatgtgcat ataaacacaa tagaacctgt caatattgat  1140
gacttgatta gagaccaagg atttcgtggt gatggaggat caaccacagg tttgtctgct  1200
acccccccctg cctcattacc tggctcacta actaacgtga aagccttaca gaaatctccc  1260
gggcctcagc gagaaaggaa gtcatcttca tcctcagaag acaggaatcg aatgaaaaca  1320
cttggtagac gggactcgag tgatgattgg gagattcctg atgggcagat tacagtggga  1380
```

-continued

```
caaagaattg gatctggatc atttgcaaca gtctacaagg gaaagtggca tggtgatgtg  1440
gcagtgaaaa tgttgaatgt gacagcacct acacctcagc agttacaagc cttcaaaaat  1500
gaagtaggag tactcaggaa aacacgacat gtgaatatcc tactcttcat gggctattcc  1560
acaaagccac aactggctat tgttacccag tggtgtgagg gctccagctt gtatcaccat  1620
ctccatatca ttgagaccaa atttgagatg atcaagctta tagatattgc acgacagact  1680
gcacagggca tggattactt acacgccaag tcaatcatcc acagagacct caagagtaat  1740
aatatatttc ttcatgaaga cctcacagta aaaataggtg attttggtct agctacagtg  1800
aaatctcgat ggagtgggtc ccatcagttt gaacagttgt ctgggtccat tttgtggatg  1860
gcaccagaag tcatcagaat gcaagataaa aatccataca gctttcagtc agatgtatat  1920
gcatttggga ttgttctgta tgaattgatg actggacagt taccttattc aaacatcaac  1980
aacagggacc agataatttt tatggtggga cgaggatacc tgtctccaga tctcagtaag  2040
gtacggagta actgtccaaa agccatgaag agattaatgg cagagtgcct caaaaagaaa  2100
agagatgaga gaccactctt tccccaaatt ctcgcctcta ttgagctgct ggcccgctca  2160
ttgccaaaaa ttcaccgcag tgcatcagaa ccctccttga atcgggctgg tttccaaaca  2220
gaggatttta gtctatatgc ttgtgcttct ccaaaaacac ccatccaggc agggggatat  2280
ggtgcgtttc ctgtccac                                                 2298

SEQ ID NO: 12           moltype = AA  length = 766
FEATURE                 Location/Qualifiers
source                  1..766
                        mol_type = protein
                        organism = Synthetic construct
SEQUENCE: 12
MAALSGGGGG GAEPGQALFN GDMEPEAGAG AGAAASSAAD PAIPEEVWNI KQMIKLTQEH  60
IEALLDKFGG EHNPPSIYLE AYEEYTSKLD ALQQREQQLL ESLGNGTDFS VSSSASMDTV  120
TSSSSSSLSV LPSSLSVFQN PTDVARSNPK SPQKPIVRVF LPNKQRTVVP ARCGVTVRDS  180
LKKALMMRGL IPECCAVYRI QDGEKKPIGW DTDISWLTGE ELHVEVLENV PLTTHNFVRK  240
TFFTLAFCDF CRKLLFQGFR CQTCGYKFHQ RCSTEVPLMC VNYDQLDLLF VSKFFEHHPI  300
PQEEASLAET ALTSGSSPSA PASDSIGPQI LTSPSPSKSI PIPQPFRPAD EDHRNQFGQR  360
DRSSSAPNVH INTIEPVNID DLIRDQGFRG DGGSTTGLSA TPPASLPGSL TNVKALQKSP  420
GPQRERKSSS SSEDRNRMKT LGRRDSSDDW EIPDGQITVG QRIGSGSFAT VYKGKWHGDV  480
AVKMLNVTAP TPQQLQAFKN EVGVLRKTRH VNILLFMGYS TKPQLAIVTQ WCEGSSLYHH  540
LHIIETKFEM IKLIDIARQT AQGMDYLHAK SIIHRDLKSN NIFLHEDLTV KIGDFGLATV  600
KSRWSGSHQF EQLSGSILWM APEVIRMQDK NPYSFQSDVY AFGIVLYELM TGQLPYSNIN  660
NRDQIIFMVG RGYLSPDLSK VRSNCPKAMK RLMAECLKKK RDERPLFPQI LASIELLARS  720
LPKIHRSASE PSLNRAGFQT EDFSLYACAS PKTPIQAGGY GAFPVH                  766

SEQ ID NO: 13           moltype = DNA  length = 2298
FEATURE                 Location/Qualifiers
source                  1..2298
                        mol_type = other DNA
                        organism = Synthetic construct
SEQUENCE: 13
atggcggcgc tgagcggtgg cggtggtggc ggcgcggagc cgggccaggc tctgttcaac  60
ggggacatgg agcccgaggc cggcgccggc gccggcgccg cggcctcttc ggctgcggac  120
cctgccattc cggaggaggt gtggaatatc aaacaaatga ttaagttgac acaggaacat  180
atagaggccc tattggacaa atttggtggg gagcataatc caccatcaat atatctggag  240
gcctatgaag aatacaccag caagctagat gcactccaac aaagagaaca acagttattg  300
gaatctctgg ggaacggaac tgatttttct gtttctagct ctgcatcaat ggataccgtt  360
acatcttctt cctcttctag cctttcagtg ctaccttcat ctctttcagt ttttcaaaat  420
cccacagatg tggcacggag caaccccaag tcaccacaaa aacctatcgt tagagtcttc  480
ctgcccaaca aacagaggac agtggtacct gcaaggtgtg gagttacagt ccgagacagt  540
ctaaagaaag cactgatgat gagaggtcta atcccagagt gctgtgctgt ttacagaatt  600
caggatggag agaagaaacc aattggttgg gacactgata tttcctggct tactggagaa  660
gaattgcatg tggaagtgtt ggagaatgtt ccacttacaa cacacaactt tgtacgaaaa  720
acgtttttca ccttagcatt ttgtgacttt tgtcgaaagc tgcttttcca gggtttccgc  780
tgtcaaacat gtggttataa atttcaccag cgttgtagta cagaagttcc actgatgtgt  840
gttaattatg accaacttga tttgctgttt gtctccaagt tctttgaaca ccacccaata  900
ccacaggaag aggcgtcctt agcagagact gccctaacat ctggatcatc cccttccgca  960
cccgcctcgg actctattgg gccccaaatt ctcaccagtc cgtctccttc aaaatccatt  1020
ccaattccac agcccttccg accagcagat gaagatcatc gaaatcaatt tgggcaacga  1080
gaccgatcct catcagctcc caatgtgcat ataaacacaa tagaacctgt caatattgat  1140
gacttgatta gagaccaagg atttcgtggt gatggaggat caaccacagg tttgtctgct  1200
acccccccctg cctcattacc tggctcacta actaacgtga aagccttaca gaaatctccc  1260
gggcctcagc gagaaaggaa gtcatcttca tcctcagaag acaggaatcg aatgaaaaca  1320
cttggtagac gggactcgag tgatgattgg gagattcctg atgggcagat tacagtggga  1380
caaagaattg gatctggatc atttggaaca gtctacaagg gaaagtggca tggtgatgtg  1440
gcagtgaaaa tgttgaatgt gacagcacct acacctcagc agttacaagc cttcaaaaat  1500
gaagtaggag tactcaggaa aacacgacat gtgaatatcc tactcttcat gggctattcc  1560
acaaagccac aactggctat tgttacccag tggtgtgagg gctccagctt gtatcaccat  1620
ctccatatca ttgagaccaa atttgagatg atcaagctta tagatattgc acgacagact  1680
gcacagggca tggattactt acacgccaag tcaatcatcc acagagacct caagagtaat  1740
aatatatttc ttcatgaaga cctcacagta aaaataggta attttggtct agctacagtg  1800
aaatctcgat ggagtgggtc ccatcagttt gaacagttgt ctgggtccat tttgtggatg  1860
gcaccagaag tcatcagaat gcaagataaa aatccataca gctttcagtc agatgtatat  1920
gcatttggga ttgttctgta tgaattgatg actggacagt taccttattc aaacatcaac  1980
aacagggacc agataatttt tatggtggga cgaggatacc tgtctccaga tctcagtaag  2040
gtacggagta actgtccaaa agccatgaag agattaatgg cagagtgcct caaaaagaaa  2100
agagatgaga gaccactctt tccccaaatt ctcgcctcta ttgagctgct ggcccgctca  2160
```

```
ttgccaaaaa ttcaccgcag tgcatcagaa ccctccttga atcgggctgg tttccaaaca  2220
gaggatttta gtctatatgc ttgtgcttct ccaaaaacac ccatccaggc agggggatat  2280
ggtgcgtttc ctgtccac                                                2298

SEQ ID NO: 14          moltype = AA  length = 766
FEATURE                Location/Qualifiers
source                 1..766
                       mol_type = protein
                       organism = Synthetic construct
SEQUENCE: 14
MAALSGGGGG GAEPGQALFN GDMEPEAGAG AGAAASSAAD PAIPEEVWNI KQMIKLTQEH  60
IEALLDKFGG EHNPPSIYLE AYEEYTSKLD ALQQREQQLL ESLGNGTDFS VSSSASMDTV  120
TSSSSSSLSV LPSSLSVFQN PTDVARSNPK SPQKPIVRVF LPNKQRTVVP ARCGVTVRDS  180
LKKALMMRGL IPECCAVYRI QDGEKKPIGW DTDISWLTGE ELHVEVLENV PLTTHNFVRK  240
TFFTLAFCDF CRKLLFQGFR CQTCGYKFHQ RCSTEVPLMC VNYDQLDLLF VSKFFEHHPI  300
PQEEASLAET ALTSGSSPSA PASDSIGPQI LTSPSPSKSI PIPQPFRPAD EDHRNQFGQR  360
DRSSSAPNVH INTIEPVNID DLIRDQGFRG DGGSTTGLSA TPPASLPGSL TNVKALQKSP  420
GPQRERKSSS SSEDRNRMKT LGRRDSSDDW EIPDGQITVG QRIGSGSFGT VYKGKWHGDV  480
AVKMLNVTAP TPQQLQAFKN EVGVLRKTRH VNILLFMGYS TKPQLAIVTQ WCEGSSLYHH  540
LHIIETKFEM IKLIDIARQT AQGMDYLHAK SIIHRDLKSN NIFLHEDLTV KIGNFGLATV  600
KSRWSGSHQF EQLSGSILWM APEVIRMQDK NPYSFQSDVY AFGIVLYELM TGQLPYSNIN  660
NRDQIIFMVG RGYLSPDLSK VRSNCPKAMK RLMAECLKKK RDERPLFPQI LASIELLARS  720
LPKIHRSASE PSLNRAGFQT EDFSLYACAS PKTPIQAGGY GAFPVH                 766

SEQ ID NO: 15          moltype = DNA  length = 2298
FEATURE                Location/Qualifiers
source                 1..2298
                       mol_type = genomic DNA
                       organism = Homo sapiens
SEQUENCE: 15
atggcggcgc tgagcggtgg cggtggtggc ggcgcggagc cgggccaggc tctgttcaac  60
ggggacatgg agcccgaggc cggcgccggc gccggcgccg cggcctcttc ggctgcggac  120
cctgccattc cggaggaggt gtggaatatc aaacaaatga ttaagttgac acaggaacat  180
atagaggccc tattggacaa atttggtggg gagcataatc caccatcaat atatctggag  240
gcctatgaag aatacaccag caagctagat gcactccaac aaagagaaca acagttattg  300
gaatctctgg ggaacggaac tgatttttct gtttctagct ctgcatcaat ggataccgtt  360
acatcttctt cctcttctag cctttcagtg ctaccttcat ctctttcagt ttttcaaaat  420
cccacagatg tggcacggag caaccccaag tcaccacaaa aacctatcgt tagagtcttc  480
ctgcccaaca aacagaggac agtggtacct gcaaggtgtg gagttacagt ccgagacagt  540
ctaaagaaag cactgatgat gagaggtcta atcccagagt gctgtgctgt ttacagaatt  600
caggatggag agaagaaacc aattggttgg gacactgata tttcctggct tactggagaa  660
gaattgcatg tggaagtgtt ggagaatgtt ccacttacaa cacacaactt tgtacgaaaa  720
acgtttttca ccttagcatt ttgtgacttt tgtcgaaagc tgcttttcca gggtttccgc  780
tgtcaaacat gtggttataa atttcaccag cgttgtagta cagaagttcc actgatgtgt  840
gttaattatg accaacttga tttgctgttt gtctccaagt tctttgaaca ccacccaata  900
ccacaggaag aggcgtcctt agcagagact gccctaacat ctggatcatc cccttccgca  960
cccgcctcgg actctattgg gccccaaatt ctcaccagtc cgtctccttc aaaatccatt  1020
ccaattccac agcccttccg accagcagat gaagatcatc gaaatcaatt tgggcaacga  1080
gaccgatcct catcagctcc caatgtgcat ataaacacaa tagaacctgt caatattgat  1140
gacttgatta gagaccaagg atttcgtggt gatggaggat caaccacagg tttgtctgct  1200
acccccccctg cctcattacc tggctcacta actaacgtga aagccttaca gaaatctccc  1260
gggcctcagc gagaaaggaa gtcatcttca tcctcagaag acaggaatcg aatgaaaaca  1320
cttggtagac gggactcgag tgatgattgg gagattcctg atgggcagat tacagtggga  1380
caaagaattg gatctggatc atttggaaca gtctacaagg gaaagtggca tggtgatgtg  1440
gcagtgaaaa tgttgaatgt gacagcacct acacctcagc agttacaagc cttcaaaaat  1500
gaagtaggag tactcaggaa aacacgacat gtgaatatcc tactcttcat gggctattcc  1560
acaaagccac aactggctat tgttacccag tggtgtgagg gctccagctt gtatcaccat  1620
ctccatatca ttgagaccaa atttgagatg atcaagctta tagatattgc acgacagact  1680
gcacagggca tggattactt acacgccaag tcaatcatcc acagagacct caagagtaat  1740
aatatatttc ttcatgaaga cctcacagta aaaataggtg attttggtct agctacagtg  1800
aaatctcgat ggagtgggtc ccatcagttt gaacagttgt ctgggtccat tttgtggatg  1860
gcaccagaag tcatcagaat gcaagataaa aatccataca gctttcagtc agatgtatat  1920
gcatttggga ttgttctgta tgaattgatg actggacagt taccttattc aaacatcaac  1980
aacagggacc agataatttt tatggtggga cgaggatacc tgtctccaga tctcagtaag  2040
gtacggagta actgtccaaa agccatgaag agattaatgg cagagtgcct caaaaagaaa  2100
agagatgaga gaccactctt tccccaaatt ctcgcctcta ttgagctgct ggcccgctca  2160
ttgccaaaaa ttcaccgcag tgcatcagaa ccctccttga atcgggctgg tttccaaaca  2220
gaggatttta gtctatatgc ttgtgcttct ccaaaaacac ccatccaggc agggggatat  2280
ggtgcgtttc ctgtccac                                                2298

SEQ ID NO: 16          moltype = AA  length = 766
FEATURE                Location/Qualifiers
source                 1..766
                       mol_type = protein
                       organism = Homo sapiens
SEQUENCE: 16
MAALSGGGGG GAEPGQALFN GDMEPEAGAG AGAAASSAAD PAIPEEVWNI KQMIKLTQEH  60
IEALLDKFGG EHNPPSIYLE AYEEYTSKLD ALQQREQQLL ESLGNGTDFS VSSSASMDTV  120
TSSSSSSLSV LPSSLSVFQN PTDVARSNPK SPQKPIVRVF LPNKQRTVVP ARCGVTVRDS  180
```

-continued

```
LKKALMMRGL IPECCAVYRI QDGEKKPIGW DTDISWLTGE ELHVEVLENV PLTTHNFVRK  240
TFFTLAFCDF CRKLLFQGFR CQTCGYKFHQ RCSTEVPLMC VNYDQLDLLF VSKFFEHHPI  300
PQEEASLAET ALTSGSSPSA PASDSIGPQI LTSPSPSKSI PIPQPFRPAD EDHRNQFGQR  360
DRSSSAPNVH INTIEPVNID DLIRDQGFRG DGGSTTGLSA TPPASLPGSL TNVKALQKSP  420
GPQRERKSSS SSEDRNRMKT LGRRDSSDDW EIPDGQITVG QRIGSGSFGT VYKGKWHGDV  480
AVKMLNVTAP TPQQLQAFKN EVGVLRKTRH VNILLFMGYS TKPQLAIVTQ WCEGSSLYHH  540
LHIIETKFEM IKLIDIARQT AQGMDYLHAK SIIHRDLKSN NIFLHEDLTV KIGDFGLATV  600
KSRWSGSHQF EQLSGSILWM APEVIRMQDK NPYSFQSDVY AFGIVLYELM TGQLPYSNIN  660
NRDQIIFMVG RGYLSPDLSK VRSNCPKAMK RLMAECLKKK RDERPLFPQI LASIELLARS  720
LPKIHRSASE PSLNRAGFQT EDFSLYACAS PKTPIQAGGY GAFPVH                766

SEQ ID NO: 17          moltype = DNA  length = 3441
FEATURE                Location/Qualifiers
source                 1..3441
                       mol_type = other DNA
                       organism = Synthetic construct
SEQUENCE: 17
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaagaac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
atcgtcaacc tggagagcaa gctgcggcgc ctctccaagg acagcaacaa cctggaccag  1320
agtctgccca ggaacctgcc agtaaccatc atctctcagg actttgggga tgccagcccc  1380
aggaccaatg gtcaagaagc tgacgattct tccacctcgg aggagtcacc tgaagacagc  1440
aagtacttcc tgccctacca tccgccccag cgcaggatga acctgaaggg catccagctg  1500
cagagagcca aatcccccat cagcctgaag cgaacatcag attttcaagc caaggggcac  1560
gaggaagaag gcacggatgc cagccctagc tcctgcggat ctctgcccat caccaactcc  1620
ttcaccaaga tgcagccccc ccggagccgc agcagcatca tgtcaatcac cgccgagccc  1680
ccgggaaacg actccatcgt cagacgctac aaggaggacg cgccccatcg cagcacagtc  1740
gaagaagaca atgacagcgg cggtttgac gccttagatc tggatgatga cagtcacgaa  1800
cgctactcct tcggaccctc ctccatccac tcctcctcct cctcccacca atccgagggc  1860
ctggatgcct acgacctgga gcaggtcaac ctcatgttca ggaagttctc tctggaaaga  1920
cccttccggc cttcggtcac ctctgtgggg cacgtgcggg gcccagggcc ctcggtgcag  1980
cacacgacgc tgaatggcga cagcctcacc tcccagctca ccctgctggg gggcaacgcg  2040
cgagggagct tcgtgcactc ggtcaagcct ggctctctgg ccgagaaagc cggcctccgt  2100
gagggccacc agctgctgct gctagaaggc tgcatccgag gcgagaggca gagtgtcccg  2160
ttggacacat gcaccaaaga ggaagcccac tggaccatcc agaggtgcag cggccccgtc  2220
acgctgcact acaaggtcaa ccacgaaggg taccggaagc tggtgaagga catggaggac  2280
ggcctgatca catcgggggga ctcgttctac atccggctga acctgaacat ctccagccag  2340
ctggacgcct gcaccatgtc cctgaagtgt gacgatgttg tgcacgtccg tgacaccatg  2400
taccaggaca ggcacgagtg gctgtgcgcg cgggtcgacc ctttcacaga ccatgacctg  2460
gatatgggca ccatacccag ctacagccga gcccagcagc tcctcctggt gaaactgcag  2520
cgcctgatgc accgaggcag ccgggaggag gtagacggca cccaccacac cctgcgggca  2580
ctccggaaca ccctgcagcc agaagaagcg ctttcaacaa gcgacccccg ggtcagcccc  2640
cgtctctcgc gagcaagctt ccttttggc cagctccttc agttcgtcag caggtccgag  2700
aacaagtata agcggatgaa cagcaacgag cgggtccgca tcatctcggg gagtccgcta  2760
gggagcctgg cccggtcctc gctggacgcc accaagctct tgactgagaa gcaggaagag  2820
ctggaccctg agagcgagct gggcaagaac ctcagcctca tcccctacag cctggtacgc  2880
gccttctact gcgagcgccg ccggcccgtg ctcttcacac ccaccgtgct ggccaagacg  2940
ctggtgcaga ggctgctcaa ctcgggaggt gccatggagt tcaccatctg caagtcagat  3000
atcgtcacaa gagatgagtt cctcagaagg cagaagacgg agaccatcat ctactcccga  3060
gagaagaacc ccaacgcgtt cgaatgcatc gcccctgcca acattgaagc tgtggccgcc  3120
aagaacaagc actgcctgct ggaggctggg atcggctgca caagagactt gatcaagtcc  3180
aacatctacc ccatcgtgct cttcatccgg gtgtgtgaga agaacatcaa gaggttcaga  3240
aagctgctgc cccgacctga gacggaggag gagttcctgc gcgtgtgccg gctgaaggag  3300
aaggagctgg aggccctgcc gtgcctgtac gccacggtgg aacctgacat gtggggcagc  3360
gtagaggagc tgctccgcgt tgtcaaggac aagatcggcg aggagcagcg caagaccatc  3420
tgggtggacg aggaccagct g                                           3441

SEQ ID NO: 18          moltype = AA  length = 1147
FEATURE                Location/Qualifiers
source                 1..1147
```

```
                        mol_type = protein
                        organism = Synthetic construct
SEQUENCE: 18
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKN CEMYKHRMNT  360
VMLQLEEVER ERDQAFHSRD EAQTQYSQCL IEKDKYRKQI RELEEKNDEM RIEMVRREAC  420
IVNLESKLRR LSKDSNNLDQ SLPRNLPVTI ISQDFGDASP RTNGQEADDS STSEESPEDS  480
KYFLPYHPPQ RRMNLKGIQL QRAKSPISLK RTSDFQAKGH EEEGTDASPS SCGSLPITNS  540
FTKMQPPRSR SSIMSITAEP PGNDSIVRRY KEDAPHRSTV EEDNDSGGFD ALDLDDDSHE  600
RYSFGPSSIH SSSSSHQSEG LDAYDLEQVN LMFRKFSLER PFRPSVTSVG HVRGPGPSVQ  660
HTTLNGDSLT SQLTLLGGNA RGSFVHSVKP GSLAEKAGLR EGHQLLLLEG CIRGERQSVP  720
LDTCTKEEAH WTIQRCSGPV TLHYKVNHEG YRKLVKDMED GLITSGDSFY IRLNLNISSQ  780
LDACTMSLKC DDVVHVRDTM YQDRHEWLCA RVDPFTDHDL DMGTIPSYSR AQQLLLVKLQ  840
RLMHRGSREE VDGTHHTLRA LRNTLQPEEA LSTSDPRVSP RLSRASFLFG QLLQFVSRSE  900
NKYKRMNSNE RVRIISGSPL GSLARSSLDA TKLLTEKQEE LDPESELGKN LSLIPYSLVR  960
AFYCERRRPV LFTPTVLAKT LVQRLLNSGG AMEFTICKSD IVTRDEFLRR QKTETIIYSR  1020
EKNPNAFECI APANIEAVAA KNKHCLLEAG IGCTRDLIKS NIYPIVLFIR VCEKNIKRFR  1080
KLLPRPETEE EFLRVCRLKE KELEALPCLY ATVEPDMWGS VEELLRVVKD KIGEEQRKTI  1140
WVDEDQL                                                           1147

SEQ ID NO: 19           moltype = DNA  length = 3441
FEATURE                 Location/Qualifiers
source                  1..3441
                        mol_type = other DNA
                        organism = Synthetic construct
SEQUENCE: 19
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
atcgtcaacc tggagagcaa gctgcggcgc ctctccaagg acagcaacaa cctggaccag  1320
agtctgccca ggaacctgcc agtaaccatc atctctcagg actttgggga tgccagcccc  1380
aggaccaatg gtcaagaagc tgacgattct tccacctcgg aggagtcacc tgaagacagc  1440
aagtacttcc tgccctacca tccgccccag cgcaggatga acctgaaggg catccagctg  1500
cagagagcca aatcccccat cagcctgaag cgaacatcag attttcaagc caaggggcac  1560
gaggaagaag gcacggatgc cagccctagc tcctgcggat ctctgcccat caccaactcc  1620
ttcaccaaga tgcagccccc ccggagccgc agcagcatca tgtcaatcac cgccgagccc  1680
ccgggaaacg actccatcgt cagacgctac aaggaggacg cgccccatcg cagcacagtc  1740
gaagaagaca atgacagcgg cgggtttgac gccttagatc tggatgatga cagtcacgaa  1800
cgctactcct tcggaccctc cttcatccac tcctcctcct cctcccacca atccgagggc  1860
ctggatgcct acgacctgga gcaggtcaac ctcatgttca ggaagttctc tctggaaaga  1920
cccttccggc cttcggtcac ctctgtgggg cacgtgcggg gcccagggcc ctcggtgcag  1980
cacacgacgc tgaatggcga cagcctcacc tcccagctca ccctgctggg gggcaacgcg  2040
cgagggagct tcgtgcactc ggtcaagcct ggctctctgg ccgagaaagc cggcctccgt  2100
gagggccacc agctgctgct gctagaaggc tgcatccgag gcgagaggca gagtgtcccg  2160
ttggacacat gcaccaaaga ggaagcccac tggaccatcc agaggtgcag cggccccgtc  2220
acgctgcact acaaggtcaa ccacgaaggg taccggaagc tggtgaagga catggaggac  2280
ggcctgatca catcggggga ctcgttctac atccggctga acctgaacat ctccagccag  2340
ctggacgcct gcaccatgtc cctgaagtgt gacgatgttg tgcacgtccg tgacaccatg  2400
taccaggaca ggcacgagtg gctgtgcgcg cgggtcgacc ctttcacaga ccatgacctg  2460
gatatgggca ccatacccag ctacagccga gcccagcagc tcctcctggt gaaactgcag  2520
cgcctgatgc accgaggcag ccgggaggag gtagacggca cccaccacac cctgcgggca  2580
ctccggaaca ccctgcagcc agaagaagcg ctttcaacaa gcgacccccg ggtcagcccc  2640
cgtctctcgc gagcaagctt cctttttggc cagctccttc agttcgtcag caggtccgag  2700
aacaagtata agcggatgaa cagcaacgag cgggtccgca tcatctcggg gagtccgcta  2760
gggagcctgg cccggtcctc gctggacgcc accaagctct tgactgagaa gcaggaagag  2820
ctggaccctg agagcgagct gggcaagaac ctcagcctca tcccctacag cctggtacgc  2880
gccttctact gcgagcgccg ccggcccgtg ctcttcacac ccaccgtgct ggccaagacg  2940
```

-continued

```
ctggtgcaga ggctgctcaa ctcgggaggt gccatggagt tcaccatctg caagtcagat  3000
atcgtcacaa gagatgagtt cctcagaagg cagaagacgg agaccatcat ctactcccga  3060
gagaagaacc ccaacgcgtt cgaatgcatc gcccctgcca acattgaagc tgtggccgcc  3120
aagaacaagc actgcctgct ggaggctggg atcggctgca caagagactt gatcaagtcc  3180
aacatctacc ccatcgtgct cttcatccgg gtgtgtgaga agaacatcaa gaggttcaga  3240
aagctgctgc cccgacctga gacggaggag gagttcctgc gcgtgtgccg gctgaaggag  3300
aaggagctgg aggccctgcc gtgcctgtac gccacggtgg aacctgacat gtggggcagc  3360
gtagaggagc tgctccgcgt tgtcaaggac aagatcggcg aggagcagcg caagaccatc  3420
tgggtggacg aggaccagct g                                            3441

SEQ ID NO: 20          moltype = AA  length = 1147
FEATURE                Location/Qualifiers
source                 1..1147
                       mol_type = protein
                       organism = Synthetic construct
SEQUENCE: 20
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMYKHRMNT  360
VMLQLEEVER ERDQAFHSRD EAQTQYSQCL IEKDKYRKQI RELEEKNDEM RIEMVRREAC  420
IVNLESKLRR LSKDSNNLDQ SLPRNLPVTI ISQDFGDASP RTNGQEADDS STSEESPEDS  480
KYFLPYHPPQ RRMNLKGIQL QRAKSPISLK RTSDFQAKGH EEEGTDASPS SCGSLPITNS  540
FTKMQPPRSR SSIMSITAEP PGNDSIVRRY KEDAPHRSTV EEDNDSGGFD ALDLDDDSHE  600
RYSFGPSFIH SSSSSHQSEG LDAYDLEQVN LMFRKFSLER PFRPSVTSVG HVRGPGPSVQ  660
HTTLNGDSLT SQLTLLGGNA RGSFVHSVKP GSLAEKAGLR EGHQLLLLEG CIRGERQSVP  720
LDTCTKEEAH WTIQRCSGPV TLHYKVNHEG YRKLVKDMED GLITSGDSFY IRLNLNISSQ  780
LDACTMSLKC DDVVHVRDTM YQDRHEWLCA RVDPFTDHDL DMGTIPSYSR AQQLLLVKLQ  840
RLMHRGSREE VDGTHHTLRA LRNTLQPEEA LSTSDPRVSP RLSRASFLFG QLLQFVSRSE  900
NKYKRMNSNE RVRIISGSPL GSLARSSLDA TKLLTEKQEE LDPESELGKN LSLIPYSLVR  960
AFYCERRRPV LFTPTVLAKT LVQRLLNSGG AMEFTICKSD IVTRDEFLRR QKTETIIYSR  1020
EKNPNAFECI APANIEAVAA KNKHCLLEAG IGCTRDLIKS NIYPIVLFIR VCEKNIKRFR  1080
KLLPRPETEE EFLRVCRLKE KELEALPCLY ATVEPDMWGS VEELLRVVKD KIGEEQRKTI  1140
WVDEDQL                                                            1147

SEQ ID NO: 21          moltype = DNA  length = 3441
FEATURE                Location/Qualifiers
source                 1..3441
                       mol_type = other DNA
                       organism = Synthetic construct
SEQUENCE: 21
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt gcaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
atcgtcaacc tggagagcaa gctgcggcgc ctctccaagg acagcaacaa cctggaccag  1320
agtctgccca ggaacctgcc agtaaccatc atctctcagg actttgggga tgccagcccc  1380
aggaccaatg gtcaagaagc tgacgattct tccacctcgg aggagtcacc tgaagacagc  1440
aagtacttcc tgccctacca tccgccccag cgcaggatga acctgaaggg catccagctg  1500
cagagagcca aatcccccat cagcctgaag cgaacatcag attttcaagc caaggggcac  1560
gaggaagaag gcacggatgc cagccctagc tcctgcggat ctctgcccat caccaactcc  1620
ttcaccaaga tgcagccccc ccggagccgc agcagcatca tgtcaatcac cgccgagccc  1680
ccgggaaacg actccatcgt cagacgctac aaggaggacg cgccccatcg cagcacagtc  1740
gaagaagaca atgacagcgg cgggtttgac gccttagatc tggatgatga cagtcacgaa  1800
cgctactcct tcggaccctc ctccatccac tcctcctcct cctcccacca atccgagggc  1860
ctggatgcct acgacctgga gcaggtcaac ctcatgttca ggaagttctc tctggaaaga  1920
cccttccggc cttcggtcac ctctgtgggg cacgtgcggg gcccagggcc ctcggtgcag  1980
cacacgacgc tgaatggcga cagcctcacc tcccagctca ccctgctggg gggcaacgcg  2040
cgagggagct tcgtgcactc ggtcaagcct ggctctctgg ccgagaaagc cggcctccgt  2100
gagggccacc agctgctgct gctagaaggc tgcatccgag gcgagaggca gagtgtcccg  2160
```

-continued

```
ttggacacat gcaccaaaga ggaagcccac tggaccatcc agaggtgcag cggccccgtc  2220
acgctgcact acaaggtcaa ccacgaaggg taccggaagc tggtgaagga catggaggac  2280
ggcctgatca catcggggga ctcgttctac atccggctga acctgaacat ctccagccag  2340
ctggacgcct gcaccatgtc cctgaagtgt gacgatgttg tgcacgtccg tgacaccatg  2400
taccaggaca ggcacgagtg gctgtgcgcg cgggtcgacc ctttcacaga ccatgacctg  2460
gatatgggca ccatacccag ctacagccga gcccagcagc tcctcctggt gaaactgcag  2520
cgcctgatgc accgaggcag ccgggaggag gtagacggca cccaccacac cctgcgggca  2580
ctccggaaca ccctgcagcc agaagaagcg ctttcaacaa gcgacccccg ggtcagcccc  2640
cgtctctcgc gagcaagctt cctttttggc cagctccttc agttcgtcag caggtccgag  2700
aacaagtata agcggatgaa cagcaacgag cgggtccgca tcatctcggg gagtccgcta  2760
gggagcctgg cccggtcctc gctggacgcc accaagctct tgactgagaa gcaggaagag  2820
ctggaccctg agagcgagct gggcaagaac ctcagcctca tccccctacag cctggtacgc  2880
gccttctact gcgagcgccg ccggcccgtg ctcttcacac ccaccgtgct ggccaagacg  2940
ctggtgcaga ggctgctcaa ctcgggaggt gccatggagt tcaccatctg caagtcagat  3000
atcgtcacaa gagatgagtt cctcagaagg cagaagacgg agaccatcat ctactcccga  3060
gagaagaacc ccaacgcgtt cgaatgcatc gcccctgcca acattgaagc tgtggccgcc  3120
aagaacaagc actgcctgct ggaggctggg atcggctgca caagagactt gatcaagtcc  3180
aacatctacc ccatcgtgct cttcatccgg gtgtgtgaga agaacatcaa gaggttcaga  3240
aagctgctgc cccgacctga gacggaggag gagttcctgc gcgtgtgccg gctgaaggag  3300
aaggagctgg aggccctgcc gtgcctgtac gccacggtgg aacctgacat gtggggcagc  3360
gtagaggagc tgctccgcgt tgtcaaggac aagatcggcg aggagcagcg caagaccatc  3420
tgggtggacg aggaccagct g                                            3441

SEQ ID NO: 22          moltype = AA  length = 1147
FEATURE                Location/Qualifiers
source                 1..1147
                       mol_type = protein
                       organism = Synthetic construct
SEQUENCE: 22
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMCKHRMNT  360
VMLQLEEVER ERDQAFHSRD EAQTQYSQCL IEKDKYRKQI RELEEKNDEM RIEMVRREAC  420
IVNLESKLRR LSKDSNNLDQ SLPRNLPVTI ISQDFGDASP RTNGQEADDS STSEESPEDS  480
KYFLPYHPPQ RRMNLKGIQL QRAKSPISLK RTSDFQAKGH EEEGTDASPS SCGSLPITNS  540
FTKMQPPRSR SSIMSITAEP PGNDSIVRRY KEDAPHRSTV EEDNDSGGFD ALDLDDDSHE  600
RYSFGPSSIH SSSSSHQSEG LDAYDLEQVN LMFRKFSLER PFRPSVTSVG HVRGPGPSVQ  660
HTTLNGDSLT SQLTLLGGNA RGSFVHSVKP GSLAEKAGLR EGHQLLLLEG CIRGERQSVP  720
LDTCTKEEAH WTIQRCSGPV TLHYKVNHEG YRKLVKDMED GLITSGDSFY IRLNLNISSQ  780
LDACTMSLKC DDVVHVRDTM YQDRHEWLCA RVDPFTDHDL DMGTIPSYSR AQQLLLVKLQ  840
RLMHRGSREE VDGTHHTLRA LRNTLQPEEA LSTSDPRVSP RLSRASFLFG QLLQFVSRSE  900
NKYKRMNSNE RVRIISGSPL GSLARSSLDA TKLLTEKQEE LDPESELGKN LSLIPYSLVR  960
AFYCERRRPV LFTPTVLAKT LVQRLLNSGG AMEFTICKSD IVTRDEFLRR QKTETIIYSR  1020
EKNPNAFECI APANIEAVAA KNKHCLLEAG IGCTRDLIKS NIYPIVLFIR VCEKNIKRFR  1080
KLLPRPETEE EFLRVCRLKE KELEALPCLY ATVEPDMWGS VEELLRVVKD KIGEEQRKTI  1140
WVDEDQL                                                            1147

SEQ ID NO: 23          moltype = DNA  length = 3441
FEATURE                Location/Qualifiers
source                 1..3441
                       mol_type = other DNA
                       organism = Synthetic construct
SEQUENCE: 23
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
atcgtcaacc tggagagcaa gctgcggcgc ctctccaagg acagcaacaa cctggaccag  1320
agtctgccca ggaacctgcc agtaaccatc atctctcagg actttgggga tgccagcccc  1380
```

aggaccaatg gtcaagaagc tgacgattct tccacctcgg aggagtcacc tgaagacagc 1440
aagtacttcc tgccctacca tccgccccag cgcaggatga acctgaaggg catccagctg 1500
cagagagcca aatcccccat cagcctgaag cgaacatcag attttcaagc caaggggcac 1560
gaggaagaag gcacggatgc cagccctagc tcctgcggat ctctgcccat caccaactcc 1620
ttcaccaaga tgcagccccc ccggagccgc agcagcatca tgtcaatcac cgccgagccc 1680
ccgggaaacg actccatcgt cagacgctac aaggaggacg cgccccatcg cagcacagtc 1740
gaagaagaca atgacagcgg cgggtttgac gccttagatc tggatgatga cagtcacgaa 1800
cgctactcct tcggaccctc ctccatccac tcctcctcct cctcccacca atccgagggc 1860
ctggatgcct acgacctgaa gcaggtcaac ctcatgttca ggaagttctc tctggaaaga 1920
cccttccggc cttcggtcac ctgtgtgggg cacgtgcggg gcccagggcc ctcggtgcag 1980
cacacgacgc tgaatggcga cagcctcacc tcccagctca ccctgctggg gggcaacgcg 2040
cgagggagct tcgtgcactc ggtcaagcct ggctctctgg ccgagaaagc cggcctccgt 2100
gagggccacc agctgctgct gctagaaggc tgcatccgag gcgagaggca gagtgtcccg 2160
ttggacacat gcaccaaaga ggaagcccac tggaccatcc agaggtgcag cggccccgtc 2220
acgctgcact acaaggtcaa ccacgaaggg taccggaagc tggtgaagga catggaggac 2280
ggcctgatca catcggggga ctcgttctac atccggctga acctgaacat ctccagccag 2340
ctggacgcct gcaccatgtc cctgaagtgt gacgatgttg tgcacgtccg tgacaccatg 2400
taccaggaca ggcacgagtg gctgtgcgcg cgggtcgacc ctttcacaga ccatgacctg 2460
gatatgggca ccatacccag ctacagccga gcccagcagc tcctcctggt gaaactgcag 2520
cgcctgatgc accgaggcag ccgggaggag gtagacggca cccaccacac cctgcgggca 2580
ctccggaaca ccctgcagcc agaagaagcg ctttcaacaa gcgacccccg ggtcagcccc 2640
cgtctctcgc gagcaagctt cctttttggc cagctccttc agttcgtcag caggtccgag 2700
aacaagtata agcggatgaa cagcaacgag cgggtccgca tcatctcggg gagtccgcta 2760
gggagcctgg cccggtcctc gctggacgcc accaagctct tgactgagaa gcaggaagag 2820
ctggaccctg agagcgagct gggcaagaac ctcagcctca tcccctacag cctggtacgc 2880
gccttctact gcgagcgccg ccggcccgtg ctcttcacac ccaccgtgct ggccaagacg 2940
ctggtgcaga ggctgctcaa ctcgggaggt gccatggagt tcaccatctg caagtcagat 3000
atcgtcacaa gagatgagtt cctcagaagg cagaagacgg agaccatcat ctactcccga 3060
gagaagaacc ccaacgcgtt cgaatgcatc gcccctgcca acattgaagc tgtggccgcc 3120
aagaacaagc actgcctgct ggaggctggg atcggctgca caagagactt gatcaagtcc 3180
aacatctacc ccatcgtgct cttcatccgg gtgtgtgaga agaacatcaa gaggttcaga 3240
aagctgctgc cccgacctga gacggaggag gagttcctgc gcgtgtgccg gctgaaggag 3300
aaggagctgg aggccctgcc gtgcctgtac gccacggtgg aacctgacat gtggggcagc 3360
gtagaggagc tgctccgcgt tgtcaaggac aagatcggcg aggagcagcg caagaccatc 3420
tgggtggacg aggaccagct g 3441

SEQ ID NO: 24 moltype = AA length = 1147
FEATURE Location/Qualifiers
source 1..1147
mol_type = protein
organism = Synthetic construct
SEQUENCE: 24
MDDYMETLKD EEDALWENVE CNRHMLSRYI NPAKLTPYLR QCKVIDEQDE DEVLNAPMLP 60
SKINRAGRLL DILHTKGQRG YVVFLESLEF YYPELYKLVT GKEPTRRFST IVVEEGHEGL 120
THFLMNEVIK LQQQMKAKDL QRCELLARLR QLEDEKKQMT LTRVELLTFQ ERYYKMKEER 180
DSYNDELVKV KDDNYNLAMR YAQLSEEKNM AVMRSRDLQL EIDQLKHRLN KMEEECKLER 240
NQSLKLKNDI ENRPKKEQVL ELERENEMLK TKNQELQSII QAGKRSLPDS DKAILDILEH 300
DRKEALEDRQ ELVNRIYNLQ EEARQAEELR DKYLEEKEDL ELKCSTLGKD CEMYKHRMNT 360
VMLQLEEVER ERDQAFHSRD EAQTQYSQCL IEKDKYRKQI RELEEKNDEM RIEMVRREAC 420
IVNLESKLRR LSKDSNNLDQ SLPRNLPVTI ISQDFGDASP RTNGQEADDS STSEESPEDS 480
KYFLPYHPPQ RRMNLKGIQL QRAKSPISLK RTSDFQAKGH EEEGTDASPS SCGSLPITNS 540
FTKMQPPRSR SSIMSITAEP PGNDSIVRRY KEDAPHRSTV EEDNDSGGFD ALDLDDDSHE 600
RYSFGPSSIH SSSSSHQSEG LDAYDLKQVN LMFRKFSLER PFRPSVTCVG HVRGPGPSVQ 660
HTTLNGDSLT SQLTLLGGNA RGSFVHSVKP GSLAEKAGLR EGHQLLLLEG CIRGERQSVP 720
LDTCTKEEAH WTIQRCSGPV TLHYKVNHEG YRKLVKDMED GLITSGDSFY IRLNLNISSQ 780
LDACTMSLKC DDVVHVRDTM YQDRHEWLCA RVDPFTDHDL DMGTIPSYSR AQQLLLVKLQ 840
RLMHRGSREE VDGTHHTLRA LRNTLQPEEA LSTSDPRVSP RLSRASFLFG QLLQFVSRSE 900
NKYKRMNSNE RVRIISGSPL GSLARSSLDA TKLLTEKQEE LDPESELGKN LSLIPYSLVR 960
AFYCERRRPV LFTPTVLAKT LVQRLLNSGG AMEFTICKSD IVTRDEFLRR QKTETIIYSR 1020
EKNPNAFECI APANIEAVAA KNKHCLLEAG IGCTRDLIKS NIYPIVLFIR VCEKNIKRFR 1080
KLLPRPETEE EFLRVCRLKE KELEALPCLY ATVEPDMWGS VEELLRVVKD KIGEEQRKTI 1140
WVDEDQL 1147

SEQ ID NO: 25 moltype = DNA length = 3441
FEATURE Location/Qualifiers
source 1..3441
mol_type = genomic DNA
organism = Homo sapiens
SEQUENCE: 25
atggatgact acatggagac gctgaaggat gaagaggacg ccttgtggga gaatgtggag 60
tgtaaccggc acatgctcag ccgctatatc aaccctgcca agctcacgcc ctacctgcgt 120
cagtgtaagg tcattgatga gcaggatgaa gatgaagtgc ttaatgcccc tatgctgcca 180
tccaagatca accgagcagg ccggctgttg gacattctac ataccaaggg gcaaaggggc 240
tatgtggtct tcttggagag cctagaattt tattacccag aactgtacaa actggtgact 300
gggaaagagc ccactcggag attctccacc attgtggtgg aggaaggcca cgagggcctc 360
acgcacttcc tgatgaacga ggtcatcaag ctgcagcagc agatgaaggc caaggacctg 420
caacgctgcg agctgctggc caggttgcgg cagctggagg atgagaagaa gcagatgacg 480
ctgacgcgcg tggagctgct aaccttccag gagcggtact acaagatgaa ggaagagcgg 540
gacagctaca atgacgagct ggtcaaggtg aaggacgaca actacaactt agccatgcgc 600

-continued

```
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
atcgtcaacc tggagagcaa gctgcggcgc ctctccaagg acagcaacaa cctggaccag  1320
agtctgccca ggaacctgcc agtaaccatc atctctcagg actttgggga tgccagcccc  1380
aggaccaatg gtcaagaagc tgacgattct tccacctcgg aggagtcacc tgaagacagc  1440
aagtacttcc tgccctacca tccgccccag cgcaggatga acctgaaggg catccagctg  1500
cagagagcca aatcccccat cagcctgaag cgaacatcag attttcaagc caaggggcac  1560
gaggaagaag gcacggatgc cagccctagc tcctgcggat ctctgcccat caccaactcc  1620
ttcaccaaga tgcagccccc ccggagccgc agcagcatca tgtcaatcac cgccgagccc  1680
ccgggaaacg actccatcgt cagacgctac aaggaggacg cgccccatcg cagcacagtc  1740
gaagaagaca atgacagcgg cgggtttgac gccttagatc tggatgatga cagtcacgaa  1800
cgctactcct tcggaccctc ctccatccac tcctcctcct cctcccacca atccgagggc  1860
ctggatgcct acgacctgga gcaggtcaac ctcatgttca ggaagttctc tctggaaaga  1920
cccttccggc cttcggtcac ctctgtgggg cacgtgcggg gcccagggcc ctcggtgcag  1980
cacacgacgc tgaatggcga cagcctcacc tcccagctca ccctgctggg gggcaacgcg  2040
cgagggagct tcgtgcactc ggtcaagcct ggctctctgg ccgagaaagc cggcctccgt  2100
gagggccacc agctgctgct gctagaaggc tgcatccgag gcgagaggca gagtgtcccg  2160
ttggacacat gcaccaaaga ggaagcccac tggaccatcc agaggtgcag cggccccgtc  2220
acgctgcact acaaggtcaa ccacgaaggg taccggaagc tggtgaagga catggaggac  2280
ggcctgatca catcggggga ctcgttctac atccggctga acctgaacat ctccagccag  2340
ctggacgcct gcaccatgtc cctgaagtgt gacgatgttg tgcacgtccg tgacaccatg  2400
taccaggaca ggcacgagtg gctgtgcgcg cgggtcgacc ctttcacaga ccatgacctg  2460
gatatgggca ccatacccag ctacagccga gcccagcagc tcctcctggt gaaactgcag  2520
cgcctgatgc accgaggcag ccgggaggag gtagacggca cccaccacac cctgcgggca  2580
ctccggaaca ccctgcagcc agaagaagcg ctttcaacaa gcgacccccg ggtcagcccc  2640
cgtctctcgc gagcaagctt cctttttggc cagctccttc agttcgtcag caggtccgag  2700
aacaagtata agcggatgaa cagcaacgag cgggtccgca tcatctcggg gagtccgcta  2760
gggagcctgg cccggtcctc gctggacgcc accaagctct tgactgagaa gcaggaagag  2820
ctggaccctg agagcgagct gggcaagaac ctcagcctca tcccctacag cctggtacgc  2880
gccttctact gcgagcgccg ccggcccgtg ctcttcacac ccaccgtgct ggccaagacg  2940
ctggtgcaga ggctgctcaa ctcgggaggt gccatggagt tcaccatctg caagtcagat  3000
atcgtcacaa gagatgagtt cctcagaagg cagaagacgg agaccatcat ctactcccga  3060
gagaagaacc ccaacgcgtt cgaatgcatc gcccctgcca acattgaagc tgtggccgcc  3120
aagaacaagc actgcctgct ggaggctggg atcggctgca caagagactt gatcaagtcc  3180
aacatctacc ccatcgtgct cttcatccgg gtgtgtgaga agaacatcaa gaggttcaga  3240
aagctgctgc cccgacctga gacggaggag gagttcctgc gcgtgtgccg gctgaaggag  3300
aaggagctgg aggccctgcc gtgcctgtac gccacggtgg aacctgacat gtggggcagc  3360
gtagaggagc tgctccgcgt tgtcaaggac aagatcggcg aggagcagcg caagaccatc  3420
tgggtggacg aggaccagct g                                          3441
```

```
SEQ ID NO: 26          moltype = AA  length = 1154
FEATURE                Location/Qualifiers
source                 1..1154
                       mol_type = protein
                       organism = Homo sapiens
SEQUENCE: 26
MPGGGPEMDD YMETLKDEED ALWENVECNR HMLSRYINPA KLTPYLRQCK VIDEQDEDEV  60
LNAPMLPSKI NRAGRLLDIL HTKGQRGYVV FLESLEFYYP ELYKLVTGKE PTRRFSTIVV  120
EEGHEGLTHF LMNEVIKLQQ QMKAKDLQRC ELLARLRQLE DEKKQMTLTR VELLTFQERY  180
YKMKEERDSY NDELVKVKDD NYNLAMRYAQ LSEEKNMAVM RSRDLQLEID QLKHRLNKME  240
EECKLERNQS LKLKNDIENR PKKEQVLELE RENEMLKTKN QELQSIIQAG KRSLPDSDKA  300
ILDILEHDRK EALEDRQELV NRIYNLQEEA RQAEELRDKY LEEKEDLELK CSTLGKDCEM  360
YKHRMNTVML QLEEVERERD QAFHSRDEAQ TQYSQCLIEK DKYRKQIREL EEKNDEMRIE  420
MVRREACIVN LESKLRRLSK DSNNLDQSLP RNLPVTIISQ DFGDASPRTN GQEADDSSTS  480
EESPEDSKYF LPYHPPQRRM NLKGIQLQRA KSPISLKRTS DFQAKGHEEE GTDASPSSCG  540
SLPITNSFTK MQPPRSRSSI MSITAEPPGN DSIVRRYKED APHRSTVEED NDSGGFDALD  600
LDDDSHERYS FGPSSIHSSS SSHQSEGLDA YDLEQVNLMF RKFSLERPFR PSVTSVGHVR  660
GPGPSVQHTT LNGDSLTSQL TLLGGNARGS FVHSVKPGSL AEKAGLREGH QLLLLEGCIR  720
GERQSVPLDT CTKEEAHWTI QRCSGPVTLH YKVNHEGYRK LVKDMEDGLI TSGDSFYIRL  780
NLNISSQLDA CTMSLKCDDV VHVRDTMYQD RHEWLCARVD PFTDHDLDMG TIPSYSRAQQ  840
LLLVKLQRLM HRGSREEVDG THHTLRALRN TLQPEEALST SDPRVSPRLS RASFLFGQLL  900
QFVSRSENKY KRMNSNERVR IISGSPLGSL ARSSLDATKL LTEKQEELDP ESELGKNLSL  960
IPYSLVRAFY CERRRPVLFT PTVLAKTLVQ RLLNSGGAME FTICKSDIVT RDEFLRRQKT  1020
ETIIYSREKN PNAFECIAPA NIEAVAAKNK HCLLEAGIGC TRDLIKSNIY PIVLFIRVCE  1080
KNIKRFRKLL PRPETEEEFL RVCRLKEKEL EALPCLYATV EPDMWGSVEE LLRVVKDKIG  1140
EEQRKTIWVD EDQL                                                  1154

SEQ ID NO: 27          moltype = DNA  length = 4305
FEATURE                Location/Qualifiers
source                 1..4305
```

```
                         mol_type = genomic DNA
                         organism = Homo sapiens
SEQUENCE: 27
atggcccaga cccccgacgg catctcctgt gagctccgag gcgagatcac caggttcctg  60
tggcccaaag aggtggagct gctgctgaaa acctggctac ccggggaggg tgctgtgcaa  120
aaccatgtcc tggcactgct acgatggaga gcctacctgc tgcacaccac ctgcctcccg  180
ctgagggtgg actgcacgtt cagctacctg gaggtccagg ccatggcgct gcaggagaca  240
ccccctcagg tcacctttga gctggagtcc ctgcgtgagc tggtcctgga gtttcctggt  300
gtggccgccc tggaacagct ggcccagcac gtggctgcag ccatcaagaa ggtcttccct  360
cgctcgaccc ttgggaagct attccggagg cccacaccag cctccatgct ggctcggctg  420
gagagaagca gcccctcgga gtccactgac ccctgcagcc cctgtggtgg cttcttggag  480
acatacgagg ctctgtgtga ctacaatggc ttccctttcc gagaggagat tcagtgggac  540
gtggacacca tttaccatcg ccagggctgc cgccatttca gcctgggaga cttcagccac  600
ctcggcagtc gggacctggc cttgagtgtg gctgccctgt cctacaacct gtggttccgg  660
tgcctctcct gtgtggacat gaagctgagc cttgaggtct cagaacagat tctgcacatg  720
atgagtcagt catcacacct ggaggagctg gtgctggaga cctgcagcct gaggggagac  780
tttgtccgac gactggccca ggcgctggcg ggacactcaa gctctgggct gcgggagctc  840
agcctcgcgg ggaacctgct ggatgaccga ggcatgactg cactcagcag acacctcgag  900
cgttgtccag gagccctgag gagactcagc ctggcccaga cagggttgac accgcgagga  960
atgagggctc tgggccgggc actggccacc aatgccgcct tcgactccac cctgacccac  1020
ctggaccttt ctgggaatcc tggggcgctg ggggcctccg aggacagtgg gggcctctat  1080
agcttcctga gccgtcctaa cgtactgtcg ttcctgaatc tcgcaggcac cgacactgcc  1140
ctggacactg tgaggggtg ctccgtgggg ggatggatga ccggcagggc ggactggagg  1200
gcgggacggg gagggctcgg tccccccgcg ggtgtagcca acagcctccc cccgcagctc  1260
ttcgcagcgg tatcccgagg ctgctgcacc agccttaccc acctcgacgc ttcgaggaac  1320
gtcttctccc gcacgaagtc ccgcgccgcg ccggccgcgc tgcagctctt cctcagccgc  1380
gcgcggacgc tgcggcacct gggcctggcg ggctgcaagc tgccgcccga cgcgctcaga  1440
gcccttttgg atggcctcgc gctcaacacg cacctccgcg acctgcacct ggacctcagc  1500
gcttgcgagc tgcgctcggc cggcgcccag gtgatacaag acttagtgtg cgacgcaggc  1560
gctgtgagct ccctggatct ggcggataac ggcttcggct cagacatggt gactctggtg  1620
ctggccatcg ggagaagccg gtccctgaga catgtggcgc ttggaaggaa cttcaacgtc  1680
cggtgcaagg agaccctgga cgacgtcctg caccggattg tccagctcat gcaggacgac  1740
gattgtcctc ttcagtctct gtcggtggct gagtctcggc tgaagctggg tgccagcgtc  1800
ctactccggg ccctagccac caatcctaac ctgaccgcgc tggatatcag cggcaacgcc  1860
atgggggacg cgggcgccaa gttgctggcc aaggcgctgc gggtcaactc gaggctccgg  1920
tctgtggtct gggaccggaa ccacacatct gctttgggtc tgctggacgt ggcgcaggcg  1980
ctggagcaga accacagcct gaaggccatg cctctgccac tgaacgacgt ggcccaggcg  2040
cagcgcagcc gcccggaact gacagcacgt gcagtccatc agatccaagc ctgtctcttg  2100
aggaacaacc gcgcagaccc tgcctcttct gaccacacga cccgccttca gccacttggt  2160
ctggtctcag acccctcaga gcaggaagtg aatgaattgt gtcagtcggt gcaggagcat  2220
gtggagctgc tgggctgtgg ggctgggccc cagggtgaag ccgctgtgcg ccaggccgag  2280
gatgccatcc aaaatgccaa cttctctctc agcattctcc ccattctata tgaagctgga  2340
agctccccaa gccatcactg gcagcttggg cagaagctgg agggccttct gagacaggtg  2400
ggcgaggtct gccgccagga catccaggac ttcactcagg ccacactgga cacagcaagg  2460
agcctctgcc cacagatgct gcagggatcc agctggaggg agcagctaga gggggtcctg  2520
gcaggctcga ggggcctccc ggagctgctc ccagagcagc tgctgcaaga tgccttcact  2580
aggctcaggg acatgcggct atcaatcacg gggaccttgg cagagagcat tgtggctcag  2640
gctttggcag gcctgagtgc agcccgggat cagctggtgg agagtctggc tcagcaggca  2700
acagtgacaa tgccccctgc cctaccagca ccggatggag gtgagcccag cctccttgag  2760
cctggggaat tggaaggtct tttcttcccc gaggagaagg aagaggagaa ggagaaggat  2820
gacagtcctc cacagaaatg gcctgagctc agccacggtc ttcacctggt ccccttcatt  2880
cacagtgctg ctgaggaagc ggagccggag cccgagctgg cggctccggg agaagatgca  2940
gagccgcagg cggggccgtc cgcgcgcggc tctccgagcc ctgccgcccc tgggcccccg  3000
gccggcccgc tgccccgcat ggacctgcca ctggcggggc agcccctgcg ccatccgacc  3060
cgggcccggc cgcggccgcg ccgccagcac caccaccgcc cgccgccggg gggcccccag  3120
gtacccccag ccttgccgca ggaagggaat gggctcagtg cccgcgtgga cgagggcgtg  3180
gaggaattct tctccaaaag gctgatccag caggatcgcc tctgggcccc cgaggaggac  3240
ccggccactg aggggggcgc cactcctgtc ccccgtacac tgcgaaagaa gctgggcacc  3300
ctctttgcct tcaagaagcc tcgttcaacg cggggtccac ggactgatct agagaccagc  3360
cctggggcag ctccccgaac ccgaaaaact acatttggcg acctactgcg gccgccaacc  3420
cgtcccagcc gtggtgagga gcttggtggg gctgaggggg acaccagcag ccctgaccct  3480
gccggcagga gccgacctcg ctacacaaga gatagcaagg cctactcgat gatactgctg  3540
cctgccgagg aggaggcaac gctgggtgcc agacccgaca agcggcggcc cctggagcgg  3600
ggagagaacag aactggctcc atcctttgaa cagcgggtac aagtaatgct gcagaggata  3660
ggcgtcagcc gaggcagcgg gggtgccgaa ggcaagagga agcaaagcaa agatggcgag  3720
atcaagaaag ctggctcaga tggtgacatt atggacagtt ccacggaggc ccctcccatc  3780
tcgatcaagt cccgcaccca ctctgtgtct gctgaccctt cctgcagacc tggcccaggg  3840
agccaggggc ctgagtctgc cacctggaag acactggggc agcagttgaa tgcggagctc  3900
aggagccgtg gttggggcca acaggatggt ccaggccctc cctcccctgg tcaaagccca  3960
agtccctgca gaaccagccc ctccccagac agcctgggcc tcccagagga cccttgcttg  4020
ggccccagaa atgaagatgg ccagctgagg ccgaggcctc tctcggcagg gcggcgagca  4080
gtgtctgtgc atgaggacca gctccaggcc cctgctgaac ggcccctgag gctgcagcgc  4140
tcccccgtcc tcaaacgcag gccaaaactc gaggcacctc catccccaag cctaggatct  4200
ggccttggaa ccgagcctct gcccccacag cccacagagc cctccagccc tgagcggagc  4260
ccaccctccc cagccacaga ccaaagaggc ggcggcccca atccc                4305

SEQ ID NO: 28            moltype = AA  length = 1435
FEATURE                  Location/Qualifiers
source                   1..1435
```

-continued

```
                        mol_type = protein
                        organism = Homo sapiens
SEQUENCE: 28
MAQTPDGISC ELRGEITRFL WPKEVELLLK TWLPGEGAVQ NHVLALLRWR AYLLHTTCLP  60
LRVDCTFSYL EVQAMALQET PPQVTFELES LRELVLEFPG VAALEQLAQH VAAAIKKVFP  120
RSTLGKLFRR PTPASMLARL ERSSPSESTD PCSPCGGFLE TYEALCDYNG FPFREEIQWD  180
VDTIYHRQGC RHFSLGDFSH LGSRDLALSV AALSYNLWFR CLSCVDMKLS LEVSEQILHM  240
MSQSSHLEEL VLETCSLRGD FVRRLAQALA GHSSSGLREL SLAGNLLDDR GMTALSRHLE  300
RCPGALRRLS LAQTGLTPRG MRALGRALAT NAAFDSTLTH LDLSGNPGAL GASEDSGGLY  360
SFLSRPNVLS FLNLAGTDTA LDTVRGCSVG GWMTGRADWR AGRGGLGPPA GVANSLPPQL  420
FAAVSRGCCT SLTHLDASRN VFSRTKSRAA PAALQLFLSR ARTLRHLGLA GCKLPPDALR  480
ALLDGLALNT HLRDLHLDLS ACELRSAGAQ VIQDLVCDAG AVSSLDLADN GFGSDMVTLV  540
LAIGRSRSLR HVALGRNFNV RCKETLDDVL HRIVQLMQDD DCPLQSLSVA ESRLKLGASV  600
LLRALATNPN LTALDISGNA MGDAGAKLLA KALRVNSRLR SVVWDRNHTS ALGLLDVAQA  660
LEQNHSLKAM PLPLNDVAQA QRSRPELTAR AVHQIQACLL RNNRADPASS DHTTRLQPLG  720
LVSDPSEQEV NELCQSVQEH VELLGCGAGP QGEAAVRQAE DAIQNANFSL SILPILYEAG  780
SSPSHHWQLG QKLEGLLRQV GEVCRQDIQD FTQATLDTAR SLCPQMLQGS SWREQLEGVL  840
AGSRGLPELL PEQLLQDAFT RLRDMRLSIT GTLAESIVAQ ALAGLSAARD QLVESLAQQA  900
TVTMPPALPA PDGGEPSLLE PGELEGLFFP EEKEEEKEKD DSPPQKWPEL SHGLHLVPFI  960
HSAAEEAEPE PELAAPGEDA EPQAGPSARG SPSPAAPGPP AGPLPRMDLP LAGQPLRHPT  1020
RARPRPRRQH HRPPPGGPQ VPPALPQEGN GLSARVDEGV EEFFSKRLIQ QDRLWAPEED  1080
PATEGGATPV PRTLRKKLGT LFAFKKPRST RGPRTDLETS PGAAPRTRKT TFGDLLRPPT  1140
RPSRGEELGG AEGDTSSPDP AGRSRPRYTR DSKAYSMILL PAEEEATLGA RPDKRRPLER  1200
GETELAPSFE QRVQVMLQRI GVSRGSGGAE GKRKQSKDGE IKKAGSDGDI MDSSTEAPPI  1260
SIKSRTHSVS ADPSCRPGPG SQGPESATWK TLGQQLNAEL RSRGWGQQDG PGPPSPGQSP  1320
SPCRTSPSPD SLGLPEDPCL GPRNEDGQLR PRPLSAGRRA VSVHEDQLQA PAERPLRLQR  1380
SPVLKRRPKL EAPPSPSLGS GLGTEPLPPQ PTEPSSPERS PPSPATDQRG GGPNP       1435

SEQ ID NO: 29           moltype = DNA  length = 4305
FEATURE                 Location/Qualifiers
source                  1..4305
                        mol_type = other DNA
                        organism = Synthetic construct
SEQUENCE: 29
atggcccaga cccccgacgg catctcctgt gagctccgag gcgagatcac caggttcctg  60
tggcccaaag aggtggagct gctgctgaaa acctggctac ccggggaggg tgctgtgcaa  120
aaccatgtcc tggcactgct acgatggaga gcctacctgc tgcacaccac ctgcctcccg  180
ctgagggtgg actgcacgtt cagctacctg gaggtccagg ccatggcgct gcaggagaca  240
ccccctcagg tcacctttga gctggagtcc ctgcgtgagc tggtcctgga gtttcctggt  300
gtggccgccc tggaacagct ggcccagcac gtggctgcag ccatcaagaa ggtcttccct  360
cgctcgaccc ttgggaagct attccggagg cccacaccag cctccatgct ggctcggctg  420
gagagaagca gcccctcgga gtccactgac ccctgcagcc cctgtggtgg cttcttggag  480
acatacgagg ctctgtgtga ctacaatggc ttccctttcc gagaggagat tcagtgggac  540
gtggacacca tttaccatcg ccagggctgc cgccatttca gcctgggaga cttcagccac  600
ctcggcagtc gggacctggc cttgagtgtg gctgccctgt cctacaacct gtggttccgg  660
tgcctctcct gtgtggacat gaagctgagc cttgaggtct cagaacagat tctgcacatg  720
atgagtcagt catcacacct ggaggagctg gtgctggaga cctgcagcct gaggggagac  780
tttgtccgac gactggccca ggcgctggcg ggacactcaa gctctgggct gcgggagctc  840
agcctcgcgg ggaacctgct ggatgaccga ggcatgactg cactcagcag acacctcgag  900
cgttgtccag gagccctgag gagactcagc ctggcccaga cagggttgac accgcgagga  960
atgagggctc tgggccgggc actggccacc aatgccgcct tcgactccac cctgacccac  1020
ctggaccttt ctgggaatcc tggggcgctg gggcctccg aggacagtgg gggcctctat  1080
agcttcctga gccgtcctaa cgtactgtcg ttcctgaatc tcgcaggcac cgacactgcc  1140
ctggacactg tgagggggtg ctccgtgggg ggatggatga ccggcagggc ggactggagg  1200
gcgggacggg gagggctcgg tccccccgcg ggtgtagcca acagcctccc cccgcagctc  1260
ttcgcagcgg tatcccgagg ctgctgcacc agccttaccc acctcgacgc ttcgaggaac  1320
gtcttctccc gcacgaagtc ccgcgccgcg ccggccgcgc tgcagctctt cctcagccgc  1380
gcgcggacgc tgcggcacct gggcctggcg ggctgcaagc tgccgcccga cgcgctcaga  1440
gccctttgg atggcctcgc gctcaacacg cacctccgcg acctgcacct ggacctcagc  1500
gcttgcgagc tgcgctcggc cggcgcccag gtgatacaag acttagtgtg cgacgcaggc  1560
gctgtgagct ccctggatct ggcggataac ggcttcggct cagacatggt gactctggtg  1620
ctggccatcg ggagaagccg gtccctgaga catgtggcgc ttggaaggaa cttcaacgtc  1680
cggtgcaagg agaccctgga cgacgtcctg caccggattg tcgagctcat gcaggacgac  1740
gattgtcctc ttcagtctct gtcggtggct gagtctcggc tgaagctggg tgccagcgtc  1800
ctactccggg ccctagccac caatcctaac ctgaccgcgc tggatatcag cggcaacgcc  1860
atgggggacg cgggcgccaa gttgctggcc aaggcgctgc gggtcaactc gaggctccgg  1920
tctgtggtct gggaccggaa ccacacatct gctttgggtc tgctggacgt ggcgcaggcg  1980
ctggagcaga accacagcct gaaggccatg cctctgccac tgaacgacgt ggcccaggcg  2040
cagcgcagcc gcccggaact gacagcacgt gcagtccatc agatccaagc ctgtctcttg  2100
aggaacaacc gcgcagaccc tgcctcttct gaccacacga cccgccttca gccacttggt  2160
ctggtctcag accccctcaga gcaggaagtg aatgaattgt gtcagtcggt gcaggagcat  2220
gtggagctgc tgggctgtgg ggctgggccc cagggtgaag ccgctgtgcg ccaggccgag  2280
gatgccatcc aaaatgccaa cttctctctc agcattctcc ccattctata tgaagctgga  2340
agctccccaa gccatcactg gcagcttggg cagaagctgg agggccttct gagacaggtg  2400
ggcgaggtct gccgccagga catccaggac ttcactcagg ccacactgga cacagcaagg  2460
agcctctgcc cacagatgct gcagggatcc agctggaggg agcagctaga gggggtcctg  2520
gcaggctcga ggggcctccc ggagctgctc ccagagcagc tgctgcaaga tgccttcact  2580
aggctcaggg acatgcggct atcaatcacg ggaccttgg cagagagcat tgtggctcag  2640
gctttggcag gcctgagtgc agcccgggat cagctggtgg agagtctggc tcagcaggca  2700
```

-continued

```
acagtgacaa tgccccctgc cctaccagca ccggatggag gtgagcccag cctccttgag  2760
cctggggaat tggaaggtct tttcttcccc gaggagaagg aagaggagaa ggagaaggat  2820
gacagtcctc cacagaaatg gcctgagctc agccacggtc ttcacctggt cccccttcatt  2880
cacagtgctg ctgaggaagc ggagccggag cccgagctgg cggctccggg agaagatgca  2940
gagccgcagg cggggccgtc cgcgcgcggc tctccgagcc ctgccgcccc tgggcccccg  3000
gccggcccgc tgccccgcat ggacctgcca ctggcggggc agcccctgcg ccatccgacc  3060
cgggcccggc cgcggccgcg ccgccagcac caccaccgcc cgccgccggg gggcccccag  3120
gtacccccag ccttgccgca ggaagggaat gggctcagtg cccgcgtgga cgagggcgtg  3180
gaggaattct tctccaaaag gctgatccag caggatcgcc tctgggcccc cgaggaggac  3240
ccggccactg agggggcgc cactcctgtc ccccgtacac tgcgaaagaa gctgggcacc  3300
ctctttgcct tcaagaagcc tcgttcaacg cggggtccac ggactgatct agagaccagc  3360
cctggggcag ctccccgaac ccgaaaaact acatttggcg acctactgcg gccgccaacc  3420
cgtcccagcc gtggtgagga gcttggtggg gctgaggggg acaccagcag ccctgaccct  3480
gccggcagga gccgacctcg ctacacaaga gatagcaagg cctactcgat gatactgctg  3540
cctgccgagg aggaggcaac gctgggtgcc agacccgaca agcggcggcc cctggagcgg  3600
ggagaaacag aactggctcc atcctttgaa cagcgggtac aagtaatgct gcagaggata  3660
ggcgtcagcc gaggcagcgg gggtgccgaa ggcaagagga agcaaagcaa agatggcgag  3720
atcaagaaag ctggctcaga tggtgacatt atggacagtt ccacggaggc ccctcccatc  3780
tcgatcaagt cccgcaccca ctctgtgtct gctgaccctt cctgcagacc tggcccaggg  3840
agccaggggc ctgagtctgc cacctggaag acactggggc agcagttgaa tgcggagctc  3900
aggagccgtg gttggggcca acaggatggt ccaggccctc cctcccctgg tcaaagccca  3960
agtccctgca gaaccagccc ctccccagac agcctgggcc tcccagagga cccttgcttg  4020
ggccccagaa atgaagatgg ccagctgagg ccgaggcctc tctcggcagg gcggcgagca  4080
gtgtctgtgc atgaggacca gctccaggcc cctgctgaac ggcccctgag gctgcagcgc  4140
tcccccgtcc tcaaacgcag gccaaaactc gaggcacctc catccccaag cctaggatct  4200
ggccttggaa ccgagcctct gcccccacag cccacagagc cctccagccc tgagcggagc  4260
ccaccctccc cagccacaga ccaaagaggc ggcggcccca atccc                  4305
```

```
SEQ ID NO: 30          moltype = AA  length = 1435
FEATURE                Location/Qualifiers
source                 1..1435
                       mol_type = protein
                       organism = Synthetic construct
SEQUENCE: 30
MAQTPDGISC ELRGEITRFL WPKEVELLLK TWLPGEGAVQ NHVLALLRWR AYLLHTTCLP  60
LRVDCTFSYL EVQAMALQET PPQVTFELES LRELVLEFPG VAALEQLAQH VAAAIKKVFP  120
RSTLGKLFRR PTPASMLARL ERSSPSESTD PCSPCGGFLE TYEALCDYNG FPFREEIQWD  180
VDTIYHRQGC RHFSLGDFSH LGSRDLALSV AALSYNLWFR CLSCVDMKLS LEVSEQILHM  240
MSQSSHLEEL VLETCSLRGD FVRRLAQALA GHSSSGLREL SLAGNLLDDR GMTALSRHLE  300
RCPGALRRLS LAQTGLTPRG MRALGRALAT NAAFDSTLTH LDLSGNPGAL GASEDSGGLY  360
SFLSRPNVLS FLNLAGTDTA LDTVRGCSVG GWMTGRADWR AGRGGLGPPA GVANSLPPQL  420
FAAVSRGCCT SLTHLDASRN VFSRTKSRAA PAALQLFLSR ARTLRHLGLA GCKLPPDALR  480
ALLDGLALNT HLRDLHLDLS ACELRSAGAQ VIQDLVCDAG AVSSLDLADN GFGSDMVTLV  540
LAIGRSRSLR HVALGRNFNV RCKETLDDVL HRIVELMQDD DCPLQSLSVA ESRLKLGASV  600
LLRALATNPN LTALDISGNA MGDAGAKLLA KALRVNSRLR SVVWDRNHTS ALGLLDVAQA  660
LEQNHSLKAM PLPLNDVAQA QRSRPELTAR AVHQIQACLL RNNRADPASS DHTTRLQPLG  720
LVSDPSEQEV NELCQSVQEH VELLGCGAGP QGEAAVRQAE DAIQNANFSL SILPILYEAG  780
SSPSHHWQLG QKLEGLLRQV GEVCRQDIQD FTQATLDTAR SLCPQMLQGS SWREQLEGVL  840
AGSRGLPELL PEQLLQDAFT RLRDMRLSIT GTLAESIVAQ ALAGLSAARD QLVESLAQQA  900
TVTMPPALPA PDGGEPSLLE PGELEGLFFP EEKEEEKEKD DSPPQKWPEL SHGLHLVPFI  960
HSAAEEAEPE PELAAPGEDA EPQAGPSARG SPSPAAPGPP AGPLPRMDLP LAGQPLRHPT  1020
RARPRPRRQH HHRPPPGGPQ VPPALPQEGN GLSARVDEGV EEFFSKRLIQ QDRLWAPEED  1080
PATEGGATPV PRTLRKKLGT LFAFKKPRST RGPRTDLETS PGAAPRTRKT TFGDLLRPPT  1140
RPSRGEELGG AEGDTSSPDP AGRSRPRYTR DSKAYSMILL PAEEEATLGA RPDKRRPLER  1200
GETELAPSFE QRVQVMLQRI GVSRGSGGAE GKRKQSKDGE IKKAGSDGDI MDSSTEAPPI  1260
SIKSRTHSVS ADPSCRPGPG SQGPESATWK TLGQQLNAEL RSRGWGQQDG PGPPSPGQSP  1320
SPCRTSPSPD SLGLPEDPCL GPRNEDGQLR PRPLSAGRRA VSVHEDQLQA PAERPLRLQR  1380
SPVLKRRPKL EAPPSPSLGS GLGTEPLPPQ PTEPSSPERS PPSPATDQRG GGPNP        1435
```

```
SEQ ID NO: 31          moltype = DNA  length = 879
FEATURE                Location/Qualifiers
source                 1..879
                       mol_type = genomic DNA
                       organism = Homo sapiens
SEQUENCE: 31
atggagctgc tgtgttgcga aggcacccgg cacgcgcccc gggccgggcc ggacccgcgg  60
ctgctggggg accagcgtgt cctgcagagc ctgctccgcc tggaggagcg ctacgtaccc  120
cgcgcctcct acttccagtg cgtgcagcgg gagatcaagc cgcacatgcg gaagatgctg  180
gcttactgga tgctggaggt atgtgaggag cagcgctgtg aggaggaagt cttccccctg  240
gccatgaact acctggatcg ctacctgtct tgcgtcccca cccgaaaggc gcagttgcag  300
ctcctgggtg cggtctgcat gctgctggcc tccaagctgc gcgagaccac gcccctgacc  360
atcgaaaaac tgtgcatcta caccgaccac gctgtctctc cccgccagtt gcgggactgg  420
gaggtgctgg tcctagggaa gctcaagtgg gacctggctg ctgtgattgc acatgatttc  480
ctggccttca ttctgcaccg gctctctctg ccccgtgacc gacaggcctt ggtcaaaaag  540
catgcccaga cctttttggc cctctgtgct acagattata cctttgccat gtacccgcca  600
tccatgatcg ccacgggcag cattggggct gcagtgcaag gcctgggtgc ctgctccatg  660
tccggggatg agctcacaga gctgctggca gggatcactg gcactgaagt ggactgcctg  720
cgggcctgtc aggagcagat cgaagctgca ctcagggaga gcctcaggga agcctctcag  780
accagctcca gcccagcgcc caaagccccc cggggctcca gcagccaagg gcccagccag  840
```

```
accagcactc ctacagatgt cacagccata cacctgttg                       879

SEQ ID NO: 32          moltype = AA  length = 293
FEATURE                Location/Qualifiers
source                 1..293
                       mol_type = protein
                       organism = Homo sapiens
SEQUENCE: 32
MELLCCEGTR HAPRAGPDPR LLGDQRVLQS LLRLEERYVP RASYFQCVQR EIKPHMRKML  60
AYWMLEVCEE QRCEEEVFPL AMNYLDRYLS CVPTRKAQLQ LLGAVCMLLA SKLRETTPLT  120
IEKLCIYTDH AVSPRQLRDW EVLVLGKLKW DLAAVIAHDF LAFILHRLSL PRDRQALVKK  180
HAQTFLALCA TDYTFAMYPP SMIATGSIGA AVQGLGACSM SGDELTELLA GITGTEVDCL  240
RACQEQIEAA LRESLREASQ TSSSPAPKAP RGSSSQGPSQ TSTPTDVTAI HLL         293

SEQ ID NO: 33          moltype = DNA  length = 879
FEATURE                Location/Qualifiers
source                 1..879
                       mol_type = other DNA
                       organism = Synthetic construct
SEQUENCE: 33
atggagctgc tgtgttgcga aggcacccgg cacgcgcccc gggccgggcc ggacccgcgg  60
ctgctggggg accagcgtgt cctgcagagc ctgctccgcc tggaggagcg ctacgtaccc  120
cgcgcctcct acttccagtg cgtgcagcgg gagatcaagc cgcacatgcg gaagatgctg  180
gcttactgga tgctggaggt atgtgaggag cagcgctgtg aggaggaagt cttccccctg  240
gccatgaact acctggatcg ctacctgtct tgcgtcccca cccgaaaggc gcagttgcag  300
ctcctgggtg cggtctgcat gctgctggcc tccaagctgc gcgagaccac gcccctgacc  360
atcgaaaaac tgtgcatcta caccgaccac gctgtctctc cccgccagtt gcgggactgg  420
gaggtgctgg tcctagggaa gctcaagtgg gacctggctg ctgtgattgc acatgatttc  480
ctggccttca ttctgcaccg gctctctctg ccccgtgacc gacaggcctt ggtcaaaaag  540
catgcccaga cctttttggc cctctgtgct acagattata cctttgccat gtacccgcca  600
tccatgatcg ccacgggcag cattggggct gcagtgcaag gcctgggtgc ctgctccatg  660
tccggggatg agctcacaga gctgctggca gggatcactg gcactgaagt ggactgcctg  720
cgggcctgtc aggagcagat cgaagctgca ctcagggaga gcctcaggga agcctctcag  780
accagctcca gcccagcgcc caaagccccc cggggctcca gcagccaagg gcccagccag  840
accagcactt ctacagatgt cacagccata cacctgttg                       879

SEQ ID NO: 34          moltype = AA  length = 293
FEATURE                Location/Qualifiers
source                 1..293
                       mol_type = protein
                       organism = Synthetic construct
SEQUENCE: 34
MELLCCEGTR HAPRAGPDPR LLGDQRVLQS LLRLEERYVP RASYFQCVQR EIKPHMRKML  60
AYWMLEVCEE QRCEEEVFPL AMNYLDRYLS CVPTRKAQLQ LLGAVCMLLA SKLRETTPLT  120
IEKLCIYTDH AVSPRQLRDW EVLVLGKLKW DLAAVIAHDF LAFILHRLSL PRDRQALVKK  180
HAQTFLALCA TDYTFAMYPP SMIATGSIGA AVQGLGACSM SGDELTELLA GITGTEVDCL  240
RACQEQIEAA LRESLREASQ TSSSPAPKAP RGSSSQGPSQ TSTSTDVTAI HLL         293

SEQ ID NO: 35          moltype = DNA  length = 660
FEATURE                Location/Qualifiers
source                 1..660
                       mol_type = other DNA
                       organism = Synthetic construct
SEQUENCE: 35
atgctcaggc tgctcttggc tctcaactta ttcccttcaa ttcaagtaac aggaaacaag  60
attttggtga agcagtcgcc catgcttgta gcgtacgaca atgcggtcaa ccttagctgc  120
aagtattcct acaatctctt ctcaagggag gtccgggcat cccttcacaa aggactggat  180
agtgctgtgg aagtctgtgt tgtatatggg aattactccc agcagcttca ggtttactca  240
aaaacggggt tcaactgtga tgggaaattg ggcaatgaat cagtgacatt ctacctccag  300
aatttgtatg ttaaccaaac agatatttac ttctgcaaaa ttgaagttat gtatcctcct  360
ccttacctag acaatgagaa gagcaatgga accattatcc atgtgaaagg gaaacacctt  420
tgtccaagtc ccctatttcc cggaccttct aagccctttt gggtgctggt ggtggttggt  480
ggagtcctgg cttgctatag cttgctagta acagtggcct ttattatttt ctgggtgagg  540
agtaagagga gcaggctcct gcacagtgac tacatgaaca tgactccccg ccgccccggg  600
cccacccgca agcattacca gccctatgcc ccaccacgcg acttcgcagc ctatcgctcc  660

SEQ ID NO: 36          moltype = AA  length = 220
FEATURE                Location/Qualifiers
source                 1..220
                       mol_type = protein
                       organism = Synthetic construct
SEQUENCE: 36
MLRLLLALNL FPSIQVTGNK ILVKQSPMLV AYDNAVNLSC KYSYNLFSRE VRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                        220

SEQ ID NO: 37          moltype = DNA  length = 660
FEATURE                Location/Qualifiers
```

```
source                 1..660
                       mol_type = other DNA
                       organism = Synthetic construct
SEQUENCE: 37
atgctcaggc tgctcttggc tctcaactta ttcccttcaa ttcaagtaac aggaaacaag  60
attttggtga agcagtcgcc catgcttgta gcgtacgaca atgcggtcaa ccttagctgc  120
aagtattcct acaatctctt ctcaagggag atccgggcat cccttcacaa aggactggat  180
agtgctgtgg aagtctgtgt tgtatatggg aattactccc agcagcttca ggtttactca  240
aaaacggggt tcaactgtga tgggaaattg ggcaatgaat cagtgacatt ctacctccag  300
aatttgtatg ttaaccaaac agatatttac ttctgcaaaa ttgaagttat gtatcctcct  360
ccttacctag acaatgagaa gagcaatgga accattatcc atgtgaaagg gaaacacctt  420
tgtccaagtc ccctatttcc cggaccttct aagccctttt gggtgctggt ggtggttggt  480
ggagtcctgg cttgctatag cttgctagta acagtggcct ttattatttt ctgggtgagg  540
agtaagagga gcaggctcct gcacagtgac tacatgaaca tgactccccg ccgccccggg  600
cccacccgca agcattacca gccctatgcc ccaccacgcg acttcgcagc ctatcgctcc  660

SEQ ID NO: 38          moltype = AA  length = 220
FEATURE                Location/Qualifiers
source                 1..220
                       mol_type = protein
                       organism = Synthetic construct
SEQUENCE: 38
MLRLLLALNL FPSIQVTGNK ILVKQSPMLV AYDNAVNLSC KYSYNLFSRE IRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                      220

SEQ ID NO: 39          moltype = DNA  length = 660
FEATURE                Location/Qualifiers
source                 1..660
                       mol_type = other DNA
                       organism = Synthetic construct
SEQUENCE: 39
atgctcaggc tgctcttggc tctcaactta ttcccttcaa ttcaagtaac aggaaacaag  60
attttggtga agcagtcgcc catgcttgta gcgtacgaca atgcggtcaa ccttagctgc  120
aagtattcct acaatctctt ctcaagggag ttccgggcat cccttcacaa aggactggat  180
agtgctgtgg aagtctgtgt tgtatatggg aattactccc agcagcttcc ggtttactca  240
aaaacggggt tcaactgtga tgggaaattg ggcaatgaat cagtgacatt ctacctccag  300
aatttgtatg ttaaccaaac agatatttac ttctgcaaaa ttgaagttat gtatcctcct  360
ccttacctag acaatgagaa gagcaatgga accattatcc atgtgaaagg gaaacacctt  420
tgtccaagtc ccctatttcc cggaccttct aagccctttt gggtgctggt ggtggttggt  480
ggagtcctgg cttgctatag cttgctagta acagtggcct ttattatttt ctgggtgagg  540
agtaagagga gcaggctcct gcacagtgac tacatgaaca tgactccccg ccgccccggg  600
cccacccgca agcattacca gccctatgcc ccaccacgcg acttcgcagc ctatcgctcc  660

SEQ ID NO: 40          moltype = AA  length = 220
FEATURE                Location/Qualifiers
source                 1..220
                       mol_type = protein
                       organism = Synthetic construct
SEQUENCE: 40
MLRLLLALNL FPSIQVTGNK ILVKQSPMLV AYDNAVNLSC KYSYNLFSRE FRASLHKGLD  60
SAVEVCVVYG NYSQQLPVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                      220

SEQ ID NO: 41          moltype = DNA  length = 660
FEATURE                Location/Qualifiers
source                 1..660
                       mol_type = genomic DNA
                       organism = Homo sapiens
SEQUENCE: 41
atgctcaggc tgctcttggc tctcaactta ttcccttcaa ttcaagtaac aggaaacaag  60
attttggtga agcagtcgcc catgcttgta gcgtacgaca atgcggtcaa ccttagctgc  120
aagtattcct acaatctctt ctcaagggag ttccgggcat cccttcacaa aggactggat  180
agtgctgtgg aagtctgtgt tgtatatggg aattactccc agcagcttca ggtttactca  240
aaaacggggt tcaactgtga tgggaaattg ggcaatgaat cagtgacatt ctacctccag  300
aatttgtatg ttaaccaaac agatatttac ttctgcaaaa ttgaagttat gtatcctcct  360
ccttacctag acaatgagaa gagcaatgga accattatcc atgtgaaagg gaaacacctt  420
tgtccaagtc ccctatttcc cggaccttct aagccctttt gggtgctggt ggtggttggt  480
ggagtcctgg cttgctatag cttgctagta acagtggcct ttattatttt ctgggtgagg  540
agtaagagga gcaggctcct gcacagtgac tacatgaaca tgactccccg ccgccccggg  600
cccacccgca agcattacca gccctatgcc ccaccacgcg acttcgcagc ctatcgctcc  660

SEQ ID NO: 42          moltype = AA  length = 220
FEATURE                Location/Qualifiers
source                 1..220
                       mol_type = protein
                       organism = Homo sapiens
```

```
SEQUENCE: 42
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                       220

SEQ ID NO: 43          moltype = DNA  length = 660
FEATURE                Location/Qualifiers
source                 1..660
                       mol_type = other DNA
                       organism = Synthetic construct
SEQUENCE: 43
atgctcaggc tgctcttggc tctcaactta ttcccttcaa ttcaagtaac aggaaacaag  60
attttggtga agcagtcgcc catgcttgta gcgtacgaca atgcggtcaa ccttagctgc  120
aagtattcct acaatctctt ctcaagggag ttccgggcat cccttcacaa aggactggat  180
agtgctgtgg aagtctgtgt tgtatatggg aattactccc agcagcttca ggtttactca  240
aaaacggggt tcaactgtga tgggaaattg ggcaatgaat cagtgacatt ctacctccag  300
aatttgtatg ttaaccaaac agatatttac ttctgcaaaa ttgaagttat gtatcctcct  360
ccttacctag acaatgagaa gagcaatgga accattatcc atgtgaaagg gaaacacctt  420
tgtccaagtc ccctatttcc cggaccttct aagccctttt gggtgctggt ggtggttggt  480
ggagtcctgg cttgctatag cttgctagta acagtggcct ttattatttt ctgggtgagg  540
agtaagagga gcaggctcct gcacagtgac tacatgaaca tgcctccccg ccgccccggg  600
cccacccgca agcattacca gccctatgcc ccaccacgcg acttcgcagc ctatcgctcc  660

SEQ ID NO: 44          moltype = AA  length = 220
FEATURE                Location/Qualifiers
source                 1..220
                       mol_type = protein
                       organism = Synthetic construct
SEQUENCE: 44
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMPPRRPG PTRKHYQPYA PPRDFAAYRS                       220

SEQ ID NO: 45          moltype = DNA  length = 621
FEATURE                Location/Qualifiers
source                 1..621
                       mol_type = genomic DNA
                       organism = Homo sapiens
SEQUENCE: 45
atgcagtcgg gcactcactg gagagttctg ggcctctgcc tcttatcagt tggcgtttgg  60
gggcaagatg gtaatgaaga aatgggtggt attacacaga caccatataa agtctccatc  120
tctggaacca cagtaatatt gacatgccct cagtatcctg gatctgaaat actatggcaa  180
cacaatgata aaaacatagg cggtgatgag gatgataaaa acataggcag tgatgaggat  240
cacctgtcac tgaaggaatt ttcagaattg gagcaaagtg gttattatgt ctgctacccc  300
agaggaagca aaccagaaga tgcgaacttt tatctctacc tgagggcaag agtgtgtgag  360
aactgcatgg agatggatgt gatgtcggta gccacaattg tcatagtgga catctgcatc  420
actgggggct tgctgctgct ggtttactac tggagcaaga atagaaaggc caaggccaag  480
cctgtgacac gaggagcagg tgctggcggc aggcaaaggg gacaaaacaa ggagaggcca  540
ccacctgttc ccaacccaga ctatgagccc atccggaaag gccagcggga cctgtattct  600
ggcctgaatc agagacgcat c                                           621

SEQ ID NO: 46          moltype = AA  length = 207
FEATURE                Location/Qualifiers
source                 1..207
                       mol_type = protein
                       organism = Homo sapiens
SEQUENCE: 46
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                     207

SEQ ID NO: 47          moltype = DNA  length = 621
FEATURE                Location/Qualifiers
source                 1..621
                       mol_type = other DNA
                       organism = Synthetic construct
SEQUENCE: 47
atgcagtcgg gcactcactg gagagttctg ggcctctgcc tcttatcagt tggcgtttgg  60
gggcaagatg gtaatgaaga aatgggtggt attacacaga caccatataa agtctccatc  120
tgcggaacca cagtaatatt gacatgccct cagtatcctg gatctgaaat actatggcaa  180
cacaatgata aaaacatagg cggtgatgag gatgataaaa acataggcag tgatgaggat  240
cacctgtcac tgaaggaatt ttcagaattg gagcaaagtg gttattatgt ctgctacccc  300
agaggaagca aaccagaaga tgcgaacttt tatctctacc tgagggcaag agtgtgtgag  360
aactgcatgg agatggatgt gatgtcggta gccacaattg tcatagtgga catctgcatc  420
actgggggct tgctgctgct ggtttactac tggagcaaga atagaaaggc caaggccaag  480
cctgtgacac gaggagcagg tgctggcggc aggcaaaggg gacaaaacaa ggagaggcca  540
```

```
ccacctgttc ccaacccaga ctatgagccc atccggaaag gccagcggga cctgtattct  600
ggcctgaatc agagacgcat c                                            621

SEQ ID NO: 48          moltype = AA  length = 207
FEATURE                Location/Qualifiers
source                 1..207
                       mol_type = protein
                       organism = Synthetic construct
SEQUENCE: 48
MQSGTHWRVL GLCLLSVGVW GQDGNEEMGG ITQTPYKVSI CGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                      207

SEQ ID NO: 49          moltype = DNA  length = 1011
FEATURE                Location/Qualifiers
source                 1..1011
                       mol_type = genomic DNA
                       organism = Homo sapiens
SEQUENCE: 49
atggcgagta gcagcggctc caaggctgaa ttcattgtcg gagggaaata taaactggta  60
cggaagatcg ggtctggctc cttcggggac atctatttgg cgatcaacat caccaacggc  120
gaggaagtgg cagtgaagct agaatctcag aaggccaggc atccccagtt gctgtacgag  180
agcaagctct ataagattct tcaaggtggg gttggcatcc cccacatacg gtggtatggt  240
caggaaaaag actacaatgt actagtcatg gatcttctgg gacctagcct cgaagacctc  300
ttcaatttct gttcaagaag gttcacaatg aaaactgtac ttatgttagc tgaccagatg  360
atcagtagaa ttgaatatgt gcatacaaag aattttatac acagagacat taaaccagat  420
aacttcctaa tgggtattgg gcgtcactgt aataagttat tccttattga ttttggtttg  480
gccaaaaagt acagagacaa caggacaagg caacacatac catacagaga agataaaaac  540
ctcactggca ctgcccgata tgctagcatc aatgcacatc ttggtattga gcagagtcgc  600
cgagatgaca tggaatcatt aggatatgtt ttgatgtatt ttaatagaac cagcctgcca  660
tggcaagggc taaaggctgc aacaaagaaa aaaaaatatg aaaagattag tgaaaagaag  720
atgtccacgc ctgttgaagt tttatgtaag ggtttcctg cagaatttgc gatgtactta  780
aactattgtc gtgggctacg ctttgaggaa gccccagatt acatgtatct gaggcagcta  840
ttccgcattc ttttcaggac cctgaaccat caatatgact acacatttga ttggacaatg  900
ttaaagcaga aagcagcaca gcaggcagcc tcttccagtg ggcagggtca gcaggcccaa  960
acccccacag gcaagcaaac tgacaaaacc aagagtaaca tgaaaggttt c           1011

SEQ ID NO: 50          moltype = AA  length = 337
FEATURE                Location/Qualifiers
source                 1..337
                       mol_type = protein
                       organism = Homo sapiens
SEQUENCE: 50
MASSSGSKAE FIVGGKYKLV RKIGSGSFGD IYLAINITNG EEVAVKLESQ KARHPQLLYE  60
SKLYKILQGG VGIPHIRWYG QEKDYNVLVM DLLGPSLEDL FNFCSRRFTM KTVLMLADQM  120
ISRIEYVHTK NFIHRDIKPD NFLMGIGRHC NKLFLIDFGL AKKYRDNRTR QHIPYREDKN  180
LTGTARYASI NAHLGIEQSR RDDMESLGYV LMYFNRTSLP WQGLKAATKK KKYEKISEKK  240
MSTPVEVLCK GFPAEFAMYL NYCRGLRFEE APDYMYLRQL FRILFRTLNH QYDYTFDWTM  300
LKQKAAQQAA SSSGQGQQAQ TPTGKQTDKT KSNMKGF                            337

SEQ ID NO: 51          moltype = DNA  length = 1011
FEATURE                Location/Qualifiers
source                 1..1011
                       mol_type = other DNA
                       organism = Synthetic construct
SEQUENCE: 51
atggcgagta gcagcggctc caaggctgaa ttcattgtcg gagggaaata taaactggta  60
cggaagatcg ggtctggctg cttcggggac atctatttgg cgatcaacat caccaacggc  120
gaggaagtgg cagtgaagct agaatctcag aaggccaggc atccccagtt gctgtacgag  180
agcaagctct ataagattct tcaaggtggg gttggcatcc cccacatacg gtggtatggt  240
caggaaaaag actacaatgt actagtcatg gatcttctgg gacctagcct cgaagacctc  300
ttcaatttct gttcaagaag gttcacaatg aaaactgtac ttatgttagc tgaccagatg  360
atcagtagaa ttgaatatgt gcatacaaag aattttatac acagagacat taaaccagat  420
aacttcctaa tgggtattgg gcgtcactgt aataagttat tccttattga ttttggtttg  480
gccaaaaagt acagagacaa caggacaagg caacacatac catacagaga agataaaaac  540
ctcactggca ctgcccgata tgctagcatc aatgcacatc ttggtattga gcagagtcgc  600
cgagatgaca tggaatcatt aggatatgtt ttgatgtatt ttaatagaac cagcctgcca  660
tggcaagggc taaaggctgc aacaaagaaa aaaaaatatg aaaagattag tgaaaagaag  720
atgtccacgc ctgttgaagt tttatgtaag ggtttcctg cagaatttgc gatgtactta  780
aactattgtc gtgggctacg ctttgaggaa gccccagatt acatgtatct gaggcagcta  840
ttccgcattc ttttcaggac cctgaaccat caatatgact acacatttga ttggacaatg  900
ttaaagcaga aagcagcaca gcaggcagcc tcttccagtg ggcagggtca gcaggcccaa  960
acccccacag gcaagcaaac tgacaaaacc aagagtaaca tgaaaggttt c           1011

SEQ ID NO: 52          moltype = AA  length = 337
FEATURE                Location/Qualifiers
source                 1..337
                       mol_type = protein
```

```
                          organism = Synthetic construct
SEQUENCE: 52
MASSSGSKAE FIVGGKYKLV RKIGSGCFGD IYLAINITNG EEVAVKLESQ KARHPQLLYE  60
SKLYKILQGG VGIPHIRWYG QEKDYNVLVM DLLGPSLEDL FNFCSRRFTM KTVLMLADQM  120
ISRIEYVHTK NFIHRDIKPD NFLMGIGRHC NKLFLIDFGL AKKYRDNRTR QHIPYREDKN  180
LTGTARYASI NAHLGIEQSR RDDMESLGYV LMYFNRTSLP WQGLKAATKK KKYEKISEKK  240
MSTPVEVLCK GFPAEFAMYL NYCRGLRFEE APDYMYLRQL FRILFRTLNH QYDYTFDWTM  300
LKQKAAQQAA SSSGQGQQAQ TPTGKQTDKT KSNMKGF                          337

SEQ ID NO: 53             moltype = DNA  length = 645
FEATURE                   Location/Qualifiers
source                    1..645
                          mol_type = genomic DNA
                          organism = Homo sapiens
SEQUENCE: 53
atgagcagct cagaggaggt gtcctggatt tcctggttct gtgggctccg tggcaatgaa  60
ttcttctgtg aagtggatga agactacatc caggacaaat ttaatcttac tggactcaat  120
gagcaggtcc ctcactatcg acaagctcta gacatgatct tggacctgga gcctgatgaa  180
gaactggaag acaaccccaa ccagagtgac ctgattgagc aggcagccga gatgctttat  240
ggattgatcc acgcccgcta catccttacc aaccgtggca tcgcccagat gttggaaaag  300
taccagcaag gagactttgg ttactgtcct cgtgtgtact gtgagaacca gccaatgctt  360
cccattggcc tttcagacat cccaggtgaa gccatggtga agctctactg ccccaagtgc  420
atggatgtgt acacacccaa gtcatcaaga caccatcaca cggatggcgc ctacttcggc  480
actggtttcc ctcacatgct cttcatggtg catcccgagt accggcccaa gagacctgcc  540
aaccagtttg tgcccaggct ctacggtttc aagatccatc cgatggccta ccagctgcag  600
ctccaagccg ccagcaactt caagagccca gtcaagacga ttcgc                 645

SEQ ID NO: 54             moltype = AA  length = 215
FEATURE                   Location/Qualifiers
source                    1..215
                          mol_type = protein
                          organism = Homo sapiens
SEQUENCE: 54
MSSSEEVSWI SWFCGLRGNE FFCEVDEDYI QDKFNLTGLN EQVPHYRQAL DMILDLEPDE  60
ELEDNPNQSD LIEQAAEMLY GLIHARYILT NRGIAQMLEK YQQGDFGYCP RVYCENQPML  120
PIGLSDIPGE AMVKLYCPKC MDVYTPKSSR HHHTDGAYFG TGFPHMLFMV HPEYRPKRPA  180
NQFVPRLYGF KIHPMAYQLQ LQAASNFKSP VKTIR                            215

SEQ ID NO: 55             moltype = DNA  length = 543
FEATURE                   Location/Qualifiers
source                    1..543
                          mol_type = other DNA
                          organism = Synthetic construct
SEQUENCE: 55
atgagcagct cagaggaggt gtcctggatt tcctggttct gtgggctccg tggcaatgaa  60
ttcttctgtg aagtggatga agactacatc caggacaaat ttaatcttac tggactcaat  120
gagcaggtcc ctcactatcg acaagctcta gacatgatct tggacctgga gcctgatgaa  180
gaactggaag acaaccccaa ccagagtgac ctgattgagc aggcagccga gatgctttat  240
ggattgatcc acgcccgcta catccttacc aaccgtggca tcgcccagat gttggaaaag  300
taccagcaag gagactttgg ttactgtcct cgtgtgtact gtgagaacca gccaatgctt  360
cccattggcc tttcagacat cccaggtgaa gccatggtga agctctactg ccccaagtgc  420
atggatgtgt acacacccaa gtcatcaaga caccatcaca cggatggcgc ctacttcggc  480
actggtttcc ctcacatgct cttcatggtg catcccgagt accggcccaa gagacctgcc  540
aac                                                               543

SEQ ID NO: 56             moltype = AA  length = 181
FEATURE                   Location/Qualifiers
source                    1..181
                          mol_type = protein
                          organism = Synthetic construct
SEQUENCE: 56
MSSSEEVSWI SWFCGLRGNE FFCEVDEDYI QDKFNLTGLN EQVPHYRQAL DMILDLEPDE  60
ELEDNPNQSD LIEQAAEMLY GLIHARYILT NRGIAQMLEK YQQGDFGYCP RVYCENQPML  120
PIGLSDIPGE AMVKLYCPKC MDVYTPKSSR HHHTDGAYFG TGFPHMLFMV HPEYRPKRPA  180
N                                                                 181

SEQ ID NO: 57             moltype = DNA  length = 1293
FEATURE                   Location/Qualifiers
source                    1..1293
                          mol_type = other DNA
                          organism = Synthetic construct
SEQUENCE: 57
atgagctggg tccaggccac cctactggcc cgaggcctct gtagggcctg gggaggcacc  60
tgcggggccg ccctcacagg aacctccatc tctcaggtcc ctcgccggct ccctcggggc  120
ctccactgca gcgcagctgc ccatagctct gaacagtccc tggttcccag cccaccggaa  180
ccccggcaga ggcccaccaa ggctctggtg ccctttgagg acctgtttgg gcaggcgcct  240
ggtggggaac gggacaaggc gagcttcctg cagacggtgc agaaatttgc ggagcacagc  300
gtgcgtaagc ggggccacat tgacttcatc tacctggccc tgcgcaagat gcgggagtat  360
ggtgtcgagc gggacctggc tgtgtacaac cagctgctca acatcttccc caaggaggcc  420
```

```
ttccggcctc gcaacatcat ccagcgcatc ttcgtccact accctcggca gcaggagtgt  480
gggattgctg tcctggagca gatggagaac cacggtgtga tgcccaacaa ggagacggag  540
ttcctgctga ttcagatctt tggacgcaaa agctacccca tgctcaagtt ggtgcgcctg  600
aagctgtggt tccctcgatt catgaacgtc aaccccttcc cagtgccccg ggacctgccc  660
caggaccctg tggagctggc catgtttggc ctgcggcaca tggagcctga ccttagtgcc  720
agggtcacca tctaccaggt tcctttgccc aaagactcaa caggtgcagc agatcccccc  780
cagccccaca tcgtaggaat ccagagtccc gatcagcagg ccgccctggc ccgccacaat  840
ccagcccggc ctgtctttgt tgagggcccc ttctccctgt ggctccgcaa caagtgtgtg  900
tattaccaca tcctcagagc tgacttgctg cccccggagg agagggaagt ggaagagacg  960
ccggaggagt ggaacctcta ctacccgatg cagctggacc tggagtatgt gaggagtggc  1020
tgggacaact acgagtttga catcaatgaa gtggaggaag gccctgtctt cgccatgtgc  1080
atggcgggtg ctcatgacca ggcgacgatg gctaagtgga tccagggcct gcaggagacc  1140
aacccaaccc tggcccagat ccccgtggtc ttccgcctcg ccgggtccac ccgggagctc  1200
cagacatcct ctgcagggct ggaggagccg cccctgcccg aggaccacca ggaagaagac  1260
gacaacctgc agcgacagca gcagggccag agc                              1293
```

```
SEQ ID NO: 58           moltype = AA  length = 431
FEATURE                 Location/Qualifiers
source                  1..431
                        mol_type = protein
                        organism = Synthetic construct
SEQUENCE: 58
MSWVQATLLA RGLCRAWGGT CGAALTGTSI SQVPRRLPRG LHCSAAAHSS EQSLVPSPPE  60
PRQRPTKALV PFEDLFGQAP GGERDKASFL QTVQKFAEHS VRKRGHIDFI YLALRKMREY  120
GVERDLAVYN QLLNIFPKEA FRPRNIIQRI FVHYPRQQEC GIAVLEQMEN HGVMPNKETE  180
FLLIQIFGRK SYPMLKLVRL KLWFPRFMNV NPFPVPRDLP QDPVELAMFG LRHMEPDLSA  240
RVTIYQVPLP KDSTGAADPP QPHIVGIQSP DQQAALARHN PARPVFVEGP FSLWLRNKCV  300
YYHILRADLL PPEEREVEET PEEWNLYYPM QLDLEYVRSG WDNYEFDINE VEEGPVFAMC  360
MAGAHDQATM AKWIQGLQET NPTLAQIPVV FRLAGSTREL QTSSAGLEEP PLPEDHQEED  420
DNLQRQQQGQ S                                                       431
```

```
SEQ ID NO: 59           moltype = DNA  length = 1293
FEATURE                 Location/Qualifiers
source                  1..1293
                        mol_type = genomic DNA
                        organism = Homo sapiens
SEQUENCE: 59
atgagctggg tccaggccac cctactggcc cgaggcctct gtagggcctg ggaggcacc  60
tgcggggccg ccctcacagg aacctccatc tctcaggtcc ctcgccggct ccctcggggc  120
ctccactgca gcgcagctgc ccatagctct gaacagtccc tggttcccag cccaccggaa  180
ccccggcaga ggcccaccaa ggctctggtg ccctttgagg acctgtttgg gcaggcgcct  240
ggtggggaac gggacaaggc gagcttcctg cagacggtgc agaaatttgc ggagcacagc  300
gtgcgtaagc ggggccacat tgacttcatc tacctggccc tgcgcaagat gcgggagtat  360
ggtgtcgagc gggacctggc tgtgtacaac cagctgctca acatcttccc caaggaggtc  420
ttccggcctc gcaacatcat ccagcgcatc ttcgtccact accctcggca gcaggagtgt  480
gggattgctg tcctggagca gatggagaac cacggtgtga tgcccaacaa ggagacggag  540
ttcctgctga ttcagatctt tggacgcaaa agctacccca tgctcaagtt ggtgcgcctg  600
aagctgtggt tccctcgatt catgaacgtc aaccccttcc cagtgccccg ggacctgccc  660
caggaccctg tggagctggc catgtttggc ctgcggcaca tggagcctga ccttagtgcc  720
agggtcacca tctaccaggt tcctttgccc aaagactcaa caggtgcagc agatcccccc  780
cagccccaca tcgtaggaat ccagagtccc gatcagcagg ccgccctggc ccgccacaat  840
ccagcccggc ctgtctttgt tgagggcccc ttctccctgt ggctccgcaa caagtgtgtg  900
tattaccaca tcctcagagc tgacttgctg cccccggagg agagggaagt ggaagagacg  960
ccggaggagt ggaacctcta ctacccgatg cagctggacc tggagtatgt gaggagtggc  1020
tgggacaact acgagtttga catcaatgaa gtggaggaag gccctgtctt cgccatgtgc  1080
atggcgggtg ctcatgacca ggcgacgatg gctaagtgga tccagggcct gcaggagacc  1140
aacccaaccc tggcccagat ccccgtggtc ttccgcctcg ccgggtccac ccgggagctc  1200
cagacatcct ctgcagggct ggaggagccg cccctgcccg aggaccacca ggaagaagac  1260
gacaacctgc agcgacagca gcagggccag agc                              1293
```

```
SEQ ID NO: 60           moltype = AA  length = 431
FEATURE                 Location/Qualifiers
source                  1..431
                        mol_type = protein
                        organism = Homo sapiens
SEQUENCE: 60
MSWVQATLLA RGLCRAWGGT CGAALTGTSI SQVPRRLPRG LHCSAAAHSS EQSLVPSPPE  60
PRQRPTKALV PFEDLFGQAP GGERDKASFL QTVQKFAEHS VRKRGHIDFI YLALRKMREY  120
GVERDLAVYN QLLNIFPKEV FRPRNIIQRI FVHYPRQQEC GIAVLEQMEN HGVMPNKETE  180
FLLIQIFGRK SYPMLKLVRL KLWFPRFMNV NPFPVPRDLP QDPVELAMFG LRHMEPDLSA  240
RVTIYQVPLP KDSTGAADPP QPHIVGIQSP DQQAALARHN PARPVFVEGP FSLWLRNKCV  300
YYHILRADLL PPEEREVEET PEEWNLYYPM QLDLEYVRSG WDNYEFDINE VEEGPVFAMC  360
MAGAHDQATM AKWIQGLQET NPTLAQIPVV FRLAGSTREL QTSSAGLEEP PLPEDHQEED  420
DNLQRQQQGQ S                                                       431
```

```
SEQ ID NO: 61           moltype = DNA  length = 945
FEATURE                 Location/Qualifiers
source                  1..945
                        mol_type = other DNA
```

```
                         organism = Synthetic construct
SEQUENCE: 61
atgccgggtc taagttgtag attttatcaa cacaaatttc ctgaggtgga agatgtagtg  60
atggtgaatg tcagatccat tgctgaaatg ggggcttatg tcagcttgct ggaatacaac  120
aacattgaag gcatgattct tcttagtgaa ttatccagaa ggcgtatccg ttctatcaac  180
aaactcatcc gaattggcag gaatgagtgt gtggttgtca ttagggtgga caaagaaaaa  240
ggatatattg atttgtcaaa aagaatcgtt tctccagagg aagcaatcaa atgtgaagac  300
aaattcacaa aatccaaaac tgtttatagc attcttcgtc atgttgctga ggtgttagaa  360
tacaccaagg atgagcagct ggaaagccta ttccagagga ctgcctgggt ctttgatgac  420
aagtacaaga gacctggata tggtgcctat gatgcattta agcatgcagt ctcagaccca  480
tctattttgg atagtttaga tttgaatgaa gatgaacggg aagtactcat taataatatt  540
aataggcgct tgaccccaca ggctgtcaaa attcgagcag atattgaagt ggcttgttat  600
ggttatgaag gcattgatgc tgtaaaagaa gccctaagag caggtttgaa ttgttctaca  660
gaaaacatgc ccattaagat taatctaata gctcctcctc ggtatgtaat gactacgaca  720
accctggaga gaacagaagg cctttctgtc ctcagtcaag ctatggctgt tatcaaagag  780
aagattgagg aaaagagggg tgtgttcaat gttcaaatgg agcccaaagt ggtcacagat  840
acagatgaga ctgaacttgc gaggcagatg gagaggcttg aaagagaaaa tgccgaagtg  900
gatggagatg atgatgcaga agaaatggaa gccaaagctg aagat                  945

SEQ ID NO: 62            moltype = AA  length = 315
FEATURE                  Location/Qualifiers
source                   1..315
                         mol_type = protein
                         organism = Synthetic construct
SEQUENCE: 62
MPGLSCRFYQ HKFPEVEDVV MVNVRSIAEM GAYVSLLEYN NIEGMILLSE LSRRRIRSIN  60
KLIRIGRNEC VVVIRVDKEK GYIDLSKRIV SPEEAIKCED KFTKSKTVYS ILRHVAEVLE  120
YTKDEQLESL FQRTAWVFDD KYKRPGYGAY DAFKHAVSDP SILDSLDLNE DEREVLINNI  180
NRRLTPQAVK IRADIEVACY GYEGIDAVKE ALRAGLNCST ENMPIKINLI APPRYVMTTT  240
TLERTEGLSV LSQAMAVIKE KIEEKRGVFN VQMEPKVVTD TDETELARQM ERLERENAEV  300
DGDDDAEEME AKAED                                                   315

SEQ ID NO: 63            moltype = DNA  length = 945
FEATURE                  Location/Qualifiers
source                   1..945
                         mol_type = genomic DNA
                         organism = Homo sapiens
SEQUENCE: 63
atgccgggtc taagttgtag attttatcaa cacaaatttc ctgaggtgga agatgtagtg  60
atggtgaatg tcagatccat tgctgaaatg ggggcttatg tcagcttgct ggaatacaac  120
aacattgaag gcatgattct tcttagtgaa ttatccagaa ggcgtatccg ttctatcaac  180
aaactcatcc gaattggcag gaatgagtgt gtggttgtca ttagggtgga caaagaaaaa  240
ggatatattg atttgtcaaa aagaagagtt tctccagagg aagcaatcaa atgtgaagac  300
aaattcacaa aatccaaaac tgtttatagc attcttcgtc atgttgctga ggtgttagaa  360
tacaccaagg atgagcagct ggaaagccta ttccagagga ctgcctgggt ctttgatgac  420
aagtacaaga gacctggata tggtgcctat gatgcattta agcatgcagt ctcagaccca  480
tctattttgg atagtttaga tttgaatgaa gatgaacggg aagtactcat taataatatt  540
aataggcgct tgaccccaca ggctgtcaaa attcgagcag atattgaagt ggcttgttat  600
ggttatgaag gcattgatgc tgtaaaagaa gccctaagag caggtttgaa ttgttctaca  660
gaaaacatgc ccattaagat taatctaata gctcctcctc ggtatgtaat gactacgaca  720
accctggaga gaacagaagg cctttctgtc ctcagtcaag ctatggctgt tatcaaagag  780
aagattgagg aaaagagggg tgtgttcaat gttcaaatgg agcccaaagt ggtcacagat  840
acagatgaga ctgaacttgc gaggcagatg gagaggcttg aaagagaaaa tgccgaagtg  900
gatggagatg atgatgcaga agaaatggaa gccaaagctg aagat                  945

SEQ ID NO: 64            moltype = AA  length = 315
FEATURE                  Location/Qualifiers
source                   1..315
                         mol_type = protein
                         organism = Homo sapiens
SEQUENCE: 64
MPGLSCRFYQ HKFPEVEDVV MVNVRSIAEM GAYVSLLEYN NIEGMILLSE LSRRRIRSIN  60
KLIRIGRNEC VVVIRVDKEK GYIDLSKRRV SPEEAIKCED KFTKSKTVYS ILRHVAEVLE  120
YTKDEQLESL FQRTAWVFDD KYKRPGYGAY DAFKHAVSDP SILDSLDLNE DEREVLINNI  180
NRRLTPQAVK IRADIEVACY GYEGIDAVKE ALRAGLNCST ENMPIKINLI APPRYVMTTT  240
TLERTEGLSV LSQAMAVIKE KIEEKRGVFN VQMEPKVVTD TDETELARQM ERLERENAEV  300
DGDDDAEEME AKAED                                                   315

SEQ ID NO: 65            moltype = DNA  length = 1614
FEATURE                  Location/Qualifiers
source                   1..1614
                         mol_type = other DNA
                         organism = Synthetic construct
SEQUENCE: 65
atgggctgtg tgcaatgtaa ggataaagaa gcaacaaaac tgacggagga gagggacggc  60
agcctgaacc agagctctgg gtaccgctat ggcacagacc ccacccctca gcactacccc  120
agcttcggtg tgacctccat ccccaactac aacaacttcc acgcagccgg gggccaagga  180
ctcaccgtct ttggaggtgt gaactcttcg tctcatacgg ggaccttgcg tacgagagga  240
ggaacaggag tgacactctt tgtggccctt tatgactatg aagcagggac agaagatgac  300
```

-continued

```
ctgagttttc acaaaggaga aaaatttcaa atattgaaca gctcggaagg agattggtgg  360
gaagcccgct ccttgacaac tggagagaca ggttacattc ccagcaatta tgtggctcca  420
gttgactcta tccaggcaga agagtggtac tttggaaaac ttggccgaaa agatgctgag  480
cgacagctat tgtcctttgg aaacccaaga ggtacctttc ttatccgcga gagtgaaacc  540
accaaaggtg cctattcact ttctatccgt gattgggatg atatgaaagg agaccatgtc  600
aaacattata aaattcgcaa acttgacaat ggtggatact acattaccac ccgggcccag  660
tttgaaacac ttcagcagct tgtacaacat tactcagaga gagctgcagg tctctgctgc  720
cgcctagtag ttccctgtca caaagggatg ccaaggctta ccgatctgtc tgtcaaaacc  780
aaagatgtct gggaaatccc tcgagaatcc ctgcagttga tcaagagact gggaaatggg  840
cagtttgggg aagtatggat gggtacctgg aatggaaaca caaaagtagc cataaagact  900
cttaaaccag gcacaatgtc cccgaatca ttccttgagg aagcgcagat catgaagaag  960
ctgaagcacg acaagctggt ccagctctat gcagtggtgt ctgaggagcc catctacatc  1020
gtcaccgagt atatgaacaa aggaagttta ctggatttct taaaagatgg agaaggaaga  1080
gctctgaaat taccaaatct tgtggacatg gcagcacagg tggctgcagg aatggcttac  1140
atcgagcgca tgaattatat ccatagagat ctgcgatcag caaacattct agtggggaat  1200
ggactcatat gcaagattgc tgacttcgga ttggcccgat tgatagaaga caatgagtac  1260
acagcaagac aaggtgcaaa gttccccatc aagtggacgg cccccgaggc agccctgtac  1320
gggaggttca caatcaagtc tgacgtgtgg tcttttggaa tcttactcac agagctggtc  1380
accaaaggaa gagtgccata cccaggcatg aacaaccggg aggtgctgga gcaggtggag  1440
cgaggctaca ggatgccctg cccgcaggac tgccccatct ctctgcatga gctcatgatc  1500
cactgctgga aaaaggaccc tgaagaacgc cccacttttg agtacttgca gagcttcctg  1560
gaagactact ttaccgcgac agagccccag tacaaacctg gtgaaaacct gttg        1614

SEQ ID NO: 66          moltype = AA  length = 538
FEATURE                Location/Qualifiers
source                 1..538
                       mol_type = protein
                       organism = Synthetic construct
SEQUENCE: 66
MGCVQCKDKE ATKLTEERDG SLNQSSGYRY GTDPTPQHYP SFGVTSIPNY NNFHAAGGQG  60
LTVFGGVNSS SHTGTLRTRG GTGVTLFVAL YDYEAGTEDD LSFHKGEKFQ ILNSSEGDWW  120
EARSLTTGET GYIPSNYVAP VDSIQAEEWY FGKLGRKDAE RQLLSFGNPR GTFLIRESET  180
TKGAYSLSIR DWDDMKGDHV KHYKIRKLDN GGYYITTRAQ FETLQQLVQH YSERAAGLCC  240
RLVVPCHKGM PRLTDLSVKT KDVWEIPRES LQLIKRLGNG QFGEVWMGTW NGNTKVAIKT  300
LKPGTMSPES FLEEAQIMKK LKHDKLVQLY AVVSEEPIYI VTEYMNKGSL LDFLKDGEGR  360
ALKLPNLVDM AAQVAAGMAY IERMNYIHRD LRSANILVGN GLICKIADFG LARLIEDNEY  420
TARQGAKFPI KWTAPEAALY GRFTIKSDVW SFGILLTELV TKGRVPYPGM NNREVLEQVE  480
RGYRMPCPQD CPISLHELMI HCWKKDPEER PTFEYLQSFL EDYFTATEPQ YKPGENLL    538

SEQ ID NO: 67          moltype = DNA  length = 1614
FEATURE                Location/Qualifiers
source                 1..1614
                       mol_type = genomic DNA
                       organism = Homo sapiens
SEQUENCE: 67
atgggctgtg tgcaatgtaa ggataaagaa gcaacaaaac tgacggagga gagggacggc  60
agcctgaacc agagctctgg gtaccgctat ggcacagacc ccacccctca gcactacccc  120
agcttcggtg tgacctccat ccccaactac aacaacttcc acgcagccgg gggccaagga  180
ctcaccgtct ttggaggtgt gaactcttcg tctcatacgg ggaccttgcg tacgagagga  240
ggaacaggag tgacactctt tgtggccctt tatgactatg aagcacggac agaagatgac  300
ctgagttttc acaaaggaga aaaatttcaa atattgaaca gctcggaagg agattggtgg  360
gaagcccgct ccttgacaac tggagagaca ggttacattc ccagcaatta tgtggctcca  420
gttgactcta tccaggcaga agagtggtac tttggaaaac ttggccgaaa agatgctgag  480
cgacagctat tgtcctttgg aaacccaaga ggtacctttc ttatccgcga gagtgaaacc  540
accaaaggtg cctattcact ttctatccgt gattgggatg atatgaaagg agaccatgtc  600
aaacattata aaattcgcaa acttgacaat ggtggatact acattaccac ccgggcccag  660
tttgaaacac ttcagcagct tgtacaacat tactcagaga gagctgcagg tctctgctgc  720
cgcctagtag ttccctgtca caaagggatg ccaaggctta ccgatctgtc tgtcaaaacc  780
aaagatgtct gggaaatccc tcgagaatcc ctgcagttga tcaagagact gggaaatggg  840
cagtttgggg aagtatggat gggtacctgg aatggaaaca caaaagtagc cataaagact  900
cttaaaccag gcacaatgtc cccgaatca ttccttgagg aagcgcagat catgaagaag  960
ctgaagcacg acaagctggt ccagctctat gcagtggtgt ctgaggagcc catctacatc  1020
gtcaccgagt atatgaacaa aggaagttta ctggatttct taaaagatgg agaaggaaga  1080
gctctgaaat taccaaatct tgtggacatg gcagcacagg tggctgcagg aatggcttac  1140
atcgagcgca tgaattatat ccatagagat ctgcgatcag caaacattct agtggggaat  1200
ggactcatat gcaagattgc tgacttcgga ttggcccgat tgatagaaga caatgagtac  1260
acagcaagac aaggtgcaaa gttccccatc aagtggacgg cccccgaggc agccctgtac  1320
gggaggttca caatcaagtc tgacgtgtgg tcttttggaa tcttactcac agagctggtc  1380
accaaaggaa gagtgccata cccaggcatg aacaaccggg aggtgctgga gcaggtggag  1440
cgaggctaca ggatgccctg cccgcaggac tgccccatct ctctgcatga gctcatgatc  1500
cactgctgga aaaaggaccc tgaagaacgc cccacttttg agtacttgca gagcttcctg  1560
gaagactact ttaccgcgac agagccccag tacaaacctg gtgaaaacct gttg        1614

SEQ ID NO: 68          moltype = AA  length = 538
FEATURE                Location/Qualifiers
source                 1..538
                       mol_type = protein
                       organism = Homo sapiens
SEQUENCE: 68
```

-continued

```
MGCVQCKDKE ATKLTEERDG SLNQSSGYRY GTDPTPQHYP SFGVTSIPNY NNFHAAGGQG  60
LTVFGGVNSS SHTGTLRTRG GTGVTLFVAL YDYEARTEDD LSFHKGEKFQ ILNSSEGDWW  120
EARSLTTGET GYIPSNYVAP VDSIQAEEWY FGKLGRKDAE RQLLSFGNPR GTFLIRESET  180
TKGAYSLSIR DWDDMKGDHV KHYKIRKLDN GGYYITTRAQ FETLQQLVQH YSERAAGLCC  240
RLVVPCHKGM PRLTDLSVKT KDVWEIPRES LQLIKRLGNG QFGEVWMGTW NGNTKVAIKT  300
LKPGTMSPES FLEEAQIMKK LKHDKLVQLY AVVSEEPIYI VTEYMNKGSL LDFLKDGEGR  360
ALKLPNLVDM AAQVAAGMAY IERMNYIHRD LRSANILVGN GLICKIADFG LARLIEDNEY  420
TARQGAKFPI KWTAPEAALY GRFTIKSDVW SFGILLTELV TKGRVPYPGM NNREVLEQVE  480
RGYRMPCPQD CPISLHELMI HCWKKDPEER PTFEYLQSFL EDYFTATEPQ YKPGENLL    538

SEQ ID NO: 69          moltype = DNA  length = 1614
FEATURE                Location/Qualifiers
source                 1..1614
                       mol_type = other DNA
                       organism = Synthetic construct
SEQUENCE: 69
atgggctgtg tgcaatgtaa ggataaagaa gcaacaaaac tgacggagga gagggacggc  60
agcctgaacc agagctctgg gtaccgctat ggcacagacc ccacccctca gcactacccc  120
agcttcggtg tgacctccat ccccaactac aacaacttcc acgcagccgg gggccaagga  180
ctcaccgtct ttggaggtgt gaactcttcg tctcatacgg ggaccttgcg tacgagagga  240
ggaacaggag tgacactctt tgtggccctt tatgactatg aagcacggac agaagatgac  300
ctgagttttc acaaaggaga aaaatttcaa atattgaaca gctcggaagg agattggtgg  360
gaagcccgct ccttgacaac tggagagaca ggttacattc ccagcaatta tgtggctcca  420
gttgactcta tccaggcaga agagtggtac tttggaaaac ttggccgaaa agatgctgag  480
cgacagctat tgtcctttgg aaacccaaga ggtacctttc ttatccgcga gagtgaaacc  540
accaaaggtg cctattcact ttctatccgt gattgggatg atatgaaagg agaccatgtc  600
aaacattata aaattcgcaa acttgacaat ggtggatact acattaccac ccgggcccag  660
tttgaaacac ttcagcagct tgtacaacat tactcagaga gagctgcagg tctctgctgc  720
cgcctagtag ttccctgtca caaagggatg ccaaggctta ccgatctgtc tgtcaaaacc  780
aaagatgtct gggaaatccc tcgagaatcc ctgcagttga tcaagagact gggaaatggg  840
cagtttgggg aagtatggat gggtacctgg aatggaaaca caaaagtagc cataaagact  900
cttaaaccag gcacaatgtc ccccgaatca ttccttgagg aagcgcagat catgaagaag  960
ctgaagcacg acaagctggt ccagctctat gcagtggtgt ctgaggagcc catctacatc  1020
gtcaccgagt atatgaacaa aggaagttta ctggatttct taaaagatgg agaaggaaga  1080
gctctgaaat taccaaatct tgtggacatg gcagcacagg tggctgcagg aatggcttac  1140
atcgagcgca tgaattatat ccatagagat ctgcgatcag caaacattct agtggggaat  1200
ggactcatat gcaagattgc tgacttcgga ttggcccgat tgatagaaga caatgagtac  1260
acagcaagac aaggtgcaaa gttccccatc aagtggacgg cccccgaggc agccctgtac  1320
gggaggttca caatcaagtc tgacgtgtgg tcttttggaa tcttactcac agagctggtc  1380
accaaaggaa gagtgccata cccaggcatg aacaaccggg aggtgctgga gcaggtggag  1440
cgaggctaca ggatgccctg cccgcaggac tgccccatct ctctgcatga gctcatgatc  1500
cactgctgga aaaaggaccc tgaagaacgc cccacttttg agtacttgca gagcttcctg  1560
gaagactact ttaccgcgac agagccccag cacaaacctg gtgaaaacct gttg        1614

SEQ ID NO: 70          moltype = AA  length = 538
FEATURE                Location/Qualifiers
source                 1..538
                       mol_type = protein
                       organism = Synthetic construct
SEQUENCE: 70
MGCVQCKDKE ATKLTEERDG SLNQSSGYRY GTDPTPQHYP SFGVTSIPNY NNFHAAGGQG  60
LTVFGGVNSS SHTGTLRTRG GTGVTLFVAL YDYEARTEDD LSFHKGEKFQ ILNSSEGDWW  120
EARSLTTGET GYIPSNYVAP VDSIQAEEWY FGKLGRKDAE RQLLSFGNPR GTFLIRESET  180
TKGAYSLSIR DWDDMKGDHV KHYKIRKLDN GGYYITTRAQ FETLQQLVQH YSERAAGLCC  240
RLVVPCHKGM PRLTDLSVKT KDVWEIPRES LQLIKRLGNG QFGEVWMGTW NGNTKVAIKT  300
LKPGTMSPES FLEEAQIMKK LKHDKLVQLY AVVSEEPIYI VTEYMNKGSL LDFLKDGEGR  360
ALKLPNLVDM AAQVAAGMAY IERMNYIHRD LRSANILVGN GLICKIADFG LARLIEDNEY  420
TARQGAKFPI KWTAPEAALY GRFTIKSDVW SFGILLTELV TKGRVPYPGM NNREVLEQVE  480
RGYRMPCPQD CPISLHELMI HCWKKDPEER PTFEYLQSFL EDYFTATEPQ HKPGENLL    538

SEQ ID NO: 71          moltype = DNA  length = 186
FEATURE                Location/Qualifiers
source                 1..186
                       mol_type = other DNA
                       organism = Synthetic construct
SEQUENCE: 71
atggaggtga cggcggacca gccgcgctgg gtgagccacc accaccccgc cgtgctcaac  60
gggcagcacc cggacacgca ccacccgggc ctcagccact cctacatgga cgcggcgcag  120
tacccgctgc cggaggaggt ggatgtgctt tttaacatcg acggtcaagg caaccacgtc  180
ccgccc                                                             186

SEQ ID NO: 72          moltype = AA  length = 62
FEATURE                Location/Qualifiers
source                 1..62
                       mol_type = protein
                       organism = Synthetic construct
SEQUENCE: 72
MEVTADQPRW VSHHHPAVLN GQHPDTHHPG LSHSYMDAAQ YPLPEEVDVL FNIDGQGNHV  60
PP                                                                 62
```

```
SEQ ID NO: 73          moltype = DNA  length = 1332
FEATURE                Location/Qualifiers
source                 1..1332
                       mol_type = genomic DNA
                       organism = Homo sapiens
SEQUENCE: 73
atggaggtga cggcggacca gccgcgctgg gtgagccacc accaccccgc cgtgctcaac  60
gggcagcacc cggacacgca ccacccgggc ctcagccact cctacatgga cgcggcgcag  120
tacccgctgc cggaggaggt ggatgtgctt tttaacatcg acggtcaagg caaccacgtc  180
ccgccctact acggaaactc ggtcagggcc acggtgcaga ggtaccctcc gacccaccac  240
gggagccagg tgtgccgccc gcctctgctt catggatccc taccctggct ggacggcggc  300
aaagccctgg gcagccacca caccgcctcc ccctggaatc tcagcccctt ctccaagacg  360
tccatccacc acggctcccc ggggcccctc tccgtctacc ccccggcctc gtcctcctcc  420
ttgtcggggg gccacgccag cccgcacctc ttcaccttcc cgcccacccc gccgaaggac  480
gtctccccgg acccatcgct gtccacccca ggctcggccg gctcggcccg gcaggacgag  540
aaagagtgcc tcaagtacca ggtgcccctg cccgacagca tgaagctgga gtcgtcccac  600
tcccgtggca gcatgaccgc cctgggtgga gcctcctcgt cgacccacca ccccatcacc  660
acctacccgc cctacgtgcc cgagtacagc tccggactct tcccccccag cagcctgctg  720
ggcggctccc ccaccggctt cggatgcaag tccaggccca aggcccggtc cagcacagaa  780
ggcagggagt gtgtgaactg tggggcaacc tcgaccccac tgtggcggcg agatggcacg  840
ggacactacc tgtgcaacgc ctgcgggctc tatcacaaaa tgaacggaca gaaccggccc  900
ctcattaagc ccaagcgaag gctgtctgca gccaggagag cagggacgtc ctgtgcgaac  960
tgtcagacca ccacaaccac actctggagg aggaatgcca atggggaccc tgtctgcaat  1020
gcctgtgggc tctactacaa gcttcacaat attaacagac ccctgactat gaagaaggaa  1080
ggcatccaga ccagaaaccg aaaaatgtct agcaaatcca aaaagtgcaa aaaagtgcat  1140
gactcactgg aggacttccc caagaacagc tcgtttaacc cggccgccct ctccagacac  1200
atgtcctccc tgagccacat ctcgcccttc agccactcca gccacatgct gaccacgccc  1260
acgccgatgc acccgccatc cagcctgtcc tttggaccac accacccctc cagcatggtc  1320
accgccatgg gt                                                     1332

SEQ ID NO: 74          moltype = AA  length = 444
FEATURE                Location/Qualifiers
source                 1..444
                       mol_type = protein
                       organism = Homo sapiens
SEQUENCE: 74
MEVTADQPRW VSHHHPAVLN GQHPDTHHPG LSHSYMDAAQ YPLPEEVDVL FNIDGQGNHV  60
PPYYGNSVRA TVQRYPPTHH GSQVCRPPLL HGSLPWLDGG KALGSHHTAS PWNLSPFSKT  120
SIHHGSPGPL SVYPPASSSS LSGGHASPHL FTFPPTPPKD VSPDPSLSTP GSAGSARQDE  180
KECLKYQVPL PDSMKLESSH SRGSMTALGG ASSSTHHPIT TYPPYVPEYS SGLFPPSSLL  240
GGSPTGFGCK SRPKARSSTE GRECVNCGAT STPLWRRDGT GHYLCNACGL YHKMNGQNRP  300
LIKPKRRLSA ARRAGTSCAN CQTTTTTLWR RNANGDPVCN ACGLYYKLHN INRPLTMKKE  360
GIQTRNRKMS SKSKKCKKVH DSLEDFPKNS SFNPAALSRH MSSLSHISPF SHSSHMLTTP  420
TPMHPPSSLS FGPHHPSSMV TAMG                                         444

SEQ ID NO: 75          moltype = DNA  length = 1077
FEATURE                Location/Qualifiers
source                 1..1077
                       mol_type = other DNA
                       organism = Synthetic construct
SEQUENCE: 75
atgactctgg agtccatcat ggcgtgctgc ctgagcgagg aggccaagga agcccggcgg  60
atcaacgacg agatcgagcg gcagctccgc agggacaagc gggacgcccg ccgggagctc  120
aagctgctgc tgctcgggac aggagagagt ggcaagagta cgtttatcaa gcagatgaga  180
atcatccatg ggtcaggata ctctgatgaa gataaaaggg gcttcaccaa gctggtgtat  240
cagaacatct tcacggccat gcaggccatg atcagagcca tggacagcct caagatccca  300
tacaagtatg agcacaataa ggctcatgca caattagttc gagaagttga tgtggagaag  360
gtgtctgctt ttgagaatcc atatgtagat gcaataaaga gtttatggaa tgatcctgga  420
atccaggaat gctatgatag acgacgagaa tatcaattat ctgactctac caaatactat  480
cttaatgact tggaccgcgt agctgaccct gcctacctgc ctacgcaaca agatgtgctt  540
agagttcgag tccccaccac agggatcatc gaatacccct ttgacttaca aagtgtcatt  600
ttcagaatgg tcgatgtagg gggccaaagg tcagagagaa gaaaatggat acactgcttt  660
gaaaatgtca cctctatcat gtttctagta gcgcttagtg aatatgatca agttctcgtg  720
gagtcagaca atgagaaccg aatggaggaa agcaaggctc tctttagaac aattatcaca  780
taccccctggt tccagaactc ctcggttatt ctgttcttaa acaagaaaga tcttctagag  840
gagaaaatca tgtattccca tctagtcgac tacttcccag aatatgatgg accccagaga  900
gatgcccagg cagcccgaga attcattctg aagatgttcg tggacctgaa cccagacagt  960
gacaaaatta tctactccca cttcacgtgc gccacagaca ccgagaatat ccgctttgtc  1020
tttgctgccg tcaaggacac catcctccag ttgaacctga aggagtacaa tctggtc     1077

SEQ ID NO: 76          moltype = AA  length = 359
FEATURE                Location/Qualifiers
source                 1..359
                       mol_type = protein
                       organism = Synthetic construct
SEQUENCE: 76
MTLESIMACC LSEEAKEARR INDEIERQLR RDKRDARREL KLLLLGTGES GKSTFIKQMR  60
IIHGSGYSDE DKRGFTKLVY QNIFTAMQAM IRAMDSLKIP YKYEHNKAHA QLVREVDVEK  120
```

-continued

```
VSAFENPYVD AIKSLWNDPG IQECYDRRRE YQLSDSTKYY LNDLDRVADP AYLPTQQDVL  180
RVRVPTTGII EYPFDLQSVI FRMVDVGGQR SERRKWIHCF ENVTSIMFLV ALSEYDQVLV  240
ESDNENRMEE SKALFRTIIT YPWFQNSSVI LFLNKKDLLE EKIMYSHLVD YFPEYDGPQR  300
DAQAAREFIL KMFVDLNPDS DKIIYSHFTC ATDTENIRFV FAAVKDTILQ LNLKEYNLV   359

SEQ ID NO: 77          moltype = DNA  length = 1077
FEATURE                Location/Qualifiers
source                 1..1077
                       mol_type = genomic DNA
                       organism = Homo sapiens
SEQUENCE: 77
atgactctgg agtccatcat ggcgtgctgc ctgagcgagg aggccaagga agcccggcgg  60
atcaacgacg agatcgagcg gcagctccgc agggacaagc gggacgcccg ccgggagctc  120
aagctgctgc tgctcgggac aggagagagt ggcaagagta cgtttatcaa gcagatgaga  180
atcatccatg ggtcaggata ctctgatgaa gataaaaggg gcttcaccaa gctggtgtat  240
cagaacatct tcacggccat gcaggccatg atcagagcca tggacacact caagatccca  300
tacaagtatg agcacaataa ggctcatgca caattagttc gagaagttga tgtggagaag  360
gtgtctgctt ttgagaatcc atatgtagat gcaataaaga gtttatggaa tgatcctgga  420
atccaggaat gctatgatag acgacgagaa tatcaattat ctgactctac caaatactat  480
cttaatgact tggaccgcgt agctgaccct gcctacctgc ctacgcaaca agatgtgctt  540
agagttcgag tccccaccac agggatcatc gaatacccct ttgacttaca aagtgtcatt  600
ttcagaatgg tcgatgtagg gggccaaagg tcagagagaa gaaaatggat acactgcttt  660
gaaaatgtca cctctatcat gtttctagta gcgcttagtg aatatgatca agttctcgtg  720
gagtcagaca atgagaaccg aatggaggaa agcaaggctc tctttagaac aattatcaca  780
tacccctggt tccagaactc ctcggttatt ctgttcttaa acaagaaaga tcttctagag  840
gagaaaatca tgtattccca tctagtcgac tacttcccag aatatgatgg accccagaga  900
gatgcccagg cagcccgaga attcattctg aagatgttcg tggacctgaa cccagacagt  960
gacaaaatta tctactccca cttcacgtgc gccacagaca ccgagaatat ccgctttgtc  1020
tttgctgccg tcaaggacac catcctccag ttgaacctga aggagtacaa tctggtc     1077

SEQ ID NO: 78          moltype = AA  length = 359
FEATURE                Location/Qualifiers
source                 1..359
                       mol_type = protein
                       organism = Homo sapiens
SEQUENCE: 78
MTLESIMACC LSEEAKEARR INDEIERQLR RDKRDARREL KLLLLGTGES GKSTFIKQMR  60
IIHGSGYSDE DKRGFTKLVY QNIFTAMQAM IRAMDTLKIP YKYEHNKAHA QLVREVDVEK  120
VSAFENPYVD AIKSLWNDPG IQECYDRRRE YQLSDSTKYY LNDLDRVADP AYLPTQQDVL  180
RVRVPTTGII EYPFDLQSVI FRMVDVGGQR SERRKWIHCF ENVTSIMFLV ALSEYDQVLV  240
ESDNENRMEE SKALFRTIIT YPWFQNSSVI LFLNKKDLLE EKIMYSHLVD YFPEYDGPQR  300
DAQAAREFIL KMFVDLNPDS DKIIYSHFTC ATDTENIRFV FAAVKDTILQ LNLKEYNLV   359

SEQ ID NO: 79          moltype = DNA  length = 1356
FEATURE                Location/Qualifiers
source                 1..1356
                       mol_type = other DNA
                       organism = Synthetic construct
SEQUENCE: 79
atgaacctgg agggcggcgg ccgaggcgga gagttcggca tgagcgcggt gagctgcggc  60
aacgggaagc tccgccagtg gctgatcgac cagatcgaca gcggcaagta ccccgggctg  120
gtgtgggaga acgaggagaa gagcatcttc cgcatcccct ggaagcacgc gggcaggcag  180
gactacaacc gcgaggagga cgccgcgctc ttcaaggctt gggcactgtt taaaggaaag  240
ttccgagaag gcatcgacaa gccggaccct cccacctgga agacgcgcct gcggtgcgct  300
ttgaacaaga gcaatgactt tgaggaactg gttgagcgga gccagctgga catctcagac  360
ccgtacaaag tgtacaggat tgttcctgag ggagccaaaa aaggagccaa gcagctcacc  420
ttggaggacc cgcagatgtc catgagccac ccctacacca tgacaacgcc ttacccttcg  480
ctcccagccc agcaggttca caactacatg atgccacccc tcgaccgaag ctggagggac  540
tacgtcccgg atcagccaca cccggaaatc ccgtaccaat gtcccatgac gtttggaccc  600
cgcggccacc actggcaagg cccagcttgt gaaaatggtt gccaggtgac aggaaccttt  660
tatgcttgtg ccccacctga gtcccaggct cccggagtcc ccacagagcc aagcataagg  720
tctgccgaag ccttggcgtt ctcagactgc cggctgcaca tctgcctgta ctaccgggaa  780
atcctcgtga aggagctgac cacgtccagc cccgagggct gccggatctc ccatggacat  840
acgtatgacg ccagcaacct ggaccaggtc ctgttcccct acccagagga caatggccag  900
aggaaaaaca ttgagaagct gctgagccac ctggagaggg gcgtggtcct ctggatggcc  960
cccgacgggc tctatgcgaa aagactgtgc cagagcagga tctactggga cgggcccctg  1020
gcgctgtgca acgaccggcc caacaaactg gagagagacc agacctgcaa gctctttgac  1080
acacagcagt tcttgtcaga gctgcaagcg tttgctcacc acggccgctc cctgccaaga  1140
ttccaggtga ctctatgctt tggagaggag tttccagacc ctcagaggca aagaaagctc  1200
atcacagctc acgtagaacc tctgctagcc agacaactat attattttgc tcaacaaaac  1260
agtggacatt tcctgagggg ctacgattta ccagaacaca tcagcaatcc agaagattac  1320
cacagatcta tccgccattc ctctattcaa gaattg                            1356

SEQ ID NO: 80          moltype = AA  length = 452
FEATURE                Location/Qualifiers
source                 1..452
                       mol_type = protein
                       organism = Synthetic construct
SEQUENCE: 80
```

-continued

```
MNLEGGGRGG EFGMSAVSCG NGKLRQWLID QIDSGKYPGL VWENEEKSIF RIPWKHAGRQ  60
DYNREEDAAL FKAWALFKGK FREGIDKPDP PTWKTRLRCA LNKSNDFEEL VERSQLDISD  120
PYKVYRIVPE GAKKGAKQLT LEDPQMSMSH PYTMTTPYPS LPAQQVHNYM MPPLDRSWRD  180
YVPDQPHPEI PYQCPMTFGP RGHHWQGPAC ENGCQVTGTF YACAPPESQA PGVPTEPSIR  240
SAEALAFSDC RLHICLYYRE ILVKELTTSS PEGCRISHGH TYDASNLDQV LFPYPEDNGQ  300
RKNIEKLLSH LERGVVLWMA PDGLYAKRLC QSRIYWDGPL ALCNDRPNKL ERDQTCKLFD  360
TQQFLSELQA FAHHGRSLPR FQVTLCFGEE FPDPQRQRKL ITAHVEPLLA RQLYYFAQQN  420
SGHFLRGYDL PEHISNPEDY HRSIRHSSIQ EL                                452

SEQ ID NO: 81          moltype = DNA  length = 1356
FEATURE                Location/Qualifiers
source                 1..1356
                       mol_type = genomic DNA
                       organism = Homo sapiens
SEQUENCE: 81
atgaacctgg agggcggcgg ccgaggcgga gagttcggca tgagcgcggt gagctgcggc  60
aacgggaagc tccgccagtg gctgatcgac cagatcgaca gcggcaagta ccccgggctg  120
gtgtgggaga acgaggagaa gagcatcttc cgcatcccct ggaagcacgc gggcaagcag  180
gactacaacc gcgaggagga cgccgcgctc ttcaaggctt gggcactgtt taaaggaaag  240
ttccgagaag gcatcgacaa gccggaccct cccacctgga agacgcgcct gcggtgcgct  300
ttgaacaaga gcaatgactt tgaggaactg gttgagcgga gccagctgga catctcagac  360
ccgtacaaag tgtacaggat tgttcctgag ggagccaaaa aaggagccaa gcagctcacc  420
ttggaggacc cgcagatgtc catgagccac ccctacacca tgacaacgcc ttacccttcg  480
ctcccagccc agcaggttca caactacatg atgccacccc tcgaccgaag ctggagggac  540
tacgtcccgg atcagccaca cccggaaatc ccgtaccaat gtcccatgac gtttggaccc  600
cgcggccacc actggcaagg cccagcttgt gaaaatggtt gccaggtgac aggaaccttt  660
tatgcttgtg ccccacctga gtcccaggct cccggagtcc ccacagagcc aagcataagg  720
tctgccgaag ccttggcgtt ctcagactgc cggctgcaca tctgcctgta ctaccgggaa  780
atcctcgtga aggagctgac cacgtccagc cccgagggct gccggatctc ccatggacat  840
acgtatgacg ccagcaacct ggaccaggtc ctgttcccct acccagagga caatggccag  900
aggaaaaaca ttgagaagct gctgagccac ctggagaggg gcgtggtcct ctggatggcc  960
cccgacgggc tctatgcgaa aagactgtgc cagagcagga tctactggga cgggcccctg  1020
gcgctgtgca acgaccggcc caacaaactg gagagagacc agacctgcaa gctctttgac  1080
acacagcagt tcttgtcaga gctgcaagcg tttgctcacc acggccgctc cctgccaaga  1140
ttccaggtga ctctatgctt tggagaggag tttccagacc ctcagaggca aagaaagctc  1200
atcacagctc acgtagaacc tctgctagcc agacaactat attattttgc tcaacaaaac  1260
agtggacatt tcctgagggg ctacgattta ccagaacaca tcagcaatcc agaagattac  1320
cacagatcta tccgccattc ctctattcaa gaattg                            1356

SEQ ID NO: 82          moltype = AA  length = 452
FEATURE                Location/Qualifiers
source                 1..452
                       mol_type = protein
                       organism = Homo sapiens
SEQUENCE: 82
MNLEGGGRGG EFGMSAVSCG NGKLRQWLID QIDSGKYPGL VWENEEKSIF RIPWKHAGKQ  60
DYNREEDAAL FKAWALFKGK FREGIDKPDP PTWKTRLRCA LNKSNDFEEL VERSQLDISD  120
PYKVYRIVPE GAKKGAKQLT LEDPQMSMSH PYTMTTPYPS LPAQQVHNYM MPPLDRSWRD  180
YVPDQPHPEI PYQCPMTFGP RGHHWQGPAC ENGCQVTGTF YACAPPESQA PGVPTEPSIR  240
SAEALAFSDC RLHICLYYRE ILVKELTTSS PEGCRISHGH TYDASNLDQV LFPYPEDNGQ  300
RKNIEKLLSH LERGVVLWMA PDGLYAKRLC QSRIYWDGPL ALCNDRPNKL ERDQTCKLFD  360
TQQFLSELQA FAHHGRSLPR FQVTLCFGEE FPDPQRQRKL ITAHVEPLLA RQLYYFAQQN  420
SGHFLRGYDL PEHISNPEDY HRSIRHSSIQ EL                                452

SEQ ID NO: 83          moltype = DNA  length = 2307
FEATURE                Location/Qualifiers
source                 1..2307
                       mol_type = other DNA
                       organism = Synthetic construct
SEQUENCE: 83
atgctgggcc tgcgcccccc acttctcgcc ctggtggggc tgctctccct cgggtgcgtc  60
ctctctcagg agtgcacgaa gttcaaggtc agcagctgcc gggaatgcat cgagtcgggg  120
cccggctgca cctggtgcca gaagctgaac ttcacagggc cgggggatcc tgactccatt  180
cgctgcgaca cccggccaca gctgctcatg aggggctgtg cggctgacga catcatggac  240
cccacaagcc tcgctgaaac ccaggaagac cacaatgggg gccagaagca gctgtcccca  300
caaaaagtga cgctttacct gcgaccaggc caggcagcag cgttcaacgt gaccttccgg  360
cgggccaagg gctaccccat cgacctgtac tatctgatgg acctctccta ctccatgctt  420
gatgacctca ggaatgtcaa gaagctaggt ggcgacctgc tccgggccct caacgagatc  480
accgagtccg gccgcattgg cttcgggtcc ttcgtggaca agaccgtgct gccgttcgtg  540
aacacgcacc ctgataagct gcgaaaccca tgccccaaca aggagaaaga gtgccagccc  600
ccgtttgcct tcaggcacgt gctgaagctg accaacaact ccaaccagtt tcagaccgag  660
gtcgggaagc agctgatttc cggaaacctg gatgcaccca agggtgggct ggacgccatg  720
atgcaggtcg ccgcctgccc ggaggaaatc ggctggcgca acgtcacgcg gctgctggtg  780
tttgccactg atgacggctt ccatttcgcg ggcgacggga agctgggcgc catcctgacc  840
cccaacgacg gccgctgtca cctggaggac aacttgtaca agaggagcaa cgaattcgac  900
tacccatcgg tgggccagct ggcgcacaag ctggctgaaa acaacatcca gcccatcttc  960
gcggtgacca gtaggatggt gaagacctac gagaaactca ccgagatcat ccccaagtca  1020
gccgtggggg agctgtctga ggactccagc aatgtggtcc atctcattaa gaatgcttac  1080
aataaactct cctccagggt attcctggat cacaacgccc tccccgacac cctgaaagtc  1140
```

-continued

```
acctacgact ccttctgcag caatggagtg acgcacagga accagcccag aggtgactgt  1200
gatggcgtgc agatcaatgt cccgatcacc ttccaggtga aggtcacggc cacagagtgc  1260
atccaggagc agtcgtttgt catccgggcg ctgggcttca cggacatagt gaccgtgcag  1320
gtccttcccc agtgtgagtg ccggtgccgg gaccagagca gagaccgcag cctctgccat  1380
ggcaagggct tcttggagtg cggcatctgc aggtgtgaca ctggctacat tgggaaaaac  1440
tgtgagtgcc agacacaggg ccggagcagc caggagctgg aaggaagctg ccggaaggac  1500
aacaactcca tcatctgctc agggctgggg gactgtgtct gcgggcagtg cctgtgccac  1560
accagcgacg tccccggcaa gctgatatac gggcagtact gcgagtgtga caccatcaac  1620
tgtgagcgct acaacggcca ggtctgcggc ggcccgggga gggggctctg cttctgcggg  1680
aagtgccgct gccacccggg ctttgagggc tcagcgtgcc agtgcgagag gaccactgag  1740
ggctgcctga acccgcggcg tgttgagtgt agtggtcgtg gccggtgccg ctgcaacgta  1800
tgcgagtgcc attcaggcta ccagctgcct ctgtgccagg agtgccccgg ctgcccctca  1860
ccctgtggca agtacatctc ctgcgccgag tgcctgaagt tcgaaaaggg cccctttggg  1920
aagaactgca gcgcggcgtg tccgggcctg cagctgtcga acaaccccgt gaagggcagg  1980
acctgcaagg agagggactc agagggctgc tgggtggcct acacgctgga gcagcaggac  2040
gggatggacc gctacctcat ctatgtggat gagagccgag agtgtgtggc aggccccaac  2100
atcgccgcca tcgtcggggg caccgtggca ggcatcgtgc tgatcggcat tctcctgctg  2160
gtcatctgga aggctctgat ccacctgagc gacctccggg agtacaggcg ctttgagaag  2220
gagaagctca agtcccagtg gaacaatgat aatccccttt tcaagagcgc caccacgacg  2280
gtcatgaacc ccaagtttgc tgagagt                                     2307

SEQ ID NO: 84          moltype = AA  length = 769
FEATURE                Location/Qualifiers
source                 1..769
                       mol_type = protein
                       organism = Synthetic construct
SEQUENCE: 84
MLGLRPPLLA LVGLLLSLGCV LSQECTKFKV SSCRECIESG PGCTWCQKLN FTGPGDPDSI  60
RCDTRPQLLM RGCAADDIMD PTSLAETQED HNGGQKQLSP QKVTLYLRPG QAAAFNVTFR  120
RAKGYPIDLY YLMDLSYSML DDLRNVKKLG GDLLRALNEI TESGRIGFGS FVDKTVLPFV  180
NTHPDKLRNP CPNKEKECQP PFAFRHVLKL TNNSNQFQTE VGKQLISGNL DAPKGGLDAM  240
MQVAACPEEI GWRNVTRLLV FATDDGFHFA GDGKLGAILT PNDGRCHLED NLYKRSNEFD  300
YPSVGQLAHK LAENNIQPIF AVTSRMVKTY EKLTEIIPKS AVGELSEDSS NVVHLIKNAY  360
NKLSSRVFLD HNALPDTLKV TYDSFCSNGV THRNQPRGDC DGVQINVPIT FQVKVTATEC  420
IQEQSFVIRA LGFTDIVTVQ VLPQCECRCR DQSRDRSLCH GKGFLECGIC RCDTGYIGKN  480
CECQTQGRSS QELEGSCRKD NNSIICSGLG DCVCGQCLCH TSDVPGKLIY GQYCECDTIN  540
CERYNGQVCG GPGRGLCFCG KCRCHPGFEG SACQCERTTE GCLNPRRVEC SGRGRCRCNV  600
CECHSGYQLP LCQECPGCPS PCGKYISCAE CLKFEKGPFG KNCSAACPGL QLSNNPVKGR  660
TCKERDSEGC WVAYTLEQQD GMDRYLIYVD ESRECVAGPN IAAIVGGTVA GIVLIGILLL  720
VIWKALIHLS DLREYRRFEK EKLKSQWNND NPLFKSATTT VMNPKFAES             769

SEQ ID NO: 85          moltype = DNA  length = 2307
FEATURE                Location/Qualifiers
source                 1..2307
                       mol_type = genomic DNA
                       organism = Homo sapiens
SEQUENCE: 85
atgctgggcc tgcgcccccc acttctcgcc ctggtggggc tgctctccct cgggtgcgtc  60
ctctctcagg agtgcacgaa gttcaaggtc agcagctgcc gggaatgcat cgagtcgggg  120
cccggctgca cctggtgcca gaagctgaac ttcacagggc cgggggatcc tgactccatt  180
cgctgcgaca cccggccaca gctgctcatg aggggctgtg cggctgacga catcatggac  240
cccacaagcc tcgctgaaac ccaggaagac cacaatgggg gccagaagca gctgtcccca  300
caaaaagtga cgctttacct gcgaccaggc caggcagcag cgttcaacgt gaccttccgg  360
cgggccaagg gctaccccat cgacctgtac tatctgatgg acctctccta ctccatgctt  420
gatgacctca ggaatgtcaa gaagctaggt ggcgacctgc tccgggccct caacgagatc  480
accgagtccg gccgcattgg cttcgggtcc ttcgtggaca agaccgtgct gccgttcgtg  540
aacacgcacc ctgataagct gcgaaaccca tgccccaaca aggagaaaga gtgccagccc  600
ccgtttgcct tcaggcacgt gctgaagctg accaacaact ccaaccagtt tcagaccgag  660
gtcgggaagc agctgatttc cggaaacctg gatgcacccg agggtgggct ggacgccatg  720
atgcaggtcg ccgcctgccc ggaggaaatc ggctggcgca acgtcacgcg gctgctggtg  780
tttgccactg atgacggctt ccatttcgcg ggcgacggga agctgggcgc catcctgacc  840
cccaacgacg gccgctgtca cctggaggac aacttgtaca agaggagcaa cgaattcgac  900
tacccatcgg tgggccagct ggcgcacaag ctggctgaaa acaacatcca gcccatcttc  960
gcggtgacca gtaggatggt gaagacctac gagaaactca ccgagatcat ccccaagtca  1020
gccgtggggg agctgtctga ggactccagc aatgtggtcc atctcattaa gaatgcttac  1080
aataaactct cctccagggt attcctggat cacaacgccc tccccgacac cctgaaagtc  1140
acctacgact ccttctgcag caatggagtg acgcacagga accagcccag aggtgactgt  1200
gatggcgtgc agatcaatgt cccgatcacc ttccaggtga aggtcacggc cacagagtgc  1260
atccaggagc agtcgtttgt catccgggcg ctgggcttca cggacatagt gaccgtgcag  1320
gtccttcccc agtgtgagtg ccggtgccgg gaccagagca gagaccgcag cctctgccat  1380
ggcaagggct tcttggagtg cggcatctgc aggtgtgaca ctggctacat tgggaaaaac  1440
tgtgagtgcc agacacaggg ccggagcagc caggagctgg aaggaagctg ccggaaggac  1500
aacaactcca tcatctgctc agggctgggg gactgtgtct gcgggcagtg cctgtgccac  1560
accagcgacg tccccggcaa gctgatatac gggcagtact gcgagtgtga caccatcaac  1620
tgtgagcgct acaacggcca ggtctgcggc ggcccgggga gggggctctg cttctgcggg  1680
aagtgccgct gccacccggg ctttgagggc tcagcgtgcc agtgcgagag gaccactgag  1740
ggctgcctga acccgcggcg tgttgagtgt agtggtcgtg gccggtgccg ctgcaacgta  1800
tgcgagtgcc attcaggcta ccagctgcct ctgtgccagg agtgccccgg ctgcccctca  1860
ccctgtggca agtacatctc ctgcgccgag tgcctgaagt tcgaaaaggg cccctttggg  1920
```

```
aagaactgca gcgcggcgtg tccgggcctg cagctgtcga acaaccccgt gaagggcagg  1980
acctgcaagg agagggactc agagggctgc tgggtggcct acacgctgga gcagcaggac  2040
gggatggacc gctacctcat ctatgtggat gagagccgag agtgtgtggc aggccccaac  2100
atcgccgcca tcgtcggggg caccgtggca ggcatcgtgc tgatcggcat tctcctgctg  2160
gtcatctgga aggctctgat ccacctgagc gacctccggg agtacaggcg ctttgagaag  2220
gagaagctca agtcccagtg gaacaatgat aatcccttt tcaagagcgc caccacgacg  2280
gtcatgaacc ccaagtttgc tgagagt                                 2307

SEQ ID NO: 86           moltype = AA  length = 769
FEATURE                 Location/Qualifiers
source                  1..769
                        mol_type = protein
                        organism = Homo sapiens
SEQUENCE: 86
MLGLRPPLLA LVGLLSLGCV LSQECTKFKV SSCRECIESG PGCTWCQKLN FTGPGDPDSI  60
RCDTRPQLLM RGCAADDIMD PTSLAETQED HNGGQKQLSP QKVTLYLRPG QAAAFNVTFR  120
RAKGYPIDLY YLMDLSYSML DDLRNVKKLG GDLLRALNEI TESGRIGFGS FVDKTVLPFV  180
NTHPDKLRNP CPNKEKECQP PFAFRHVLKL TNNSNQFQTE VGKQLISGNL DAPEGGLDAM  240
MQVAACPEEI GWRNVTRLLV FATDDGFHFA GDGKLGAILT PNDGRCHLED NLYKRSNEFD  300
YPSVGQLAHK LAENNIQPIF AVTSRMVKTY EKLTEIIPKS AVGELSEDSS NVVHLIKNAY  360
NKLSSRVFLD HNALPDTLKV TYDSFCSNGV THRNQPRGDC DGVQINVPIT FQVKVTATEC  420
IQEQSFVIRA LGFTDIVTVQ VLPQCECRCR DQSRDRSLCH GKGFLECGIC RCDTGYIGKN  480
CECQTQGRSS QELEGSCRKD NNSIICSGLG DCVCGQCLCH TSDVPGKLIY GQYCECDTIN  540
CERYNGQVCG GPGRGLCFCG KCRCHPGFEG SACQCERTTE GCLNPRRVEC SGRGRCRCNV  600
CECHSGYQLP LCQECPGCPS PCGKYISCAE CLKFEKGPFG KNCSAACPGL QLSNNPVKGR  660
TCKERDSEGC WVAYTLEQQD GMDRYLIYVD ESRECVAGPN IAAIVGGTVA GIVLIGILLL  720
VIWKALIHLS DLREYRRFEK EKLKSQWNND NPLFKSATTT VMNPKFAES             769

SEQ ID NO: 87           moltype = DNA  length = 3462
FEATURE                 Location/Qualifiers
source                  1..3462
                        mol_type = other DNA
                        organism = Synthetic construct
SEQUENCE: 87
atgcagtatc taaatataaa agaggactgc aatgccatgg ctttctgtgc taaaatgagg  60
agctccaaga agactgaggt gaacctggag gcccctgagc caggggtgga agtgatcttc  120
tatctgtcgg acagggagcc cctccggctg ggcagtggag agtacacagc agaggaactg  180
tgcatcaggg ctgcacaggc atgccgtatc tctcctcttt gtcacaacct ctttgccctg  240
tatgacgaga acaccaagct ctggtatgct ccaaatcgca ccatcaccgt tgatgacaag  300
atgtccctcc ggctccacta ccggatgagg ttctatttca ccaattggca tggaaccaac  360
gacaatgagc agtcagtgtg gcgtcattct ccaaagaagc agaaaaatgg ctacgagaaa  420
aaaaagattc cagatgcaac ccctctcctt gatgccagct cactggagta tctgtttgct  480
cagggacagt atgatttggt gaaatgcctg gctcctattc gagaccccaa gaccgagcag  540
gatggacatg atattgagaa cgagtgtcta gggatggctg tcctggccat ctcacactat  600
gccatgatga agaagatgca gttgccagaa ctgcccaagg acatcagcta caagcgatat  660
attccagaaa cattgaataa gtccatcaga cagaggaacc ttctcaccag gatgcggata  720
aataatgttt tcaaggattt cctaaaggaa tttaacaaca agaccatttg tgacagcagc  780
gtgtccacgc atgacctgaa ggtgaaatac ttggctacct tggaaacttt gacaaaacat  840
tacggtgctg aaatatttga gacttccatg ttactgattt catcagaaaa tgagatgaat  900
tggtttcatt cgaatgacgg tggaaacgtt ctctactacg aagtgatggt gactgggaat  960
cttggaatcc agtggaggca taaaccaaat gttgtttctg ttgaaaagga aaaaaataaa  1020
ctgaagcgga aaaaactgga aaataaacac aagaaggatg aggagaaaaa caagatccgg  1080
gaagagtgga acaatttttc ttacttccct gaaatcactc acattgtaat aaaggagtct  1140
gtggtcagca ttaacaagca ggacaacaag aaaatggaac tgaagctctc ttcccacgag  1200
gaggccttgt cctttgtgtc cctggtagat ggctacttcc ggctcacagc agatgcccat  1260
cattacctct gcaccgacgt ggcccccccg ttgatcgtcc acaacataca gaatggctgt  1320
catggtccaa tctgtacaga atacgccatc aataaattgc ggcaagaagg aagcgaggag  1380
gggatgtacg tgctgaggtg gagctgcacc gactttgaca acatcctcat gaccgtcacc  1440
tgctttgaga agtctgagca ggtgcagggt gcccagaagc agttcaagaa ctttcagatc  1500
gaggtgcaga agggccgcta cagtctgcac ggttcggacc gcagcttccc cagcttggga  1560
gacctcatga gccacctcaa gaagcagatc ctgcgcacgg ataacatcag cttcatgcta  1620
aaacgctgct gccagcccaa gccccgagaa atctccaacc tgctggtggc tactaagaaa  1680
gcccaggagt ggcagcccgt ctaccccatg agccagctga gtttcgatcg gatcctcaag  1740
aaggatctgg tgcagggcga gcaccttggg agaggcacga gaacacacat ctattctggg  1800
accctgatgg attacaagga tgacgaagga acttctgaag agaagaagat aaaagtgatc  1860
ctcaaagtct tagaccccag ccacagggat atttccctgg ccttcttcga ggcagccagc  1920
atgatgagac aggtctccca caaacacatc gtgtacctct atggcgtctg tgtccgcgac  1980
gtggagaata tcatggtgga agagtttgtg gaagggggtc ctctggatct cttcatgcac  2040
cggaaaagcg atgtccttac cacaccatgg aaattcaaag ttgccaaaca gctggccagt  2100
gccctgagct acttggagga taaagacctg gtccatggaa atgtgtgtac taaaaacctc  2160
ctcctggccc gtgagggcat cgacagtgag tgtggcccat tcatcaagct cagtgacccc  2220
ggcatcccca ttacggtgct gtctaggcaa gaatgcattg aacgaatccc atggattgct  2280
cctgagtgtg ttgaggactc caagaacctg agtgtggctg ctgacaagtg gagctttgga  2340
accacgctct gggaaatctg ctacaatggc gagatcccct tgaaagacaa gacgctgatt  2400
gagaaagaga gattctatga aagccggtgc aggccagtga caccatcatg taaggagctg  2460
gctgacctca tgacccgctg catgaactat gaccccaatc agaggccttt cttccgagcc  2520
atcatgagag acattaataa gcttgaagag cagaatccag atattgtttc agaaaaaaaa  2580
ccagcaactg aagtggaccc cacacatttt gaaaagcgct tcctaaagag gatccgtgac  2640
ttgggagagg gccactttgg gaaggttgag ctctgcaggt atgaccccga aggggacaat  2700
```

-continued

```
acaggggagc aggtggctgt taaatctctg aagcctgaga gtggaggtaa ccacatagct  2760
gatctgaaaa aggaaatcga gatcttaagg aacctctatc atgagaacat tgtgaagtac  2820
aaaggaatct gcacagaaga cggaggaaat ggtattaagc tcatcatgga atttctgcct  2880
tcgggaagcc ttaaggaata tcttccaaag aataagaaca aaataaacct caaacagcag  2940
ctaaaatatg ccgttcagat ttgtaagggg atggactatt tgggttctcg gcaatacgtt  3000
caccgggact tggcagcaag aaatgtcctt gttgagagtg aacaccaagt gaaaattgga  3060
gacttcggtt taaccaaagc aattgaaacc gataaggagt attacaccgt caaggatgac  3120
cgggacagcc ctgtgttttg gtatgctcca gaatgtttaa tgcaatctaa attttatatt  3180
gcctctgacg tctggtcttt tggagtcact ctgcatgagc tgctgactta ctgtgattca  3240
gattctagtc ccatggcttt gttcctgaaa atgataggcc caacccatgc ccagatgaca  3300
gtcacaagac ttgtgaatac gttaaaagaa ggaaaacgcc tgccgtgccc acctaactgt  3360
ccagatgagg tttatcaact tatgaggaaa tgctgggaat tccaaccatc caatcggaca  3420
agctttcaga accttattga aggatttgaa gcacttttaa aa                    3462

SEQ ID NO: 88          moltype = AA  length = 1154
FEATURE                Location/Qualifiers
source                 1..1154
                       mol_type = protein
                       organism = Synthetic construct
SEQUENCE: 88
MQYLNIKEDC NAMAFCAKMR SSKKTEVNLE APEPGVEVIF YLSDREPLRL GSGEYTAEEL  60
CIRAAQACRI SPLCHNLFAL YDENTKLWYA PNRTITVDDK MSLRLHYRMR FYFTNWHGTN  120
DNEQSVWRHS PKKQKNGYEK KKIPDATPLL DASSLEYLFA QGQYDLVKCL APIRDPKTEQ  180
DGHDIENECL GMAVLAISHY AMMKKMQLPE LPKDISYKRY IPETLNKSIR QRNLLTRMRI  240
NNVFKDFLKE FNNKTICDSS VSTHDLKVKY LATLETLTKH YGAEIFETSM LLISSENEMN  300
WFHSNDGGNV LYYEVMVTGN LGIQWRHKPN VVSVEKEKNK LKRKKLENKH KKDEEKNKIR  360
EEWNNFSYFP EITHIVIKES VVSINKQDNK KMELKLSSHE EALSFVSLVD GYFRLTADAH  420
HYLCTDVAPP LIVHNIQNGC HGPICTEYAI NKLRQEGSEE GMYVLRWSCT DFDNILMTVT  480
CFEKSEQVQG AQKQFKNFQI EVQKGRYSLH GSDRSFPSLG DLMSHLKKQI LRTDNISFML  540
KRCCQPKPRE ISNLLVATKK AQEWQPVYPM SQLSFDRILK KDLVQGEHLG RGTRTHIYSG  600
TLMDYKDDEG TSEEKKIKVI LKVLDPSHRD ISLAFFEAAS MMRQVSHKHI VYLYGVCVRD  660
VENIMVEEFV EGGPLDLFMH RKSDVLTTPW KFKVAKQLAS ALSYLEDKDL VHGNVCTKNL  720
LLAREGIDSE CGPFIKLSDP GIPITVLSRQ ECIERIPWIA PECVEDSKNL SVAADKWSFG  780
TTLWEICYNG EIPLKDKTLI EKERFYESRC RPVTPSCKEL ADLMTRCMNY DPNQRPFFRA  840
IMRDINKLEE QNPDIVSEKK PATEVDPTHF EKRFLKRIRD LGEGHFGKVE LCRYDPEGDN  900
TGEQVAVKSL KPESGGNHIA DLKKEIEILR NLYHENIVKY KGICTEDGGN GIKLIMEFLP  960
SGSLKEYLPK NKNKINLKQQ LKYAVQICKG MDYLGSRQYV HRDLAARNVL VESEHQVKIG  1020
DFGLTKAIET DKEYYTVKDD RDSPVFWYAP ECLMQSKFYI ASDVWSFGVT LHELLTYCDS  1080
DSSPMALFLK MIGPTHAQMT VTRLVNTLKE GKRLPCPPNC PDEVYQLMRK CWEFQPSNRT  1140
SFQNLIEGFE ALLK                                                   1154

SEQ ID NO: 89          moltype = DNA  length = 3462
FEATURE                Location/Qualifiers
source                 1..3462
                       mol_type = genomic DNA
                       organism = Homo sapiens
SEQUENCE: 89
atgcagtatc taaatataaa agaggactgc aatgccatgg ctttctgtgc taaaatgagg  60
agctccaaga agactgaggt gaacctggag gcccctgagc caggggtgga agtgatcttc  120
tatctgtcgg acagggagcc cctccggctg ggcagtggag agtacacagc agaggaactg  180
tgcatcaggg ctgcacaggc atgccgtatc tctcctcttt gtcacaacct ctttgccctg  240
tatgacgaga acaccaagct ctggtatgct ccaaatcgca ccatcaccgt tgatgacaag  300
atgtccctcc ggctccacta ccggatgagg ttctatttca ccaattggca tggaaccaac  360
gacaatgagc agtcagtgtg gcgtcattct ccaaagaagc agaaaaatgg ctacgagaaa  420
aaaaagattc cagatgcaac ccctctcctt gatgccagct cactggagta tctgtttgct  480
cagggacagt atgatttggt gaaatgcctg gctcctattc gagaccccaa gaccgagcag  540
gatggacatg atattgagaa cgagtgtcta gggatggctg tcctggccat ctcacactat  600
gccatgatga agaagatgca gttgccagaa ctgcccaagg acatcagcta caagcgatat  660
attccagaaa cattgaataa gtccatcaga cagaggaacc ttctcaccag gatgcggata  720
aataatgttt tcaaggattt cctaaaggaa tttaacaaca agaccatttg tgacagcagc  780
gtgtccacgc atgacctgaa ggtgaaatac ttggctacct tggaaacttt gacaaaacat  840
tacggtgctg aaatatttga gacttccatg ttactgattt catcagaaaa tgagatgaat  900
tggtttcatt cgaatgacgg tggaaacgtt ctctactacg aagtgatggt gactgggaat  960
cttggaatcc agtggaggca taaaccaaat gttgtttctg ttgaaaagga aaaaaataaa  1020
ctgaagcgga aaaaactgga aaataaacac aagaaggatg aggagaaaaa caagatccgg  1080
gaagagtgga acaatttttc ttacttccct gaaatcactc acattgtaat aaaggagtct  1140
gtggtcagca ttaacaagca ggacaacaag aaaatggaac tgaagctctc ttcccacgag  1200
gaggccttgt cctttgtgtc cctggtagat ggctacttcc ggctcacagc agatgcccat  1260
cattacctct gcaccgacgt ggcccccccg ttgatcgtcc acaacataca gaatggctgt  1320
catggtccaa tctgtacaga atacgccatc aataaattgc ggcaagaagg aagcgaggag  1380
gggatgtacg tgctgaggtg gagctgcacc gactttgaca acatcctcat gaccgtcacc  1440
tgctttgaga agtctgagca ggtgcagggt gcccagaagc agttcaagaa ctttcagatc  1500
gaggtgcaga agggccgcta cagtctgcac ggttcggacc gcagcttccc cagcttggga  1560
gacctcatga gccacctcaa gaagcagatc ctgcgcacgg ataacatcag cttcatgcta  1620
aaacgctgct gccagcccaa gccccgagaa atctccaacc tgctggtggc tactaagaaa  1680
gcccaggagt ggcagcccgt ctaccccatg agccagctga gtttcgatcg gatcctcaag  1740
aaggatctgg tgcagggcga gcaccttggg agaggcacga gaacacacat ctattctggg  1800
accctgatgg attacaagga tgacgaagga acttctgaag agaagaagat aaaagtgatc  1860
ctcaaagtct tagaccccag ccacagggat atttccctgg ccttcttcga ggcagccagc  1920
```

-continued

```
atgatgagac aggtctccca caaacacatc gtgtacctct atggcgtctg tgtccgcgac  1980
gtggagaata tcatggtgga agagtttgtg gaagggggtc ctctggatct cttcatgcac  2040
cggaaaagcg atgtccttac cacaccatgg aaattcaaag ttgccaaaca gctggccagt  2100
gccctgagct acttggagga taaagacctg gtccatggaa atgtgtgtac taaaaacctc  2160
ctcctggccc gtgagggcat cgacagtgag tgtggcccat tcatcaagct cagtgacccc  2220
ggcatcccca ttacggtgct gtctaggcaa gaatgcattg aacgaatccc atggattgct  2280
cctgagtgtg ttgaggactc caagaacctg agtgtggctg ctgacaagtg gagctttgga  2340
accacgctct gggaaatctg ctacaatggc gagatcccct tgaaagacaa gacgctgatt  2400
gagaaagaga gattctatga aagccggtgc aggccagtga caccatcatg taaggagctg  2460
gctgacctca tgacccgctg catgaactat gaccccaatc agaggccttt cttccgagcc  2520
atcatgagag acattaataa gcttgaagag cagaatccag atattgtttc agaaaaaaaa  2580
ccagcaactg aagtggaccc cacacatttt gaaaagcgct tcctaaagag gatccgtgac  2640
ttgggagagg gccactttgg gaaggttgag ctctgcaggt atgaccccga aggggacaat  2700
acaggggagc aggtggctgt taaatctctg aagcctgaga gtggaggtaa ccacatagct  2760
gatctgaaaa aggaaatcga gatcttaagg aacctctatc atgagaacat tgtgaagtac  2820
aaaggaatct gcacagaaga cggaggaaat ggtattaagc tcatcatgga atttctgcct  2880
tcgggaagcc ttaaggaata tcttccaaag aataagaaca aaataaacct caaacagcag  2940
ctaaaatatg ccgttcagat ttgtaagggg atggactatt tgggttctcg gcaatacgtt  3000
caccgggact tggcagcaag aaatgtcctt gttgagagtg aacaccaagt gaaaattgga  3060
gacttcggtt taaccaaagc aattgaaacc gataaggagt attacaccgt caaggatgac  3120
cgggacagcc ctgtgttttg gtatgctcca gaatgtttaa tgcaatctaa attttatatt  3180
gcctctgacg tctggtcttt tggagtcact ctgcatgagc tgctgactta ctgtgattca  3240
gattctagtc ccatggcttt gttcctgaaa atgataggcc caacccatgg ccagatgaca  3300
gtcacaagac ttgtgaatac gttaaaagaa ggaaaacgcc tgccgtgccc acctaactgt  3360
ccagatgagg tttatcaact tatgaggaaa tgctgggaat tccaaccatc caatcggaca  3420
agctttcaga accttattga aggatttgaa gcacttttaa aa                    3462

SEQ ID NO: 90          moltype = AA  length = 1154
FEATURE                Location/Qualifiers
source                 1..1154
                       mol_type = protein
                       organism = Homo sapiens
SEQUENCE: 90
MQYLNIKEDC NAMAFCAKMR SSKKTEVNLE APEPGVEVIF YLSDREPLRL GSGEYTAEEL  60
CIRAAQACRI SPLCHNLFAL YDENTKLWYA PNRTITVDDK MSLRLHYRMR FYFTNWHGTN  120
DNEQSVWRHS PKKQKNGYEK KKIPDATPLL DASSLEYLFA QGQYDLVKCL APIRDPKTEQ  180
DGHDIENECL GMAVLAISHY AMMKKMQLPE LPKDISYKRY IPETLNKSIR QRNLLTRMRI  240
NNVFKDFLKE FNNKTICDSS VSTHDLKVKY LATLETLTKH YGAEIFETSM LLISSENEMN  300
WFHSNDGGNV LYYEVMVTGN LGIQWRHKPN VVSVEKEKNK LKRKKLENKH KKDEEKNKIR  360
EEWNNFSYFP EITHIVIKES VVSINKQDNK KMELKLSSHE EALSFVSLVD GYFRLTADAH  420
HYLCTDVAPP LIVHNIQNGC HGPICTEYAI NKLRQEGSEE GMYVLRWSCT DFDNILMTVT  480
CFEKSEQVQG AQKQFKNFQI EVQKGRYSLH GSDRSFPSLG DLMSHLKKQI LRTDNISFML  540
KRCCQPKPRE ISNLLVATKK AQEWQPVYPM SQLSFDRILK KDLVQGEHLG RGTRTHIYSG  600
TLMDYKDDEG TSEEKKIKVI LKVLDPSHRD ISLAFFEAAS MMRQVSHKHI VYLYGVCVRD  660
VENIMVEEFV EGGPLDLFMH RKSDVLTTPW KFKVAKQLAS ALSYLEDKDL VHGNVCTKNL  720
LLAREGIDSE CGPFIKLSDP GIPITVLSRQ ECIERIPWIA PECVEDSKNL SVAADKWSFG  780
TTLWEICYNG EIPLKDKTLI EKERFYESRC RPVTPSCKEL ADLMTRCMNY DPNQRPFFRA  840
IMRDINKLEE QNPDIVSEKK PATEVDPTHF EKRFLKRIRD LGEGHFGKVE LCRYDPEGDN  900
TGEQVAVKSL KPESGGNHIA DLKKEIEILR NLYHENIVKY KGICTEDGGN GIKLIMEFLP  960
SGSLKEYLPK NKNKINLKQQ LKYAVQICKG MDYLGSRQYV HRDLAARNVL VESEHQVKIG  1020
DFGLTKAIET DKEYYTVKDD RDSPVFWYAP ECLMQSKFYI ASDVWSFGVT LHELLTYCDS  1080
DSSPMALFLK MIGPTHGQMT VTRLVNTLKE GKRLPCPPNC PDEVYQLMRK CWEFQPSNRT  1140
SFQNLIEGFE ALLK                                                    1154

SEQ ID NO: 91          moltype = DNA  length = 3375
FEATURE                Location/Qualifiers
source                 1..3375
                       mol_type = other DNA
                       organism = Synthetic construct
SEQUENCE: 91
atggcacctc caagtgaaga gacgcccctg atccctcagc gttcatgcag cctcttgtcc  60
acggaggctg gtgccctgca tgtgctgctg cccgctcggg gccccgggcc cccccagcgc  120
ctatctttct cctttgggga ccacttggct gaggacctgt gcgtgcaggc tgccaaggcc  180
agcggcatcc tgcctgtgta ccactccctc tttgctctgg ccacggagga cctgtcctgc  240
tggttccccc cgagccacat cttctccgtg gaggatgcca gcacccaagt cctgctgtac  300
aggattcgct tttacttccc caattggttt gggctggaga agtgccaccg cttcgggcta  360
cgcaaggatt tggccagtgc tatccttgac ctgccagtcc tggagcacct ctttgcccag  420
caccgcagtg acctggtgag tgggcgcctc cccgtgggcc tcagtctcaa ggagcagggt  480
gagtgtctca gcctggccgt gttggacctg gcccggatgg cgcgagagca ggcccagcgg  540
ccgggagagc tgctgaagac tgtcagctac aaggcctgcc taccccaag cctgcgcgac  600
ctgatccagg gcctgagctt cgtgacgcgg aggcgtattc ggaggacggt gcgcagagcc  660
ctgcgccgcg tggccgcctg ccaggcagac cggcactcgc tcatggccaa gtacatcatg  720
gacctggagc ggctggatcc agccggggcc gccgagacct tccacgtggg cctccctggg  780
gcccttggtg gccacgacgg gctggggctg ctccgcgtgg ctggtgacgg cggcatcgcc  840
tggacccagg gagaacagga ggtcctccag cccttctgcg actttccaga aatcgtagac  900
attagcatca agcaggcccc gcgcgttggc ccggccggag agcaccgcct ggtcactgtt  960
accaggacag acaaccagat tttagaggcc gagttcccag ggctgcccga ggctctgtcg  1020
ttcgtggcgc tcgtggacgg ctacttccgg ctgaccacgg actcccagca cttcttctgc  1080
aaggaggtgg caccgccgag gctgctggag gaagtggccg agcagtgcca cggccccatc  1140
```

-continued

```
actctggact ttgccatcaa caagctcaag actgggggct cacgtcctgg ctcctatgtt  1200
ctccgccgca gcccccagga ctttgacagc ttcctcctca ctgtctgtgt ccagaacccc  1260
cttggtcctg attataaggg ctgcctcatc cggcgcagcc ccacaggaac cttccttctg  1320
gttggcctca gccgacccca cagcagtctt cgagagctcc tggcaacctg ctgggatggg  1380
gggctgcacg tagatggggt ggcagtgacc ctcacttcct gctgtatccc cagacccaaa  1440
gaaaagtcca acctgatcgt ggtccagaga ggtcacagcc cacccacatc atccttggtt  1500
cagccccaat cccaatacca gctgagtcag atgacatttc acaagatccc tgctgacagc  1560
ctggagtggc atgagaacct gggccatggg tccttcacca agatttaccg gggctgtcgc  1620
catgaggtgg tggatgggga ggcccgaaag acagaggtgc tgctgaaggt catggatgcc  1680
aagcacaaga actgcatgga gtcattcctg gaagcagtga gcttgatgag ccaagtgtcg  1740
taccggcatc tcgtgctgct ccacggcgtg tgcatggctg gagacagcac catggtgcag  1800
gaatttgtac acctgggggc catagacatg tatctgcgaa aacgtggcca cctggtgcca  1860
gccagctgga agctgcaggt ggtcaaacag ctggcctacg ccctcaacta tctggaggac  1920
aaaggcctgc cccatggcaa tgtctctgcc cggaaggtgc tcctggctcg ggagggggct  1980
gatgggagcc cgcccttcat caagctgagt gaccctgggg tcagccccgc tgtgttaagc  2040
ctggagatgc tcaccgacag gatcccctgg gtggcccccg agtgtctccg ggaggcgcag  2100
acacttagct tggaagctga caagtggggc ttcggcgcca cggtctggga agtgtttagt  2160
ggcgtcacca tgcccatcag tgccctggat cctgctaaga aactccaatt ttatgaggac  2220
cggcagcagc tgccggcccc caagtggaca gagctggccc tgctgattca acagtgcatg  2280
gcctatgagc cggtccagag gccctccttc cgagccgtca ttcgtgacct caatagcctc  2340
atctcttcag actatgagct cctctcagac cccacacctg gtgccctggc acctcgtgat  2400
gggctgtgga atggtgccca gctctatgcc tgccaagacc ccacgatctt cgaggagaga  2460
cacctcaagt acatctcaca gctgggcaag ggcaactttg gcagcgtgga gctgtgccgc  2520
tatgacccgc taggcgacaa tacaggtgcc ctggtggccg tgaaacagct gcagcacagc  2580
gggccagacc agcagaggga ctttcagcgg gagattcaga tcctcaaagc actgcacagt  2640
gatttcattg tcaagtatcg tggtgtcagc tatggcccgg gccgccagag cctgcggctg  2700
gtcatggagt acctgcccag cggctgcttg cgcgacttcc tgcagcggca ccgcgcgcgc  2760
ctcgatgcca gccgcctcct tctctattcc tcgcagatct gcaagggcat ggagtacctg  2820
ggctcccgcc gctgcgtgca ccgcgacctg gccgcccgaa acatcctcgt ggagagcgag  2880
gcacacgtca agatcgctga cttcggccta gctaagctgc tgccgcttga caaagactac  2940
tacgtggtcc gcgagccagg ccagagcccc attttctggt atgcccccga atccctctcg  3000
gacaacatct tctctcgcca gtcagacgtc tggagcttcg gggtcgtcct gtacgagctc  3060
ttcacctact gcgacaaaag ctgcagcccc tcggccgagt tcctgcggat gatgggatgt  3120
gagcgggatg tccccgccct ctgccgcctc ttggaactgc tggaggaggg ccagaggctg  3180
ccggcgcctc ctgcctgccc tgctgaggtt cacgagctca tgaagctgtg ctgggcccct  3240
agcccacagg accggccatc attcagcgcc ctgggccccc agctggacat gctgtggagc  3300
ggaagccggg ggtgtgagac tcatgccttc actgctcacc cagagggcaa acaccactcc  3360
ctgtcctttt cattg                                                  3375

SEQ ID NO: 92          moltype = AA  length = 1125
FEATURE                Location/Qualifiers
source                 1..1125
                       mol_type = protein
                       organism = Synthetic construct
SEQUENCE: 92
MAPPSEETPL IPQRSCSLLS TEAGALHVLL PARGPGPPQR LSFSFGDHLA EDLCVQAAKA  60
SGILPVYHSL FALATEDLSC WFPPSHIFSV EDASTQVLLY RIRFYFPNWF GLEKCHRFGL  120
RKDLASAILD LPVLEHLFAQ HRSDLVSGRL PVGLSLKEQG ECLSLAVLDL ARMAREQAQR  180
PGELLKTVSY KACLPPSLRD LIQGLSFVTR RRIRRTVRRA LRRVAACQAD RHSLMAKYIM  240
DLERLDPAGA AETFHVGLPG ALGGHDGLGL LRVAGDGGIA WTQGEQEVLQ PFCDFPEIVD  300
ISIKQAPRVG PAGEHRLVTV TRTDNQILEA EFPGLPEALS FVALVDGYFR LTTDSQHFFC  360
KEVAPPRLLE EVAEQCHGPI TLDFAINKLK TGGSRPGSYV LRRSPQDFDS FLLTVCVQNP  420
LGPDYKGCLI RRSPTGTFLL VGLSRPHSSL RELLATCWDG GLHVDGVAVT LTSCCIPRPK  480
EKSNLIVVQR GHSPPTSSLV QPQSQYQLSQ MTFHKIPADS LEWHENLGHG SFTKIYRGCR  540
HEVVDGEARK TEVLLKVMDA KHKNCMESFL EAVSLMSQVS YRHLVLLHGV CMAGDSTMVQ  600
EFVHLGAIDM YLRKRGHLVP ASWKLQVVKQ LAYALNYLED KGLPHGNVSA RKVLLAREGA  660
DGSPPFIKLS DPGVSPAVLS LEMLTDRIPW VAPECLREAQ TLSLEADKWG FGATVWEVFS  720
GVTMPISALD PAKKLQFYED RQQLPAPKWT ELALLIQQCM AYEPVQRPSF RAVIRDLNSL  780
ISSDYELLSD PTPGALAPRD GLWNGAQLYA CQDPTIFEER HLKYISQLGK GNFGSVELCR  840
YDPLGDNTGA LVAVKQLQHS GPDQQRDFQR EIQILKALHS DFIVKYRGVS YGPGRQSLRL  900
VMEYLPSGCL RDFLQRHRAR LDASRLLLYS SQICKGMEYL GSRRCVHRDL AARNILVESE  960
AHVKIADFGL AKLLPLDKDY YVVREPGQSP IFWYAPESLS DNIFSRQSDV WSFGVVLYEL  1020
FTYCDKSCSP SAEFLRMMGC ERDVPALCRL LELLEEGQRL PAPPACPAEV HELMKLCWAP  1080
SPQDRPSFSA LGPQLDMLWS GSRGCETHAF TAHPEGKHHS LSFSL                 1125

SEQ ID NO: 93          moltype = DNA  length = 3375
FEATURE                Location/Qualifiers
source                 1..3375
                       mol_type = genomic DNA
                       organism = Homo sapiens
SEQUENCE: 93
atggcacctc caagtgaaga gacgcccctg atccctcagc gttcatgcag cctcttgtcc  60
acggaggctg gtgccctgca tgtgctgctg cccgctcggg gccccgggcc cccccagcgc  120
ctatctttct cctttgggga ccacttggct gaggacctgt gcgtgcaggc tgccaaggcc  180
agcggcatcc tgcctgtgta ccactccctc tttgctctgg ccacggagga cctgtcctgc  240
tggttccccc cgagccacat cttctccgtg gaggatgcca gcacccaagt cctgctgtac  300
aggattcgct tttacttccc caattggttt gggctggaga agtgccaccg cttcgggcta  360
cgcaaggatt tggccagtgc tatccttgac ctgccagtcc tggagcacct ctttgcccag  420
caccgcagtg acctggtgag tgggcgcctc cccgtgggcc tcagtctcaa ggagcagggt  480
```

-continued

```
gagtgtctca gcctggccgt gttggacctg gcccggatgg cgcgagagca ggcccagcgg  540
ccgggagagc tgctgaagac tgtcagctac aaggcctgcc tacccccaag cctgcgcgac  600
ctgatccagg gcctgagctt cgtgacgcgg aggcgtattc ggaggacggt gcgcagagcc  660
ctgcgccgcg tggccgcctg ccaggcagac cggcactcgc tcatggccaa gtacatcatg  720
gacctggagc ggctggatcc agccggggcc gccgagacct tccacgtggg cctccctggg  780
gcccttggtg gccacgacgg gctggggctg ctccgcgtgg ctggtgacgg cggcatcgcc  840
tggacccagg gagaacagga ggtcctccag cccttctgcg actttccaga aatcgtagac  900
attagcatca agcaggcccc gcgcgttggc ccggccggag agcaccgcct ggtcactgtt  960
accaggacag acaaccagat tttagaggcc gagttcccag ggctgcccga ggctctgtcg  1020
ttcgtggcgc tcgtggacgg ctacttccgg ctgaccacgg actcccagca cttcttctgc  1080
aaggaggtgg caccgccgag gctgctggag gaagtggccg agcagtgcca cggccccatc  1140
actctggact ttgccatcaa caagctcaag actgggggct cacgtcctgg ctcctatgtt  1200
ctccgccgca gcccccagga ctttgacagc ttcctcctca ctgtctgtgt ccagaacccc  1260
cttggtcctg attataaggg ctgcctcatc cggcgcagcc ccacaggaac cttccttctg  1320
gttggcctca gccgacccca cagcagtctt cgagagctcc tggcaacctg ctgggatggg  1380
gggctgcacg tagatggggt ggcagtgacc ctcacttcct gctgtatccc cagacccaaa  1440
gaaaagtcca acctgatcgt ggtccagaga ggtcacagcc cacccacatc atccttggtt  1500
cagccccaat cccaatacca gctgagtcag atgacatttc acaagatccc tgctgacagc  1560
ctggagtggc atgagaacct gggccatggg tccttcacca agatttaccg gggctgtcgc  1620
catgaggtgg tggatgggga ggcccgaaag acagaggtgc tgctgaaggt catggatgcc  1680
aagcacaaga actgcatgga gtcattcctg gaagcagcga gcttgatgag ccaagtgtcg  1740
taccggcatc tcgtgctgct ccacggcgtg tgcatggctg gagacagcac catggtgcag  1800
gaatttgtac acctgggggc catagacatg tatctgcgaa aacgtggcca cctggtgcca  1860
gccagctgga agctgcaggt ggtcaaacag ctggcctacg ccctcaacta tctggaggac  1920
aaaggcctgc cccatggcaa tgtctctgcc cggaaggtgc tcctggctcg ggagggggct  1980
gatgggagcc cgcccttcat caagctgagt gaccctgggg tcagccccgc tgtgttaagc  2040
ctggagatgc tcaccgacag gatcccctgg gtggcccccg agtgtctccg ggaggcgcag  2100
acacttagct tggaagctga caagtggggc ttcggcgcca cggtctggga agtgtttagt  2160
ggcgtcacca tgcccatcag tgccctggat cctgctaaga aactccaatt ttatgaggac  2220
cggcagcagc tgccggcccc caagtggaca gagctggccc tgctgattca acagtgcatg  2280
gcctatgagc cggtccagag gccctccttc cgagccgtca ttcgtgacct caatagcctc  2340
atctcttcag actatgagct cctctcagac cccacacctg gtgccctggc acctcgtgat  2400
gggctgtgga atggtgccca gctctatgcc tgccaagacc ccacgatctt cgaggagaga  2460
cacctcaagt acatctcaca gctgggcaag ggcaactttg gcagcgtgga gctgtgccgc  2520
tatgacccgc taggcgacaa tacaggtgcc ctggtggccg tgaaacagct gcagcacagc  2580
gggccagacc agcagaggga ctttcagcgg gagattcaga tcctcaaagc actgcacagt  2640
gatttcattg tcaagtatcg tggtgtcagc tatggcccgg gccgccagag cctgcggctg  2700
gtcatggagt acctgcccag cggctgcttg cgcgacttcc tgcagcggca ccgcgcgcgc  2760
ctcgatgcca gccgcctcct tctctattcc tcgcagatct gcaagggcat ggagtacctg  2820
ggctcccgcc gctgcgtgca ccgcgacctg gccgcccgaa acatcctcgt ggagagcgag  2880
gcacacgtca agatcgctga cttcggccta gctaagctgc tgccgcttga caaagactac  2940
tacgtggtcc gcgagccagg ccagagcccc attttctggt atgcccccga atccctctcg  3000
gacaacatct tctctcgcca gtcagacgtc tggagcttcg gggtcgtcct gtacgagctc  3060
ttcacctact gcgacaaaag ctgcagcccc tcggccgagt tcctgcggat gatgggatgt  3120
gagcgggatg tccccgccct ctgccgcctc ttggaactgc tggaggaggg ccagaggctg  3180
ccggcgcctc ctgcctgccc tgctgaggtt cacgagctca tgaagctgtg ctgggcccct  3240
agcccacagg accggccatc attcagcgcc ctgggccccc agctggacat gctgtggagc  3300
ggaagccggg ggtgtgagac tcatgccttc actgctcacc cagagggcaa acaccactcc  3360
ctgtcctttt cattg                                                   3375
```

SEQ ID NO: 94 moltype = AA length = 1125
FEATURE Location/Qualifiers
source 1..1125
mol_type = protein
organism = Homo sapiens

SEQUENCE: 94

```
MAPPSEETPL IPQRSCSLLS TEAGALHVLL PARGPGPPQR LSFSFGDHLA EDLCVQAAKA  60
SGILPVYHSL FALATEDLSC WFPPSHIFSV EDASTQVLLY RIRFYFPNWF GLEKCHRFGL  120
RKDLASAILD LPVLEHLFAQ HRSDLVSGRL PVGLSLKEQG ECLSLAVLDL ARMAREQAQR  180
PGELLKTVSY KACLPPSLRD LIQGLSFVTR RRIRRTVRRA LRRVAACQAD RHSLMAKYIM  240
DLERLDPAGA AETFHVGLPG ALGGHDGLGL LRVAGDGGIA WTQGEQEVLQ PFCDFPEIVD  300
ISIKQAPRVG PAGEHRLVTV TRTDNQILEA EFPGLPEALS FVALVDGYFR LTTDSQHFFC  360
KEVAPPRLLE EVAEQCHGPI TLDFAINKLK TGGSRPGSYV LRRSPQDFDS FLLTVCVQNP  420
LGPDYKGCLI RRSPTGTFLL VGLSRPHSSL RELLATCWDG GLHVDGVAVT LTSCCIPRPK  480
EKSNLIVVQR GHSPPTSSLV QPQSQYQLSQ MTFHKIPADS LEWHENLGHG SFTKIYRGCR  540
HEVVDGEARK TEVLLKVMDA KHKNCMESFL EASLMSQVS YRHLVLLHGV CMAGDSTMVQ  600
EFVHLGAIDM YLRKRGHLVP ASWKLQVVKQ LAYALNYLED KGLPHGNVSA RKVLLAREGA  660
DGSPPFIKLS DPGVSPAVLS LEMLTDRIPW VAPECLREAQ TLSLEADKWG FGATVWEVFS  720
GVTMPISALD PAKKLQFYED RQQLPAPKWT ELALLIQQCM AYEPVQRPSF RAVIRDLNSL  780
ISSDYELLSD PTPGALAPRD GLWNGAQLYA CQDPTIFEER HLKYISQLGK GNFGSVELCR  840
YDPLGDNTGA LVAVKQLQHS GPDQQRDFQR EIQILKALHS DFIVKYRGVS YGPGRQSLRL  900
VMEYLPSGCL RDFLQRHRAR LDASRLLLYS SQICKGMEYL GSRRCVHRDL AARNILVESE  960
AHVKIADFGL AKLLPLDKDY YVVREPGQSP IFWYAPESLS DNIFSRQSDV WSFGVVLYEL  1020
FTYCDKSCSP SAEFLRMMGC ERDVPALCRL LELLEEGQRL PAPPACPAEV HELMKLCWAP  1080
SPQDRPSFSA LGPQLDMLWS GSRGCETHAF TAHPEGKHHS LSFSL                  1125
```

SEQ ID NO: 95 moltype = DNA length = 1041
FEATURE Location/Qualifiers
source 1..1041

```
                        mol_type = other DNA
                        organism = Synthetic construct
SEQUENCE: 95
atgtgcacta aaatggaaca gcccttctac cacgacgact catacacagc tacgggatac  60
ggccgggccc ctggtggcct ctctctacac gactacaaac tcctgaaacc gagcctggcg  120
gtcaacctgg ccgaccccta ccggagtctc aaagcgcctg gggctcgcgg acccggccca  180
gagggcggcg gtggcggcag ctacttttct ggtcagggct cggacaccgg cgcgtctctc  240
aagctcgcct cttcggagct ggaacgcctg attgtcccca acagcaacgg cgtgatcacg  300
acgacgccta cacccccggg acagtacttt tacccccgcg gggtggcag cggtggaggt  360
gcagggggcg cagggggcgg cgtcaccgag gagcaggagg gcttcgccga cggctttgtc  420
aaagccctgg acgatctgca caagatgaac cacgtgacac cccccaacgt gtccctgggc  480
gctaccgggg ggcccccggc tgggcccggg ggcgtctacg ccggcccgga gccacctccc  540
gtttacacca acctcagcag ctactcccca gcctctgcgt cctcgggagg cgccggggct  600
gccgtcggga ccgggagctc gtacccgacg accaccatca gctacctccc acacgcgccg  660
cccttcgccg gtggccaccc ggcgcagctg ggcttgggcc gcggcgcctc caccttcaag  720
gaggaaccgc agaccgtgcc ggaggcgcgc agccgggacg ccacgccgcc ggtgtccccc  780
atcaacatgg aagaccaaga gcgcatcaaa gtggagcgca agcggctgcg gaaccggctg  840
gcggtcacca agtgccggaa gcggaagctg gagcgcatcg cgcgcctgga ggacaaggtg  900
aagacgctca aggccgagaa cgcggggctg tcgagtaccg ccggcctcct ccgggagcag  960
gtggcccagc tcaaacagaa ggtcatgacc cacgtcagca acggctgtca gctgctgctt  1020
ggggtcaagg gacacgcctt c                                            1041

SEQ ID NO: 96           moltype = AA  length = 347
FEATURE                 Location/Qualifiers
source                  1..347
                        mol_type = protein
                        organism = Synthetic construct
SEQUENCE: 96
MCTKMEQPFY HDDSYTATGY GRAPGGLSLH DYKLLKPSLA VNLADPYRSL KAPGARGPGP  60
EGGGGGSYFS GQGSDTGASL KLASSELERL IVPNSNGVIT TTPTPPGQYF YPRGGGSGGG  120
AGGAGGGVTE EQEGFADGFV KALDDLHKMN HVTPPNVSLG ATGGPPAGPG GVYAGPEPPP  180
VYTNLSSYSP ASASSGGAGA AVGTGSSYPT TTISYLPHAP PFAGGHPAQL GLGRGASTFK  240
EEPQTVPEAR SRDATPPVSP INMEDQERIK VERKRLRNRL AVTKCRKRKL ERIARLEDKV  300
KTLKAENAGL SSTAGLLREQ VAQLKQKVMT HVSNGCQLLL GVKGHAF                347

SEQ ID NO: 97           moltype = DNA  length = 1041
FEATURE                 Location/Qualifiers
source                  1..1041
                        mol_type = genomic DNA
                        organism = Homo sapiens
SEQUENCE: 97
atgtgcacta aaatggaaca gcccttctac cacgacgact catacacagc tacgggatac  60
ggccgggccc ctggtggcct ctctctacac gactacaaac tcctgaaacc gagcctggcg  120
gtcaacctgg ccgaccccta ccggagtctc aaagcgcctg gggctcgcgg acccggccca  180
gagggcggcg gtggcggcag ctacttttct ggtcagggct cggacaccgg cgcgtctctc  240
aagctcgcct cttcggagct ggaacgcctg attgtcccca acagcaacgg cgtgatcacg  300
acgacgccta cacccccggg acagtacttt tacccccgcg gggtggcag cggtggaggt  360
gcagggggcg cagggggcgg cgtcaccgag gagcaggagg gcttcgccga cggctttgtc  420
aaagccctgg acgatctgca caagatgaac cacgtgacac cccccaacgt gtccctgggc  480
gctaccgggg ggcccccggc tgggcccggg ggcgtctacg ccggcccgga gccacctccc  540
gtttacacca acctcagcag ctactcccca gcctctgcgt cctcgggagg cgccggggct  600
gccgtcggga ccgggagctc gtacccgacg accaccatca gctacctccc acacgcgccg  660
cccttcgccg gtggccaccc ggcgcagctg ggcttgggcc gcggcgcctc caccttcaag  720
gaggaaccgc agaccgtgcc ggaggcgcgc agccgggacg ccacgccgcc ggtgtccccc  780
atcaacatgg aagaccaaga gcgcatcaaa gtggagcgca agcggctgcg gaaccggctg  840
gcggccacca agtgccggaa gcggaagctg gagcgcatcg cgcgcctgga ggacaaggtg  900
aagacgctca aggccgagaa cgcggggctg tcgagtaccg ccggcctcct ccgggagcag  960
gtggcccagc tcaaacagaa ggtcatgacc cacgtcagca acggctgtca gctgctgctt  1020
ggggtcaagg gacacgcctt c                                            1041

SEQ ID NO: 98           moltype = AA  length = 347
FEATURE                 Location/Qualifiers
source                  1..347
                        mol_type = protein
                        organism = Homo sapiens
SEQUENCE: 98
MCTKMEQPFY HDDSYTATGY GRAPGGLSLH DYKLLKPSLA VNLADPYRSL KAPGARGPGP  60
EGGGGGSYFS GQGSDTGASL KLASSELERL IVPNSNGVIT TTPTPPGQYF YPRGGGSGGG  120
AGGAGGGVTE EQEGFADGFV KALDDLHKMN HVTPPNVSLG ATGGPPAGPG GVYAGPEPPP  180
VYTNLSSYSP ASASSGGAGA AVGTGSSYPT TTISYLPHAP PFAGGHPAQL GLGRGASTFK  240
EEPQTVPEAR SRDATPPVSP INMEDQERIK VERKRLRNRL AATKCRKRKL ERIARLEDKV  300
KTLKAENAGL SSTAGLLREQ VAQLKQKVMT HVSNGCQLLL GVKGHAF                347

SEQ ID NO: 99           moltype = DNA  length = 2028
FEATURE                 Location/Qualifiers
source                  1..2028
                        mol_type = other DNA
                        organism = Synthetic construct
SEQUENCE: 99
```

-continued

```
atggccgcgg cctcctcccc gcccagggcc gagaggaagc gctggggttg gggccgcctg  60
ccaggcgccc ggcggggcag cgcgggcctg gccaagaagt gccccttctc gctggagctg  120
gcggagggcg gcccggcggg cggcgcgctc tacgcgccca tcgcgcccgg cgccccaggt  180
cccgcgcccc ctgcgtcccc ggccgcgccc gccgcgcccc cagttgcctc cgaccttggc  240
ccgcggccgc cggtgagcct agacccgcgc gtctccatct acagcacgcg ccgcccggtg  300
ttggcgcgca cccacgtcca gggccgcgtc tacaacttcc tcgagcgtcc caccggctgg  360
aaatgcttcg tttaccactt cgccgtcttc ctcatcgtcc tggtctgcct catcttcagc  420
gtgctgtcca ccatcgagca gtatgccgcc ctggccacgg ggactctctt ctggatggag  480
atcgtgctgg tggtgttctt cgggacggag tacgtggtcc gcctctggtc cgccggctgc  540
cgcagcaagt acgtgggcct ctgggggcgg ctgcgctttg cccggaagcc catttccatc  600
atcgacctca tcgtggtcgt ggcctccatg gtggtcctct gcgtgggctc caaggggcag  660
gtgtttgcca cgtcggccat caggggcatc cgcttcctgc agatcctgag gatgctacac  720
gtcgaccgcc agggaggcac ctggaggctc ctgggctccg tggtcttcat ccaccgccag  780
gagctgataa ccaccctgta catcggcttc ctgggcctca tcttctcctc gtactttgtg  840
tacctggctg agaaggacgc ggtgaacgag tcaggccgcg tggagttcgg cagctacgca  900
gatgcgctgt ggtggggggt ggtcacagtc accaccatcg gctatgggga caaggtgccc  960
cagacgtggg tcgggaagac catcgcctcc tgcttctctg tctttgccat ctccttcttt  1020
gcgctcccag cggggattct tggctcgggg tttgccctga aggtgcagca gaagcagagg  1080
cagaagcact tcaaccggca gatcccggcg gcagcctcac tcattcagac cgcatggagg  1140
tgctatgctg ccgagaaccc cgactcctcc acctggaaga tctacatccg gaaggccccc  1200
cggagccaca ctctgctgtc acccagcccc aaacccaaga agtctgtggt ggtaaagaaa  1260
aaaaagttca agctggacaa agacaatggg gtgactcctg gagagaagat gctcacagtc  1320
ccccatatca cgtgcgaccc cccagaagag cggcggctgg accacttctc tgtcgacggc  1380
tatgacagtt ctgtaaggaa gagcccaaca ctgctggaag tgagcatgcc ccatttcatg  1440
agaaccaaca gcttcgccga ggacctggac ctggaagggg agactctgct gacacccatc  1500
acccacatct cacagctgcg ggaacaccat cgggccacca ttaaggtcat tcgacgcatg  1560
cagtactttg tggccaagaa gaaattccag caagcgcgga agccttacga tgtgcgggac  1620
gtcattgagc agtactcgca gggccacctc aacctcatgg tgcgcatcaa ggagctgcag  1680
aggaggctgg accagtccat tgggaagccc tcactgttca tctccgtctc agaaaagagc  1740
aaggattgcg gcagcaacac gatcggcgcc cgcctgaacc gagtagaaga caaggtgacg  1800
cagctggacc agaggctggc actcatcacc gacatgcttc accagctgct ctccttgcac  1860
ggtggcagca cccccggcag cggcggcccc cccagagagg gcggggccca catcacccag  1920
ccctgcggca gtggcggctc cgtcgaccct gagctcttcc tgcccagcaa caccctgccc  1980
acctacgagc agctgaccgt gcccaggagg ggccccgatg aggggtcc  2028

SEQ ID NO: 100         moltype = AA  length = 676
FEATURE                Location/Qualifiers
source                 1..676
                       mol_type = protein
                       organism = Synthetic construct
SEQUENCE: 100
MAAASSPPRA ERKRWGWGRL PGARRGSAGL AKKCPFSLEL AEGGPAGGAL YAPIAPGAPG  60
PAPPASPAAP AAPPVASDLG PRPPVSLDPR VSIYSTRRPV LARTHVQGRV YNFLERPTGW  120
KCFVYHFAVF LIVLVCLIFS VLSTIEQYAA LATGTLFWME IVLVVFFGTE YVVRLWSAGC  180
RSKYVGLWGR LRFARKPISI IDLIVVVASM VVLCVGSKGQ VFATSAIRGI RFLQILRMLH  240
VDRQGGTWRL LGSVVFIHRQ ELITTLYIGF LGLIFSSYFV YLAEKDAVNE SGRVEFGSYA  300
DALWWGVVTV TTIGYGDKVP QTWVGKTIAS CFSVFAISFF ALPAGILGSG FALKVQQKQR  360
QKHFNRQIPA AASLIQTAWR CYAAENPDSS TWKIYIRKAP RSHTLLSPSP KPKKSVVVKK  420
KKFKLDKDNG VTPGEKMLTV PHITCDPPEE RRLDHFSVDG YDSSVRKSPT LLEVSMPHFM  480
RTNSFAEDLD LEGETLLTPI THISQLREHH RATIKVIRRM QYFVAKKKFQ QARKPYDVRD  540
VIEQYSQGHL NLMVRIKELQ RRLDQSIGKP SLFISVSEKS KDCGSNTIGA RLNRVEDKVT  600
QLDQRLALIT DMLHQLLSLH GGSTPGSGGP PREGGAHITQ PCGSGGSVDP ELFLPSNTLP  660
TYEQLTVPRR GPDEGS                                              676

SEQ ID NO: 101         moltype = DNA  length = 2028
FEATURE                Location/Qualifiers
source                 1..2028
                       mol_type = genomic DNA
                       organism = Homo sapiens
SEQUENCE: 101
atggccgcgg cctcctcccc gcccagggcc gagaggaagc gctggggttg gggccgcctg  60
ccaggcgccc ggcggggcag cgcgggcctg gccaagaagt gccccttctc gctggagctg  120
gcggagggcg gcccggcggg cggcgcgctc tacgcgccca tcgcgcccgg cgccccaggt  180
cccgcgcccc ctgcgtcccc ggccgcgccc gccgcgcccc cagttgcctc cgaccttggc  240
ccgcggccgc cggtgagcct agacccgcgc gtctccatct acagcacgcg ccgcccggtg  300
ttggcgcgca cccacgtcca gggccgcgtc tacaacttcc tcgagcgtcc caccggctgg  360
aaatgcttcg tttaccactt cgccgtcttc ctcatcgtcc tggtctgcct catcttcagc  420
gtgctgtcca ccatcgagca gtatgccgcc ctggccacgg ggactctctt ctggatggag  480
atcgtgctgg tggtgttctt cgggacggag tacgtggtcc gcctctggtc cgccggctgc  540
cgcagcaagt acgtgggcct ctgggggcgg ctgcgctttg cccggaagcc catttccatc  600
atcgacctca tcgtggtcgt ggcctccatg gtggtcctct gcgtgggctc caaggggcag  660
gtgtttgcca cgtcggccat caggggcatc cgcttcctgc agatcctgag gatgctacac  720
gtcgaccgcc agggaggcac ctggaggctc ctgggctccg tggtcttcat ccaccgccag  780
gagctgataa ccaccctgta catcggcttc ctgggcctca tcttctcctc gtactttgtg  840
tacctggctg agaaggacgc ggtgaacgag tcaggccgcg tggagttcgg cagctacgca  900
gatgcgctgt ggtggggggt ggtcacagtc accaccatcg gctatgggga caaggtgccc  960
cagacgtggg tcgggaagac catcgcctcc tgcttctctg tctttgccat ctccttcttt  1020
gcgctcccag cggggattct tggctcgggg tttgccctga aggtgcagca gaagcagagg  1080
cagaagcact tcaaccggca gatcccggcg gcagcctcac tcattcagac cgcatggagg  1140
```

-continued

```
tgctatgctg ccgagaaccc cgactcctcc acctggaaga tctacatccg gaaggccccc  1200
cggagccaca ctctgctgtc acccagcccc aaacccaaga agtctgtggt ggtaaagaaa  1260
aaaaagttca agctggacaa agacaatggg gtgactcctg gagagaagat gctcacagtc  1320
ccccatatca cgtgcgaccc cccagaagag cggcggctgg accacttctc tgtcgacggc  1380
tatgacagtt ctgtaaggaa gagcccaaca ctgctggaag tgagcatgcc ccatttcatg  1440
agaaccaaca gcttcgccga ggacctggac ctggaagggg agactctgct gacacccatc  1500
acccacatct cacagctgcg ggaacaccat cgggccacca ttaaggtcat tcgacgcatg  1560
cagtactttg tggccaagaa gaaattccag caagcgcgga agccttacga tgtgcgggac  1620
gtcattgagc agtactcgca gggccacctc aacctcatgg tgcgcatcaa ggagctgcag  1680
aggaggctgg accagtccat tgggaagccc tcactgttca tctccgtctc agaaaagagc  1740
aaggatcgcg gcagcaacac gatcggcgcc cgcctgaacc gagtagaaga caaggtgacg  1800
cagctggacc agaggctggc actcatcacc gacatgcttc accagctgct ctccttgcac  1860
ggtggcagca cccccggcag cggcggcccc cccagagagg gcggggccca catcacccag  1920
ccctgcggca gtggcggctc cgtcgaccct gagctcttcc tgcccagcaa caccctgccc  1980
acctacgagc agctgaccgt gcccaggagg ggccccgatg aggggtcc             2028

SEQ ID NO: 102          moltype = AA  length = 676
FEATURE                 Location/Qualifiers
source                  1..676
                        mol_type = protein
                        organism = Homo sapiens
SEQUENCE: 102
MAAASSPPRA ERKRWGWGRL PGARRGSAGL AKKCPFSLEL AEGGPAGGAL YAPIAPGAPG  60
PAPPASPAAP AAPPVASDLG PRPPVSLDPR VSIYSTRRPV LARTHVQGRV YNFLERPTGW  120
KCFVYHFAVF LIVLVCLIFS VLSTIEQYAA LATGTLFWME IVLVVFFGTE YVVRLWSAGC  180
RSKYVGLWGR LRFARKPISI IDLIVVVASM VVLCVGSKGQ VFATSAIRGI RFLQILRMLH  240
VDRQGGTWRL LGSVVFIHRQ ELITTLYIGF LGLIFSSYFV YLAEKDAVNE SGRVEFGSYA  300
DALWWGVVTV TTIGYGDKVP QTWVGKTIAS CFSVFAISFF ALPAGILGSG FALKVQQKQR  360
QKHFNRQIPA AASLIQTAWR CYAAENPDSS TWKIYIRKAP RSHTLLSPSP KPKKSVVVKK  420
KKFKLDKDNG VTPGEKMLTV PHITCDPPEE RRLDHFSVDG YDSSVRKSPT LLEVSMPHFM  480
RTNSFAEDLD LEGETLLTPI THISQLREHH RATIKVIRRM QYFVAKKKFQ QARKPYDVRD  540
VIEQYSQGHL NLMVRIKELQ RRLDQSIGKP SLFISVSEKS KDRGSNTIGA RLNRVEDKVT  600
QLDQRLALIT DMLHQLLSLH GGSTPGSGGP PREGGAHITQ PCGSGGSVDP ELFLPSNTLP  660
TYEQLTVPRR GPDEGS                                                 676

SEQ ID NO: 103          moltype = DNA  length = 3390
FEATURE                 Location/Qualifiers
source                  1..3390
                        mol_type = other DNA
                        organism = Synthetic construct
SEQUENCE: 103
atgaagagga gtgaaaagcc agaaggatat agacaaatga ggcctaagac ctttcctgcc  60
agtaactata ctgtcagtag ccggcaaatg ttacaagaaa ttcgggaatc ccttaggaat  120
ttatctaaac catctgatgc tgctaaggct gagcataaca tgagtaaaat gtcaaccgaa  180
gatcctcgac aagtcagaaa tccacccaaa tttgggacgc atcataaagc cttgcaggaa  240
attcgaaact ctctgcttcc atttgcaaat gaaacaaatt cttctcggag tacttcagaa  300
gttaatccac aaatgcttca agacttgcaa gctgctggat ttgatgagga tatggttata  360
caagctcttc agaaaactaa caacagaagt atagaagcag caattgaatt cattagtaaa  420
atgagttacc aagatcctcg acgagagcag atggctgcag cagctgccag acctattaat  480
gccagcatga aacagggaa tgtgcagcaa tcagttaacc gcaaacagag ctggaaaggt  540
tctaaagaat ccttagttcc tcagaggcat ggcccgccac taggagaaag tgtggcctat  600
cattctgaga gtcccaactc acagacagat gtaggaagac ctttgtctgg atctggtata  660
tcagcatttg ttcaagctca ccctagcaac ggacagagag tgaacccccc accaccacct  720
caagtaagga gtgttactcc tccaccacct ccaagaggcc agactccccc tccaagaggt  780
acaactccac ctcccccttc atgggaacca aactctcaaa caaagcgcta ttctggaaac  840
atggaatacg taatctcccg aatctctcct gtcccacctg gggcatggca agagggctat  900
cctccaccac ctctcaacac ttcccccatg aatcctccta atcaaggaca gagaggcatt  960
agttctgttc ctgttggcag acaaccaatc atcatgcaga gttctagcaa atttaacttt  1020
ccatcaggga gacctggaat gcagaatggt actggacaaa ctgatttcat gatacaccaa  1080
aatgttgtcc ctgctggcac tgtgaatcgg cagccaccac ctccatatcc tctgacagca  1140
gctaatggac aaagcccttc tgctttacaa acagggggat ctgctgctcc ttcgtcatat  1200
acaaatggaa gtattcctca gtctatgatg gtgccaaaca gaaatagtca taacatggaa  1260
ctatataaca ttagtgtacc tggactgcaa acaaattggc ctcagtcatc ttctgctcca  1320
gcccagtcat ccccgagcag tgggcatgaa atccctacat ggcaacctaa cataccagtg  1380
aggtcaaatt cttttaataa cccattagga aatagagcaa gtcactctgc taattctcag  1440
ccttctgcta caacagtcac tgcaattaca ccagctccta ttcaacagcc tgtgaaaagt  1500
atgcgtgtat taaaaccaga gctacagact gctttagcac ctacacaccc ttcttggata  1560
ccacagccaa ttcaaactgt tcaacccagt cctttttcctg agggaaccgc ttcaaatgtg  1620
actgtgatgc cacctgttgc tgaagctcca aactatcaag gaccaccacc accctaccca  1680
aaacatctgc tgcaccaaaa cccatctgtt cctccatacg agtcaatcag taagcctagc  1740
aaagaggatc agccaagctt gcccaaggaa gatgagagtg aaaagagtta tgaaaatgtt  1800
gatagtgggg ataaagaaaa gaaacagatt acaacttcac ctattactgt taggaaaaac  1860
aagaaagatg aagagcgaag ggaatctcgt attcaaagtt attctcctca agcatttaaa  1920
ttctttatgg agcaacatgt agaaaatgta ctcaaatctc atcagcagcg tctacatcgt  1980
aaaaaacaat tagagaatga aatgatgcgg gttggattat ctcaagatgc ccaggatcaa  2040
atgagaaaga tgctttgcca aaaagaatct aattacatcc gtcttaaaag ggctaaaatg  2100
gacaagtcta tgtttgtgaa gataaagaca ctaggaatag gagcatttgg tgaagtctgt  2160
ctagcaagaa aagtagatac taaggctttg tatgcaacaa aaactcttcg aaagaaagat  2220
gttcttcttc gaaatcaagt cgctcatgtt aaggctgaga gagatatcct ggctgaagct  2280
```

```
gacaatgaat gggtagttcg tctatattat tcattccaag ataaggacaa tttatacttt  2340
gtaatggact acattcctgg gggtgatatg atgagcctat taattagaat gggcatcttt  2400
ccagaaagtc tggcacgatt ctacatagca gaacttacct gtgcagttga aagtgttcat  2460
aaaatgggtt ttattcatag agatattaaa cctgataata ttttgattga tcgtgatggt  2520
catattaaat tgactgactt tggcctctgc actggcttca gatggacaca cgattctaag  2580
tactatcaga gtggtgacca tccacggcaa gatagcatgg atttcagtaa tgaatggggg  2640
gatccctcaa gctgtcgatg tggagacaga ctgaagccat tagagcggag agctgcacgc  2700
cagcaccagc gatgtctagc acattctttg gttgggactc ccaattatat tgcacctgaa  2760
gtgttgctac gaacaggata cacacagttg tgtgattggt ggagtgttgg tgttattctt  2820
tttgaaatgt tggtgggaca acctcctttc ttggcacaaa caccattaga aacacaaatg  2880
aaggttatca actggcaaac atctcttcac attccaccac aagctaaact cagtcctgaa  2940
gcttctgatc ttattattaa actttgccga ggacccgaag atcgcttagg caagaatggt  3000
gctgatgaaa taaaagctca tccatttttt aaaacaattg acttctccag tgacctgaga  3060
cagcagtctg cttcatacat tcctaaaatc acacacccaa cagatacatc aaattttgat  3120
cctgttgatc ctgataaatt atggagtgat gataacgagg aagaaaatgt aaatgacact  3180
ctcaatggat ggtataaaaa tggaaagcat cctgaacatg cattctatga atttaccttc  3240
cgaaggtttt ttgatgacaa tggctaccca tataattatc cgaagcctat tgaatatgaa  3300
tacattaatt cacaaggctc agagcagcag tcggatgaag atgatcaaaa cacaggctca  3360
gagattaaaa atcgcgatct agtatatgtt                                   3390

SEQ ID NO: 104          moltype = AA  length = 1130
FEATURE                 Location/Qualifiers
source                  1..1130
                        mol_type = protein
                        organism = Synthetic construct
SEQUENCE: 104
MKRSEKPEGY RQMRPKTFPA SNYTVSSRQM LQEIRESLRN LSKPSDAAKA EHNMSKMSTE  60
DPRQVRNPPK FGTHHKALQE IRNSLLPFAN ETNSSRSTSE VNPQMLQDLQ AAGFDEDMVI  120
QALQKTNNRS IEAAIEFISK MSYQDPRREQ MAAAAARPIN ASMKTGNVQQ SVNRKQSWKG  180
SKESLVPQRH GPPLGESVAY HSESPNSQTD VGRPLSGSGI SAFVQAHPSN GQRVNPPPPP  240
QVRSVTPPPP PRGQTPPPRG TTPPPPSWEP NSQTKRYSGN MEYVISRISP VPPGAWQEGY  300
PPPPLNTSPM NPPNQGQRGI SSVPVGRQPI IMQSSSKFNF PSGRPGMQNG TGQTDFMIHQ  360
NVVPAGTVNR QPPPPYPLTA ANGQSPSALQ TGGSAAPSSY TNGSIPQSMM VPNRNSHNME  420
LYNISVPGLQ TNWPQSSSAP AQSSPSSGHE IPTWQPNIPV RSNSFNNPLG NRASHSANSQ  480
PSATTVTAIT PAPIQQPVKS MRVLKPELQT ALAPTHPSWI PQPIQTVQPS PFPEGTASNV  540
TVMPPVAEAP NYQGPPPPYP KHLLHQNPSV PPYESISKPS KEDQPSLPKE DESEKSYENV  600
DSGDKEKKQI TTSPITVRKN KKDEERRESR IQSYSPQAFK FFMEQHVENV LKSHQQRLHR  660
KKQLENEMMR VGLSQDAQDQ MRKMLCQKES NYIRLKRAKM DKSMFVKIKT LGIGAFGEVC  720
LARKVDTKAL YATKTLRKKD VLLRNQVAHV KAERDILAEA DNEWVVRLYY SFQDKDNLYF  780
VMDYIPGGDM MSLLIRMGIF PESLARFYIA ELTCAVESVH KMGFIHRDIK PDNILIDRDG  840
HIKLTDFGLC TGFRWTHDSK YYQSGDHPRQ DSMDFSNEWG DPSSCRCGDR LKPLERRAAR  900
QHQRCLAHSL VGTPNYIAPE VLLRTGYTQL CDWWSVGVIL FEMLVGQPPF LAQTPLETQM  960
KVINWQTSLH IPPQAKLSPE ASDLIIKLCR GPEDRLGKNG ADEIKAHPFF KTIDFSSDLR  1020
QQSASYIPKI THPTDTSNFD PVDPDKLWSD DNEEENVNDT LNGWYKNGKH PEHAFYEFTF  1080
RRFFDDNGYP YNYPKPIEYE YINSQGSEQQ SDEDDQNTGS EIKNRDLVYV             1130

SEQ ID NO: 105          moltype = DNA  length = 3390
FEATURE                 Location/Qualifiers
source                  1..3390
                        mol_type = genomic DNA
                        organism = Homo sapiens
SEQUENCE: 105
atgaagagga gtgaaaagcc agaaggatat agacaaatga ggcctaagac ctttcctgcc  60
agtaactata ctgtcagtag ccggcaaatg ttacaagaaa ttcgggaatc ccttaggaat  120
ttatctaaac catctgatgc tgctaaggct gagcataaca tgagtaaaat gtcaaccgaa  180
gatcctcgac aagtcagaaa tccacccaaa tttgggacgc atcataaagc cttgcaggaa  240
attcgaaact ctctgcttcc atttgcaaat gaaacaaatt cttctcggag tacttcagaa  300
gttaatccac aaatgcttca agacttgcaa gctgctggat ttgatgagga tatggttata  360
caagctcttc agaaaactaa caacagaagt atagaagcag caattgaatt cattagtaaa  420
atgagttacc aagatcctcg acgagagcag atggctgcag cagctgccag acctattaat  480
gccagcatga aaccagggaa tgtgcagcaa tcagttaacc gcaaacagag ctggaaaggt  540
tctaaagaat ccttagttcc tcagaggcat ggcccgccac taggagaaag tgtggcctat  600
cattctgaga gtcccaactc acagacagat gtaggaagac ctttgtctgg atctggtata  660
tcagcatttg ttcaagctca ccctagcaac ggacagagag tgaacccccc accaccacct  720
caagtaagga gtgttactcc tccaccacct ccaagaggcc agactccccc tccaagaggt  780
acaactccac ctccccottc atgggaacca aactctcaaa caaagcgcta ttctggaaac  840
atggaatacg taatctcccg aatctctcct gtcccacctg ggcatggca agagggctat  900
cctccaccac ctctcaacac ttcccccatg aatcctccta atcaaggaca gagaggcatt  960
agttctgttc ctgttggcag acaaccaatc atcatgcaga gttctagcaa atttaacttt  1020
ccatcaggga gacctggaat gcagaatggt actggacaaa ctgatttcat gatacaccaa  1080
aatgttgtcc ctgctggcac tgtgaatcgg cagccaccac ctccatatcc tctgacagca  1140
gctaatggac aaagcccttc tgctttacaa acagggggat ctgctgctcc ttcgtcatat  1200
acaaatggaa gtattcctca gtctatgatg gtgccaaaca gaaatagtca taacatggaa  1260
ctatataaca ttagtgtacc tggactgcaa acaaattggc ctcagtcatc ttctgctcca  1320
gcccagtcat ccccgagcag tgggcatgaa atccctacat ggcaacctaa cataccagtg  1380
aggtcaaatt cttttaataa cccattagga aatagagcaa gtcactctgc taattctcag  1440
ccttctgcta caacagtcac tgcaattaca ccagctccta ttcaacagcc tgtgaaaagt  1500
atgcgtgtat taaaaccaga gctacagact gctttagcac ctacacaccc ttcttggata  1560
ccacagccaa ttcaaactgt tcaacccagt ccttttcctg agggaaccgc ttcaaatgtg  1620
```

-continued

```
actgtgatgc cacctgttgc tgaagctcca aactatcaag gaccaccacc accctaccca  1680
aaacatctgc tgcaccaaaa cccatctgtt cctccatacg agtcaatcag taagcctagc  1740
aaagaggatc agccaagctt gcccaaggaa gatgagagtg aaaagagtta tgaaaatgtt  1800
gatagtgggg ataaagaaaa gaaacagatt acaacttcac ctattactgt taggaaaaac  1860
aagaaagatg aagagcgaag ggaatctcgt attcaaagtt attctcctca agcatttaaa  1920
ttctttatgg agcaacatgt agaaaatgta ctcaaatctc atcagcagcg tctacatcgt  1980
aaaaaacaat tagagaatga aatgatgcgg gttggattat ctcaagatgc ccaggatcaa  2040
atgagaaaga tgctttgcca aaaagaatct aattacatcc gtcttaaaag ggctaaaatg  2100
gacaagtcta tgtttgtgaa gataaagaca ctaggaatag gagcatttgg tgaagtctgt  2160
ctagcaagaa aagtagatac taaggctttg tatgcaacaa aaactcttcg aaagaaagat  2220
gttcttcttc gaaatcaagt cgctcatgtt aaggctgaga gagatatcct ggctgaagct  2280
gacaatgaat gggtagttcg tctatattat tcattccaag ataaggacaa tttatacttt  2340
gtaatggact acattcctgg gggtgatatg atgagcctat taattagaat gggcatcttt  2400
ccagaaagtc tggcacgatt ctacatagca gaacttacct gtgcagttga aagtgttcat  2460
aaaatgggtt ttattcatag agatattaaa cctgataata ttttgattga tcgtgatggt  2520
catattaaat tgactgactt tggcctctgc actggcttca gatggacaca cgattctaag  2580
tactatcaga gtggtgacca tccacggcaa gatagcatgg atttcagtaa tgaatggggg  2640
gatccctcaa gctgtcgatg tggagacaga ctgaagccat tagagcggag agctgcacgc  2700
cagcaccagc gatgtctagc acattctttg gttgggactc ccaattatat tgcacctgaa  2760
gtgttgctac gaacaggata cacacagttg tgtgattggt ggagtgttgg tgttattctt  2820
tttgaaatgt tggtgggaca acctcctttc ttggcacaaa caccattaga aacacaaatg  2880
aaggttatca actggcaaac atctcttcac attccaccac aagctaaact cagtcctgaa  2940
gcttctgatc ttattattaa actttgccga ggacccgaag atcgcttagg caagaatggt  3000
gctgatgaaa taaaagctca tccatttttt aaaacaattg acttctccag tgacctgaga  3060
cagcagtctg cttcatacat tcctaaaatc acacacccaa cagatacatc aaattttgat  3120
cctgttgatc ctgataaatt atggagtgat gataacgagg aagaaaatgt aaatgacact  3180
ctcaatggat ggtataaaaa tggaaagcat cctgaacatg cattctatga atttaccttc  3240
cgaaggtttt ttgatgacaa tggctaccca tataattatc cgaagcctat tgaatatgaa  3300
tacattaatt cacaaggctc agagcagcag tcggatgaag atgatcaaaa cacaggctca  3360
gagattaaaa atcgcgatct agtatatgtt                                   3390

SEQ ID NO: 106          moltype = AA  length = 1130
FEATURE                 Location/Qualifiers
source                  1..1130
                        mol_type = protein
                        organism = Homo sapiens
SEQUENCE: 106
MKRSEKPEGY RQMRPKTFPA SNYTVSSRQM LQEIRESLRN LSKPSDAAKA EHNMSKMSTE  60
DPRQVRNPPK FGTHHKALQE IRNSLLPFAN ETNSSRSTSE VNPQMLQDLQ AAGFDEDMVI  120
QALQKTNNRS IEAAIEFISK MSYQDPRREQ MAAAAARPIN ASMKPGNVQQ SVNRKQSWKG  180
SKESLVPQRH GPPLGESVAY HSESPNSQTD VGRPLSGSGI SAFVQAHPSN GQRVNPPPPP  240
QVRSVTPPPP PRGQTPPPRG TTPPPPSWEP NSQTKRYSGN MEYVISRISP VPPGAWQEGY  300
PPPPLNTSPM NPPNQGQRGI SSVPVGRQPI IMQSSSKFNF PSGRPGMQNG TGQTDFMIHQ  360
NVVPAGTVNR QPPPPYPLTA ANGQSPSALQ TGGSAAPSSY TNGSIPQSMM VPNRNSHNME  420
LYNISVPGLQ TNWPQSSSAP AQSSPSSGHE IPTWQPNIPV RSNSFNNPLG NRASHSANSQ  480
PSATTVTAIT PAPIQQPVKS MRVLKPELQT ALAPTHPSWI PQPIQTVQPS PFPEGTASNV  540
TVMPPVAEAP NYQGPPPPYP KHLLHQNPSV PPYESISKPS KEDQPSLPKE DESEKSYENV  600
DSGDKEKKQI TTSPITVRKN KKDEERRESR IQSYSPQAFK FFMEQHVENV LKSHQQRLHR  660
KKQLENEMMR VGLSQDAQDQ MRKMLCQKES NYIRLKRAKM DKSMFVKIKT LGIGAFGEVC  720
LARKVDTKAL YATKTLRKKD VLLRNQVAHV KAERDILAEA DNEWVVRLYY SFQDKDNLYF  780
VMDYIPGGDM MSLLIRMGIF PESLARFYIA ELTCAVESVH KMGFIHRDIK PDNILIDRDG  840
HIKLTDFGLC TGFRWTHDSK YYQSGDHPRQ DSMDFSNEWG DPSSCRCGDR LKPLERRAAR  900
QHQRCLAHSL VGTPNYIAPE VLLRTGYTQL CDWWSVGVIL FEMLVGQPPF LAQTPLETQM  960
KVINWQTSLH IPPQAKLSPE ASDLIIKLCR GPEDRLGKNG ADEIKAHPFF KTIDFSSDLR  1020
QQSASYIPKI THPTDTSNFD PVDPDKLWSD DNEEENVNDT LNGWYKNGKH PEHAFYEFTF  1080
RRFFDDNGYP YNYPKPIEYE YINSQGSEQQ SDEDDQNTGS EIKNRDLVYV             1130

SEQ ID NO: 107          moltype = DNA  length = 618
FEATURE                 Location/Qualifiers
source                  1..618
                        mol_type = other DNA
                        organism = Synthetic construct
SEQUENCE: 107
atgagcacgg gctccgtaag cgaccctgag gagatggagc ttcgcggtct ccaacgagaa  60
taccctgttc ccgcgagtaa gagaccgccg ctgcggggtg ttgaaagatc ctatgcatct  120
ccctctgata actcctctgc ggaggaggag gatcctgatg ggaagagga gcgctgcgca  180
ttgggcaccg ctggctcagc tgaaggttgc aaaaggaaga ggccacgcgt tgcaggtgga  240
ggcggtgcgg gtggctcagc aggcggtggt gggaaaaaac cccttcccgc taagggttct  300
gccgccgagt gtaagcagtc ccaacgaaat gctgcgaatg cacggaaaag ggccagaatg  360
agagtgctta gcaaagcctt tagccggttg aagacatcac tcccttgggt cccgccagat  420
acaaagctca gtaagcttga taccttgaga cttgcctcct catatatcgc tcacctgaga  480
caactgcttc aggaggacag gtacgagaat ggatacgttc acccggtaaa tcttacttgg  540
cctttcgtcg tctcaggaag accggattcc gataccaaag aggtatccgc cgcgaaccgg  600
ttgtgcggga ccacggca                                                618

SEQ ID NO: 108          moltype = AA  length = 206
FEATURE                 Location/Qualifiers
source                  1..206
                        mol_type = protein
```

```
                        organism = Synthetic construct
SEQUENCE: 108
MSTGSVSDPE EMELRGLQRE YPVPASKRPP LRGVERSYAS PSDNSSAEEE DPDGEEERCA  60
LGTAGSAEGC KRKRPRVAGG GGAGGSAGGG GKKPLPAKGS AAECKQSQRN AANARKRARM  120
RVLSKAFSRL KTSLPWVPPD TKLSKLDTLR LASSYIAHLR QLLQEDRYEN GYVHPVNLTW  180
PFVVSGRPDS DTKEVSAANR LCGTTA                                        206

SEQ ID NO: 109          moltype = DNA  length = 618
FEATURE                 Location/Qualifiers
source                  1..618
                        mol_type = genomic DNA
                        organism = Homo sapiens
SEQUENCE: 109
atgagcacgg gctccgtaag cgaccctgag gagatggagc ttcgcggtct ccaacgagaa  60
taccctgttc ccgcgagtaa gagaccgccg ctgcggggtg ttgaaagatc ctatgcatct  120
ccctctgata actcctctgc ggaggaggag gatcctgatg gggaagagga gcgctgcgca  180
ttgggcaccg ctggctcagc tgaaggttgc aaaaggaaga ggccacgcgt tgcaggtgga  240
ggcggtgcgg gtggctcagc aggcggtggt gggaaaaaac cccttcccgc taagggttct  300
gccgccgagt gtaagcagtc ccaacgaaat gctgcgaatg cacgggaaag ggccagaatg  360
agagtgctta gcaaagcctt tagccggttg aagacatcac tcccttgggt cccgccagat  420
acaaagctca gtaagcttga taccttgaga cttgcctcct catatatcgc tcacctgaga  480
caactgcttc aggaggacag gtacgagaat ggatacgttc acccggtaaa tcttacttgg  540
cctttcgtcg tctcaggaag accggattcc gataccaaag aggtatccgc cgcgaaccgg  600
ttgtgcggga ccacggca                                                 618

SEQ ID NO: 110          moltype = AA  length = 206
FEATURE                 Location/Qualifiers
source                  1..206
                        mol_type = protein
                        organism = Homo sapiens
SEQUENCE: 110
MSTGSVSDPE EMELRGLQRE YPVPASKRPP LRGVERSYAS PSDNSSAEEE DPDGEEERCA  60
LGTAGSAEGC KRKRPRVAGG GGAGGSAGGG GKKPLPAKGS AAECKQSQRN AANARERARM  120
RVLSKAFSRL KTSLPWVPPD TKLSKLDTLR LASSYIAHLR QLLQEDRYEN GYVHPVNLTW  180
PFVVSGRPDS DTKEVSAANR LCGTTA                                        206

SEQ ID NO: 111          moltype = DNA  length = 1392
FEATURE                 Location/Qualifiers
source                  1..1392
                        mol_type = other DNA
                        organism = Synthetic construct
SEQUENCE: 111
atgccgagct gctccacgtc caccatgccg ggcatgatct gcaagaaccc agacctcgag  60
tttgactcgc tacagccctg cttctacccg gacgaagatg acttctactt cggcggcccc  120
gactcgaccc tcccggggga ggacatctgg aagaagtttg agctgctgcc cacgcccccg  180
ctgtcgccca gccgtggctt cgcggagcac agctccgagc ccccgagctg ggtcacggag  240
atgctgcttg agaacgagct gtggggcagc ccggccgagg aggacgcgtt cggcctgggg  300
ggactgggtg gcctcacccc caacccggtc atcctccagg actgcatgtg gagcggcttc  360
tccgcccgcg agaagctgga gcgcgccgtg agcgagaagc tgcagcacgg ccgcgggccg  420
ccaaccgccg gttccaccgc ccagtccccg ggagccggcg ccgccagccc tgcgggtcgc  480
gggcacggcg gggctgcggg agccggccgc gccggggccg ccctgcccgc cgagctcgcc  540
cacccggccg ccgagtgcgt ggatcccgcc gtggtcttcc cctttcccgt gaacaagcgc  600
gagccagcgc ccgtgcccgc agccccggcc agtgccccgg cggcgggccc tgcggtcgcc  660
tcgggggcgg gtattgccgc cccagccggg gccccggggg tcgcccctcc gcgcccaggc  720
ggccgccaga ccagcggcgg cgaccacaag gccctcagta cctccggaga ggacaccctg  780
agcgattcag atgatgaaga tgatgaagag gaagatgaag aggaagaaat cgacgtggtc  840
actgtggaga agcggcgttc ctcctccaac accaaggctg tcaccacatt caccatcact  900
gtgcgtccca agaacgcagc cctgggtccc gggagggctc agtccagcga gctgatcctc  960
aaacgatgcc ttcccatcca ccagcagcac aactatgccg cccccctctcc ctacgtggag  1020
agtgaggatg caccccccaca gaagaagata aagagcgagg cgtccccacg tccgctcaag  1080
agtgtcatcc ccccaaaggc taagagcttg agcccccgaa actctgactc ggaggacagt  1140
gagcgtcgca gaaaccacaa catcctggag cgccagcgcc gcaacgacct tcggtccagc  1200
tttctcacgc tcagggacca cgtgccggag ttggtaaaga atgagaaggc cgccaaggtg  1260
gtcattttga aaaaggccac tgagtatgtc cactccctcc aggccgagga gcaccagctt  1320
ttgctggaaa aggaaaaatt gcaggcaaga cagcagcagt tgctaaagaa aattgaacac  1380
gctcggactt gc                                                       1392

SEQ ID NO: 112          moltype = AA  length = 464
FEATURE                 Location/Qualifiers
source                  1..464
                        mol_type = protein
                        organism = Synthetic construct
SEQUENCE: 112
MPSCSTSTMP GMICKNPDLE FDSLQPCFYP DEDDFYFGGP DSTLPGEDIW KKFELLPTPP  60
LSPSRGFAEH SSEPPSWVTE MLLENELWGS PAEEDAFGLG GLGGLTPNPV ILQDCMWSGF  120
SAREKLERAV SEKLQHGRGP PTAGSTAQSP GAGAASPAGR GHGGAAGAGR AGAALPAELA  180
HPAAECVDPA VVFPFPVNKR EPAPVPAAPA SAPAAGPAVA SGAGIAAPAG APGVAPPRPG  240
GRQTSGGDHK ALSTSGEDTL SDSDDEDDEE EDEEEEIDVV TVEKRRSSSN TKAVTTFTIT  300
VRPKNAALGP GRAQSSELIL KRCLPIHQQH NYAAPSPYVE SEDAPPQKKI KSEASPRPLK  360
```

-continued

```
SVIPPKAKSL SPRNSDSEDS ERRRNHNILE RQRRNDLRSS FLTLRDHVPE LVKNEKAAKV  420
VILKKATEYV HSLQAEEHQL LLEKEKLQAR QQQLLKKIEH ARTC                   464

SEQ ID NO: 113          moltype = DNA  length = 1392
FEATURE                 Location/Qualifiers
source                  1..1392
                        mol_type = genomic DNA
                        organism = Homo sapiens
SEQUENCE: 113
atgccgagct gctccacgtc caccatgccg ggcatgatct gcaagaaccc agacctcgag  60
tttgactcgc tacagccctg cttctacccg gacgaagatg acttctactt cggcggcccc  120
gactcgaccc ccccggggga ggacatctgg aagaagtttg agctgctgcc cacgcccccg  180
ctgtcgccca gccgtggctt cgcggagcac agctccgagc ccccgagctg ggtcacggag  240
atgctgcttg agaacgagct gtggggcagc ccggccgagg aggacgcgtt cggcctgggg  300
ggactgggtg gcctcacccc caacccggtc atcctccagg actgcatgtg gagcggcttc  360
tccgcccgcg agaagctgga gcgcgccgtg agcgagaagc tgcagcacgg ccgcgggccg  420
ccaaccgccg gttccaccgc ccagtccccg ggagccggcg ccgccagccc tgcgggtcgc  480
gggcacggcg gggctgcggg agccggccgc gccggggccg ccctgcccgc cgagctcgcc  540
cacccggccg ccgagtgcgt ggatcccgcc gtggtcttcc cctttcccgt gaacaagcgc  600
gagccagcgc ccgtgcccgc agccccggcc agtgccccgg cggcgggccc tgcggtcgcc  660
tcgggggcgg gtattgccgc cccagccggg gccccggggg tcgcccctcc gcgcccaggc  720
ggccgccaga ccagcggcgg cgaccacaag gccctcagta cctccggaga ggacaccctg  780
agcgattcag atgatgaaga tgatgaagag gaagatgaag aggaagaaat cgacgtggtc  840
actgtggaga agcggcgttc ctcctccaac accaaggctg tcaccacatt caccatcact  900
gtgcgtccca agaacgcagc cctgggtccc gggagggctc agtccagcga gctgatcctc  960
aaacgatgcc ttcccatcca ccagcagcac aactatgccg cccccctctcc ctacgtggag  1020
agtgaggatg cacccccaca gaagaagata aagagcgagg cgtccccacg tccgctcaag  1080
agtgtcatcc ccccaaaggc taagagcttg agccccccgaa actctgactc ggaggacagt  1140
gagcgtcgca gaaaccacaa catcctggag cgccagcgcc gcaacgacct tcggtccagc  1200
tttctcacgc tcagggacca cgtgccggag ttggtaaaga atgagaaggc cgccaaggtg  1260
gtcattttga aaaaggccac tgagtatgtc cactccctcc aggccgagga gcaccagctt  1320
ttgctggaaa aggaaaaatt gcaggcaaga cagcagcagt tgctaaagaa aattgaacac  1380
gctcggactt gc                                                      1392

SEQ ID NO: 114          moltype = AA  length = 464
FEATURE                 Location/Qualifiers
source                  1..464
                        mol_type = protein
                        organism = Homo sapiens
SEQUENCE: 114
MPSCSTSTMP GMICKNPDLE FDSLQPCFYP DEDDFYFGGP DSTPPGEDIW KKFELLPTPP  60
LSPSRGFAEH SSEPPSWVTE MLLENELWGS PAEEDAFGLG GLGGLTPNPV ILQDCMWSGF  120
SAREKLERAV SEKLQHGRGP PTAGSTAQSP GAGAASPAGR GHGGAAGAGR AGAALPAELA  180
HPAAECVDPA VVFPFPVNKR EPAPVPAAPA SAPAAGPAVA SGAGIAAPAG APGVAPPRPG  240
GRQTSGGDHK ALSTSGEDTL SDSDDEDDEE EDEEEEIDVV TVEKRRSSSN TKAVTTFTIT  300
VRPKNAALGP GRAQSSELIL KRCLPIHQQH NYAAPSPYVE SEDAPPQKKI KSEASPRPLK  360
SVIPPKAKSL SPRNSDSEDS ERRRNHNILE RQRRNDLRSS FLTLRDHVPE LVKNEKAAKV  420
VILKKATEYV HSLQAEEHQL LLEKEKLQAR QQQLLKKIEH ARTC                   464

SEQ ID NO: 115          moltype = DNA  length = 2910
FEATURE                 Location/Qualifiers
source                  1..2910
                        mol_type = other DNA
                        organism = Synthetic construct
SEQUENCE: 115
atggcagaag atgatccata tttgggaagg cctgaacaaa tgtttcattt ggatccttct  60
ttgactcata caatatttaa tccagaagta tttcaaccac agatggcact gccaacagca  120
gatggcccat accttcaaat attagagcaa cctaaacaga gaggatttcg tttccgttat  180
gtatgtgaag gcccatccta tggtggacta cctggtgcct ctagtgaaaa gaacaagaag  240
tcttaccctc aggtcaaaat ctgcaactat gtgggaccag caaaggttat tgttcagttg  300
gtcacaaatg gaaaaaatat ccacctgcat gcccacagcc tggtgggaaa acactgtgag  360
gatgggatct gcactgtaac tgctggaccc aaggacatgg tggtcggctt cgcaaacctg  420
ggtatacttc atgtgacaaa gaaaaaagta tttgaaacac tggaagcacg aatgacagag  480
gcgtgtataa ggggccataa tcctggactc ttggtgcacc ctgaccttgc ctatttgcaa  540
gcagaaggtg gaggggaccg gcagctggga gatcgggaaa aagagctaat ccgccaagca  600
gctctgcagc agaccaagga gatggacctc agcgtggtgc ggctcatgtt tacagctttt  660
cttccggata gcactggcag cttcacaagg cgcctggaac ccgtggtatc agacgccatc  720
tatgacagta aagcccccaa tgcatccaac ttgaaaattg taagaatgga caggacagct  780
ggatgtgtga ctggagggga ggaaatttat cttctttgtg acaaagttca gaaagatgac  840
atccagattc gattttatga agaggaagaa aatggtggag tctgggaagg atttggagat  900
ttttccccca cagatgttca tagacaattt gccattgtct tcaaaactcc aaagtataaa  960
gatattaata ttacaaaacc agcctctgtg tttgtccagc ttcggaggaa atctgacttg  1020
gaaactagtg aaccaaaacc tttcctctac tatcctgaaa tcaaagataa agaagaagtg  1080
cagaggaaac gtcagaagct catgcccaat ttttcggata gtttcggcgg tggtagtggt  1140
gccggagctg gaggcggagg catgtttggt agtggcggtg gaggaggggg cactggaagt  1200
acaggtccag ggtatagctt cccacactat ggatttccta cttatggtgg gattactttc  1260
catcctggaa ctactaaatc taatgctggg atgaagcatg gaaccatgga cactgaatct  1320
aaaaaggacc ctgaaggttg tgacaaaagt gatgacaaaa acactgtaaa cctctttggg  1380
aaagttattg aaaccacaga gcaagatcag gagcccagcg aggccaccgt tgggaatggt  1440
```

```
gaggtcactc taacgtatgc aacaggaaca aaagaagaga gtgctggagt tcaggataac  1500
ctctttctag agaaggctat gcagcttgca aagaggcatg ccaatgccct tttcgactac  1560
gcggtgacag gagacgtgaa gatgctgctg gccgtccagc gccatctcac tgctgtgcag  1620
gatgagaatg gggacagtgt cttacactta gcaatcatcc accttcattc tcaacttgtg  1680
agggatctac tagaagtcac atctggtttg atttctgatg acattatcaa catgagaaat  1740
gatctgtacc agacgccctt gcacttggca gtgatcacta agcaggaaga tgtggtggag  1800
gatttgctga gggctggggc cgacctgagc cttctggacc gcttgggtaa ctctgttttg  1860
cacctagctg ccaaagaagg acatgataaa gttctcagta tcttactcaa gcacaaaaag  1920
gcagcactac ttcttgacca ccccaacggg gacggtctga atgccattca tctagccatg  1980
atgagcaata gcctgccatg tttgctgctg ctggtggccg ctggggctga cgtcaatgct  2040
caggagcaga agtccgggcg cacagcactg cacctggctg tggagcacga caacatctca  2100
ttggcaggct gcctgctcct ggagggtgat gcccatgtgg acagtactac ctacgatgga  2160
accacacccc tgcatatagc agctgggaga gggtccacca ggctggcagc tcttctcaaa  2220
gcagcaggag cagatcccct ggtggagaac tttgagcctc tctatgacct ggatgactct  2280
tgggaaaatg caggagagga tgaaggagtt gtgcctggaa ccacgcctct agatatggcc  2340
accagctggc aggtatttga catattaaat gggaaaccat atgagccaga gtttacatct  2400
gatgatttac tagcacaagg agacatgaaa cagctggctg aagatgtgaa gctgcagctg  2460
tataagttac tagaaattcc tgatccagac aaaaactggg ctactctggc gcagaaatta  2520
ggtctgggga tacttaataa tgccttccgg ctgagtcctg ctccttccaa aacacttatg  2580
gacaactatg aggtctctgg gggtacagtc agagagctgg tggaggccct gagacaaatg  2640
ggctacaccg aagcaattga agtgatccag gcagcctcca gcccagtgaa gaccacctct  2700
caggcccact cgctgcctct ctcgcctgcc tccacaaggc agcaaataga cgagctccga  2760
gacagtgaca gtgtctgcga cagcggcgtg gagacatcct tccgcaaact cagctttacc  2820
gagtctctga ccagtggtgc ctcactgcta actctcaaca aaatgcccca tgattatggg  2880
caggaaggac ctctagaagg caaaattttg                                  2910

SEQ ID NO: 116         moltype = AA  length = 970
FEATURE                Location/Qualifiers
source                 1..970
                       mol_type = protein
                       organism = Synthetic construct
SEQUENCE: 116
MAEDDPYLGR PEQMFHLDPS LTHTIFNPEV FQPQMALPTA DGPYLQILEQ PKQRGFRFRY  60
VCEGPSYGGL PGASSEKNKK SYPQVKICNY VGPAKVIVQL VTNGKNIHLH AHSLVGKHCE  120
DGICTVTAGP KDMVVGFANL GILHVTKKKV FETLEARMTE ACIRGHNPGL LVHPDLAYLQ  180
AEGGGDRQLG DREKELIRQA ALQQTKEMDL SVVRLMFTAF LPDSTGSFTR RLEPVVSDAI  240
YDSKAPNASN LKIVRMDRTA GCVTGGEEIY LLCDKVQKDD IQIRFYEEEE NGGVWEGFGD  300
FSPTDVHRQF AIVFKTPKYK DINITKPASV FVQLRRKSDL ETSEPKPFLY YPEIKDKEEV  360
QRKRQKLMPN FSDSFGGGSG AGAGGGGMFG SGGGGGGTGS TGPGYSFPHY GFPTYGGITF  420
HPGTTKSNAG MKHGTMDTES KKDPEGCDKS DDKNTVNLFG KVIETTEQDQ EPSEATVGNG  480
EVTLTYATGT KEESAGVQDN LFLEKAMQLA KRHANALFDY AVTGDVKMLL AVQRHLTAVQ  540
DENGDSVLHL AIIHLHSQLV RDLLEVTSGL ISDDIINMRN DLYQTPLHLA VITKQEDVVE  600
DLLRAGADLS LLDRLGNSVL HLAAKEGHDK VLSILLKHKK AALLLDHPNG DGLNAIHLAM  660
MSNSLPCLLL LVAAGADVNA QEQKSGRTAL HLAVEHDNIS LAGCLLLEGD AHVDSTTYDG  720
TTPLHIAAGR GSTRLAALLK AAGADPLVEN FEPLYDLDDS WENAGEDEGV VPGTTPLDMA  780
TSWQVFDILN GKPYEPEFTS DDLLAQGDMK QLAEDVKLQL YKLLEIPDPD KNWATLAQKL  840
GLGILNNAFR LSPAPSKTLM DNYEVSGGTV RELVEALRQM GYTEAIEVIQ AASSPVKTTS  900
QAHSLPLSPA STRQQIDELR DSDSVCDSGV ETSFRKLSFT ESLTSGASLL TLNKMPHDYG  960
QEGPLEGKIL                                                        970

SEQ ID NO: 117         moltype = DNA  length = 2910
FEATURE                Location/Qualifiers
source                 1..2910
                       mol_type = genomic DNA
                       organism = Homo sapiens
SEQUENCE: 117
atggcagaag atgatccata tttgggaagg cctgaacaaa tgtttcattt ggatccttct  60
ttgactcata caatatttaa tccagaagta tttcaaccac agatggcact gccaacagca  120
gatggcccat accttcaaat attagagcaa cctaaacaga gaggatttcg tttccgttat  180
gtatgtgaag gcccatccca tggtggacta cctggtgcct ctagtgaaaa gaacaagaag  240
tcttaccctc aggtcaaaat ctgcaactat gtgggaccag caaaggttat tgttcagttg  300
gtcacaaatg gaaaaaatat ccacctgcat gcccacagcc tggtgggaaa acactgtgag  360
gatgggatct gcactgtaac tgctggaccc aaggacatgg tggtcggctt cgcaaacctg  420
ggtatacttc atgtgacaaa gaaaaaagta tttgaaacac tggaagcacg aatgacagag  480
gcgtgtataa ggggccataa tcctggactc ttggtgcacc ctgaccttgc ctatttgcaa  540
gcagaaggtg gaggggaccg gcagctggga gatcgggaaa aagagctaat ccgccaagca  600
gctctgcagc agaccaagga gatggacctc agcgtggtgc ggctcatgtt tacagctttt  660
cttccggata gcactggcag cttcacaagg cgcctggaac ccgtggtatc agacgccatc  720
tatgacagta aagcccccaa tgcatccaac ttgaaaattg taagaatgga caggacagct  780
ggatgtgtga ctggagggga ggaaatttat cttctttgtg acaaagttca gaaagatgac  840
atccagattc gattttatga agaggaagaa aatggtggag tctgggaagg atttggagat  900
ttttccccca cagatgttca tagacaattt gccattgtct tcaaaactcc aaagtataaa  960
gatattaata ttacaaaacc agcctctgtg tttgtccagc ttcggaggaa atctgacttg  1020
gaaactagtg aaccaaaacc tttcctctac tatcctgaaa tcaaagataa agaagaagtg  1080
cagaggaaac gtcagaagct catgcccaat tttcggata gtttcggcgg tggtagtggt  1140
gccggagctg gaggcggagg catgtttggt agtggcggtg gaggaggggg cactggaagt  1200
acaggtccag ggtatagctt ccccactat ggatttccta cttatggtgg gattactttc  1260
catcctggaa ctactaaatc taatgctggg atgaagcatg gaaccatgga cactgaatct  1320
aaaaaggacc ctgaaggttg tgacaaaagt gatgacaaaa acactgtaaa cctctttggg  1380
```

```
aaagttattg aaaccacaga gcaagatcag gagcccagcg aggccaccgt tgggaatggt  1440
gaggtcactc taacgtatgc aacaggaaca aaagaagaga gtgctggagt tcaggataac  1500
ctctttctag agaaggctat gcagcttgca aagaggcatg ccaatgccct tttcgactac  1560
gcggtgacag gagacgtgaa gatgctgctg gccgtccagc gccatctcac tgctgtgcag  1620
gatgagaatg gggacagtgt cttacactta gcaatcatcc accttcattc tcaacttgtg  1680
agggatctac tagaagtcac atctggtttg atttctgatg acattatcaa catgagaaat  1740
gatctgtacc agacgccctt gcacttggca gtgatcacta agcaggaaga tgtggtggag  1800
gatttgctga gggctggggc cgacctgagc cttctggacc gcttgggtaa ctctgttttg  1860
cacctagctg ccaaagaagg acatgataaa gttctcagta tcttactcaa gcacaaaaag  1920
gcagcactac ttcttgacca ccccaacggg gacggtctga atgccattca tctagccatg  1980
atgagcaata gcctgccatg tttgctgctg ctggtggccg ctggggctga cgtcaatgct  2040
caggagcaga agtccgggcg cacagcactg cacctggctg tggagcacga caacatctca  2100
ttggcaggct gcctgctcct ggagggtgat gcccatgtgg acagtactac ctacgatgga  2160
accacacccc tgcatatagc agctgggaga gggtccacca ggctggcagc tcttctcaaa  2220
gcagcaggag cagatcccct ggtggagaac tttgagcctc tctatgacct ggatgactct  2280
tgggaaaatg caggagagga tgaaggagtt gtgcctggaa ccacgcctct agatatggcc  2340
accagctggc aggtatttga catattaaat gggaaaccat atgagccaga gtttacatct  2400
gatgatttac tagcacaagg agacatgaaa cagctggctg aagatgtgaa gctgcagctg  2460
tataagttac tagaaattcc tgatccagac aaaaactggg ctactctggc gcagaaatta  2520
ggtctgggga tacttaataa tgccttccgg ctgagtcctg ctccttccaa aacacttatg  2580
gacaactatg aggtctctgg gggtacagtc agagagctgg tggaggccct gagacaaatg  2640
ggctacaccg aagcaattga agtgatccag gcagcctcca gcccagtgaa gaccacctct  2700
caggcccact cgctgcctct ctcgcctgcc tccacaaggc agcaaataga cgagctccga  2760
gacagtgaca gtgtctgcga cagcggcgtg gagacatcct tccgcaaact cagctttacc  2820
gagtctctga ccagtggtgc ctcactgcta actctcaaca aaatgcccca tgattatggg  2880
caggaaggac ctctagaagg caaaattttg                                  2910

SEQ ID NO: 118         moltype = AA  length = 970
FEATURE                Location/Qualifiers
source                 1..970
                       mol_type = protein
                       organism = Homo sapiens
SEQUENCE: 118
MAEDDPYLGR PEQMFHLDPS LTHTIFNPEV FQPQMALPTA DGPYLQILEQ PKQRGFRFRY  60
VCEGPSHGGL PGASSEKNKK SYPQVKICNY VGPAKVIVQL VTNGKNIHLH AHSLVGKHCE  120
DGICTVTAGP KDMVVGFANL GILHVTKKKV FETLEARMTE ACIRGHNPGL LVHPDLAYLQ  180
AEGGGDRQLG DREKELIRQA ALQQTKEMDL SVVRLMFTAF LPDSTGSFTR RLEPVVSDAI  240
YDSKAPNASN LKIVRMDRTA GCVTGGEEIY LLCDKVQKDD IQIRFYEEEE NGGVWEGFGD  300
FSPTDVHRQF AIVFKTPKYK DINITKPASV FVQLRRKSDL ETSEPKPFLY YPEIKDKEEV  360
QRKRQKLMPN FSDSFGGGSG AGAGGGGMFG SGGGGGGTGS TGPGYSFPHY GFPTYGGITF  420
HPGTTKSNAG MKHGTMDTES KKDPEGCDKS DDKNTVNLFG KVIETTEQDQ EPSEATVGNG  480
EVTLTYATGT KEESAGVQDN LFLEKAMQLA KRHANALFDY AVTGDVKMLL AVQRHLTAVQ  540
DENGDSVLHL AIIHLHSQLV RDLLEVTSGL ISDDIINMRN DLYQTPLHLA VITKQEDVVE  600
DLLRAGADLS LLDRLGNSVL HLAAKEGHDK VLSILLKHKK AALLLDHPNG DGLNAIHLAM  660
MSNSLPCLLL LVAAGADVNA QEQKSGRTAL HLAVEHDNIS LAGCLLLEGD AHVDSTTYDG  720
TTPLHIAAGR GSTRLAALLK AAGADPLVEN FEPLYDLDDS WENAGEDEGV VPGTTPLDMA  780
TSWQVFDILN GKPYEPEFTS DDLLAQGDMK QLAEDVKLQL YKLLEIPDPD KNWATLAQKL  840
GLGILNNAFR LSPAPSKTLM DNYEVSGGTV RELVEALRQM GYTEAIEVIQ AASSPVKTTS  900
QAHSLPLSPA STRQQIDELR DSDSVCDSGV ETSFRKLSFT ESLTSGASLL TLNKMPHDYG  960
QEGPLEGKIL                                                        970

SEQ ID NO: 119         moltype = DNA  length = 1966
FEATURE                Location/Qualifiers
source                 1..1966
                       mol_type = other DNA
                       organism = Synthetic construct
SEQUENCE: 119
atggagagtt gctacaaccc aggtctggat ggtattattg aatatgatga tttcaaattg  60
aactcctcca ttgtggaacc caaggagcca gccccagaaa cagctgatgg cccctacctg  120
gtgatcgtgg aacagcctaa gcagagaggc ttccgatttc gatatggctg tgaaggcccc  180
tcccatggag gactgcccgg tgcctccagt gagaagggcc gaaagaccta tcccactgtc  240
aagatctgta actacgaggg accagccaag atcgaggtgg acctggtaac acacagtgac  300
ccacctcgtg ctcatgccca cagtctggtg ggcaagcaat gctcggagct ggggatctgc  360
gccgtttctg tggggcccaa ggacatgact gcccaattta acaacctggg tgtcctgcat  420
gtgactaaga agaacatgat ggggactatg atacaaaaac ttcagaggca gcggctccgc  480
tctaggcccc agggccttac ggaggccgag cagcgggagc tggagcaaga ggccaaagaa  540
ctgaagaagg tgatggatct gagtatagtg cggctgcgct tctctgcctt ccttagagcc  600
agtgatggct ccttctccct gcccctgaag ccagtcatct cccagcccat ccatgacagc  660
aaatctccgg gggcatcaaa cctgaagatt tctcgaatgg acaagacagc aggctctgtg  720
cggggtggag atgaagttta tctgctttgt gacaaggtgc agaaagatga cattgaggtt  780
cggttctatg aggatgatga gaatggatgg caggcctttg gggacttctc tcccacagat  840
gtgcataaac agtatgccat tgtgttccgg acaccccccct atcacaagat gaagattgag  900
cggcctgtaa cagtgtttct gcaactgaaa cgcaagcgag gaggggacgt gtctgattcc  960
aaacagttca cctattaccc tctggtggaa gacaaggaag aggtgcagcg gaagcggagg  1020
aaggccttgc ccaccttctc ccagcccttc gggggtggct cccacatggg tggaggctct  1080
gggggtgcag ccgggggcta cggaggagct ggaggaggtg gcagcctcgg tttcttcccc  1140
tcctccctgg cctacagccc ctaccagtcc ggcgcgggcc ccatgggctg ctacccggga  1200
ggcgggggcg gggcgcagat ggccgccacg gtgcccagca gggactccgg ggaggaagcc  1260
gcggagccga gcgcccctc caggaccccc cagtgcgagc cgcaggcccc ggagatgctg  1320
```

```
cagcgagctc gagagtacaa cgcgcgcctg ttcggcctgg cgcagcgcag cgcccgagcc  1380
ctactcgact acggcgtcac cgcggacgcg cgcgcgctgc tggcgggaca gcgccacctg  1440
ctgacggcgc aggacgagaa cggagacaca ccactgcacc tagccatcat ccacgggcag  1500
accagtgtca ttgagcagat agtctatgtc atccaccacg cccaggacct cggcgttgtc  1560
aacctcacca accacctgca ccagacgccc ctgcacctgg cggtgatcac ggggcagacg  1620
agtgtggtga gctttctgct gcgggtaggt gcagacccag ctctgctgga tcggcatgga  1680
gactcagcca tgcatctggc gctgcgggca ggcgctggtg ctcctgagct gctgcgtgca  1740
ctgcttcaga gtggagctcc tgctgtgccc cagctgttgc atatgcctga ctttgaggga  1800
ctgtatccag tacacctggc ggtccgagcc cgaagccctg agtgcctgga tctgctggtg  1860
gacagtgggg ctgaagtgga ggccactgag cggcaggggg gacgaacagc cttgcatcta  1920
gccacagaga tggaggagct ggggttggtc acccatctgg tcaccg                 1966

SEQ ID NO: 120         moltype = AA  length = 655
FEATURE                Location/Qualifiers
source                 1..655
                       mol_type = protein
                       organism = Synthetic construct
SEQUENCE: 120
MESCYNPGLD GIIEYDDFKL NSSIVEPKEP APETADGPYL VIVEQPKQRG FRFRYGCEGP  60
SHGGLPGASS EKGRKTYPTV KICNYEGPAK IEVDLVTHSD PPRAHAHSLV GKQCSELGIC  120
AVSVGPKDMT AQFNNLGVLH VTKKNMMGTM IQKLQRQRLR SRPQGLTEAE QRELEQEAKE  180
LKKVMDLSIV RLRFSAFLRA SDGSFSLPLK PVISQPIHDS KSPGASNLKI SRMDKTAGSV  240
RGGDEVYLLC DKVQKDDIEV RFYEDDENGW QAFGDFSPTD VHKQYAIVFR TPPYHKMKIE  300
RPVTVFLQLK RKRGGDVSDS KQFTYYPLVE DKEEVQRKRR KALPTFSQPF GGGSHMGGGS  360
GGAAGGYGGA GGGGSLGFFP SSLAYSPYQS GAGPMGCYPG GGGGAQMAAT VPSRDSGEEA  420
AEPSAPSRTP QCEPQAPEML QRAREYNARL FGLAQRSARA LLDYGVTADA RALLAGQRHL  480
LTAQDENGDT PLHLAIIHGQ TSVIEQIVYV IHHAQDLGVV NLTNHLHQTP LHLAVITGQT  540
SVVSFLLRVG ADPALLDRHG DSAMHLALRA GAGAPELLRA LLQSGAPAVP QLLHMPDFEG  600
LYPVHLAVRA RSPECLDLLV DSGAEVEATE RQGGRTALHL ATEMEELGLV THLVT       655

SEQ ID NO: 121         moltype = DNA  length = 2697
FEATURE                Location/Qualifiers
source                 1..2697
                       mol_type = genomic DNA
                       organism = Homo sapiens
SEQUENCE: 121
atggagagtt gctacaaccc aggtctggat ggtattattg aatatgatga tttcaaattg  60
aactcctcca ttgtggaacc caaggagcca gccccagaaa cagctgatgg cccctacctg  120
gtgatcgtgg aacagcctaa gcagagaggc ttccgatttc gatatggctg tgaaggcccc  180
tcccatggag gactgcccgg tgcctccagt gagaagggcc gaaagaccta tcccactgtc  240
aagatctgta actacgaggg accagccaag atcgaggtgg acctggtaac acacagtgac  300
ccacctcgtg ctcatgccca cagtctggtg ggcaagcaat gctcggagct ggggatctgc  360
gccgtttctg tggggcccaa ggacatgact gcccaattta acaacctggg tgtcctgcat  420
gtgactaaga agaacatgat ggggactatg atacaaaaac ttcagaggca gcggctccgc  480
tctaggcccc agggccttac ggaggccgag cagcgggagc tggagcaaga ggccaaagaa  540
ctgaagaagg tgatggatct gagtatagtg cggctgcgct tctctgcctt ccttagagcc  600
agtgatggct ccttctccct gcccctgaag ccagtcatct cccagcccat ccatgacagc  660
aaatctccgg gggcatcaaa cctgaagatt tctcgaatgg acaagacagc aggctctgtg  720
cggggtggag atgaagttta tctgctttgt gacaaggtgc agaaagatga cattgaggtt  780
cggttctatg aggatgatga gaatggatgg caggcctttg gggacttctc tcccacagat  840
gtgcataaac agtatgccat tgtgttccgg acaccccccct atcacaagat gaagattgag  900
cggcctgtaa cagtgtttct gcaactgaaa cgcaagcgag gaggggacgt gtctgattcc  960
aaacagttca cctattaccc tctggtggaa gacaaggaag aggtgcagcg gaagcggagg  1020
aaggccttgc ccaccttctc ccagcccttc ggggggtggct cccacatggg tggaggctct  1080
gggggtgcag ccgggggcta cggaggagct ggaggaggtg gcagcctcgg tttcttcccc  1140
tcctccctgg cctacagccc ctaccagtcc ggcgcgggcc ccatgggctg ctacccggga  1200
ggcgggggcg gggcgcagat ggccgccacg gtgcccagca gggactccgg ggaggaagcc  1260
gcggagccga gcgcccccctc caggaccccc cagtgcgagc cgcaggcccc ggagatgctg  1320
cagcgagctc gagagtacaa cgcgcgcctg ttcggcctgg cgcagcgcag cgcccgagcc  1380
ctactcgact acggcgtcac cgcggacgcg cgcgcgctgc tggcgggaca gcgccacctg  1440
ctgacggcgc aggacgagaa cggagacaca ccactgcacc tagccatcat ccacgggcag  1500
accagtgtca ttgagcagat agtctatgtc atccaccacg cccaggacct cggcgttgtc  1560
aacctcacca accacctgca ccagacgccc ctgcacctgg cggtgatcac ggggcagacg  1620
agtgtggtga gctttctgct gcgggtaggt gcagacccag ctctgctgga tcggcatgga  1680
gactcagcca tgcatctggc gctgcgggca ggcgctggtg ctcctgagct gctgcgtgca  1740
ctgcttcaga gtggagctcc tgctgtgccc cagctgttgc atatgcctga ctttgaggga  1800
ctgtatccag tacacctggc ggtccgagcc cgaagccctg agtgcctgga tctgctggtg  1860
gacagtgggg ctgaagtgga ggccactgag cggcaggggg gacgaacagc cttgcatcta  1920
gccacagaga tggaggagct ggggttggtc acccatctgg tcaccaagct ccgggccaac  1980
gtgaacgctc gcacctttgc gggaaacaca cccctgcacc tggcagctgg actggggtac  2040
ccgaccctca cccgcctcct tctgaaggct ggtgctgaca tccatgctga aaacgaggag  2100
cccctgtgcc cactgccttc acccccctacc tctgatagcg actcggactc tgaagggcct  2160
gagaaggaca cccgaagcag cttccggggc cacacgcctc ttgacctcac ttgcagcacc  2220
aaggtgaaga ccttgctgct aaatgctgct cagaacacca tggagccacc cctgaccccg  2280
cccagcccag cagggccggg actgtcactt ggtgatacag ctctgcagaa cctggagcag  2340
ctgctagacg ggccagaagc ccagggcagc tgggcagagc tggcagagcg tctggggctg  2400
cgcagcctgg tagacacgta ccgacagaca acctcaccca gtggcagcct cctgcgcagc  2460
tacgagctgg ctggcgggga cctggcaggt ctactggagg ccctgtctga catgggccta  2520
gaggagggag tgaggctgct gaggggtcca gaaacccgag acaagctgcc cagcacagag  2580
```

-continued

```
gtgaaggaag acagtgcgta cgggagccag tcagtggagc aggaggcaga gaagctgggc  2640
ccaccccctg agccaccagg agggctctgc cacgggcacc cccagcctca ggtgcac     2697

SEQ ID NO: 122          moltype = AA  length = 899
FEATURE                 Location/Qualifiers
source                  1..899
                        mol_type = protein
                        organism = Homo sapiens
SEQUENCE: 122
MESCYNPGLD GIIEYDDFKL NSSIVEPKEP APETADGPYL VIVEQPKQRG FRFRYGCEGP  60
SHGGLPGASS EKGRKTYPTV KICNYEGPAK IEVDLVTHSD PPRAHAHSLV GKQCSELGIC  120
AVSVGPKDMT AQFNNLGVLH VTKKNMMGTM IQKLQRQRLR SRPQGLTEAE QRELEQEAKE  180
LKKVMDLSIV RLRFSAFLRA SDGSFSLPLK PVISQPIHDS KSPGASNLKI SRMDKTAGSV  240
RGGDEVYLLC DKVQKDDIEV RFYEDDENGW QAFGDFSPTD VHKQYAIVFR TPPYHKMKIE  300
RPVTVFLQLK RKRGGDVSDS KQFTYYPLVE DKEEVQRKRR KALPTFSQPF GGGSHMGGGS  360
GGAAGGYGGA GGGGSLGFFP SSLAYSPYQS GAGPMGCYPG GGGGAQMAAT VPSRDSGEEA  420
AEPSAPSRTP QCEPQAPEML QRAREYNARL FGLAQRSARA LLDYGVTADA RALLAGQRHL  480
LTAQDENGDT PLHLAIIHGQ TSVIEQIVYV IHHAQDLGVV NLTNHLHQTP LHLAVITGQT  540
SVVSFLLRVG ADPALLDRHG DSAMHLALRA GAGAPELLRA LLQSGAPAVP QLLHMPDFEG  600
LYPVHLAVRA RSPECLDLLV DSGAEVEATE RQGGRTALHL ATEMEELGLV THLVTKLRAN  660
VNARTFAGNT PLHLAAGLGY PTLTRLLLKA GADIHAENEE PLCPLPSPPT SDSDSDSEGP  720
EKDTRSSFRG HTPLDLTCST KVKTLLLNAA QNTMEPPLTP PSPAGPGLSL GDTALQNLEQ  780
LLDGPEAQGS WAELAERLGL RSLVDTYRQT TSPSGSLLRS YELAGGDLAG LLEALSDMGL  840
EEGVRLLRGP ETRDKLPSTE VKEDSAYGSQ SVEQEAEKLG PPPEPPGGLC HGHPQPQVH   899

SEQ ID NO: 123          moltype = DNA  length = 567
FEATURE                 Location/Qualifiers
source                  1..567
                        mol_type = other DNA
                        organism = Synthetic construct
SEQUENCE: 123
atgactgagt ataagctcgt tgtagtgggt gcaggaggtg ttggcaaatc cgccttgact  60
atccaattga ttcaaaatca tttcgtcgac gagtacgacc ctaccataga ggattcctat  120
cgcaagcagg tagtaatcga cggcgagaca tgccttcttg atattctgga tacggcggga  180
cacgaggaat actctgcaat gcgcgaccag tatatgcgaa ccggtgaggg ttttttgtgt  240
gtttttgcga taaataattc caagtcattt gcggacataa atctgtatcg ggagcagatc  300
aagcgcgtta aggattcaga cgatgtgcct atggtcctcg tggggaataa gtgtgacctt  360
cctacccgaa cagtcgacac aaaacaggcc catgaactgg ctaaaagcta cgggataccg  420
tttattgaaa catcagcaaa aactagacag ggagttgaag acgcgttcta tacccttgtc  480
agggagatac gacaatacag aatgaaaaaa ctcaatagtt ccgacgatgg cactcaaggt  540
tgtatgggtt tgccgtgtgt ggttatg                                     567

SEQ ID NO: 124          moltype = AA  length = 189
FEATURE                 Location/Qualifiers
source                  1..189
                        mol_type = protein
                        organism = Synthetic construct
SEQUENCE: 124
MTEYKLVVVG AGGVGKSALT IQLIQNHFVD EYDPTIEDSY RKQVVIDGET CLLDILDTAG  60
HEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 125          moltype = DNA  length = 567
FEATURE                 Location/Qualifiers
source                  1..567
                        mol_type = other DNA
                        organism = Synthetic construct
SEQUENCE: 125
atgactgagt ataagctcgt tgtagtgggt gcaggagatg ttggcaaatc cgccttgact  60
atccaattga ttcaaaatca tttcgtcgac gagtacgacc ctaccataga ggattcctat  120
cgcaagcagg tagtaatcga cggcgagaca tgccttcttg atattctgga tacggcggga  180
caggaggaat actctgcaat gcgcgaccag tatatgcgaa ccggtgaggg ttttttgtgt  240
gtttttgcga taaataattc caagtcattt gcggacataa atctgtatcg ggagcagatc  300
aagcgcgtta aggattcaga cgatgtgcct atggtcctcg tggggaataa gtgtgacctt  360
cctacccgaa cagtcgacac aaaacaggcc catgaactgg ctaaaagcta cgggataccg  420
tttattgaaa catcagcaaa aactagacag ggagttgaag acgcgttcta tacccttgtc  480
agggagatac gacaatacag aatgaaaaaa ctcaatagtt ccgacgatgg cactcaaggt  540
tgtatgggtt tgccgtgtgt ggttatg                                     567

SEQ ID NO: 126          moltype = AA  length = 189
FEATURE                 Location/Qualifiers
source                  1..189
                        mol_type = protein
                        organism = Synthetic construct
SEQUENCE: 126
MTEYKLVVVG AGDVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
```

```
CMGLPCVVM                                                  189

SEQ ID NO: 127         moltype = DNA  length = 567
FEATURE                Location/Qualifiers
source                 1..567
                       mol_type = genomic DNA
                       organism = Homo sapiens
SEQUENCE: 127
atgactgagt ataagctcgt tgtagtgggt gcaggaggtg ttggcaaatc cgccttgact  60
atccaattga ttcaaaatca tttcgtcgac gagtacgacc ctaccataga ggattcctat  120
cgcaagcagg tagtaatcga cggcgagaca tgccttcttg atattctgga tacggcggga  180
caggaggaat actctgcaat gcgcgaccag tatatgcgaa ccggtgaggg ttttttgtgt  240
gtttttgcga taaataattc caagtcattt gcggacataa atctgtatcg ggagcagatc  300
aagcgcgtta aggattcaga cgatgtgcct atggtcctcg tggggaataa gtgtgacctt  360
cctacccgaa cagtcgacac aaaacaggcc catgaactgg ctaaaagcta cgggataccg  420
tttattgaaa catcagcaaa aactagacag ggagttgaag acgcgttcta tacccttgtc  480
agggagatac gacaatacag aatgaaaaaa ctcaatagtt ccgacgatgg cactcaaggt  540
tgtatgggtt tgccgtgtgt ggttatg                              567

SEQ ID NO: 128         moltype = AA  length = 189
FEATURE                Location/Qualifiers
source                 1..189
                       mol_type = protein
                       organism = Homo sapiens
SEQUENCE: 128
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                  189

SEQ ID NO: 129         moltype = DNA  length = 690
FEATURE                Location/Qualifiers
source                 1..690
                       mol_type = other DNA
                       organism = Synthetic construct
SEQUENCE: 129
atgcagatcc cacaggcgcc ctggccagtc gtctgggcgg tgctacaact gggctggcgg  60
ccaggatggt tcttagactc cccagacagg ccctggaacc cccccacctt ctccccagcc  120
ctgctcgtgg tgaccgaagg ggacaacgcc accttcacct gcagcttctc caacacatcg  180
gagagcttcg tgctaaactg gtaccgcatg agccccagca accagacgga caagctggcc  240
gctttccccg aggaccgcag ccagcccggc caggactgcc gcttccgtgt cacacaactg  300
cccaacgggc gtgacttcca catgagcgtg gtcagggccc ggcgcaatga cagcggcacc  360
tacctctgtg gggccatctc cctggccccc aaggcgcaga tcaaagagag cctgcgggca  420
gagctcaggg tgacagagag aagggcagaa gtgcccacag cccaccccag cccctcaccc  480
aggccagccg gccagttcca aaccctggtg gttggtgtcg tgggcggcct gctgggcagc  540
ctggtgctgc tagtctgggt cctggccgtc atctgctccc gggccgcacg agggacaata  600
ggagccaggc gcaccggcca gcccctgaag gaggacccct cagccgtgcc tgtgttctct  660
gtggactatg gggagctgga tttccagtgg                           690

SEQ ID NO: 130         moltype = AA  length = 230
FEATURE                Location/Qualifiers
source                 1..230
                       mol_type = protein
                       organism = Synthetic construct
SEQUENCE: 130
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW         230

SEQ ID NO: 131         moltype = DNA  length = 864
FEATURE                Location/Qualifiers
source                 1..864
                       mol_type = genomic DNA
                       organism = Homo sapiens
SEQUENCE: 131
atgcagatcc cacaggcgcc ctggccagtc gtctgggcgg tgctacaact gggctggcgg  60
ccaggatggt tcttagactc cccagacagg ccctggaacc cccccacctt ctccccagcc  120
ctgctcgtgg tgaccgaagg ggacaacgcc accttcacct gcagcttctc caacacatcg  180
gagagcttcg tgctaaactg gtaccgcatg agccccagca accagacgga caagctggcc  240
gctttccccg aggaccgcag ccagcccggc caggactgcc gcttccgtgt cacacaactg  300
cccaacgggc gtgacttcca catgagcgtg gtcagggccc ggcgcaatga cagcggcacc  360
tacctctgtg gggccatctc cctggccccc aaggcgcaga tcaaagagag cctgcgggca  420
gagctcaggg tgacagagag aagggcagaa gtgcccacag cccaccccag cccctcaccc  480
aggccagccg gccagttcca aaccctggtg gttggtgtcg tgggcggcct gctgggcagc  540
ctggtgctgc tagtctgggt cctggccgtc atctgctccc gggccgcacg agggacaata  600
ggagccaggc gcaccggcca gcccctgaag gaggacccct cagccgtgcc tgtgttctct  660
gtggactatg gggagctgga tttccagtgg cgagagaaga ccccggagcc ccccgtgccc  720
tgtgtccctg agcagacgga gtatgccacc attgtctttc ctagcggaat gggcacctca  780
```

```
tcccccgccc gcaggggctc agccgacggc cctcggagtg cccagccact gaggcctgag  840
gatggacact gctcttggcc cctc                                          864

SEQ ID NO: 132         moltype = AA  length = 288
FEATURE                Location/Qualifiers
source                 1..288
                       mol_type = protein
                       organism = Homo sapiens
SEQUENCE: 132
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL                288

SEQ ID NO: 133         moltype = DNA  length = 3873
FEATURE                Location/Qualifiers
source                 1..3873
                       mol_type = other DNA
                       organism = Synthetic construct
SEQUENCE: 133
atggcgggcg ccgcgtcccc ttgcgccaac ggctgcgggc ccggcgcgcc ctcggacgcc  60
gaggtgctgc acctctgccg cagcctcgag gtgggcaccg tcatgacttt gttctactcc  120
aagaagtcgc agcgacccaa gcggaagacc ttccaggtca agctggagac gcgccagatc  180
acgtggagcc ggggcgccga caagatcgag gggccattg acattcgtga aattaaggag  240
atccgcccag ggaagacctc acgggacttt gatcgctatc aagaggaccc agctttccgg  300
ccggaccagt cacattgctt tgtcattctc tatggaatgg aatttcgcct gaaaacgctg  360
agcctgcaag ccacatctga ggatgaagtg aacatgtgga tcaagggctt aacttggctg  420
atggaggata cattgcaggc acccacaccc ctgcagattg agaggtggct ccggaagcag  480
ttttactcag tggatcggaa tcgtgaggat cgtatatcag ccaaggacct gaagaacatg  540
ctgtcccagg tcaactaccg ggtccccaac atgcgcttcc tccgagagcg gctgacggac  600
ctggagcagc gcagcgggga catcacctac gggcagtttg ctcagctgta ccgcagcctc  660
atgtacagcg cccagaagac gatggacctc cccttcttgg aagccagtac tctgagggct  720
ggggagcggc cggagctttg ccgagtgtcc cttcctgagt tccagcagtt ccttcttgac  780
taccaggggg agctgtgggc tgttgatcgc ctccaggtgc aggagttcat gctcagcttc  840
ctccgagacc ccttacgaga gatcgaggag ccatacttct tcctggatga gtttgtcacc  900
ttcctgttct ccaaagagaa cagtgtgtgg aactcgcagc tggatgcagt atgcccggac  960
accatgaaca accctctttc ccactactgg atctcctcct cgcacaacac gtacctgacc  1020
ggggaccagt tctccagtga gtcctccttg gaagcctatg ctcgctgcct gcggatgggc  1080
tgtcgctgca ttgagttgga ctgctgggac ggcccggatg ggatgccagt tatttaccat  1140
gggcacaccc ttaccaccaa gatcaagttc tcagatgtcc tgcacaccat caaggagcat  1200
gcctttgtgg cctcagagta cccagtcatc ctgtccattg aggaccactg cagcattgcc  1260
cagcagagaa acatggccca atacttcaag aaggtgctgg gggacacact cctcaccaag  1320
cccgtggaga tctctgccga cgggctcccc tcacccaacc agcttaagag gaagatcctc  1380
atcaagcaca agaagctggc tgagggcagt gcctacgagg aggtgcctac atccatgatg  1440
tactctgaga acgacatcag caactctatc aagaatggca tcctctacct ggaggaccct  1500
gtgaaccacg aatggtatcc ccactacttt gttctgacca gcagcaagat ctactactct  1560
gaggagacca gcagtgacca gggcaacgag gatgaggagg agcccaagga ggtcagcagc  1620
agcacagagc tgcactccaa tgagaagtgg ttccatggga agctaggggc agggcgtgac  1680
gggcgtcaca tcgctgagcg cctgcttact gagtactgca tcgagaccgg agcccctgac  1740
ggctccttcc tcgtgcgaga gagtgagacc ttcgtgggcg actacacgct ctctttctgg  1800
cggaacggga aagtccagca ctgccgtatc cactcccggc aagatgctgg gacccccaag  1860
ttcttcttga cagacaacct cgtctttgac tccctctatg acctcatcac gcactaccag  1920
caggtgcccc tgcgctgtaa tgagtttgag atgcgacttt cagagcctgt cccacagacc  1980
aacgcccacg agagcaaaga gtggtaccac gcgagcctga ccagagcaca ggctgagcac  2040
atgctaatgc gcgtccctcg tgatggggcc ttcctggtgc ggaagcggaa tgaacccaac  2100
tcatatgcca tctctttccg ggctgagggc aagatcaagc attgccgtgt ccagcaagag  2160
ggccagacag tgatgctagg gaactcggag ttcgacagcc ttgttgacct catcagctac  2220
tatgagaaac acccgctata ccgcaagatg aagctgcgct atcccatcaa cgaggaggca  2280
ctggagaaga ttggcacagc tgagcctgac tacggggccc tgtatgaggg acgcaaccct  2340
ggcttctatg tagaggcaaa ccctatgcca actttcaagt gtgcagtcaa agccctcttt  2400
gactacaagg cccagaggga ggacgagctg accttcacca agagcgccat catccagaat  2460
gtggagaagc aagagggagg ctggtggcga ggggactacg gagggaagaa gcagctgtgg  2520
ttcccatcaa actacgtgga agagatggtc aaccccgtgg ccctggagcc ggagagggag  2580
cacttggacg agaacagccc cctaggggac ttgctgcggg gggtcttgga tgtgccggct  2640
tgtcagattg ccatccgtcc tgagggcaag aacaaccggc tcttcgtctt ctccatcagc  2700
atggcgtcgg tggcccactg gtccctggat gttgctgccg actcacagga ggagctgcag  2760
gactgggtga aaaagatccg tgaagtggcc cagacagcag acgccaggct cactgaaggg  2820
aagataatgg aacggaggaa gaagattgcc ctggagctct ctgaacttgt cgtctactgc  2880
cggcctgttc cctttgatga agagaagatt ggcacagaac gtgcttgcta ccgggacatg  2940
tcatccttcc cggaaaccaa ggctgagaaa tacgtgaaca aggccaaagg caagaagttc  3000
cttcagtaca atcgactgca gctctcccgc atctacccca agggccagcg actggattcc  3060
tccaactacg atcctttgcc catgtggatc tgtggcagtc agcttgtggc cctcaacttc  3120
cagacccctg acaagcctat gcagatgaac caggccctct tcatgacggg caggcactgt  3180
ggctacgtgc tgcagccaag caccatgcgg gatgaggcct tcgacccctt tgacaagagc  3240
agcctccgcg ggctggagcc atgtgccatc tctattgagg tgctgggggc ccgacatctg  3300
ccaaagaatg gccgaggcat tgtgtgtcct tttgtggaga ttgaggtggc tggagctgag  3360
tatgacagca ccaagcagaa gacagagttt gtggtggaca atggactcaa ccctgtatgg  3420
ccagccaagc ccttccactt ccagatcagt aaccctgaat ttgcctttct gcgcttcgtg  3480
```

-continued

```
gtgtatgagg aagacatgtt tagtgaccag aatttcctgg ctcaggctac tttcccagta  3540
aaaggcctga agacaggata cagagcagtg cctttgaaga acaactacag tgaggacctg  3600
gagttggcct ccctgctgat caagattgac atttccctgg ccaagcagga gaatggtgac  3660
ctcagtccct tcagtggtac gtccctgcgg gagcggggct cagatgcctc aggccagctg  3720
tttcatggcc gagcccggga aggctccttt gaatcccgct accagcagcc gtttgaggac  3780
ttccgcatct cccaggagca tctcgcagac cattttgaca gtcgagaacg aagggcccca  3840
agaaggactc gggtcaatgg agacaaccgc ctc                               3873

SEQ ID NO: 134          moltype = AA  length = 1291
FEATURE                 Location/Qualifiers
source                  1..1291
                        mol_type = protein
                        organism = Synthetic construct
SEQUENCE: 134
MAGAASPCAN GCGPGAPSDA EVLHLCRSLE VGTVMTLFYS KKSQRPKRKT FQVKLETRQI  60
TWSRGADKIE GAIDIREIKE IRPGKTSRDF DRYQEDPAFR PDQSHCFVIL YGMEFRLKTL  120
SLQATSEDEV NMWIKGLTWL MEDTLQAPTP LQIERWLRKQ FYSVDRNRED RISAKDLKNM  180
LSQVNYRVPN MRFLRERLTD LEQRSGDITY GQFAQLYRSL MYSAQKTMDL PFLEASTLRA  240
GERPELCRVS LPEFQQFLLD YQGELWAVDR LQVQEFMLSF LRDPLREIEE PYFFLDEFVT  300
FLFSKENSVW NSQLDAVCPD TMNNPLSHYW ISSSHNTYLT GDQFSSESSL EAYARCLRMG  360
CRCIELDCWD GPDGMPVIYH GHTLTTKIKF SDVLHTIKEH AFVASEYPVI LSIEDHCSIA  420
QQRNMAQYFK KVLGDTLLTK PVEISADGLP SPNQLKRKIL IKHKKLAEGS AYEEVPTSMM  480
YSENDISNSI KNGILYLEDP VNHEWYPHYF VLTSSKIYYS EETSSDQGNE DEEEPKEVSS  540
STELHSNEKW FHGKLGAGRD GRHIAERLLT EYCIETGAPD GSFLVRESET FVGDYTLSFW  600
RNGKVQHCRI HSRQDAGTPK FFLTDNLVFD SLYDLITHYQ QVPLRCNEFE MRLSEPVPQT  660
NAHESKEWYH ASLTRAQAEH MLMRVPRDGA FLVRKRNEPN SYAISFRAEG KIKHCRVQQE  720
GQTVMLGNSE FDSLVDLISY YEKHPLYRKM KLRYPINEEA LEKIGTAEPD YGALYEGRNP  780
GFYVEANPMP TFKCAVKALF DYKAQREDEL TFTKSAIIQN VEKQEGGWWR GDYGGKKQLW  840
FPSNYVEEMV NPVALEPERE HLDENSPLGD LLRGVLDVPA CQIAIRPEGK NNRLFVFSIS  900
MASVAHWSLD VAADSQEELQ DWVKKIREVA QTADARLTEG KIMERRKKIA LELSELVVYC  960
RPVPFDEEKI GTERACYRDM SSFPETKAEK YVNKAKGKKF LQYNRLQLSR IYPKGQRLDS  1020
SNYDPLPMWI CGSQLVALNF QTPDKPMQMN QALFMTGRHC GYVLQPSTMR DEAFDPFDKS  1080
SLRGLEPCAI SIEVLGARHL PKNGRGIVCP FVEIEVAGAE YDSTKQKTEF VVDNGLNPVW  1140
PAKPFHFQIS NPEFAFLRFV VYEEDMFSDQ NFLAQATFPV KGLKTGYRAV PLKNNYSEDL  1200
ELASLLIKID IFPAKQENGD LSPFSGTSLR ERGSDASGQL FHGRAREGSF ESRYQQPFED  1260
FRISQEHLAD HFDSRERRAP RRTRVNGDNR L                                 1291

SEQ ID NO: 135          moltype = DNA  length = 3873
FEATURE                 Location/Qualifiers
source                  1..3873
                        mol_type = other DNA
                        organism = Synthetic construct
SEQUENCE: 135
atggcgggcg ccgcgtcccc ttgcgccaac ggctgcgggc ccggcgcgcc ctcggacgcc  60
gaggtgctgc acctctgccg cagcctcgag gtgggcaccg tcatgacttt gttctactcc  120
aagaagtcgc agcgacccga gcggaagacc ttccaggtca agctggagac gcgccagatc  180
acgtggagcc ggggcgccga caagatcgag gggcgccattg acattcgtga aattaaggag  240
atccgcccag ggaagacctc acgggacttt gatcgctatc aagaggaccc agctttccgg  300
ccggaccagt cacattgctt tgtcattctc tatggaatgg aatttcgcct gaaaacgctg  360
agcctgcaag ccacatctga ggatgaagtg aacatgtgga tcaagggctt aacttggctg  420
atggaggata cattgcaggc acccacaccc ctgcagattg agaggtggct ccggaagcag  480
ttttactcag tggatcggaa tcgtgaggat cgtatatcag ccaaggacct gaagaacatg  540
ctgtcccagg tcaactaccg ggtccccaac atgcgcttcc tccgagagcg gctgacggac  600
ctggagcagc gcagcgggga catcacctac gggcagtttg ctcagctgta ccgcagcctc  660
atgtacagcg cccagaagac gatggacctc cccttcttgg aagccagtac tctgagggct  720
ggggagcggc cggagctttg ccgagtgtcc cttcctgagt tccagcagtt ccttcttgac  780
taccaggggg agctgtgggc tgttgatcgc ctccaggtgc aggagttcat gctcagcttc  840
ctccgagacc ccttacgaga gatcgaggag ccatacttct tcctggatga gtttgtcacc  900
ttcctgttct ccaaagagaa cagtgtgtgg aactcgcagc tggatgcagt atgcccggac  960
accatgaaca accctctttc ccactactgg atctcctcct cgcacaacac gtacctgacc  1020
ggggaccagt tctccagtga gtcctccttg gaagcctatg ctcgctgcct gcggatgggc  1080
tgtcgctgca ttgagttgga ctgctgggac ggcccggatg ggatgccagt tatttaccat  1140
gggcacaccc ttaccaccaa gatcaagttc tcagatgtcc tgcacaccat caaggagcat  1200
gcctttgtgg cctcagagta cccagtcatc ctgtccattg aggaccactg cagcattgcc  1260
cagcagagaa acatggccca atacttcaag aaggtgctgg gggacacact cctcaccaag  1320
cccgtggaga tctctgccga cggctcccc tcacccaacc agcttaagag gaagatcctc  1380
atcaagcaca agaagctggc tgagggcagt gcctacgagg aggtgcctac atccatgatg  1440
tactctgaga acgacatcag caactctatc aagaatggca tcctctacct ggaggaccct  1500
gtgaaccacg aatggtatcc ccactacttt gttctgacca gcagcaagat ctactacttt  1560
gaggagacca gcagtgacca gggcaacgag gatgaggagg agcccaagga ggtcagcagc  1620
agcacagagc tgcactccaa tgagaagtgg ttccatggga agctaggggc agggcgtgac  1680
gggcgtcaca tcgctgagcg cctgcttact gagtactgca tcgagaccgg agcccctgac  1740
ggctccttcc tcgtgcgaga gagtgagacc ttcgtgggcg actacacgct ctctttctgg  1800
cggaacggga aagtccagca ctgccgtatc cactcccggc aagatgctgg gacccccaag  1860
ttcttcttga cagacaacct cgtctttgac tccctctatg acctcatcac gcactaccag  1920
caggtgcccc tgcgctgtaa tgagtttgag atgcgacttt cagagcctgt cccacagacc  1980
aacgcccacg agagcaaaga gtggtaccac gcgagcctga ccagagcaca ggctgagcac  2040
atgctaatgc gcgtccctcg tgatggggcc ttcctggtgc ggaagcggaa tgaacccaac  2100
tcatatgcca tctctttccg ggctgagggc aagatcaagc attgccgtgt ccagcaagag  2160
```

-continued

```
ggccagacag tgatgctagg gaactcggag ttcgacagcc ttgttgacct catcagctac  2220
tatgagaaac acccgctata ccgcaagatg aagctgcgct atcccatcaa cgaggaggca  2280
ctggagaaga ttggcacagc tgagcctgac tacggggccc tgtatgaggg acgcaaccct  2340
ggcttctatg tagaggcaaa ccctatgcca actttcaagt gtgcagtcaa agccctcttt  2400
gactacaagg cccagaggga ggacgagctg accttcacca agagcgccat catccagaat  2460
gtggagaagc aagagggagg ctggtggcga ggggactacg gagggaagaa gcagctgtgg  2520
ttcccatcaa actacgtgga agagatggtc aaccccgtgg ccctggagcc ggagagggag  2580
cacttggacg agaacagccc cctaggggac ttgctgcggg gggtcttgga tgtgccggct  2640
tgtcagattg ccatccgtcc tgagggcaag aacaaccggc tcttcgtctt ctccatcagc  2700
atggcgtcgg tggcccactg gtccctggat gttgctgccg actcacagga ggagctgcag  2760
gactgggtga aaaagatccg tgaagtggcc cagacagcag acgccaggct cactgaaggg  2820
aagataatgg aacggaggaa gaagattgcc ctggagctct ctgaacttgt cgtctactgc  2880
cggcctgttc cctttgatga agagaagatt ggcacagaac gtgcttgcta ccgggacatg  2940
tcatccttcc cggaaaccaa ggctgagaaa tacgtgaaca aggccaaagg caagaagttc  3000
cttcagtaca atcgactgca gctctcccgc atctacccca agggccagcg actggattcc  3060
tccaactacg atcctttgcc catgtggatc tgtggcagtc agcttgtggc cctcaacttc  3120
cagacccctg acaagcctat gcagatgaac caggccctct tcatgacggg caggcactgt  3180
ggctacgtgc tgcagccaag caccatgcgg gatgaggcct tcgacccctt tgacaagagc  3240
agcctccgcg ggctggagcc atgtgccatc tctattgagg tgctgggggc ccgacatctg  3300
ccaaagaatg gccgaggcat tgtgtgtcct tttgtggaga ttgaggtggc tggagctgag  3360
tatgacagca ccaagcagaa gacagagttt gtggtggaca atggactcaa ccctgtatgg  3420
ccagccaagc ccttccactt ccagatcagt aaccctgaat ttgcctttct gcgcttcgtg  3480
gtgtatgagg aagacatgtt tagtgaccag aatttcctgg ctcaggctac tttcccagta  3540
aaaggcctga agacaggata cagagcagtg cctttgaaga acaactacag tgaggacctg  3600
gagttggcct ccctgctgat caagattgac attttccctg ccaagcagga gaatggtgac  3660
ctcagtccct tcagtggtac gtccctgcgg gagcggggct cagatgcctc aggccagctg  3720
tttcatggcc gagcccggga aggctccttt gaatcccgct accagcagcc gtttgaggac  3780
ttccgcatct cccaggagca tctcgcagac catttttgaca gtcgagaacg aagggcccca  3840
agaaggactc gggtcaatgg agacaaccgc ctc                                3873

SEQ ID NO: 136          moltype = AA  length = 1291
FEATURE                 Location/Qualifiers
source                  1..1291
                        mol_type = protein
                        organism = Synthetic construct
SEQUENCE: 136
MAGAASPCAN GCGPGAPSDA EVLHLCRSLE VGTVMTLFYS KKSQRPERKT FQVKLETRQI  60
TWSRGADKIE GAIDIREIKE IRPGKTSRDF DRYQEDPAFR PDQSHCFVIL YGMEFRLKTL  120
SLQATSEDEV NMWIKGLTWL MEDTLQAPTP LQIERWLRKQ FYSVDRNRED RISAKDLKNM  180
LSQVNYRVPN MRFLRERLTD LEQRSGDITY GQFAQLYRSL MYSAQKTMDL PFLEASTLRA  240
GERPELCRVS LPEFQQFLLD YQGELWAVDR LQVQEFMLSF LRDPLREIEE PYFFLDEFVT  300
FLFSKENSVW NSQLDAVCPD TMNNPLSHYW ISSSHNTYLT GDQFSSESSL EAYARCLRMG  360
CRCIELDCWD GPDGMPVIYH GHTLTTKIKF SDVLHTIKEH AFVASEYPVI LSIEDHCSIA  420
QQRNMAQYFK KVLGDTLLTK PVEISADGLP SPNQLKRKIL IKHKKLAEGS AYEEVPTSMM  480
YSENDISNSI KNGILYLEDP VNHEWYPHYF VLTSSKIYYF EETSSDQGNE DEEEPKEVSS  540
STELHSNEKW FHGKLGAGRD GRHIAERLLT EYCIETGAPD GSFLVRESET FVGDYTLSFW  600
RNGKVQHCRI HSRQDAGTPK FFLTDNLVFD SLYDLITHYQ QVPLRCNEFE MRLSEPVPQT  660
NAHESKEWYH ASLTRAQAEH MLMRVPRDGA FLVRKRNEPN SYAISFRAEG KIKHCRVQQE  720
GQTVMLGNSE FDSLVDLISY YEKHPLYRKM KLRYPINEEA LEKIGTAEPD YGALYEGRNP  780
GFYVEANPMP TFKCAVKALF DYKAQREDEL TFTKSAIIQN VEKQEGGWWR GDYGGKKQLW  840
FPSNYVEEMV NPVALEPERE HLDENSPLGD LLRGVLDVPA CQIAIRPEGK NNRLFVFSIS  900
MASVAHWSLD VAADSQEELQ DWVKKIREVA QTADARLTEG KIMERRKKIA LELSELVVYC  960
RPVPFDEEKI GTERACYRDM SSFPETKAEK YVNKAKGKKF LQYNRLQLSR IYPKGQRLDS  1020
SNYDPLPMWI CGSQLVALNF QTPDKPMQMN QALFMTGRHC GYVLQPSTMR DEAFDPFDKS  1080
SLRGLEPCAI SIEVLGARHL PKNGRGIVCP FVEIEVAGAE YDSTKQKTEF VVDNGLNPVW  1140
PAKPFHFQIS NPEFAFLRFV VYEEDMFSDQ NFLAQATFPV KGLKTGYRAV PLKNNYSEDL  1200
ELASLLIKID IFPAKQENGD LSPFSGTSLR ERGSDASGQL FHGRAREGSF ESRYQQPFED  1260
FRISQEHLAD HFDSRERRAP RRTRVNGDNR L                                  1291

SEQ ID NO: 137          moltype = DNA  length = 3873
FEATURE                 Location/Qualifiers
source                  1..3873
                        mol_type = other DNA
                        organism = Synthetic construct
SEQUENCE: 137
atggcgggcg ccgcgtcccc ttgcgccaac ggctgcgggc ccggcgcgcc ctcggacgcc  60
gaggtgctgc acctctgccg cagcctcgag gtgggcaccg tcatgacttt gttctactcc  120
aagaagtcgc agcgacccga gcggaagacc ttccaggtca agctggagac gcgccagatc  180
acgtggagcc ggggcgccga caagatcgag ggggccattg acattcgtga aattaaggag  240
atccgcccag ggaagacctc acgggacttt gatcgctatc aagaggaccc agctttccgg  300
ccggaccagt cacattgctt tgtcattctc tatggaatgg aatttcgcct gaaaacgctg  360
agcctgcaag ccacatctga ggatgaagtg aacatgtgga tcaagggctt aacttggctg  420
atggaggata cattgcaggc acccacaccc ctgcagattg agaggtggct ccggaagcag  480
ttttactcag tggatcggaa tcgtgaggat cgtatatcag ccaaggacct gaagaacatg  540
ctgtcccagg tcaactaccg ggtccccaac atgcgcttcc tccgagagcg gctgacggac  600
ctggagcagc gcagcgggga catcacctac gggcagtttg ctcagctgta ccgcagcctc  660
atgtacagcg cccagaagac gatggacctc cccttcttgg aagccagtac tctgagggct  720
ggggagcggc cggagctttg ccgagtgtcc cttcctgagt tccagcagtt ccttcttgac  780
taccaggggg agctgtgggc tgttgatcgc ctccaggtgc aggagttcat gctcagcttc  840
```

-continued

```
ctccgagacc ccttacgaga gatcgaggag ccatacttct tcctggatga gtttgtcacc  900
ttcctgttct ccaaagagaa cagtgtgtgg aactcgcagc tggatgcagt atgcccggac  960
accatgaaca accctctttc ccactactgg atctcctcct cgcacaacac gtacctgacc  1020
ggggaccagt tctccagtga gtcctccttg gaagcctatg ctcgctgcct gcggatgggc  1080
tgtcgctgca ttgagttgga ctgctgggac ggcccggatg ggatgccagt tatttaccat  1140
gggcacaccc ttaccaccaa gatcaagttc tcagatgtcc tgcacaccat caaggagcat  1200
gcctttgtgg cctcagagta cccagtcatc ctgtccattg aggaccactg cagcattgcc  1260
cagcagagaa acatggccca atacttcaag aaggtgctgg gggacacact cctcaccaag  1320
cccgtggaga tctctgccga cggctcccc  tcacccaacc agcttaagag gaagatcctc  1380
atcaagcaca agaagctggc tgagggcagt gcctacgagg aggtgcctac atccatgatg  1440
tactctgaga acgacatcag caactctatc aagaatggca tcctctacct ggaggaccct  1500
gtgaaccacg aatggtatcc ccactacttt gttctgacca gcagcaagat ctactactct  1560
gaggagacca gcagtgacca gggcaacgag gatgaggagg agcccaagga ggtcagcagc  1620
agcacagagc tgcactccaa tgagaagtgg ttccatggga agctaggggc agggcgtgac  1680
gggcgtcaca tcgctgagcg cctgcttact gagtactgca tcgagaccgg agcccctgac  1740
ggctccttcc tcgtgcgaga gagtgagacc ttcgtgggcg actacacgct ctctttctgg  1800
cggaacggga aagtccagca ctgccgtatc cactcccggc aagatgctgg gacccccaag  1860
ttcttcttga cagacaacct cgtctttgac tccctctatg acctcatcac gcactaccag  1920
caggtgcccc tgcgctgtaa tgagtttgag atgcgacttt cagagcctgt cccacagacc  1980
aacgcccacg agagcaaaga gtggtaccac gcgagcctga ccagagcaca ggctgagcac  2040
atgctaatgc gcgtccctcg tgatggggcc ttcctggtgc ggaagcggaa tgaacccaac  2100
tcatatgcca tctctttccg ggctgagggc aagatcaagc attgccgtgt ccagcaagag  2160
ggccagacag tgatgctagg gaactcggag ttcgacagcc ttgttgacct catcagctac  2220
tatgagaaac acccgctata ccgcaagatg aagctgcgct atcccatcaa cgaggaggca  2280
ctggagaaga ttggcacagc tgagcctgac tacggggccc tgtatgaggg acgcaaccct  2340
ggcttctatg tagaggcaaa ccctatgcca actttcaagt gtgcagtcaa agccctcttt  2400
gactacaagg cccagaggga ggacgagctg accttcacca agagcgccat catccagaat  2460
gtggagaagc aagagggagg ctggtggcga ggggactacg gagggaagaa gcagctgtgg  2520
ttcccatcaa actacgtgga agagatggtc aaccccgtgg ccctggagcc ggagagggag  2580
cacttggacg agaacagccc cctaggggac ttgctgcggg gggtcttgga tgtgccggct  2640
tgtcagattg ccatccgtcc tgagggcaag aacaaccggc tcttcgtctt ctccatcagc  2700
atggcgtcgg tggcccactg gtccctggat gttgctgccg actcacagga ggagctgcag  2760
gactgggtga aaaagatccg tgaagtggcc cagacagcag acgccaggct cactgaaggg  2820
aagataatgg aacggaggaa gaagattgcc ctggagctct ctgaacttgt cgtctactgc  2880
cggcctgttc cctttgatga agagaagatt ggcacagaac gtgcttgcta ccgggacatg  2940
tcatccttcc cggaaaccaa ggctgagaaa tacgtgaaca aggccaaagg caagaagttc  3000
cttcagtaca atcgactgca gctctcccgc atctacccca agggccagcg actggattcc  3060
tccaactacg atcctttgcc catgtggatc tgtggcagtc agcttgtggc cctcaacttc  3120
cagacccctg acaagcctat gcagatgaac caggccctct tcatgacggg caggcactgt  3180
ggctacgtgc tgcagccaag caccatgcgg gatgaggcct tcgacccctt tgacaagagc  3240
agcctccgcg ggctggagcc atgtgccatc tctattgagg tgctgggggc ccgacatctg  3300
ccaaagaatg gccgaggcat tgtgtgtcct tttgtggaga ttgaggtggc tggagctgag  3360
tatgacagca ccaagcagaa gacagagttt gtggtggaca atggactcaa ccctgtatgg  3420
ccagccaagc ccttccactt ccagatcagt aaccctgaat ttgcctttct gcgcttcgtg  3480
gtgtataagg aagacatgtt tagtgaccag aatttcctgg ctcaggctac tttcccagta  3540
aaaggcctga agacaggata cagagcagtg cctttgaaga acaactacag tgaggacctg  3600
gagttggcct ccctgctgat caagattgac attttccctg ccaagcagga gaatggtgac  3660
ctcagtccct tcagtggtac gtccctgcgg gagcggggct cagatgcctc aggccagctg  3720
tttcatggcc gagcccggga aggctccttt gaatcccgct accagcagcc gtttgaggac  3780
ttccgcatct cccaggagca tctcgcagac cattttgaca gtcgagaaacg aagggcccca  3840
agaaggactc gggtcaatgg agacaaccgc ctc                               3873
```

```
SEQ ID NO: 138         moltype = AA  length = 1291
FEATURE                Location/Qualifiers
source                 1..1291
                       mol_type = protein
                       organism = Synthetic construct
SEQUENCE: 138
MAGAASPCAN GCGPGAPSDA EVLHLCRSLE VGTVMTLFYS KKSQRPERKT FQVKLETRQI  60
TWSRGADKIE GAIDIREIKE IRPGKTSRDF DRYQEDPAFR PDQSHCFVIL YGMEFRLKTL  120
SLQATSEDEV NMWIKGLTWL MEDTLQAPTP LQIERWLRKQ FYSVDRNRED RISAKDLKNM  180
LSQVNYRVPN MRFLRERLTD LEQRSGDITY GQFAQLYRSL MYSAQKTMDL PFLEASTLRA  240
GERPELCRVS LPEFQQFLLD YQGELWAVDR LQVQEFMLSF LRDPLREIEE PYFFLDEFVT  300
FLFSKENSVW NSQLDAVCPD TMNNPLSHYW ISSSHNTYLT GDQFSSESSL EAYARCLRMG  360
CRCIELDCWD GPDGMPVIYH GHTLTTKIKF SDVLHTIKEH AFVASEYPVI LSIEDHCSIA  420
QQRNMAQYFK KVLGDTLLTK PVEISADGLP SPNQLKRKIL IKHKKLAEGS AYEEVPTSMM  480
YSENDISNSI KNGILYLEDP VNHEWYPHYF VLTSSKIYYS EETSSDQGNE DEEEPKEVSS  540
STELHSNEKW FHGKLGAGRD GRHIAERLLT EYCIETGAPD GSFLVRESET FVGDYTLSFW  600
RNGKVQHCRI HSRQDAGTPK FFLTDNLVFD SLYDLITHYQ QVPLRCNEFE MRLSEPVPQT  660
NAHESKEWYH ASLTRAQAEH MLMRVPRDGA FLVRKRNEPN SYAISFRAEG KIKHCRVQQE  720
GQTVMLGNSE FDSLVDLISY YEKHPLYRKM KLRYPINEEA LEKIGTAEPD YGALYEGRNP  780
GFYVEANPMP TFKCAVKALF DYKAQREDEL TFTKSAIIQN VEKQEGGWWR GDYGGKKQLW  840
FPSNYVEEMV NPVALEPERE HLDENSPLGD LLRGVLDVPA CQIAIRPEGK NNRLFVFSIS  900
MASVAHWSLD VAADSQEELQ DWVKKIREVA QTADARLTEG KIMERRKKIA LELSELVVYC  960
RPVPFDEEKI GTERACYRDM SSFPETKAEK YVNKAKGKKF LQYNRLQLSR IYPKGQRLDS  1020
SNYDPLPMWI CGSQLVALNF QTPDKPMQMN QALFMTGRHC GYVLQPSTMR DEAFDPFDKS  1080
SLRGLEPCAI SIEVLGARHL PKNGRGIVCP FVEIEVAGAE YDSTKQKTEF VVDNGLNPVW  1140
PAKPFHFQIS NPEFAFLRFV VYKEDMFSDQ NFLAQATFPV KGLKTGYRAV PLKNNYSEDL  1200
ELASLLIKID IFPAKQENGD LSPFSGTSLR ERGSDASGQL FHGRAREGSF ESRYQQPFED  1260
```

-continued

```
FRISQEHLAD HFDSRERRAP RRTRVNGDNR L                             1291

SEQ ID NO: 139          moltype = DNA  length = 3873
FEATURE                 Location/Qualifiers
source                  1..3873
                        mol_type = other DNA
                        organism = Synthetic construct
SEQUENCE: 139
atggcgggcg ccgcgtcccc ttgcgccaac ggctgcgggc ccggcgcgcc ctcggacgcc  60
gaggtgctgc acctctgccg cagcctcgag gtgggcaccg tcatgacttt gttctactcc  120
aagaagtcgc agcgacccga gcggaagacc ttccaggtca agctggagac gcgccagatc  180
acgtggagcc ggggcgccga caagatcgag ggggccattg acattcgtga aattaaggag  240
atccgcccag ggaagacctc acgggacttt gatcgctatc aagaggaccc agctttccgg  300
ccggaccagt cacattgctt tgtcattctc tatggaatgg aatttcgcct gaaaacgctg  360
agcctgcaag ccacatctga ggatgaagtg aacatgtgga tcaagggctt aacttggctg  420
atggaggata cattgcaggc acccacaccc ctgcagattg agaggtggct ccggaagcag  480
ttttactcag tggatcggaa tcgtgaggat cgtatatcag ccaaggacct gaagaacatg  540
ctgtcccagg tcaactaccg ggtccccaac atgcgcttcc tccgagagcg gctgacggac  600
ctggagcagc gcagcgggga catcacctac gggcagtttg ctcagctgta ccgcagcctc  660
atgtacagcg cccagaagac gatggacctc cccttcttgg aagccagtac tctgagggct  720
ggggagcggc cggagctttg ccgagtgtcc cttcctgagt tccagcagtt ccttcttgac  780
taccaggggg agctgtgggc tgttgatcgc ctccaggtgc aggagttcat gctcagcttc  840
ctccgagacc ccttacgaga gatcgaggag ccatacttct tcctggatga gtttgtcacc  900
ttcctgttct ccaaagagaa cagtgtgtgg aactcgcagc tggatgcagt atgcccggac  960
accatgaaca accctctttc ccactactgg atctcctcct cgcacaacac gtacctgacc  1020
ggggaccagt tctccagtga gtcctccttg gaagcctatg ctcgctgcct gcggatgggc  1080
tgtcgctgca ttgagttgga ctgctgggac ggcccggatg ggatgccagt tatttaccat  1140
gggcacaccc ttaccaccaa gatcaagttc tcagatgtcc tgcacaccat caaggagcat  1200
gcctttgtgg cctcagagta cccagtcatc ctgtccattg aggaccactg cagcattgcc  1260
cagcagagaa acatggccca atacttcaag aaggtgctgg gggacacact cctcaccaag  1320
cccgtggaga tctctgccga cgggctcccc tcacccaacc agcttaagag gaagatcctc  1380
atcaagcaca agaagctggc tgagggcagt gcctacgagg aggtgcctac atccatgatg  1440
tactctgaga acgacatcag caactctatc aagaatggca tcctctacct ggaggaccct  1500
gtgaaccacg aatggtatcc ccactacttt gttctgacca gcagcaagat ctactactct  1560
gaggagacca gcagtgacca gggcaacgag gatgaggagg agcccaagga ggtcagcagc  1620
agcacagagc tgcactccaa tgagaagtgg ttccatggga agctaggggc agggcgtgac  1680
gggcgtcaca tcgctgagcg cctgcttact gagtactgca tcgagaccgg agcccctgac  1740
ggctccttcc tcgtgcgaga gagtgagacc ttcgtgggcg actacacgct ctctttctgg  1800
cggaacggga aagtccagca ctgccgtatc cactcccggc aagatgctgg gacccccaag  1860
ttcttcttga cagacaacct cgtctttgac tccctctatg acctcatcac gcactaccag  1920
caggtgcccc tgcgctgtaa tgagtttgag atgcgacttt cagagcctgt cccacagacc  1980
aacgcccacg agagcaaaga gtggtaccac gcgagcctga ccagagcaca ggctgagcac  2040
atgctaatgc gcgtccctcg tgatggggcc ttcctggtgc ggaagcggaa tgaacccaac  2100
tcatatgcca tctctttccg ggctgagggc aagatcaagc attgccgtgt ccagcaagag  2160
ggccagacag tgatgctagg gaactcggag ttcgacagcc ttgttgacct catcagctac  2220
tatgagaaac acccgctata ccgcaagatg aagctgcgct atcccatcaa cgaggaggca  2280
ctggagaaga ttggcacagc tgagcctgac tacggggccc tgtatgaggg acgcaaccct  2340
ggcttctatg tagaggcaaa ccctatgcca actttcaagt gtgcagtcaa agccctcttt  2400
gactacaagg cccagaggga ggacgagctg accttcacca agagcgccat catccagaat  2460
gtggagaagc aagagggagg ctggtggcga ggggactacg gagggaagaa gcagctgtgg  2520
ttcccatcaa actacgtgga agagatggtc aaccccgtgg ccctggagcc ggagagggag  2580
cacttggacg agaacagccc cctaggggac ttgctgcggg gggtcttgga tgtgccggct  2640
tgtcagattg ccatccgtcc tgagggcaag aacaaccggc tcttcgtctt ctccatcagc  2700
atggcgtcgg tggcccactg gtccctggat gttgctgccg actcacagga ggagctgcag  2760
gactgggtga aaaagatccg tgaagtggcc cagacagcag acgccaggct cactgaaggg  2820
aagataatgg aacggaggaa gaagattgcc ctggagctct ctgaacttgt cgtctactgc  2880
cggcctgttc cctttgatga agagaagatt ggcacagaac gtgcttgcta ccgggacatg  2940
tcatccttcc cggaaaccaa ggctgagaaa tacgtgaaca aggccaaagg caagaagttc  3000
cttcagtaca atcgactgca gctctcccgc atctacccca agggccagcg actggattcc  3060
tccaactacg atcctttgcc catgtggatc tgtggcagtc agcttgtggc cctcaacttc  3120
cagacccctg acaagcctat gcagatgaac caggccctct tcatgacggg caggcactgt  3180
ggctacgtgc tgcagccaag caccatgcgg gatgaggcct tcgacccctt tgacaagagc  3240
agcctccgcg ggctggagcc atgtgccatc tctattgagg tgctgggggc ccgacatctg  3300
ccaaagaatg gccgaggcat tgtgtgtcct tttgtggaga ttgaggtggc tggagctgag  3360
tatgacagca ccaagcagaa gacagagttt gtggtggaca atggactcaa ccctgtatgg  3420
ccagccaagc ccttccactt ccagatcagt aaccctgaat ttgcctttct gcgcttcgtg  3480
gtgtatgagg aacacatgtt tagtgaccag aatttcctgg ctcaggctac tttcccagta  3540
aaaggcctga agacaggata cagagcagtg cctttgaaga acaactacag tgaggacctg  3600
gagttggcct ccctgctgat caagattgac attttccctg ccaagcagga gaatggtgac  3660
ctcagtccct tcagtggtac gtccctgcgg gagcggggct cagatgcctc aggccagctg  3720
tttcatggcc gagcccggga aggctccttt gaatcccgct accagcagcc gtttgaggac  3780
ttccgcatct cccaggagca tctcgcagac cattttgaca gtcgagaacg aagggcccca  3840
agaaggactc gggtcaatgg agacaaccgc ctc                              3873

SEQ ID NO: 140          moltype = AA  length = 1291
FEATURE                 Location/Qualifiers
source                  1..1291
                        mol_type = protein
                        organism = Synthetic construct
```

```
SEQUENCE: 140
MAGAASPCAN GCGPGAPSDA EVLHLCRSLE VGTVMTLFYS KKSQRPERKT FQVKLETRQI  60
TWSRGADKIE GAIDIREIKE IRPGKTSRDF DRYQEDPAFR PDQSHCFVIL YGMEFRLKTL  120
SLQATSEDEV NMWIKGLTWL MEDTLQAPTP LQIERWLRKQ FYSVDRNRED RISAKDLKNM  180
LSQVNYRVPN MRFLRERLTD LEQRSGDITY GQFAQLYRSL MYSAQKTMDL PFLEASTLRA  240
GERPELCRVS LPEFQQFLLD YQGELWAVDR LQVQEFMLSF LRDPLREIEE PYFFLDEFVT  300
FLFSKENSVW NSQLDAVCPD TMNNPLSHYW ISSSHNTYLT GDQFSSESSL EAYARCLRMG  360
CRCIELDCWD GPDGMPVIYH GHTLTTKIKF SDVLHTIKEH AFVASEYPVI LSIEDHCSIA  420
QQRNMAQYFK KVLGDTLLTK PVEISADGLP SPNQLKRKIL IKHKKLAEGS AYEEVPTSMM  480
YSENDISNSI KNGILYLEDP VNHEWYPHYF VLTSSKIYYS EETSSDQGNE DEEEPKEVSS  540
STELHSNEKW FHGKLGAGRD GRHIAERLLT EYCIETGAPD GSFLVRESET FVGDYTLSFW  600
RNGKVQHCRI HSRQDAGTPK FFLTDNLVFD SLYDLITHYQ QVPLRCNEFE MRLSEPVPQT  660
NAHESKEWYH ASLTRAQAEH MLMRVPRDGA FLVRKRNEPN SYAISFRAEG KIKHCRVQQE  720
GQTVMLGNSE FDSLVDLISY YEKHPLYRKM KLRYPINEEA LEKIGTAEPD YGALYEGRNP  780
GFYVEANPMP TFKCAVKALF DYKAQREDEL TFTKSAIIQN VEKQEGGWWR GDYGGKKQLW  840
FPSNYVEEMV NPVALEPERE HLDENSPLGD LLRGVLDVPA CQIAIRPEGK NNRLFVFSIS  900
MASVAHWSLD VAADSQEELQ DWVKKIREVA QTADARLTEG KIMERRKKIA LELSELVVYC  960
RPVPFDEEKI GTERACYRDM SSFPETKAEK YVNKAKGKKF LQYNRLQLSR IYPKGQRLDS  1020
SNYDPLPMWI CGSQLVALNF QTPDKPMQMN QALFMTGRHC GYVLQPSTMR DEAFDPFDKS  1080
SLRGLEPCAI SIEVLGARHL PKNGRGIVCP FVEIEVAGAE YDSTKQKTEF VVDNGLNPVW  1140
PAKPFHFQIS NPEFAFLRFV VYEEHMFSDQ NFLAQATFPV KGLKTGYRAV PLKNNYSEDL  1200
ELASLLIKID IFPAKQENGD LSPFSGTSLR ERGSDASGQL FHGRAREGSF ESRYQQPFED  1260
FRISQEHLAD HFDSRERRAP RRTRVNGDNR L                                1291

SEQ ID NO: 141          moltype = DNA  length = 3873
FEATURE                 Location/Qualifiers
source                  1..3873
                        mol_type = genomic DNA
                        organism = Homo sapiens
SEQUENCE: 141
atggcgggcg ccgcgtcccc ttgcgccaac ggctgcgggc ccggcgcgcc ctcggacgcc  60
gaggtgctgc acctctgccg cagcctcgag gtgggcaccg tcatgacttt gttctactcc  120
aagaagtcgc agcgacccga gcggaagacc ttccaggtca agctggagac gcgccagatc  180
acgtggagcc ggggcgccga caagatcgag gggcccattg acattcgtga aattaaggag  240
atccgcccag ggaagacctc acgggacttt gatcgctatc aagaggaccc agctttccgg  300
ccggaccagt cacattgctt tgtcattctc tatggaatgg aatttcgcct gaaaacgctg  360
agcctgcaag ccacatctga ggatgaagtg aacatgtgga tcaagggctt aacttggctg  420
atggaggata cattgcaggc acccacaccc ctgcagattg agaggtggct ccggaagcag  480
ttttactcag tggatcggaa tcgtgaggat cgtatatcag ccaaggacct gaagaacatg  540
ctgtcccagg tcaactaccg ggtccccaac atgcgcttcc tccgagagcg gctgacggac  600
ctggagcagc gcagcgggga catcacctac gggcagtttg ctcagctgta ccgcagcctc  660
atgtacagcg cccagaagac gatggacctc cccttcttgg aagccagtac tctgagggct  720
ggggagcggc cggagctttg ccgagtgtcc cttcctgagt tccagcagtt ccttcttgac  780
taccaggggg agctgtgggc tgttgatcgc ctccaggtgc aggagttcat gctcagcttc  840
ctccgagacc ccttacgaga gatcgaggag ccatacttct tcctggatga gtttgtcacc  900
ttcctgttct ccaaagagaa cagtgtgtgg aactcgcagc tggatgcagt atgcccggac  960
accatgaaca accctctttc ccactactgg atctcctcct cgcacaacac gtacctgacc  1020
ggggaccagt tctccagtga gtcctccttg gaagcctatg ctcgctgcct gcggatgggc  1080
tgtcgctgca ttgagttgga ctgctgggac ggcccggatg ggatgccagt tatttaccat  1140
gggcacaccc ttaccaccaa gatcaagttc tcagatgtcc tgcacaccat caaggagcat  1200
gcctttgtgg cctcagagta cccagtcatc ctgtccattg aggaccactg cagcattgcc  1260
cagcagagaa acatggccca atacttcaag aaggtgctgg gggacacact cctcaccaag  1320
cccgtggaga tctctgccga cgggctcccc tcacccaacc agcttaagag gaagatcctc  1380
atcaagcaca agaagctggc tgagggcagt gcctacgagg aggtgcctac atccatgatg  1440
tactctgaga acgacatcag caactctatc aagaatggca tcctctacct ggaggaccct  1500
gtgaaccacg aatggtatcc ccactacttt gttctgacca gcagcaagat ctactactct  1560
gaggagacca gcagtgacca gggcaacgag gatgaggagg agcccaagga ggtcagcagc  1620
agcacagagc tgcactccaa tgagaagtgg ttccatggga agctaggggc agggcgtgac  1680
gggcgtcaca tcgctgagcg cctgcttact gagtactgca tcgagaccgg agcccctgac  1740
ggctccttcc tcgtgcgaga gagtgagacc ttcgtgggcg actacacgct ctctttctgg  1800
cggaacggga aagtccagca ctgccgtatc cactcccggc aagatgctgg gacccccaag  1860
ttcttcttga cagacaacct cgtctttgac tccctctatg acctcatcac gcactaccag  1920
caggtgcccc tgcgctgtaa tgagtttgag atgcgacttt cagagcctgt cccacagacc  1980
aacgcccacg agagcaaaga gtggtaccac gcgagcctga ccagagcaca ggctgagcac  2040
atgctaatgc gcgtccctcg tgatggggcc ttcctggtgc ggaagcggaa tgaacccaac  2100
tcatatgcca tctctttccg ggctgagggc aagatcaagc attgccgtgt ccagcaagag  2160
ggccagacag tgatgctagg gaactcggag ttcgacagcc ttgttgacct catcagctac  2220
tatgagaaac acccgctata ccgcaagatg aagctgcgct atcccatcaa cgaggaggca  2280
ctggagaaga ttggcacagc tgagcctgac tacggggccc tgtatgaggg acgcaaccct  2340
ggcttctatg tagaggcaaa ccctatgcca actttcaagt gtgcagtcaa agccctcttt  2400
gactacaagg cccagaggga ggacgagctg accttcacca agagcgccat catccagaat  2460
gtggagaagc aagagggagg ctggtggcga ggggactacg gagggaagaa gcagctgtgg  2520
ttcccatcaa actacgtgga agagatggtc aaccccgtgg ccctggagcc ggagagggag  2580
cacttggacg agaacagccc cctaggggac ttgctgcggg gggtcttgga tgtgccggct  2640
tgtcagattg ccatccgtcc tgagggcaag aacaaccggc tcttcgtctt ctccatcagc  2700
atggcgtcgg tggcccactg gtccctggat gttgctgccg actcacagga ggagctgcag  2760
gactgggtga aaaagatccg tgaagtggcc cagacagcag acgccaggct cactgaaggg  2820
aagataatgg aacggaggaa gaagattgcc ctggagctct ctgaacttgt cgtctactgc  2880
cggcctgttc cctttgatga agagaagatt ggcacagaac gtgcttgcta ccgggacatg  2940
```

```
tcatccttcc cggaaaccaa ggctgagaaa tacgtgaaca aggccaaagg caagaagttc  3000
cttcagtaca atcgactgca gctctcccgc atctacccca agggccagcg actggattcc  3060
tccaactacg atcctttgcc catgtggatc tgtggcagtc agcttgtggc cctcaacttc  3120
cagacccctg acaagcctat gcagatgaac caggccctct tcatgacggg caggcactgt  3180
ggctacgtgc tgcagccaag caccatgcgg gatgaggcct tcgacccctt tgacaagagc  3240
agcctccgcg ggctggagcc atgtgccatc tctattgagg tgctgggggc ccgacatctg  3300
ccaaagaatg gccgaggcat tgtgtgtcct tttgtggaga ttgaggtggc tggagctgag  3360
tatgacagca ccaagcagaa gacagagttt gtggtggaca atggactcaa ccctgtatgg  3420
ccagccaagc ccttccactt ccagatcagt aaccctgaat ttgcctttct gcgcttcgtg  3480
gtgtatgagg aagacatgtt tagtgaccag aatttcctgg ctcaggctac tttcccagta  3540
aaaggcctga agacaggata cagagcagtg cctttgaaga acaactacag tgaggacctg  3600
gagttggcct ccctgctgat caagattgac attttccctg ccaagcagga gaatggtgac  3660
ctcagtccct tcagtggtac gtccctgcgg gagcggggct cagatgcctc aggccagctg  3720
tttcatggcc gagcccggga aggctccttt gaatcccgct accagcagcc gtttgaggac  3780
ttccgcatct cccaggagca tctcgcagac cattttgaca gtcgagaacg aagggcccca  3840
agaaggactc gggtcaatgg agacaaccgc ctc                                3873

SEQ ID NO: 142          moltype = AA  length = 1291
FEATURE                 Location/Qualifiers
source                  1..1291
                        mol_type = protein
                        organism = Homo sapiens
SEQUENCE: 142
MAGAASPCAN GCGPGAPSDA EVLHLCRSLE VGTVMTLFYS KKSQRPERKT FQVKLETRQI  60
TWSRGADKIE GAIDIREIKE IRPGKTSRDF DRYQEDPAFR PDQSHCFVIL YGMEFRLKTL  120
SLQATSEDEV NMWIKGLTWL MEDTLQAPTP LQIERWLRKQ FYSVDRNRED RISAKDLKNM  180
LSQVNYRVPN MRFLRERLTD LEQRSGDITY GQFAQLYRSL MYSAQKTMDL PFLEASTLRA  240
GERPELCRVS LPEFQQFLLD YQGELWAVDR LQVQEFMLSF LRDPLREIEE PYFFLDEFVT  300
FLFSKENSVW NSQLDAVCPD TMNNPLSHYW ISSSHNTYLT GDQFSSESSL EAYARCLRMG  360
CRCIELDCWD GPDGMPVIYH GHTLTTKIKF SDVLHTIKEH AFVASEYPVI LSIEDHCSIA  420
QQRNMAQYFK KVLGDTLLTK PVEISADGLP SPNQLKRKIL IKHKKLAEGS AYEEVPTSMM  480
YSENDISNSI KNGILYLEDP VNHEWYPHYF VLTSSKIYYS EETSSDQGNE DEEEPKEVSS  540
STELHSNEKW FHGKLGAGRD GRHIAERLLT EYCIETGAPD GSFLVRESET FVGDYTLSFW  600
RNGKVQHCRI HSRQDAGTPK FFLTDNLVFD SLYDLITHYQ QVPLRCNEFE MRLSEPVPQT  660
NAHESKEWYH ASLTRAQAEH MLMRVPRDGA FLVRKRNEPN SYAISFRAEG KIKHCRVQQE  720
GQTVMLGNSE FDSLVDLISY YEKHPLYRKM KLRYPINEEA LEKIGTAEPD YGALYEGRNP  780
GFYVEANPMP TFKCAVKALF DYKAQREDEL TFTKSAIIQN VEKQEGGWWR GDYGGKKQLW  840
FPSNYVEEMV NPVALEPERE HLDENSPLGD LLRGVLDVPA CQIAIRPEGK NNRLFVFSIS  900
MASVAHWSLD VAADSQEELQ DWVKKIREVA QTADARLTEG KIMERRKKIA LELSELVVYC  960
RPVPFDEEKI GTERACYRDM SSFPETKAEK YVNKAKGKKF LQYNRLQLSR IYPKGQRLDS  1020
SNYDPLPMWI CGSQLVALNF QTPDKPMQMN QALFMTGRHC GYVLQPSTMR DEAFDPFDKS  1080
SLRGLEPCAI SIEVLGARHL PKNGRGIVCP FVEIEVAGAE YDSTKQKTEF VVDNGLNPVW  1140
PAKPFHFQIS NPEFAFLRFV VYEEDMFSDQ NFLAQATFPV KGLKTGYRAV PLKNNYSEDL  1200
ELASLLIKID IFPAKQENGD LSPFSGTSLR ERGSDASGQL FHGRAREGSF ESRYQQPFED  1260
FRISQEHLAD HFDSRERRAP RRTRVNGDNR L                                  1291

SEQ ID NO: 143          moltype = DNA  length = 3873
FEATURE                 Location/Qualifiers
source                  1..3873
                        mol_type = other DNA
                        organism = Synthetic construct
SEQUENCE: 143
atggcgggcg ccgcgtcccc ttgcgccaac ggctgcgggc ccggcgcgcc ctcggacgcc  60
gaggtgctgc acctctgccg cagcctcgag gtgggcaccg tcatgacttt gttctactcc  120
aagaagtcgc agcgacccga gtggaagacc ttccaggtca agctggagac gcgccagatc  180
acgtggagcc ggggcgccga caagatcgag ggggccattg acattcgtga aattaaggag  240
atccgcccag ggaagacctc acgggacttt gatcgctatc aagaggaccc agctttccgg  300
ccggaccagt cacattgctt tgtcattctc tatggaatgg aatttcgcct gaaaacgctg  360
agcctgcaag ccacatctga ggatgaagtg aacatgtgga tcaagggctt aacttggctg  420
atggaggata cattgcaggc acccacaccc ctgcagattg agaggtggct ccggaagcag  480
ttttactcag tggatcggaa tcgtgaggat cgtatatcag ccaaggacct gaagaacatg  540
ctgtcccagg tcaactaccg ggtccccaac atgcgcttcc tccgagagcg gctgacggac  600
ctggagcagc gcagcgggga catcacctac gggcagtttg ctcagctgta ccgcagcctc  660
atgtacagcg cccagaagac gatggacctc cccttcttgg aagccagtac tctgagggct  720
ggggagcggc cggagctttg ccgagtgtcc cttcctgagt tccagcagtt ccttcttgac  780
taccaggggg agctgtgggc tgttgatcgc ctccaggtgc aggagttcat gctcagcttc  840
ctccgagacc ccttacgaga gatcgaggag ccatacttct tcctggatga gtttgtcacc  900
ttcctgttct ccaaagagaa cagtgtgtgg aactcgcagc tggatgcagt atgcccggac  960
accatgaaca accctcttc ccactactgg atctcctcct cgcacaacac gtacctgacc  1020
ggggaccagt tctccagtga gtcctccttg gaagcctatg ctcgctgcct gcggatgggc  1080
tgtcgctgca ttgagttgga ctgctgggac ggcccggatg ggatgccagt tatttaccat  1140
gggcacaccc ttaccaccaa gatcaagttc tcagatgtcc tgcacaccat caaggagcat  1200
gcctttgtgg cctcagagta cccagtcatc ctgtccattg aggaccactg cagcattgcc  1260
cagcagagaa acatggccca atacttcaag aaggtgctgg gggacacact cctcaccaag  1320
cccgtggaga tctctgccga cgggctcccc tcacccaacc agcttaagag gaagatcctc  1380
atcaagcaca agaagctggc tgagggcagt gcctacgagg aggtgcctac atccatgatg  1440
tactctgaga acgacatcag caactctatc aagaatggca tcctctacct ggaggaccct  1500
gtgaaccacg aatggtatcc ccactacttt gttctgacca gcagcaagat ctactactct  1560
gaggagacca gcagtgacca gggcaacgag gatgaggagg agcccaagga ggtcagcagc  1620
```

-continued

```
agcacagagc tgcactccaa tgagaagtgg ttccatggga agctaggggc agggcgtgac  1680
gggcgtcaca tcgctgagcg cctgcttact gagtactgca tcgagaccgg agcccctgac  1740
ggctccttcc tcgtgcgaga gagtgagacc ttcgtgggcg actacacgct ctctttctgg  1800
cggaacggga aagtccagca ctgccgtatc cactcccggc aagatgctgg gacccccaag  1860
ttcttcttga cagacaacct cgtctttgac tccctctatg acctcatcac gcactaccag  1920
caggtgcccc tgcgctgtaa tgagtttgag atgcgacttt cagagcctgt cccacagacc  1980
aacgcccacg agagcaaaga gtggtaccac gcgagcctga ccagagcaca ggctgagcac  2040
atgctaatgc gcgtccctcg tgatggggcc ttcctggtgc ggaagcggaa tgaacccaac  2100
tcatatgcca tctctttccg ggctgagggc aagatcaagc attgccgtgt ccagcaagag  2160
ggccagacag tgatgctagg gaactcggag ttcgacagcc ttgttgacct catcagctac  2220
tatgagaaac acccgctata ccgcaagatg aagctgcgct atcccatcaa cgaggaggca  2280
ctggagaaga ttggcacagc tgagcctgac tacggggccc tgtatgaggg acgcaaccct  2340
ggcttctatg tagaggcaaa ccctatgcca actttcaagt gtgcagtcaa agccctcttt  2400
gactacaagg cccagaggga ggacgagctg accttcacca agagcgccat catccagaat  2460
gtggagaagc aagagggagg ctggtggcga ggggactacg gagggaagaa gcagctgtgg  2520
ttcccatcaa actacgtgga agagatggtc aaccccgtgg ccctggagcc ggagagggag  2580
cacttggacg agaacagccc cctaggggac ttgctgcggg gggtcttgga tgtgccggct  2640
tgtcagattg ccatccgtcc tgagggcaag aacaaccggc tcttcgtctt ctccatcagc  2700
atggcgtcgg tggcccactg gtccctggat gttgctgccg actcacagga ggagctgcag  2760
gactgggtga aaaagatccg tgaagtggcc cagacagcag acgccaggct cactgaaggg  2820
aagataatgg aacggaggaa gaagattgcc ctggagctct ctgaacttgt cgtctactgc  2880
cggcctgttc cctttgatga agagaagatt ggcacagaac gtgcttgcta ccgggacatg  2940
tcatccttcc cggaaaccaa ggctgagaaa tacgtgaaca aggccaaagg caagaagttc  3000
cttcagtaca atcgactgca gctctcccgc atctacccca agggccagcg actggattcc  3060
tccaactacg atcctttgcc catgtggatc tgtggcagtc agcttgtggc cctcaacttc  3120
cagacccctg acaagcctat gcagatgaac caggccctct tcatgacggg caggcactgt  3180
ggctacgtgc tgcagccaag caccatgcgg gatgaggcct tcgacccctt tgacaagagc  3240
agcctccgcg ggctggagcc atgtgccatc tctattgagg tgctgggggc ccgacatctg  3300
ccaaagaatg gccgaggcat tgtgtgtcct tttgtggaga ttgaggtggc tggagctgag  3360
tatgacagca ccaagcagaa gacagagttt gtggtggaca atggactcaa ccctgtatgg  3420
ccagccaagc ccttccactt ccagatcagt aaccctgaat ttgcctttct gcgcttcgtg  3480
gtgtatgagg aagacatgtt tagtgaccag aatttcctgg ctcaggctac tttcccagta  3540
aaaggcctga agacaggata cagagcagtg cctttgaaga acaactacag tgaggacctg  3600
gagttggcct ccctgctgat caagattgac attttccctg ccaagcagga gaatggtgac  3660
ctcagtccct tcagtggtac gtccctgcgg gagcggggct cagatgcctc aggccagctg  3720
tttcatggcc gagcccggga aggctccttt gaatcccgct accagcagcc gtttgaggac  3780
ttccgcatct cccaggagca tctcgcagac catttgaca gtcgagaacg aagggcccca  3840
agaaggactc gggtcaatgg agacaaccgc ctc                               3873
```

```
SEQ ID NO: 144          moltype = AA  length = 1291
FEATURE                 Location/Qualifiers
source                  1..1291
                        mol_type = protein
                        organism = Synthetic construct
SEQUENCE: 144
MAGAASPCAN GCGPGAPSDA EVLHLCRSLE VGTVMTLFYS KKSQRPEWKT FQVKLETRQI  60
TWSRGADKIE GAIDIREIKE IRPGKTSRDF DRYQEDPAFR PDQSHCFVIL YGMEFRLKTL  120
SLQATSEDEV NMWIKGLTWL MEDTLQAPTP LQIERWLRKQ FYSVDRNRED RISAKDLKNM  180
LSQVNYRVPN MRFLRERLTD LEQRSGDITY GQFAQLYRSL MYSAQKTMDL PFLEASTLRA  240
GERPELCRVS LPEFQQFLLD YQGELWAVDR LQVQEFMLSF LRDPLREIEE PYFFLDEFVT  300
FLFSKENSVW NSQLDAVCPD TMNNPLSHYW ISSSHNTYLT GDQFSSESSL EAYARCLRMG  360
CRCIELDCWD GPDGMPVIYH GHTLTTKIKF SDVLHTIKEH AFVASEYPVI LSIEDHCSIA  420
QQRNMAQYFK KVLGDTLLTK PVEISADGLP SPNQLKRKIL IKHKKLAEGS AYEEVPTSMM  480
YSENDISNSI KNGILYLEDP VNHEWYPHYF VLTSSKIYYS EETSSDQGNE DEEEPKEVSS  540
STELHSNEKW FHGKLGAGRD GRHIAERLLT EYCIETGAPD GSFLVRESET FVGDYTLSFW  600
RNGKVQHCRI HSRQDAGTPK FFLTDNLVFD SLYDLITHYQ QVPLRCNEFE MRLSEPVPQT  660
NAHESKEWYH ASLTRAQAEH MLMRVPRDGA FLVRKRNEPN SYAISFRAEG KIKHCRVQQE  720
GQTVMLGNSE FDSLVDLISY YEKHPLYRKM KLRYPINEEA LEKIGTAEPD YGALYEGRNP  780
GFYVEANPMP TFKCAVKALF DYKAQREDEL TFTKSAIIQN VEKQEGGWWR GDYGGKKQLW  840
FPSNYVEEMV NPVALEPERE HLDENSPLGD LLRGVLDVPA CQIAIRPEGK NNRLFVFSIS  900
MASVAHWSLD VAADSQEELQ DWVKKIREVA QTADARLTEG KIMERRKKIA LELSELVVYC  960
RPVPFDEEKI GTERACYRDM SSFPETKAEK YVNKAKGKKF LQYNRLQLSR IYPKGQRLDS  1020
SNYDPLPMWI CGSQLVALNF QTPDKPMQMN QALFMTGRHC GYVLQPSTMR DEAFDPFDKS  1080
SLRGLEPCAI SIEVLGARHL PKNGRGIVCP FVEIEVAGAE YDSTKQKTEF VVDNGLNPVW  1140
PAKPFHFQIS NPEFAFLRFV VYEEDMFSDQ NFLAQATFPV KGLKTGYRAV PLKNNYSEDL  1200
ELASLLIKID IFPAKQENGD LSPFSGTSLR ERGSDASGQL FHGRAREGSF ESRYQQPFED  1260
FRISQEHLAD HFDSRERRAP RRTRVNGDNR L                                 1291
```

```
SEQ ID NO: 145          moltype = DNA  length = 2019
FEATURE                 Location/Qualifiers
source                  1..2019
                        mol_type = other DNA
                        organism = Synthetic construct
SEQUENCE: 145
atggctgacc cggctgcggg gccgccgccg agcgagggcg aggagagcac cgtgcgcttc  60
gcccgcaaag gcgccctccg gcagaagaac gtgcatgagg tcaagaacca caaattcacc  120
gcccgcttct tcaagcagcc caccttctgc agccactgca ccgacttcat ctggggcttc  180
gggaagcagg gattccagtg ccaagtttgc tgctttgtgg tgcacaagcg gtgccatgaa  240
tttgtcacat tctcctgccc tggcgctgac aagggtccag cctccgatga cccccgcagc  300
```

-continued

```
aaacacaagt ttaagatcca cacgtactcc agccccacgt tttgtgacca ctgtgggtca  360
ctgctgtatg gactcatcca ccaggggatg aaatgtgaca cctgcatgat gaatgtgcac  420
aagcgctgcg tgatgaatgt tcccagcctg tgtggcacgg accacacgga gcgccgcggc  480
cgcatctaca tccaggccca catcgacagg gacgtcctca ttgtcctcgt aagagatgct  540
aaaaaccttg tacctatgga ccccaatggc ctgtcagatc cctacgtaaa actgaaactg  600
attcccgatc ccaaaagtga gagcaaacag aagaccaaaa ccatcaaatg ctccctcaac  660
cctgagtgga atgagacatt tagatttcag ctgaaagaat cggacaaaga cagaagactg  720
tcagtagaga tttgggattg ggatttgacc agcaggaatg acttcatggg atctttgtcc  780
tttgggattt ctgaacttca gaaagccagt gttgatggct ggtttaagtt actgagccag  840
gaggaaggcg agtacttcaa tgtgcctgtg ccaccagaag gaagtgaggc caatgaagaa  900
ctgcggcaga aatttgagag ggccaagatc agtcagggaa ccaaggtccc ggaagaaaag  960
acgaccaaca ctgtctccaa atttgacaac aatggcaaca gagaccggat gaaactgacc  1020
gattttaact tcctaatggt gctggggaaa ggcagctttg gcaaggtcat gctttcagaa  1080
cgaaaaggca cagatgagct ctatgctgtg aagatcctga agaaggacgt tgtgatccaa  1140
gatgatgacg tggagtgcac tatggtggag aagcgggtgt tggccctgcc tgggaagccg  1200
cccttcctga cccagctcca ctcctgcttc cagaccatgg accgcctgta ctttgtgatg  1260
gagtacgtga atgggggcga cctcatgtat cacatccagc aagtcggccg gttcaaggag  1320
ccccatgctg tattttacgc tgcagaaatt gccatcggtc tgttcttctt acagagtaag  1380
ggcatcattt accgtgacct aaaacttgac aacgtgatgc tcgattctga gggacacatc  1440
aagattgccg attttggcat gtgtaaggaa aacatctggg atggggtgac aaccaagaca  1500
ttctgtggca ctccagacta catcgccccc gagataattg cttatcagcc ctatgggaag  1560
tccgtggatt ggtgggcatt tggagtcctg ctgtatgaaa tgttggctgg gcaggcaccc  1620
tttgaagggg aggatgaaga tgaactcttc caatccatca tggaacacaa cgtagcctat  1680
cccaagtcta tgtccaagga agctgtggcc atctgcaaag ggctgatgac caaacaccca  1740
ggcaaacgtc tgggttgtgg acctgaaggc gaacgtgata tcaaagagca tgcatttttc  1800
cggtatattg attgggagaa acttgaacgc aaagagatcc agccccctta taagccaaaa  1860
gcttgtgggc gaaatgctga aaacttctac cgattttca cccgccatcc accagtccta  1920
acacctcccg accaggaagt catcaggaat attgaccaat cagaattcga aggattttcc  1980
tttgttaact ctgaattttt aaaacccgaa gtcaagagc                        2019

SEQ ID NO: 146          moltype = AA  length = 673
FEATURE                 Location/Qualifiers
source                  1..673
                        mol_type = protein
                        organism = Synthetic construct
SEQUENCE: 146
MADPAAGPPP SEGEESTVRF ARKGALRQKN VHEVKNHKFT ARFFKQPTFC SHCTDFIWGF  60
GKQGFQCQVC CFVVHKRCHE FVTFSCPGAD KGPASDDPRS KHKFKIHTYS SPTFCDHCGS  120
LLYGLIHQGM KCDTCMMNVH KRCVMNVPSL CGTDHTERRG RIYIQAHIDR DVLIVLVRDA  180
KNLVPMDPNG LSDPYVKLKL IPDPKSESKQ KTKTIKCSLN PEWNETFRFQ LKESDKDRRL  240
SVEIWDWDLT SRNDFMGSLS FGISELQKAS VDGWFKLLSQ EEGEYFNVPV PPEGSEANEE  300
LRQKFERAKI SQGTKVPEEK TTNTVSKFDN NGNRDRMKLT DFNFLMVLGK GSFGKVMLSE  360
RKGTDELYAV KILKKDVVIQ DDDVECTMVE KRVLALPGKP PFLTQLHSCF QTMDRLYFVM  420
EYVNGGDLMY HIQQVGRFKE PHAVFYAAEI AIGLFFLQSK GIIYRDLKLD NVMLDSEGHI  480
KIADFGMCKE NIWDGVTTKT FCGTPDYIAP EIIAYQPYGK SVDWWAFGVL LYEMLAGQAP  540
FEGEDEDELF QSIMEHNVAY PKSMSKEAVA ICKGLMTKHP GKRLGCGPEG ERDIKEHAFF  600
RYIDWEKLER KEIQPPYKPK ACGRNAENFY RFFTRHPPVL TPPDQEVIRN IDQSEFEGFS  660
FVNSEFLKPE VKS                                                    673

SEQ ID NO: 147          moltype = DNA  length = 2019
FEATURE                 Location/Qualifiers
source                  1..2019
                        mol_type = genomic DNA
                        organism = Homo sapiens
SEQUENCE: 147
atggctgacc cggctgcggg gccgccgccg agcgagggcg aggagagcac cgtgcgcttc  60
gcccgcaaag gcgccctccg gcagaagaac gtgcatgagg tcaagaacca caaattcacc  120
gcccgcttct tcaagcagcc caccttctgc agccactgca ccgacttcat ctggggcttc  180
gggaagcagg gattccagtg ccaagtttgc tgctttgtgg tgcacaagcg gtgccatgaa  240
tttgtcacat tctcctgccc tggcgctgac aagggtccag cctccgatga cccccgcagc  300
aaacacaagt ttaagatcca cacgtactcc agccccacgt tttgtgacca ctgtgggtca  360
ctgctgtatg gactcatcca ccaggggatg aaatgtgaca cctgcatgat gaatgtgcac  420
aagcgctgcg tgatgaatgt tcccagcctg tgtggcacgg accacacgga gcgccgcggc  480
cgcatctaca tccaggccca catcgacagg gacgtcctca ttgtcctcgt aagagatgct  540
aaaaaccttg tacctatgga ccccaatggc ctgtcagatc cctacgtaaa actgaaactg  600
attcccgatc ccaaaagtga gagcaaacag aagaccaaaa ccatcaaatg ctccctcaac  660
cctgagtgga atgagacatt tagatttcag ctgaaagaat cggacaaaga cagaagactg  720
tcagtagaga tttgggattg ggatttgacc agcaggaatg acttcatggg atctttgtcc  780
tttgggattt ctgaacttca gaaagccagt gttgatggct ggtttaagtt actgagccag  840
gaggaaggcg agtacttcaa tgtgcctgtg ccaccagaag gaagtgaggc caatgaagaa  900
ctgcggcaga aatttgagag ggccaagatc agtcagggaa ccaaggtccc ggaagaaaag  960
acgaccaaca ctgtctccaa atttgacaac aatggcaaca gagaccggat gaaactgacc  1020
gattttaact tcctaatggt gctggggaaa ggcagctttg gcaaggtcat gctttcagaa  1080
cgaaaaggca cagatgagct ctatgctgtg aagatcctga agaaggacgt tgtgatccaa  1140
gatgatgacg tggagtgcac tatggtggag aagcgggtgt tggccctgcc tgggaagccg  1200
cccttcctga cccagctcca ctcctgcttc cagaccatgg accgcctgta ctttgtgatg  1260
gagtacgtga atgggggcga cctcatgtat cacatccagc aagtcggccg gttcaaggag  1320
ccccatgctg tattttacgc tgcagaaatt gccatcggtc tgttcttctt acagagtaag  1380
ggcatcattt accgtgacct aaaacttgac aacgtgatgc tcgattctga gggacacatc  1440
```

-continued

```
aagattgccg attttggcat gtgtaaggaa aacatctggg atggggtgac aaccaagaca  1500
ttctgtggca ctccagacta catcgccccc gagataattg cttatcagcc ctatgggaag  1560
tccgtggatt ggtgggcatt tggagtcctg ctgtatgaaa tgttggctgg gcaggcaccc  1620
tttgaagggg aggatgaaga tgaactcttc caatccatca tggaacacaa cgtagcctat  1680
cccaagtcta tgtccaagga agctgtggcc atctgcaaag ggctgatgac caaacaccca  1740
ggcaaacgtc tgggttgtgg acctgaaggc gaacgtgata tcaaagagca tgcatttttc  1800
cggtatattg attgggagaa acttgaacgc aaagagatcc agcccccctta taagccaaaa  1860
gcttgtgggc gaaatgctga aaacttcgac cgatttttca cccgccatcc accagtccta  1920
acacctcccg accaggaagt catcaggaat attgaccaat cagaattcga aggattttcc  1980
tttgttaact ctgaattttt aaaacccgaa gtcaagagc                         2019

SEQ ID NO: 148          moltype = AA  length = 673
FEATURE                 Location/Qualifiers
source                  1..673
                        mol_type = protein
                        organism = Homo sapiens
SEQUENCE: 148
MADPAAGPPP SEGEESTVRF ARKGALRQKN VHEVKNHKFT ARFFKQPTFC SHCTDFIWGF  60
GKQGFQCQVC CFVVHKRCHE FVTFSCPGAD KGPASDDPRS KHKFKIHTYS SPTFCDHCGS  120
LLYGLIHQGM KCDTCMMNVH KRCVMNVPSL CGTDHTERRG RIYIQAHIDR DVLIVLVRDA  180
KNLVPMDPNG LSDPYVKLKL IPDPKSESKQ KTKTIKCSLN PEWNETFRFQ LKESDKDRRL  240
SVEIWDWDLT SRNDFMGSLS FGISELQKAS VDGWFKLLSQ EEGEYFNVPV PPEGSEANEE  300
LRQKFERAKI SQGTKVPEEK TTNTVSKFDN NGNRDRMKLT DFNFLMVLGK GSFGKVMLSE  360
RKGTDELYAV KILKKDVVIQ DDDVECTMVE KRVLALPGKP PFLTQLHSCF QTMDRLYFVM  420
EYVNGGDLMY HIQQVGRFKE PHAVFYAAEI AIGLFFLQSK GIIYRDLKLD NVMLDSEGHI  480
KIADFGMCKE NIWDGVTTKT FCGTPDYIAP EIIAYQPYGK SVDWWAFGVL LYEMLAGQAP  540
FEGEDEDELF QSIMEHNVAY PKSMSKEAVA ICKGLMTKHP GKRLGCGPEG ERDIKEHAFF  600
RYIDWEKLER KEIQPPYKPK ACGRNAENFD RFFTRHPPVL TPPDQEVIRN IDQSEFEGFS  660
FVNSEFLKPE VKS                                                     673

SEQ ID NO: 149          moltype = DNA  length = 2019
FEATURE                 Location/Qualifiers
source                  1..2019
                        mol_type = other DNA
                        organism = Synthetic construct
SEQUENCE: 149
atggctgacc cggctgcggg gccgccgccg agcgagggcg aggagagcac cgtgcgcttc  60
gcccgcaaag gcgccctccg gcagaagaac gtgcatgagg tcaagaacca caaattcacc  120
gcccgcttct tcaagcagcc caccttctgc agccactgca ccgacttcat ctggggcttc  180
gggaagcagg gattccagtg ccaagtttgc tgctttgtgg tgcacaagcg gtgccatgaa  240
tttgtcacat tctcctgccc tggcgctgac aagggtccag cctccgatga cccccgcagc  300
aaacacaagt ttaagatcca cacgtactcc agccccacgt tttgtgacca ctgtgggtca  360
ctgctgtatg gactcatcca ccaggggatg aaatgtgaca cctgcatgat gaatgtgcac  420
aagcgctgcg tgatgaatgt tcccagcctg tgtggcacgg accacacgga gcgccgcggc  480
cgcatctaca tccaggccca catcgacagg gacgtcctca ttgtcctcgt aagagatgct  540
aaaaaccttg tacctatgga ccccaatggc ctgtcagatc cctacgtaaa actgaaactg  600
attcccgatc ccaaaagtga gagcaaacag aagaccaaaa ccatcaaatg ctccctcaac  660
cctgagtgga atgagacatt tagatttcag ctgaaagaat cggacaaaga cagaagactg  720
tcagtagaga tttgggattg ggatttgacc agcaggaatg acttcatggg atctttgtcc  780
tttgggattt ctgaacttca gaaagccagt gttgatggct ggtttaagtt actgagccag  840
gaggaaggcg agtacttcaa tgtgcctgtg ccaccagaag gaagtgaggc caatgaagaa  900
ctgcggcaga aatttgagag ggccaagatc agtcagggaa ccaaggtccc ggaagaaaag  960
acgaccaaca ctgtctccaa atttgacaac aatggcaaca gagaccggat gaaactgacc  1020
gattttaact tcctaatggt gctggggaaa ggcagctttg gcaaggtcat gctttcagaa  1080
cgaaaaggca cagatgagct ctatgctgtg aagatcctga agaaggacgt tgtgatccaa  1140
gatgatgacg tggagtgcac tatggtggag aagcgggtgt tggccctgcc tgggaagccg  1200
cccttcctga cccagctcca ctcctgcttc cagaccatgg accgcctgta ctttgtgatg  1260
gagtacgtga atgggggcaa cctcatgtat cacatccagc aagtcggccg gttcaaggag  1320
ccccatgctg tattttacgc tgcagaaatt gccatcggtc tgttcttctt acagagtaag  1380
ggcatcattt accgtgacct aaaacttgac aacgtgatgc tcgattctga gggacacatc  1440
aagattgccg attttggcat gtgtaaggaa aacatctggg atggggtgac aaccaagaca  1500
ttctgtggca ctccagacta catcgccccc gagataattg cttatcagcc ctatgggaag  1560
tccgtggatt ggtgggcatt tggagtcctg ctgtatgaaa tgttggctgg gcaggcaccc  1620
tttgaagggg aggatgaaga tgaactcttc caatccatca tggaacacaa cgtagcctat  1680
cccaagtcta tgtccaagga agctgtggcc atctgcaaag ggctgatgac caaacaccca  1740
ggcaaacgtc tgggttgtgg acctgaaggc gaacgtgata tcaaagagca tgcatttttc  1800
cggtatattg attgggagaa acttgaacgc aaagagatcc agcccccctta taagccaaaa  1860
gcttgtgggc gaaatgctga aaacttcgac cgatttttca cccgccatcc accagtccta  1920
acacctcccg accaggaagt catcaggaat attgaccaat cagaattcga aggattttcc  1980
tttgttaact ctgaattttt aaaacccgaa gtcaagagc                         2019

SEQ ID NO: 150          moltype = AA  length = 673
FEATURE                 Location/Qualifiers
source                  1..673
                        mol_type = protein
                        organism = Synthetic construct
SEQUENCE: 150
MADPAAGPPP SEGEESTVRF ARKGALRQKN VHEVKNHKFT ARFFKQPTFC SHCTDFIWGF  60
GKQGFQCQVC CFVVHKRCHE FVTFSCPGAD KGPASDDPRS KHKFKIHTYS SPTFCDHCGS  120
```

-continued

```
LLYGLIHQGM KCDTCMMNVH KRCVMNVPSL CGTDHTERRG RIYIQAHIDR DVLIVLVRDA  180
KNLVPMDPNG LSDPYVKLKL IPDPKSESKQ KTKTIKCSLN PEWNETFRFQ LKESDKDRRL  240
SVEIWDWDLT SRNDFMGSLS FGISELQKAS VDGWFKLLSQ EEGEYFNVPV PPEGSEANEE  300
LRQKFERAKI SQGTKVPEEK TTNTVSKFDN NGNRDRMKLT DFNFLMVLGK GSFGKVMLSE  360
RKGTDELYAV KILKKDVVIQ DDDVECTMVE KRVLALPGKP PFLTQLHSCF QTMDRLYFVM  420
EYVNGGNLMY HIQQVGRFKE PHAVFYAAEI AIGLFFLQSK GIIYRDLKLD NVMLDSEGHI  480
KIADFGMCKE NIWDGVTTKT FCGTPDYIAP EIIAYQPYGK SVDWWAFGVL LYEMLAGQAP  540
FEGEDEDELF QSIMEHNVAY PKSMSKEAVA ICKGLMTKHP GKRLGCGPEG ERDIKEHAFF  600
RYIDWEKLER KEIQPPYKPK ACGRNAENFD RFFTRHPPVL TPPDQEVIRN IDQSEFEGFS  660
FVNSEFLKPE VKS                                                    673

SEQ ID NO: 151         moltype = DNA  length = 1386
FEATURE                Location/Qualifiers
source                 1..1386
                       mol_type = genomic DNA
                       organism = Homo sapiens
SEQUENCE: 151
atggccagca acagcagctc ctgcccgaca cctgggggcg ggcacctcaa tgggtacccg  60
gtgcctccct acgccttctt cttccccct atgctgggtg gactctcccc gccaggcgct  120
ctgaccactc tccagcacca gcttccagtt agtggatata gcacaccatc cccagccacc  180
attgagaccc agagcagcag ttctgaagag atagtgccca gccctccctc gccacccccct 240
ctaccccgca tctacaagcc ttgctttgtc tgtcaggaca agtcctcagg ctaccactat  300
ggggtcagcg cctgtgaggg ctgcaagggc ttcttccgcc gcagcatcca gaagaacatg  360
gtgtacacgt gtcaccggga caagaactgc atcatcaaca aggtgacccg gaaccgctgc  420
cagtactgcc gactgcagaa gtgctttgaa gtgggcatgt ccaaggagtc tgtgagaaac  480
gaccgaaaca agaagaagaa ggaggtgccc aagcccgagt gctctgagag ctacacgctg  540
acgccggagg tgggggagct cattgagaag gtgcgcaaag cgcaccagga aaccttccct  600
gccctctgcc agctgggcaa atacactacg aacaacagct cagaacaacg tgtctctctg  660
gacattgacc tctgggacaa gttcagtgaa ctctccacca agtgcatcat taagactgtg  720
gagttcgcca agcagctgcc cggcttcacc accctcacca tcgccgacca gatcaccctc  780
ctcaaggctg cctgcctgga catcctgatc ctgcggatct gcacgcggta cacgcccgag  840
caggacacca tgaccttctc ggacgggctg accctgaacc ggacccagat gcacaacgct  900
ggcttcggcc ccctcaccga cctggtcttt gccttcgcca accagctgct gcccctggag  960
atggatgatg cggagacggg gctgctcagc gccatctgcc tcatctgcgg agaccgccag  1020
gacctggagc agccggaccg ggtggacatg ctgcaggagc cgctgctgga ggcgctaaag  1080
gtctacgtgc ggaagcggag gcccagccgc ccccacatgt tccccaagat gctaatgaag  1140
attactgacc tgcgaagcat cagcgccaag gggctgagc gggtgatcac gctgaagatg  1200
gagatcccgg gctccatgcc gcctctcatc caggaaatgt tggagaactc agagggcctg  1260
gacactctga gcggacagcc ggggggtggg gggcgggacg gggtggcct ggcccccccg  1320
ccaggcagct gtagccccag cctcagcccc agctccaaca gaagcagccc ggccacccac  1380
tccccg                                                            1386

SEQ ID NO: 152         moltype = AA  length = 462
FEATURE                Location/Qualifiers
source                 1..462
                       mol_type = protein
                       organism = Homo sapiens
SEQUENCE: 152
MASNSSSCPT PGGGHLNGYP VPPYAFFFPP MLGGLSPPGA LTTLQHQLPV SGYSTPSPAT  60
IETQSSSSEE IVPSPPSPPP LPRIYKPCFV CQDKSSGYHY GVSACEGCKG FFRRSIQKNM  120
VYTCHRDKNC IINKVTRNRC QYCRLQKCFE VGMSKESVRN DRNKKKKEVP KPECSESYTL  180
TPEVGELIEK VRKAHQETFP ALCQLGKYTT NNSSEQRVSL DIDLWDKFSE LSTKCIIKTV  240
EFAKQLPGFT TLTIADQITL LKAACLDILI LRICTRYTPE QDTMTFSDGL TLNRTQMHNA  300
GFGPLTDLVF AFANQLLPLE MDDAETGLLS AICLICGDRQ DLEQPDRVDM LQEPLLEALK  360
VYVRKRRPSR PHMFPKMLMK ITDLRSISAK GAERVITLKM EIPGSMPPLI QEMLENSEGL  420
DTLSGQPGGG GRDGGGLAPP PGSCSPSLSP SSNRSSPATH SP                    462

SEQ ID NO: 153         moltype = DNA  length = 1386
FEATURE                Location/Qualifiers
source                 1..1386
                       mol_type = other DNA
                       organism = Synthetic construct
SEQUENCE: 153
atggccagca acagcagctc ctgcccgaca cctgggggcg ggcacctcaa tgggtacccg  60
gtgcctccct acgccttctt cttccccct atgctgggtg gactctcccc gccaggcgct  120
ctgaccactc tccagcacca gcttccagtt agtggatata gcacaccatc cccagccacc  180
attgagaccc agagcagcag ttctgaagag atagtgccca gccctccctc gccacccccct 240
ctaccccgca tctacaagcc ttgctttgtc tgtcaggaca agtcctcagg ctaccactat  300
ggggtcagcg cctgtgaggg ctgcaagggc ttcttccgcc gcagcatcca gaagaacatg  360
gtgtacacgt gtcaccggga caagaactgc atcatcaaca aggtgacccg gaaccgctgc  420
cagtactgcc gactgcagaa gtgctttgaa gtgggcatgt ccaaggagtc tgtgagaaac  480
gaccgaaaca agaagaagaa ggaggtgccc aagcccgagt gctctgagag ctacacgctg  540
acgccggagg tgggggagct cattgagaag gtgcgcaaag cgcaccagga aaccttccct  600
gccctctgcc agctgagcaa atacactacg aacaacagct cagaacaacg tgtctctctg  660
gacattgacc tctgggacaa gttcagtgaa ctctccacca agtgcatcat taagactgtg  720
gagttcgcca agcagctgcc cggcttcacc accctcacca tcgccgacca gatcaccctc  780
ctcaaggctg cctgcctgga catcctgatc ctgcggatct gcacgcggta cacgcccgag  840
caggacacca tgaccttctc ggacgggctg accctgaacc ggacccagat gcacaacgct  900
ggcttcggcc ccctcaccga cctggtcttt gccttcgcca accagctgct gcccctggag  960
```

```
atggatgatg cggagacggg gctgctcagc gccatctgcc tcatctgcgg agaccgccag  1020
gacctggagc agccggaccg ggtggacatg ctgcaggagc cgctgctgga ggcgctaaag  1080
gtctacgtgc ggaagcggag gcccagccgc ccccacatgt tccccaagat gctaatgaag  1140
attactgacc tgcgaagcat cagcgccaag ggggctgagc gggtgatcac gctgaagatg  1200
gagatcccgg gctccatgcc gcctctcatc caggaaatgt tggagaactc agagggcctg  1260
gacactctga gcggacagcc ggggggtggg gggcgggacg ggggtggcct ggcccccccg  1320
ccaggcagct gtagccccag cctcagcccc agctccaaca gaagcagccc ggccacccac  1380
tccccg                                                              1386

SEQ ID NO: 154         moltype = AA  length = 462
FEATURE                Location/Qualifiers
source                 1..462
                       mol_type = protein
                       organism = Synthetic construct
SEQUENCE: 154
MASNSSSCPT PGGGHLNGYP VPPYAFFFPP MLGGLSPPGA LTTLQHQLPV SGYSTPSPAT  60
IETQSSSSEE IVPSPPSPPP LPRIYKPCFV CQDKSSGYHY GVSACEGCKG FFRRSIQKNM  120
VYTCHRDKNC IINKVTRNRC QYCRLQKCFE VGMSKESVRN DRNKKKKEVP KPECSESYTL  180
TPEVGELIEK VRKAHQETFP ALCQLSKYTT NNSSEQRVSL DIDLWDKFSE LSTKCIIKTV  240
EFAKQLPGFT TLTIADQITL LKAACLDILI LRICTRYTPE QDTMTFSDGL TLNRTQMHNA  300
GFGPLTDLVF AFANQLLPLE MDDAETGLLS AICLICGDRQ DLEQPDRVDM LQEPLLEALK  360
VYVRKRRPSR PHMFPKMLMK ITDLRSISAK GAERVITLKM EIPGSMPPLI QEMLENSEGL  420
DTLSGQPGGG GRDGGGLAPP PGSCSPSLSP SSNRSSPATH SP                      462

SEQ ID NO: 155         moltype = DNA  length = 2391
FEATURE                Location/Qualifiers
source                 1..2391
                       mol_type = other DNA
                       organism = Synthetic construct
SEQUENCE: 155
atgggcaccc tgggcaaggc gagagaggct ccgcggaaac cttcccatgg ctgcagagct  60
gcctctaaag caagactaga ggcaaagcca gccaacagcc ccttcccctc ccatcccagc  120
ttggcccaca tcacccagtt ccgaatgatg gtgtctctgg gacatttagc caaaggagcc  180
agcctggacg atctcattga cagctgcatt caatcttttg atgcagatgg aaacctgtgt  240
cgaagtaacc aactgttgca agtcatgctg accatgcacc gaattgtcat ctcctctgca  300
gaactgctcc aaaaagttat caccctctat aaggatgctt tggcaaagaa ttcaccagga  360
ctttgcctga agatctgtta ttttgtaagg tattggataa cagaattctg ggtcatgttt  420
aaaatggacg ccagcttgac agacactatg gaggagtttc aggaactggt gaaagctaag  480
ggtgaggagt tacattgccg cctgattgac acaactcaaa tcaatgcccg tgactggtcc  540
aggaaactta ctcaaaggat aaaatcaaat accagcaaga aacggaaagt ctccctgctc  600
tttgaccatc tggaaccaga agagctatcc gagcacctca cctaccttga gttcaagtct  660
ttccggagga tatcgttctc tgattatcag aattaccttg taaatagctg tgtgaaggaa  720
aaccccacca tggagcgatc tattgctctg tgcaacggca tctcccagtg ggtacaactg  780
atcgttctca gccgccccac gccgcagctc cgagcagaag tcttcatcaa gttcatccag  840
gtggctcaga agctccacca actacagaac ttcaatacac tgatggctgt gataggtggg  900
ctgtgtcaca gctcaatctc gaggctcaag gagacaagtt cgcatgtccc acatgaaatc  960
aataaggttc tcggtgagat gactgagctg ctgtcctcct ccagaaacta cgacaattac  1020
cggcgagcct atggagagtg caccgacttc aagatcccca ttctgggtgt gcatctcaag  1080
gacctcatct ccctgtatga agccatgcct gactatctgg aggacgggaa agtgaacgtc  1140
cataagctac tggccctata caatcatatc agtgaattgg tccagctgca agaggtggcc  1200
ccacccttgg aggctaacaa ggacttggta cacttgctga cgttatccct ggatctttac  1260
tacactgagg atgaaatcta tgagctttcc tatgcccggg aaccaaggaa ccacagagct  1320
ccaccactaa caccttcaaa gccaccagta gtagtggact gggcttctgg agtgtctccc  1380
aaacctgatc caaaaaccat tagcaaacac gtccagagga tggtggattc tgtcttcaag  1440
aactatgatc acgaccagga tggatacatt tctcaggaag aatttgaaaa gattgctgcg  1500
agttttccat ttccttctg tgtgatggac aaagacaggg aaggcctcat cagcagggat  1560
gagatcacag cctacttcat gagagccagc tcaatctatt ccaagctggg cctgggcttt  1620
cctcacaact tccaagagac cacctacctg aagcccactt tttgtgacaa ctgtgctgga  1680
tttctctggg gagtgatcaa acaaggatat cgatgtaaag actgcgggat gaactgtcac  1740
aaacaatgca aagatctggt tgtgtttgag tgtaagaagc gagccaagaa cccagtagct  1800
cccacagaga acaacacttc tgtggggcca gtgtccaacc tttgctcatt gggagccaaa  1860
gatctgctcc atgcacctga ggaaggacct tttacattcc ctaatgggga ggctgtggaa  1920
catggtgagg agagtaagga tcggaccatc atgctgatgg gagtgtcctc acagaagatt  1980
tctcttcggc tgaagagggc tgttgcccac aaggccaccc agactgaatc acagccttgg  2040
attggcagtg agggcccttc aggtcccttt gtgctgtctt ccccaaggaa gacagcccag  2100
gatactctat atgtgcttcc cagtcccacc tctccatgtc ctagcccagt cttggtcaga  2160
aagcgggctt ttgtcaagtg ggagaataaa gactccctca taaaatcaaa ggaggagctc  2220
cgtcacctca gactgcctac ctaccaagaa ctggaacagg aaataaatac tctgaaagca  2280
gataatgatg ccctaaagat ccaactgaaa tatgcacaga agaaaataga atccctccag  2340
cttgaaaaaa gcaatcatgt cttagctcaa atggagcagg gtgactgttc t            2391

SEQ ID NO: 156         moltype = AA  length = 797
FEATURE                Location/Qualifiers
source                 1..797
                       mol_type = protein
                       organism = Synthetic construct
SEQUENCE: 156
MGTLGKAREA PRKPSHGCRA ASKARLEAKP ANSPFPSHPS LAHITQFRMM VSLGHLAKGA  60
SLDDLIDSCI QSFDADGNLC RSNQLLQVML TMHRIVISSA ELLQKVITLY KDALAKNSPG  120
```

-continued

```
LCLKICYFVR YWITEFWVMF KMDASLTDTM EEFQELVKAK GEELHCRLID TTQINARDWS  180
RKLTQRIKSN TSKKRKVSLL FDHLEPEELS EHLTYLEFKS FRRISFSDYQ NYLVNSCVKE  240
NPTMERSIAL CNGISQWVQL IVLSRPTPQL RAEVFIKFIQ VAQKLHQLQN FNTLMAVIGG  300
LCHSSISRLK ETSSHVPHEI NKVLGEMTEL LSSSRNYDNY RRAYGECTDF KIPILGVHLK  360
DLISLYEAMP DYLEDGKVNV HKLLALYNHI SELVQLQEVA PPLEANKDLV HLLTLSLDLY  420
YTEDEIYELS YAREPRNHRA PPLTPSKPPV VVDWASGVSP KPDPKTISKH VQRMVDSVFK  480
NYDHDQDGYI SQEEFEKIAA SFPFSFCVMD KDREGLISRD EITAYFMRAS SIYSKLGLGF  540
PHNFQETTYL KPTFCDNCAG FLWGVIKQGY RCKDCGMNCH KQCKDLVVFE CKKRAKNPVA  600
PTENNTSVGP VSNLCSLGAK DLLHAPEEGP FTFPNGEAVE HGEESKDRTI MLMGVSSQKI  660
SLRLKRAVAH KATQTESQPW IGSEGPSGPF VLSSPRKTAQ DTLYVLPSPT SPCPSPVLVR  720
KRAFVKWENK DSLIKSKEEL RHLRLPTYQE LEQEINTLKA DNDALKIQLK YAQKKIESLQ  780
LEKSNHVLAQ MEQGDCS                                                 797

SEQ ID NO: 157          moltype = DNA  length = 2391
FEATURE                 Location/Qualifiers
source                  1..2391
                        mol_type = genomic DNA
                        organism = Homo sapiens
SEQUENCE: 157
atgggcaccc tgggcaaggc gagagaggct ccgcggaaac cttcccatgg ctgcagagct  60
gcctctaaag caagactaga ggcaaagcca gccaacagcc ccttcccctc ccatcccagc  120
ttggcccaca tcacccagtt ccgaatgatg gtgtctctgg gacatttagc caaaggagcc  180
agcctggacg atctcattga cagctgcatt caatcttttg atgcagatgg aaacctgtgt  240
cgaagtaacc aactgttgca agtcatgctg accatgcacc gaattgtcat ctcctctgca  300
gaactgctcc aaaaagttat caccctctat aaggatgctt tggcaaagaa ttcaccagga  360
ctttgcctga agatctgtta ttttgtaagg tattggataa cagaattctg ggtcatgttt  420
aaaatggacg ccagcttgac agacactatg gaggagtttc aggaactggt gaaagctaag  480
ggtgaggagt tacattgccg cctgattgac acaactcaaa tcaatgcccg tgactggtcc  540
aggaaactta ctcaaaggat aaaatcaaat accagcaaga aacggaaagt ctccctgctc  600
tttgaccatc tggaaccaga agagctatcc gagcacctca cctaccttga gttcaagtct  660
ttccggagga tatcgttctc tgattatcag aattaccttg taaatagctg tgtgaaggaa  720
aaccccacca tggagcgatc tattgctctg tgcaacggca tctcccagtg ggtacaactg  780
atggttctca gccgccccac gccgcagctc cgagcagaag tcttcatcaa gttcatccag  840
gtggctcaga agctccacca actacagaac ttcaatacac tgatggctgt gataggtggg  900
ctgtgtcaca gctcaatctc gaggctcaag gagacaagtt cgcatgtccc acatgaaatc  960
aataaggttc tcggtgagat gactgagctg ctgtcctcct ccagaaacta cgacaattac  1020
cggcgagcct atggagagtg caccgacttc aagatcccca ttctgggtgt gcatctcaag  1080
gacctcatct ccctgtatga agccatgcct gactatctgg aggacgggaa agtgaacgtc  1140
cataagctac tggccctata caatcatatc agtgaattgg tccagctgca agaggtggcc  1200
ccaccccttgg aggctaacaa ggacttggta cacttgctga cgttatccct ggatctttac  1260
tacactgagg atgaaatcta tgagctttcc tatgcccggg aaccaaggaa ccacagagct  1320
ccaccactaa caccttcaaa gccaccagta gtagtggact gggcttctgg agtgtctccc  1380
aaacctgatc caaaaaccat tagcaaacac gtccagagga tggtggattc tgtcttcaag  1440
aactatgatc acgaccagga tggatacatt tctcaggaag aatttgaaaa gattgctgcg  1500
agttttccat ttccttctg tgtgatggac aaagacaggg aaggcctcat cagcagggat  1560
gagatcacag cctacttcat gagagccagc tcaatctatt ccaagctggg cctgggcttt  1620
cctcacaact tccaagagac cacctacctg aagcccactt tttgtgacaa ctgtgctgga  1680
tttctctggg gagtgatcaa acaaggatat cgatgtaaag actgcgggat gaactgtcac  1740
aaacaatgca aagatctggt tgtgtttgag tgtaagaagc gagccaagaa cccagtagct  1800
cccacagaga acaacacttc tgtggggcca gtgtccaacc tttgctcatt gggagccaaa  1860
gatctgctcc atgcacctga ggaaggacct tttacattcc ctaatgggga ggctgtggaa  1920
catggtgagg agagtaagga tcggaccatc atgctgatgg gagtgtcctc acagaagatt  1980
tctcttcggc tgaagagggc tgttgcccac aaggccaccc agactgaatc acagccttgg  2040
attggcagtg agggccttc aggtcccttt gtgctgtctt ccccaaggaa gacagcccag  2100
gatactctat atgtgcttcc cagtcccacc tctccatgtc ctagcccagt cttggtcaga  2160
aagcgggctt ttgtcaagtg ggagaataaa gactccctca taaaatcaaa ggaggagctc  2220
cgtcacctca gactgcctac ctaccaagaa ctggaacagg aaataaatac tctgaaagca  2280
gataatgatg ccctaaagat ccaactgaaa tatgcacaga agaaaataga atccctccag  2340
cttgaaaaaa gcaatcatgt cttagctcaa atggagcagg gtgactgttc t           2391

SEQ ID NO: 158          moltype = AA  length = 797
FEATURE                 Location/Qualifiers
source                  1..797
                        mol_type = protein
                        organism = Homo sapiens
SEQUENCE: 158
MGTLGKAREA PRKPSHGCRA ASKARLEAKP ANSPFPSHPS LAHITQFRMM VSLGHLAKGA  60
SLDDLIDSCI QSFDADGNLC RSNQLLQVML TMHRIVISSA ELLQKVITLY KDALAKNSPG  120
LCLKICYFVR YWITEFWVMF KMDASLTDTM EEFQELVKAK GEELHCRLID TTQINARDWS  180
RKLTQRIKSN TSKKRKVSLL FDHLEPEELS EHLTYLEFKS FRRISFSDYQ NYLVNSCVKE  240
NPTMERSIAL CNGISQWVQL MVLSRPTPQL RAEVFIKFIQ VAQKLHQLQN FNTLMAVIGG  300
LCHSSISRLK ETSSHVPHEI NKVLGEMTEL LSSSRNYDNY RRAYGECTDF KIPILGVHLK  360
DLISLYEAMP DYLEDGKVNV HKLLALYNHI SELVQLQEVA PPLEANKDLV HLLTLSLDLY  420
YTEDEIYELS YAREPRNHRA PPLTPSKPPV VVDWASGVSP KPDPKTISKH VQRMVDSVFK  480
NYDHDQDGYI SQEEFEKIAA SFPFSFCVMD KDREGLISRD EITAYFMRAS SIYSKLGLGF  540
PHNFQETTYL KPTFCDNCAG FLWGVIKQGY RCKDCGMNCH KQCKDLVVFE CKKRAKNPVA  600
PTENNTSVGP VSNLCSLGAK DLLHAPEEGP FTFPNGEAVE HGEESKDRTI MLMGVSSQKI  660
SLRLKRAVAH KATQTESQPW IGSEGPSGPF VLSSPRKTAQ DTLYVLPSPT SPCPSPVLVR  720
KRAFVKWENK DSLIKSKEEL RHLRLPTYQE LEQEINTLKA DNDALKIQLK YAQKKIESLQ  780
```

-continued

```
LEKSNHVLAQ MEQGDCS                                              797

SEQ ID NO: 159          moltype = DNA  length = 579
FEATURE                 Location/Qualifiers
source                  1..579
                        mol_type = other DNA
                        organism = Synthetic construct
SEQUENCE: 159
atggctgcga taagaaagaa actcgtcatt gttggcgatg gggcttgtgt taaaacttgt  60
cttctcatag ttttcagtaa agatcagttt ccggaagttt atgtgcctac agtcttcgag  120
aattatgttg ccgacatcga agtggatggc aaacaggtgg aacttgcttt gtgggatacc  180
gcaggacaag aagattacga ccgcctccga cctctctctt accccgatac ggatgtcata  240
cttatgtgct tctccataga cagcccggat tcactggaaa atatacccga aaagtggacc  300
ccagaggtta aacatttctg tccgaacgtg ccaatcatcc ttgtcggtaa caaaaaggat  360
cttaggaatg atgagcacac tcgccgcgaa cttgcgaaga tgaagcaaga gcctgtcaaa  420
cctgaggaag gtagagatat ggcaaatcga ataggcgcgt ttggctacat ggaatgttct  480
gcaaaaaacaa aggacggtgt acgagaagtt tttgagatgg ctactcgggc agcgttgcag  540
gctagaagag gtaagaaaaa atcaggctgt ttggtgttg                      579

SEQ ID NO: 160          moltype = AA  length = 193
FEATURE                 Location/Qualifiers
source                  1..193
                        mol_type = protein
                        organism = Synthetic construct
SEQUENCE: 160
MAAIRKKLVI VGDGACVKTC LLIVFSKDQF PEVYVPTVFE NYVADIEVDG KQVELALWDT  60
AGQEDYDRLR PLSYPDTDVI LMCFSIDSPD SLENIPEKWT PEVKHFCPNV PIILVGNKKD  120
LRNDEHTRRE LAKMKQEPVK PEEGRDMANR IGAFGYMECS AKTKDGVREV FEMATRAALQ  180
ARRGKKKSGC LVL                                                  193

SEQ ID NO: 161          moltype = DNA  length = 579
FEATURE                 Location/Qualifiers
source                  1..579
                        mol_type = other DNA
                        organism = Synthetic construct
SEQUENCE: 161
atggctgcga taagaaagaa actcgtcatt gttggcgatg gggctcgtgg gaaaacttgt  60
cttctcatag ttttcagtaa agatcagttt ccggaagttt atgtgcctac agtcttcgag  120
aattatgttg ccgacatcga agtggatggc aaacaggtgg aacttgcttt gtgggatacc  180
gcaggacaag aagattacga ccgcctccga cctctctctt accccgatac ggatgtcata  240
cttatgtgct tctccataga cagcccggat tcactggaaa atatacccga aaagtggacc  300
ccagaggtta aacatttctg tccgaacgtg ccaatcatcc ttgtcggtaa caaaaaggat  360
cttaggaatg atgagcacac tcgccgcgaa cttgcgaaga tgaagcaaga gcctgtcaaa  420
cctgaggaag gtagagatat ggcaaatcga ataggcgcgt ttggctacat ggaatgttct  480
gcaaaaaacaa aggacggtgt acgagaagtt tttgagatgg ctactcgggc agcgttgcag  540
gctagaagag gtaagaaaaa atcaggctgt ttggtgttg                      579

SEQ ID NO: 162          moltype = AA  length = 193
FEATURE                 Location/Qualifiers
source                  1..193
                        mol_type = protein
                        organism = Synthetic construct
SEQUENCE: 162
MAAIRKKLVI VGDGARGKTC LLIVFSKDQF PEVYVPTVFE NYVADIEVDG KQVELALWDT  60
AGQEDYDRLR PLSYPDTDVI LMCFSIDSPD SLENIPEKWT PEVKHFCPNV PIILVGNKKD  120
LRNDEHTRRE LAKMKQEPVK PEEGRDMANR IGAFGYMECS AKTKDGVREV FEMATRAALQ  180
ARRGKKKSGC LVL                                                  193

SEQ ID NO: 163          moltype = DNA  length = 579
FEATURE                 Location/Qualifiers
source                  1..579
                        mol_type = genomic DNA
                        organism = Homo sapiens
SEQUENCE: 163
atggctgcga taagaaagaa actcgtcatt gttggcgatg gggcttgtgg gaaaacttgt  60
cttctcatag ttttcagtaa agatcagttt ccggaagttt atgtgcctac agtcttcgag  120
aattatgttg ccgacatcga agtggatggc aaacaggtgg aacttgcttt gtgggatacc  180
gcaggacaag aagattacga ccgcctccga cctctctctt accccgatac ggatgtcata  240
cttatgtgct tctccataga cagcccggat tcactggaaa atatacccga aaagtggacc  300
ccagaggtta aacatttctg tccgaacgtg ccaatcatcc ttgtcggtaa caaaaaggat  360
cttaggaatg atgagcacac tcgccgcgaa cttgcgaaga tgaagcaaga gcctgtcaaa  420
cctgaggaag gtagagatat ggcaaatcga ataggcgcgt ttggctacat ggaatgttct  480
gcaaaaaacaa aggacggtgt acgagaagtt tttgagatgg ctactcgggc agcgttgcag  540
gctagaagag gtaagaaaaa atcaggctgt ttggtgttg                      579

SEQ ID NO: 164          moltype = AA  length = 193
FEATURE                 Location/Qualifiers
source                  1..193
                        mol_type = protein
```

```
                          organism = Homo sapiens
SEQUENCE: 164
MAAIRKKLVI VGDGACGKTC LLIVFSKDQF PEVYVPTVFE NYVADIEVDG KQVELALWDT  60
AGQEDYDRLR PLSYPDTDVI LMCFSIDSPD SLENIPEKWT PEVKHFCPNV PIILVGNKKD  120
LRNDEHTRRE LAKMKQEPVK PEEGRDMANR IGAFGYMECS AKTKDGVREV FEMATRAALQ  180
ARRGKKKSGC LVL                                                    193

SEQ ID NO: 165            moltype = DNA  length = 1101
FEATURE                   Location/Qualifiers
source                    1..1101
                          mol_type = other DNA
                          organism = Synthetic construct
SEQUENCE: 165
atgatgatga tggcgctgag caagaccttc gggcagaagc ccgtgaagtt ccagctggag  60
gacgacggcg agttctacat gatcggctcc gaggtgggaa actacctccg tatgttccga  120
ggttctctgt acaagagata cccctcactc tggaggcgac tagccactgt ggaagagagg  180
aagaaaatag ttgcatcgtc acatggtaaa aaaacaaaac ctaacactaa ggatcacgga  240
tacacgactc tagccaccag tgtgaccctg ttaaaagcct cggaagtgga agagattctg  300
gatggcaacg atgagaagta caaggctgtg tccatcagca cagagccccc cacctacctc  360
agggaacaga aggccaagag gaacagccag tgggtaccca ccctgcccaa cagctcccac  420
cacttagatg ccgtgccatg ctccacaacc atcaacagga accgcatggg ccgagacaag  480
aagagaacct tccccctttg ctttgatgac catgacccag ctgtgatcca tgagaacgca  540
tctcagcccg aggtgctggt ccccatccgg ctggacatgg agatcgatgg gcagaagctg  600
cgagacgcct tcacctggaa catgaatgag aagttgatga cgcctgagat gttttcagaa  660
atcctctgtg acgatctgga tttgaacccg ctgacgtttg tgccagccat cgcctctgcc  720
atcagacagc agatcgagtc ctaccccacg gacagcatcc tggaggacca gtcagaccag  780
cgcgtcatca tcaagctgaa catccatgtg ggaaacattt ccctggtgga ccagtttgag  840
tgggacatgt cagagaagga gaactcacca gagaagtttg ccctgaagct gtgctcggag  900
ctggggttgg gcggggagtt tgtcaccacc atcgcataca gcatccgggg acagctgagc  960
tggcatcaga agacctacgc cttcagcgag aaccctctgc ccacagtgga gattgccatc  1020
cggaacacgg gcgatgcgga ccagtggtgc ccactgctgg agactctgac agacgctgag  1080
atggagaaga agatccgcga c                                           1101

SEQ ID NO: 166            moltype = AA  length = 367
FEATURE                   Location/Qualifiers
source                    1..367
                          mol_type = protein
                          organism = Synthetic construct
SEQUENCE: 166
MMMMALSKTF GQKPVKFQLE DDGEFYMIGS EVGNYLRMFR GSLYKRYPSL WRRLATVEER  60
KKIVASSHGK KTKPNTKDHG YTTLATSVTL LKASEVEEIL DGNDEKYKAV SISTEPPTYL  120
REQKAKRNSQ WVPTLPNSSH HLDAVPCSTT INRNRMGRDK KRTFPLCFDD HDPAVIHENA  180
SQPEVLVPIR LDMEIDGQKL RDAFTWNMNE KLMTPEMFSE ILCDDLDLNP LTFVPAIASA  240
IRQQIESYPT DSILEDQSDQ RVIIKLNIHV GNISLVDQFE WDMSEKENSP EKFALKLCSE  300
LGLGGEFVTT IAYSIRGQLS WHQKTYAFSE NPLPTVEIAI RNTGDADQWC PLLETLTDAE  360
MEKKIRD                                                           367

SEQ ID NO: 167            moltype = DNA  length = 1155
FEATURE                   Location/Qualifiers
source                    1..1155
                          mol_type = genomic DNA
                          organism = Homo sapiens
SEQUENCE: 167
atgatgatga tggcgctgag caagaccttc gggcagaagc ccgtgaagtt ccagctggag  60
gacgacggcg agttctacat gatcggctcc gaggtgggaa actacctccg tatgttccga  120
ggttctctgt acaagagata cccctcactc tggaggcgac tagccactgt ggaagagagg  180
aagaaaatag ttgcatcgtc acatggtaaa aaaacaaaac ctaacactaa ggatcacgga  240
tacacgactc tagccaccag tgtgaccctg ttaaaagcct cggaagtgga agagattctg  300
gatggcaacg atgagaagta caaggctgtg tccatcagca cagagccccc cacctacctc  360
agggaacaga aggccaagag gaacagccag tgggtaccca ccctgcccaa cagctcccac  420
cacttagatg ccgtgccatg ctccacaacc atcaacagga accgcatggg ccgagacaag  480
aagagaacct tccccctttg ctttgatgac catgacccag ctgtgatcca tgagaacgca  540
tctcagcccg aggtgctggt ccccatccgg ctggacatgg agatcgatgg gcagaagctg  600
cgagacgcct tcacctggaa catgaatgag aagttgatga cgcctgagat gttttcagaa  660
atcctctgtg acgatctgga tttgaacccg ctgacgtttg tgccagccat cgcctctgcc  720
atcagacagc agatcgagtc ctaccccacg gacagcatcc tggaggacca gtcagaccag  780
cgcgtcatca tcaagctgaa catccatgtg ggaaacattt ccctggtgga ccagtttgag  840
tgggacatgt cagagaagga gaactcacca gagaagtttg ccctgaagct gtgctcggag  900
ctggggttgg gcggggagtt tgtcaccacc atcgcataca gcatccgggg acagctgagc  960
tggcatcaga agacctacgc cttcagcgag aaccctctgc ccacagtgga gattgccatc  1020
cggaacacgg gcgatgcgga ccagtggtgc ccactgctgg agactctgac agacgctgag  1080
atggagaaga agatccgcga ccaggacagg aacacgaggc ggatgaggcg tcttgccaac  1140
acggccccgg cctgg                                                  1155

SEQ ID NO: 168            moltype = AA  length = 385
FEATURE                   Location/Qualifiers
source                    1..385
                          mol_type = protein
                          organism = Homo sapiens
```

SEQUENCE: 168
MMMMALSKTF GQKPVKFQLE DDGEFYMIGS EVGNYLRMFR GSLYKRYPSL WRRLATVEER 60
KKIVASSHGK KTKPNTKDHG YTTLATSVTL LKASEVEEIL DGNDEKYKAV SISTEPPTYL 120
REQKAKRNSQ WVPTLPNSSH HLDAVPCSTT INRNRMGRDK KRTFPLCFDD HDPAVIHENA 180
SQPEVLVPIR LDMEIDGQKL RDAFTWNMNE KLMTPEMFSE ILCDDLDLNP LTFVPAIASA 240
IRQQIESYPT DSILEDQSDQ RVIIKLNIHV GNISLVDQFE WDMSEKENSP EKFALKLCSE 300
LGLGGEFVTT IAYSIRGQLS WHQKTYAFSE NPLPTVEIAI RNTGDADQWC PLLETLTDAE 360
MEKKIRDQDR NTRRMRRLAN TAPAW 385

SEQ ID NO: 169 moltype = DNA length = 2310
FEATURE Location/Qualifiers
source 1..2310
mol_type = other DNA
organism = Synthetic construct
SEQUENCE: 169
atggcccaat ggaatcagct acagcagctt gacacacggt acctggagca gctccatcag 60
ctctacagtg acagcttccc aatggagctg cggcagtttc tggccccttg gattgagagt 120
caagattggg catatgcggc cagcaaagaa tcacatgcca ctttggtgtt tcataatctc 180
ctgggagaga ttgaccagca gtatagccgc ttcctgcaag agtcgaatgt tctctatcag 240
cacaatctac gaagaatcaa gcagtttctt cagagcaggt atcttgagaa gccaatggag 300
attgcccgga ttgtggcccg gtgcctgtgg gaagaatcac gccttctaca gactgcagcc 360
actgcggccc agcaaggggg ccaggccaac caccccacag cagccgtggt gacggagaag 420
cagcagatgc tggagcagca ccttcaggat gtccggaaga gagtgcagga tctagaacag 480
aaaatgaaag tggtagagaa tctccaggat gactttgatt tcaactataa aaccctcaag 540
agtcaaggag acatgcaaga tctgaatgga aacaaccagt cagtgaccag gcagaagatg 600
cagcagctgg aacagatgct cactgcgctg gaccagatgc ggagaagcat cgtgagtgag 660
ctggcggggc ttttgtcagc gatggagtac gtgcagaaaa ctctcacgga cgaggagctg 720
gctgactgga agaggcggca acagattgcc tgcattggag gcccgcccaa catctgccta 780
gatcggctag aaaactggat aacgtcatta gcagaatctc aacttcagac ccgtcaacaa 840
attaagaaac tggaggagtt gcagcaaaaa gtttcctaca aaggggaccc cattgtacag 900
caccggccga tgctggagga gagaatcgtg gagctgttta gaaacttaat gaaaagtgcc 960
tttgtggtgg agcggcagcc ctgcatgccc atgcatcctg accggcccct cgtcatcaag 1020
accggcgtcc agttcactac taaagtcagg ttgctggtca aattccctga gttgaattat 1080
cagcttaaaa ttaaagtgtg cattgacaaa gactctgggg acgttgcagc tctcagagga 1140
tcccggaaat ttaacattct gggcacaaac acaaaagtga tgaacatgga agaatccaac 1200
aacggcagcc tctctgcaga attcaaacac ttgaccctga gggagcagag atgtgggaat 1260
gggggccgag ccaattgtga tgcttccctg attgtgactg aggagctgca cctgatcacc 1320
tttgagaccg aggtgtatca ccaaggcctc aagattgacc tagagaccca ctccttgcca 1380
gttgtggtga tctccaacat ctgtcagatg ccaaatgcct gggcgtccat cctgtggtac 1440
aacatgctga ccaacaatcc caagaatgta aactttttta ccaagccccc aattggaacc 1500
tgggatcaag tggccgaggt cctgagctgg cagttctcct ccaccaccaa gcgaggactg 1560
agcatcgagc agctgactac actggcagag aaactcttgg gacctggtgt gaattattca 1620
gggtgtcaga tcacatgggc taaattttgc aaagaaaaca tggctggcaa gggcttctcc 1680
ttctgggtct ggctggacaa tatcattgac cttgtgaaaa agtacatcct ggccctttgg 1740
aacgaagggt acatcatggg ctttatcagt aaggagcggg agcgggccat cttgagcact 1800
aagcctccag gcaccttcct gctaagattc agtgaaagca gcaaagaagg aggcgtcact 1860
ttcacttggg tggagaagga catcagcggt aagacccaga tccagtccgt ggaaccatac 1920
acaaagcagc agctgaacat catgtcattt gctgaaatca tcatgggcta taagatcatg 1980
gatgctacca atatcctggt gtctccactg gtctatctct atcctgacat tcccaaggag 2040
gaggcattcg gaaagtattg tcggccagag agccaggagc atcctgaagc tgacccaggt 2100
agcgctgccc catacctgaa gaccaagttt atctgtgtga caccaacgac ctgcagcaat 2160
accattgacc tgccgatgtc cccccgcact ttagattcat tgatgcagtt tggaaataat 2220
ggtgaaggtg ctgaaccctc agcaggaggg cagtttgagt ccctcacctt tgacatggag 2280
ttgacctcgg agtgcgctac ctcccccatg 2310

SEQ ID NO: 170 moltype = AA length = 770
FEATURE Location/Qualifiers
source 1..770
mol_type = protein
organism = Synthetic construct
SEQUENCE: 170
MAQWNQLQQL DTRYLEQLHQ LYSDSFPMEL RQFLAPWIES QDWAYAASKE SHATLVFHNL 60
LGEIDQQYSR FLQESNVLYQ HNLRRIKQFL QSRYLEKPME IARIVARCLW EESRLLQTAA 120
TAAQQGGQAN HPTAAVVTEK QQMLEQHLQD VRKRVQDLEQ KMKVVENLQD DFDFNYKTLK 180
SQGDMQDLNG NNQSVTRQKM QQLEQMLTAL DQMRRSIVSE LAGLLSAMEY VQKTLTDEEL 240
ADWKRRQQIA CIGGPPNICL DRLENWITSL AESQLQTRQQ IKKLEELQQK VSYKGDPIVQ 300
HRPMLEERIV ELFRNLMKSA FVVERQPCMP MHPDRPLVIK TGVQFTTKVR LLVKFPELNY 360
QLKIKVCIDK DSGDVAALRG SRKFNILGTN TKVMNMEESN NGSLSAEFKH LTLREQRCGN 420
GGRANCDASL IVTEELHLIT FETEVYHQGL KIDLETHSLP VVVISNICQM PNAWASILWY 480
NMLTNNPKNV NFFTKPPIGT WDQVAEVLSW QFSSTTKRGL SIEQLTTLAE KLLGPGVNYS 540
GCQITWAKFC KENMAGKGFS FWVWLDNIID LVKKYILALW NEGYIMGFIS KERERAILST 600
KPPGTFLLRF SESSKEGGVT FTWVEKDISG KTQIQSVEPY TKQQLNIMSF AEIIMGYKIM 660
DATNILVSPL VYLYPDIPKE EAFGKYCRPE SQEHPEADPG SAAPYLKTKF ICVTPTTCSN 720
TIDLPMSPRT LDSLMQFGNN GEGAEPSAGG QFESLTFDME LTSECATSPM 770

SEQ ID NO: 171 moltype = DNA length = 2310
FEATURE Location/Qualifiers
source 1..2310
mol_type = other DNA

```
                         organism = Synthetic construct
SEQUENCE: 171
atggcccaat ggaatcagct acagcagctt gacacacggt acctggagca gctccatcag  60
ctctacagtg acagcttccc aatggagctg cggcagtttc tggccccttg gattgagagt  120
caagattggg catatgcggc cagcaaagaa tcacatgcca ctttggtgtt tcataatctc  180
ctgggagaga ttgaccagca gtatagccgc ttcctgcaag agtcgaatgt tctctatcag  240
cacaatctac gaagaatcaa gcagtttctt cagagcaggt atcttgagaa gccaatggag  300
attgcccgga ttgtggcccg gtgcctgtgg gaagaatcac gccttctaca gactgcagcc  360
actgcggccc agcaaggggg ccaggccaac caccccacag cagccgtggt gacggagaag  420
cagcagatgc tggagcagca ccttcaggat gtccggaaga gagtgcagga tctagaacag  480
aaaatgaaag tggtagagaa tctccaggat gactttgatt tcaactataa aaccctcaag  540
agtcaaggag acatgcaaga tctgaatgga aacaaccagt cagtgaccag gcagaagatg  600
cagcagctgg aacagatgct cactgcgctg gaccagatgc ggagaagcat cgtgagtgag  660
ctggcggggc ttttgtcagc gatggagtac gtgcagaaaa ctctcacgga cgaggagctg  720
gctgactgga agaggcggca acagattgcc tgcattggag gcccgcccaa catctgccta  780
gatcggctag aaaactggat aacgtcatta gcagaatctc aacttcagac ccgtcaacaa  840
attaagaaac tggaggagtt gcagcaaaaa gtttcctaca aggggaccc cattgtacag  900
caccggccga tgctggagga gagaatcgtg gagctgttta gaaacttaat gaaaagtgcc  960
tttgtggtgg agcggcagcc ctgcatgccc atgcatcctg accggcccct cgtcatcaag  1020
accggcgtcc agttcactac taaagtcagg ttgctggtca aattccctga gttgaattat  1080
cagcttaaaa ttaaagtgtg cattgacaaa gactctgggg acgttgcagc tctcagagga  1140
tcccggaaat ttaacattct gggcacaaac acaaaagtga tgaacatgga agaatccaac  1200
aacggcagcc tctctgcaga attcaaacac ttgaccctga gggagcagag atgtgggaat  1260
gggggccgag ccaattgtga tgcttccctg attgtgactg aggagctgca cctgatcacc  1320
tttgagaccg aggtgtatca ccaaggcctc aagattgacc tagagaccca ctccttgcca  1380
gttgtggtga tctccaacat ctgtcagatg ccaaatgcct gggcgtccat cctgtggtac  1440
aacatgctga ccaacaatcc caagaatgta aactttttta ccaagccccc aattggaacc  1500
tgggatcaag tggccgaggt cctgagctgg cagttctcct ccaccaccaa gcgaggactg  1560
agcatcgagc agctgactac actggcagag aaactcttgg gacctggtgt gaattattca  1620
gggtgtcaga tcacatgggc taaattttgc aaagaaaaca tggctggcaa gggcttctcc  1680
ttctgggtct ggctggacaa tatcattgac cttgtgaaaa agtacatcct ggccctttgg  1740
aacgaagggt acatcatggg ctttatcagt aaggagcggg agcgggccat cttgagcact  1800
aagcctccag gcaccttcct gctaagattc agtgaaagca gcaaagaagg acgcgtcact  1860
ttcacttggg tggagaagga catcagcggt aagacccaga tccagtccgt ggaaccatac  1920
acaaagcagc agctgaacaa catgtcattt gctgaaatca tcatgggcta taagatcatg  1980
gatgctacca atatcctggt gtctccactg gtctatctct atcctgacat tcccaaggag  2040
gaggcattcg gaaagtattg tcggccagag agccaggagc atcctgaagc tgacccaggt  2100
agcgctgccc catacctgaa gaccaagttt atctgtgtga caccaacgac ctgcagcaat  2160
accattgacc tgccgatgtc cccccgcact ttagattcat tgatgcagtt tggaaataat  2220
ggtgaaggtg ctgaaccctc agcaggaggg cagtttgagt ccctcacctt tgacatggag  2280
ttgacctcgg agtgcgctac ctcccccatg                                   2310

SEQ ID NO: 172           moltype = AA  length = 770
FEATURE                  Location/Qualifiers
source                   1..770
                         mol_type = protein
                         organism = Synthetic construct
SEQUENCE: 172
MAQWNQLQQL DTRYLEQLHQ LYSDSFPMEL RQFLAPWIES QDWAYAASKE SHATLVFHNL  60
LGEIDQQYSR FLQESNVLYQ HNLRRIKQFL QSRYLEKPME IARIVARCLW EESRLLQTAA  120
TAAQQGGQAN HPTAAVVTEK QQMLEQHLQD VRKRVQDLEQ KMKVVENLQD DFDFNYKTLK  180
SQGDMQDLNG NNQSVTRQKM QQLEQMLTAL DQMRRSIVSE LAGLLSAMEY VQKTLTDEEL  240
ADWKRRQQIA CIGGPPNICL DRLENWITSL AESQLQTRQQ IKKLEELQQK VSYKGDPIVQ  300
HRPMLEERIV ELFRNLMKSA FVVERQPCMP MHPDRPLVIK TGVQFTTKVR LLVKFPELNY  360
QLKIKVCIDK DSGDVAALRG SRKFNILGTN TKVMNMEESN NGSLSAEFKH LTLREQRCGN  420
GGRANCDASL IVTEELHLIT FETEVYHQGL KIDLETHSLP VVVISNICQM PNAWASILWY  480
NMLTNNPKNV NFFTKPPIGT WDQVAEVLSW QFSSTTKRGL SIEQLTTLAE KLLGPGVNYS  540
GCQITWAKFC KENMAGKGFS FWVWLDNIID LVKKYILALW NEGYIMGFIS KERERAILST  600
KPPGTFLLRF SESSKEGRVT FTWVEKDISG KTQIQSVEPY TKQQLNNMSF AEIIMGYKIM  660
DATNILVSPL VYLYPDIPKE EAFGKYCRPE SQEHPEADPG SAAPYLKTKF ICVTPTTCSN  720
TIDLPMSPRT LDSLMQFGNN GEGAEPSAGG QFESLTFDME LTSECATSPM             770

SEQ ID NO: 173           moltype = DNA  length = 2310
FEATURE                  Location/Qualifiers
source                   1..2310
                         mol_type = other DNA
                         organism = Synthetic construct
SEQUENCE: 173
atggcccaat ggaatcagct acagcagctt gacacacggt acctggagca gctccatcag  60
ctctacagtg acagcttccc aatggagctg cggcagtttc tggccccttg gattgagagt  120
caagattggg catatgcggc cagcaaagaa tcacatgcca ctttggtgtt tcataatctc  180
ctgggagaga ttgaccagca gtatagccgc ttcctgcaag agtcgaatgt tctctatcag  240
cacaatctac gaagaatcaa gcagtttctt cagagcaggt atcttgagaa gccaatggag  300
attgcccgga ttgtggcccg gtgcctgtgg gaagaatcac gccttctaca gactgcagcc  360
actgcggccc agcaaggggg ccaggccaac caccccacag cagccgtggt gacggagaag  420
cagcagatgc tggagcagca ccttcaggat gtccggaaga gagtgcagga tctagaacag  480
aaaatgaaag tggtagagaa tctccaggat gactttgatt tcaactataa aaccctcaag  540
agtcaaggag acatgcaaga tctgaatgga aacaaccagt cagtgaccag gcagaagatg  600
cagcagctgg aacagatgct cactgcgctg gaccagatgc ggagaagcat cgtgagtgag  660
```

```
ctggcggggc ttttgtcagc gatggagtac gtgcagaaaa ctctcacgga cgaggagctg  720
gctgactgga agaggcggca acagattgcc tgcattggag gcccgcccaa catctgccta  780
gatcggctag aaaactggat aacgtcatta gcagaatctc aacttcagac ccgtcaacaa  840
attaagaaac tggaggagtt gcagcaaaaa gtttcctaca aaggggaccc cattgtacag  900
caccggccga tgctggagga gagaatcgtg gagctgttta gaaacttaat gaaaagtgcc  960
tttgtggtgg agcggcagcc ctgcatgccc atgcatcctg accggcccct cgtcatcaag  1020
accggcgtcc agttcactac taaagtcagg ttgctggtca aattccctga gttgaattat  1080
cagcttaaaa ttaaagtgtg cattgacaaa gactctgggg acgttgcagc tctcagagga  1140
tcccggaaat ttaacattct gggcacaaac acaaaagtga tgaacatgga agaatccaac  1200
aacggcagcc tctctgcaga attcaaacac ttgaccctga gggagcagag atgtgggaat  1260
gggggccgag ccaattgtga tgcttccctg attgtgactg aggagctgca cctgatcacc  1320
tttgagaccg aggtgtatca ccaaggcctc aagattgacc tagagaccca ctccttgcca  1380
gttgtggtga tctccaacat ctgtcagatg ccaaatgcct gggcgtccat cctgtggtac  1440
aacatgctga ccaacaatcc caagaatgta aacttttta ccaagccccc aattggaacc  1500
tgggatcaag tggccgaggt cctgagctgg cagttctcct ccaccaccaa gcgaggactg  1560
agcatcgagc agctgactac actggcagag aaactcttgg gacctggtgt gaattattca  1620
gggtgtcaga tcacatgggc taaattttgc aaagaaaaca tggctggcaa gggcttctcc  1680
ttctgggtct ggctggacaa tatcattgac cttgtgaaaa agtacatcct ggccctttgg  1740
aacgaagggt acatcatggg ctttatcagt aaggagcggg agcgggccat cttgagcact  1800
aagcctccag gcaccttcct gctaagattc agtgaaagca gcaaagaagg aggcgtcact  1860
ttcacttggg tggagaagga catcagcggt aagacccaga tccagtccgt ggaaccatac  1920
acaaagcagc agctgaacaa catgtcattt gctgaaatca tcatgggcta taagatcatg  1980
attgctacca atatcctggt gtctccactg gtctatctct atcctgacat tcccaaggag  2040
gaggcattcg gaaagtattg tcggccagag agccaggagc atcctgaagc tgacccaggt  2100
agcgctgccc catacctgaa gaccaagttt atctgtgtga caccaacgac ctgcagcaat  2160
accattgacc tgccgatgtc cccccgcact ttagattcat tgatgcagtt tggaaataat  2220
ggtgaaggtg ctgaaccctc agcaggaggg cagtttgagt ccctcacctt tgacatggag  2280
ttgacctcgg agtgcgctac ctcccccatg                                  2310

SEQ ID NO: 174          moltype = AA  length = 770
FEATURE                 Location/Qualifiers
source                  1..770
                        mol_type = protein
                        organism = Synthetic construct
SEQUENCE: 174
MAQWNQLQQL DTRYLEQLHQ LYSDSFPMEL RQFLAPWIES QDWAYAASKE SHATLVFHNL  60
LGEIDQQYSR FLQESNVLYQ HNLRRIKQFL QSRYLEKPME IARIVARCLW EESRLLQTAA  120
TAAQQGGQAN HPTAAVVTEK QQMLEQHLQD VRKRVQDLEQ KMKVVENLQD DFDFNYKTLK  180
SQGDMQDLNG NNQSVTRQKM QQLEQMLTAL DQMRRSIVSE LAGLLSAMEY VQKTLTDEEL  240
ADWKRRQQIA CIGGPPNICL DRLENWITSL AESQLQTRQQ IKKLEELQQK VSYKGDPIVQ  300
HRPMLEERIV ELFRNLMKSA FVVERQPCMP MHPDRPLVIK TGVQFTTKVR LLVKFPELNY  360
QLKIKVCIDK DSGDVAALRG SRKFNILGTN TKVMNMEESN NGSLSAEFKH LTLREQRCGN  420
GGRANCDASL IVTEELHLIT FETEVYHQGL KIDLETHSLP VVVISNICQM PNAWASILWY  480
NMLTNNPKNV NFFTKPPIGT WDQVAEVLSW QFSSTTKRGL SIEQLTTLAE KLLGPGVNYS  540
GCQITWAKFC KENMAGKGFS FWVWLDNIID LVKKYILALW NEGYIMGFIS KERERAILST  600
KPPGTFLLRF SESSKEGGVT FTWVEKDISG KTQIQSVEPY TKQQLNNMSF AEIIMGYKIM  660
IATNILVSPL VYLYPDIPKE EAFGKYCRPE SQEHPEADPG SAAPYLKTKF ICVTPTTCSN  720
TIDLPMSPRT LDSLMQFGNN GEGAEPSAGG QFESLTFDME LTSECATSPM              770

SEQ ID NO: 175          moltype = DNA  length = 2310
FEATURE                 Location/Qualifiers
source                  1..2310
                        mol_type = genomic DNA
                        organism = Homo sapiens
SEQUENCE: 175
atggcccaat ggaatcagct acagcagctt gacacacggt acctggagca gctccatcag  60
ctctacagtg acagcttccc aatggagctg cggcagtttc tggccccttg gattgagagt  120
caagattggg catatgcggc cagcaaagaa tcacatgcca ctttggtgtt tcataatctc  180
ctgggagaga ttgaccagca gtatagccgc ttcctgcaag agtcgaatgt tctctatcag  240
cacaatctac gaagaatcaa gcagtttctt cagagcaggt atcttgagaa gccaatggag  300
attgcccgga ttgtggcccg gtgcctgtgg gaagaatcac gccttctaca gactgcagcc  360
actgcggccc agcaaggggg ccaggccaac caccccacag cagccgtggt gacggagaag  420
cagcagatgc tggagcagca ccttcaggat gtccggaaga gagtgcagga tctagaacag  480
aaaatgaaag tggtagagaa tctccaggat gactttgatt tcaactataa aaccctcaag  540
agtcaaggag acatgcaaga tctgaatgga aacaaccagt cagtgaccag gcagaagatg  600
cagcagctgg aacagatgct cactgcgctg gaccagatgc ggagaagcat cgtgagtgag  660
ctggcggggc ttttgtcagc gatggagtac gtgcagaaaa ctctcacgga cgaggagctg  720
gctgactgga agaggcggca acagattgcc tgcattggag gcccgcccaa catctgccta  780
gatcggctag aaaactggat aacgtcatta gcagaatctc aacttcagac ccgtcaacaa  840
attaagaaac tggaggagtt gcagcaaaaa gtttcctaca aaggggaccc cattgtacag  900
caccggccga tgctggagga gagaatcgtg gagctgttta gaaacttaat gaaaagtgcc  960
tttgtggtgg agcggcagcc ctgcatgccc atgcatcctg accggcccct cgtcatcaag  1020
accggcgtcc agttcactac taaagtcagg ttgctggtca aattccctga gttgaattat  1080
cagcttaaaa ttaaagtgtg cattgacaaa gactctgggg acgttgcagc tctcagagga  1140
tcccggaaat ttaacattct gggcacaaac acaaaagtga tgaacatgga agaatccaac  1200
aacggcagcc tctctgcaga attcaaacac ttgaccctga gggagcagag atgtgggaat  1260
gggggccgag ccaattgtga tgcttccctg attgtgactg aggagctgca cctgatcacc  1320
tttgagaccg aggtgtatca ccaaggcctc aagattgacc tagagaccca ctccttgcca  1380
gttgtggtga tctccaacat ctgtcagatg ccaaatgcct gggcgtccat cctgtggtac  1440
```

```
aacatgctga ccaacaatcc caagaatgta aactttttta ccaagccccc aattggaacc  1500
tgggatcaag tggccgaggt cctgagctgg cagttctcct ccaccaccaa gcgaggactg  1560
agcatcgagc agctgactac actggcagag aaactcttgg gacctggtgt gaattattca  1620
gggtgtcaga tcacatgggc taaattttgc aaagaaaaca tggctggcaa gggcttctcc  1680
ttctgggtct ggctggacaa tatcattgac cttgtgaaaa agtacatcct ggccctttgg  1740
aacgaagggt acatcatggg ctttatcagt aaggagcggg agcgggccat cttgagcact  1800
aagcctccag gcaccttcct gctaagattc agtgaaagca gcaaagaagg aggcgtcact  1860
ttcacttggg tggagaagga catcagcggt aagacccaga tccagtccgt ggaaccatac  1920
acaaagcagc agctgaacaa catgtcattt gctgaaatca tcatgggcta taagatcatg  1980
gatgctacca atatcctggt gtctccactg gtctatctct atcctgacat tcccaaggag  2040
gaggcattcg gaaagtattg tcggccagag agccaggagc atcctgaagc tgacccaggt  2100
agcgctgccc catacctgaa gaccaagttt atctgtgtga caccaacgac ctgcagcaat  2160
accattgacc tgccgatgtc cccccgcact ttagattcat tgatgcagtt tggaaataat  2220
ggtgaaggtg ctgaaccctc agcaggaggg cagtttgagt ccctcacctt tgacatggag  2280
ttgacctcgg agtgcgctac ctcccccatg                                   2310
```

```
SEQ ID NO: 176          moltype = AA  length = 770
FEATURE                 Location/Qualifiers
source                  1..770
                        mol_type = protein
                        organism = Homo sapiens
SEQUENCE: 176
MAQWNQLQQL DTRYLEQLHQ LYSDSFPMEL RQFLAPWIES QDWAYAASKE SHATLVFHNL  60
LGEIDQQYSR FLQESNVLYQ HNLRRIKQFL QSRYLEKPME IARIVARCLW EESRLLQTAA  120
TAAQQGGQAN HPTAAVVTEK QQMLEQHLQD VRKRVQDLEQ KMKVVENLQD DFDFNYKTLK  180
SQGDMQDLNG NNQSVTRQKM QQLEQMLTAL DQMRRSIVSE LAGLLSAMEY VQKTLTDEEL  240
ADWKRRQQIA CIGGPPNICL DRLENWITSL AESQLQTRQQ IKKLEELQQK VSYKGDPIVQ  300
HRPMLEERIV ELFRNLMKSA FVVERQPCMP MHPDRPLVIK TGVQFTTKVR LLVKFPELNY  360
QLKIKVCIDK DSGDVAALRG SRKFNILGTN TKVMNMEESN NGSLSAEFKH LTLREQRCGN  420
GGRANCDASL IVTEELHLIT FETEVYHQGL KIDLETHSLP VVVISNICQM PNAWASILWY  480
NMLTNNPKNV NFFTKPPIGT WDQVAEVLSW QFSSTTKRGL SIEQLTTLAE KLLGPGVNYS  540
GCQITWAKFC KENMAGKGFS FWVWLDNIID LVKKYILALW NEGYIMGFIS KERERAILST  600
KPPGTFLLRF SESSKEGGVT FTWVEKDISG KTQIQSVEPY TKQQLNNMSF AEIIMGYKIM  660
DATNILVSPL VYLYPDIPKE EAFGKYCRPE SQEHPEADPG SAAPYLKTKF ICVTPTTCSN  720
TIDLPMSPRT LDSLMQFGNN GEGAEPSAGG QFESLTFDME LTSECATSPM             770
```

```
SEQ ID NO: 177          moltype = DNA  length = 2364
FEATURE                 Location/Qualifiers
source                  1..2364
                        mol_type = other DNA
                        organism = Synthetic construct
SEQUENCE: 177
atggctgtgt ggatacaagc tcagcagctc caaggagaag cccttcatca gatgcaagcg  60
ttatatggcc agcattttcc cattgaggtg cggcattatt tatcccagtg gattgaaagc  120
caagcatggg actcagtaga tcttgataat ccacaggaga acattaaggc cacccagctc  180
ctggagggcc tggtgcagga gctgcagaag aaggcagagc accaggtggg ggaagatggg  240
tttttactga agatcaagct ggggcactat gccacacagc tccagaacac gtatgaccgc  300
tgccccatgg agctggtccg ctgcatccgc catatattgt acaatgaaca gaggttggtc  360
cgagaagcca acaatggtag ctctccagct ggaagccttg ctgatgccat gtcccagaaa  420
cacctccaga tcaaccagac gtttgaggag ctgcgactgg tcacgcagga cacagagaat  480
gagttaaaaa agctgcagca gactcaggag tacttcatca tccagtacca ggagagcctg  540
aggatccaag ctcagtttgg cccgctggcc cagctgagcc cccaggagcg tctgagccgg  600
gagacggccc tccagcagaa gcaggtgtct ctggaggcct ggttgcagcg tgaggcacag  660
acactgcagc agtaccgcgt ggagctggcc gagaagcacc agaagaccct gcagctgctg  720
cggaagcagc agaccatcat cctggatgac gagctgatcc agtggaagcg gcggcagcag  780
ctggccggga acggcgggcc ccccgagggc agcctggacg tgctacagtc ctggtgtgag  840
aagttggccg agatcatctg gcagaaccgg cagcagatcc gcagggctga gcacctctgc  900
cagcagctgc ccatccccgg cccagtggag gagatgctgg ccgaggtcaa cgccaccatc  960
acggacatta tctcagccct ggtgaccagc acgttcatca ttgagaagca gcctcctcag  1020
gtcctgaaga cccagaccaa gtttgcagcc actgtgcgcc tgctggtggg cgggaagctg  1080
aacgtgcaca tgaacccccc ccaggtgaag gccaccatca tcagtgagca gcaggccaag  1140
tctctgctca agaacgagaa cacccgcaat gattacagtg gcgagatctt gaacaactgc  1200
tgcgtcatgg agtaccacca agccacaggc acccttagtg cccacttcag gaatatgtcc  1260
ctgaaacgaa ttaagaggtc agaccgtcgt ggggcagagt cggtgacaga agaaaaattt  1320
acaatcctgt ttgaatccca gttcagtgtt ggtggaaatg agctggtttt tcaagtcaag  1380
accctgtccc tgccagtggt ggtgatcgtt catggcagcc aggacaacaa tgcgacggcc  1440
actgttctct gggacaatgc ttttgcagag cctggcaggg tgccatttgc cgtgcctgac  1500
aaagtgctgt ggccacagct gtgtgaggcg ctcaacatga aattcaaggc cgaagtgcag  1560
agcaaccggg gcctgaccaa ggagaacctc gtgttcctgg cgcagaaact gttcaacaac  1620
agcagcagcc acctggagga ctacagtggc ctgtctgtgt cctggtccca gttcaacagg  1680
gagaatttac caggacggaa ttacactttc tggcaatggt ttgacggtgt gatggaagtg  1740
ttaaaaaaac atctcaagcc tcattggaat gatggggcca ttttggggtt tgtaaacaag  1800
caacaggccc atgacctact cattaacaag ccagatggga ccttcctcct gagattcagt  1860
gactcagaaa ttggcggcat cagcattgct tggaagtttg attctcagga aagaatgttt  1920
tggaatctga tgccttttac caccagagac ttctccattc ggtccctagc cgaccgcttg  1980
ggagacttga attaccttat ctacgtgttt cctgatcggc caaaagatga agtatactcc  2040
aaatactaca caccagttcc ctgcgagtct gctactgcta aagctgttga tggatacgtg  2100
aagccacaga tcaagcaagt ggtccctgag tttgtgaacg catctgcaga tgccgggggc  2160
ggcagcgcca cgtacatgga ccaggccccc tccccagctg tgtgtcccca ggctcactat  2220
```

```
aacatgtacc cacagaaccc tgactcagtc cttgacaccg atggggactt cgatctggag  2280
gacacaatgg acgtagcgcg gcgtgtggag gagctcctgg gccggccaat ggacagtcag  2340
tggatcccgc acgcacaatc gttg                                         2364

SEQ ID NO: 178         moltype = AA  length = 788
FEATURE                Location/Qualifiers
source                 1..788
                       mol_type = protein
                       organism = Synthetic construct
SEQUENCE: 178
MAVWIQAQQL QGEALHQMQA LYGQHFPIEV RHYLSQWIES QAWDSVDLDN PQENIKATQL  60
LEGLVQELQK KAEHQVGEDG FLLKIKLGHY ATQLQNTYDR CPMELVRCIR HILYNEQRLV  120
REANNGSSPA GSLADAMSQK HLQINQTFEE LRLVTQDTEN ELKKLQQTQE YFIIQYQESL  180
RIQAQFGPLA QLSPQERLSR ETALQQKQVS LEAWLQREAQ TLQQYRVELA EKHQKTLQLL  240
RKQQTIILDD ELIQWKRRQQ LAGNGGPPEG SLDVLQSWCE KLAEIIWQNR QQIRRAEHLC  300
QQLPIPGPVE EMLAEVNATI TDIISALVTS TFIIEKQPPQ VLKTQTKFAA TVRLLVGGKL  360
NVHMNPPQVK ATIISEQQAK SLLKNENTRN DYSGEILNNC CVMEYHQATG TLSAHFRNMS  420
LKRIKRSDRR GAESVTEEKF TILFESQFSV GGNELVFQVK TLSLPVVVIV HGSQDNNATA  480
TVLWDNAFAE PGRVPFAVPD KVLWPQLCEA LNMKFKAEVQ SNRGLTKENL VFLAQKLFNN  540
SSSHLEDYSG LSVSWSQFNR ENLPGRNYTF WQWFDGVMEV LKKHLKPHWN DGAILGFVNK  600
QQAHDLLINK PDGTFLLRFS DSEIGGISIA WKFDSQERMF WNLMPFTTRD FSIRSLADRL  660
GDLNYLIYVF PDRPKDEVYS KYYTPVPCES ATAKAVDGYV KPQIKQVVPE FVNASADAGG  720
GSATYMDQAP SPAVCPQAHY NMYPQNPDSV LDTDGDFDLE DTMDVARRVE ELLGRPMDSQ  780
WIPHAQSL                                                           788

SEQ ID NO: 179         moltype = DNA  length = 2364
FEATURE                Location/Qualifiers
source                 1..2364
                       mol_type = other DNA
                       organism = Synthetic construct
SEQUENCE: 179
atggctgtgt ggatacaagc tcagcagctc caaggagaag cccttcatca gatgcaagcg  60
ttatatggcc agcatttccc cattgaggtg cggcattatt tatcccagtg gattgaaagc  120
caagcatggg actcagtaga tcttgataat ccacaggaga acattaaggc cacccagctc  180
ctggagggcc tggtgcagga gctgcagaag aaggcagagc accaggtggg ggaagatggg  240
tttttactga agatcaagct ggggcactat gccacacagc tccagaacac gtatgaccgc  300
tgccccatgg agctggtccg ctgcatccgc catatattgt acaatgaaca gaggttggtc  360
cgagaagcca acaatggtag ctctccagct ggaagccttg ctgatgccat gtcccagaaa  420
cacctccaga tcaaccagac gtttgaggag ctgcgactgg tcacgcagga cacagagaat  480
gagttaaaaa agctgcagca gactcaggag tacttcatca tccagtacca ggagagcctg  540
aggatccaag ctcagtttgg cccgctggcc cagctgagcc cccaggagcg tctgagccgg  600
gagacggccc tccagcagaa gcaggtgtct ctggaggcct ggttgcagcg tgaggcacag  660
acactgcagc agtaccgcgt ggagctggcc gagaagcacc agaagaccct gcagctgctg  720
cggaagcagc agaccatcat cctggatgac gagctgatcc agtggaagcg gcggcagcag  780
ctggccggga acggcgggcc ccccgagggc agcctggacg tgctacagtc ctggtgtgag  840
aagttggccg agatcatctg gcagaaccgg cagcagatcc gcagggctga gcacctctgc  900
cagcagctgc ccatccccgg cccagtggag gagatgctgg ccgaggtcaa cgccaccatc  960
acggacatta tctcagccct ggtgaccagc acgttcatca ttgagaagca gcctcctcag  1020
gtcctgaaga cccagaccaa gtttgcagcc actgtgcgcc tgctggtggg cgggaagctg  1080
aacgtgcaca tgaacccccc ccaggtgaag gccaccatca tcagtgagca gcaggccaag  1140
tctctgctca agaacgagaa cacccgcaat gattacagtg gcgagatctt gaacaactgc  1200
tgcgtcatgg agtaccacca agccacaggc acccttagtg cccacttcag gaatatgtcc  1260
ctgaaacgaa ttaagaggtc agaccgtcgt ggggcagagt cggtgacaga agaaaaattt  1320
acaatcctgt ttgaatccca gttcagtgtt ggtggaaatg agctggtttt tcaagtcaag  1380
accctgtccc tgccagtggt ggtgatcgtt catggcagcc aggacaacaa tgcgacggcc  1440
actgttctct gggacaatgc ttttgcagag cctggcaggg tgccatttgc cgtgcctgac  1500
aaagtgctgt ggccacagct gtgtgaggcg ctcaacatga aattcaaggc cgaagtgcag  1560
agcaaccggg gcctgaccaa ggagaacctc gtgttcctgg cgcagaaact gttcaacaac  1620
agcagcagcc acctggagga ctacagtggc ctgtctgtgt cctggtccca gttcaacagg  1680
gagaatttac caggacggaa ttacactttc tggcaatggt ttgacggtgt gatggaagtg  1740
ttaaaaaaac atctcaagcc tcattggaat gatggggcca ttttggggtt tgtaaacaag  1800
caacaggccc atgacctact cattaacaag ccagatggga ccttcctcct gagattcagt  1860
gactcagaaa ttggcggcat caccattgct tggaagtttg attctcagga aagaatgttt  1920
tggaatctga tgccttttac caccagagac ttctccattc ggtccctagc cgaccgcttg  1980
ggagacttga atttccttat ctacgtgttt cctgatcggc caaaagatga agtatactcc  2040
aaatactaca caccagttcc ctgcgagtct gctactgcta aagctgttga tggatacgtg  2100
aagccacaga tcaagcaagt ggtccctgag tttgtgaacg catctgcaga tgccgggggc  2160
ggcagcgcca cgtacatgga ccaggccccc tccccagctg tgtgtcccca ggctcactat  2220
aacatgtacc cacagaaccc tgactcagtc cttgacaccg atggggactt cgatctggag  2280
gacacaatgg acgtagcgcg gcgtgtggag gagctcctgg gccggccaat ggacagtcag  2340
tggatcccgc acgcacaatc gttg                                         2364

SEQ ID NO: 180         moltype = AA  length = 788
FEATURE                Location/Qualifiers
source                 1..788
                       mol_type = protein
                       organism = Synthetic construct
SEQUENCE: 180
MAVWIQAQQL QGEALHQMQA LYGQHFPIEV RHYLSQWIES QAWDSVDLDN PQENIKATQL  60
```

-continued

```
LEGLVQELQK KAEHQVGEDG FLLKIKLGHY ATQLQNTYDR CPMELVRCIR HILYNEQRLV  120
REANNGSSPA GSLADAMSQK HLQINQTFEE LRLVTQDTEN ELKKLQQTQE YFIIQYQESL  180
RIQAQFGPLA QLSPQERLSR ETALQQKQVS LEAWLQREAQ TLQQYRVELA EKHQKTLQLL  240
RKQQTIILDD ELIQWKRRQQ LAGNGGPPEG SLDVLQSWCE KLAEIIWQNR QQIRRAEHLC  300
QQLPIPGPVE EMLAEVNATI TDIISALVTS TFIIEKQPPQ VLKTQTKFAA TVRLLVGGKL  360
NVHMNPPQVK ATIISEQQAK SLLKNENTRN DYSGEILNNC CVMEYHQATG TLSAHFRNMS  420
LKRIKRSDRR GAESVTEEKF TILFESQFSV GGNELVFQVK TLSLPVVVIV HGSQDNNATA  480
TVLWDNAFAE PGRVPFAVPD KVLWPQLCEA LNMKFKAEVQ SNRGLTKENL VFLAQKLFNN  540
SSSHLEDYSG LSVSWSQFNR ENLPGRNYTF WQWFDGVMEV LKKHLKPHWN DGAILGFVNK  600
QQAHDLLINK PDGTFLLRFS DSEIGGITIA WKFDSQERMF WNLMPFTTRD FSIRSLADRL  660
GDLNFLIYVF PDRPKDEVYS KYYTPVPCES ATAKAVDGYV KPQIKQVVPE FVNASADAGG  720
GSATYMDQAP SPAVCPQAHY NMYPQNPDSV LDTDGDFDLE DTMDVARRVE ELLGRPMDSQ  780
WIPHAQSL                                                           788

SEQ ID NO: 181          moltype = DNA  length = 2364
FEATURE                 Location/Qualifiers
source                  1..2364
                        mol_type = genomic DNA
                        organism = Homo sapiens
SEQUENCE: 181
atggctgtgt ggatacaagc tcagcagctc caaggagaag cccttcatca gatgcaagcg  60
ttatatggcc agcattttcc cattgaggtg cggcattatt tatcccagtg gattgaaagc  120
caagcatggg actcagtaga tcttgataat ccacaggaga acattaaggc cacccagctc  180
ctggagggcc tggtgcagga gctgcagaag aaggcagagc accaggtggg ggaagatggg  240
tttttactga agatcaagct ggggcactat gccacacagc tccagaacac gtatgaccgc  300
tgccccatgg agctggtccg ctgcatccgc catatattgt acaatgaaca gaggttggtc  360
cgagaagcca acaatggtag ctctccagct ggaagccttg ctgatgccat gtcccagaaa  420
cacctccaga tcaaccagac gtttgaggag ctgcgactgg tcacgcagga cacagagaat  480
gagttaaaaa agctgcagca gactcaggag tacttcatca tccagtacca ggagagcctg  540
aggatccaag ctcagtttgg cccgctggcc cagctgagcc cccaggagcg tctgagccgg  600
gagacggccc tccagcagaa gcaggtgtct ctggaggcct ggttgcagcg tgaggcacag  660
acactgcagc agtaccgcgt ggagctggcc gagaagcacc agaagaccct gcagctgctg  720
cggaagcagc agaccatcat cctggatgac gagctgatcc agtggaagcg gcggcagcag  780
ctggccggga acggcgggcc ccccgagggc agcctggacg tgctacagtc ctggtgtgag  840
aagttggccg agatcatctg gcagaaccgg cagcagatcc gcagggctga gcacctctgc  900
cagcagctgc ccatccccgg cccagtggag gagatgctgg ccgaggtcaa cgccaccatc  960
acggacatta tctcagccct ggtgaccagc acgttcatca ttgagaagca gcctcctcag  1020
gtcctgaaga cccagaccaa gtttgcagcc actgtgcgcc tgctggtggg cgggaagctg  1080
aacgtgcaca tgaacccccc ccaggtgaag gccaccatca tcagtgagca gcaggccaag  1140
tctctgctca agaacgagaa cacccgcaat gattacagtg gcgagatctt gaacaactgc  1200
tgcgtcatgg agtaccacca agccacaggc acccttagtg cccacttcag gaatatgtcc  1260
ctgaaacgaa ttaagaggtc agaccgtcgt ggggcagagt cggtgacaga agaaaaattt  1320
acaatcctgt ttgaatccca gttcagtgtt ggtggaaatg agctggtttt tcaagtcaag  1380
accctgtccc tgccagtggt ggtgatcgtt catggcagcc aggacaacaa tgcgacggcc  1440
actgttctct gggacaatgc ttttgcagag cctggcaggg tgccatttgc cgtgcctgac  1500
aaagtgctgt ggccacagct gtgtgaggcg ctcaacatga aattcaaggc cgaagtgcag  1560
agcaaccggg gcctgaccaa ggagaacctc gtgttcctgg cgcagaaact gttcaacaac  1620
agcagcagcc acctggagga ctacagtggc ctgtctgtgt cctggtccca gttcaacagg  1680
gagaatttac caggacggaa ttacactttc tggcaatggt ttgacggtgt gatggaagtg  1740
ttaaaaaaac atctcaagcc tcattggaat gatggggcca ttttggggtt tgtaaacaag  1800
caacaggccc atgacctact cattaacaag ccagatggga ccttcctcct gagattcagt  1860
gactcagaaa ttggcggcat caccattgct tggaagtttg attctcagga aagaatgttt  1920
tggaatctga tgccttttac caccagagac ttctccattc ggtccctagc cgaccgcttg  1980
ggagacttga attaccttat ctacgtgttt cctgatcggc caaaagatga agtatactcc  2040
aaatactaca caccagttcc ctgcgagtct gctactgcta aagctgttga tggatacgtg  2100
aagccacaga tcaagcaagt ggtccctgag tttgtgaacg catctgcaga tgccgggggc  2160
ggcagcgcca cgtacatgga ccaggccccc tccccagctg tgtgtcccca ggctcactat  2220
aacatgtacc cacagaaccc tgactcagtc cttgacaccg atggggactt cgatctggag  2280
gacacaatgg acgtagcgcg gcgtgtggag gagctcctgg gccggccaat ggacagtcag  2340
tggatcccgc acgcacaatc gttg                                         2364

SEQ ID NO: 182          moltype = AA  length = 788
FEATURE                 Location/Qualifiers
source                  1..788
                        mol_type = protein
                        organism = Homo sapiens
SEQUENCE: 182
MAVWIQAQQL QGEALHQMQA LYGQHFPIEV RHYLSQWIES QAWDSVDLDN PQENIKATQL  60
LEGLVQELQK KAEHQVGEDG FLLKIKLGHY ATQLQNTYDR CPMELVRCIR HILYNEQRLV  120
REANNGSSPA GSLADAMSQK HLQINQTFEE LRLVTQDTEN ELKKLQQTQE YFIIQYQESL  180
RIQAQFGPLA QLSPQERLSR ETALQQKQVS LEAWLQREAQ TLQQYRVELA EKHQKTLQLL  240
RKQQTIILDD ELIQWKRRQQ LAGNGGPPEG SLDVLQSWCE KLAEIIWQNR QQIRRAEHLC  300
QQLPIPGPVE EMLAEVNATI TDIISALVTS TFIIEKQPPQ VLKTQTKFAA TVRLLVGGKL  360
NVHMNPPQVK ATIISEQQAK SLLKNENTRN DYSGEILNNC CVMEYHQATG TLSAHFRNMS  420
LKRIKRSDRR GAESVTEEKF TILFESQFSV GGNELVFQVK TLSLPVVVIV HGSQDNNATA  480
TVLWDNAFAE PGRVPFAVPD KVLWPQLCEA LNMKFKAEVQ SNRGLTKENL VFLAQKLFNN  540
SSSHLEDYSG LSVSWSQFNR ENLPGRNYTF WQWFDGVMEV LKKHLKPHWN DGAILGFVNK  600
QQAHDLLINK PDGTFLLRFS DSEIGGITIA WKFDSQERMF WNLMPFTTRD FSIRSLADRL  660
GDLNYLIYVF PDRPKDEVYS KYYTPVPCES ATAKAVDGYV KPQIKQVVPE FVNASADAGG  720
```

-continued

```
GSATYMDQAP SPAVCPQAHY NMYPQNPDSV LDTDGDFDLE DTMDVARRVE ELLGRPMDSQ  780
WIPHAQSL                                                           788

SEQ ID NO: 183          moltype = DNA  length = 1542
FEATURE                 Location/Qualifiers
source                  1..1542
                        mol_type = genomic DNA
                        organism = Homo sapiens
SEQUENCE: 183
atgagtataa gcagtgatga ggtcaacttc ttggtatata gatacttgca agagtcagga  60
ttttctcatt cagcatttac ctttggtata gaaagccata tcagtcagtc caatataaat  120
ggtgccctcg tcccacccgc tgcattgatt tctatcatcc agaaaggtct acagtatgta  180
gaagcagaag ttagtattaa tgaggatggt accttgtttg atggtcgacc aatagagtct  240
ctgtccctga tagatgccgt aatgcctgat gtagtacaaa caagacaaca agcttataga  300
gataagcttg cacagcaaca ggcagcagct gctgcagctg ccgcagctgc agccagccaa  360
caaggatctg caaaaaatgg agaaaacaca gcaaatgggg aggagaatgg agcacatact  420
atagcaaata atcatactga tatgatggaa gtggatgggg atgttgaaat ccctcctaat  480
aaagctgttg tgttgcgggg ccatgaatct gaagttttta tctgtgcctg gaaccctgtt  540
agtgatctcc tagcatcagg gtctggagac tcaacagcaa gaatatggaa tcttagtgag  600
aacagcacca gtggctctac acagttagta cttagacatt gtatacgaga aggagggcaa  660
gatgttccaa gcaacaagga tgtcacatct ctagattgga atagtgaagg tacacttcta  720
gcaactggtt cctatgatgg gtttgccaga atatggacta aagatggtaa ccttgctagc  780
accttagggc agcataaagg ccctatattt gcattaaaat ggaataagaa aggaaatttc  840
atcctaagtg ctggagtaga caagactaca attatttggg acgcacatac tggtgaagcc  900
aagcaacagt ttccttttca ttcagcacca gcattggatg ttgattggca gagcaacaac  960
acctttgctt cttgtagtac agatatgtgc attcatgtct gtaaattagg acaagacaga  1020
cctattaaaa cattccaagg acatacgaat gaagtaaatg ctatcaaatg ggacccaact  1080
ggcaatctct tggcctcctg ttctgacgac atgactttaa agatatggag tatgaaacaa  1140
gacaattgtg tccatgattt gcaagcacat aataaagaaa tttatactat caaatggagt  1200
ccaacaggac cagggactaa taatccaaat gccaacctta tgttagcaag tgcatccttt  1260
gattctactg ttaggttatg ggatgtagac cgagggatat gcatccatac tttgacaaaa  1320
caccaagagc ctgtgtacag tgtagctttc agtcctgatg gcaggtatct ggcaagtggt  1380
tcttttgaca aatgtgtaca catctggaac acgcagacag gtgctctagt tcacagctat  1440
aggggaacag gtggaatatt tgaagtttgc tggaatgcag caggagacaa agttggagcc  1500
agtgcatcag atggttcagt ttgtgtatta gaccttcgga aa                     1542

SEQ ID NO: 184          moltype = AA  length = 514
FEATURE                 Location/Qualifiers
source                  1..514
                        mol_type = protein
                        organism = Homo sapiens
SEQUENCE: 184
MSISSDEVNF LVYRYLQESG FSHSAFTFGI ESHISQSNIN GALVPPAALI SIIQKGLQYV  60
EAEVSINEDG TLFDGRPIES LSLIDAVMPD VVQTRQQAYR DKLAQQQAAA AAAAAAASQ  120
QGSAKNGENT ANGEENGAHT IANNHTDMME VDGDVEIPPN KAVVLRGHES EVFICAWNPV  180
SDLLASGSGD STARIWNLSE NSTSGSTQLV LRHCIREGGQ DVPSNKDVTS LDWNSEGTLL  240
ATGSYDGFAR IWTKDGNLAS TLGQHKGPIF ALKWNKKGNF ILSAGVDKTT IIWDAHTGEA  300
KQQFPFHSAP ALDVDWQSNN TFASCSTDMC IHVCKLGQDR PIKTFQGHTN EVNAIKWDPT  360
GNLLASCSDD MTLKIWSMKQ DNCVHDLQAH NKEIYTIKWS PTGPGTNNPN ANLMLASASF  420
DSTVRLWDVD RGICIHTLTK HQEPVYSVAF SPDGRYLASG SFDKCVHIWN TQTGALVHSY  480
RGTGGIFEVC WNAAGDKVGA SASDGSVCVL DLRK                              514

SEQ ID NO: 185          moltype = DNA  length = 1542
FEATURE                 Location/Qualifiers
source                  1..1542
                        mol_type = other DNA
                        organism = Synthetic construct
SEQUENCE: 185
atgagtataa gcagtgatga ggtcaacttc ttggtatata gatacttgca agagtcagga  60
ttttctcatt cagcatttac ctttggtata gaaagccata tcagtcagtc caatataaat  120
ggtgccctcg tcccacccgc tgcattgatt tctatcatcc agaaaggtct acagtatgta  180
gaagcagaag ttagtattaa tgaggatggt accttgtttg atggtcgacc aatagagtct  240
ctgtccctga tagatgccgt aatgcctgat gtagtacaaa caagacaaca agcttataga  300
gataagcttg cacagcaaca ggcagcagct gctgcagctg ccgcagctgc agccagccaa  360
caaggatctg caaaaaatgg agaaaacaca gcaaatgggg aggagaatgg agcacatact  420
atagcaaata atcatactga tatgatggaa gtggatgggg atgttgaaat ccctcctaat  480
aaagctgttg tgttgcgggg ccatgaatct gaagttttta tctgtgcctg gaaccctgtt  540
agtgatctcc tagcatcagg gtctggagac tcaacagcaa gaatatggaa tcttagtgag  600
aacagcacca gtggctctac acagttagta cttagacatt gtatacgaga aggagggcaa  660
gatgttccaa gcaacaagga tgtcacatct ctagattgga atagtgaagg tacacttcta  720
gcaactggtt cctatgatgg gtttgccaga atatggacta aagatggtaa ccttgctagc  780
accttagggc agcataaagg ccctatattt gcattaaaat ggaataagaa aggaaatttc  840
atcctaagtg ctggagtaga caagactaca attatttggg acgcacatac tggtgaagcc  900
aagcaacagt ttccttttcg ttcagcacca gcattggatg ttgattggca gagcaacaac  960
acctttgctt cttgtagtac agatatgtgc attcatgtct gtaaattagg acaagacaga  1020
cctattaaaa cattccaagg acatacgaat gaagtaaatg ctatcaaatg ggacccaact  1080
ggcaatctct tggcctcctg ttctgacgac atgactttaa agatatggag tatgaaacaa  1140
gacaattgtg tccatgattt gcaagcacat aataaagaaa tttatactat caaatggagt  1200
ccaacaggac cagggactaa taatccaaat gccaacctta tgttagcaag tgcatccttt  1260
```

```
gattctactg ttaggttatg ggatgtagac cgagggatat gcatccatac tttgacaaaa  1320
caccaagagc ctgtgtacag tgtagctttc agtcctgatg gcaggtatct ggcaagtggt  1380
tcttttgaca aatgtgtaca catctggaac acgcagacag gtgctctagt tcacagctat  1440
aggggaacag gtggaatatt tgaagtttgc tggaatgcag caggagacaa agttggagcc  1500
agtgcatcag atggttcagt ttgtgtatta gaccttcgga aa                     1542

SEQ ID NO: 186         moltype = AA  length = 514
FEATURE                Location/Qualifiers
source                 1..514
                       mol_type = protein
                       organism = Synthetic construct
SEQUENCE: 186
MSISSDEVNF LVYRYLQESG FSHSAFTFGI ESHISQSNIN GALVPPAALI SIIQKGLQYV  60
EAEVSINEDG TLFDGRPIES LSLIDAVMPD VVQTRQQAYR DKLAQQQAAA AAAAAAAASQ  120
QGSAKNGENT ANGEENGAHT IANNHTDMME VDGDVEIPPN KAVVLRGHES EVFICAWNPV  180
SDLLASGSGD STARIWNLSE NSTSGSTQLV LRHCIREGGQ DVPSNKDVTS LDWNSEGTLL  240
ATGSYDGFAR IWTKDGNLAS TLGQHKGPIF ALKWNKKGNF ILSAGVDKTT IIWDAHTGEA  300
KQQFPFRSAP ALDVDWQSNN TFASCSTDMC IHVCKLGQDR PIKTFQGHTN EVNAIKWDPT  360
GNLLASCSDD MTLKIWSMKQ DNCVHDLQAH NKEIYTIKWS PTGPGTNNPN ANLMLASASF  420
DSTVRLWDVD RGICIHTLTK HQEPVYSVAF SPDGRYLASG SFDKCVHIWN TQTGALVHSY  480
RGTGGIFEVC WNAAGDKVGA SASDGSVCVL DLRK                              514

SEQ ID NO: 187         moltype = DNA  length = 1383
FEATURE                Location/Qualifiers
source                 1..1383
                       mol_type = other DNA
                       organism = Synthetic construct
SEQUENCE: 187
atggcgcccg tcgccgtctg ggccgcgctg gccgtcggac tggagctctg ggctgcggcg  60
cacgccttgc ccgcccaggt ggcatttaca ccctacgccc cggagcccgg gagcacatgc  120
cggctcagag aatactatga ccagacagct cagatgtgct gcagcaaatg ctcgccgggc  180
caacatgcaa aagtcttctg taccaagacc tcggacaccg tgtgtgactc ctgtgaggac  240
agcacataca cccagctctg gaactgggtt cccgagtgct tgagctgtgg ctcccgctgt  300
agctctgacc aggtggaaac tcaagcctgc actcgggaac agaaccgcat ctgcacctgc  360
aggcccggct ggtactgcgc gctgagcaag caggaggggt gccggctgtg cgcgccgctg  420
cgcaagtgcc gcccgggctt cggcgtggcc agaccaggaa ctgaaacatc agacgtggtg  480
tgcaagccct gtgccccggg gacgttctcc aacacgactt catccacgga tatttgcagg  540
ccccaccaga tctgtaacgt ggtggccatc cctgggaatg caagcatgga tgcagtctgc  600
acgtccacgt cccccacccg gagtatggcc ccaggggcag tacacttacc ccagccagtg  660
tccacacgat cccaacacac gcagccaact ccagaaccca gcactgctcc aagcacctcc  720
ttcctgctcc caatgggccc cagccccccca gctgaaggga gcactggcga cttcgctctt  780
ccagttggac tgattgtggg tgtgacagcc ttgggtctac taataatagg agtggtgaac  840
tgtgtcatca tgacccaggt gaaaaagaag cccttgtgcc tgcagagaga agccaaggtg  900
cctcacttgc ctgccgataa ggcccggggt acacagggcc ccgagcagca gcacctgctg  960
atcacagcgc cgagctccag cagcagctcc ctggagagct cggccagtgc gttggacaga  1020
agggcgccca ctcggaacca gccacaggca ccaggcgtgg aggccagtgg ggccggggag  1080
gcccgggcca gcaccgggag ctcagattct tcccctggtg gccatgggat ccaggtcaat  1140
gtcacctgca tcgtgaacgt ctgtagcagc tctgaccaca gctcacagtg ctcctcccaa  1200
gccagctcca caatgggaga cacagattcc agcccctcgg agtccccgaa ggacgagcag  1260
gtccccttct ccaaggagga atgtgccttt cggtcacagc tggagacgcc agagaccctg  1320
ctggggagca ccgaagagaa gcccctgccc cttggagtgc ctgatgctgg gatgaagccc  1380
agt                                                                1383

SEQ ID NO: 188         moltype = AA  length = 461
FEATURE                Location/Qualifiers
source                 1..461
                       mol_type = protein
                       organism = Synthetic construct
SEQUENCE: 188
MAPVAVWAAL AVGLELWAAA HALPAQVAFT PYAPEPGSTC RLREYYDQTA QMCCSKCSPG  60
QHAKVFCTKT SDTVCDSCED STYTQLWNWV PECLSCGSRC SSDQVETQAC TREQNRICTC  120
RPGWYCALSK QEGCRLCAPL RKCRPGFGVA RPGTETSDVV CKPCAPGTFS NTTSSTDICR  180
PHQICNVVAI PGNASMDAVC TSTSPTRSMA PGAVHLPQPV STRSQHTQPT PEPSTAPSTS  240
FLLPMGPSPP AEGSTGDFAL PVGLIVGVTA LGLLIIGVVN CVIMTQVKKK PLCLQREAKV  300
PHLPADKARG TQGPEQQHLL ITAPSSSSSS LESSASALDR RAPTRNQPQA PGVEASGAGE  360
ARASTGSSDS SPGGHGIQVN VTCIVNVCSS SDHSSQCSSQ ASSTMGDTDS SPSESPKDEQ  420
VPFSKEECAF RSQLETPETL LGSTEEKPLP LGVPDAGMKP S                       461

SEQ ID NO: 189         moltype = DNA  length = 1383
FEATURE                Location/Qualifiers
source                 1..1383
                       mol_type = other DNA
                       organism = Synthetic construct
SEQUENCE: 189
atggcgcccg tcgccgtctg ggccgcgctg gccgtcggac tggagctctg ggctgcggcg  60
cacgccttgc ccgcccaggt ggcatttaca ccctacgccc cggagcccgg gagcacatgc  120
cggctcagag aatactatga ccagacagct cagatgtgct gcagcaaatg ctcgccgggc  180
caacatgcaa aagtcttctg taccaagacc tcggacaccg tgtgtgactc ctgtgaggac  240
agcacataca cccagctctg gaactgggtt cccgagtgct tgagctgtgg ctcccgctgt  300
```

-continued

```
agctctgacc aggtggaaac tcaagcctgc actcgggaac agaaccgcat ctgcacctgc  360
aggcccggct ggtactgcgc gctgagcaag caggaggggt gccggctgtg cgcgccgctg  420
cgcaagtgcc gcccgggctt cggcgtggcc agaccaggaa ctgaaacatc agacgtggtg  480
tgcaagccct gtgccccggg gacgttctcc aacacgactt catccacgga tatttgcagg  540
ccccaccaga tctgtaacgt ggtggccatc cctgggaatg caagcatgga tgcagtctgc  600
acgtccacgt cccccacccg gagtatggcc ccaggggcag tacacttacc ccagccagtg  660
tccacacgat cccaacacac gcagccaact ccagaaccca gcactgctcc aagcacctcc  720
ttcctgctcc caatgggccc cagcccccca gctgaaggga gcacttgcga cttcgctctt  780
ccagttggac tgattgtggg tgtgacagcc ttgggtctac taataatagg agtggtgaac  840
tgtgtcatca tgacccaggt gaaaaagaag cccttgtgcc tgcagagaga agccaaggtg  900
cctcacttgc ctgccgataa ggcccggggt acacagggcc ccgagcagca gcacctgctg  960
atcacagcgc cgagctccag cagcagctcc ctggagagct cggccagtgc gttggacaga  1020
agggcgccca ctcggaacca gccacaggca ccaggcgtgg aggccagtgg ggccggggag  1080
gcccgggcca gcaccgggag ctcagattct tcccctggtg gccatgggac ccaggtcaat  1140
gtcacctgca tcgtgaacgt ctgtagcagc tctgaccaca gctcacagtg ctcctcccaa  1200
gccagctcca caatgggaga cacagattcc agcccctcgg agtccccgaa ggacgagcag  1260
gtccccttct ccaaggagga atgtgccttt cggtcacagc tggagacgcc agagaccctg  1320
ctggggagca ccgaagagaa gcccctgccc cttggagtgc ctgatgctgg gatgaagccc  1380
agt                                                                1383

SEQ ID NO: 190          moltype = AA  length = 461
FEATURE                 Location/Qualifiers
source                  1..461
                        mol_type = protein
                        organism = Synthetic construct
SEQUENCE: 190
MAPVAVWAAL AVGLELWAAA HALPAQVAFT PYAPEPGSTC RLREYYDQTA QMCCSKCSPG  60
QHAKVFCTKT SDTVCDSCED STYTQLWNWV PECLSCGSRC SSDQVETQAC TREQNRICTC  120
RPGWYCALSK QEGCRLCAPL RKCRPGFGVA RPGTETSDVV CKPCAPGTFS NTTSSTDICR  180
PHQICNVVAI PGNASMDAVC TSTSPTRSMA PGAVHLPQPV STRSQHTQPT PEPSTAPSTS  240
FLLPMGPSPP AEGSTCDFAL PVGLIVGVTA LGLLIIGVVN CVIMTQVKKK PLCLQREAKV  300
PHLPADKARG TQGPEQQHLL ITAPSSSSSS LESSASALDR RAPTRNQPQA PGVEASGAGE  360
ARASTGSSDS SPGGHGTQVN VTCIVNVCSS SDHSSQCSSQ ASSTMGDTDS SPSESPKDEQ  420
VPFSKEECAF RSQLETPETL LGSTEEKPLP LGVPDAGMKP S                      461

SEQ ID NO: 191          moltype = DNA  length = 1383
FEATURE                 Location/Qualifiers
source                  1..1383
                        mol_type = genomic DNA
                        organism = Homo sapiens
SEQUENCE: 191
atggcgcccg tcgccgtctg ggccgcgctg gccgtcggac tggagctctg ggctgcggcg  60
cacgccttgc ccgcccaggt ggcatttaca ccctacgccc cggagcccgg gagcacatgc  120
cggctcagag aatactatga ccagacagct cagatgtgct gcagcaaatg ctcgccgggc  180
caacatgcaa aagtcttctg taccaagacc tcggacaccg tgtgtgactc ctgtgaggac  240
agcacataca cccagctctg gaactgggtt cccgagtgct tgagctgtgg ctcccgctgt  300
agctctgacc aggtggaaac tcaagcctgc actcgggaac agaaccgcat ctgcacctgc  360
aggcccggct ggtactgcgc gctgagcaag caggaggggt gccggctgtg cgcgccgctg  420
cgcaagtgcc gcccgggctt cggcgtggcc agaccaggaa ctgaaacatc agacgtggtg  480
tgcaagccct gtgccccggg gacgttctcc aacacgactt catccacgga tatttgcagg  540
ccccaccaga tctgtaacgt ggtggccatc cctgggaatg caagcatgga tgcagtctgc  600
acgtccacgt cccccacccg gagtatggcc ccaggggcag tacacttacc ccagccagtg  660
tccacacgat cccaacacac gcagccaact ccagaaccca gcactgctcc aagcacctcc  720
ttcctgctcc caatgggccc cagcccccca gctgaaggga gcactggcga cttcgctctt  780
ccagttggac tgattgtggg tgtgacagcc ttgggtctac taataatagg agtggtgaac  840
tgtgtcatca tgacccaggt gaaaaagaag cccttgtgcc tgcagagaga agccaaggtg  900
cctcacttgc ctgccgataa ggcccggggt acacagggcc ccgagcagca gcacctgctg  960
atcacagcgc cgagctccag cagcagctcc ctggagagct cggccagtgc gttggacaga  1020
agggcgccca ctcggaacca gccacaggca ccaggcgtgg aggccagtgg ggccggggag  1080
gcccgggcca gcaccgggag ctcagattct tcccctggtg gccatgggac ccaggtcaat  1140
gtcacctgca tcgtgaacgt ctgtagcagc tctgaccaca gctcacagtg ctcctcccaa  1200
gccagctcca caatgggaga cacagattcc agcccctcgg agtccccgaa ggacgagcag  1260
gtccccttct ccaaggagga atgtgccttt cggtcacagc tggagacgcc agagaccctg  1320
ctggggagca ccgaagagaa gcccctgccc cttggagtgc ctgatgctgg gatgaagccc  1380
agt                                                                1383

SEQ ID NO: 192          moltype = AA  length = 461
FEATURE                 Location/Qualifiers
source                  1..461
                        mol_type = protein
                        organism = Homo sapiens
SEQUENCE: 192
MAPVAVWAAL AVGLELWAAA HALPAQVAFT PYAPEPGSTC RLREYYDQTA QMCCSKCSPG  60
QHAKVFCTKT SDTVCDSCED STYTQLWNWV PECLSCGSRC SSDQVETQAC TREQNRICTC  120
RPGWYCALSK QEGCRLCAPL RKCRPGFGVA RPGTETSDVV CKPCAPGTFS NTTSSTDICR  180
PHQICNVVAI PGNASMDAVC TSTSPTRSMA PGAVHLPQPV STRSQHTQPT PEPSTAPSTS  240
FLLPMGPSPP AEGSTGDFAL PVGLIVGVTA LGLLIIGVVN CVIMTQVKKK PLCLQREAKV  300
PHLPADKARG TQGPEQQHLL ITAPSSSSSS LESSASALDR RAPTRNQPQA PGVEASGAGE  360
ARASTGSSDS SPGGHGTQVN VTCIVNVCSS SDHSSQCSSQ ASSTMGDTDS SPSESPKDEQ  420
```

```
VPFSKEECAF RSQLETPETL LGSTEEKPLP LGVPDAGMKP S                461

SEQ ID NO: 193          moltype = DNA  length = 1179
FEATURE                 Location/Qualifiers
source                  1..1179
                        mol_type = other DNA
                        organism = Synthetic construct
SEQUENCE: 193
atggaggagc cgcagtcaga tcctagcgtc gagcccccctc tgagtcagga aacattttca  60
gacctatgga aactacttcc tgaaaacaac gttctgtccc ccttgccgtc ccaagcaatg  120
gatgatttga tgctgtcccc ggacgatatt gaacaatggt tcactgaaga cccaggtcca  180
gatgaagctc ccagaatgcc agaggctgct ccccgcgtgg cccctgcacc agcagctcct  240
acaccggcgg cccctgcacc agcccccctcc tggcccctgt catcttctgt cccttcccag  300
aaaacctacc agggcagcta cggtttccgt ctgggcttct tgcattctgg gacagccaag  360
tctgtgactt gcacgtactc ccctgccctc aacaagatgt tttgccaact ggccaagacc  420
tgccctgtgc agctgtgggt tgattccaca cccccgcccg gcacccgcgt ccgcgccatg  480
gccatctaca agcagtcaca gcacatgacg gaggttgtga ggcgctgccc ccatcatgag  540
cgctgctcag atagcgatgg tctggcccct cctcagcatc ttatccgagt ggaaggaaat  600
ttgcgtgtgg agtatttgga tgacagaaac acttttcgac atagtgtggt ggtgccctat  660
gagccgcctg aggttggctc tgactgtacc accatccact acaactacat gtgtaacagt  720
tcctgcatgg gcggcatgaa ccggaggccc atcctcacca tcatcacact ggaagactcc  780
agtggtaatc tactgggacg gaacagcttt gaggtgcctg tttgtgcctg tcctgggaga  840
gaccggcgca cagaggaaga gaatctccgt aagaaagggg agcctcacca cgagctgccc  900
ccagggagca ctaagcgagc actgcccaac aacaccagct cctctcccca gccaaagaag  960
aaaccactgg atggagaata tttcaccctt cagatccgtg ggcgtgagcg cttcgagatg  1020
ttccgagagc tgaatgaggc cttggaactc aaggatgccc aggctgggaa ggagccaggg  1080
gggagcaggg ctcactccag ccacctgaag tccaaaaagg gtcagtctac ctcccgccat  1140
aaaaaactca tgttcaagac agaagggcct gactcagac                       1179

SEQ ID NO: 194          moltype = AA  length = 393
FEATURE                 Location/Qualifiers
source                  1..393
                        mol_type = protein
                        organism = Synthetic construct
SEQUENCE: 194
MEEPQSDPSV EPPLSQETFS DLWKLLPENN VLSPLPSQAM DDLMLSPDDI EQWFTEDPGP  60
DEAPRMPEAA PRVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVPVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                              393

SEQ ID NO: 195          moltype = DNA  length = 1179
FEATURE                 Location/Qualifiers
source                  1..1179
                        mol_type = genomic DNA
                        organism = Homo sapiens
SEQUENCE: 195
atggaggagc cgcagtcaga tcctagcgtc gagcccccctc tgagtcagga aacattttca  60
gacctatgga aactacttcc tgaaaacaac gttctgtccc ccttgccgtc ccaagcaatg  120
gatgatttga tgctgtcccc ggacgatatt gaacaatggt tcactgaaga cccaggtcca  180
gatgaagctc ccagaatgcc agaggctgct ccccgcgtgg cccctgcacc agcagctcct  240
acaccggcgg cccctgcacc agcccccctcc tggcccctgt catcttctgt cccttcccag  300
aaaacctacc agggcagcta cggtttccgt ctgggcttct tgcattctgg gacagccaag  360
tctgtgactt gcacgtactc ccctgccctc aacaagatgt tttgccaact ggccaagacc  420
tgccctgtgc agctgtgggt tgattccaca cccccgcccg gcacccgcgt ccgcgccatg  480
gccatctaca agcagtcaca gcacatgacg gaggttgtga ggcgctgccc ccatcatgag  540
cgctgctcag atagcgatgg tctggcccct cctcagcatc ttatccgagt ggaaggaaat  600
ttgcgtgtgg agtatttgga tgacagaaac acttttcgac atagtgtggt ggtgccctat  660
gagccgcctg aggttggctc tgactgtacc accatccact acaactacat gtgtaacagt  720
tcctgcatgg gcggcatgaa ccggaggccc atcctcacca tcatcacact ggaagactcc  780
agtggtaatc tactgggacg gaacagcttt gaggtgcgtg tttgtgcctg tcctgggaga  840
gaccggcgca cagaggaaga gaatctccgt aagaaagggg agcctcacca cgagctgccc  900
ccagggagca ctaagcgagc actgcccaac aacaccagct cctctcccca gccaaagaag  960
aaaccactgg atggagaata tttcaccctt cagatccgtg ggcgtgagcg cttcgagatg  1020
ttccgagagc tgaatgaggc cttggaactc aaggatgccc aggctgggaa ggagccaggg  1080
gggagcaggg ctcactccag ccacctgaag tccaaaaagg gtcagtctac ctcccgccat  1140
aaaaaactca tgttcaagac agaagggcct gactcagac                       1179

SEQ ID NO: 196          moltype = AA  length = 393
FEATURE                 Location/Qualifiers
source                  1..393
                        mol_type = protein
                        organism = Homo sapiens
SEQUENCE: 196
MEEPQSDPSV EPPLSQETFS DLWKLLPENN VLSPLPSQAM DDLMLSPDDI EQWFTEDPGP  60
DEAPRMPEAA PRVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
```

```
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVRVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                               393

SEQ ID NO: 197          moltype = DNA  length = 2370
FEATURE                 Location/Qualifiers
source                  1..2370
                        mol_type = other DNA
                        organism = Synthetic construct
SEQUENCE: 197
atgattgtgc taccactgta ctccagactg gacaaaagat tcctgtgcct taagaacatt  60
agaaccttcc tgtccacctg ctgtgagaag ttcggcctca agcggagcga gctcttcgaa  120
gcctttgacc tcttcgatgt gcaggatttt ggcaaggtca tctacaccct gtctgctctg  180
tcctggaccc cgatcgccca gaacaggggg atcatgccct tccccaccga ggaggagagt  240
gtaggtgatg aagacatcta cagtggcctg tccgaccaga tcgacgacac ggtggaggag  300
gatgaggacc tgtatgactg cgtggagaat gaggaggcgg aaggcgacga gatctatgag  360
gacctcatgc gctcggagcc cgtgtccatg ccgcccaaga tgacagagta tgacaagcgc  420
tgctgctgcc tgcgggagat ccagcagacg gaggagaagt acactgacac gctgggctcc  480
atccagcagc atttcttgaa gcccctgcaa cggttcctga aacctcaaga cattgagatc  540
atctttatca acattgagga cctgcttcgt gttcatactc acttcctaaa ggagatgaag  600
gaagccctgg gcacccctgg cgcagccaat ctctaccagg tcttcatcaa atacaaggag  660
aggttcctcg tctatggccg ctactgcagc caggtggagt cagccagcaa acacctggac  720
cgtgtggccg cagcccggga ggacgtgcag atgaagctgg aggaatgttc tcagagagcc  780
aacaacggga ggttcaccct gcgggacctg ctgatggtgc ctatgcagcg agttctcaaa  840
tatcacctcc ttctccagga gctggtgaaa cacacgcagg aggcgatgga gaaggagaac  900
ctgcggctgg ccctggatgc catgagggac ctggctcagt gcgtgaacga ggtcaagcga  960
gacaacgaga cactgcgaca gatcaccaat ttccagctgt ccattgagaa cctggaccag  1020
tctctggctc actatggccg gcccaagatc gacggggaac tcaagatcac ctcggtggaa  1080
cggcgctcca agatggacag gtatgccttc ctgctcgaca aagctctact catctgtaag  1140
cgcaggggag actcctatga cctcaaggac tttgtaaacc tgcacagctt ccaggttcgg  1200
gatgactctt caggagaccg agacaacaag aagtggagcc acatgttcct cctgatcgag  1260
gaccaaggtg cccagggcta tgagctgttc ttcaagacaa gagaattgaa gaagaagtgg  1320
atggagcagt ttgagatggc catctccaac atctatccgg agaatgccac cgccaacggg  1380
catgacttcc agatgttctc ctttgaggag accacatcct gcaaggcctg tcagatgctg  1440
cttagaggta ccttctatca gggctaccgc tgccatcggt gccgggcatc tgcacacaag  1500
gagtgtctgg ggagggtccc tccatgtggc cgacatgggc aagatttccc aggaactatg  1560
aagaaggaca aactacatcg cagggctcag gacaaaaaga ggaatgagct gggtctgccc  1620
aagatggagg tgtttcagga atactacggg cttcctccac cccctggagc cattggaccc  1680
tttctacggc tcaaccctgg agacattgtg gagctcacga aggctgaggc tgaacagaac  1740
tggtgggagg gcagaaatac atctactaat gaaattggct ggtttccttg taacagggtg  1800
aagccctatg tccatggccc tcctcaggac ctgtctgttc atctctggta cgcaggcccc  1860
atggagcggg caggggcaga gagcatcctg gccaaccgct cggacgggac tttcttggtg  1920
cggcagaggg tgaaggatgc agcagaattt gccatcagca ttaaatataa cgtcgaggtc  1980
aagcacatta aaatcatgac agcagaagga ctgtaccgga tcacagagaa aaaggctttc  2040
cgggggctta cggagctggt ggagttttac cagcagaact ctctaaagga ttgcttcaag  2100
tctctggaca ccaccttgca gttccccttc aaggagcctg aaaagagaac catcagcagg  2160
ccagcagtgg gaagcacaaa gtattttggc acagccaaag cccgctatga cttctgcgcc  2220
cgacaccgat cagagctgtc gctcaaggag ggtgacatca tcaagatcct taacaagaag  2280
ggacagcaag gctggtggcg aggggagatc tatggccggg ttggctggtt ccctgccaac  2340
tacgtggagg aagattattc tgaatactgc                                  2370

SEQ ID NO: 198          moltype = AA  length = 790
FEATURE                 Location/Qualifiers
source                  1..790
                        mol_type = protein
                        organism = Synthetic construct
SEQUENCE: 198
MIVLPLYSRL DKRFLCLKNI RTFLSTCCEK FGLKRSELFE AFDLFDVQDF GKVIYTLSAL  60
SWTPIAQNRG IMPFPTEEES VGDEDIYSGL SDQIDDTVEE DEDLYDCVEN EEAEGDEIYE  120
DLMRSEPVSM PPKMTEYDKR CCCLREIQQT EEKYTDTLGS IQQHFLKPLQ RFLKPQDIEI  180
IFINIEDLLR VHTHFLKEMK EALGTPGAAN LYQVFIKYKE RFLVYGRYCS QVESASKHLD  240
RVAAAREDVQ MKLEECSQRA NNGRFTLRDL LMVPMQRVLK YHLLLQELVK HTQEAMEKEN  300
LRLALDAMRD LAQCVNEVKR DNETLRQITN FQLSIENLDQ SLAHYGRPKI DGELKITSVE  360
RRSKMDRYAF LLDKALLICK RRGDSYDLKD FVNLHSFQVR DDSSGDRDNK KWSHMFLLIE  420
DQGAQGYELF FKTRELKKKW MEQFEMAISN IYPENATANG HDFQMFSFEE TTSCKACQML  480
LRGTFYQGYR CHRCRASAHK ECLGRVPPCG RHGQDFPGTM KKDKLHRRAQ DKKRNELGLP  540
KMEVFQEYYG LPPPPGAIGP FLRLNPGDIV ELTKAEAEQN WWEGRNTSTN EIGWFPCNRV  600
KPYVHGPPQD LSVHLWYAGP MERAGAESIL ANRSDGTFLV RQRVKDAAEF AISIKYNVEV  660
KHIKIMTAEG LYRITEKKAF RGLTELVEFY QQNSLKDCFK SLDTTLQFPF KEPEKRTISR  720
PAVGSTKYFG TAKARYDFCA RHRSELSLKE GDIIKILNKK GQQGWWRGEI YGRVGWFPAN  780
YVEEDYSEYC                                                         790

SEQ ID NO: 199          moltype = DNA  length = 2370
FEATURE                 Location/Qualifiers
source                  1..2370
                        mol_type = other DNA
                        organism = Synthetic construct
SEQUENCE: 199
```

```
atgattgtgc taccactgta ctccagactg gacaaaagat tcctgtgcct taagaacatt  60
agaaccttcc tgtccacctg ctgtgagaag ttcggcctca agcggagcga gctcttcgaa  120
gcctttgacc tcttcgatgt gcaggatttt ggcaaggtca tctacaccct gtctgctctg  180
tcctggaccc cgatcgccca gaacaggggg atcatgccct tccccaccga ggaggagagt  240
gtaggtgatg aagacatcta cagtggcctg tccgaccaga tcgacgacac ggtggaggag  300
gatgaggacc tgtatgactg cgtggagaat gaggaggcgg aaggcgacga gatctatgag  360
gacctcatgc gctcggagcc cgtgtccatg ccgcccaaga tgacagagta tgacaagcgc  420
tgctgctgcc tgcgggagat ccagcagacg gaggagaagt acactgacac gctgggctcc  480
atccagcagc atttcttgaa gcccctgcaa cggttcctga aacctcaaga cattgagatc  540
atctttatca acattgagga cctgcttcgt gttcatactc acttcctaaa ggagatgaag  600
gaagccctgg gcacccctgg cgcagccaat ctctaccagg tcttcatcaa atacaaggag  660
aggttcctcg tctatggccg ctactgcagc caggtggagt cagccagcaa acacctggac  720
cgtgtggccg cagcccggga ggacgtgcag atgaagctgg aggaatgttc tcagagagcc  780
aacaacggga ggttcaccct gcgggacctg ctgatggtgc ctatgcagcg agttctcaaa  840
tatcacctcc ttctccagga gctggtgaaa cacacgcagg aggcgatgga gaaggagaac  900
ctgcggctgg ccctggatgc catgagggac ctggctcagt gcgtgaacga ggtcaagcga  960
gacaacgaga cactgcgaca gatcaccaat ttccagctgt ccattgagaa cctggaccag  1020
tctctggctc actatggccg gcccaagatc gacggggaac tcaagatcac ctcggtggaa  1080
cggcgctcca agatggacag gtatgccttc ctgctcgaca aagctctact catctgtaag  1140
cgcaggggag actcctatga cctcaaggac tttgtaaacc tgcacagctt ccaggttcgg  1200
gatgactctt caggagaccg agacaacaag aagtggagcc acatgttcct cctgatcgag  1260
gaccaaggtg cccagggcta tgagctgttc ttcaagacaa gagaattgaa gaagaagtgg  1320
atggagcagt ttgagatggc catctccaac atctatccgg agaatgccac cgccaacggg  1380
catgacttcc agatgttctc ctttgaggag accacatcct gcaaggcctg tcagatgctg  1440
cttagaggta ccttctatca gggctaccgc tgccatcggt gccgggcatc tgcacacaag  1500
gactgtctgg ggagggtccc tccatgtggc cgacatgggc aagatttccc aggaactatg  1560
aagaaggaca aactacatcg cagggctcag gacaaaaaga ggaatgagct gggtctgccc  1620
aagatggagg tgtttcagga atactacggg cttcctccac cccctggagc cattggaccc  1680
tttctacggc tcaaccctgg agacattgtg gagctcacga aggctgaggc tgaacagaac  1740
tggtgggagg gcagaaatac atctactaat gaaattggct ggtttccttg taacagggtg  1800
aagccctatg tccatggccc tcctcaggac ctgtctgttc atctctggta cgcaggcccc  1860
atggagcggg caggggcaga gagcatcctg gccaaccgct cggacgggac tttcttggtg  1920
cggcagaggg tgaaggatgc agcagaattt gccatcagca ttaaatataa cgtcgaggtc  1980
aagcacatta aaatcatgac agcagaagga ctgtaccgga tcacagagaa aaaggctttc  2040
cgggggctta cggagctggt ggagttttac cagcagaact ctctaaagga ttgcttcaag  2100
tctctggaca ccaccttgca gttcccettc aaggagcctg aaaagagaac catcagcagg  2160
ccagcagtgg gaagcacaaa gtattttggc acagccaaag cccgctatga cttctgcgcc  2220
cgagaccgat cagagctgtc gctcaaggag ggtgacatca tcaagatcct taacaagaag  2280
ggacagcaag gctggtggcg aggggagatc tatggccggg ttggctggtt ccctgccaac  2340
tacgtggagg aagattattc tgaatactgc                                  2370

SEQ ID NO: 200          moltype = AA  length = 790
FEATURE                 Location/Qualifiers
source                  1..790
                        mol_type = protein
                        organism = Synthetic construct
SEQUENCE: 200
MIVLPLYSRL DKRFLCLKNI RTFLSTCCEK FGLKRSELFE AFDLFDVQDF GKVIYTLSAL  60
SWTPIAQNRG IMPFPTEEES VGDEDIYSGL SDQIDDTVEE DEDLYDCVEN EEAEGDEIYE  120
DLMRSEPVSM PPKMTEYDKR CCCLREIQQT EEKYTDTLGS IQQHFLKPLQ RFLKPQDIEI  180
IFINIEDLLR VHTHFLKEMK EALGTPGAAN LYQVFIKYKE RFLVYGRYCS QVESASKHLD  240
RVAAAREDVQ MKLEECSQRA NNGRFTLRDL LMVPMQRVLK YHLLLQELVK HTQEAMEKEN  300
LRLALDAMRD LAQCVNEVKR DNETLRQITN FQLSIENLDQ SLAHYGRPKI DGELKITSVE  360
RRSKMDRYAF LLDKALLICK RRGDSYDLKD FVNLHSFQVR DDSSGDRDNK KWSHMFLLIE  420
DQGAQGYELF FKTRELKKKW MEQFEMAISN IYPENATANG HDFQMFSFEE TTSCKACQML  480
LRGTFYQGYR CHRCRASAHK DCLGRVPPCG RHGQDFPGTM KKDKLHRRAQ DKKRNELGLP  540
KMEVFQEYYG LPPPPGAIGP FLRLNPGDIV ELTKAEAEQN WWEGRNTSTN EIGWFPCNRV  600
KPYVHGPPQD LSVHLWYAGP MERAGAESIL ANRSDGTFLV RQRVKDAAEF AISIKYNVEV  660
KHIKIMTAEG LYRITEKKAF RGLTELVEFY QQNSLKDCFK SLDTTLQFPF KEPEKRTISR  720
PAVGSTKYFG TAKARYDFCA RDRSELSLKE GDIIKILNKK GQQGWWRGEI YGRVGWFPAN  780
YVEEDYSEYC                                                        790

SEQ ID NO: 201          moltype = DNA  length = 2370
FEATURE                 Location/Qualifiers
source                  1..2370
                        mol_type = other DNA
                        organism = Synthetic construct
SEQUENCE: 201
atgattgtgc taccactgta ctccagactg gacaaaagat tcctgtgcct taagaacatt  60
agaaccttcc tgtccacctg ctgtgagaag ttcggcctca agcggagcga gctcttcgaa  120
gcctttgacc tcttcgatgt gcaggatttt ggcaaggtca tctacaccct gtctgctctg  180
tcctggaccc cgatcgccca gaacaggggg atcatgccct tccccaccga ggaggagagt  240
gtaggtgatg aagacatcta cagtggcctg tccgaccaga tcgacgacac ggtggaggag  300
gatgaggacc tgtatgactg cgtggagaat gaggaggcgg aaggcgacga gatctatgag  360
gacctcatgc gctcggagcc cgtgtccatg ccgcccaaga tgacagagta tgacaagcgc  420
tgctgctgcc tgcgggagat ccagcagacg gaggagaagt acactgacac gctgggctcc  480
atccagcagc atttcttgaa gcccctgcaa cggttcctga aacctcaaga cattgagatc  540
atctttatca acattgagga cctgcttcgt gttcatactc acttcctaaa ggagatgaag  600
gaagccctgg gcacccctgg cgcagccaat ctctaccagg tcttcatcaa atacaaggag  660
```

```
aggttcctcg tctatggccg ctactgcagc caggtggagt cagccagcaa acacctggac  720
cgtgtggccg cagcccggga ggacgtgcag atgaagctgg aggaatgttc tcagagagcc  780
aacaacggga ggttcaccct gcgggacctg ctgatggtgc ctatgcagcg agttctcaaa  840
tatcacctcc ttctccagga gctggtgaaa cacacgcagg aggcgatgga gaaggagaac  900
ctgcggctgg ccctggatgc catgagggac ctggctcagt gcgtgaacga ggtcaagcga  960
gacaacgaga cactgcgaca gatcaccaat ttccagctgt ccattgagaa cctggaccag  1020
tctctggctc actatggccg gcccaagatc gacggggaac tcaagatcac ctcggtggaa  1080
cggcgctcca agatggacag gtatgccttc ctgctcgaca aagctctact catctgtaag  1140
cgcaggggag actcctatga cctcaaggac tttgtaaacc tgcacagctt ccaggttcgg  1200
gatgactctt caggagaccg agacaacaag aagtggagcc acatgttcct cctgatcgag  1260
gaccaaggtg cccagggcta tgagctgttc ttcaagacaa gagaattgaa gaagaagtgg  1320
atggagcagt ttgagatggc catctccaac atctatccgg agaatgccac cgccaacggg  1380
catgacttcc agatgttctc ctttgaggag accacatcct gcaaggcctg tcagatgctg  1440
cttagaggta ccttctatca gggctaccgc tgccatcggt gccgggcatc tgcacacaag  1500
gagtgtctgg ggagggtccc tccatgtggc cgacatgggc aagatttccc aggaactatg  1560
aagaaggaca aactacatcg cagggctcag gacaaaaaga ggaatgagct gggtctgccc  1620
aagatggagg tgtttcagga atactacggg cttcctccac cccctggagc cattggaccc  1680
tttctacggc tcaaccctgg agacattgtg gagctcacga aggctgaggc tgaacagaac  1740
tggtgggagg gcagaaatac atctactaat gaaattggct ggtttccttg taacagggtg  1800
aagccctatg tccatggccc tcctcaggac ctgtctgttc atctctggta cgcaggcccc  1860
atggagcggg caggggcaga gagcatcctg gccaaccgct cggacgggac tttcttggtg  1920
cggcagaggg tgaaggatgc agcagaattt gccatcagca ttaaatataa cgtcgaggtc  1980
aagcacatta aaatcatgac agcagaagga ctgtaccgga tcacagagaa aaaggctttc  2040
cgggggctta cggagctggt ggagttttac cagcagaact ctctaaagga ttgcttcaag  2100
tctctggaca ccaccttgca gttccccttc aaggagcctg aaaagagaac catcagcagg  2160
ccagcagtgg gaagcacaaa gtattttggc acagccaaag cccgctatga cttctgcgcc  2220
cgagaccaat cagagctgtc gctcaaggag ggtgacatca tcaagatcct taacaagaag  2280
ggacagcaag gctggtggcg aggggagatc tatggccggg ttggctggtt ccctgccaac  2340
tacgtggagg aagattattc tgaatactgc                                  2370

SEQ ID NO: 202         moltype = AA  length = 790
FEATURE                Location/Qualifiers
source                 1..790
                       mol_type = protein
                       organism = Synthetic construct
SEQUENCE: 202
MIVLPLYSRL DKRFLCLKNI RTFLSTCCEK FGLKRSELFE AFDLFDVQDF GKVIYTLSAL  60
SWTPIAQNRG IMPFPTEEES VGDEDIYSGL SDQIDDTVEE DEDLYDCVEN EEAEGDEIYE  120
DLMRSEPVSM PPKMTEYDKR CCCLREIQQT EEKYTDTLGS IQQHFLKPLQ RFLKPQDIEI  180
IFINIEDLLR VHTHFLKEMK EALGTPGAAN LYQVFIKYKE RFLVYGRYCS QVESASKHLD  240
RVAAAREDVQ MKLEECSQRA NNGRFTLRDL LMVPMQRVLK YHLLLQELVK HTQEAMEKEN  300
LRLALDAMRD LAQCVNEVKR DNETLRQITN FQLSIENLDQ SLAHYGRPKI DGELKITSVE  360
RRSKMDRYAF LLDKALLICK RRGDSYDLKD FVNLHSFQVR DDSSGDRDNK KWSHMFLLIE  420
DQGAQGYELF FKTRELKKKW MEQFEMAISN IYPENATANG HDFQMFSFEE TTSCKACQML  480
LRGTFYQGYR CHRCRASAHK ECLGRVPPCG RHGQDFPGTM KKDKLHRRAQ DKKRNELGLP  540
KMEVFQEYYG LPPPPGAIGP FLRLNPGDIV ELTKAEAEQN WWEGRNTSTN EIGWFPCNRV  600
KPYVHGPPQD LSVHLWYAGP MERAGAESIL ANRSDGTFLV RQRVKDAAEF AISIKYNVEV  660
KHIKIMTAEG LYRITEKKAF RGLTELVEFY QQNSLKDCFK SLDTTLQFPF KEPEKRTISR  720
PAVGSTKYFG TAKARYDFCA RDQSELSLKE GDIIKILNKK GQQGWWRGEI YGRVGWFPAN  780
YVEEDYSEYC                                                        790

SEQ ID NO: 203         moltype = DNA  length = 2370
FEATURE                Location/Qualifiers
source                 1..2370
                       mol_type = genomic DNA
                       organism = Homo sapiens
SEQUENCE: 203
atgattgtgc taccactgta ctccagactg gacaaaagat tcctgtgcct taagaacatt  60
agaaccttcc tgtccacctg ctgtgagaag ttcggcctca agcggagcga gctcttcgaa  120
gcctttgacc tcttcgatgt gcaggatttt ggcaaggtca tctacaccct gtctgctctg  180
tcctggaccc cgatcgccca gaacaggggg atcatgccct tccccaccga ggaggagagt  240
gtaggtgatg aagacatcta cagtggcctg tccgaccaga tcgacgacac ggtggaggag  300
gatgaggacc tgtatgactg cgtggagaat gaggaggcgg aaggcgacga gatctatgag  360
gacctcatgc gctcggagcc cgtgtccatg ccgcccaaga tgacagagta tgacaagcgc  420
tgctgctgcc tgcgggagat ccagcagacg gaggagaagt acactgacac gctgggctcc  480
atccagcagc atttcttgaa gcccctgcaa cggttcctga aacctcaaga cattgagatc  540
atctttatca acattgagga cctgcttcgt gttcatactc acttcctaaa ggagatgaag  600
gaagccctgg gcacccctgg cgcagccaat ctctaccagg tcttcatcaa atacaaggag  660
aggttcctcg tctatggccg ctactgcagc caggtggagt cagccagcaa acacctggac  720
cgtgtggccg cagcccggga ggacgtgcag atgaagctgg aggaatgttc tcagagagcc  780
aacaacggga ggttcaccct gcgggacctg ctgatggtgc ctatgcagcg agttctcaaa  840
tatcacctcc ttctccagga gctggtgaaa cacacgcagg aggcgatgga gaaggagaac  900
ctgcggctgg ccctggatgc catgagggac ctggctcagt gcgtgaacga ggtcaagcga  960
gacaacgaga cactgcgaca gatcaccaat ttccagctgt ccattgagaa cctggaccag  1020
tctctggctc actatggccg gcccaagatc gacggggaac tcaagatcac ctcggtggaa  1080
cggcgctcca agatggacag gtatgccttc ctgctcgaca aagctctact catctgtaag  1140
cgcaggggag actcctatga cctcaaggac tttgtaaacc tgcacagctt ccaggttcgg  1200
gatgactctt caggagaccg agacaacaag aagtggagcc acatgttcct cctgatcgag  1260
gaccaaggtg cccagggcta tgagctgttc ttcaagacaa gagaattgaa gaagaagtgg  1320
```

```
atggagcagt ttgagatggc catctccaac atctatccgg agaatgccac cgccaacggg  1380
catgacttcc agatgttctc ctttgaggag accacatcct gcaaggcctg tcagatgctg  1440
cttagaggta ccttctatca gggctaccgc tgccatcggt gccgggcatc tgcacacaag  1500
gagtgtctgg ggagggtccc tccatgtggc cgacatgggc aagatttccc aggaactatg  1560
aagaaggaca aactacatcg cagggctcag gacaaaaaga ggaatgagct gggtctgccc  1620
aagatggagg tgtttcagga atactacggg cttcctccac cccctggagc cattggaccc  1680
tttctacggc tcaaccctgg agacattgtg gagctcacga aggctgaggc tgaacagaac  1740
tggtgggagg gcagaaatac atctactaat gaaattggct ggtttccttg taacagggtg  1800
aagccctatg tccatggccc tcctcaggac ctgtctgttc atctctggta cgcaggcccc  1860
atggagcggg caggggcaga gagcatcctg gccaaccgct cggacgggac tttcttggtg  1920
cggcagaggg tgaaggatgc agcagaattt gccatcagca ttaaatataa cgtcgaggtc  1980
aagcacatta aaatcatgac agcagaagga ctgtaccgga tcacagagaa aaaggctttc  2040
cgggggctta cggagctggt ggagttttac cagcagaact ctctaaagga ttgcttcaag  2100
tctctggaca ccaccttgca gttccccttc aaggagcctg aaaagagaac catcagcagg  2160
ccagcagtgg gaagcacaaa gtattttggc acagccaaag cccgctatga cttctgcgcc  2220
cgagaccgat cagagctgtc gctcaaggag ggtgacatca tcaagatcct taacaagaag  2280
ggacagcaag gctggtggcg aggggagatc tatggccggg ttggctggtt ccctgccaac  2340
tacgtggagg aagattattc tgaatactgc                                   2370

SEQ ID NO: 204         moltype = AA  length = 790
FEATURE                Location/Qualifiers
source                 1..790
                       mol_type = protein
                       organism = Homo sapiens
SEQUENCE: 204
MIVLPLYSRL DKRFLCLKNI RTFLSTCCEK FGLKRSELFE AFDLFDVQDF GKVIYTLSAL  60
SWTPIAQNRG IMPFPTEEES VGDEDIYSGL SDQIDDTVEE DEDLYDCVEN EEAEGDEIYE  120
DLMRSEPVSM PPKMTEYDKR CCCLREIQQT EEKYTDTLGS IQQHFLKPLQ RFLKPQDIEI  180
IFINIEDLLR VHTHFLKEMK EALGTPGAAN LYQVFIKYKE RFLVYGRYCS QVESASKHLD  240
RVAAAREDVQ MKLEECSQRA NNGRFTLRDL LMVPMQRVLK YHLLLQELVK HTQEAMEKEN  300
LRLALDAMRD LAQCVNEVKR DNETLRQITN FQLSIENLDQ SLAHYGRPKI DGELKITSVE  360
RRSKMDRYAF LLDKALLICK RRGDSYDLKD FVNLHSFQVR DDSSGDRDNK KWSHMFLLIE  420
DQGAQGYELF FKTRELKKKW MEQFEMAISN IYPENATANG HDFQMFSFEE TTSCKACQML  480
LRGTFYQGYR CHRCRASAHK ECLGRVPPCG RHGQDFPGTM KKDKLHRRAQ DKKRNELGLP  540
KMEVFQEYYG LPPPPGAIGP FLRLNPGDIV ELTKAEAEQN WWEGRNTSTN EIGWFPCNRV  600
KPYVHGPPQD LSVHLWYAGP MERAGAESIL ANRSDGTFLV RQRVKDAAEF AISIKYNVEV  660
KHIKIMTAEG LYRITEKKAF RGLTELVEFY QQNSLKDCFK SLDTTLQPFF KEPEKRTISR  720
PAVGSTKYFG TAKARYDFCA RDRSELSLKE GDIIKILNKK GQQGWWRGEI YGRVGWFPAN  780
YVEEDYSEYC                                                         790

SEQ ID NO: 205         moltype = DNA  length = 2175
FEATURE                Location/Qualifiers
source                 1..2175
                       mol_type = genomic DNA
                       organism = Homo sapiens
SEQUENCE: 205
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
atcgtcaacc tggagagcaa gctgcggcgc ctctccaagg acagcaacaa cctggaccag  1320
agtctgccca ggaacctgcc agtaaccatc atctctcagg actttgggga tgccagcccc  1380
aggaccaatg gtcaagaagc tgacgattct tccacctcgg aggagtcacc tgaagacagc  1440
aagtacttcc tgccctacca tccgccccag cgcaggatga acctgaaggg catccagctg  1500
cagagagcca aatcccccat cagcctgaag cgaacatcag attttcaagc caaggggcac  1560
gaggaagaag gcacggatgc cagccctagc tcctgcggat ctctgcccat caccaactcc  1620
ttcaccaaga tgcagccccc ccggagccgc agcagcatca tgtcaatcac cgccgagccc  1680
ccgggaaacg actccatcgt cagacgctac aaggaggacg cgccccatcg cagatggctc  1740
aatcacaaag gagtgagaca gaaacgcctg aatgtctggc tgggaattaa gaatgaggat  1800
gctgctgaga actattttat caatgaggaa gatgaaaacc tgccccatta tgatgagaaa  1860
acctggtttg ttgaggatat caatcgagta caagcagagg acttgcttta tgggaaacct  1920
gatggtgcat tcttaattcg tgagagtagc aagaaaggat gctatgcttg ctctgtggtg  1980
```

```
gccgatgggg aagtgaagca ctgtgtgatc tacagcactg ctcggggcta tggctttgca  2040
gagccctaca acctgtacag ctctctgaag gagctagtgc tccattacca gcagacatcc  2100
ttggttcagc acaacgactc cctcaacgtc aggcttgcct accctgttca tgcacagatg  2160
ccctcgcttt gcaga                                                   2175

SEQ ID NO: 206          moltype = AA  length = 725
FEATURE                 Location/Qualifiers
source                  1..725
                        mol_type = protein
                        organism = Homo sapiens
SEQUENCE: 206
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMYKHRMNT  360
VMLQLEEVER ERDQAFHSRD EAQTQYSQCL IEKDKYRKQI RELEEKNDEM RIEMVRREAC  420
IVNLESKLRR LSKDSNNLDQ SLPRNLPVTI ISQDFGDASP RTNGQEADDS STSEESPEDS  480
KYFLPYHPPQ RRMNLKGIQL QRAKSPISLK RTSDFQAKGH EEEGTDASPS SCGSLPITNS  540
FTKMQPPRSR SSIMSITAEP PGNDSIVRRY KEDAPHRRWL NHKGVRQKRL NVWLGIKNED  600
AAENYFINEE DENLPHYDEK TWFVEDINRV QAEDLLYGKP DGAFLIRESS KKGCYACSVV  660
ADGEVKHCVI YSTARGYGFA EPYNLYSSLK ELVLHYQQTS LVQHNDSLNV RLAYPVHAQM  720
PSLCR                                                              725

SEQ ID NO: 207          moltype = DNA  length = 2040
FEATURE                 Location/Qualifiers
source                  1..2040
                        mol_type = genomic DNA
                        organism = Homo sapiens
SEQUENCE: 207
atggaagatt cgatggacat ggacatgagc cccctgaggc cccagaacta tcttttcggt  60
tgtgaactaa aggccgacaa agattatcac tttaaggtgg ataatgatga aaatgagcac  120
cagttatctt taagaacggt cagtttaggg gctggtgcaa aggatgagtt gcacattgtt  180
gaagcagagg caatgaatta cgaaggcagt ccaattaaag taacactggc aactttgaaa  240
atgtctgtac agccaacggt ttcccttggg ggctttgaaa taacaccacc agtggtctta  300
aggttgaagt gtggttcagg gccagtgcat attagtggac agcacttagt agtgtaccgc  360
cggaagcacc aggagctgca agccatgcag atggagctgc agagccctga gtacaagctg  420
agcaagctcc gcacctcgac catcatgacc gactacaacc ccaactactg ctttgctggc  480
aagacctcct ccatcagtga cctgaaggag gtgccgcgga aaaacatcac cctcattcgg  540
ggtctgggcc atggcgcctt tggggaggtg tatgaaggcc aggtgtccgg aatgcccaac  600
gacccaagcc ccctgcaagt ggctgtgaag acgctgcctg aagtgtgctc tgaacaggac  660
gaactggatt tcctcatgga agccctgatc atcagcaaat tcaaccacca gaacattgtt  720
cgctgcattg gggtgagcct gcaatccctg ccccggttca tcctgctgga gctcatggcg  780
gggggagacc tcaagtcctt cctccgagag acccgccctc gcccgagcca gccctcctcc  840
ctggccatgc tggaccttct gcacgtggct cgggacattg cctgtggctg tcagtatttg  900
gaggaaaacc acttcatcca ccgagacatt gctgccagaa actgcctctt gacctgtcca  960
ggccctggaa gagtggccaa gattggagac ttcgggatgg cccgagacat ctacagggcg  1020
agctactata gaaagggagg ctgtgccatg ctgccagtta agtggatgcc cccagaggcc  1080
ttcatggaag gaatattcac ttctaaaaca gacacatggt cctttggagt gctgctatgg  1140
gaaatctttt ctcttggata tatgccatac cccagcaaaa gcaaccagga agttctggag  1200
tttgtcacca gtggaggccg gatggaccca cccaagaact gccctgggcc tgtataccgg  1260
ataatgactc agtgctggca acatcagcct gaagacaggc ccaactttgc catcattttg  1320
gagaggattg aatactgcac ccaggacccg gatgtaatca acaccgcttt gccgatagaa  1380
tatggtccac ttgtggaaga ggaagagaaa gtgcctgtga ggcccaagga ccctgagggg  1440
gttcctcctc tcctggtctc tcaacaggca aaacgggagg aggagcgcag cccagctgcc  1500
ccaccacctc tgcctaccac ctcctctggc aaggctgcaa agaaacccac agctgcagag  1560
gtctctgttc gagtccctag agggccggcc gtggaagggg gacacgtgaa tatggcattc  1620
tctcagtcca accctccttc ggagttgcac aaggtccacg gatccagaaa caagcccacc  1680
agcttgtgga acccaacgta cggctcctgg tttacagaga aacccaccaa aaagaataat  1740
cctatagcaa agaaggagcc acacgacagg ggtaacctgg ggctggaggg aagctgtact  1800
gtcccaccta acgttgcaac tgggagactt ccgggggcct cactgctcct agagccctct  1860
tcgctgactg ccaatatgaa ggaggtacct ctgttcaggc tacgtcactt cccttgtggg  1920
aatgtcaatt acggctacca gcaacagggc ttgcccttag aagccgctac tgcccctgga  1980
gctggtcatt acgaggatac cattctgaaa agcaagaata gcatgaacca gcctgggccc  2040

SEQ ID NO: 208          moltype = AA  length = 680
FEATURE                 Location/Qualifiers
source                  1..680
                        mol_type = protein
                        organism = Homo sapiens
SEQUENCE: 208
MEDSMDMDMS PLRPQNYLFG CELKADKDYH FKVDNDENEH QLSLRTVSLG AGAKDELHIV  60
EAEAMNYEGS PIKVTLATLK MSVQPTVSLG GFEITPPVVL RLKCGSGPVH ISGQHLVVYR  120
RKHQELQAMQ MELQSPEYKL SKLRTSTIMT DYNPNYCFAG KTSSISDLKE VPRKNITLIR  180
GLGHGAFGEV YEGQVSGMPN DPSPLQVAVK TLPEVCSEQD ELDFLMEALI ISKFNHQNIV  240
RCIGVSLQSL PRFILLELMA GGDLKSFLRE TRPRPSQPSS LAMLDLLHVA RDIACGCQYL  300
EENHFIHRDI AARNCLLTCP GPGRVAKIGD FGMARDIYRA SYYRKGGCAM LPVKWMPPEA  360
FMEGIFTSKT DTWSFGVLLW EIFSLGYMPY PSKSNQEVLE FVTSGGRMDP PKNCPGPVYR  420
```

```
IMTQCWQHQP EDRPNFAIIL ERIEYCTQDP DVINTALPIE YGPLVEEEEK VPVRPKDPEG  480
VPPLLVSQQA KREEERSPAA PPPLPTTSSG KAAKKPTAAE VSVRVPRGPA VEGGHVNMAF  540
SQSNPPSELH KVHGSRNKPT SLWNPTYGSW FTEKPTKKNN PIAKKEPHDR GNLGLEGSCT  600
VPPNVATGRL PGASLLLEPS SLTANMKEVP LFRLRHFPCG NVNYGYQQQG LPLEAATAPG  660
AGHYEDTILK SKNSMNQPGP                                            680

SEQ ID NO: 209          moltype = DNA  length = 1458
FEATURE                 Location/Qualifiers
source                  1..1458
                        mol_type = genomic DNA
                        organism = Homo sapiens
SEQUENCE: 209
atgaacaact ttatcctcct ggaagaacag ctcatcaaga aatcccaaca aaagagaaga  60
acttctccct cgaactttaa agtccgcttc tttgtgttaa ccaaagccag cctggcatac  120
tttgaagatc gtcatgggaa gaagcgcacg ctgaaggggt ccattgagct ctcccgaatc  180
aaatgtgttg agattgtgaa aagtgacatc agcatcccat gccactataa atacccgttt  240
caggtggtgc atgacaacta cctcctatat gtgtttgctc cagatcgtga gagccggcag  300
cgctgggtgc tggcccttaa agaagaaacg aggaataata acagtttggt gcctaaatat  360
catcctaatt tctggatgga tgggaagtgg aggtgctgtt ctcagctgga gaagcttgca  420
acaggctgtg cccaatatga tccaaccaag aatgcttcaa agaagcctct tcctcctact  480
cctgaagaca acaggtcctc ccctgcccaa gggaaccggc aagagagtac tgtgtcattc  540
aatccgtatg agccagaact tgcaccctgg gctgcagaca aaggccccca gagagaagcc  600
ctacccatgg acacagaggt gtacgagagc ccctacgcgg accctgagga gatcaggccc  660
aaggaggttt acctggaccg aaagctgctg acgctggaag acaaagaact gggctctggt  720
aattttggaa ctgtgaaaaa gggctactac caaatgaaaa aagttgtgaa aaccgtggct  780
gtgaaaatac tgaaaaacga ggccaatgac cccgctctta aagatgagtt attagcagaa  840
gcaaatgtca tgcagcagct ggacaacccg tacatcgtgc gcatgatcgg gatatgcgag  900
gccgagtcct ggatgctagt tatggagatg gcagaacttg gtcccctcaa taagtatttg  960
cagcagaaca gacatgtcaa ggataagaac atcatagaac tggttcatca ggtttccatg  1020
ggcatgaagt acttggagga gagcaatttt gtgcacagag atctggctgc aagaaatgtg  1080
ttgctagtta cccaacatta tgccaagatc agtgatttcg gactctccaa agcactgcgt  1140
gctgatgaaa actactacaa ggcccagacc catggaaagt ggcctgtcaa gtggtacgct  1200
ccggaatgca tcaactacta caagttctcc agcaaaagcg atgtctggag ctttggagtg  1260
ttgatgtggg aagcattctc ctatgggcag aagccatatc gagggatgaa aggaagtgaa  1320
gtcaccgcta tgttagagaa aggagagcgg atggggtgcc ctgcagggtg tccaagagag  1380
atgtacgatc tcatgaatct gtgctggaca tacgatgtgg aaaacaggcc cggattcgca  1440
gcagtggaac tgcggctg                                               1458

SEQ ID NO: 210          moltype = AA  length = 486
FEATURE                 Location/Qualifiers
source                  1..486
                        mol_type = protein
                        organism = Homo sapiens
SEQUENCE: 210
MNNFILLEEQ LIKKSQQKRR TSPSNFKVRF FVLTKASLAY FEDRHGKKRT LKGSIELSRI  60
KCVEIVKSDI SIPCHYKYPF QVVHDNYLLY VFAPDRESRQ RWVLALKEET RNNNSLVPKY  120
HPNFWMDGKW RCCSQLEKLA TGCAQYDPTK NASKKPLPPT PEDNRSSPAQ GNRQESTVSF  180
NPYEPELAPW AADKGPQREA LPMDTEVYES PYADPEEIRP KEVYLDRKLL TLEDKELGSG  240
NFGTVKKGYY QMKKVVKTVA VKILKNEAND PALKDELLAE ANVMQQLDNP YIVRMIGICE  300
AESWMLVMEM AELGPLNKYL QQNRHVKDKN IIELVHQVSM GMKYLEESNF VHRDLAARNV  360
LLVTQHYAKI SDFGLSKALR ADENYYKAQT HGKWPVKWYA PECINYYKFS SKSDVWSFGV  420
LMWEAFSYGQ KPYRGMKGSE VTAMLEKGER MGCPAGCPRE MYDLMNLCWT YDVENRPGFA  480
AVELRL                                                            486

SEQ ID NO: 211          moltype = DNA  length = 1998
FEATURE                 Location/Qualifiers
source                  1..1998
                        mol_type = genomic DNA
                        organism = Homo sapiens
SEQUENCE: 211
atgaacaact ttatcctcct ggaagaacag ctcatcaaga aatcccaaca aaagagaaga  60
acttctccct cgaactttaa agtccgcttc tttgtgttaa ccaaagccag cctggcatac  120
tttgaagatc gtcatgggaa gaagcgcacg ctgaaggggt ccattgagct ctcccgaatc  180
aaatgtgttg agattgtgaa aagtgacatc agcatcccat gccactataa atacccgttt  240
caggtggtgc atgacaacta cctcctatat gtgtttgctc cagatcgtga gagccggcag  300
cgctgggtgc tggcccttaa agaagaaacg aggaataata acagtttggt gcctaaatat  360
catcctaatt tctggatgga tgggaagtgg aggtgctgtt ctcagctgga gaagcttgca  420
acaggctgtg cccaatatga tccaaccaag aatgcttcaa agaagcctct tcctcctact  480
cctgaagaca acaggcgacc actttgggaa cctgaagaaa ctgtggtcat tgccttatat  540
gactaccaaa ccaatgatcc tcaggaactc gcactgcggc gcaacgaaga gtactgcctg  600
ctggacagtt ctgagattca ctggtggaga gtccaggaca ggaatgggca tgaaggatat  660
gtaccaagca gttatctggt ggaaaaatct ccaaataatc tggaaaccta tgagtggtac  720
aataagagta tcagccgaga caaagctgaa aaacttcttt tggacacaga aagaaaggag  780
aggctatcca aatttgaatc tattcgtcat tcaattgctg gaataattag gtctccaaaa  840
tctgcactgg gctcttcagc actttctgat atgatctcca tcagtgagaa gcctttggca  900
gaacaggact ggtaccatgg tgcaattccc agaatagaag ctcaagaact gttaaaaaaa  960
caaggagact ttttggtgcg agagagtcat gggaaacctg gtgaatatgt cctttctgta  1020
tattctgatg gacagaggag acattttatc atacaatatg ttgataacat gtatcgattc  1080
gagggcactg ggttttcaaa cattcctcaa cttatagatc atcactatac aacaaaacag  1140
```

-continued

```
gtcatcacta agaaatcagg tgtagttctg ctgaatccta ttcctaagga caagaaatgg  1200
attctcagtc atgaagatgt catattggga gaattactgg gcaagggaaa ttttggtgaa  1260
gtatataagg gcacattaaa ggataaaact tctgttgctg ttaaaacatg taaagaagat  1320
cttcctcagg aattgaaaat aaaattttta caagaagcca aaattctcaa gcaatatgat  1380
catcccaata ttgtcaaact tataggagtt tgcacacaaa gacagcctgt ctacatcatt  1440
atggaactgg tttcaggagg tgatttcctc acctttctga gaaggaagaa ggatgaacta  1500
aaactcaaac agttagtgaa attttcatta gacgctgctg ctggtatgtt gtatctcgag  1560
agtaaaaact gtatacacag ggaccttgct gcaagaaact gcctggtagg tgaaaataat  1620
gttctgaaaa tcagtgactt tggaatgtct cgtcaagagg atggtggagt gtattcatct  1680
tctggcttaa agcagattcc cattaaatgg acagcaccgg aagctcttaa ttatgggaga  1740
tacagttcag agagtgacgt gtggagcttt gtcatccttc tctgggagac cttcagctta  1800
ggggtttgtc cgtaccctgg aatgacaaat cagcaagcaa gagagcaagt agaaagagga  1860
taccggatgt cagctcccca gcactgtcca gaggatattt ccaaaattat gatgaagtgt  1920
tgggattata aacctgaaaa tcgccctaag ttcagtgaac ttcagaaaga gctcactatc  1980
ataaagagaa aactcaca                                               1998
```

```
SEQ ID NO: 212         moltype = AA  length = 666
FEATURE                Location/Qualifiers
source                 1..666
                       mol_type = protein
                       organism = Homo sapiens
SEQUENCE: 212
MNNFILLEEQ LIKKSQQKRR TSPSNFKVRF FVLTKASLAY FEDRHGKKRT LKGSIELSRI  60
KCVEIVKSDI SIPCHYKYPF QVVHDNYLLY VFAPDRESRQ RWVLALKEET RNNNSLVPKY  120
HPNFWMDGKW RCCSQLEKLA TGCAQYDPTK NASKKPLPPT PEDNRRPLWE PEETVVIALY  180
DYQTNDPQEL ALRRNEEYCL LDSSEIHWWR VQDRNGHEGY VPSSYLVEKS PNNLETYEWY  240
NKSISRDKAE KLLLDTERKE RLSKFESIRH SIAGIIRSPK SALGSSALSD MISISEKPLA  300
EQDWYHGAIP RIEAQELLKK QGDFLVRESH GKPGEYVLSV YSDGQRRHFI IQYVDNMYRF  360
EGTGFSNIPQ LIDHHYTTKQ VITKKSGVVL LNPIPKDKKW ILSHEDVILG ELLGKGNFGE  420
VYKGTLKDKT SVAVKTCKED LPQELKIKFL QEAKILKQYD HPNIVKLIGV CTQRQPVYII  480
MELVSGGDFL TFLRRKKDEL KLKQLVKFSL DAAAGMLYLE SKNCIHRDLA ARNCLVGENN  540
VLKISDFGMS RQEDGGVYSS SGLKQIPIKW TAPEALNYGR YSSESDVWSF VILLWETFSL  600
GVCPYPGMTN QQAREQVERG YRMSAPQHCP EDISKIMMKC WDYKPENRPK FSELQKELTI  660
IKRKLT                                                            666
```

```
SEQ ID NO: 213         moltype = DNA  length = 3597
FEATURE                Location/Qualifiers
source                 1..3597
                       mol_type = genomic DNA
                       organism = Homo sapiens
SEQUENCE: 213
atgattgtgc taccactgta ctccagactg gacaaaagat tcctgtgcct taagaacatt  60
agaaccttcc tgtccacctg ctgtgagaag ttcggcctca agcggagcga gctcttcgaa  120
gcctttgacc tcttcgatgt gcaggatttt ggcaaggtca tctacaccct gtctgctctg  180
tcctggaccc cgatcgccca gaacaggggg atcatgccct tccccaccga ggaggagagt  240
gtaggtgatg aagacatcta cagtggcctg tccgaccaga tcgacgacac ggtggaggag  300
gatgaggacc tgtatgactg cgtggagaat gaggaggcgg aaggcgacga gatctatgag  360
gacctcatgc gctcggagcc cgtgtccatg ccgcccaaga tgacagagta tgacaagcgc  420
tgctgctgcc tgcgggagat ccagcagacg gaggagaagt acactgacac gctgggctcc  480
atccagcagc atttcttgaa gcccctgcaa cggttcctga aacctcaaga cattgagatc  540
atctttatca acattgagga cctgcttcgt gttcatactc acttcctaaa ggagatgaag  600
gaagccctgg gcacccctgg cgcagccaat ctctaccagg tcttcatcaa atacaaggag  660
aggttcctcg tctatggccg ctactgcagc caggtggagt cagccagcaa acacctggac  720
cgtgtggccg cagcccggga ggacgtgcag atgaagctgg aggaatgttc tcagagagcc  780
aacaacggga ggttcaccct gcgggacctg ctgatggtgc ctatgcagcg agttctcaaa  840
tatcacctcc ttctccagga gctggtgaaa cacacgcagg aggcgatgga gaaggagaac  900
ctgcggctgg ccctggatgc catgagggac ctggctcagt gcgtgaacga ggtcaagcga  960
gacaacgaga cactgcgaca gatcaccaat ttccagctgt ccattgagaa cctggaccag  1020
tctctggctc actatggccg gcccaagatc gacgggggaac tcaagatcac ctcggtggaa  1080
cggcgctcca agatggacag gtatgccttc ctgctcgaca aagctctact catctgtaag  1140
cgcaggggag actcctatga cctcaaggac tttgtaaacc tgcacagctt ccaggttcgg  1200
gatgactctt caggagaccg agacaacaag aagtggagcc acatgttcct cctgatcgag  1260
gaccaaggtg cccagggcta tgagctgttc ttcaagacaa gagaattgaa gaagaagtgg  1320
atggagcagt ttgagatggc catctccaac atctatccgg agaatgccac cgccaacggg  1380
catgacttcc agatgttctc ctttgaggag accacatcct gcaaggcctg tcagatgctg  1440
cttagaggta ccttctatca gggctaccgc tgccatcggt gccgggcatc tgcacacaag  1500
gagtgtctgg ggagggtccc tccatgtggc cgacatgggc aagatttccc aggaactatg  1560
aagaaggaca aactacatcg cagggctcag gacaaaaaga ggaatgagct gggtctgccc  1620
aagatggagg tgtttcagga atactacggg cttcctccac cccctggagc cattggaccc  1680
tttctacggc tcaaccctgg agacattgtg gagctcacga aggctgaggc tgaacagaac  1740
tggtgggagg gcagaaatac atctactaat gaaattggct ggtttccttg taacagggtg  1800
aagccctatg tccatggccc tcctcaggac ctgtctgttc atctctggta cgcaggcccc  1860
atggagcggg caggggcaga gagcatcctg gccaaccgct cggacgggac tttcttggtg  1920
cggcagaggg tgaaggatgc agcagaattt gccatcagca ttaaatataa cgtcgaggtc  1980
aagcacatta aaatcatgac agcagaagga ctgtaccgga tcacagagaa aaaggctttc  2040
cgggggctta cggagctggt ggagttttac cagcagaact ctctaaagga ttgcttcaag  2100
tctctggaca ccaccttgca gttccccttc aaggagcctg aaaagagaac catcagcagg  2160
ccagcaggtg ttgggatggc caccaactgg gggagcctct tgcaggataa acagcagcta  2220
gaggagctgg cacggcaggc cgtggaccgg gccctggctg agggagtatt gctgaggacc  2280
```

-continued

```
tcacaggagc ccacttcctc ggaggtggtg agctatgccc cattcacgct cttcccctca  2340
ctggtcccca gtgccctgct ggagcaagcc tatgctgtgc agatggactt caacctgcta  2400
gtggatgctg tcagccagaa cgctgccttc ctggagcaaa ctctttccag caccatcaaa  2460
caggatgact ttaccgctcg tctctttgac atccacaagc aagtcctaaa agagggcatt  2520
gcccagactg tgttcctggg cctgaatcgc tcagactaca tgttccagcg cagcgcagat  2580
ggctccccag ccctgaaaca gatcgaaatc aacaccatct ctgccagctt tgggggcctg  2640
gcctcccgga ccccagctgt gcaccgacat gttctcagtg tcctgagtaa gaccaaagaa  2700
gctggcaaga tcctctctaa taatcccagc aagggactgg ccctgggaat tgccaaagcc  2760
tgggagctct acggctcacc caatgctctg gtgctactga ttgctcaaga gaaggaaaga  2820
aacatatttg accagcgtgc catagagaat gagctactgg ccaggaacat ccatgtgatc  2880
cgacgaacat ttgaagatat ctctgaaaag gggtctctgg accaagaccg aaggctgttt  2940
gtggatggcc aggaaattgc tgtggtttac ttccgggatg gctacatgcc tcgtcagtac  3000
agtctacaga attgggaagc acgtctactg ctggagaggt cacatgctgc caagtgccca  3060
gacattgcca cccagctggc tggactaagg aaggtgcagc aggagctaag caggccgggc  3120
atgctggaga tgttgctccc tggccagcct gaggctgtgg cccgcctccg cgccaccttt  3180
gctggcctct actcactgga tgtgggtgaa gaaggggacc aggccatcgc cgaggccctt  3240
gctgccccta gccggtttgt gctaaagccc cagagagagg gtggaggtaa caacctatat  3300
ggggaggaaa tggtacaggc cctgaaacag ctgaaggaca gtgaggagag ggcctcctac  3360
atcctcatgg agaagatcga acctgagcct tttgagaatt gcctgctacg gcctggcagc  3420
cctgcccgag tggtccagtg catttcagag ctgggcatct ttggggtcta tgtcaggcag  3480
gaaaagacac tcgtgatgaa caagcacgtg ggcatctac ttcgaaccaa agccatcgag  3540
catgcagatg gtggtgtggc agcgggagtg gcagtcctgg acaacccata ccctgtg     3597
```

```
SEQ ID NO: 214         moltype = AA  length = 1199
FEATURE                Location/Qualifiers
source                 1..1199
                       mol_type = protein
                       organism = Homo sapiens
SEQUENCE: 214
MIVLPLYSRL DKRFLCLKNI RTFLSTCCEK FGLKRSELFE AFDLFDVQDF GKVIYTLSAL  60
SWTPIAQNRG IMPFPTEEES VGDEDIYSGL SDQIDDTVEE DEDLYDCVEN EEAEGDEIYE  120
DLMRSEPVSM PPKMTEYDKR CCCLREIQQT EEKYTDTLGS IQQHFLKPLQ RFLKPQDIEI  180
IFINIEDLLR VHTHFLKEMK EALGTPGAAN LYQVFIKYKE RFLVYGRYCS QVESASKHLD  240
RVAAAREDVQ MKLEECSQRA NNGRFTLRDL LMVPMQRVLK YHLLLQELVK HTQEAMEKEN  300
LRLALDAMRD LAQCVNEVKR DNETLRQITN FQLSIENLDQ SLAHYGRPKI DGELKITSVE  360
RRSKMDRYAF LLDKALLICK RRGDSYDLKD FVNLHSFQVR DDSSGDRDNK KWSHMFLLIE  420
DQGAQGYELF FKTRELKKKW MEQFEMAISN IYPENATANG HDFQMFSFEE TTSCKACQML  480
LRGTFYQGYR CHRCRASAHK ECLGRVPPCG RHGQDFPGTM KKDKLHRRAQ DKKRNELGLP  540
KMEVFQEYYG LPPPPGAIGP FLRLNPGDIV ELTKAEAEQN WWEGRNTSTN EIGWFPCNRV  600
KPYVHGPPQD LSVHLWYAGP MERAGAESIL ANRSDGTFLV RQRVKDAAEF AISIKYNVEV  660
KHIKIMTAEG LYRITEKKAF RGLTELVEFY QQNSLKDCFK SLDTTLQFPF KEPEKRTISR  720
PAGVGMATNW GSLLQDKQQL EELARQAVDR ALAEGVLLRT SQEPTSSEVV SYAPFTLFPS  780
LVPSALLEQA YAVQMDFNLL VDAVSQNAAF LEQTLSSTIK QDDFTARLFD IHKQVLKEGI  840
AQTVFLGLNR SDYMFQRSAD GSPALKQIEI NTISASFGGL ASRTPAVHRH VLSVLSKTKE  900
AGKILSNNPS KGLALGIAKA WELYGSPNAL VLLIAQEKER NIFDQRAIEN ELLARNIHVI  960
RRTFEDISEK GSLDQDRRLF VDGQEIAVVY FRDGYMPRQY SLQNWEARLL LERSHAAKCP  1020
DIATQLAGTK KVQQELSRPG MLEMLLPGQP EAVARLRATF AGLYSLDVGE EGDQAIAEAL  1080
AAPSRFVLKP QREGGGNNLY GEEMVQALKQ LKDSEERASY ILMEKIEPEP FENCLLRPGS  1140
PARVVQCISE LGIFGVYVRQ EKTLVMNKHV GHLLRTKAIE HADGGVAAGV AVLDNPYPV   1199
```

```
SEQ ID NO: 215         moltype = DNA  length = 2157
FEATURE                Location/Qualifiers
source                 1..2157
                       mol_type = genomic DNA
                       organism = Homo sapiens
SEQUENCE: 215
atggaagatt cgatggacat ggacatgagc cccctgaggc cccagaacta tcttttcggt  60
tgtgaactaa aggccgacaa agattatcac tttaaggtgg ataatgatga aaatgagcac  120
cagttatctt taagaacggt cagtttaggg gctggtgcaa aggatgagtt gcacattgtt  180
gaagcagagg caatgaatta cgaaggcagt ccaattaaag taacactggc aactttgaaa  240
atgtctgtac agccaacggt ttcccttggg ggctttgaaa taacaccacc agtggtctta  300
aggttgaagt gtggttcagg gccagtgcat attagtggac agcacttagt agctgtggag  360
gaagatgcag agtcagaaga tgaagaggag gaggatgtga aactcttaag tatatctgga  420
aagcggtctg cccctggagg tggtagcaag gttccacaga aaaaagtaaa acttgctgct  480
gatgaagatg atgacgatga tgatgaagag gatgatgatg aagatgatga tgatgatgat  540
tttgatgatg aggaagctga agaaaaagcg ccagtgaaga aatctatacg agatactcca  600
gccaaaaatg cacaaaagtc aaatcagaat ggaaaagact caaaaccatc atcaacacca  660
agatcaaaag gacaagaatc cttcaagaaa caggaaaaaa ctcctaaaac accaaaagga  720
cctagttctg tagaagacat taaagcaaaa atgcaagcaa gtatagaaaa agagaacaag  780
aacctggttc atggtaatgt gtgtggccgg aacatcctgc tggcccggct ggggttggca  840
gagggcacca gccccttcat caagctgagt gatcctggcg tgggcctggg cgccctctcc  900
agggaggagc gggtggagag gatcccctgg ctggcccccg aatgcctacc aggtggggcc  960
aacagcctaa gcaccgccat ggacaagtgg gggtttggcg ccaccctcct ggagatctgc  1020
tttgacggag aggcccctct gcagagccgc agtccctccg agaaggagca tttctaccag  1080
aggcagcacc ggctgcccga gccctcctgc ccacagctgg ccacactcac cagccagtgt  1140
ctgacctatg agccaaccca gaggccatca ttccgcacca tcctgcgtga cctcacccgg  1200
ctgcagcccc acaatcttgc tgacgtcttg actgtgaacc cggactcacc ggcgtcggac  1260
cctacggttt tccacaagcg ctatttgaaa aagatccgag atctgggcga gggtcacttc  1320
ggcaaggtca gcttgtactg ctacgatccg accaacgacg gcactggcga gatggtggcg  1380
```

```
gtgaaagccc tcaaggcaga ctgcggcccc cagcaccgct cgggctggaa gcaggagatt  1440
gacattctgc gcacgctcta ccacgagcac atcatcaagt acaagggctg ctgcgaggac  1500
caaggcgaga agtcgctgca gctggtcatg gagtacgtgc cctgggcag cctccgagac  1560
tacctgcccc ggcacagcat cgggctggcc cagctgctgc tcttcgccca gcagatctgc  1620
gagggcatgg cctatctgca ctcgcagcac tacatccacc gagacctagc cgcgcgcaac  1680
gtgctgctgg acaacgacag gctggtcaag atcggggact ttggcctagc caaggccgtg  1740
cccgaaggcc acgagtacta ccgcgtgcgc gaggatgggg acagccccgt gttctggtat  1800
gccccagagt gcctgaagga gtataagttc tactatgcgt cagatgtctg gtccttcggg  1860
gtgaccctgt atgagctgct gacgcactgt gactccagcc agagcccccc cacgaaattc  1920
cttgagctca taggcattgc tcagggtcag atgacagttc tgagactcac tgagttgctg  1980
gaacgagggg agaggctgcc acggcccgac aaatgtccct gtgaggtcta tcatctcatg  2040
aagaactgct gggagacaga ggcgtccttt cgcccaacct tcgagaacct catacccatt  2100
ctgaagacag tccatgagaa gtaccaaggc caggcccctt cagtgttcag cgtgtgc     2157

SEQ ID NO: 216         moltype = AA  length = 719
FEATURE                Location/Qualifiers
source                 1..719
                       mol_type = protein
                       organism = Homo sapiens
SEQUENCE: 216
MEDSMDMDMS PLRPQNYLFG CELKADKDYH FKVDNDENEH QLSLRTVSLG AGAKDELHIV  60
EAEAMNYEGS PIKVTLATLK MSVQPTVSLG GFEITPPVVL RLKCGSGPVH ISGQHLVAVE  120
EDAESEDEEE EDVKLLSISG KRSAPGGGSK VPQKKVKLAA DEDDDDDDEE DDDEDDDDDD  180
FDDEEAEEKA PVKKSIRDTP AKNAQKSNQN GKDSKPSSTP RSKGQESFKK QEKTPKTPKG  240
PSSVEDIKAK MQASIEKENK NLVHGNVCGR NILLARLGLA EGTSPFIKLS DPGVGLGALS  300
REERVERIPW LAPECLPGGA NSLSTAMDKW GFGATLLEIC FDGEAPLQSR SPSEKEHFYQ  360
RQHRLPEPSC PQLATLTSQC LTYEPTQRPS FRTILRDLTR LQPHNLADVL TVNPDSPASD  420
PTVFHKRYLK KIRDLGEGHF GKVSLYCYDP TNDGTGEMVA VKALKADCGP QHRSGWKQEI  480
DILRTLYHEH IIKYKGCCED QGEKSLQLVM EYVPLGSLRD YLPRHSIGLA QLLLFAQQIC  540
EGMAYLHSQH YIHRDLAARN VLLDNDRLVK IGDFGLAKAV PEGHEYYRVR EDGDSPVFWY  600
APECLKEYKF YYASDVWSFG VTLYELLTHC DSSQSPPTKF LELIGIAQGQ MTVLRLTELL  660
ERGERLPRPD KCPCEVYHLM KNCWETEASF RPTFENLIPI LKTVHEKYQG QAPSVFSVC   719

SEQ ID NO: 217         moltype = DNA  length = 600
FEATURE                Location/Qualifiers
source                 1..600
                       mol_type = genomic DNA
                       organism = Homo sapiens
SEQUENCE: 217
atgctcaggc tgctcttggc tctcaactta ttcccttcaa ttcaagtaac aggaaacaag  60
attttggtga agcagtcgcc catgcttgta gcgtacgaca atgcggtcaa ccttagctgc  120
aagtattcct acaatctctt ctcaagggag ttccgggcat cccttcacaa aggactggat  180
agtgctgtgg aagtctgtgt tgtatatggg aattactccc agcagcttca ggtttactca  240
aaaacggggt tcaactgtga tgggaaattg ggcaatgaat cagtgacatt ctacctccag  300
aatttgtatg ttaaccaaac agatatttac ttctgcaaaa ttgaagttat gtatcctcct  360
ccttacctag agaatgagaa gagcaatgga accattatcc atgtgaaagg gaaacacctt  420
tgtccaagtc ccctatttcc cggaccttct aagccctttt gggtgctggt ggtggttggt  480
ggagtcctgg cttgctatag cttgctagta acagtggcct ttattatttt ctgggaccct  540
gaaccgtgcc ctgattctga ctttcttttg tggatattgg ctgccgtctc aagtgggctg  600

SEQ ID NO: 218         moltype = AA  length = 200
FEATURE                Location/Qualifiers
source                 1..200
                       mol_type = protein
                       organism = Homo sapiens
SEQUENCE: 218
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLENEKSNG TIIHVKGKHL CPSPLFPGPS KPFWVLVVVG GVLACYSLLV TVAFIIFWDP  180
EPCPDSDFLL WILAAVSSGL                                             200

SEQ ID NO: 219         moltype = DNA  length = 666
FEATURE                Location/Qualifiers
source                 1..666
                       mol_type = genomic DNA
                       organism = Homo sapiens
SEQUENCE: 219
atgaaatccg gtttgtggta tttctttctt ttctgccttc gcatcaaggt tttgacggga  60
aacaagattt tggtgaagca gtcgcccatg cttgtagcgt acgacaatgc ggtcaacctt  120
agctgcaagt attcctacaa tctcttctca agggagttcc gggcatccct tcacaaagga  180
ctggatagtg ctgtggaagt ctgtgttgta tatgggaatt actcccagca gcttcaggtt  240
tactcaaaaa cggggttcaa ctgtgatggg aaattgggca atgaatcagt gacattctac  300
ctccagaatt tgtatgttaa ccaaacagat atttacttct gcaaaattga agttatgtat  360
cctcctcctt acctagagaa tgagaagagc aatggaacca ttatccatgt gaaagggaaa  420
cacctttgtc caagtcccct atttcccgga ccttctaagc ccttttgggt gctggtggtg  480
gttggtggag tcctggcttg ctatagcttg ctagtaacag tggcctttat tattttctgg  540
gtgaggagta agaggagcag gctcctgcac agtgactaca tgaacatgac tccccgccgc  600
cccgggccca cccgcaagca ttaccagccc tatgccccac cacgcgactt cgcagcctat  660
cgctcc                                                            666
```

```
SEQ ID NO: 220         moltype = AA  length = 222
FEATURE                Location/Qualifiers
source                 1..222
                       mol_type = protein
                       organism = Homo sapiens
SEQUENCE: 220
MKSGLWYFFL FCLRIKVLTG NKILVKQSPM LVAYDNAVNL SCKYSYNLFS REFRASLHKG  60
LDSAVEVCVV YGNYSQQLQV YSKTGFNCDG KLGNESVTFY LQNLYVNQTD IYFCKIEVMY  120
PPPYLENEKS NGTIIHVKGK HLCPSPLFPG PSKPFWVLVV VGGVLACYSL LVTVAFIIFW  180
VRSKRSRLLH SDYMNMTPRR PGPTRKHYQP YAPPRDFAAY RS                    222

SEQ ID NO: 221         moltype = DNA  length = 1215
FEATURE                Location/Qualifiers
source                 1..1215
                       mol_type = genomic DNA
                       organism = Homo sapiens
SEQUENCE: 221
atgctccaag catgtaagat ggaaggtttc cccettgttc cacctccttc tgaagacctg  60
gtgccctacg acaccgacct ctatcaacga caaacgcatg agtactaccc ctatctgagt  120
agtgatggag aaagccattc agaccattac tgggatttcc atcctcatca cgttcatagt  180
gagtttgaga gtttcgctga gaacaacttc acagaattgc agagcgttca accaccccag  240
ctccagcaac tttacaggca catggaactt gagcagatgc acgttctgga tactccaatg  300
gttcctccgc atccgtcact tggccatcaa gtttcttatc tgcctcgaat gtgcctccaa  360
tacccctctc tcagtccggc gcagcctagt agtgacgaag aagaaggcga gcgacagtca  420
cctccccttgg aggtgtcaga tggtgaagcg gacgggctgg aaccaggacc gggacttctt  480
ccgggagaaa ctggttctaa aaaaaagatt cggctgtatc aatttctttt ggacctcctg  540
agaagcctgg cagagttgaa gtcaagcctg gtcaacgaaa gcgaaggtgc ggccgggggt  600
gccggcattc ctggagttcc tggggcgggt gctggcgcga gaggggaagc ggaagccctt  660
gggagagaac acgcggcaca gcgattgttc ccggacaaac tccctgaacc tttggaggat  720
ggacttaaag ccccagagtg cacttctggt atgtacaagg aaaccgtgta ctccgcattt  780
aatctcctga tgcactaccc tccaccaagt ggggccggac agcatccaca gccgcaacca  840
cccttgcaca aagctaatca gccgccccac ggagtgcccc agctgagtct ttacgagcat  900
tttaatagtc cacacccgac gccagcccca gcagacataa gccaaaaaca ggtccaccgg  960
ccactccaga ccccagacct gagcggattt tatagcctta cctcaggctc tatgggacag  1020
ttgccacata ctgtaagctg gtttactcac ccgtctctta tgcttggatc cggtgtgccg  1080
ggtcatcccg ctgcaattcc acatcctgca attgtgccgc cgtcaggtaa acaagagctc  1140
cagcctttcg accgaaacct caagacccag gcggaatcaa aagcagaaaa agaagcgaag  1200
aagccgacaa tcaaa                                                  1215

SEQ ID NO: 222         moltype = AA  length = 405
FEATURE                Location/Qualifiers
source                 1..405
                       mol_type = protein
                       organism = Homo sapiens
SEQUENCE: 222
MLQACKMEGF PLVPPPSEDL VPYDTDLYQR QTHEYYPYLS SDGESHSDHY WDFHPHHVHS  60
EFESFAENNF TELQSVQPPQ LQQLYRHMEL EQMHVLDTPM VPPHPSLGHQ VSYLPRMCLQ  120
YPSLSPAQPS SDEEEGERQS PPLEVSDGEA DGLEPGPGLL PGETGSKKKI RLYQFLLDLL  180
RSLAELKSSL VNESEGAAGG AGIPGVPGAG AGARGEAEAL GREHAAQRLF PDKLPEPLED  240
GLKAPECTSG MYKETVYSAF NLLMHYPPPS GAGQHPQPQP PLHKANQPPH GVPQLSLYEH  300
FNSPHPTPAP ADISQKQVHR PLQTPDLSGF YSLTSGSMGQ LPHTVSWFTH PSLMLGSGVP  360
GHPAAIPHPA IVPPSGKQEL QPFDRNLKTQ AESKAEKEAK KPTIK                 405

SEQ ID NO: 223         moltype = DNA  length = 2817
FEATURE                Location/Qualifiers
source                 1..2817
                       mol_type = genomic DNA
                       organism = Homo sapiens
SEQUENCE: 223
atggctggct acgaatacgt gagcccggag cagctggctg gctttgataa gtacaagacc  60
acgctccatt atccagcccc aaagcgcaac aagcccactg tctatggtgt gtccccccaac  120
tacgacaagt gggagatgga acgcacggac atcaccatga agcacaagct gggcgggggc  180
cagtacgggg aggtgtacga gggcgtgtgg aagaaataca gcctgacggt ggccgtgaag  240
accttgaagg aggacaccat ggaggtggaa gagttcttga aagaagctgc agtcatgaaa  300
gagatcaaac accctaacct ggtgcagctc cttggggtct gcacccggga gcccccgttc  360
tatatcatca ctgagttcat gacctacggg aacctcctgg actacctgag ggagtgcaac  420
cggcaggagg tgaacgccgt ggtgctgctg tacatggcca ctcagatctc gtcagccatg  480
gagtacctgg agaagaaaaa cttcatccac agagatcttg ctgcccgaaa ctgcctggta  540
ggggagaacc acttggtgaa ggtagctgat tttggcctga gcaggttgat gacaggggac  600
acctacacag cccatgctgg agccaagttc cccatcaaat ggactgcacc cgagagcctg  660
gcctacaaca agttctccat caagtccgac gtctgggcat ttggagtatt gctttgggaa  720
attgctacct atggcatgtc cccttacccg ggaattgacc tgtcccaggt gtatgagctg  780
ctagagaagg actaccgcat ggagcgccca gaaggctgcc cagagaaggt ctatgaactc  840
atgcgagcat gttggcagtg gaatccctct gaccggccct cctttgctga aatccaccaa  900
gcctttgaaa caatgttcca ggaatccagt atctcagacg aagtggaaaa ggagctgggg  960
aaacaaggcg tccgtggggc tgtgagtacc ttgctgcagg ccccagagct gcccaccaag  1020
acgaggacct ccaggagagc tgcagagcac agagacacca ctgacgtgcc tgagatgcct  1080
cactccaagg gccagggaga gagcgatcct ctggaccatg agcctgccgt gtctccattg  1140
```

```
ctccctcgaa aagagcgagg tcccccggag ggcggcctga atgaagatga gcgccttctc  1200
cccaaagaca aaaagaccaa cttgttcagc gccttgatca agaagaagaa gaagacagcc  1260
ccaacccctc ccaaacgcag cagctccttc cgggagatgg acggccagcc ggagcgcaga  1320
ggggccggcg aggaagaggg ccgagacatc agcaacgggg cactggcttt cacccccttg  1380
gacacagctg acccagccaa gtccccaaag cccagcaatg gggctggggt ccccaatgga  1440
gccctccggg agtccggggg ctcaggcttc cggtctcccc acctgtggaa gaagtccagc  1500
acgctgacca gcagccgcct agccaccggc gaggaggagg gcggtggcag ctccagcaag  1560
cgcttcctgc gctcttgctc cgcctcctgc gttccccatg gggccaagga cacggagtgg  1620
aggtcagtca cgctgcctcg ggacttgcag tccacgggaa gacagtttga ctcgtccaca  1680
tttggagggc acaaaagtga gaagccggct ctgcctcgga agagggcagg ggagaacagg  1740
tctgaccagg tgacccgagg cacagtaacg cctcccccca ggctggtgaa aaagaatgag  1800
gaagctgctg atgaggtctt caaagacatc atggagtcca gcccgggctc cagcccgccc  1860
aacctgactc caaaacccct ccggcggcag gtcaccgtgg cccctgcctc gggcctcccc  1920
cacaaggaag aagctggaaa gggcagtgcc ttagggaccc ctgctgcagc tgagccagtg  1980
acccccacca gcaaagcagg ctcaggtgca ccagggggca ccagcaaggg ccccgccgag  2040
gagtccagag tgaggaggca caagcactcc tctgagtcgc cagggaggga caaggggaaa  2100
ttgtccaggc tcaaacctgc cccgccgccc ccaccagcag cctctgcagg gaaggctgga  2160
ggaaagccct cgcagagccc gagccaggag gcggccgggg aggcagtcct gggcgcaaag  2220
acaaaagcca cgagtctggt tgatgctgtg aacagtgacg ctgccaagcc cagccagccg  2280
ggagagggcc tcaaaaagcc cgtgctcccg gccactccaa agccacagtc cgccaagccg  2340
tcggggaccc ccatcagccc agcccccgtt ccctccacgt tgccatcagc atcctcggcc  2400
ctggcagggg accagccgtc ttccaccgcc ttcatccctc tcatatcaac ccgagtgtct  2460
cttcggaaaa cccgccagcc tccagagcgg atcgccagcg gtgccatcac caagggcgtg  2520
gtcctggaca gcaccgaggc gctgtgcctc gccatctcta ggaactccga gcagatggcc  2580
agccacagcg cagtgctgga ggccggcaaa aacctctaca cgttctgcgt gagctatgtg  2640
gattccatcc agcaaatgag gaacaagttt gccttccgag aggccatcaa caaactggag  2700
aataatctcc gggagcttca gatctgcccg gcgacagcag gcagtggtcc agcggccact  2760
caggacttca gcaagctcct cagttcggtg aaggaaatca gtgacatagt gcagagg     2817
```

```
SEQ ID NO: 224          moltype = AA  length = 939
FEATURE                 Location/Qualifiers
source                  1..939
                        mol_type = protein
                        organism = Homo sapiens
SEQUENCE: 224
MAGYEYVSPE QLAGFDKYKT TLHYPAPKRN KPTVYGVSPN YDKWEMERTD ITMKHKLGGG  60
QYGEVYEGVW KKYSLTVAVK TLKEDTMEVE EFLKEAAVMK EIKHPNLVQL LGVCTREPPF  120
YIITEFMTYG NLLDYLRECN RQEVNAVVLL YMATQISSAM EYLEKKNFIH RDLAARNCLV  180
GENHLVKVAD FGLSRLMTGD TYTAHAGAKF PIKWTAPESL AYNKFSIKSD VWAFGVLLWE  240
IATYGMSPYP GIDLSQVYEL LEKDYRMERP EGCPEKVYEL MRACWQWNPS DRPSFAEIHQ  300
AFETMFQESS ISDEVEKELG KQGVRGAVST LLQAPELPTK TRTSRRAAEH RDTTDVPEMP  360
HSKGQGESDP LDHEPAVSPL LPRKERGPPE GGLNEDERLL PKDKKTNLFS ALIKKKKKTA  420
PTPPKRSSSF REMDGQPERR GAGEEEGRDI SNGALAFTPL DTADPAKSPK PSNGAGVPNG  480
ALRESGGSGF RSPHLWKKSS TLTSSRLATG EEEGGGSSSK RFLRSCSASC VPHGAKDTEW  540
RSVTLPRDLQ STGRQFDSST FGGHKSEKPA LPRKRAGENR SDQVTRGTVT PPPRLVKKNE  600
EAADEVFKDI MESSPGSSPP NLTPKPLRRQ VTVAPASGLP HKEEAGKGSA LGTPAAAEPV  660
TPTSKAGSGA PGGTSKGPAE ESRVRRHKHS SESPGRDKGK LSRLKPAPPP PPAASAGKAG  720
GKPSQSPSQE AAGEAVLGAK TKATSLVDAV NSDAAKPSQP GEGLKKPVLP ATPKPQSAKP  780
SGTPISPAPV PSTLPSASSA LAGDQPSSTA FIPLISTRVS LRKTRQPPER IASGAITKGV  840
VLDSTEALCL AISRNSEQMA SHSAVLEAGK NLYTFCVSYV DSIQQMRNKF AFREAINKLE  900
NNLRELQICP ATAGSGPAAT QDFSKLLSSV KEISDIVQR                         939
```

```
SEQ ID NO: 225          moltype = DNA  length = 1791
FEATURE                 Location/Qualifiers
source                  1..1791
                        mol_type = other DNA
                        organism = Synthetic construct
SEQUENCE: 225
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
```

```
atcgtcaacc tggagagcaa gctgcggcgc ctctccaagg acagcaacaa cctggaccag  1320
agtctgccca ggaacctgcc agtaaccatc tggctcaatc acaaaggagt gagacagaaa  1380
cgcctgaatg tctggctggg aattaagaat gaggatgctg ctgagaacta ttttatcaat  1440
gaggaagatg aaaacctgcc ccattatgat gagaaaacct ggtttgttga ggatatcaat  1500
cgagtacaag cagaggactt gctttatggg aaacctgatg gtgcattctt aattcgtgag  1560
agtagcaaga aaggatgcta tgcttgctct gtggtggccg atggggaagt gaagcactgt  1620
gtgatctaca gcactgctcg gggctatggc tttgcagagc cctacaacct gtacagctct  1680
ctgaaggagc tagtgctcca ttaccagcag acatccttgg ttcagcacaa cgactccctc  1740
aacgtcaggc ttgcctaccc tgttcatgca cagatgccct cgctttgcag a           1791

SEQ ID NO: 226          moltype = AA  length = 597
FEATURE                 Location/Qualifiers
source                  1..597
                        mol_type = protein
                        organism = Synthetic construct
SEQUENCE: 226
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMYKHRMNT  360
VMLQLEEVER ERDQAFHSRD EAQTQYSQCL IEKDKYRKQI RELEEKNDEM RIEMVRREAC  420
IVNLESKLRR LSKDSNNLDQ SLPRNLPVTI WLNHKGVRQK RLNVWLGIKN EDAAENYFIN  480
EEDENLPHYD EKTWFVEDIN RVQAEDLLYG KPDGAFLIRE SSKKGCYACS VVADGEVKHC  540
VIYSTARGYG FAEPYNLYSS LKELVLHYQQ TSLVQHNDSL NVRLAYPVHA QMPSLCR     597

SEQ ID NO: 227          moltype = DNA  length = 1707
FEATURE                 Location/Qualifiers
source                  1..1707
                        mol_type = other DNA
                        organism = Synthetic construct
SEQUENCE: 227
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagctgg aggagaagaa cgatgagatg aggatcgaga tggtgcggcg ggaggcctgc  1260
atcgtctggc tcaatcacaa aggagtgaga cagaaacgcc tgaatgtctg gctgggaatt  1320
aagaatgagg atgctgctga gaactatttt atcaatgagg aagatgaaaa cctgccccat  1380
tatgatgaga aaacctggtt tgttgaggat atcaatcgag tacaagcaga ggacttgctt  1440
tatgggaaac ctgatggtgc attcttaatt cgtgagagta gcaagaaagg atgctatgct  1500
tgctctgtgg tggccgatgg ggaagtgaag cactgtgtga tctacagcac tgctcggggc  1560
tatggctttg cagagcccta caacctgtac agctctctga aggagctagt gctccattac  1620
cagcagacat ccttggttca gcacaacgac tccctcaacg tcaggcttgc ctaccctgtt  1680
catgcacaga tgccctcgct ttgcaga                                      1707

SEQ ID NO: 228          moltype = AA  length = 569
FEATURE                 Location/Qualifiers
source                  1..569
                        mol_type = protein
                        organism = Synthetic construct
SEQUENCE: 228
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMYKHRMNT  360
VMLQLEEVER ERDQAFHSRD EAQTQYSQCL IEKDKYRKQI RELEEKNDEM RIEMVRREAC  420
IVWLNHKGVR QKRLNVWLGI KNEDAAENYF INEEDENLPH YDEKTWFVED INRVQAEDLL  480
YGKPDGAFLI RESSKKGCYA CSVVADGEVK HCVIYSTARG YGFAEPYNLY SSLKELVLHY  540
QQTSLVQHND SLNVRLAYPV HAQMPSLCR                                    569
```

```
SEQ ID NO: 229          moltype = DNA  length = 1647
FEATURE                 Location/Qualifiers
source                  1..1647
                        mol_type = other DNA
                        organism = Synthetic construct
SEQUENCE: 229
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagctcaga cacagtactc gcagtgctta atcgaaaagg acaagtacag gaagcagatc  1200
cgcgagtggc tcaatcacaa aggagtgaga cagaaacgcc tgaatgtctg gctgggaatt  1260
aagaatgagg atgctgctga gaactatttt atcaatgagg aagatgaaaa cctgccccat  1320
tatgatgaga aaacctggtt tgttgaggat atcaatcgag tacaagcaga ggacttgctt  1380
tatgggaaac ctgatggtgc attcttaatt cgtgagagta gcaagaaagg atgctatgct  1440
tgctctgtgg tggccgatgg ggaagtgaag cactgtgtga tctacagcac tgctcggggc  1500
tatggctttg cagagcccta caacctgtac agctctctga aggagctagt gctccattac  1560
cagcagacat ccttggttca gcacaacgac tccctcaacg tcaggcttgc ctaccctgtt  1620
catgcacaga tgccctcgct ttgcaga                                     1647

SEQ ID NO: 230          moltype = AA  length = 549
FEATURE                 Location/Qualifiers
source                  1..549
                        mol_type = protein
                        organism = Synthetic construct
SEQUENCE: 230
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMYKHRMNT  360
VMLQLEEVER ERDQAFHSRD EAQTQYSQCL IEKDKYRKQI REWLNHKGVR QKRLNVWLGI  420
KNEDAAENYF INEEDENLPH YDEKTWFVED INRVQAEDLL YGKPDGAFLI RESSKKGCYA  480
CSVVADGEVK HCVIYSTARG YGFAEPYNLY SSLKELVLHY QQTSLVQHND SLNVRLAYPV  540
HAQMPSLCR                                                         549

SEQ ID NO: 231          moltype = DNA  length = 1587
FEATURE                 Location/Qualifiers
source                  1..1587
                        mol_type = other DNA
                        organism = Synthetic construct
SEQUENCE: 231
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgctgc agctggagga ggtggagcgg gagcgggacc aggccttcca ctcccgagat  1140
gaagcttggc tcaatcacaa aggagtgaga cagaaacgcc tgaatgtctg gctgggaatt  1200
```

```
aagaatgagg atgctgctga gaactatttt atcaatgagg aagatgaaaa cctgccccat  1260
tatgatgaga aaacctggtt tgttgaggat atcaatcgag tacaagcaga ggacttgctt  1320
tatgggaaac ctgatggtgc attcttaatt cgtgagagta gcaagaaagg atgctatgct  1380
tgctctgtgg tggccgatgg ggaagtgaag cactgtgtga tctacagcac tgctcggggc  1440
tatggctttg cagagcccta caacctgtac agctctctga aggagctagt gctccattac  1500
cagcagacat ccttggttca gcacaacgac tccctcaacg tcaggcttgc ctaccctgtt  1560
catgcacaga tgccctcgct ttgcaga                                      1587

SEQ ID NO: 232          moltype = AA  length = 529
FEATURE                 Location/Qualifiers
source                  1..529
                        mol_type = protein
                        organism = Synthetic construct
SEQUENCE: 232
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMYKHRMNT  360
VMLQLEEVER ERDQAFHSRD EAWLNHKGVR QKRLNVWLGI KNEDAAENYF INEEDENLPH  420
YDEKTWFVED INRVQAEDLL YGKPDGAFLI RESSKKGCYA CSVVADGEVK HCVIYSTARG  480
YGFAEPYNLY SSLKELVLHY QQTSLVQHND SLNVRLAYPV HAQMPSLCR              529

SEQ ID NO: 233          moltype = DNA  length = 1527
FEATURE                 Location/Qualifiers
source                  1..1527
                        mol_type = other DNA
                        organism = Synthetic construct
SEQUENCE: 233
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctcaagt gctcgaccct gggaaaggac tgtgaaatgt acaagcaccg catgaacacg  1080
gtcatgtggc tcaatcacaa aggagtgaga cagaaacgcc tgaatgtctg gctgggaatt  1140
aagaatgagg atgctgctga gaactatttt atcaatgagg aagatgaaaa cctgccccat  1200
tatgatgaga aaacctggtt tgttgaggat atcaatcgag tacaagcaga ggacttgctt  1260
tatgggaaac ctgatggtgc attcttaatt cgtgagagta gcaagaaagg atgctatgct  1320
tgctctgtgg tggccgatgg ggaagtgaag cactgtgtga tctacagcac tgctcggggc  1380
tatggctttg cagagcccta caacctgtac agctctctga aggagctagt gctccattac  1440
cagcagacat ccttggttca gcacaacgac tccctcaacg tcaggcttgc ctaccctgtt  1500
catgcacaga tgccctcgct ttgcaga                                      1527

SEQ ID NO: 234          moltype = AA  length = 509
FEATURE                 Location/Qualifiers
source                  1..509
                        mol_type = protein
                        organism = Synthetic construct
SEQUENCE: 234
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELKCSTLGKD CEMYKHRMNT  360
VMWLNHKGVR QKRLNVWLGI KNEDAAENYF INEEDENLPH YDEKTWFVED INRVQAEDLL  420
YGKPDGAFLI RESSKKGCYA CSVVADGEVK HCVIYSTARG YGFAEPYNLY SSLKELVLHY  480
QQTSLVQHND SLNVRLAYPV HAQMPSLCR                                    509

SEQ ID NO: 235          moltype = DNA  length = 1467
FEATURE                 Location/Qualifiers
source                  1..1467
                        mol_type = other DNA
                        organism = Synthetic construct
SEQUENCE: 235
```

-continued

```
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggaggccc gccaggcaga ggagctgcga gacaagtacc tggaggagaa ggaggacctg  1020
gagctctggc tcaatcacaa aggagtgaga cagaaacgcc tgaatgtctg gctgggaatt  1080
aagaatgagg atgctgctga gaactatttt atcaatgagg aagatgaaaa cctgccccat  1140
tatgatgaga aaacctggtt tgttgaggat atcaatcgag tacaagcaga ggacttgctt  1200
tatgggaaac ctgatggtgc attcttaatt cgtgagagta gcaagaaagg atgctatgct  1260
tgctctgtgg tggccgatgg ggaagtgaag cactgtgtga tctacagcac tgctcggggc  1320
tatggctttg cagagcccta caacctgtac agctctctga aggagctagt gctccattac  1380
cagcagacat ccttggttca gcacaacgac tccctcaacg tcaggcttgc ctaccctgtt  1440
catgcacaga tgccctcgct ttgcaga                                       1467
```

```
SEQ ID NO: 236          moltype = AA  length = 489
FEATURE                 Location/Qualifiers
source                  1..489
                        mol_type = protein
                        organism = Synthetic construct
SEQUENCE: 236
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEARQAEELR DKYLEEKEDL ELWLNHKGVR QKRLNVWLGI  360
KNEDAAENYF INEEDENLPH YDEKTWFVED INRVQAEDLL YGKPDGAFLI RESSKKGCYA  420
CSVVADGEVK HCVIYSTARG YGFAEPYNLY SSLKELVLHY QQTSLVQHND SLNVRLAYPV  480
HAQMPSLCR                                                           489
```

```
SEQ ID NO: 237          moltype = DNA  length = 1407
FEATURE                 Location/Qualifiers
source                  1..1407
                        mol_type = other DNA
                        organism = Synthetic construct
SEQUENCE: 237
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgcaagg aggccctgga ggacaggcag gagctggtca acaggatcta caacctgcag  960
gaggagtggc tcaatcacaa aggagtgaga cagaaacgcc tgaatgtctg gctgggaatt  1020
aagaatgagg atgctgctga gaactatttt atcaatgagg aagatgaaaa cctgccccat  1080
tatgatgaga aaacctggtt tgttgaggat atcaatcgag tacaagcaga ggacttgctt  1140
tatgggaaac ctgatggtgc attcttaatt cgtgagagta gcaagaaagg atgctatgct  1200
tgctctgtgg tggccgatgg ggaagtgaag cactgtgtga tctacagcac tgctcggggc  1260
tatggctttg cagagcccta caacctgtac agctctctga aggagctagt gctccattac  1320
cagcagacat ccttggttca gcacaacgac tccctcaacg tcaggcttgc ctaccctgtt  1380
catgcacaga tgccctcgct ttgcaga                                       1407
```

```
SEQ ID NO: 238          moltype = AA  length = 469
FEATURE                 Location/Qualifiers
source                  1..469
                        mol_type = protein
                        organism = Synthetic construct
SEQUENCE: 238
```

-continued

```
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRKEALEDRQ ELVNRIYNLQ EEWLNHKGVR QKRLNVWLGI KNEDAAENYF INEEDENLPH  360
YDEKTWFVED INRVQAEDLL YGKPDGAFLI RESSKKGCYA CSVVADGEVK HCVIYSTARG  420
YGFAEPYNLY SSLKELVLHY QQTSLVQHND SLNVRLAYPV HAQMPSLCR              469

SEQ ID NO: 239          moltype = DNA  length = 1347
FEATURE                 Location/Qualifiers
source                  1..1347
                        mol_type = other DNA
                        organism = Synthetic construct
SEQUENCE: 239
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggccggga agcgcagcct gccagactca gacaaggcca tcctggacat cttggaacac  900
gaccgctggc tcaatcacaa aggagtgaga cagaaacgcc tgaatgtctg gctgggaatt  960
aagaatgagg atgctgctga gaactatttt atcaatgagg aagatgaaaa cctgccccat  1020
tatgatgaga aaacctggtt tgttgaggat atcaatcgag tacaagcaga ggacttgctt  1080
tatgggaaac ctgatggtgc attcttaatt cgtgagagta gcaagaaagg atgctatgct  1140
tgctctgtgg tggccgatgg ggaagtgaag cactgtgtga tctacagcac tgctcggggc  1200
tatggctttg cagagcccta caacctgtac agctctctga aggagctagt gctccattac  1260
cagcagacat ccttggttca gcacaacgac tccctcaacg tcaggcttgc ctaccctgtt  1320
catgcacaga tgccctcgct ttgcaga                                    1347

SEQ ID NO: 240          moltype = AA  length = 449
FEATURE                 Location/Qualifiers
source                  1..449
                        mol_type = protein
                        organism = Synthetic construct
SEQUENCE: 240
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAGKRSLPDS DKAILDILEH  300
DRWLNHKGVR QKRLNVWLGI KNEDAAENYF INEEDENLPH YDEKTWFVED INRVQAEDLL  360
YGKPDGAFLI RESSKKGCYA CSVVADGEVK HCVIYSTARG YGFAEPYNLY SSLKELVLHY  420
QQTSLVQHND SLNVRLAYPV HAQMPSLCR                                  449

SEQ ID NO: 241          moltype = DNA  length = 1287
FEATURE                 Location/Qualifiers
source                  1..1287
                        mol_type = other DNA
                        organism = Synthetic construct
SEQUENCE: 241
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactggagc gggagaatga aatgctgaag accaaaaacc aggagctgca gtccatcatc  840
caggcctggc tcaatcacaa aggagtgaga cagaaacgcc tgaatgtctg gctgggaatt  900
aagaatgagg atgctgctga gaactatttt atcaatgagg aagatgaaaa cctgccccat  960
tatgatgaga aaacctggtt tgttgaggat atcaatcgag tacaagcaga ggacttgctt  1020
tatgggaaac ctgatggtgc attcttaatt cgtgagagta gcaagaaagg atgctatgct  1080
tgctctgtgg tggccgatgg ggaagtgaag cactgtgtga tctacagcac tgctcggggc  1140
```

```
tatggctttg cagagcccta caacctgtac agctctctga aggagctagt gctccattac  1200
cagcagacat ccttggttca gcacaacgac tccctcaacg tcaggcttgc ctaccctgtt  1260
catgcacaga tgccctcgct ttgcaga                                      1287

SEQ ID NO: 242         moltype = AA  length = 429
FEATURE                Location/Qualifiers
source                 1..429
                       mol_type = protein
                       organism = Synthetic construct
SEQUENCE: 242
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELERENEMLK TKNQELQSII QAWLNHKGVR QKRLNVWLGI  300
KNEDAAENYF INEEDENLPH YDEKTWFVED INRVQAEDLL YGKPDGAFLI RESSKKGCYA  360
CSVVADGEVK HCVIYSTARG YGFAEPYNLY SSLKELVLHY QQTSLVQHND SLNVRLAYPV  420
HAQMPSLCR                                                          429

SEQ ID NO: 243         moltype = DNA  length = 1227
FEATURE                Location/Qualifiers
source                 1..1227
                       mol_type = other DNA
                       organism = Synthetic construct
SEQUENCE: 243
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
aatcagtctc taaaactgaa gaatgacatt gaaaatcggc ccaagaagga gcaggttctg  780
gaactgtggc tcaatcacaa aggagtgaga cagaaacgcc tgaatgtctg gctgggaatt  840
aagaatgagg atgctgctga gaactatttt atcaatgagg aagatgaaaa cctgccccat  900
tatgatgaga aaacctggtt tgttgaggat atcaatcgag tacaagcaga ggacttgctt  960
tatgggaaac ctgatggtgc attcttaatt cgtgagagta gcaagaaagg atgctatgct  1020
tgctctgtgg tggccgatgg ggaagtgaag cactgtgtga tctacagcac tgctcggggc  1080
tatggctttg cagagcccta caacctgtac agctctctga aggagctagt gctccattac  1140
cagcagacat ccttggttca gcacaacgac tccctcaacg tcaggcttgc ctaccctgtt  1200
catgcacaga tgccctcgct ttgcaga                                      1227

SEQ ID NO: 244         moltype = AA  length = 409
FEATURE                Location/Qualifiers
source                 1..409
                       mol_type = protein
                       organism = Synthetic construct
SEQUENCE: 244
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQSLKLKNDI ENRPKKEQVL ELWLNHKGVR QKRLNVWLGI KNEDAAENYF INEEDENLPH  300
YDEKTWFVED INRVQAEDLL YGKPDGAFLI RESSKKGCYA CSVVADGEVK HCVIYSTARG  360
YGFAEPYNLY SSLKELVLHY QQTSLVQHND SLNVRLAYPV HAQMPSLCR             409

SEQ ID NO: 245         moltype = DNA  length = 1167
FEATURE                Location/Qualifiers
source                 1..1167
                       mol_type = other DNA
                       organism = Synthetic construct
SEQUENCE: 245
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatcgatc agctaaagca ccggttgaat aagatggagg aggaatgtaa gctggagaga  720
```

```
aatcagtggc tcaatcacaa aggagtgaga cagaaacgcc tgaatgtctg gctgggaatt  780
aagaatgagg atgctgctga gaactatttt atcaatgagg aagatgaaaa cctgccccat  840
tatgatgaga aaacctggtt tgttgaggat atcaatcgag tacaagcaga ggacttgctt  900
tatgggaaac ctgatggtgc attcttaatt cgtgagagta gcaagaaagg atgctatgct  960
tgctctgtgg tggccgatgg ggaagtgaag cactgtgtga tctacagcac tgctcggggc  1020
tatggctttg cagagcccta caacctgtac agctctctga aggagctagt gctccattac  1080
cagcagacat ccttggttca gcacaacgac tccctcaacg tcaggcttgc ctaccctgtt  1140
catgcacaga tgccctcgct ttgcaga                                    1167

SEQ ID NO: 246         moltype = AA  length = 389
FEATURE                Location/Qualifiers
source                 1..389
                       mol_type = protein
                       organism = Synthetic construct
SEQUENCE: 246
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIDQLKHRLN KMEEECKLER  240
NQWLNHKGVR QKRLNVWLGI KNEDAAENYF INEEDENLPH YDEKTWFVED INRVQAEDLL  300
YGKPDGAFLI RESSKKGCYA CSVVADGEVK HCVIYSTARG YGFAEPYNLY SSLKELVLHY  360
QQTSLVQHND SLNVRLAYPV HAQMPSLCR                                  389

SEQ ID NO: 247         moltype = DNA  length = 1107
FEATURE                Location/Qualifiers
source                 1..1107
                       mol_type = other DNA
                       organism = Synthetic construct
SEQUENCE: 247
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
tacgcacagc tcagtgagga gaagaacatg gcggtcatga ggagccgaga cctccaactc  660
gagatctggc tcaatcacaa aggagtgaga cagaaacgcc tgaatgtctg gctgggaatt  720
aagaatgagg atgctgctga gaactatttt atcaatgagg aagatgaaaa cctgccccat  780
tatgatgaga aaacctggtt tgttgaggat atcaatcgag tacaagcaga ggacttgctt  840
tatgggaaac ctgatggtgc attcttaatt cgtgagagta gcaagaaagg atgctatgct  900
tgctctgtgg tggccgatgg ggaagtgaag cactgtgtga tctacagcac tgctcggggc  960
tatggctttg cagagcccta caacctgtac agctctctga aggagctagt gctccattac  1020
cagcagacat ccttggttca gcacaacgac tccctcaacg tcaggcttgc ctaccctgtt  1080
catgcacaga tgccctcgct ttgcaga                                    1107

SEQ ID NO: 248         moltype = AA  length = 369
FEATURE                Location/Qualifiers
source                 1..369
                       mol_type = protein
                       organism = Synthetic construct
SEQUENCE: 248
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAQLSEEKNM AVMRSRDLQL EIWLNHKGVR QKRLNVWLGI  240
KNEDAAENYF INEEDENLPH YDEKTWFVED INRVQAEDLL YGKPDGAFLI RESSKKGCYA  300
CSVVADGEVK HCVIYSTARG YGFAEPYNLY SSLKELVLHY QQTSLVQHND SLNVRLAYPV  360
HAQMPSLCR                                                        369

SEQ ID NO: 249         moltype = DNA  length = 1047
FEATURE                Location/Qualifiers
source                 1..1047
                       mol_type = other DNA
                       organism = Synthetic construct
SEQUENCE: 249
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctaca atgacgagct ggtcaaggtg aaggacgaca actacaactt agccatgcgc  600
```

```
tacgcatggc tcaatcacaa aggagtgaga cagaaacgcc tgaatgtctg gctgggaatt  660
aagaatgagg atgctgctga gaactatttt atcaatgagg aagatgaaaa cctgccccat  720
tatgatgaga aaacctggtt tgttgaggat atcaatcgag tacaagcaga ggacttgctt  780
tatgggaaac ctgatggtgc attcttaatt cgtgagagta gcaagaaagg atgctatgct  840
tgctctgtgg tggccgatgg ggaagtgaag cactgtgtga tctacagcac tgctcggggc  900
tatggctttg cagagcccta caacctgtac agctctctga aggagctagt gctccattac  960
cagcagacat ccttggttca gcacaacgac tccctcaacg tcaggcttgc ctaccctgtt  1020
catgcacaga tgccctcgct ttgcaga                                      1047

SEQ ID NO: 250         moltype = AA  length = 349
FEATURE                Location/Qualifiers
source                 1..349
                       mol_type = protein
                       organism = Synthetic construct
SEQUENCE: 250
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSYNDELVKV KDDNYNLAMR YAWLNHKGVR QKRLNVWLGI KNEDAAENYF INEEDENLPH  240
YDEKTWFVED INRVQAEDLL YGKPDGAFLI RESSKKGCYA CSVVADGEVK HCVIYSTARG  300
YGFAEPYNLY SSLKELVLHY QQTSLVQHND SLNVRLAYPV HAQMPSLCR              349

SEQ ID NO: 251         moltype = DNA  length = 987
FEATURE                Location/Qualifiers
source                 1..987
                       mol_type = other DNA
                       organism = Synthetic construct
SEQUENCE: 251
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgcgcg tggagctgct aaccttccag gagcggtact acaagatgaa ggaagagcgg  540
gacagctggc tcaatcacaa aggagtgaga cagaaacgcc tgaatgtctg gctgggaatt  600
aagaatgagg atgctgctga gaactatttt atcaatgagg aagatgaaaa cctgccccat  660
tatgatgaga aaacctggtt tgttgaggat atcaatcgag tacaagcaga ggacttgctt  720
tatgggaaac ctgatggtgc attcttaatt cgtgagagta gcaagaaagg atgctatgct  780
tgctctgtgg tggccgatgg ggaagtgaag cactgtgtga tctacagcac tgctcggggc  840
tatggctttg cagagcccta caacctgtac agctctctga aggagctagt gctccattac  900
cagcagacat ccttggttca gcacaacgac tccctcaacg tcaggcttgc ctaccctgtt  960
catgcacaga tgccctcgct ttgcaga                                      987

SEQ ID NO: 252         moltype = AA  length = 329
FEATURE                Location/Qualifiers
source                 1..329
                       mol_type = protein
                       organism = Synthetic construct
SEQUENCE: 252
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTRVELLTFQ ERYYKMKEER  180
DSWLNHKGVR QKRLNVWLGI KNEDAAENYF INEEDENLPH YDEKTWFVED INRVQAEDLL  240
YGKPDGAFLI RESSKKGCYA CSVVADGEVK HCVIYSTARG YGFAEPYNLY SSLKELVLHY  300
QQTSLVQHND SLNVRLAYPV HAQMPSLCR                                    329

SEQ ID NO: 253         moltype = DNA  length = 927
FEATURE                Location/Qualifiers
source                 1..927
                       mol_type = other DNA
                       organism = Synthetic construct
SEQUENCE: 253
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctgcg agctgctggc caggttgcgg cagctggagg atgagaagaa gcagatgacg  480
ctgacgtggc tcaatcacaa aggagtgaga cagaaacgcc tgaatgtctg gctgggaatt  540
aagaatgagg atgctgctga gaactatttt atcaatgagg aagatgaaaa cctgccccat  600
tatgatgaga aaacctggtt tgttgaggat atcaatcgag tacaagcaga ggacttgctt  660
tatgggaaac ctgatggtgc attcttaatt cgtgagagta gcaagaaagg atgctatgct  720
tgctctgtgg tggccgatgg ggaagtgaag cactgtgtga tctacagcac tgctcggggc  780
tatggctttg cagagcccta caacctgtac agctctctga aggagctagt gctccattac  840
```

```
cagcagacat ccttggttca gcacaacgac tccctcaacg tcaggcttgc ctaccctgtt  900
catgcacaga tgccctcgct ttgcaga                                      927

SEQ ID NO: 254         moltype = AA  length = 309
FEATURE                Location/Qualifiers
source                 1..309
                       mol_type = protein
                       organism = Synthetic construct
SEQUENCE: 254
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRCELLARLR QLEDEKKQMT LTWLNHKGVR QKRLNVWLGI  180
KNEDAAENYF INEEDENLPH YDEKTWFVED INRVQAEDLL YGKPDGAFLI RESSKKGCYA  240
CSVVADGEVK HCVIYSTARG YGFAEPYNLY SSLKELVLHY QQTSLVQHND SLNVRLAYPV  300
HAQMPSLCR                                                          309

SEQ ID NO: 255         moltype = DNA  length = 867
FEATURE                Location/Qualifiers
source                 1..867
                       mol_type = other DNA
                       organism = Synthetic construct
SEQUENCE: 255
atggatgact acatggagac gctgaaggat gaagaggacg ccttgtggga gaatgtggag  60
tgtaaccggc acatgctcag ccgctatatc aaccctgcca agctcacgcc ctacctgcgt  120
cagtgtaagg tcattgatga gcaggatgaa gatgaagtgc ttaatgcccc tatgctgcca  180
tccaagatca accgagcagg ccggctgttg gacattctac ataccaaggg gcaaaggggc  240
tatgtggtct tcttggagag cctagaattt tattacccag aactgtacaa actggtgact  300
gggaaagagc ccactcggag attctccacc attgtggtgg aggaaggcca cgagggcctc  360
acgcacttcc tgatgaacga ggtcatcaag ctgcagcagc agatgaaggc caaggacctg  420
caacgctggc tcaatcacaa aggagtgaga cagaaacgcc tgaatgtctg gctgggaatt  480
aagaatgagg atgctgctga gaactatttt atcaatgagg aagatgaaaa cctgccccat  540
tatgatgaga aaacctggtt tgttgaggat atcaatcgag tacaagcaga ggacttgctt  600
tatgggaaac ctgatggtgc attcttaatt cgtgagagta gcaagaaagg atgctatgct  660
tgctctgtgg tggccgatgg ggaagtgaag cactgtgtga tctacagcac tgctcggggc  720
tatggctttg cagagcccta caacctgtac agctctctga aggagctagt gctccattac  780
cagcagacat ccttggttca gcacaacgac tccctcaacg tcaggcttgc ctaccctgtt  840
catgcacaga tgccctcgct ttgcaga                                      867

SEQ ID NO: 256         moltype = AA  length = 289
FEATURE                Location/Qualifiers
source                 1..289
                       mol_type = protein
                       organism = Synthetic construct
SEQUENCE: 256
MDDYMETLKD EEDALWENVE CNRHMLSRYI NPAKLTPYLR QCKVIDEQDE DEVLNAPMLP  60
SKINRAGRLL DILHTKGQRG YVVFLESLEF YYPELYKLVT GKEPTRRFST IVVEEGHEGL  120
THFLMNEVIK LQQQMKAKDL QRWLNHKGVR QKRLNVWLGI KNEDAAENYF INEEDENLPH  180
YDEKTWFVED INRVQAEDLL YGKPDGAFLI RESSKKGCYA CSVVADGEVK HCVIYSTARG  240
YGFAEPYNLY SSLKELVLHY QQTSLVQHND SLNVRLAYPV HAQMPSLCR              289

SEQ ID NO: 257         moltype =   length =
SEQUENCE: 257
000

SEQ ID NO: 258         moltype = AA  length = 585
FEATURE                Location/Qualifiers
source                 1..585
                       mol_type = protein
                       organism = Synthetic construct
SEQUENCE: 258
MPGGGPEMDD YMETLKDEED ALWENVECNR HMLSRYINPA KLTPYLRQCK VIDEQDEDEV  60
LNAPMLPSKI NRAGRLLDIL HTKGQRGYVV FLESLEFYYP ELYKLVTGKE PTRRFSTIVV  120
EEGHEGLTHF LMNEVIKLQQ QMKAKDLQRC ELLARLRQLE DEKKQMTLTR VELLTFQERY  180
YKMKEERDSY NDELVKVKDD NYNLAMRYAQ LSEEKNMAVM RSRDLQLEID QLKHRLNKME  240
EECKLERNQS LKLKNDIENR PKKEQVLELE RENEMLKTKN QELQSIIQAG KRSLPDSDKA  300
ILDILEHDRK EALEDRQELV NRIYNLQEEA RQAEELRDKY LEEKEDLELK CSTLGKDCEM  360
YKHRMNTVML QLEEVERERD QAFHSRDEAQ TQYSQCLIEK DKYRKQIREL EEKNDEMRIE  420
MVRREACIVN LESKLRRLSK DSNNLDQSLP RNLPVTIISQ DFGDASPRTN GQEADDSSTS  480
EESPEDSKYF LPYHPPQRRM NLKGIQLQRA KSPISLKRTS DFQAKGHEEE GTDASPSSCG  540
SLPITNSFTK MQPPRSRSSI MSITAEPPGN DSIVRRYKED APHRS                  585

SEQ ID NO: 259         moltype =   length =
SEQUENCE: 259
000

SEQ ID NO: 260         moltype = AA  length = 147
FEATURE                Location/Qualifiers
source                 1..147
                       mol_type = protein
```

```
                         organism = Synthetic construct
SEQUENCE: 260
WLNHKGVRQK RLNVWLGIKN EDADENYFIN EEDENLPHYD EKTWFVEDIN RVQAEDLLYG  60
KPDGAFLIRE SSKKGCYACS VVADGEVKHC VIYSTARGYG FAEPYNLYSS LKELVLHYQQ  120
TSLVQHNDSL NVRLAYPVHA QMPSLCR                                     147

SEQ ID NO: 261           moltype = AA  length = 93
FEATURE                  Location/Qualifiers
source                   1..93
                         mol_type = protein
                         organism = Homo sapiens
SEQUENCE: 261
NDDECWSVLE GFRVTLTSVI DPSRITPYLR QCKVLNPDDE EQVLSDPNLV IRKRKVGVLL  60
DILQRTGHKG YVAFLESLEL YYPQLYKKVT GKE                              93

SEQ ID NO: 262           moltype = AA  length = 93
FEATURE                  Location/Qualifiers
source                   1..93
                         mol_type = protein
                         organism = Homo sapiens
SEQUENCE: 262
EEDALWERIE GVRHRLARAL NPAKLTPYLR QCRVIDEQDE EEVLSTYRFP CRVNRTGRLM  60
DILRCRGKRG YEAFLEALEF YYPEHFTLLT GQE                              93

SEQ ID NO: 263           moltype = AA  length = 93
FEATURE                  Location/Qualifiers
source                   1..93
                         mol_type = protein
                         organism = Homo sapiens
SEQUENCE: 263
EEDALWENVE CNRHMLSRYI NPAKLTPYLR QCKVIDEQDE DEVLNAPMLP SKINRAGRLL  60
DILHTKGQRG YVVFLESLEF YYPELYKLVT GKE                              93

SEQ ID NO: 264           moltype = AA  length = 93
FEATURE                  Location/Qualifiers
source                   1..93
                         mol_type = protein
                         organism = Homo sapiens
SEQUENCE: 264
DEETLWEMME SHRHRIVRCI CPSRLTPYLR QAKVLCQLDE EEVLHSPRLT NSAMRAGHLL  60
DLLKTRGKNG AIAFLESLKF HNPDVYTLVT GLQ                              93

SEQ ID NO: 265           moltype = AA  length = 69
FEATURE                  Location/Qualifiers
source                   1..69
                         mol_type = protein
                         organism = Homo sapiens
SEQUENCE: 265
IERERKKLLE ILQHDPDSIL DTLTSRRLIS EEEYETLENV TDLLKKSRKL LILVQKKGEA  60
TCQHFLKCL                                                         69

SEQ ID NO: 266           moltype = AA  length = 83
FEATURE                  Location/Qualifiers
source                   1..83
                         mol_type = protein
                         organism = Homo sapiens
SEQUENCE: 266
FVKENHRQLQ ARMGDLKGVL DDLQDNEVLT ENEKELVEQE KTRQSKNEAL LSMVEKKGDL  60
ALDVLFRSIS ERDPYLVSYL RQQ                                         83

SEQ ID NO: 267           moltype = AA  length = 83
FEATURE                  Location/Qualifiers
source                   1..83
                         mol_type = protein
                         organism = Homo sapiens
SEQUENCE: 267
VLKEKRKLFI HSMGEGTING LLDELLQTRV LNQEEMEKVK RENATVMDKT RALIDSVIPK  60
GAQACQICIT YICEEDSYLA ETL                                         83

SEQ ID NO: 268           moltype = AA  length = 83
FEATURE                  Location/Qualifiers
source                   1..83
                         mol_type = protein
                         organism = Homo sapiens
SEQUENCE: 268
VLKEKRKQFI RSVGEGTING LLGELLETRV LSQEEIEIVK CENATVMDKA RALLDSVIRK  60
GAPACQICIT YICEEDSHLA GTL                                         83

SEQ ID NO: 269           moltype = AA  length = 82
```

-continued

```
FEATURE                Location/Qualifiers
source                 1..82
                       mol_type = protein
                       organism = Homo sapiens
SEQUENCE: 269
LRKKRRIFIH SVGAGTINAL LDCLLEDEVI SQEDMNKVRD ENDTVMDKAR VLIDLVTGKG  60
PKSCCKFIKH LCEEDPQLAS KM                                           82

SEQ ID NO: 270         moltype = AA  length = 92
FEATURE                Location/Qualifiers
source                 1..92
                       mol_type = protein
                       organism = Homo sapiens
SEQUENCE: 270
DRLVQDTPFL TGHGRLSEQQ VDRIILQLNR YYPQILTNKE AEKFRNPKAS LRVRLCDLLS  60
HLQRSGERDC QEFYRALYIH AQPLHSRLPS RH                                92

SEQ ID NO: 271         moltype = AA  length = 83
FEATURE                Location/Qualifiers
source                 1..83
                       mol_type = protein
                       organism = Homo sapiens
SEQUENCE: 271
VLKEKRKLFI RSMGEGTING LLDELLQTRV LNKEEMEKVK RENATVMDKT RALIDSVIPK  60
GAQACQICIT YICEEDSYLA GTL                                          83

SEQ ID NO: 272         moltype = AA  length = 87
FEATURE                Location/Qualifiers
source                 1..87
                       mol_type = protein
                       organism = Homo sapiens
SEQUENCE: 272
MHPHHQETLK KNRVVLAKQL LLSELLEHLL EKDIITLEMR ELIQAKVGSF SQNVELLNLL  60
PKRGPQAFDA FCEALRETKQ GHLEDML                                      87

SEQ ID NO: 273         moltype = AA  length = 77
FEATURE                Location/Qualifiers
source                 1..77
                       mol_type = protein
                       organism = Homo sapiens
SEQUENCE: 273
NHRKKPLKVL ESLGKDFLTG VLDNLVEQNV LNWKEEEKKK YYDAKTEDKV RVMADSMQEK  60
QRMAGQMLLQ TFFNIDQ                                                 77

SEQ ID NO: 274         moltype = AA  length = 80
FEATURE                Location/Qualifiers
source                 1..80
                       mol_type = protein
                       organism = Homo sapiens
SEQUENCE: 274
NHKKKTVKML EYLGKDVLHG VFNYLAKHDV LTLKEEEKKK YYDTKIEDKA LILVDSLRKN  60
RVAHQMFTQT LLNMDQKITS                                              80

SEQ ID NO: 275         moltype = AA  length = 74
FEATURE                Location/Qualifiers
source                 1..74
                       mol_type = protein
                       organism = Homo sapiens
SEQUENCE: 275
VEELQVDQLW DALLSRELFR PHMIEDIQRA GSGSRRDQAR QLIIDLETRG SQALPLFISC  60
LEDTGQDMLA SFLR                                                    74

SEQ ID NO: 276         moltype = AA  length = 92
FEATURE                Location/Qualifiers
source                 1..92
                       mol_type = protein
                       organism = Homo sapiens
SEQUENCE: 276
MASDDLSLIR KNRMALFQQL TCVLPILDNL LKANVINKQE HDIIKQKTQI PLQARELIDT  60
ILVKGNAAAN IFKNCLKEID STLYKNLFVD KN                                92

SEQ ID NO: 277         moltype = AA  length = 90
FEATURE                Location/Qualifiers
source                 1..90
                       mol_type = protein
                       organism = Homo sapiens
SEQUENCE: 277
SNDLLLIRKN RMALFQHLTC VIPILDSLLT AGIINEQEHD VIKQKTQTSL QARELIDTIL  60
VKGNIAATVF RNSLQEAEAV LYEHLFVQQD                                   90
```

```
SEQ ID NO: 278         moltype = AA  length = 94
FEATURE                Location/Qualifiers
source                 1..94
                       mol_type = protein
                       organism = Homo sapiens
SEQUENCE: 278
MEARDKQVLR SLRLELGAEV LVEGLVLQYL YQEGILTENH IQEINAQTTG LRKTMLLLDI  60
LPSRGPKAFD TFLDSLQEFP WVREKLKKAR EEAM                              94

SEQ ID NO: 279         moltype = AA  length = 83
FEATURE                Location/Qualifiers
source                 1..83
                       mol_type = protein
                       organism = Homo sapiens
SEQUENCE: 279
SDRQINQLAQ RLGPEWEPMV LSLGLSQTDI YRCKANHPHN VQSQVVEAFI RWRQRFGKQA  60
TFQSLHNGLR AVEVDPSLLL HML                                         83

SEQ ID NO: 280         moltype = AA  length = 85
FEATURE                Location/Qualifiers
source                 1..85
                       mol_type = protein
                       organism = Homo sapiens
SEQUENCE: 280
QLLKSNRELL VTHIRNTQCL VDNLLKNDYF SAEDAEIVCA CPTQPDKVRK ILDLVQSKGE  60
EVSEFFLYLL QQLADAYVDL RPWLL                                       85

SEQ ID NO: 281         moltype = AA  length = 86
FEATURE                Location/Qualifiers
source                 1..86
                       mol_type = protein
                       organism = Homo sapiens
SEQUENCE: 281
FQAQRSQLVE LLVSGSLEGF ESVLDWLLSW EVLSWEDYEG FHLLGQPLSH LARRLLDTVW  60
NKGTWACQKL IAAAQEAQAD SQSPKL                                      86

SEQ ID NO: 282         moltype = AA  length = 81
FEATURE                Location/Qualifiers
source                 1..81
                       mol_type = protein
                       organism = Homo sapiens
SEQUENCE: 282
LQSHRPAIVR RLHSHVENML DLAWERGFVS QYECDEIRLP IFTPSQRARR LLDLATVKAN  60
GLAAFLLQHV QELPVPLALP L                                           81

SEQ ID NO: 283         moltype = AA  length = 87
FEATURE                Location/Qualifiers
source                 1..87
                       mol_type = protein
                       organism = Homo sapiens
SEQUENCE: 283
QWIQSKREDI VNQMTEACLN QSLDALLSRD LIMKEDYELV STKPTRTSKV RQLLDTTDIQ  60
GEEFAKVIVQ KLKDNKQMGL QPYPEIL                                     87

SEQ ID NO: 284         moltype = AA  length = 87
FEATURE                Location/Qualifiers
source                 1..87
                       mol_type = protein
                       organism = Homo sapiens
SEQUENCE: 284
MHPHHQETLK KNRVVLAKQL LLSELLEHLL EKDIITLEMR ELIQAKVGSF SQNVELLNLL  60
PKRGPQAFDA FCEALRETKQ GHLEDML                                     87

SEQ ID NO: 285         moltype = AA  length = 94
FEATURE                Location/Qualifiers
source                 1..94
                       mol_type = protein
                       organism = Homo sapiens
SEQUENCE: 285
MEARDKQVLR SLRLELGAEV LVEGLVLQYL YQEGILTENH IQEIKAQTTG LRKTMLLLDI  60
LPSRGPKAFD TFLDSLQEFP WVREKLEKAR EEVT                              94

SEQ ID NO: 286         moltype = AA  length = 90
FEATURE                Location/Qualifiers
source                 1..90
                       mol_type = protein
                       organism = Homo sapiens
SEQUENCE: 286
```

```
MDAKARNCLL QHREALEKDI KTSYIMDHMI SDGFLTISEE EKVRNEPTQQ QRAAMLIKMI  60
LKKDNDSYVS FYNALLHEGY KDLAALLHDG                                   90

SEQ ID NO: 287         moltype = AA  length = 89
FEATURE                Location/Qualifiers
source                 1..89
                       mol_type = protein
                       organism = Homo sapiens
SEQUENCE: 287
AAKPGLHFID QHRAALIARV TNVEWLLDAL YGKVLTDEQY QAVRAEPTNP SKMRKLFSFT  60
PAWNWTCKDL LLQALRESQS YLVEDLERS                                    89

SEQ ID NO: 288         moltype = AA  length = 87
FEATURE                Location/Qualifiers
source                 1..87
                       mol_type = protein
                       organism = Homo sapiens
SEQUENCE: 288
MTTEQRRSLQ AFQDYIRKTL DPTYILSYMA PWFREEEVQY IQAEKNNKGP MEAATLFLKF  60
LLELQEEGWF RGFLDALDHA GYSGLYE                                      87

SEQ ID NO: 289         moltype = AA  length = 81
FEATURE                Location/Qualifiers
source                 1..81
                       mol_type = protein
                       organism = Homo sapiens
SEQUENCE: 289
WDFKKIEKLE EYRLLLKRLQ PEFKTRIIPT DIISDLSECL INQECEEILQ ICSTKGMMAG  60
AEKLVECLLR SDKENWPKTL K                                            81

SEQ ID NO: 290         moltype = AA  length = 320
FEATURE                Location/Qualifiers
source                 1..320
                       mol_type = protein
                       organism = Homo sapiens
SEQUENCE: 290
FLMNEVIKLQ QQMKAKDLQR CELLARLRQL EDEKKQMTLT RVELLTFQER YYKMKEERDS  60
YNDELVKVKD DNYNLAMRYA QLSEEKNMAV MRSRDLQLEI DQLKHRLNKM EEECKLERNQ  120
SLKLKNDIEN RPKKEQVLEL ERENEMLKTK NQELQSIIQA GKRSLPDSDK AILDILEHDR  180
KEALEDRQEL VNRIYNLQEE ARQAEELRDK YLEEKEDLEL KCSTLGKDCE MYKHRMNTVM  240
LQLEEVERER DQAFHSRDEA QTQYSQCLIE KDKYRKQIRE LEEKNDEMRI EMVRREACIV  300
NLESKLRRLS KDSNNLDQSL                                              320

SEQ ID NO: 291         moltype = AA  length = 161
FEATURE                Location/Qualifiers
source                 1..161
                       mol_type = protein
                       organism = Homo sapiens
SEQUENCE: 291
QLLMTEVMKL QKKVQDLTAL LSSKDDFIKE LRVKDSLLRK HQERVQRLKE ECEAGSRELK  60
RCKEENYDLA MRLAHQSEEK GAALMRNRDL QLEIDQLKHS LMKAEDDCKV ERKHTLKLRH  120
AMEQRPSQEL LWELQQEKAL LQARVQELEA SVQEGKLDRS S                      161

SEQ ID NO: 292         moltype = AA  length = 319
FEATURE                Location/Qualifiers
source                 1..319
                       mol_type = protein
                       organism = Homo sapiens
SEQUENCE: 292
TEVRRLREAR KSQLQREQQL QARGRVLEEE RAGLEQRLRD QQQAQERCQR LREDWEAGSL  60
ELLRLKDENY MIAMRLAQLS EEKNSAVLRS RDLQLAVDQL KLKVSRLEEE CALLRRARGP  120
PPGAEEKEKE KEKEKEPDNV DLVSELRAEN QRLTASLREL QEGLQQEASR PGAPGSERIL  180
LDILEHDWRE AQDSRQELCQ KLHAVQGELQ WAEELRDQYL QEMEDLRLKH RTLQKDCDLY  240
KHRMATVLAQ LEEIEKERDQ AIQSRDRIQL QYSQSLIEKD QYRKQVRGLE AERDELLTTL  300
TSLEGTKALL EVQLQRAQG                                               319

SEQ ID NO: 293         moltype = AA  length = 282
FEATURE                Location/Qualifiers
source                 1..282
                       mol_type = protein
                       organism = Homo sapiens
SEQUENCE: 293
LAGAIGSLQE ELNQEKGQKE VLLRRCQQLQ EHLGLAETRA EGLHQLEADH SRMKREVSAH  60
FHEVLRLKDE MLSLSLHYSN ALQEKELAAS RCRSLQEELY LLKQELQRAN MVSSCELELQ  120
EQSLRTASDQ ESGDEELNRL KEENEKLRSL TFSLAEKDIL EQSLDEARGS RQELVERIHS  180
LRERAVAAER QREQYWEEKE QTLLQFQKSK MACQLYREKV NALQAQVCEL QKERDQAYSA  240
RDSAQREISQ SLVEKDSLRR QVFELTDQVC ELRTQLRQLQ AE                     282

SEQ ID NO: 294         moltype = AA  length = 135
```

```
FEATURE                Location/Qualifiers
source                 1..135
                       mol_type = protein
                       organism = Homo sapiens
SEQUENCE: 294
PRNLPVTIIS QDFGDASPRT NGQEADDSST SEESPEDSKY FLPYHPPQRR MNLKGIQLQR  60
AKSPISLKRT SDFQAKGHEE EGTDASPSSC GSLPITNSFT KMQPPRSRSS IMSITAEPPG  120
NDSIVRRYKE DAPHR                                                   135

SEQ ID NO: 295         moltype = AA  length = 217
FEATURE                Location/Qualifiers
source                 1..217
                       mol_type = protein
                       organism = Homo sapiens
SEQUENCE: 295
PRNLPVTIIS QDFGDASPRT NGQEADDSST SEESPEDSKY FLPYHPPQRR MNLKGIQLQR  60
AKSPISLKRT SDFQAKGHEE EGTDASPSSC GSLPITNSFT KMQPPRSRSS IMSITAEPPG  120
NDSIVRRYKE DAPHRSTVEE DNDSGGFDAL DLDDDSHERY SFGPSSIHSS SSSHQSEGLD  180
AYDLEQVNLM FRKFSLERPF RPSVTSVGHV RGPGPSV                           217

SEQ ID NO: 296         moltype = DNA  length = 507
FEATURE                Location/Qualifiers
source                 1..507
                       mol_type = other DNA
                       organism = Synthetic construct
SEQUENCE: 296
gatgaacctg aagggcatcc agctgcagag agccaaatcc cccatcagcc tgaagcgaac  60
atcagatttt caagccaagg ggcacgagga agaaggcacg gacgccagcc ctagctcctg  120
cggatctctg cccatcacca actccttcac caagatgcag cccccccgga gccgcagcag  180
catcatgtca atcaccgccg agcccccggg aaacgactcc atcgtcagac gctacaagga  240
ggacgcgccc catcgcagat ggctcaatca caaaggagtg agacagaaac gcctgaatgt  300
ctggctggga attaagaatg aggatgctga tgagaactat tttatcaatg aggaagatga  360
aaacctgccc cattatgatg agaaaacctg gtttgttgag gatatcaatc gagtacaagc  420
agaggacttg ctttatggga aacctgatgg tgcattctta attcgtgaga gtagcaagaa  480
aggatgctat gcttgctctg tggtggc                                      507

SEQ ID NO: 297         moltype = AA  length = 168
FEATURE                Location/Qualifiers
source                 1..168
                       mol_type = protein
                       organism = Synthetic construct
SEQUENCE: 297
MNLKGIQLQR AKSPISLKRT SDFQAKGHEE EGTDASPSSC GSLPITNSFT KMQPPRSRSS  60
IMSITAEPPG NDSIVRRYKE DAPHRRWLNH KGVRQKRLNV WLGIKNEDAD ENYFINEEDE  120
NLPHYDEKTW FVEDINRVQA EDLLYGKPDG AFLIRESSKK GCYACSVV                168

SEQ ID NO: 298         moltype = AA  length = 1068
FEATURE                Location/Qualifiers
source                 1..1068
                       mol_type = protein
                       organism = Homo sapiens
SEQUENCE: 298
MPPRPSSGEL WGIHLMPPRI LVECLLPNGM IVTLECLREA TLITIKHELF KEARKYPLHQ  60
LLQDESSYIF VSVTQEAERE EFFDETRRLC DLRLFQPFLK VIEPVGNREE KILNREIGFA  120
IGMPVCEFDM VKDPEVQDFR RNILNVCKEA VDLRDLNSPH SRAMYVYPPN VESSPELPKH  180
IYNKLDKGQI IVVIWVIVSP NNDKQKYTLK INHDCVPEQV IAEAIRKKTR SMLLSSEQLK  240
LCVLEYQGKY ILKVCGCDEY FLEKYPLSQY KYIRSCIMLG RMPNLMLMAK ESLYSQLPMD  300
CFTMPSYSRR ISTATPYMNG ETSTKSLWVI NSALRIKILC ATYVNVNIRD IDKIYVRTGI  360
YHGGEPLCDN VNTQRVPCSN PRWNEWLNYD IYIPDLPRAA RLCLSICSVK GRKGAKEEHC  420
PLAWGNINLF DYTDTLVSGK MALNLWPVPH GLEDLLNPIG VTGSNPNKET PCLELEFDWF  480
SSVVKFPDMS VIEEHANWSV SREAGFSYSH AGLSNRLARD NELRENDKEQ LKAISTRDPL  540
SEITEQEKDF LWSHRHYCVT IPEILPKLLL SVKWNSRDEV AQMYCLVKDW PPIKPEQAME  600
LLDCNYPDPM VRGFAVRCLE KYLTDDKLSQ YLIQLVQVLK YEQYLDNLLV RFLLKKALTN  660
QRIGHFFFWH LKSEMHNKTV SQRFGLLLES YCRACGMYLK HLNRQVEAME KLINLTDILK  720
QEKKDETQKV QMKFLVEQMR RPDFMDALQG FLSPLNPAHQ LGNLRLEECR IMSSAKRPLW  780
LNWENPDIMS ELLFQNNEII FKNGDDLRQD MLTLQIIRIM ENIWQNQGLD LRMLPYGCLS  840
IGDCVGLIEV VRNSHTIMQI QCKGGLKGAL QFNSHTLHQW LKDKNKGEIY DAAIDLFTRS  900
CAGYCVATFI LGIGDRHNSN IMVKDDGQLF HIDFGHFLDH KKKKFGYKRE RVPFVLTQDF  960
LIVISKGAQE CTKTREFERF QEMCYKAYLA IRQHANLFIN LFSMMLGSGM PELQSFDDIA  1020
YIRKTLALDK TEQEALEYFM KQMNDAHHGG WTTKMDWIFH TIKQHALN               1068

SEQ ID NO: 299         moltype = AA  length = 1070
FEATURE                Location/Qualifiers
source                 1..1070
                       mol_type = protein
                       organism = Homo sapiens
SEQUENCE: 299
MCFSFIMPPA MADILDIWAV DSQIASDGSI PVDFLLPTGI YIQLEVPREA TISYIKQMLW  60
KQVHNYPMFN LLMDIDSYMF ACVNQTAVYE ELEDETRRLC DVRPFLPVLK LVTRSCDPGE  120
```

```
KLDSKIGVLI GKGLHEFDSL KDPEVNEFRR KMRKFSEEKI LSLVGLSWMD WLKQTYPPEH  180
EPSIPENLED KLYGGKLIVA VHFENCQDVF SFQVSPNMNP IKVNELAIQK RLTIHGKEDE  240
VSPYDYVLQV SGRVEYVFGD HPLIQFQYIR NCVMNRALPH FILVECCKIK KMYEQEMIAI  300
EAAINRNSSN LPLPLPPKKT RIISHVWENN NPFQIVLVKG NKLNTEETVK VHVRAGLFHG  360
TELLCKTIVS SEVSGKNDHI WNEPLEFDIN ICDLPRMARL CFAVYAVLDK VKTKKSTKTI  420
NPSKYQTIRK AGKVHYPVAW VNTMVFDFKG QLRTGDIILH SWSSFPDELE EMLNPMGTVQ  480
TNPYTENATA LHVKFPENKK QPYYYPPFDK IIEKAAEIAS SDSANVSSRG GKKFLPVLKE  540
ILDRDPLSQL CENEMDLIWT LRQDCREIFP QSLPKLLLSI KWNKLEDVAQ LQALLQIWPK  600
LPPREALELL DFNYPDQYVR EYAVGCLRQM SDEELSQYLL QLVQVLKYEP FLDCALSRFL  660
LERALGNRRI GQFLFWHLRS EVHIPAVSVQ FGVILEAYCR GSVGHMKVLS KQVEALNKLK  720
TLNSLIKLNA VKLNRAKGKE AMHTCLKQSA YREALSDLQS PLNPCVILSE LYVEKCKYMD  780
SKMKPLWLVY NNKVFGEDSV GVIFKNGDDL RQDMLTLQML RLMDLLWKEA GLDLRMLPYG  840
CLATGDRSGL IEVVSTSETI ADIQLNSSNV AAAAAFNKDA LLNWLKEYNS GDDLDRAIEE  900
FTLSCAGYCV ASYVLGIGDR HSDNIMVKKT GQLFHIDFGH ILGNFKSKFG IKRERVPFIL  960
TYDFIHVIQQ GKTGNTEKFG RFRQCCEDAY LILRRHGNLF ITLFALMLTA GLPELTSVKD  1020
IQYLKDSLAL GKSEEEALKQ FKQKFDEALR ESWTTKVNWM AHTVRKDYRS             1070

SEQ ID NO: 300         moltype = AA  length = 1044
FEATURE                Location/Qualifiers
source                 1..1044
                       mol_type = protein
                       organism = Homo sapiens
SEQUENCE: 300
MPPGVDCPME FWTKEENQSV VVDFLLPTGV YLNFPVSRNA NLSTIKQLLW HRAQYEPLFH  60
MLSGPEAYVF TCINQTAEQQ ELEDEQRRLC DVQPFLPVLR LVAREGDRVK KLINSQISLL  120
IGKGLHEFDS LCDPEVNDFR AKMCQFCEEA AARRQQLGWE AWLQYSFPLQ LEPSAQTWGP  180
GTLRLPNRAL LVNVKFEGSE ESFTFQVSTK DVPLALMACA LRKKATVFRQ PLVEQPEDYT  240
LQVNGRHEYL YGSYPLCQFQ YICSCLHSGL TPHLTMVHSS SILAMRDEQS NPAPQVQKPR  300
AKPPPIPAKK PSSVSLWSLE QPFRIELIQG SKVNADERMK LVVQAGLFHG NEMLCKTVSS  360
SEVSVCSEPV WKQRLEFDIN ICDLPRMARL CFALYAVIEK AKKARSTKKK SKKADCPIAW  420
ANLMLFDYKD QLKTGERCLY MWPSVPDEKG ELLNPTGTVR SNPNTDSAAA LLICLPEVAP  480
HPVYYPALEK ILELGRHSEC VHVTEEEQLQ LREILERRGS GELYEHEKDL VWKLRHEVQE  540
HFPEALARLL LVTKWNKHED VAQMLYLLCS WPELPVLSAL ELLDFSFPDC HVGSFAIKSL  600
RKLTDDELFQ YLLQLVQVLK YESYLDCELT KFLLDRALAN RKIGHFLFWH LRSEMHVPSV  660
ALRFGLILEA YCRGSTHHMK VLMKQGEALS KLKALNDFVK LSSQKTPKPQ TKELMHLCMR  720
QEAYLEALSH LQSPLDPSTL LAEVCVEQCT FMDSKMKPLW IMYSNEEAGS GGSVGIIFKN  780
GDDLRQDMLT LQMIQLMDVL WKQEGLDLRM TPYGCLPTGD RTGLIEVVLR SDTIANIQLN  840
KSNMAATAAF NKDALLNWLK SKNPGEALDR AIEEFTLSCA GYCVATYVLG IGDRHSDNIM  900
IRESGQLFHI DFGHFLGNFK TKFGINRERV PFILTYDFVH VIQQGKTNNS EKFERFRGYC  960
ERAYTILRRH GLLFLHLFAL MRAAGLPELS CSKDIQYLKD SLALGKTEEE ALKHFRVKFN  1020
EALRESWKTK VNWLAHNVSK DNRQ                                         1044

SEQ ID NO: 301         moltype = AA  length = 1367
FEATURE                Location/Qualifiers
source                 1..1367
                       mol_type = protein
                       organism = Homo sapiens
SEQUENCE: 301
MKSGSGGGSP TSLWGLLFLS AALSLWPTSG EICGPGIDIR NDYQQLKRLE NCTVIEGYLH  60
ILLISKAEDY RSYRFPKLTV ITEYLLLFRV AGLESLGDLF PNLTVIRGWK LFYNYALVIF  120
EMTNLKDIGL YNLRNITRGA IRIEKNADLC YLSTVDWSLI LDAVSNNYIV GNKPPKECGD  180
LCPGTMEEKP MCEKTTINNE YNYRCWTTNR CQKMCPSTCG KRACTENNEC CHPECLGSCS  240
APDNDTACVA CRHYYYAGVC VPACPPNTYR FEGWRCVDRD FCANILSAES SDSEGFVIHD  300
GECMQECPSG FIRNGSQSMY CIPCEGPCPK VCEEEKKTKT IDSVTSAQML QGCTIFKGNL  360
LINIRRGNNI ASELENFMGL IEVVTGYVKI RHSHALVSLS FLKNLRLILG EEQLEGNYSF  420
YVLDNQNLQQ LWDWDHRNLT IKAGKMYFAF NPKLCVSEIY RMEEVTGTKG RQSKGDINTR  480
NNGERASCES DVLHFTSTTT SKNRIIITWH RYRPPDYRDL ISFTVYYKEA PFKNVTEYDG  540
QDACGSNSWN MVDVDLPPNK DVEPGILLHG LKPWTQYAVY VKAVTLTMVE NDHIRGAKSE  600
ILYIRTNASV PSIPLDVLSA SNSSSQLIVK WNPPSLPNGN LSYYIVRWQR QPQDGYLYRH  660
NYCSKDKIPI RKYADGTIDI EEVTENPKTE VCGGEKGPCC ACPKTEAEKQ AEKEEAEYRK  720
VFENFLHNSI FVPRPERKRR DVMQVANTTM SSRSRNTTAA DTYNITDPEE LETEYPFFES  780
RVDNKERTVI SNLRPFTLYR IDIHSCNHEA EKLGCSASNF VFARTMPAEG ADDIPGPVTW  840
EPRPENSIFL KWPEPENPNG LILMYEIKYG SQVEDQRECV SRQEYRKYGG AKLNRLNPGN  900
YTARIQATSL SGNGSWTDPV FFYVQAKTGY ENFIHLIIAL PVAVLLIVGG LVIMLYVFHR  960
KRNNSRLGNG VLYASVNPEY FSAADVYVPD EWEVAREKIT MSRELGQGSF GMVYEGVAKG  1020
VVKDEPETRV AIKTVNEAAS MRERIEFLNE ASVMKEFNCH HVVRLLGVVS QGQPTLVIME  1080
LMTRGDLKSY LRSLRPEMEN NPVLAPPSLS KMIQMAGEIA DGMAYLNANK FVHRDLAARN  1140
CMVAEDFTVK IGDFGMTRDI YETDYYRKGG KGLLPVRWMS PESLKDGVFT TYSDVWSFGV  1200
VLWEIATLAE QPYQGLSNEQ VLRFVMEGGL LDKPDNCPDM LFELMRMCWQ YNPKMRPSFL  1260
EIISSIKEEM EPGFREVSFY YSEENKLPEP EELDLEPENM ESVPLDPSAS SSSLPLPDRH  1320
SGHKAENGPG PGVLVLRASF DERQPYAHMN GGRKNERALP LPQSSTC                1367

SEQ ID NO: 302         moltype = AA  length = 1255
FEATURE                Location/Qualifiers
source                 1..1255
                       mol_type = protein
                       organism = Homo sapiens
SEQUENCE: 302
MELAALCRWG LLLALLPPGA ASTQVCTGTD MKLRLPASPE THLDMLRHLY QGCQVVQGNL  60
```

```
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERP KTLSPGKNGV VKDVFAFGGA VENPEYLTPQ  1200
GGAAPQPHPP PAFSPAFDNL YYWDQDPPER GAPPSTFKGT PTAENPEYLG LDVPV       1255

SEQ ID NO: 303         moltype = AA  length = 220
FEATURE                Location/Qualifiers
source                 1..220
                       mol_type = protein
                       organism = Homo sapiens
SEQUENCE: 303
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                       220

SEQ ID NO: 304         moltype = AA  length = 223
FEATURE                Location/Qualifiers
source                 1..223
                       mol_type = protein
                       organism = Homo sapiens
SEQUENCE: 304
MACLGFQRHK AQLNLATRTW PCTLLFFLLF IPVFCKAMHV AQPAVVLASS RGIASFVCEY  60
ASPGKATEVR VTVLRQADSQ VTEVCAATYM MGNELTFLDD SICTGTSSGN QVNLTIQGLR  120
AMDTGLYICK VELMYPPPYY LGIGNGTQIY VIDPEPCPDS DFLLWILAAV SSGLFFYSFL  180
LTAVSLSKML KKRSPLTTGV YVKMPPTEPE CEKQFQPYFI PIN                   223

SEQ ID NO: 305         moltype = AA  length = 95
FEATURE                Location/Qualifiers
source                 1..95
                       mol_type = protein
                       organism = Homo sapiens
SEQUENCE: 305
WFVEDINRVQ AEDLLYGKPD GAFLIRESSK KGCYACSVVA DGEVKHCVIY STARGYGFAE  60
PYNLYSSLKE LVLHYQQTSL VQHNDSLNVR LAYPV                             95

SEQ ID NO: 306         moltype = AA  length = 13
FEATURE                Location/Qualifiers
source                 1..13
                       mol_type = protein
                       organism = Homo sapiens
SEQUENCE: 306
FDNLYYWDQD PPE                                                     13

SEQ ID NO: 307         moltype = AA  length = 95
FEATURE                Location/Qualifiers
source                 1..95
                       mol_type = protein
                       organism = Homo sapiens
SEQUENCE: 307
WFVEDINRVQ AEDLLYGKPD GAFLIRESSK KGCYACSVVA DGEVKHCVIY STARGYGFAE  60
PYNLYSSLKE LVLHYQQTSL VQHNDSLNVR LAYPV                             95

SEQ ID NO: 308         moltype = AA  length = 95
FEATURE                Location/Qualifiers
source                 1..95
                       mol_type = protein
                       organism = Homo sapiens
SEQUENCE: 308
WYVGKINRTQ AEEMLSGKRD GTFLIRESSQ RGCYACSVVV DGDTKHCVIY RTATGFGFAE  60
PYNLYGSLKE LVLHYQHASL VQHNDALTVT LAHPV                             95

SEQ ID NO: 309         moltype = AA  length = 95
```

```
FEATURE                Location/Qualifiers
source                 1..95
                       mol_type = protein
                       organism = Homo sapiens
SEQUENCE: 309
WNVGSSNRNK AENLLRGKRD GTFLVRESSK QGCYACSVVV DGEVKHCVIN KTATGYGFAE  60
PYNLYSSLKE LVLHYQHTSL VQHNDSLNVT LAYPV                             95

SEQ ID NO: 310         moltype = AA  length = 103
FEATURE                Location/Qualifiers
source                 1..103
                       mol_type = protein
                       organism = Homo sapiens
SEQUENCE: 310
QPWGSILRNW NFLAVTHPGY MAFLTYDEVK ARLQKYSTKP GSYIFRLSCT RLGQWAIGYV  60
TGDGNILQTI PHNKPLFQAL IDGSREGFYL YPDGRSYNPD LTG                    103

SEQ ID NO: 311         moltype = AA  length = 98
FEATURE                Location/Qualifiers
source                 1..98
                       mol_type = protein
                       organism = Homo sapiens
SEQUENCE: 311
WFFKNLSRKD AERQLLAPGN THGSFLIRES ESTAGSFSLS VRDFDQNQGE VVKHYKIRNL  60
DNGGFYISPR ITFPGLHELV RHYTNASDGL CTRLSRPC                          98

SEQ ID NO: 312         moltype = AA  length = 97
FEATURE                Location/Qualifiers
source                 1..97
                       mol_type = protein
                       organism = Homo sapiens
SEQUENCE: 312
WFHRDLSGLD AETLLKGRGV HGSFLARPSR KNQGDFSLSV RVGDQVTHIR IQNSGDFYDL  60
YGGEKFATLT ELVEYYTQQQ GVLQDRDGTI IHLKYPL                           97

SEQ ID NO: 313         moltype = AA  length = 101
FEATURE                Location/Qualifiers
source                 1..101
                       mol_type = protein
                       organism = Synthetic construct
SEQUENCE: 313
QAEEWYFGKL GRKDAERQLL SFGNPRGTFL IRESETVKGA YALSIRDWDD MKGDHVKHYL  60
IRKLDNGGYY IWLGAQFETL QQLVQHYSER AVPGSCRLVV P                      101

SEQ ID NO: 314         moltype = AA  length = 101
FEATURE                Location/Qualifiers
source                 1..101
                       mol_type = protein
                       organism = Synthetic construct
SEQUENCE: 314
QAEEWYFGKL GRKDAERQLL SFGNPRGTFL IRESETVKGA YALSIRDWDD MKGDHVKHYL  60
IRKLDNGGYY IPGGAQFETL QQLVQHYSER AWYWCCRLVV P                      101

SEQ ID NO: 315         moltype = AA  length = 101
FEATURE                Location/Qualifiers
source                 1..101
                       mol_type = protein
                       organism = Synthetic construct
SEQUENCE: 315
QAEEWYFGKL GRKDAERQLL SFGNPRGTFL IRESETVKGA YALSIRDWDD MKGDHVKHYL  60
IRKLDNGGYY IRRRAQFETL QQLVQHYSER ALPGCCRLVV P                      101

SEQ ID NO: 316         moltype = AA  length = 121
FEATURE                Location/Qualifiers
source                 1..121
                       mol_type = protein
                       organism = Homo sapiens
SEQUENCE: 316
KRSDRKDVQH NEWYIGEYSR QAVEEAFMKE NKDGSFLVRD CSTKSKEEPY VLAVFYENKV  60
YNVKIRFLER NQQFALGTGL RGDEKFDSVE DIIEHYKNFP IILIDGKDKT GVHRKQCHLT  120
Q                                                                  121

SEQ ID NO: 317         moltype = AA  length = 118
FEATURE                Location/Qualifiers
source                 1..118
                       mol_type = protein
                       organism = Homo sapiens
SEQUENCE: 317
FDSEERSSWY WGRLSRQEAV ALLQGQRHGV FLVRDSSTSP GDYVLSVSEN SRVSHYIINS  60
```

```
SGPRPPVPPS PAQPPPGVSP SRLRIGDQEF DSLPALLEFY KIHYLDTTTL IEPVSRSR    118

SEQ ID NO: 318         moltype = AA  length = 101
FEATURE                Location/Qualifiers
source                 1..101
                       mol_type = protein
                       organism = Homo sapiens
SEQUENCE: 318
FDSSDRSAWY MGPVSRQEAQ TRLQGQRHGM FLVRDSSTCP GDYVLSVSEN SRVSHYIINS  60
LPNRRFKIGD QEFDHLPALL EFYKIHYLDT TTLIEPAPRY P                      101

SEQ ID NO: 319         moltype = AA  length = 95
FEATURE                Location/Qualifiers
source                 1..95
                       mol_type = protein
                       organism = Homo sapiens
SEQUENCE: 319
KPHPWYSGRI SRQLAEEILM KRNHLGAFLI RESESSPGEF SVSVNYGDQV QHFKVLREAS  60
GKYFLWEEKF NSLNELVDFY RTTTIAKKRQ IFLRD                             95

SEQ ID NO: 320         moltype = AA  length = 94
FEATURE                Location/Qualifiers
source                 1..94
                       mol_type = protein
                       organism = Homo sapiens
SEQUENCE: 320
QFPKWFHEGL SRHQAENLLM GKEVGFFIIR ASQSSPGDFS ISVRHEDDVQ HFKVMRDNKG  60
NYFLWTEKFP SLNKLVDYYR TNSISRQKQI FLRD                              94

SEQ ID NO: 321         moltype = AA  length = 95
FEATURE                Location/Qualifiers
source                 1..95
                       mol_type = protein
                       organism = Homo sapiens
SEQUENCE: 321
KPHPWFFGKI PRAKAEEMLS KQRHDGAFLI RESESAPGDF SLSVKFGNDV QHFKVLRDGA  60
GKYFLWVVKF NSLNELVDYH RSTSVSRNQQ IFLRD                             95

SEQ ID NO: 322         moltype = AA  length = 97
FEATURE                Location/Qualifiers
source                 1..97
                       mol_type = protein
                       organism = Homo sapiens
SEQUENCE: 322
NPWYYGKVTR HQAEMALNER GHEGDFLIRD SESSPNDFSV SLKAQGKNKH FKVQLKETVY  60
CIGQRKFSTM EELVEHYKKA PIFTSEQGEK LYLVKHL                           97

SEQ ID NO: 323         moltype = AA  length = 98
FEATURE                Location/Qualifiers
source                 1..98
                       mol_type = protein
                       organism = Homo sapiens
SEQUENCE: 323
REWYYGNVTR HQAECALNER GVEGDFLIRD SESSPSDFSV SLKASGKNKH FKVQLVDNVY  60
CIGQRRFHTM DELVEHYKKA PIFTSEHGEK LYLVRALQ                          98

SEQ ID NO: 324         moltype = AA  length = 98
FEATURE                Location/Qualifiers
source                 1..98
                       mol_type = protein
                       organism = Homo sapiens
SEQUENCE: 324
PGICVARVYH GWLFEGLGRD KAEELLQLPD TKVGSFMIRE SETKKGFYSL SVRHRQVKHY  60
RIFRLPNNWY YISPRLTFQC LEDLVNHYSE VADGLCCV                          98

SEQ ID NO: 325         moltype = AA  length = 104
FEATURE                Location/Qualifiers
source                 1..104
                       mol_type = protein
                       organism = Homo sapiens
SEQUENCE: 325
PSVHVAKVSH GWLYEGLSRE KAEELLLLPG NPGGAFLIRE SQTRRGSYSL SVRLSRPASW  60
DRIRHYRIHC LDNGWLYISP RLTFPSLQAL VDHYSELADD ICCL                   104

SEQ ID NO: 326         moltype = AA  length = 225
FEATURE                Location/Qualifiers
source                 1..225
                       mol_type = protein
                       organism = Homo sapiens
```

```
SEQUENCE: 326
RVPKPKGVLP SHYYESFLEK KGPCDRDYKK FWAGLQGLTI YFYNSNRDFQ HVEKLNLGAF  60
EKLTDEIPWG SSRDPGTHFS LILRDQEIKF KVETLECREM WKGFILTVVE LRVPTDLTLL  120
PGHLYMMSPS CFLKVSRLEA QLLLERYPEC GNLLLRPSGD GADGVSVTTR QMHNGTHVVR  180
HYKVKREGPK YVIDVEQPFS CTSLDAVVNY FVSHTKKALV PFLLD                 225

SEQ ID NO: 327         moltype = AA  length = 205
FEATURE                Location/Qualifiers
source                 1..205
                       mol_type = protein
                       organism = Homo sapiens
SEQUENCE: 327
ADHKQEEDMK RKQQRTTYIK RVIAHPSFHN INFKQAEKMM ETMDQGDVII RPSSKGENHL  60
TVTWKVSDGI YQHVDVREEG KENAFSLGAT LWINSEEFED LDEIVARYVQ PMASFARDLL  120
NHKYYQDCSG GDRKKLEELL IKTKKEKPTF IPYFICACKE LPGKFLLGYQ PRGKPRIEYV  180
TVTPEGFRYR GQIFPTVNGL FRWFK                                       205

SEQ ID NO: 328         moltype = AA  length = 159
FEATURE                Location/Qualifiers
source                 1..159
                       mol_type = protein
                       organism = Homo sapiens
SEQUENCE: 328
DLVYVTERII AVSFPSTANE ENFRSNLREV AQMLKSKHGG NYLLFNLSER RPDITKLHAK  60
VLEFGWPDLH TPALEKICSI CKAMDTWLNA DPHNVVVLHN KGNRGRIGVV IAAYMHYSNI  120
SASADQALDR FAMKRFYEDK IVPIGQPSQR RYVHYFSGL                        159

SEQ ID NO: 329         moltype = AA  length = 116
FEATURE                Location/Qualifiers
source                 1..116
                       mol_type = protein
                       organism = Homo sapiens
SEQUENCE: 329
TSKYWYKPEI SREQAIALLK DQEPGAFIIR DSHSFRGAYG LAMKVSSPPP TIMQQNKKGD  60
MTHELVRHFL IETGPRGVKL KGCPNEPNFG SLSALVYQHS IIPLALPCKL VIPNRD      116

SEQ ID NO: 330         moltype = AA  length = 114
FEATURE                Location/Qualifiers
source                 1..114
                       mol_type = protein
                       organism = Homo sapiens
SEQUENCE: 330
TSKFWYKPHL SRDQAIALLK DKDPGAFLIR DSHSFQGAYG LALKVATPPP SAQPWKGDPV  60
EQLVRHFLIE TGPKGVKIKG CPSEPYFGSL SALVSQHSIS PISLPCCLRI PSKD        114

SEQ ID NO: 331         moltype = AA  length = 117
FEATURE                Location/Qualifiers
source                 1..117
                       mol_type = protein
                       organism = Homo sapiens
SEQUENCE: 331
TSKFWYKADI SREQAIAMLK DKEPGSFIVR DSHSFRGAYG LAMKVATPPP SVLQLNKKAG  60
DLANELVRHF LIECTPKGVR LKGCSNEPYF GSLTALVCQH SITPLALPCK LLIPERD     117

SEQ ID NO: 332         moltype = AA  length = 114
FEATURE                Location/Qualifiers
source                 1..114
                       mol_type = protein
                       organism = Homo sapiens
SEQUENCE: 332
TSKYWFKPNI TREQAIELLR KEEPGAFVIR DSSSYRGSFG LALKVQEVPA SAQSRPGEDS  60
NDLIRHFLIE SSAKGVHLKG ADEEPYFGSL SAFVCQHSIM ALALPCKLTI PQRE        114

SEQ ID NO: 333         moltype = AA  length = 94
FEATURE                Location/Qualifiers
source                 1..94
                       mol_type = protein
                       organism = Homo sapiens
SEQUENCE: 333
EKHSWYHGPV SRNAAEYLLS SGINGSFLVR ESESSPGQRS ISLRYEGRVY HYRINTASDG  60
KLYVSSESRF NTLAELVHHH STVADGLITT LHYP                              94

SEQ ID NO: 334         moltype = AA  length = 94
FEATURE                Location/Qualifiers
source                 1..94
                       mol_type = protein
                       organism = Homo sapiens
SEQUENCE: 334
EKHSWYHGPV SRSAAEYLLS SLINGSFLVR ESESSPGQLS ISLRYEGRVY HYRINTTADG  60
```

```
KVYVTAESRF STLAELVHHH STVADGLVTT LHYP                           94

SEQ ID NO: 335         moltype = AA  length = 100
FEATURE                Location/Qualifiers
source                 1..100
                       mol_type = protein
                       organism = Homo sapiens
SEQUENCE: 335
EMERWFFRSQ GRKEAERQLL APINKAGSFL IRESETNKGA FSLSVKDVTT QGELIKHYKI  60
RCLDEGGYYI SPRITFPSLQ ALVQHYSKKG DGLCQRLTLP                     100

SEQ ID NO: 336         moltype = AA  length = 106
FEATURE                Location/Qualifiers
source                 1..106
                       mol_type = protein
                       organism = Homo sapiens
SEQUENCE: 336
ENLDDYDWFA GNISRSQSEQ LLRQKGKEGA FMVRNSSQVG MYTVSLFSKA VNDKKGTVKH  60
YHVHTNAENK LYLAENYCFD SIPKLIHYHQ HNSAGMITRL RHPVST              106

SEQ ID NO: 337         moltype = AA  length = 106
FEATURE                Location/Qualifiers
source                 1..106
                       mol_type = protein
                       organism = Homo sapiens
SEQUENCE: 337
DSIEMYEWYS KHMTRSQAEQ LLKQEGKEGG FIVRDSSKAG KYTVSVFAKS TGDPQGVIRH  60
YVVCSTPQSQ YYLAEKHLFS TIPELINYHQ HNSAGLISRL KYPVSQ              106

SEQ ID NO: 338         moltype = AA  length = 98
FEATURE                Location/Qualifiers
source                 1..98
                       mol_type = protein
                       organism = Homo sapiens
SEQUENCE: 338
SLMPWFHGKI TREQAERLLY PPETGLFLVR ESTNYPGDYT LCVSCDGKVE HYRIMYHASK  60
LSIDEEVYFE NLMQLVEHYT SDADGLCTRL IKPKVMEG                       98

SEQ ID NO: 339         moltype = AA  length = 86
FEATURE                Location/Qualifiers
source                 1..86
                       mol_type = protein
                       organism = Homo sapiens
SEQUENCE: 339
KPLAEQDWYH GAIPRIEAQE LLKKQGDFLV RESHGKPGEY VLSVYSDGQR RHFIIQYVDN  60
MYRFEGTGFS NIPQLIDHHY TTKQVI                                    86

SEQ ID NO: 340         moltype = AA  length = 85
FEATURE                Location/Qualifiers
source                 1..85
                       mol_type = protein
                       organism = Homo sapiens
SEQUENCE: 340
KPLHEQLWYH GAIPRAEVAE LLVHSGDFLV RESQGKQEYV LSVLWDGLPR HFIIQSLDNL  60
YRLEGEGFPS IPLLIDHLLS TQQPL                                     85

SEQ ID NO: 341         moltype = AA  length = 101
FEATURE                Location/Qualifiers
source                 1..101
                       mol_type = protein
                       organism = Homo sapiens
SEQUENCE: 341
QAEEWYFGKI GRKDAERQLL SPGNPQGAFL IRESETTKGA YSLSIRDWDQ TRGDHVKHYK  60
IRKLDMGGYY ITTRVQFNSV QELVQHYMEV NDGLCNLLIA P                   101

SEQ ID NO: 342         moltype = AA  length = 96
FEATURE                Location/Qualifiers
source                 1..96
                       mol_type = protein
                       organism = Homo sapiens
SEQUENCE: 342
QAEPWFFGAI GRSDAEKQLL YSENKTGSFL IRESESQKGE FSLSVLDGAV VKHYRIKRLD  60
EGGFFLTRRR IFSTLNEFVS HYTKTSDGLC VKLGKP                         96

SEQ ID NO: 343         moltype = AA  length = 101
FEATURE                Location/Qualifiers
source                 1..101
                       mol_type = protein
                       organism = Homo sapiens
```

```
SEQUENCE: 343
QAEEWYFGKL GRKDAERQLL SFGNPRGTFL IRESETTKGA YSLSIRDWDD MKGDHVKHYK  60
IRKLDNGGYY ITTRAQFETL QQLVQHYSER AAGLCCRLVV P                     101

SEQ ID NO: 344         moltype = AA  length = 104
FEATURE                Location/Qualifiers
source                 1..104
                       mol_type = protein
                       organism = Homo sapiens
SEQUENCE: 344
ETEEWFFKGI SRKDAERQLL APGNMLGSFM IRDSETTKGS YSLSVRDYDP RQGDTVKHYK  60
IRTLDNGGFY ISPRSTFSTL QELVDHYKKG NDGLCQKLSV PCMS                  104

SEQ ID NO: 345         moltype = AA  length = 109
FEATURE                Location/Qualifiers
source                 1..109
                       mol_type = protein
                       organism = Homo sapiens
SEQUENCE: 345
NNLETYEWYN KSISRDKAEK LLLDTGKEGA FMVRDSRTAG TYTVSVFTKA VVSENNPCIK  60
HYHIKETNDN PKRYYVAEKY VFDSIPLLIN YHQHNGGGLV TRLRYPVCF             109

SEQ ID NO: 346         moltype = AA  length = 102
FEATURE                Location/Qualifiers
source                 1..102
                       mol_type = protein
                       organism = Homo sapiens
SEQUENCE: 346
DVAPPLIVHN IQNGCHGPIC TEYAINKLRQ EGSEEGMYVL RWSCTDFDNI LMTVTCFEKS  60
EQVQGAQKQF KNFQIEVQKG RYSLHGSDRS FPSLGDLMSH LK                    102

SEQ ID NO: 347         moltype = AA  length = 97
FEATURE                Location/Qualifiers
source                 1..97
                       mol_type = protein
                       organism = Homo sapiens
SEQUENCE: 347
EVAPPAVLEN IQSNCHGPIS MDFAISKLKK AGNQTGLYVL RCSPKDFNKY FLTFAVEREN  60
VIEYKHCLIT KNENEEYNLS GTKKNFSSLK DLLNCYQ                          97

SEQ ID NO: 348         moltype = AA  length = 97
FEATURE                Location/Qualifiers
source                 1..97
                       mol_type = protein
                       organism = Homo sapiens
SEQUENCE: 348
EVAPPRLLEE VAEQCHGPIT LDFAINKLKT GGSRPGSYVL RRSPQDFDSF LLTVCVQNPL  60
GPDYKGCLIR RSPTGTFLLV GLSRPHSSLR ELLATCW                          97

SEQ ID NO: 349         moltype = AA  length = 101
FEATURE                Location/Qualifiers
source                 1..101
                       mol_type = protein
                       organism = Homo sapiens
SEQUENCE: 349
EPEPWFFKNL SRKDAERQLL APGNTHGSFL IRESESTAGS FSLSVRDFDQ NQGEVVKHYK  60
IRNLDNGGFY ISPRITFPGL HELVRHYTNA SDGLCTRLSR P                     101

SEQ ID NO: 350         moltype = AA  length = 101
FEATURE                Location/Qualifiers
source                 1..101
                       mol_type = protein
                       organism = Homo sapiens
SEQUENCE: 350
ETEEWFFKDI TRKDAERQLL APGNSAGAFL IRESETLKGS FSLSVRDFDP VHGDVIKHYK  60
IRSLDNGGYY ISPRITFPCI SDMIKHYQKQ ADGLCRRLEK A                     101

SEQ ID NO: 351         moltype = AA  length = 98
FEATURE                Location/Qualifiers
source                 1..98
                       mol_type = protein
                       organism = Homo sapiens
SEQUENCE: 351
SLMPWFHGKI SGQEAVQQLQ PPEDGLFLVR ESARHPGDYV LCVSFGRDVI HYRVLHRDGH  60
LTIDEAVFFC NLMDMVEHYS KDKGAICTKL VRPKRKHG                         98

SEQ ID NO: 352         moltype = AA  length = 128
FEATURE                Location/Qualifiers
source                 1..128
```

```
                         mol_type = protein
                         organism = Homo sapiens
SEQUENCE: 352
DNIEAVGKKL HEYNTQFQEK SREYDRLYEE YTRTSQEIQM KRTAIEAFNE TIKIFEEQCQ  60
TQERYSKEYI EKFKREGNEK EIQRIMHNYD KLKSRISEII DSRRRLEEDL KKQAAEYREI  120
DKRMNSIK                                                          128

SEQ ID NO: 353           moltype = AA  length = 104
FEATURE                  Location/Qualifiers
source                   1..104
                         mol_type = protein
                         organism = Homo sapiens
SEQUENCE: 353
PHHDEKTWNV GSSNRNKAEN LLRGKRDGTF LVRESSKQGC YACSVVVDGE VKHCVINKTA  60
TGYGFAEPYN LYSSLKELVL HYQHTSLVQH NDSLNVTLAY PVYA                  104

SEQ ID NO: 354           moltype = AA  length = 111
FEATURE                  Location/Qualifiers
source                   1..111
                         mol_type = protein
                         organism = Homo sapiens
SEQUENCE: 354
NMSLQDAEWY WGDISREEVN EKLRDTADGT FLVRDASTKM HGDYTLTLRK GGNNKLIKIF  60
HRDGKYGFSD PLTFSSVVEL INHYRNESLA QYNPKLDVKL LYPVSKYQQD Q           111

SEQ ID NO: 355           moltype = AA  length = 100
FEATURE                  Location/Qualifiers
source                   1..100
                         mol_type = protein
                         organism = Homo sapiens
SEQUENCE: 355
SEPWFFGCIS RSEAVRRLQA EGNATGAFLI RVSEKPSADY VLSVRDTQAV RHYKIWRRAG  60
GRLHLNEAVS FLSLPELVNY HRAQSLSHGL RLAAPCRKHE                       100

SEQ ID NO: 356           moltype = AA  length = 101
FEATURE                  Location/Qualifiers
source                   1..101
                         mol_type = protein
                         organism = Homo sapiens
SEQUENCE: 356
QAEEWYFGKI TRRESERLLL NAENPRGTFL VRESETTKGA YCLSVSDFDN AKGLNVKHYK  60
IRKLDSGGFY ITSRTQFNSL QQLVAYYSKH ADGLCHRLTT V                     101

SEQ ID NO: 357           moltype = AA  length = 79
FEATURE                  Location/Qualifiers
source                   1..79
                         mol_type = protein
                         organism = Homo sapiens
SEQUENCE: 357
PWYFSGVSRT QAQQLLLSPP NEPGAFLIRP SESSLGGYSL SVRAQAKVCH YRVSMAADGS  60
LYLQKGRLFP GLEELLTYY                                              79

SEQ ID NO: 358           moltype = AA  length = 203
FEATURE                  Location/Qualifiers
source                   1..203
                         mol_type = protein
                         organism = Homo sapiens
SEQUENCE: 358
LPFFFGNITR EEAEDYLVQG GMSDGLYLLR QSRNYLGGFA LSVAHGRKAH HYTIERELNG  60
TYAIAGGRTH ASPADLCHYH SQESDGLVCL LKKPFNRPQG VQPKEKMPWF HGKISREESE  120
QIVLIGSKTN GKFLIRARDN NGSYALCLLH EGKVLHYRID KDKTGKLSIP EGKKFDTLWQ  180
LVEHYSYKAD GLLRVLTVPC QKI                                         203

SEQ ID NO: 359           moltype = AA  length = 99
FEATURE                  Location/Qualifiers
source                   1..99
                         mol_type = protein
                         organism = Homo sapiens
SEQUENCE: 359
EKMPWFHGKI SREESEQIVL IGSKTNGKFL IRARDNNGSY ALCLLHEGKV LHYRIDKDKT  60
GKLSIPEGKK FDTLWQLVEH YSYKADGLLR VLTVPCQKI                        99

SEQ ID NO: 360           moltype = AA  length = 107
FEATURE                  Location/Qualifiers
source                   1..107
                         mol_type = protein
                         organism = Homo sapiens
SEQUENCE: 360
NNLDQYEWYC RNMNRSKAEQ LLRSEDKEGG FMVRDSSQPG LYTVSLYTKF GGEGSSGFRH  60
```

-continued

```
YHIKETTTSP KKYYLAEKHA FGSIPEIIEY HKHNAAGLVT RLRYPVS               107

SEQ ID NO: 361         moltype = AA  length = 106
FEATURE                Location/Qualifiers
source                 1..106
                       mol_type = protein
                       organism = Homo sapiens
SEQUENCE: 361
TNLEIYEWYH RNITRNQAEH LLRQESKEGA FIVRDSRHLG SYTISVFMGA RRSTEAAIKH  60
YQIKKNDSGQ WYVAERHAFQ SIPELIWYHQ HNAAGLMTRL RYPVGL                 106

SEQ ID NO: 362         moltype = AA  length = 98
FEATURE                Location/Qualifiers
source                 1..98
                       mol_type = protein
                       organism = Homo sapiens
SEQUENCE: 362
EVAPPRLVMS IRDGIHGPLL EPFVQAKLRP EDGLYLIHWS TSHPYRLILT VAQRSQAPDG  60
MQSLRLRKFP IEQQDGAFVL EGWGRSFPSV RELGAALQ                         98

SEQ ID NO: 363         moltype = AA  length = 100
FEATURE                Location/Qualifiers
source                 1..100
                       mol_type = protein
                       organism = Homo sapiens
SEQUENCE: 363
QAEEWYFGKM GRKDAERLLL NPGNQRGIFL VRESETTKGA YSLSIRDWDE IRGDNVKHYK  60
IRKLDNGGYY ITTRAQFDTL QKLVKHYTEH ADGLCHKLTT                       100

SEQ ID NO: 364         moltype = AA  length = 104
FEATURE                Location/Qualifiers
source                 1..104
                       mol_type = protein
                       organism = Homo sapiens
SEQUENCE: 364
LIATTAHERM PWYHSSLTRE EAERKLYSGA QTDGKFLLRP RKEQGTYALS LIYGKTVYHY  60
LISQDKAGKY CIPEGTKFDT LWQLVEYLKL KADGLIYCLK EACP                  104

SEQ ID NO: 365         moltype = AA  length = 104
FEATURE                Location/Qualifiers
source                 1..104
                       mol_type = protein
                       organism = Homo sapiens
SEQUENCE: 365
LPFFYGSISR AEAEEHLKLA GMADGLFLLR QCLRSLGGYV LSLVHDVRFH HFPIERQLNG  60
TYAIAGGKAH CGPAELCEFY SRDPDGLPCN LRKPCNRPSG LEPQ                  104

SEQ ID NO: 366         moltype = AA  length = 99
FEATURE                Location/Qualifiers
source                 1..99
                       mol_type = protein
                       organism = Homo sapiens
SEQUENCE: 366
RWFHPNITGV EAENLLLTRG VDGSFLARPS KSNPGDFTLS VRRNGAVTHI KIQNTGDYYD  60
LYGGEKFATL AELVQYYMEH HGQLKEKNGD VIELKYPLN                        99

SEQ ID NO: 367         moltype = AA  length = 108
FEATURE                Location/Qualifiers
source                 1..108
                       mol_type = protein
                       organism = Homo sapiens
SEQUENCE: 367
RWFHGHLSGK EAEKLLTEKG KHGSFLVRES QSHPGDFVLS VRTGDDKGES NDGKSKVTHV  60
MIRCQELKYD VGGGERFDSL TDLVEHYKKN PMVETLGTVL QLKQPLNT              108

SEQ ID NO: 368         moltype = AA  length = 99
FEATURE                Location/Qualifiers
source                 1..99
                       mol_type = protein
                       organism = Homo sapiens
SEQUENCE: 368
RWFHRDLSGL DAETLLKGRG VHGSFLARPS RKNQGDFSLS VRVGDQVTHI RIQNSGDFYD  60
LYGGEKFATL TELVEYYTQQ QGVLQDRDGT IIHLKYPLN                        99

SEQ ID NO: 369         moltype = AA  length = 107
FEATURE                Location/Qualifiers
source                 1..107
                       mol_type = protein
                       organism = Homo sapiens
```

```
SEQUENCE: 369
RWYHGHMSGG QAETLLQAKG EPWTFLVRES LSQPGDFVLS VLSDQPKAGP GSPLRVTHIK  60
VMCEGGRYTV GGLETFDSLT DLVEHFKKTG IEEASGAFVY LRQPYYA                107

SEQ ID NO: 370         moltype = AA  length = 102
FEATURE                Location/Qualifiers
source                 1..102
                       mol_type = protein
                       organism = Homo sapiens
SEQUENCE: 370
MVPCWNHGNI TRSKAEELLS RTGKDGSFLV RASESISRAY ALCVLYRNCV YTYRILPNED  60
DKFTVQASEG VSMRFFTKLD QLIEFYKKEN MGLVTHLQYP VP                     102

SEQ ID NO: 371         moltype = AA  length = 103
FEATURE                Location/Qualifiers
source                 1..103
                       mol_type = protein
                       organism = Homo sapiens
SEQUENCE: 371
QAPSWYHRDL SRAAAEELLA RAGRDGSFLV RDSESVAGAF ALCVLYQKHV HTYRILPDGE  60
DFLAVQTSQG VPVRRFQTLG ELIGLYAQPN QGLVCALLLP VEG                    103

SEQ ID NO: 372         moltype = AA  length = 111
FEATURE                Location/Qualifiers
source                 1..111
                       mol_type = protein
                       organism = Homo sapiens
SEQUENCE: 372
PPSLQDAEWY WGDISREEVN EKLRDTPDGT FLVRDASSKI QGEYTLTLRK GGNNKLIKVF  60
HRDGHYGFSE PLTFCSVVDL INHYRHESLA QYNAKLDTRL LYPVSKYQQD Q            111

SEQ ID NO: 373         moltype = AA  length = 103
FEATURE                Location/Qualifiers
source                 1..103
                       mol_type = protein
                       organism = Homo sapiens
SEQUENCE: 373
PHHEERTWYV GKINRTQAEE MLSGKRDGTF LIRESSQRGC YACSVVVDGD TKHCVIYRTA  60
TGFGFAEPYN LYGSLKELVL HYQHASLVQH NDALTVTLAH PVR                    103

SEQ ID NO: 374         moltype = AA  length = 128
FEATURE                Location/Qualifiers
source                 1..128
                       mol_type = protein
                       organism = Homo sapiens
SEQUENCE: 374
DNIDAVGKKL QEYHSQYQEK SKEYDRLYEE YTRTSQEIQM KRTAIEAFNE TIKIFEEQCH  60
TQEQHSKEYI ERFRREGNEK EIERIMMNYD KLKSRLGEIH DSKMRLEQDL KNQALDNREI  120
DKKMNSIK                                                           128

SEQ ID NO: 375         moltype = AA  length = 109
FEATURE                Location/Qualifiers
source                 1..109
                       mol_type = protein
                       organism = Homo sapiens
SEQUENCE: 375
SLQDAEWYWG DISREEVNDK LRDMPDGTFL VRDASTKMQG DYTLTLRKGG NNKLIKIYHR  60
DGKYGFSDPL TFNSVVELIN HYHHESLAQY NPKLDVKLMY PVSRYQQDQ              109

SEQ ID NO: 376         moltype = AA  length = 104
FEATURE                Location/Qualifiers
source                 1..104
                       mol_type = protein
                       organism = Homo sapiens
SEQUENCE: 376
PHYDEKTWFV EDINRVQAED LLYGKPDGAF LIRESSKKGC YACSVVADGE VKHCVIYSTA  60
RGYGFAEPYN LYSSLKELVL HYQQTSLVQH NDSLNVRLAY PVHA                   104

SEQ ID NO: 377         moltype = AA  length = 103
FEATURE                Location/Qualifiers
source                 1..103
                       mol_type = protein
                       organism = Homo sapiens
SEQUENCE: 377
HESKEWYHAS LTRAQAEHML MRVPRDGAFL VRKRNEPNSY AISFRAEGKI KHCRVQQEGQ  60
TVMLGNSEFD SLVDLISYYE KHPLYRKMKL RYPINEEALE KIG                    103

SEQ ID NO: 378         moltype = AA  length = 105
FEATURE                Location/Qualifiers
```

```
source                  1..105
                        mol_type = protein
                        organism = Homo sapiens
SEQUENCE: 378
HSNEKWFHGK LGAGRDGRHI AERLLTEYCI ETGAPDGSFL VRESETFVGD YTLSFWRNGK  60
VQHCRIHSRQ DAGTPKFFLT DNLVFDSLYD LITHYQQVPL RCNEF                  105

SEQ ID NO: 379          moltype = AA  length = 104
FEATURE                 Location/Qualifiers
source                  1..104
                        mol_type = protein
                        organism = Homo sapiens
SEQUENCE: 379
HESKPWYYDS LSRGEAEDML MRIPRDGAFL IRKREGSDSY AITFRARGKV KHCRINRDGR  60
HFVLGTSAYF ESLVELVSYY EKHSLYRKMR LRYPVTPELL ERYN                   104

SEQ ID NO: 380          moltype = AA  length = 101
FEATURE                 Location/Qualifiers
source                  1..101
                        mol_type = protein
                        organism = Homo sapiens
SEQUENCE: 380
HFGEKWFHKK VEKRTSAEKL LQEYCMETGG KDGTFLVRES ETFPNDYTLS FWRSGRVQHC  60
RIRSTMEGGT LKYYLTDNLT FSSIYALIQH YRETHLRCAE F                      101

SEQ ID NO: 381          moltype = AA  length = 84
FEATURE                 Location/Qualifiers
source                  1..84
                        mol_type = protein
                        organism = Homo sapiens
SEQUENCE: 381
WYAGACDRKS AEEALHRSNK DGSFLIRKSS GHDSKQPYTL VVFFNKRVYN IPVRFIEATK  60
QYALGRKKNG EEYFGSVAEI IRNH                                         84

SEQ ID NO: 382          moltype = AA  length = 121
FEATURE                 Location/Qualifiers
source                  1..121
                        mol_type = protein
                        organism = Homo sapiens
SEQUENCE: 382
PAEEENSLNE EWYVSYITRP EAEAALRKIN QDGTFLVRDS SKKTTTNPYV LMVLYKDKVY  60
NIQIRYQKES QVYLLGTGLR GKEDFLSVSD IIDYFRKMPL LLIDGKNRGS RYQCTLTHAA  120
G                                                                  121

SEQ ID NO: 383          moltype = AA  length = 77
FEATURE                 Location/Qualifiers
source                  1..77
                        mol_type = protein
                        organism = Homo sapiens
SEQUENCE: 383
WAFAGISRPC ALALLRRDVL GAFLLWPELG ASGQWCLSVR TQCGVVPHQV FRNHLGRYCL  60
EHLPAEFPSL EALVENH                                                 77

SEQ ID NO: 384          moltype = AA  length = 104
FEATURE                 Location/Qualifiers
source                  1..104
                        mol_type = protein
                        organism = Homo sapiens
SEQUENCE: 384
AEQLRGEPWF HGKLSRREAE ALLQLNGDFL VRESTTTPGQ YVLTGLQSGQ PKHLLLVDPE  60
GVVRTKDHRF ESVSHLISYH MDNHLPIISA GSELCLQQPV ERKL                   104

SEQ ID NO: 385          moltype = AA  length = 104
FEATURE                 Location/Qualifiers
source                  1..104
                        mol_type = protein
                        organism = Homo sapiens
SEQUENCE: 385
EEQLRQEPWY HGRMSRRAAE RMLRADGDFL VRDSVTNPGQ YVLTGMHAGQ PKHLLLVDPE  60
GVVRTKDVLF ESISHLIDHH LQNGQPIVAA ESELHLRGVV SREP                   104

SEQ ID NO: 386          moltype = AA  length = 103
FEATURE                 Location/Qualifiers
source                  1..103
                        mol_type = protein
                        organism = Homo sapiens
SEQUENCE: 386
EELQAETWYQ GEMSRKEAEG LLEKDGDFLV RKSTTNPGSF VLTGMHNGQA KHLLLVDPEG  60
TIRTKDRVFD SISHLINHHL ESSLPIVSAG SELCLQQPVE RKQ                    103
```

```
SEQ ID NO: 387         moltype = AA  length = 101
FEATURE                Location/Qualifiers
source                 1..101
                       mol_type = protein
                       organism = Homo sapiens
SEQUENCE: 387
KQQLWSEECY HGKLSRKAAE SLLVKDGDFL VRESATSPGQ YVLSGLQGGQ AKHLLLVDPE  60
GKVRTKDHVF DNVGHLIRYH MDNSLPIISS GSEVSLKQPV R                      101

SEQ ID NO: 388         moltype = AA  length = 85
FEATURE                Location/Qualifiers
source                 1..85
                       mol_type = protein
                       organism = Homo sapiens
SEQUENCE: 388
WYSGNCDRYA VESALLHLQK DGAYTVRPSS GPHGSQPFTL AVLLRGRVFN IPIRRLDGGR  60
HYALGREGRN REELFSSVAA MVQHF                                        85

SEQ ID NO: 389         moltype = AA  length = 88
FEATURE                Location/Qualifiers
source                 1..88
                       mol_type = protein
                       organism = Homo sapiens
SEQUENCE: 389
LRESGWYWGS ITASEARQHL QKMPEGTFLV RDSTHPSYLF TLSVKTTRGP TNVRIEYADS  60
SFRLDSNCLS RPRILAFPDV VSLVQHYV                                     88

SEQ ID NO: 390         moltype = AA  length = 92
FEATURE                Location/Qualifiers
source                 1..92
                       mol_type = protein
                       organism = Homo sapiens
SEQUENCE: 390
ELLQDLGWYH GNLTRHAAEA LLLSNGCDGS YLLRDSNETT GLYSLSVRAK DSVKHFHVEY  60
TGYSFKFGFN EFSSLKDFVK HFANQPLIGS ET                                92

SEQ ID NO: 391         moltype = AA  length = 108
FEATURE                Location/Qualifiers
source                 1..108
                       mol_type = protein
                       organism = Homo sapiens
SEQUENCE: 391
IHRTQHWFHG RISREESHRI IKQQGLVDGL FLLRDSQSNP KAFVLTLCHH QKIKNFQILP  60
CEDDGQTFFS LDDGNTKFSD LIQLVDFYQL NKGVLPCKLK HHCIRVAL               108

SEQ ID NO: 392         moltype = AA  length = 108
FEATURE                Location/Qualifiers
source                 1..108
                       mol_type = protein
                       organism = Homo sapiens
SEQUENCE: 392
IHRSQPWFHH KISRDEAQRL IIQQGLVDGV FLVRDSQSNP KTFVLSMSHG QKIKHFQIIP  60
VEDDGEMFHT LDDGHTRFTD LIQLVEFYQL NKGVLPCKLK HYCARIAL               108

SEQ ID NO: 393         moltype = AA  length = 108
FEATURE                Location/Qualifiers
source                 1..108
                       mol_type = protein
                       organism = Homo sapiens
SEQUENCE: 393
IHRTQLWFHG RISREESQRL IGQQGLVDGL FLVRESQRNP QGFVLSLCHL QKVKHYLILP  60
SEEEGRLYFS MDDGQTRFTD LLQLVEFHQL NRGILPCLLR HCCTRVAL               108

SEQ ID NO: 394         moltype = AA  length = 102
FEATURE                Location/Qualifiers
source                 1..102
                       mol_type = protein
                       organism = Homo sapiens
SEQUENCE: 394
LAQDGVPEWF HGAISREDAE NLLESQPLGS FLIRVSHSHV GYTLSYKAQS SCCHFMVKLL  60
DDGTFMIPGE KVAHTSLDAL VTFHQQKPIE PRRELLTQPC RQ                     102

SEQ ID NO: 395         moltype = AA  length = 97
FEATURE                Location/Qualifiers
source                 1..97
                       mol_type = protein
                       organism = Homo sapiens
SEQUENCE: 395
```

```
GDQPLSGYPW FHGMLSRLKA AQLVLTGGTG SHGVFLVRQS ETRRGEYVLT FNFQGKAKHL  60
RLSLNEEGQC RVQHLWFQSI FDMLEHFRVH PIPLESG                           97

SEQ ID NO: 396          moltype = AA  length = 96
FEATURE                 Location/Qualifiers
source                  1..96
                        mol_type = protein
                        organism = Homo sapiens
SEQUENCE: 396
ELELSDYPWF HGTLSRVKAA QLVLAGGPRN HGLFVIRQSE TRPGEYVLTF NFQGKAKHLR  60
LSLNGHGQCH VQHLWFQSVL DMLRHFHTHP IPLESG                            96

SEQ ID NO: 397          moltype = AA  length = 97
FEATURE                 Location/Qualifiers
source                  1..97
                        mol_type = protein
                        organism = Homo sapiens
SEQUENCE: 397
TDHFLSCYPW FHGPISRVKA AQLVQLQGPD AHGVFLVRQS ETRRGEYVLT FNFQGIAKHL  60
RLSLTERGQC RVQHLHFPSV VDMLHHFQRS PIPLECG                           97

SEQ ID NO: 398          moltype = AA  length = 103
FEATURE                 Location/Qualifiers
source                  1..103
                        mol_type = protein
                        organism = Homo sapiens
SEQUENCE: 398
DAVAVYHGKI SRETGEKLLL ATGLDGSYLL RDSESVPGVY CLCVLYHGYI YTYRVSQTET  60
GSWSAETAPG VHKRYFRKIK NLISAFQKPD QGIVIPLQYP VEK                    103

SEQ ID NO: 399          moltype = AA  length = 103
FEATURE                 Location/Qualifiers
source                  1..103
                        mol_type = protein
                        organism = Homo sapiens
SEQUENCE: 399
MDLPYYHGRL TKQDCETLLL KEGVDGNFLL RDSESIPGVL CLCVSFKNIV YTYRIFREKH  60
GYYRIQTAEG SPKQVFPSLK ELISKFEKPN QGMVVHLLKP IKR                    103

SEQ ID NO: 400          moltype = AA  length = 102
FEATURE                 Location/Qualifiers
source                  1..102
                        mol_type = protein
                        organism = Homo sapiens
SEQUENCE: 400
LQHGAAPAWF HGFITRREAE RLLEPKPQGC YLVRFSESAV TFVLTYRSRT CCRHFLLAQL  60
RDGRHVVLGE DSAHARLQDL LLHYTAHPLS PYGETLTEPL AR                     102

SEQ ID NO: 401          moltype = AA  length = 104
FEATURE                 Location/Qualifiers
source                  1..104
                        mol_type = protein
                        organism = Homo sapiens
SEQUENCE: 401
KTSDTIAPWF HGILTLKKAN ELLLSTGMPG SFLIRVSERI KGYALSYLSE DGCKHFLIDA  60
SADAYSFLGV DQLQHATLAD LVEYHKEEPI TSLGKELLLY PCGQ                   104

SEQ ID NO: 402          moltype = AA  length = 103
FEATURE                 Location/Qualifiers
source                  1..103
                        mol_type = protein
                        organism = Homo sapiens
SEQUENCE: 402
RNTKFIAPWF HGIISREDAE ALLENMTEGA FLVRVSEKIW GYTLSYRLQK GFKHFLVDAS  60
GDFYSFLGVD PNRHATLTDL VDFHKEEIIT VSGGELLQEP CGQ                    103

SEQ ID NO: 403          moltype = AA  length = 101
FEATURE                 Location/Qualifiers
source                  1..101
                        mol_type = protein
                        organism = Homo sapiens
SEQUENCE: 403
SVFVNTTESC EVERLFKATS PRGEPQDGLY CIRNSSTKSG KVLVVWDETS NKVRNYRIFE  60
KDSKFYLEGE VLFVSVGSMV EHYHTHVLPS HQSLLLRHPY G                      101

SEQ ID NO: 404          moltype = AA  length = 97
FEATURE                 Location/Qualifiers
source                  1..97
                        mol_type = protein
```

```
                         organism = Homo sapiens
SEQUENCE: 404
QIWYHGAISR GDAENLLRLC KECSYLVRNS QTSKHDYSLS LRSNQGFMHM KLAKTKEKYV  60
LGQNSPPFDS VPEVIHYYTT RKLPIKGAEH LSLLYPV                           97

SEQ ID NO: 405           moltype = AA  length = 98
FEATURE                  Location/Qualifiers
source                   1..98
                         mol_type = protein
                         organism = Homo sapiens
SEQUENCE: 405
QPWFHGPLNR ADAESLLSLC KEGSYLVRLS ETNPQDCSLS LRSSQGFLHL KFARTRENQV  60
VLGQHSGPFP SVPELVLHYS SRPLPVQGAE HLALLYPV                          98

SEQ ID NO: 406           moltype = AA  length = 73
FEATURE                  Location/Qualifiers
source                   1..73
                         mol_type = protein
                         organism = Homo sapiens
SEQUENCE: 406
QPWYHGAISR AEAESRLQPC KEAGYLVRNS ESGNSRYSIA LKTSQGCVHI IVAQTKDNKY  60
TLNQTSAVFD SIP                                                     73

SEQ ID NO: 407           moltype = AA  length = 98
FEATURE                  Location/Qualifiers
source                   1..98
                         mol_type = protein
                         organism = Homo sapiens
SEQUENCE: 407
QVWYHGAISR TDAENLLRLC KEASYLVRNS ETSKNDFSLS LKSSQGFMHM KLSRTKEHKY  60
VLGQNSPPFS SVPEIVHHYA SRKLPIKGAE HMSLLYPV                          98

SEQ ID NO: 408           moltype = AA  length = 98
FEATURE                  Location/Qualifiers
source                   1..98
                         mol_type = protein
                         organism = Homo sapiens
SEQUENCE: 408
TRASALLDAC GFYWGPLSVH GAHERLRAEP VGTFLVRDSR QRNCFFALSV KMASGPTSIR  60
VHFQAGRFHL DGSRESFDCL FELLEHYVAA PRRMLGAP                          98

SEQ ID NO: 409           moltype = AA  length = 103
FEATURE                  Location/Qualifiers
source                   1..103
                         mol_type = protein
                         organism = Homo sapiens
SEQUENCE: 409
LRELGQTGWY WGSMTVNEAK EKLKEAPEGT FLIRDSSHSD YLLTISVKTS AGPTNLRIEY  60
QDGKFRLDSI ICVKSKLKQF DSVVHLIDYY VQMCKDKRTG PEA                    103

SEQ ID NO: 410           moltype = AA  length = 101
FEATURE                  Location/Qualifiers
source                   1..101
                         mol_type = protein
                         organism = Homo sapiens
SEQUENCE: 410
VNAVRKLQES GFYWSAVTGG EANLLLSAEP AGTFLIRDSS DQRHFFTLSV KTQSGTKNLR  60
IQCEGGSFSL QSDPRSTQPV PRFDCVLKLV HHYMPPPGAP S                      101

SEQ ID NO: 411           moltype = AA  length = 101
FEATURE                  Location/Qualifiers
source                   1..101
                         mol_type = protein
                         organism = Homo sapiens
SEQUENCE: 411
VPDLLQINNN PCYWGVMDKY AAEALLEGKP EGTFLLRDSA QEDYLFSVSF RRYSRSLHAR  60
IEQWNHNFSF DAHDPCVFHS PDITGLLEHY KDPSACMFFE P                      101

SEQ ID NO: 412           moltype = AA  length = 101
FEATURE                  Location/Qualifiers
source                   1..101
                         mol_type = protein
                         organism = Homo sapiens
SEQUENCE: 412
VPDLLQITGN PCYWGVMDRY EAEALLEGKP EGTFLLRDSA QEDYLFSVSF RRYNRSLHAR  60
IEQWNHNFSF DAHDPCVFHS STVTGLLEHY KDPSSCMFFE P                      101

SEQ ID NO: 413           moltype = AA  length = 100
FEATURE                  Location/Qualifiers
```

```
source                  1..100
                        mol_type = protein
                        organism = Homo sapiens
SEQUENCE: 413
TEELKKLAKQ GWYWGPITRW EAEGKLANVP DGSFLVRDSS DDRYLLSLSF RSHGKTLHTR  60
IEHSNGRFSF YEQPDVEGHT SIVDLIEHSI RDSENGAFCY                       100

SEQ ID NO: 414          moltype = AA  length = 101
FEATURE                 Location/Qualifiers
source                  1..101
                        mol_type = protein
                        organism = Homo sapiens
SEQUENCE: 414
AASLRELEKC GWYWGPMNWE DAEMKLKGKP DGSFLVRDSS DPRYILSLSF RSQGITHHTR  60
MEHYRGTFSL WCHPKFEDRC QSVVEFIKRA IMHSKNGKFL Y                     101

SEQ ID NO: 415          moltype = AA  length = 136
FEATURE                 Location/Qualifiers
source                  1..136
                        mol_type = protein
                        organism = Homo sapiens
SEQUENCE: 415
EDLRSHAWYH GRIPRQVSEN LVQRDGDFLV RDSLSSPGNF VLTCQWKNLA QHFKINRTVL  60
RLSEAYSRVQ YQFEMESFDS IPGLVRCYVG NRRPISQQSG AIIFQPINRT VPLRCLEEHY  120
GTSPGQAREG SLTKGR                                                 136

SEQ ID NO: 416          moltype = AA  length = 87
FEATURE                 Location/Qualifiers
source                  1..87
                        mol_type = protein
                        organism = Homo sapiens
SEQUENCE: 416
RPKYYGREFH GMISREAADQ LLIVAEGSYL IRESQRQPGT YTLALRFGSQ TRNFRLYYDG  60
KHFVGEKRFE SIHDLVTDGL ITLYIET                                     87

SEQ ID NO: 417          moltype = AA  length = 87
FEATURE                 Location/Qualifiers
source                  1..87
                        mol_type = protein
                        organism = Homo sapiens
SEQUENCE: 417
RPKYYGREFH GIISREQADE LLGGVEGAYI LRESQRQPGC YTLALRFGNQ TLNYRLFHDG  60
KHFVGEKRFE SIHDLVTDGL ITLYIET                                     87

SEQ ID NO: 418          moltype = AA  length = 181
FEATURE                 Location/Qualifiers
source                  1..181
                        mol_type = protein
                        organism = Homo sapiens
SEQUENCE: 418
GPEYEEEEVA IPLTAPPTNQ WYHGKLDRTI AEERLRQAGK SGSYLIRESD RRPGSFVLSF  60
LSQMNVVNHF RIIAMCGDYY IGGRRFSSLS DLIGYYSHVS CLLKIWFHGK ISKQEAYNLL  120
MTVGQVCSFL VRPSDNTPGD YSLYFRTNEN IQRFKICPTP NNQFMMGGRY YNSIGDIIDH  180
Y                                                                 181

SEQ ID NO: 419          moltype = AA  length = 101
FEATURE                 Location/Qualifiers
source                  1..101
                        mol_type = protein
                        organism = Homo sapiens
SEQUENCE: 419
LRERLLLTRP VWLQLQANAA AALHMLRTEP PGTFLVRKSN TRQCQALCMR LPEASGPSFV  60
SSHYILESPG GVSLEGSELM FPDLVQLICA YCHTRDILLL P                     101

SEQ ID NO: 420          moltype = AA  length = 100
FEATURE                 Location/Qualifiers
source                  1..100
                        mol_type = protein
                        organism = Homo sapiens
SEQUENCE: 420
ILDRLLHTHP IWLQLSLSEE EAAEVLQAQP PGIFLVHKST KMQKKVLSLR LPCEFGAPLK  60
EFAIKESTYT FSLEGSGISF ADLFRLIAFY CISRDVLPFT                       100

SEQ ID NO: 421          moltype = AA  length = 102
FEATURE                 Location/Qualifiers
source                  1..102
                        mol_type = protein
                        organism = Homo sapiens
SEQUENCE: 421
```

```
ILEKLIKTCP VWLQLSLGQA EVARILHRVV AGMFLVRRDS SSKQLVLCVH FPSLNESSAE  60
VLEYTIKEEK SILYLEGSAL VFEDIFRLIA FYCVSRDLLP FT                    102

SEQ ID NO: 422          moltype = AA  length = 136
FEATURE                 Location/Qualifiers
source                  1..136
                        mol_type = protein
                        organism = Homo sapiens
SEQUENCE: 422
EDLAGQPWYH GLLSRQKAEA LLQQNGDFLV RASGSRGGNP VISCRWRGSA LHFEVFRVAL  60
RPRPGRPTAL FQLEDEQFPS IPALVHSYMT GRRPLSQATG AVVSRPVTWQ GPLRRSFSED  120
TLMDGPARIE PLRARK                                                 136

SEQ ID NO: 423          moltype = AA  length = 135
FEATURE                 Location/Qualifiers
source                  1..135
                        mol_type = protein
                        organism = Homo sapiens
SEQUENCE: 423
TDLRSHAWYH GRIPREVSET LVQRNGDFLI RDSLTSLGDY VLTCRWRNQA LHFKINKVVV  60
KAGESYTHIQ YLFEQESFDH VPALVRYHVG SRKAVSEQSG AIIYCPVNRT FPLRYLEASY  120
GLGQGSSKPA SPVSP                                                  135

SEQ ID NO: 424          moltype = AA  length = 103
FEATURE                 Location/Qualifiers
source                  1..103
                        mol_type = protein
                        organism = Homo sapiens
SEQUENCE: 424
DLSVHLWYAG PMERAGAESI LANRSDGTFL VRQRVKDAAE FAISIKYNVE VKHIKIMTAE  60
GLYRITEKKA FRGLTELVEF YQQNSLKDCF KSLDTTLQFP FKE                   103

SEQ ID NO: 425          moltype = AA  length = 103
FEATURE                 Location/Qualifiers
source                  1..103
                        mol_type = protein
                        organism = Homo sapiens
SEQUENCE: 425
DYTAYPWFAG NMERQQTDNL LKSHASGTYL IRERPAEAER FAISIKFNDE VKHIKVVEKD  60
NWIHITEAKK FDSLLELVEY YQCHSLKESF KQLDTTLKYP YKS                   103

SEQ ID NO: 426          moltype = AA  length = 103
FEATURE                 Location/Qualifiers
source                  1..103
                        mol_type = protein
                        organism = Homo sapiens
SEQUENCE: 426
DYSCQPWYAG AMERLQAETE LINRVNSTYL VRHRTKESGE YAISIKYNNE AKHIKILTRD  60
GFFHIAENRK FKSLMELVEY YKHHSLKEGF RTLDTTLQFP YKE                   103

SEQ ID NO: 427          moltype = AA  length = 93
FEATURE                 Location/Qualifiers
source                  1..93
                        mol_type = protein
                        organism = Homo sapiens
SEQUENCE: 427
PACFYTVSRK EATEMLQKNP SLGNMILRPG SDSRNYSITI RQEIDIPRIK HYKVMSVGQN  60
YTIELEKPVT LPNLFSVIDY FVKETRGNLR PFI                              93

SEQ ID NO: 428          moltype = AA  length = 151
FEATURE                 Location/Qualifiers
source                  1..151
                        mol_type = protein
                        organism = Homo sapiens
SEQUENCE: 428
WIESILELIK KHLLPLWNDG CIMGFISKER ERALLKDQQP GTFLLRFSES SREGAITFTW  60
VERSQNGGEP DFHAVEPYTK KELSAVTFPD IIRNYKVMAA ENIPENPLKY LYPNIDKDHA  120
FGKYYSRPKE APEPMELDGP KGTGYIKTEL I                                151

SEQ ID NO: 429          moltype = AA  length = 151
FEATURE                 Location/Qualifiers
source                  1..151
                        mol_type = protein
                        organism = Homo sapiens
SEQUENCE: 429
WLDKILELVH DHLKDLWNDG RIMGFVSRSQ ERRLLKKTMS GTFLLRFSES SEGGITCSWV  60
EHQDDDKVLI YSVQPYTKEV LQSLPLTEII RHYQLLTEEN IPENPLRFLY PRIPRDEAFG  120
CYYQEKVNLQ ERRKYLKHRL IVVSNRQVDE L                                151
```

-continued

```
SEQ ID NO: 430         moltype = AA  length = 162
FEATURE                Location/Qualifiers
source                 1..162
                       mol_type = protein
                       organism = Homo sapiens
SEQUENCE: 430
MAGKGFSFWV WLDNIIDLVK KYILALWNEG YIMGFISKER ERAILSTKPP GTFLLRFSES  60
SKEGGVTFTW VEKDISGKTQ IQSVEPYTKQ QLNNMSFAEI IMGYKIMDAT NILVSPLVYL  120
YPDIPKEEAF GKYCRPESQE HPEADPGSAA PYLKTKFICV TP                     162

SEQ ID NO: 431         moltype = AA  length = 148
FEATURE                Location/Qualifiers
source                 1..148
                       mol_type = protein
                       organism = Homo sapiens
SEQUENCE: 431
WLEAILDLIK KHILPLWIDG YVMGFVSKEK ERLLLKDKMP GTFLLRFSES HLGGITFTWV  60
DHSESGEVRF HSVEPYNKGR LSALPFADIL RDYKVIMAEN IPENPLKYLY PDIPKDKAFG  120
KHYSSQPCEV SRPTERGDKG YVPSVFIP                                     148

SEQ ID NO: 432         moltype = AA  length = 140
FEATURE                Location/Qualifiers
source                 1..140
                       mol_type = protein
                       organism = Homo sapiens
SEQUENCE: 432
WFDGVMEVLK KHHKPHWNDG AILGFVNKQQ AHDLLINKPD GTFLLRFSDS EIGGITIAWK  60
FDSPERNLWN LKPFTTRDFS IRSLADRLGD LSYLIYVFPD RPKDEVFSKY YTPVLAKAVD  120
GYVKPQIKQV VPEFVNASAD                                              140

SEQ ID NO: 433         moltype = AA  length = 145
FEATURE                Location/Qualifiers
source                 1..145
                       mol_type = protein
                       organism = Homo sapiens
SEQUENCE: 433
WFDGVMEVLK KHLKPHWNDG AILGFVNKQQ AHDLLINKPD GTFLLRFSDS EIGGITIAWK  60
FDSQERMFWN LMPFTTRDFS IRSLADRLGD LNYLIYVFPD RPKDEVYSKY YTPVPCESAT  120
AKAVDGYVKP QIKQVVPEFV NASAD                                        145

SEQ ID NO: 434         moltype = AA  length = 130
FEATURE                Location/Qualifiers
source                 1..130
                       mol_type = protein
                       organism = Homo sapiens
SEQUENCE: 434
WFDGVLDLTK RCLRSYWSDR LIIGFISKQY VTSLLLNEPD GTFLLRFSDS EIGGITIAHV  60
IRGQDGSPQI ENIQPFSAKD LSIRSLGDRI RDLAQLKNLY PKKPKDEAFR SHYKPEQMGK  120
DGRGYVPATI                                                         130

SEQ ID NO: 435         moltype = AA  length = 97
FEATURE                Location/Qualifiers
source                 1..97
                       mol_type = protein
                       organism = Homo sapiens
SEQUENCE: 435
RNWNSLAVTH PGYMAFLTYD EVKARLQKFI HKPGSYIFRL SCTRLGQWAI GYVTADGNIL  60
QTIPHNKPLF QALIDGFREG FYLFPDGRNQ NPDLTGL                           97

SEQ ID NO: 436         moltype = AA  length = 97
FEATURE                Location/Qualifiers
source                 1..97
                       mol_type = protein
                       organism = Homo sapiens
SEQUENCE: 436
RNWNFLAVTH PGYMAFLTYD EVKARLQKYS TKPGSYIFRL SCTRLGQWAI GYVTGDGNIL  60
QTIPHNKPLF QALIDGSREG FYLYPDGRSY NPDLTGL                           97

SEQ ID NO: 437         moltype = AA  length = 97
FEATURE                Location/Qualifiers
source                 1..97
                       mol_type = protein
                       organism = Homo sapiens
SEQUENCE: 437
KNWQLLAVNH PGYMAFLTYD EVQERLQACR DKPGSYIFRP SCTRLGQWAI GYVSSDGSIL  60
QTIPANKPLS QVLLEGQKDG FYLYPDGKTH NPDLTEL                           97
```